United States Patent
Deng et al.

(10) Patent No.: US 11,319,322 B2
(45) Date of Patent: May 3, 2022

(54) SUBSTITUTED ARYL ETHER COMPOUND, PREPARATION METHOD THEREOF, PHARMACEUTICAL COMPOSITION AND USE THEREOF

(71) Applicant: Xiamen University, Xiamen (CN)

(72) Inventors: Xianming Deng, Xiamen (CN); Ting Zhang, Xiamen (CN); Qiaofeng Kang, Xiamen (CN); Yanru Yang, Xiamen (CN); Xihuan Sun, Xiamen (CN); Zaiyou Yang, Xiamen (CN); Xiaoyang Li, Xiamen (CN); Jingfang Zhang, Xiamen (CN); Jiaji Zhong, Xiamen (CN); Zhou Deng, Xiamen (CN); Chao Dong, Xiamen (CN); Shuang Liu, Xiamen (CN); Li Li, Xiamen (CN); Qingyan Xu, Xiamen (CN); Zhiyu Hu, Xiamen (CN)

(73) Assignee: Xiamen University, Xiamen (CN)

(*) Notice: Subject to any disclaimer, the term of this patent is extended or adjusted under 35 U.S.C. 154(b) by 0 days.

(21) Appl. No.: 16/626,015

(22) PCT Filed: Jun. 29, 2018

(86) PCT No.: PCT/CN2018/093544
§ 371 (c)(1),
(2) Date: Dec. 23, 2019

(87) PCT Pub. No.: WO2019/001556
PCT Pub. Date: Jan. 3, 2019

(65) Prior Publication Data
US 2020/0123162 A1    Apr. 23, 2020

(30) Foreign Application Priority Data

Jun. 30, 2017 (CN) .......................... 201710523136.4

(51) Int. Cl.
| | | |
|---|---|---|
| *C07D 487/04* | (2006.01) | |
| *A61P 35/00* | (2006.01) | |
| *C07D 471/04* | (2006.01) | |
| *C07D 473/18* | (2006.01) | |
| *C07D 473/30* | (2006.01) | |
| *C07D 495/04* | (2006.01) | |

(52) U.S. Cl.
CPC ............ *C07D 487/04* (2013.01); *A61P 35/00* (2018.01); *C07D 471/04* (2013.01); *C07D 473/18* (2013.01); *C07D 473/30* (2013.01); *C07D 495/04* (2013.01)

(58) Field of Classification Search
CPC .................................................. C07D 487/04
See application file for complete search history.

(56) References Cited

U.S. PATENT DOCUMENTS

2015/0315191 A1    11/2015    Yang et al.

FOREIGN PATENT DOCUMENTS

| CN | 103570723 | * | 2/2014 |
| CN | 103570723 A | | 2/2014 |
| WO | WO2007/004749 | * | 1/2007 |
| WO | WO 2007/004749 A1 | | 1/2007 |
| WO | WO2011/090738 | * | 12/2009 |
| WO | WO 2011/090738 A2 | | 7/2011 |
| WO | WO 2015/089479 A1 | | 6/2015 |
| WO | WO2016/130920 | * | 8/2016 |
| WO | WO 2016/130920 A2 | | 8/2016 |

OTHER PUBLICATIONS

Pinedo et al. (2000) McMahon et al. (2000).*
J'nal of Med. Chem. 2015, 58, 183-196 J'nal of Med. Chem 2013, 56, 1641-1655.*
Vippagunta et al. (2001).*
J'nal of Het. Chem., 46, 459 (2009) J'nal of Med. Chem., 2015 58, 7431-7448.*
International Preliminary Report on Patentability for Application No. PCT/CN2018/093544, dated Jan. 9, 2020.
PCT/CN2018/093544, Jan. 9, 2020, International Preliminary Report on Patentability.
International Search Report and Written Opinion dated Aug. 8, 2018, in connection with PCT/CN2018/093544.
Lawhorn et al., Identification of Purines and 7-Deazapurines as Potent and Selective Type I Inhibitors of Troponin I-Interacting Kinase (TNNI3K). J Med Chem. Sep. 24, 2015;58(18):7431-48. doi: 10.1021/acs.jmedchem.5b00931. Epub Sep. 10, 2015.
Perspicace et al., Unexpected C—O Bond Formation in Suzuki Coupling of 4-Chlorothieno[2-3-d]pyrimidines. J. Heterocyclic. Chem., May 2009;46:459-64. doi: 10.1002/jhet.107.

(Continued)

*Primary Examiner* — Paul V Ward
(74) *Attorney, Agent, or Firm* — Wolf, Greenfield & Sacks, P.C.

(57) ABSTRACT

The present invention relates to a compound having the following formula, or a stereoisomer thereof, a prodrug thereof, a pharmaceutically acceptable salt thereof or a pharmaceutically acceptable solvate thereof, preparation method thereof, pharmaceutical composition comprising the same and use of the compound in the manufacture of a medicament for preventing or treating tumor, wherein the substituents are as defined in the specification.

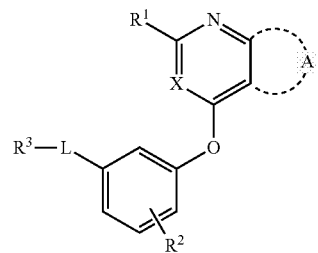

12 Claims, No Drawings

(56) References Cited

OTHER PUBLICATIONS

Tan et al., Discovery of type II inhibitors of TGFβ-activated kinase 1 (TAK1) and mitogen-activated protein kinase kinase kinase kinase 2 (MAP4K2). J Med Chem. Jan. 8, 2015;58(1):183-96. doi: 10.1021/jm500480k. Epub Jul. 30, 2014.
Wang et al., Development of an UPLC-MS/MS method for quantification of Avitinib (AC0010) and its five metabolites in human cerebrospinal fluid: Application to a study of the blood-brain barrier penetration rate of non-small cell lung cancer patients. J Pharm Biomed Anal. May 30, 2017;139:205-214. doi: 10.1016/j.jpba.2017.02.057. Epub Mar. 4, 2017.
Yang et al., Structure-activity relationship studies of pyrazolo[3,4-d]pyrimidine derivatives leading to the discovery of a novel multikinase inhibitor that potently inhibits FLT3 and VEGFR2 and evaluation of its activity against acute myeloid leukemia in vitro and in vivo. J Med Chem. Feb. 28, 2013;56(4):1641-55. doi: 10.1021/jm301537p. Epub Feb. 19, 2013.
PCT/CN2018/093544, Aug. 8, 2018, International Search Report and Written Opinion.

* cited by examiner

SUBSTITUTED ARYL ETHER COMPOUND, PREPARATION METHOD THEREOF, PHARMACEUTICAL COMPOSITION AND USE THEREOF

RELATED APPLICATIONS

This application is a national stage filing under 35 U.S.C. § 371 of International PCT Application, PCT/CN2018/093544, filed Jun. 29, 2018, which claims priority to Chinese Application No. 201710523136.4, filed on Jun. 30, 2017, the entire contents of each of which is incorporated herein by reference.

TECHNICAL FIELD

The invention relates to the field of medicinal chemistry, and in particular to a type of compounds having RET kinase selective inhibitory activity, a method for the preparation thereof, a pharmaceutical composition comprising the same, and use of these compounds in the manufacture of a medicament for preventing or treating a disease associated with RET kinase in vivo, and in the manufacture of a medicament for preventing or treating a disease associated with angiogenesis or cancer metastasis, in particular in the manufacture of a medicament for preventing or treating tumor growth and metastasis.

BACKGROUND ART

Lung cancer is the first killer to threat human health today. At present, the use of targeted drugs for the treatment of lung cancer has made a great progress. A series of small molecule drugs targeting kinases, such as Imatinib, Gefitinib, Ceritinib and Sunitinib, have been successfully used in clinical practice. Also, there are more kinase inhibitors in development or in clinical trials.

Personalized treatment based on biomarkers has progressed from the laboratory to the clinic, and has made a great clinical progress in the treatment of patients with advanced non-small cell lung cancer. This means that, in addition to the traditional histopathological classification of NSCLC, molecular phenotypic classification can be performed based on different expression levels of different molecular markers of specific patients. NSCLC patients are tested in the aspect of relevant molecular markers prior to treatment. In the clinic, doctors can carry out targeted treatment according to the phenotypic characteristics of their tumor molecules, thereby improving the therapeutic effect. Under such a background, research and development of new drugs targeting driver genes or their encoded proteins closely related to tumor development and progression has become a hot spot in anti-tumor drug research.

RET kinase is a receptor tyrosine kinase expressed by RET proto-oncogene. The protein structure includes, in the order from N-terminus to C-terminus, an extracellular receptor domain, a transmembrane domain, and an intracellular tyrosine kinase domain. The protein consists of 1114 amino acids, of which 724 to 1016 are kinase domains.

Studies have shown that, in lung adenocarcinoma (LADC), RET kinase protein fused to other proteins can be used as a potential therapeutic target. Currently known proteins that can be fused to RET kinase are kinesin family member 5B (KIF5B), coiled-coli domain containing 6 (CCDC6), tripartite motif-containing 33 (TRIM33), and nuclear receptor coactivator 4 (NOCA4). Among them, KIF5B-RET fusion protein accounts for 90% of all RET fusion proteins. In addition, RET fusion proteins are independent of other cancer driver factors such as EGFR, HER2, BRAF or ELM4-ALK. And there is evidence to suggest that the expression of exogenous KIF5B-RET protein in NIH3T3 cells can lead to morphological changes and non-dependent growth of cells. These findings all indicate that RET fusion protein is a potential therapeutic target for lung adenocarcinoma. Therefore, the development of small molecule kinase inhibitors that can inhibit the kinase activity of RET fusion proteins has become a focus of research.

There have been no reports of selective inhibitors targeting RET kinase. However, for example, Danusertib (pan-Aurora kinase inhibitor, Carpinelli P, et al. *Mol. Cancer Ther.*, 2007, 3158-3168.), Regorafenib (VEGFR inhibitor) developed by Bayer, Gefitinib (EGFR inhibitor, Pedersen M W, et al. *Br. J. Cancer*, 2005, 915-923.) developed by AstraZeneca and Sunitinib (VEGFR and PDGFR inhibitor, Sun L, et al. *J. Med. Chem.*, 2003, 1116-1119.) developed by Pfizer have a relatively strong inhibitory effect on RET. However, for various reasons, the above several small molecule inhibitors have not been used in the treatment of lung adenocarcinoma patients with RET fusion protein. Therefore, there is a great need for a selective small molecule inhibitor targeting RET that can be used in the clinical practice of treating such patients.

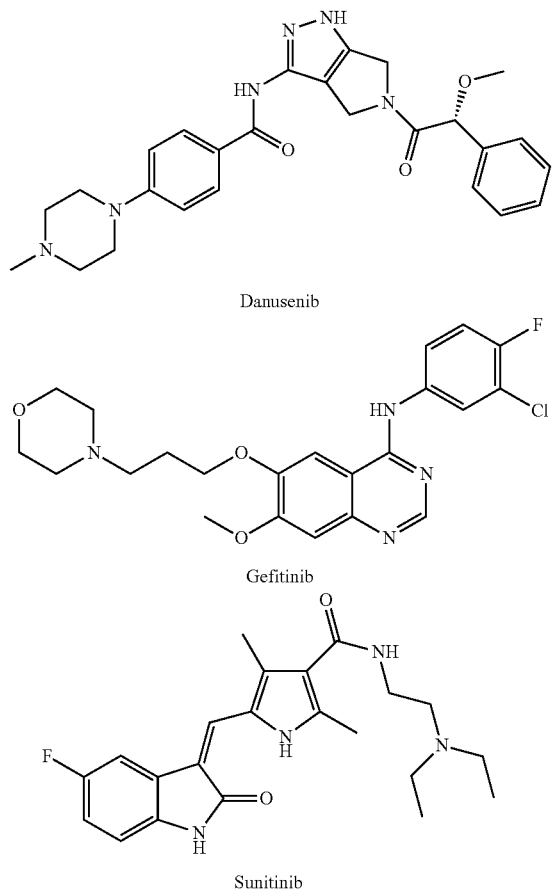

Danusenib

Gefitinib

Sunitinib

SUMMARY OF INVENTION

In order to find new RET inhibitors, after extensive and in-depth research, the inventors of the present invention have designed and synthesized a series of substituted aryl ether derivatives having novel structures, high safety and high activity for RET, and have studied antitumor activity of this novel type of derivatives.

The compound has the general formula:

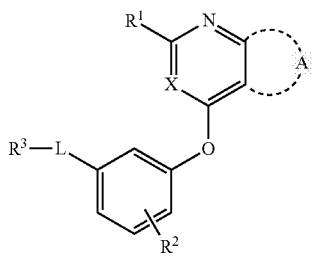

The definitions of substituents and symbols are described in detail below.

One object of the present invention is to provide a compound having RET selective inhibitory activity, and a stereoisomer thereof, a prodrug thereof, a pharmaceutically acceptable salt thereof or a pharmaceutically acceptable solvate thereof.

Another object of the present invention is to provide a method for the preparation of the above compound.

Another object of the present invention is to provide a pharmaceutical composition comprising the above compound.

Another object of the present invention is to provide use of the above compound in the manufacture of a medicament for preventing or treating a disease associated with RET kinase accompanied by abnormal cell proliferation, morphological changes, hyperkinesia and the like in vivo, and in the manufacture of a medicament for preventing or treating a disease associated with angiogenesis or cancer metastasis, in particular in the manufacture of a medicament for preventing or treating tumor growth and metastasis.

Specific Modes for Carrying Out the Invention

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In one aspect, the present invention provides a compound having the general formula, or a stereoisomer thereof, a prodrug thereof, a pharmaceutically acceptable salt thereof or a pharmaceutically acceptable solvate thereof,

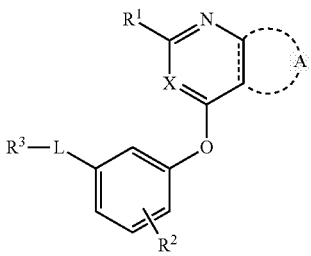

wherein, $R^1$ is selected from:

1) hydrogen, C1-C6 amido, optionally substituted C1-C6 alkyl, C1-C6 alkoxy, C1-C6 oxygen-containing alkyl, C1-C6 fluorine-containing alkyl, C1-C6 fluorine-containing alkoxy; C2-C6 alkenyl, C2-C6 alkynyl, optionally substituted C3-C7 cycloalkyl, nitro, cyano, hydroxy, halogen, optionally substituted aryl; optionally substituted heteroaryl, optionally substituted heterocyclyl, the substituent thereof being selected from: halogen atom, C1-C6 alkyl, C1-C6 alkoxy; C1-C6 oxygen-containing alkyl; C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

2) amino or amino bearing one or two substituent(s) on the nitrogen, the substituent thereof being selected from C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl; or 2-N,N-dimethylaminoethylamino, 2-hydroxyethylamino, 2-morpholinoethylamino; 2-thiomorpholinylethylamino, 2-(4-N-methylpiperazinyl)ethylamino, N-dimethylaminopropylamino, 3-N, N-diethylaminopropylamino, 3-N,N-diisopropylaminopropylamino; 3-hydroxypropylamino, 3-morpholinopropylamino, 3-thiomorpholinylpropylamino, 3-(4-N-methylpiperazinyl)propylamino, N-methylpiperidyl-4-amino, N-ethylpiperidyl-4-amino, N-isopropylpiperidyl-4-amino; N-acetylpiperidyl-4-amino;

3) arylamino or heteroarylamino; wherein the aryl or heteroaryl is optionally substituted by C1-C6 alkyl, C1-C6 alkoxy, C1-C6 oxygen-containing alkyl, C1-C3 fluorine-containing alkyl; C3-C6 cycloalkyl, halogen; nitro, cyano, hydroxy, optionally substituted heterocyclyl, C1-C6 alkoxycarbonyl, C1-C6 acyl;

4) a five- or six-membered heterocyclic ring comprising one or more heteroatoms selected from N, O and S, said five- or six-membered heterocyclic ring being optionally substituted by C1-C6 alkyl, C1-C6 alkoxy, hydroxy; amino; C1-C6 alkoxycarbonyl, C1-C6 acyl, cyano, optionally substituted heterocyclyl, including but not limited to: morpholine, 3,5-dimethylmorpholino, thiomorpholinyl, tetrahydropyrrolyl, 3-N,N-dimethyltetrahydropyrrolyl, 3-N,N-diethyltetrahydropyrrolyl;

piperidinyl, 4-N,N-dimethylaminopiperidinyl, 4-N,N-diethylaminopiperidinyl, 4-N,N-diisopropylaminopiperidinyl, 4-hydroxypiperidinyl, 4-(N-methylpiperazinyl)piperidinyl, 4-(N-ethylpiperazinyl)piperidinyl, 4-(N-isopropylpiperazinyl)piperidinyl, 4-(N-acetylpiperazinyl)piperidinyl; 4-(N-t-butoxyformylpiperazinyl)piperidinyl, 4-(N-methanesulfonylpiperazinyl)piperidinyl, 4-(N-(2-hydroxyethyl)piperazinyl)piperidinyl, 4-(N-(2-cyanoethyl)piperazinyl)piperidinyl, 4-(N-(3-hydroxypropyl)piperazinyl)piperidinyl, 4-(N-(2-N,N-dimethylethyl)piperazinyl)piperidinyl; 4-(N-(2-N,N-diethylethyl)piperazinyl)piperidinyl, 4-(N-(3-N,N-dimethylpropyl)piperazinyl)piperidinyl, 4-(N-(3-N,N-diethylpropyl)piperazinyl)piperidinyl, 4-(tetrahydropyrrolyl) piperidinyl; 4-(3-N,N-dimethyltetrahydropyrrolyl) piperidinyl;

N-methylpiperazinyl, N-ethylpiperazinyl; N-isopropylpiperazinyl, N-acetylpiperazinyl, N-t-butoxyformylpiperazinyl, N-methanesulfonylpiperazinyl, N-(2-hydroxyethyl)piperazinyl, N-(2-cyanoethyl)piperazinyl, N-(3-hydroxypropyl)piperazinyl, N-(2-N,N-dimethylethyl)piperazinyl, N-(2-N,N-diethylethyl)piperazinyl, N-(3-N,N-dimethylpropl)piperazinyl, N-(3-N,N-diethylpropyl)piperazinyl, 2-oxo-piperazin-4-yl, N—(N-methyl-4-piperidinyl)piperazinyl, N—(N-ethyl-4-piperidinyl)piperazinyl, N—(N-acetyl-4-piperidinyl)piperazinyl;

preferably, $R^1$ is selected from:

1) hydrogen; C1-C6 amido, optionally substituted C1-C6 alkyl; C1-C6 alkoxy, C1-C6 fluorine-containing alkyl, optionally substituted C3-C7 cycloalkyl, hydroxy, halogen, optionally substituted C6-C10 aryl, optionally substituted heteroaryl, optionally substituted heterocyclyl; the substituent thereof being selected from: halogen atom, amino, hydroxy, C1-C6 alkyl, C1-C6 alkoxy, C1-C6 fluorine-containing alkyl;

2) amino or amino bearing one or two substituent(s) on the nitrogen, the substituent thereof being selected from C1-C6 alkyl, C1-C6 alkoxy, C1-C6 fluorine-containing alkyl, C3-C7 cycloalkyl;

3) arylamino or heteroarylamino, wherein the aryl or heteroaryl is optionally substituted by C1-C6 alkyl, 01-C6 alkoxy, C1-C3 fluorine-containing alkyl, C3-C6 cycloalkyl, halogen, amino; hydroxy, optionally substituted heterocyclyl;

$R^2$ is selected from: hydrogen, halogen atom, C1-C6 alkylamino, di(C1-C6 alkyl) amino; optionally substituted C1-C6 alkyl, optionally substituted 03-C7 cycloalkyl, the substituent thereof being selected from halogen atom, amino; hydroxy, optionally substituted C6-C10 aryl or optionally substituted heteroaryl, the substituent thereof being selected from halogen atom, C1-C6 alkyl, C1-C6 alkoxy; C1-C6 fluorine-containing alkyl;

preferably, $R^2$ is selected from: hydrogen, halogen atom, optionally substituted 01-C6 alkyl, optionally substituted C3-C7 cycloalkyl, C1-C6 fluorine-containing alkyl, optionally substituted C6-C10 aryl or optionally substituted heteroaryl;

$R^3$ is selected from optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl; optionally substituted heteroaryl, optionally substituted heterocyclyl, C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, $R^3$ is selected from optionally substituted 06-010 aryl or optionally substituted heteroaryl, optionally substituted C1-C6 alkyl, optionally substituted C3-C7 cycloalkyl, optionally substituted heterocyclyl, the substituent thereof being selected from: optionally substituted heterocyclyl, hydroxy, C1-C6 fluorine-containing alkyl, optionally substituted C6-C10 aryl, optionally substituted heteroaryl;

A is selected from —NR$_4$—CH=N—, —NR$_5$—N=CH—, —CH=CH—NR$_6$—, =N—NR$_7$—CH=, —NR$_6$—CH=CH—, —CH=CH—S—, —S—CH=CH—, the dotted line denotes that when A is: —NR$_4$—CH=N—, —NR$_5$—N=CH—, —CH=CH—NR$_8$—, —NR$_8$—CH=CH—, —CH=CH—S—, —S—CH=CH—, there is a double bond at this site;

X is N or CH; preferably N;

L is selected from: —NHCO—, —CONH—, —CO—, —NHSO$_2$—, —SO$_2$NH—, —NHCONH—, —NHCSNH—, —COO—, —OCO—; preferably —NHCO—, —CONH—, —CO—.

The pharmaceutically acceptable salt is preferably an inorganic acid salt or an organic acid salt, wherein the inorganic acid salt is selected from hydrochloride, hydrobromide, nitrate, sulfate or phosphate; the organic acid salt is selected from formate, acetate, propionate, benzoate, maleate, fumarate, succinate, tartrate, citrate, alkyl sulfonate or aryl sulfonate; preferably, said alkyl sulfonate is methyl sulfonate or ethyl sulfonate; said aryl sulfonate is benzenesulfonate or p-toluenesulfonate.

The present invention is further achieved by the following technical solution; wherein as for the compound, or a stereoisomer thereof, a prodrug thereof, a pharmaceutically acceptable salt thereof or a pharmaceutically acceptable solvate thereof, the compound has the following general formulas I-VII:

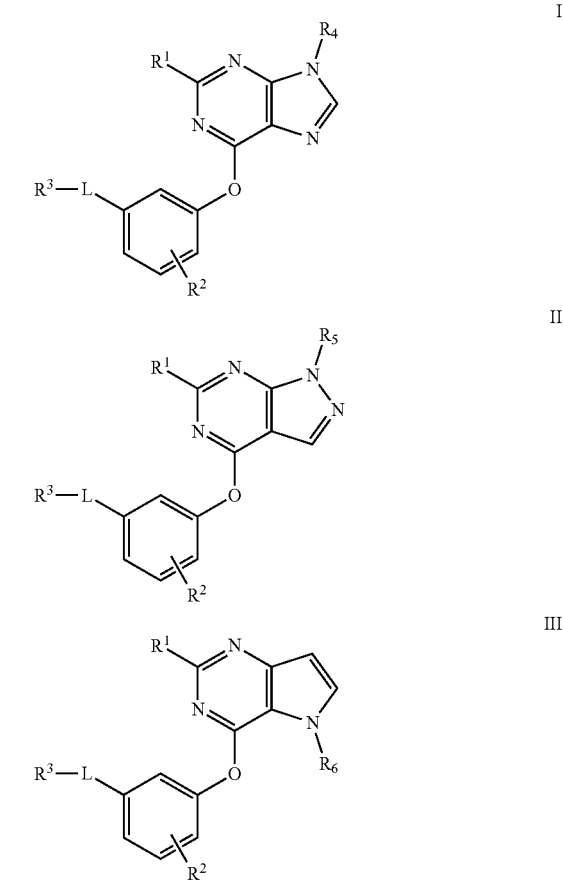

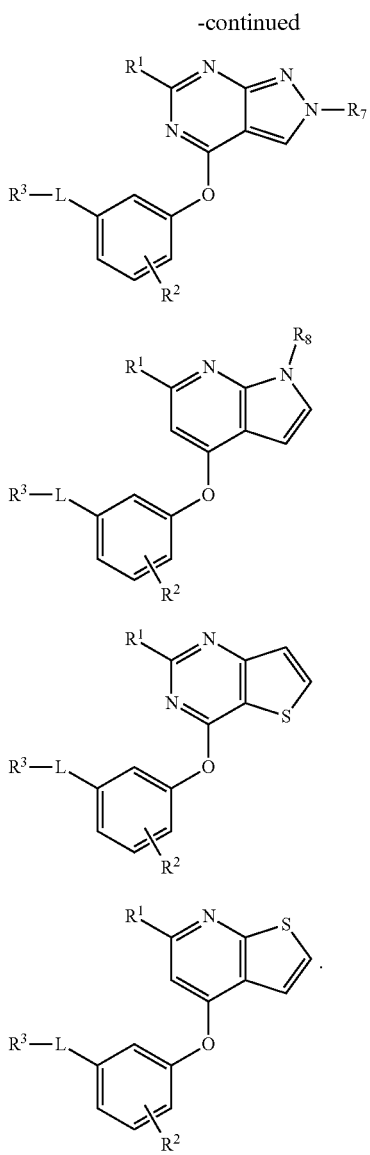

In a first aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

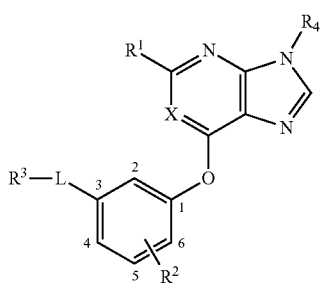

wherein, R¹ is selected from: hydrogen, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, amino, hydroxy, optionally substituted aryl, optionally substituted heteroaryl, optionally substituted heterocyclyl, the substituent thereof being selected from: halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

preferably, R¹ is selected from: hydrogen, optionally substituted C1-C6 alkyl, C1-C6 alkoxy, C1-C6 fluorine-containing alkyl, optionally substituted C3-C7 cycloalkyl, hydroxy, amino, optionally substituted C6-C10 aryl, optionally substituted heteroaryl, optionally substituted heterocyclyl, the substituent thereof being selected from: halogen atom, amino, hydroxy, C1-C6 alkyl, C1-C6 alkoxy, C1-C6 fluorine-containing alkyl;

more preferably, R¹ is selected from: hydrogen, C1-C6 alkoxy, optionally substituted C3-C7 cycloalkyl, hydroxy, amino, optionally substituted C6-C10 aryl, optionally substituted heteroaryl, optionally substituted heterocyclyl, the substituent thereof being selected from: fluoro, chloro, bromo, amino, hydroxy, methyl, ethyl, propyl, isopropyl, methoxy, ethoxy, propoxy, isopropoxy, fluoromethyl, difluoromethyl, trifluoromethyl, trifluoroethyl;

most preferably, R¹ is selected from:

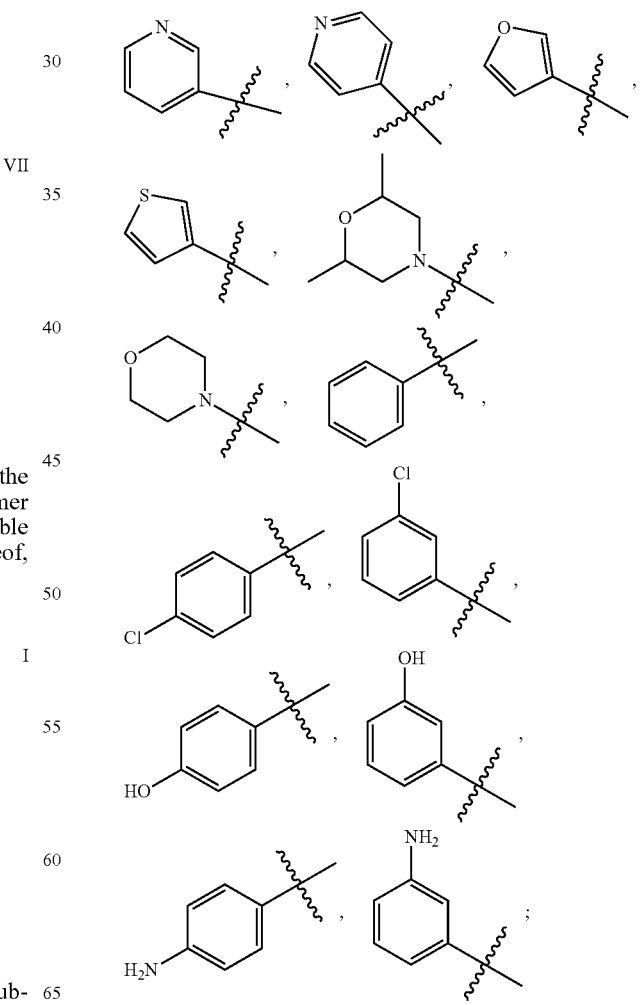

R² is selected from: hydrogen, halogen atom, optionally substituted C1-C6 alkyl, optionally substituted C3-C7 cycloalkyl, the substituent thereof being selected from halogen atom;

preferably, R² is selected from: hydrogen, halogen atom, C1-C6 alkyl, C1-C6 fluorine-containing alkyl;

more preferably, R² is selected from: hydrogen, fluoro, chloro, bromo, methyl, ethyl, propyl, isopropyl, trifluoromethyl;

most preferably, R² is selected from: H, 4-Cl, 4-CH₃, 6-CH₃;

R³ is selected from optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from: halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, R³ is selected from: mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl, heterocyclyl substituted by C1-C6 alkyl;

more preferably, R³ is

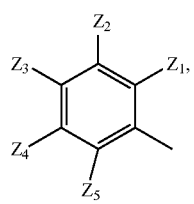

wherein one of $Z_1$-$Z_5$ is $CF_3$—, the rest being H; or any two of $Z_2$, $Z_3$, $Z_4$ each are independently selected from $CF_3$—,

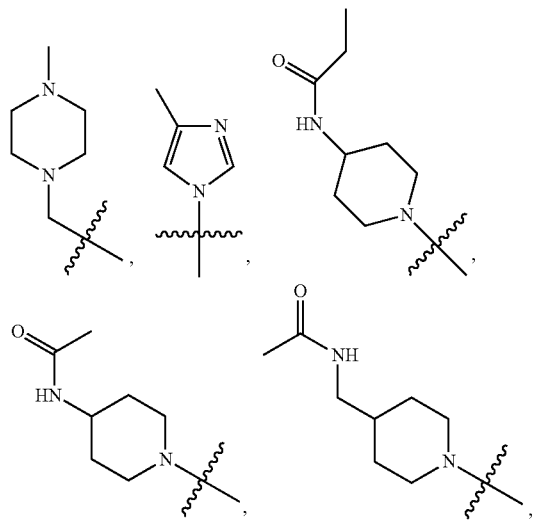

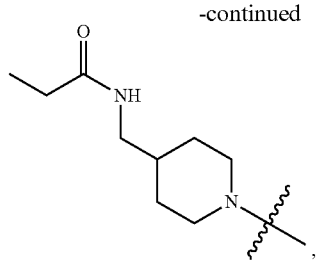

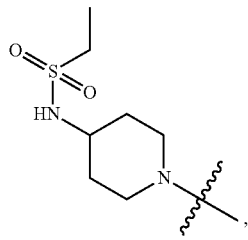

the rest one and $Z_1$, $Z_5$ being H;

most preferably, R³ is

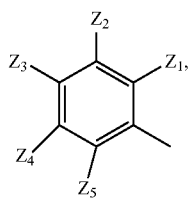

wherein $Z_4$ is $CF_3$—, the rest being H; or $Z_4$ is $CF_3$—, one of $Z_2$, $Z_3$ is

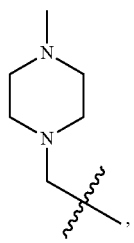

the rest one and $Z_1$, $Z_5$ being H;

R₄ is selected from: hydrogen, C1-C6 alkyl, C1-C6 fluorine-containing alkyl, tri(C1-C6 alkyl) silyl C1-C6 alkoxy C1-C6 alkyl;

preferably, R₄ is selected from: hydrogen, methyl, ethyl, propyl, isopropyl, trifluoromethyl, tri(C1-C6 alkyl) silyl C1-C6 alkoxy C1-C6 alkyl;

R₄, most preferably, is selected from hydrogen, methyl, isopropyl, trimethylsilylethoxymethyl (-SEM);

L is selected from: —NHCO—, —CONH—, —NHSO₂—, —SO₂NH—, —NHCONH—, —NHCSNH—, —COO—, —OCO—; L, preferably, is selected from: —NHCO—, —CONH—.

In a second aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

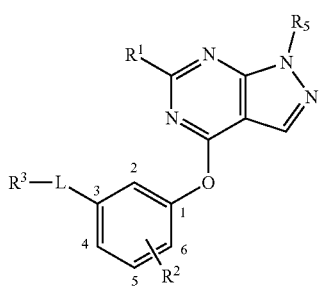

wherein, R¹ is selected from:
1) hydrogen, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, hydroxy;
2) optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy; 3) amino or amino bearing one or two substituent(s) on the nitrogen, the substituent thereof being selected from C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl;
4) arylamino or heteroarylamino, wherein the aryl or heteroaryl is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, hydroxy, optionally substituted heterocyclyl, C1-C6 alkoxycarbonyl, C1-C6 acyl;

preferably, R¹ is selected from:
1) hydrogen, optionally substituted C1-C6 alkyl, C1-C6 alkoxy, C1-C6 fluorine-containing alkyl, optionally substituted C3-C7 cycloalkyl, hydroxy;
2) optionally substituted aryl, optionally substituted heteroaryl, optionally substituted heterocyclyl, the substituent thereof being selected from halogen atom, C1-C6 alkyl, C1-C6 alkoxy, C1-C6 fluorine-containing alkyl, C1-C6 fluorine-containing alkoxy, amino, hydroxy;
3) amino or amino bearing one or two substituent(s) on the nitrogen, the substituent thereof being selected from C1-C6 alkyl, C1-C6 alkoxy, C1-C6 fluorine-containing alkyl, C3-C7 cycloalkyl;
4) arylamino or heteroarylamino, wherein the aryl or heteroaryl is optionally substituted by C1-C6 alkyl, C1-C6 alkoxy, C1-C3 fluorine-containing alkyl, C3-C6 cycloalkyl, halogen, amino, hydroxy, optionally substituted heterocyclyl;

more preferably, R¹ is selected from:
1) hydrogen, hydroxy;
2) optionally substituted aryl, optionally substituted heteroaryl, optionally substituted heterocyclyl, the substituent thereof being selected from fluoro, chloro, bromo, methyl, ethyl, propyl, isopropyl, methoxy, ethoxy, propoxy, isopropoxy, fluoromethyl, difluoromethyl, trifluoromethyl, trifluoroethyl, amino, hydroxy;
3) amino or amino bearing one or two substituent(s) on the nitrogen, the substituent thereof being selected from methyl, ethyl, propyl, isopropyl, methoxy, ethoxy, propoxy, isopropoxy, fluoromethyl, difluoromethyl, trifluoromethyl, trifluoroethyl, cyclopropyl, cyclobutyl, cyclopentyl, cyclohexyl;
4) arylamino or heteroarylamino, wherein the aryl or heteroaryl is optionally substituted by methyl, ethyl, propyl, isopropyl, methoxy, ethoxy, propoxy, isopropoxy, fluoromethyl, difluoromethyl, trifluoromethyl, trifluoroethylcyclopropyl, cyclobutyl, cyclopentyl, cyclohexyl, fluoro, chloro, bromo, hydroxy, optionally substituted heterocyclyl;

most preferably, R¹ is selected from: —H,

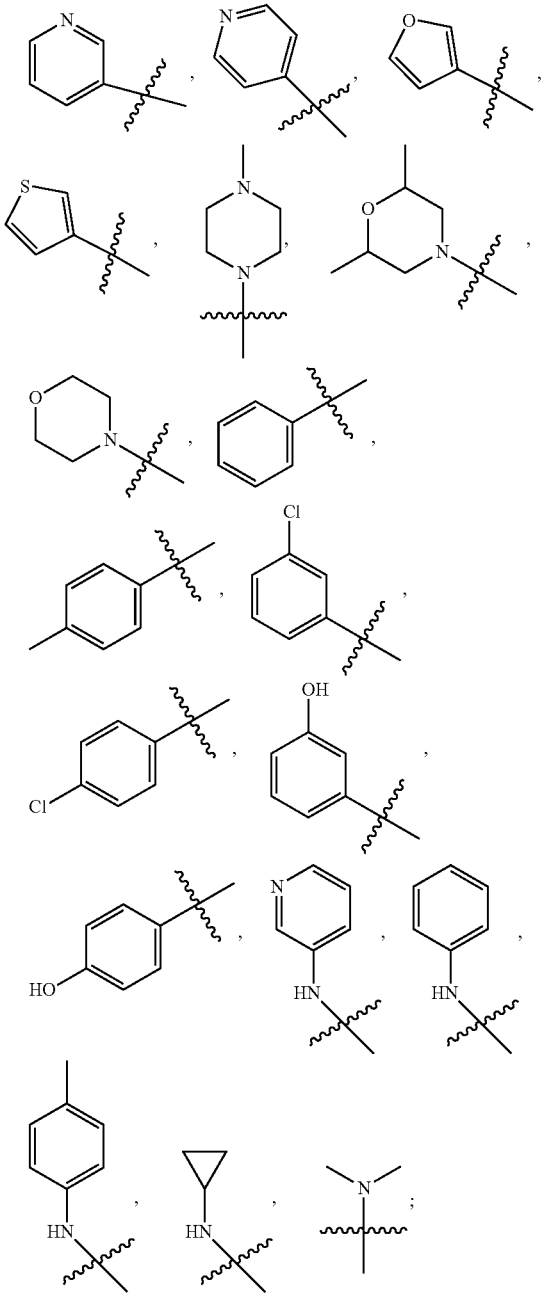

R² is selected from: hydrogen, halogen atom, optionally substituted C1-C6 alkyl, optionally substituted C3-C7 cycloalkyl, the substituent thereof being selected from halogen atom;

preferably, R² is selected from: hydrogen, halogen atom, C₁₋₆ alkyl, C1-C6 fluorine-containing alkyl;

more preferably, R² is selected from: hydrogen, fluoro, chloro, bromo, methyl, ethyl, propyl, isopropyl, trifluoromethyl;

most preferably, R² is selected from: H, 4-Cl, 4-CH₃, 6-CH₃;

R³ is selected from optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, R³ is selected from optionally substituted C6-C10 aryl or optionally substituted heteroaryl, optionally substituted C1-C6 alkyl, the substituent thereof being selected from: optionally substituted C1-C6 alkyl, optionally substituted heterocyclyl, hydroxy, C1-C6 fluorine-containing alkyl, optionally substituted C6-C10 aryl, optionally substituted heteroaryl;

more preferably, R³ is selected from: optionally substituted or unsubstituted C1-C6 alkyl, the substituent thereof being selected from: optionally substituted heterocyclyl, hydroxy; mono- or di-substituted or unsubstituted C6-C10 aryl, the substituent thereof being selected from: optionally substituted C1-C6 alkyl, the substituent on the C1-C6 alkyl being heterocyclyl substituted by C1-C6 alkyl; C1-C6 fluorine-containing alkyl, heterocyclyl substituted by one of C1-C6 amido, C1-C6 amido C1-C6 alkyl or C1-C6 alkyl, heteroaryl substituted by C1-C6 alkyl;

most preferably, R³ is selected from: 1)

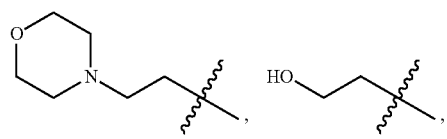

2)

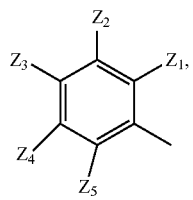

wherein Z₁, Z₂, Z₃, Z₄, Z₅ are all H: or Z₄ is CF₃—, the rest being H: or Z₄ is CF₃—, one of Z₂, Z₃ is selected from CF₃—,

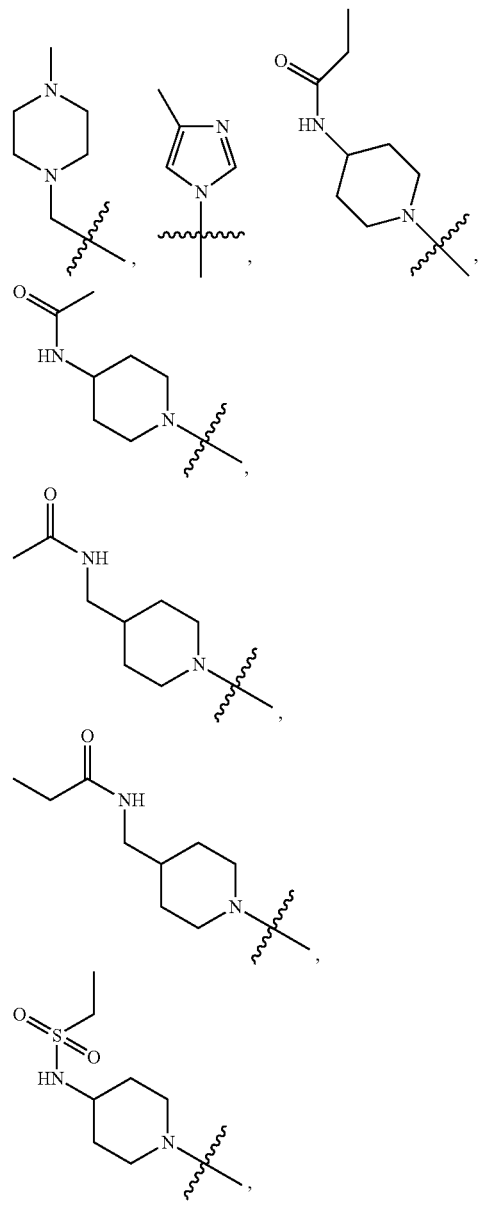

the rest one and Z₁, Z₅ being H; or, when L is —CO—, R³ is

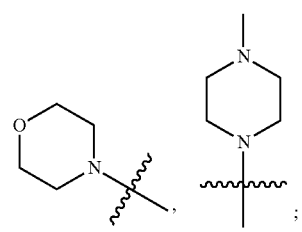

R₅ is selected from: hydrogen, C₁₋₆ alkyl, C1-C6 fluorine-containing alkyl;

preferably, R₅ is selected from: hydrogen, methyl, ethyl, propyl, isopropyl, trifluoromethyl;

most preferably, R₅ is hydrogen, methyl, ethyl, isopropyl;

L is selected from: —NHCO—, —CONH—, —CO—, —NHSO₂—, —SO₂NH—, —NHCONH—,

—NHCSNH—, —COO—, —OCO—; L, preferably, is selected from: —NHCO—, —CONH—, —CO—.

In a third aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

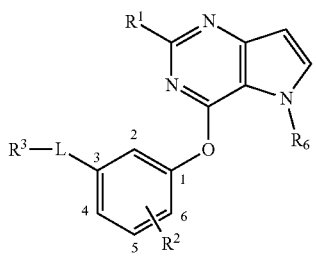

III wherein, $R^1$ is selected from:

1) hydrogen, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, hydroxy;

2) optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

3) amino or amino bearing one or two substituent(s) on the nitrogen, the substituent thereof being selected from C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl;

4) arylamino or heteroarylamino, wherein the aryl or heteroaryl is optionally substituted by C1-C6 alkyl, C1-C6 alkoxy, C1-C6 oxygen-containing alkyl, C1-C3 fluorine-containing alkyl, C3-C6 cycloalkyl, halogen, nitro, cyano, hydroxy, optionally substituted heterocyclyl, C1-C6 alkoxycarbonyl, C1-C6 acyl;

preferably, $R^1$ is selected from:

1) hydrogen, hydroxy, optionally substituted C1-C6 alkyl, C1-C6 alkoxy, C1-C6 oxygen-containing alkyl, C1-C6 fluorine-containing alkyl, optionally substituted C3-C7 cycloalkyl;

2) optionally substituted aryl, optionally substituted heteroaryl, optionally substituted heterocyclyl, the substituent thereof being selected from halogen atom, C1-C6 alkyl, C1-C6 alkoxy, C1-C6 fluorine-containing alkyl, C1-C6 fluorine-containing alkoxy, amino, hydroxy;

3) amino or amino bearing one or two substituent(s) on the nitrogen, the substituent thereof being selected from C1-C6 alkyl, C1-C6 alkoxy, C1-C6 fluorine-containing alkyl, C3-C7 cycloalkyl;

4) arylamino or heteroarylamino, wherein the aryl or heteroaryl is optionally substituted by C1-C6 alkyl, C1-C6 alkoxy, C1-C3 fluorine-containing alkyl, C3-C6 cycloalkyl, halogen, hydroxy, optionally substituted heterocyclyl;

more preferably, $R^1$ is selected from:

1) hydrogen, hydroxy;

2) optionally substituted aryl, optionally substituted heteroaryl, optionally substituted heterocyclyl, the substituent thereof being selected from fluoro, chloro, bromo, methyl, ethyl, propyl, isopropyl, methoxy, ethoxy, propoxy, isopropoxy, fluoromethyl, difluoromethyl, trifluoromethyl, trifluoroethyl, amino, hydroxy;

3) amino or amino bearing one or two substituent(s) on the nitrogen, the substituent thereof being selected from methyl, ethyl, propyl, isopropyl, methoxy, ethoxy, propoxy, isopropoxy, fluoromethyl, difluoromethyl, trifluoromethyl, trifluoroethyl, cyclopropyl, cyclobutyl, cyclopentyl, cyclohexyl;

most preferably, $R^1$ is selected from: —H, —OH,

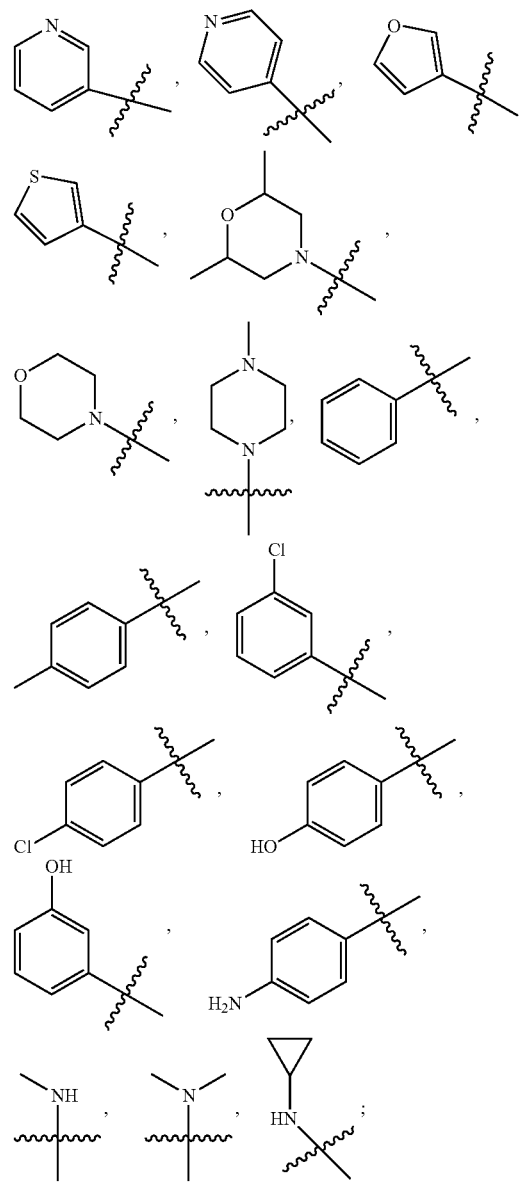

$R^2$ is selected from: hydrogen, halogen atom, optionally substituted C1-C6 alkyl, optionally substituted C3-C7 cycloalkyl, optionally substituted C6-C10 aryl or optionally substituted heteroaryl, the substituent thereof being selected from halogen atom, C1-C6 alkyl, C1-C6 alkoxy, C1-C6 fluorine-containing alkyl;

preferably, R² is selected from: hydrogen, halogen atom, optionally substituted C1-C6 alkyl, C1-C6 fluorine-containing alkyl, optionally substituted C6-C10 aryl or optionally substituted heteroaryl;

more preferably, R² is selected from: hydrogen, fluoro, chloro, bromo, methyl, ethyl, propyl, isopropyl, trifluoromethyl, pyridyl, pyrazinyl, pyrimidinyl, pyridazinyl, imidazolyl, thiazolyl, isothiazolyl, thioxazolyl, pyrrolyl, furyl, oxazolyl, isoxazolyl, pyrazolyl, thienyl, indazolyl, quinolyl, isoquinolyl;

most preferably, R² is selected from: H,

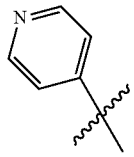 [SMILES: *c1ccncc1]

at 4-position, 4-Cl, 4-CH₃, 6-CH₃;

R³ is selected from optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, R³ is selected from mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl, heterocyclyl substituted by one of C1-C6 amido, C1-C6 amido C1-C6 alkyl or C1-C6 alkyl, heteroaryl substituted by C1-C6 alkyl;

more preferably, R³ is

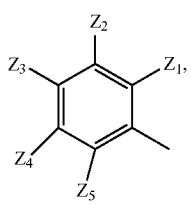

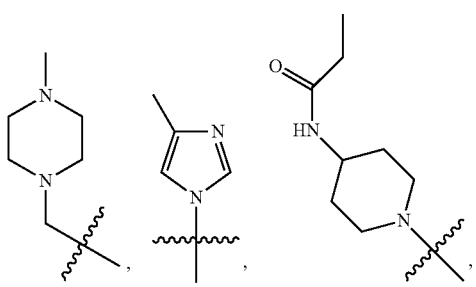

wherein one of $Z_1$-$Z_5$ is $CF_3$—, the rest being H; or any two of $Z_2$, $Z_3$, $Z_4$ each are independently selected from $CF_3$—,

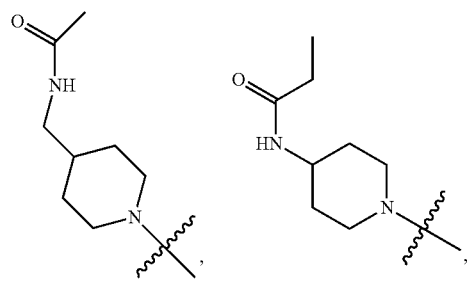

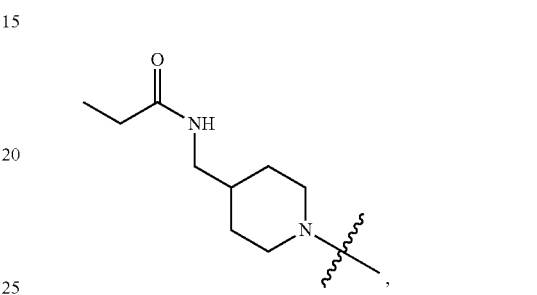

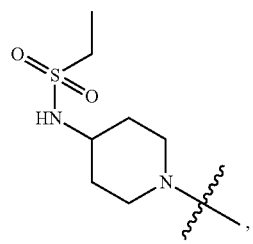

the rest one and $Z_1$, $Z_5$ being H;

most preferably, R³ is

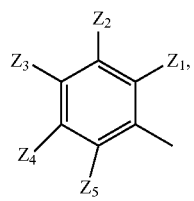

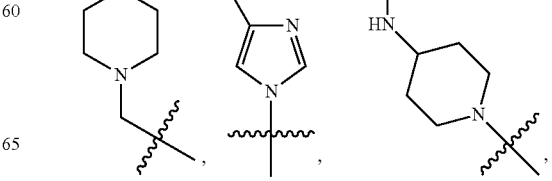

wherein $Z_4$ is $CF_3$—, the rest being H; or $Z_4$ is $CF_3$—, one of $Z_2$, $Z_3$ is

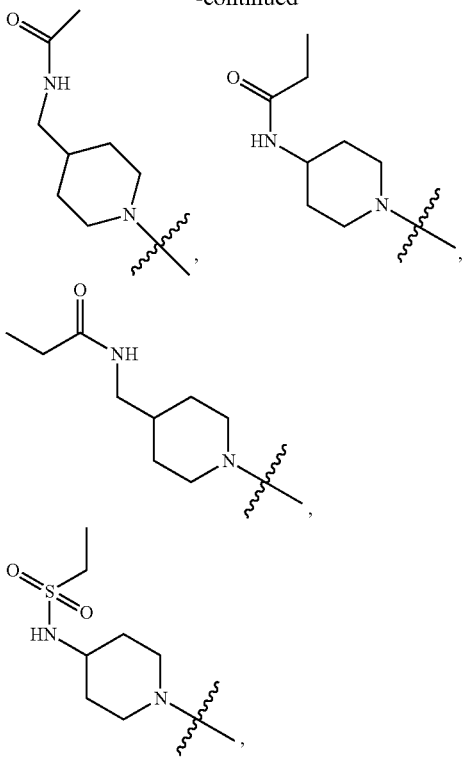

the rest one and $Z_1$, $Z_5$ being H;

$R_6$ is selected from: hydrogen, $C_{1-6}$ alkyl, C1-C6 fluorine-containing alkyl;

preferably, $R_6$ is selected from: hydrogen, methyl, ethyl, propyl, isopropyl, trifluoromethyl;

$R_6$, most preferably, is hydrogen, methyl;

L is selected from: —NHCO—, —CONH—, —NHSO$_2$—, —SO$_2$NH—, —NHCONH—, —NHCSNH—, —COO—, —OCO—; L, preferably, is selected from: —NHCO—, —CONH—.

In a fourth aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

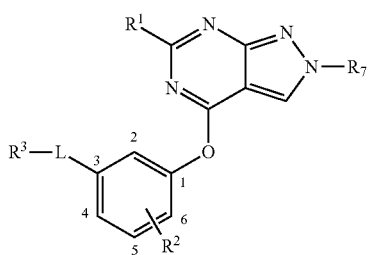

IV wherein, $R^1$ is selected from: hydrogen, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, amino, hydroxy, optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

preferably, $R^1$ is selected from: hydrogen, optionally substituted C1-C6 alkyl, C1-C6 alkoxy, C1-C6 fluorine-containing alkyl, optionally substituted C3-C7 cycloalkyl, hydroxy, amino, optionally substituted C6-C10 aryl, optionally substituted heteroaryl, optionally substituted heterocyclyl, the substituent thereof being selected from halogen atom, amino, hydroxy, C1-C6 alkyl, C1-C6 alkoxy, C1-C6 fluorine-containing alkyl;

more preferably, $R^1$ is selected from: hydrogen, C1-C6 alkoxy, optionally substituted C3-C7 cycloalkyl, hydroxy, amino, optionally substituted C6-C10 aryl, optionally substituted heteroaryl, optionally substituted heterocyclyl, the substituent thereof being selected from fluoro, chloro, bromo, amino, hydroxy, methyl, ethyl, propyl, isopropyl, methoxy, ethoxy, propoxy, isopropoxy, fluoromethyl, difluoromethyl, trifluoromethyl, trifluoroethyl;

most preferably, $R^1$ is selected from: —H,

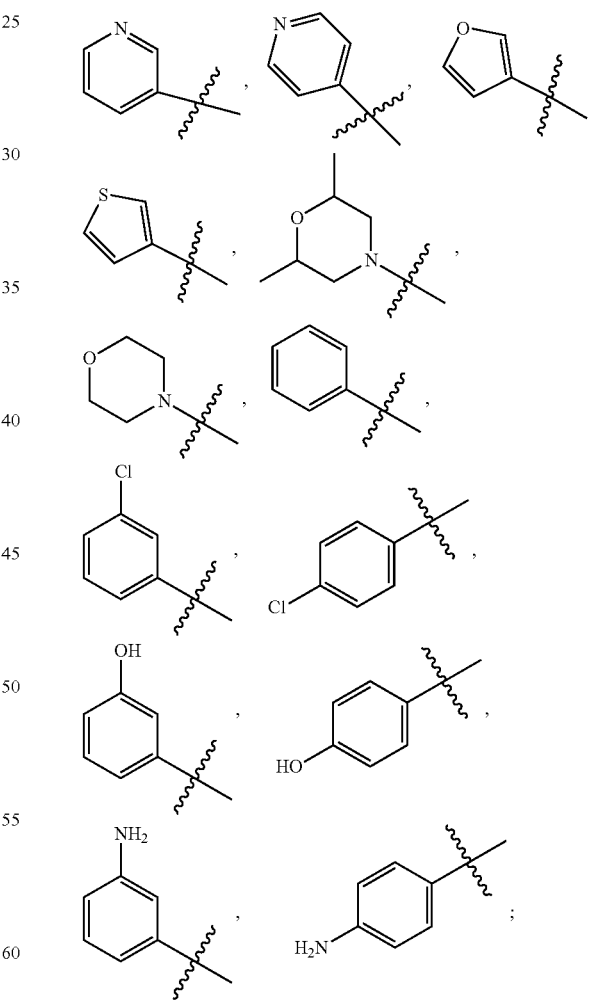

$R^2$ is selected from: hydrogen, halogen atom, optionally substituted C1-C6 alkyl, optionally substituted C3-C7 cycloalkyl, the substituent thereof being selected from halogen atom;

preferably, $R^2$ is selected from: hydrogen, halogen atom, $C_{1-6}$ alkyl, C1-C6 fluorine-containing alkyl;

more preferably, $R^2$ is selected from: hydrogen, fluoro, chloro, bromo, methyl, ethyl, propyl, isopropyl, trifluoromethyl;

$R^2$, most preferably, is selected from: H, 4-Cl, 4-CH$_3$, 6-CH$_3$;

$R^3$ is selected from: optionally substituted C1-C6 alkyl, the substituent thereof being halogen atom, optionally substituted heterocyclyl, C1-C6 alkyl, C1-C6 alkoxy, C1-C6 fluorine-containing alkyl, C1-C6 fluorine-containing alkoxy, nitro, cyano, amino, hydroxy; optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, $R^3$ is selected from mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl, C1-C6 fluorine-containing alkoxy, heterocyclyl substituted by C1-C6 alkyl, heteroaryl substituted by C1-C6 alkyl;

more preferably, $R^3$ is

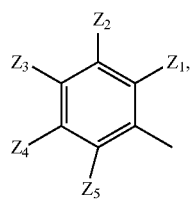

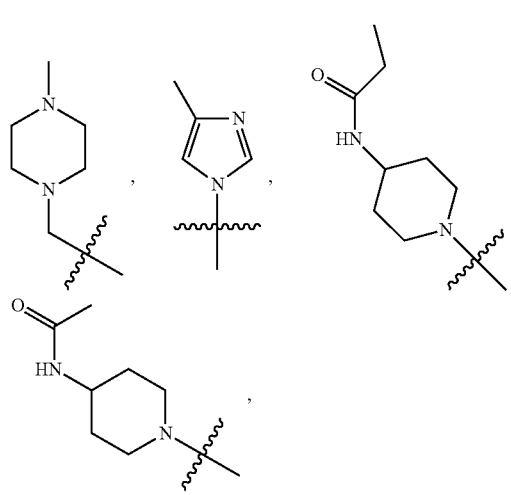

wherein one of $Z_1$-$Z_5$ is CF$_3$— or CF$_3$O—, the rest being H; or any two of $Z_2$, $Z_3$, $Z_4$ each are independently selected from CF$_3$—,

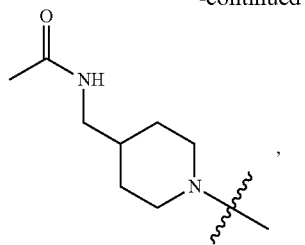

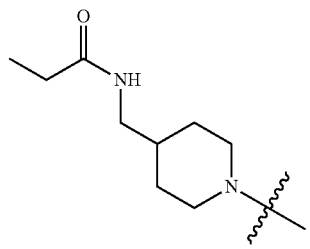

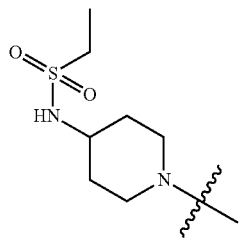

the rest one and $Z_1$, $Z_5$ being H;

$R^3$, most preferably, is

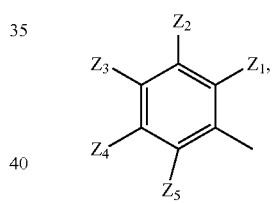

wherein $Z_4$ is CF$_3$— or CF$_3$O—, the rest being H; or $Z_4$ is CF$_3$—, one of $Z_2$, $Z_3$ is

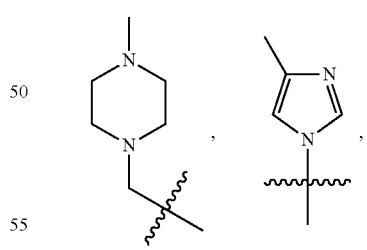

the rest one and $Z_1$, $Z_5$ being H;

$R_7$ is selected from: C1-C6 alkyl, C1-C6 fluorine-containing alkyl;

preferably, $R_7$ is selected from: methyl, ethyl, propyl, isopropyl, trifluoromethyl;

most preferably, $R_7$ is selected from methyl;

L is selected from: —NHCO—, —CONH—, —NHSO$_2$—, —SO$_2$NH—, —NHCONH—, —NHCSNH—, —COO—, —OCO—; L, preferably, is selected from: —NHCO—, —CONH—.

In a fifth aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

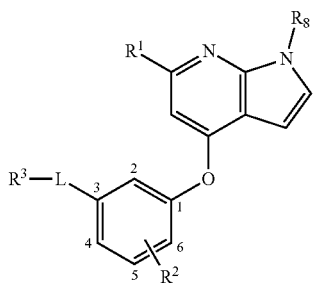

V wherein, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, amino, hydroxy, optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

preferably, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, optionally substituted C3-C7 cycloalkyl, hydroxy, amino, optionally substituted C6-C10 aryl, optionally substituted heteroaryl, optionally substituted heterocyclyl, the substituent thereof being selected from halogen atom, amino, hydroxy, C1-C6 alkyl, C1-C6 alkoxy, C1-C6 fluorine-containing alkyl;

more preferably, $R^1$ is selected from: hydrogen, C1-C6 amido, C1-C6 alkoxy, optionally substituted C3-C7 cycloalkyl, hydroxy, amino, optionally substituted C6-C10 aryl, optionally substituted heteroaryl, optionally substituted heterocyclyl, the substituent thereof being selected from fluoro, chloro, bromo, amino, hydroxy, methyl, ethyl, propyl, isopropyl, methoxy, ethoxy, propoxy, isopropoxy, fluoromethyl, difluoromethyl, trifluoromethyl, trifluoroethyl; most preferably, $R^1$ is selected from:

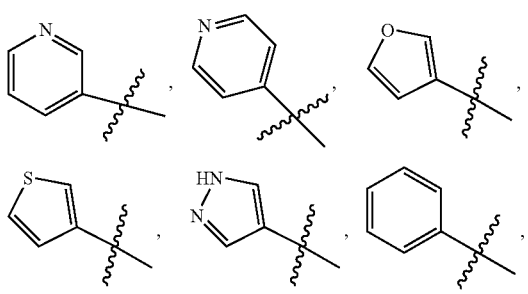

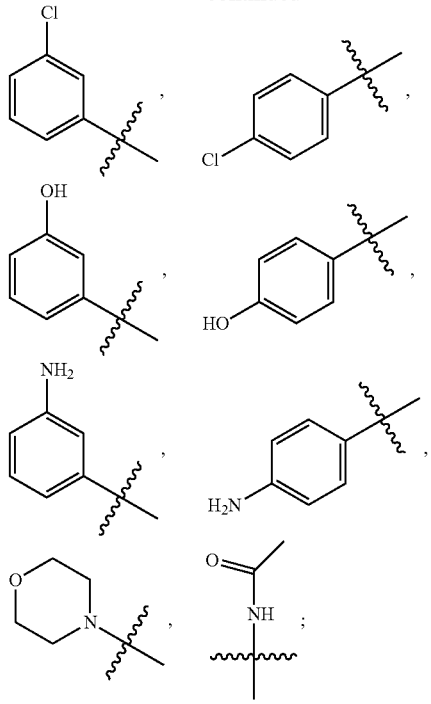

$R^2$ is selected from: hydrogen, halogen atom, optionally substituted C1-C6 alkyl, optionally substituted C3-C7 cycloalkyl, the substituent thereof being selected from halogen atom;

preferably, $R^2$ is selected from: hydrogen, halogen atom, $C_{1-6}$ alkyl, C1-C6 fluorine-containing alkyl;

more preferably, $R^2$ is selected from: hydrogen, fluoro, chloro, bromo, methyl, ethyl, propyl, isopropyl, trifluoromethyl;

$R^2$, most preferably, is selected from: H, 4-$CH_3$, 6-$CH_3$;

$R^3$ is selected from: optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from: halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, $R^3$ is selected from: mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl, heterocyclyl substituted by C1-C6 alkyl;

more preferably, $R^3$ is

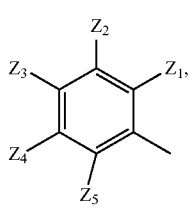

wherein one of $Z_1$-$Z_5$ is $CF_3$—, the rest being H; or any two of $Z_2$, $Z_3$, $Z_4$ each are independently selected from $CF_3$—,

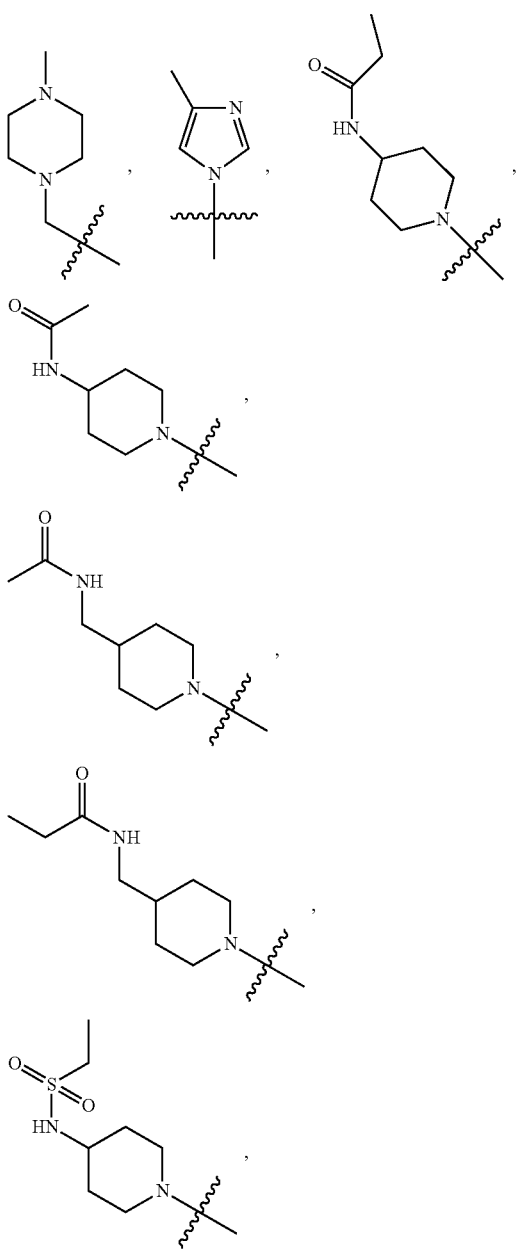

the rest one and $Z_1$, $Z_5$ being H;
$R^3$, most preferably, is

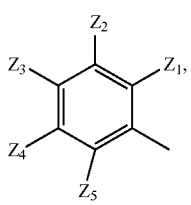

wherein $Z_4$ is $CF_3$—, the rest being H; or $Z_4$ is $CF_3$—, one of $Z_2$, $Z_3$ is

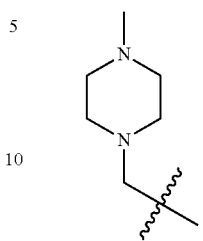

the rest one and $Z_1$, $Z_5$ being H;
$R_8$ is selected from: hydrogen, C1-C6 alkyl, C1-C6 fluorine-containing alkyl;
preferably, $R_8$ is selected from: hydrogen, methyl, ethyl, propyl, isopropyl, trifluoromethyl;
most preferably, $R_8$ is selected from hydrogen, methyl;
L is selected from: —NHCO—, —CONH—, —NHSO$_2$—, —SO$_2$NH—, —NHCONH—, —NHCSNH—, —COO—, —OCO—; L, preferably, is selected from: —NHCO—, —CONH—.

In a sixth aspect, according to a specific embodiment of the present invention, as for the compound, or a stereoisomer thereof, a prodrug thereof, a pharmaceutically acceptable salt thereof or a pharmaceutically acceptable solvate thereof, the compound f has the following structure:

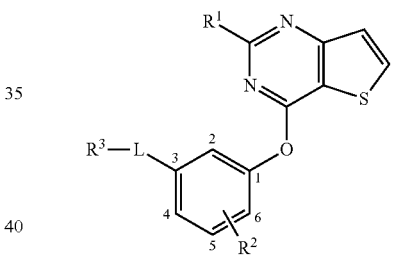

VI wherein, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, amino, hydroxy, optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;
preferably, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, optionally substituted C3-C7 cycloalkyl, hydroxy, amino, optionally substituted C6-C10 aryl, optionally substituted heteroaryl, optionally substituted heterocyclyl, the substituent thereof being selected from halogen atom, amino, hydroxy, C1-C6 alkyl, C1-C6 alkoxy, C1-C6 fluorine-containing alkyl;
more preferably, $R^1$ is selected from: hydrogen, C1-C6 alkoxy, optionally substituted C3-C7 cycloalkyl, hydroxy, amino, optionally substituted C6-C10 aryl, optionally substituted heteroaryl, optionally substituted heterocyclyl, the substituent thereof being selected from fluoro, chloro, bromo, amino, hydroxy, methyl, ethyl, propyl, isopropyl, methoxy, ethoxy, propoxy, isopropoxy, fluoromethyl, difluoromethyl, trifluoromethyl, trifluoroethyl;

most preferably, $R^1$ is selected from:

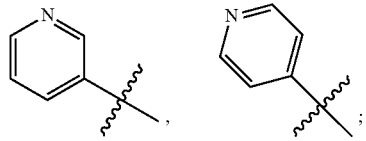 [SMILES: *c1cccnc1 ; *c1ccncc1]

$R^2$ is selected from: hydrogen, halogen atom, optionally substituted C1-C6 alkyl, optionally substituted C3-C7 cycloalkyl, the substituent thereof being selected from halogen atom;

preferably, $R^2$ is selected from: hydrogen, halogen atom, $C_{1-6}$ alkyl, C1-C6 fluorine-containing alkyl;

more preferably, $R^2$ is selected from: hydrogen, fluoro, chloro, bromo, methyl, ethyl, propyl, isopropyl, trifluoromethyl;

$R^2$, most preferably, is selected from: H, 4-Cl, 4-$CH_3$, 6-$CH_3$;

$R^3$ is selected from: optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, $R^3$ is selected from: mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl, heterocycyl substituted by C1-C6 alkyl;

more preferably, $R^3$ is

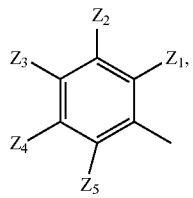

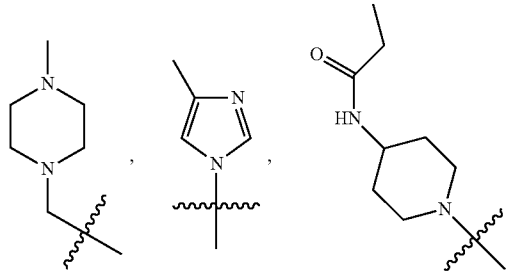

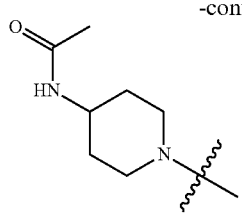

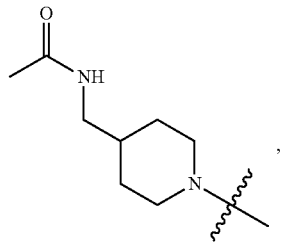

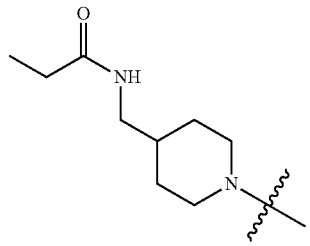

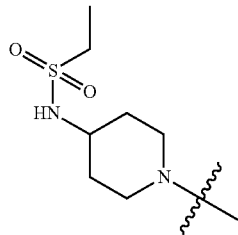

the rest one and $Z_1$, $Z_5$ being H;

$R^3$, most preferably, is

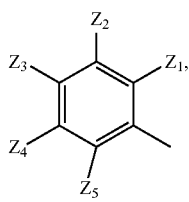

wherein $Z_4$ is $CF_3$—, one of $Z_2$, $Z_3$ is

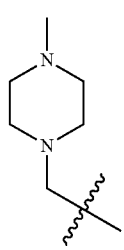

the rest one and $Z_1$, $Z_5$ being H;

L is selected from: —NHCO—, —CONH—, —$NHSO_2$—, —$SO_2NH$—, —NHCONH—,

—NHCSNH—, —COO—, —OCO—; L, preferably, is selected from: —NHCO—, —CONH—.

In a seventh aspect, according to a specific embodiment of the present invention, as for the compound, or a stereoisomer thereof, a prodrug thereof, a pharmaceutically acceptable salt thereof or a pharmaceutically acceptable solvate thereof, the compound has the following structure:

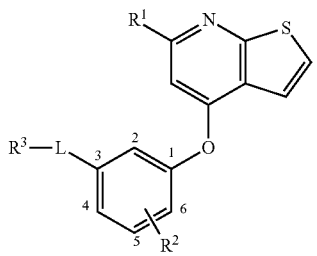

VII wherein, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, optionally substituted C3-C7 cycloalkyl, nitro, cyano, amino, hydroxy, optionally substituted aryl, optionally substituted heteroaryl, optionally substituted heterocyclyl, the substituent thereof being selected from halogen atom, C1-C6 alkyl, C1-C6 alkoxy, C1-C6 oxygen-containing alkyl, C1-C6 fluorine-containing alkyl, C1-C6 fluorine-containing alkoxy, C2-C6 alkenyl, C2-C6 alkynyl, C3-C7 cycloalkyl, nitro, cyano, amino, hydroxy;

preferably, $R^1$ is selected from: hydrogen, C1-C6 amido, optionally substituted C1-C6 alkyl, C1-C6 alkoxy, C1-C6 oxygen-containing alkyl, C1-C6 fluorine-containing alkyl, optionally substituted C3-C7 cycloalkyl, hydroxy, amino, optionally substituted C6-C10 aryl, optionally substituted heteroaryl, optionally substituted heterocyclyl, the substituent thereof being selected from fluoro, chloro, bromo, amino, hydroxy, C1-C6 alkyl, C1-C6 alkoxy, C1-C6 fluorine-containing alkyl;

more preferably, $R^1$ is selected from: hydrogen, C1-C6 alkoxy, optionally substituted C3-C7 cycloalkyl, hydroxy, amino, optionally substituted C6-C10 aryl, optionally substituted heteroaryl, optionally substituted heterocyclyl, the substituent thereof being selected from fluoro, chloro, bromo, amino, hydroxy, methyl, ethyl, propyl, isopropyl, methoxy, ethoxy, propoxy, isopropoxy, fluoromethyl, difluoromethyl, trifluoromethyl;

most preferably, $R^1$ is selected from:

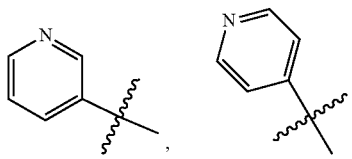

$R^2$ is selected from: hydrogen, halogen atom, optionally substituted C1-C6 alkyl, optionally substituted C3-C7 cycloalkyl, the substituent thereof being selected from halogen atom;

preferably, $R^2$ is selected from: hydrogen, halogen atom, C1-C6 alkyl, C1-C6 fluorine-containing alkyl;

more preferably, $R^2$ is selected from: hydrogen, fluoro, chloro, bromo, methyl, ethyl, propyl, isopropyl, trifluoromethyl;

most preferably, $R^2$ is selected from: H, 4-Cl, 4-$CH_3$, 6-$CH_3$;

$R^3$ is selected from: optionally substituted C6-C10 aryl, optionally substituted heteroaryl, optionally substituted heterocyclyl, optionally substituted C1-C6 alkyl, optionally substituted C3-C7 cycloalkyl, the substituent thereof being selected from halogen atom, optionally substituted C6-C10 aryl, optionally substituted heteroaryl, optionally substituted heterocyclyl, optionally substituted C1-C6 alkyl, C1-C6 alkoxy, C1-C6 oxygen-containing alkyl, C1-C6 fluorine-containing alkyl, C1-C6 fluorine-containing alkoxy, nitro, cyano, amino, hydroxy;

preferably, $R^3$ is selected from: mono- or di-substituted or unsubstituted C6-C10 aryl or heteroaryl, the substituent thereof being: optionally substituted C1-C6 alkyl, the substituent on the C1-C6 alkyl being heterocyclyl substituted by C1-C6 alkyl; C1-C6 fluorine-containing alkyl; heterocyclyl substituted by C1-C6 alkyl; heteroaryl substituted by C1-C6 alkyl;

more preferably, $R^3$ is

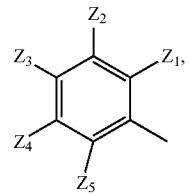

wherein any two of $Z_2$, $Z_3$, $Z_4$ each are independently selected from $CF_3$—,

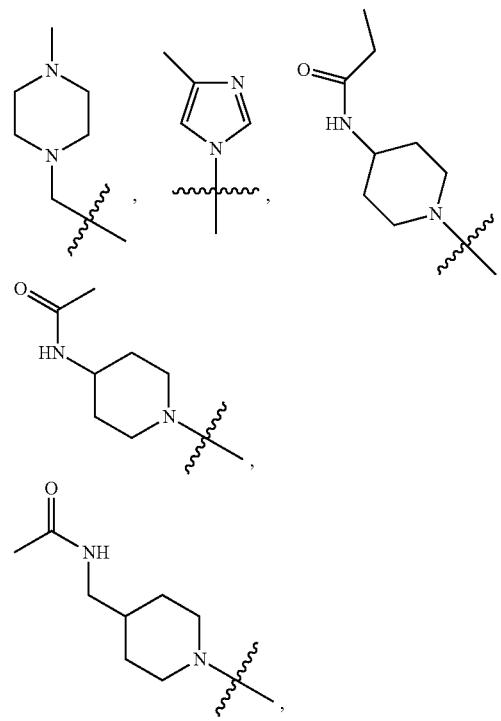

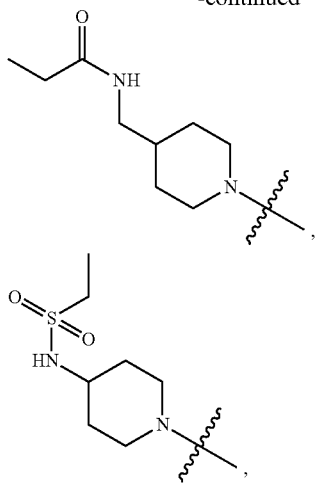

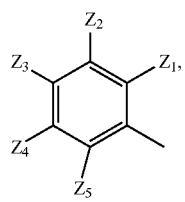

the rest one and $Z_1$, $Z_5$ being H;
$R^3$, most preferably, is

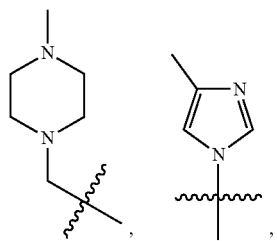

wherein $Z_4$ is $CF_3$—, one of $Z_2$, $Z_3$ is

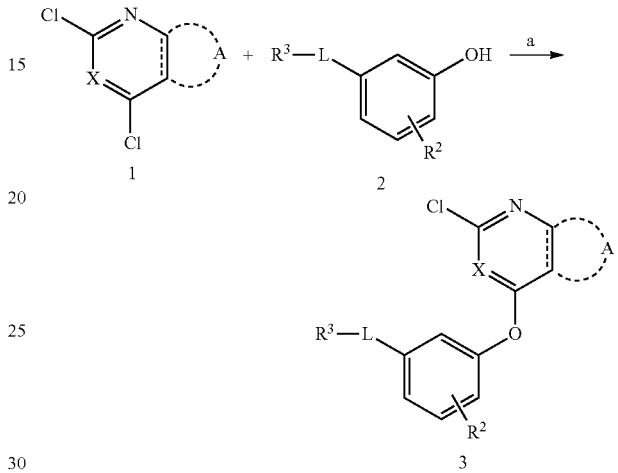

the rest one and $Z_1$, $Z_5$ being H;
L is selected from: —NHCO—, —CONH—, —NHSO$_2$—, —SO$_2$NH—, —NHCONH—, —NHCSNH—, —COO—, —OCO—; L, preferably, is selected from: —NHCO—, —CONH—.

The present invention is further achieved by the following technical solution, wherein the compounds of formulas I-VII form, with a certain amount (e.g., equal amount of substance) of an acid, a pharmaceutically acceptable salt, wherein the pharmaceutically acceptable salt is an inorganic acid salt or an organic acid salt, wherein the inorganic acid salt is selected from hydrochloride, hydrobromide, nitrate, sulfate or phosphate; the organic acid salt is selected from formate, acetate, propionate, benzoate, maleate, fumarate, succinate, tartrate, citrate, alkyl sulfonate or aryl sulfonate; preferably, said alkyl sulfonate is methyl sulfonate or ethyl sulfonate; said aryl sulfonate is benzenesulfonate or p-toluenesulfonate.

The present invention is further achieved by the following technical solution wherein the compounds of formulas I-VII are formed into a pharmaceutical composition, comprising a pharmaceutically acceptable solvate and a pharmaceutically acceptable carrier, diluent or excipient.

The present invention is further achieved by the following technical solution, which provides a preparation method of the compounds of formulas I-VII and salts thereof, comprising the following steps:

a) reacting a compound of formula 1 with a compound of formula 2 under alkaline conditions to obtain a compound of formula 3

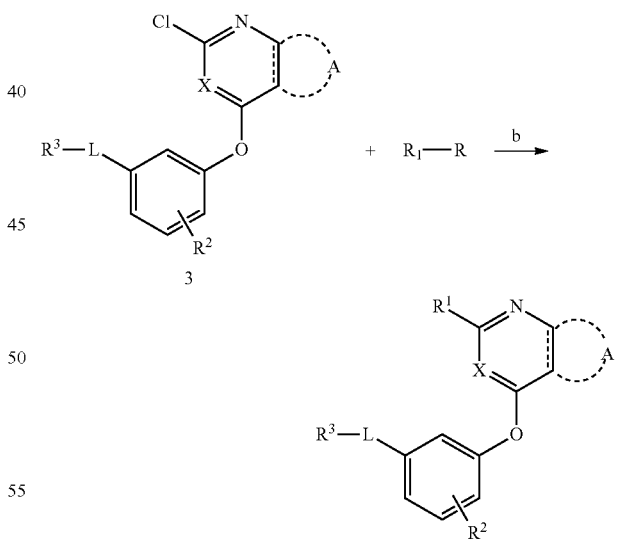

b) reacting the compound of formula 3 under Suzuki coupling reaction or Buchwald coupling reaction or basic conditions to obtain compounds of formulas I-VII wherein $R_1$, $R_2$, $R_3$, A, X, L are as defined above; R refers to a reactive group, selected from hydrogen, boric acid group or borate ester group and the like.

The present invention is further achieved by the following technical solution, which provides a preparation method of the compounds of formulas I-VII and salts thereof, characterized in the following aspects.

a) In the step of preparing the compound of formula 3, the base used is selected from an organic base (such as n-butyl lithium, sodium methoxide, sodium ethoxide, potassium t-butoxide and the like) or an inorganic base (such as sodium carbonate, potassium carbonate, cesium carbonate and the like), preferably sodium carbonate or potassium carbonate.

b) In the step of preparing the compounds of formulas I-VII, when the reaction is Suzuki coupling reaction, the metal catalyst used is a zero-valent transition metal catalyst (such as $Pd(dppf)Cl_2 \cdot CH_2Cl_2$, $Pd(OAc)_2$, $Pd(PPh_3)_4$, $Ni(cod)_2$, $Ni(dppf)Cl_2$ and the like), preferably $Pd(dppf)Cl_2 \cdot CH_2Cl_2$; the solvent used is, but not limited to, toluene, tetrahydrofuran, N,N-dimethylformamide, water or a mixed solvent, preferably tetrahydrofuran/water mixed solvent; the base used is, but not limited to, sodium carbonate, potassium carbonate, cesium carbonate, potassium phosphate, sodium hydroxide, barium hydroxide, potassium fluoride, cesium fluoride, sodium tert-butoxide, preferably sodium carbonate or potassium carbonate.

c) In the step of preparing the compounds of formulas I-VII, when the reaction is Buchwald coupling reaction, the metal catalyst used is a zero-valent transition metal catalyst (such as $Pd_2(dba)_3$, $Pd(OAc)_2$, $Pd(dppf)Cl_2 \cdot CH_2Cl_2$ and the like), preferably $Pd_2(dba)_3$; the phosphorus ligand used is but not limited to; the solvent used is, but not limited to, toluene, tetrahydrofuran, N,N-dimethylformamide, tert-butanol, preferably tert-butanol; the base used is, but not limited to, potassium carbonate, cesium carbonate, sodium tert-butoxide, lithium hexamethyldisilazide (LHMDS), preferably potassium carbonate or cesium carbonate.

d) In the step of preparing the compounds of formulas I-VII, when the reaction is under alkaline conditions, the base used is selected from an organic base (such as triethylamine, pyridine, 4-dimethylaminopyridine, diisopropylethylamine and the like) or an inorganic base (such as sodium carbonate, potassium carbonate, cesium carbonate and the like), preferably triethylamine or diisopropylethylamine; the solvent used is, but not limited to, toluene, tetrahydrofuran, N,N-dimethylformamide, tert-butanol, preferably tetrahydrofuran.

Unless otherwise indicated, the above groups and substituents have the ordinary meanings in the field of medicinal chemistry. The term "C1-C6 alkyl" refers to any straight-chain or branched-chain group having 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "C2-C6 alkenyl" refers to any straight-chain or branched-chain group containing 2 to 6 carbon atoms and containing at least one alkenyl, such as vinyl, allyl, 1-propenyl, isopropenyl, 1-butenyl, 2-butenyl, 3-butenyl, 2-pentenyl, 1-hexenyl and the like.

The term "C2-C6 alkynyl" refers to any straight-chain or branched-chain group containing 2 to 6 carbon atoms and containing at least one alkynyl, such as ethynyl, 2-propynyl, 4-pentynyl and the like.

The term "C1-C6 amido" refers to any straight-chain or branched-chain group containing amido ($CONH_2$), having 1 to 6 carbon atoms and, such as formamide, acetamido, propionamide, butanamide, valeramide, caproamide and the like.

The term "C3-C7 cycloalkyl" refers to a 3- to 7-membered all-carbon monocyclic ring that may contain one or more double bonds, but does not have a fully conjugated π-electron system. Examples of cycloalkyl include, but are not limited to, cyclopropyl, cyclobutyl, cyclopentyl, cyclopentenyl, cyclohexyl, cyclohexenyl, cyclohexadienyl, cycloheptyl.

The term "silyl" refers to a silyl group, r1r2r3r4-Si, that is, $SiH_4$ wherein H atom(s) is (are) substituted by 1 to 4 organic groups mentioned in the present invention, such as "C1-C6 alkyl", "C1-C3 alkyl", "C2-C6 alkenyl", "C2-C6 alkynyl", "C3-C7 cycloalkyl", "C1-C6 amido", "C1-C6 amido C1-C6 alkyl", "halogen atom", hydroxy, amino, nitro, cyano and the like. The term "fluorine-containing alkyl" or "polyfluorinated alkyl" refers to a group in which alkyl skeleton is substituted by one or more fluoro groups, for example, fluoromethyl, difluoromethyl, trifluoromethyl, trifluoroethyl and the like.

The term "C1-C6 acyl" refers to $-C(=O)-H$ and $-C(=O)-C1$-C5 alkyl, such as formyl, acetyl, propionyl, butanoyl and the like.

It should be noted that C1-C6 oxygen-containing alkyl refers to a group in which C1-C6 alkyl skeleton is substituted by one or more C1-C6 alkoxy groups, for example, methoxyethyl, methoxyethoxymethyl and the like.

The term "halogen" refers to a fluoro (F), chloro (Cl), bromo (Br) or iodine (I) atom.

The term "cyano" refers to —CN residue.

The term "nitro" refers to $-NO_2$ group.

The term "aryl" or "C6-C10 aryl" refers to a C6-C10 mono-, di- or poly-carbocyclic hydrocarbon having from 1 to 2 ring systems which are optionally further fused or attached to each other by a single bond, wherein at least one of the carbon rings is "aromatic", and the term "aromatic" refers to a fully conjugated π-electron bond system. The aryl ring may be optionally further fused or attached to aromatic or non-aromatic carbocyclic rings or heterocyclic rings. Non-limiting examples of the aryl group are phenyl, α- or β-naphthyl.

The term "heteroaryl" refers to an aromatic heterocyclic ring, which is usually a 5- to 8-membered heterocyclic ring having from 1 to 3 heteroatoms selected from N, O or S; a heteroaryl ring may be optionally further fused or attached to aromatic or non-aromatic carbocyclic rings or heterocyclic rings. Non-limiting examples of the heteroaryl group are, for example, pyridyl, pyrazinyl, pyrimidinyl, pyridazinyl, indolyl, imidazolyl, thiazolyl, isothiazolyl, thioxazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolyl, isoquinolyl, 1,2,3-triazolyl, 1-phenyl-1,2,3-triazolyl, 2,3-indolinyl, 2,3-dihydrobenzofuryl, 2,3-dihydrobenzothienyl, benzopyranyl, 2,3-dihydrobenzoxazinyl, 2,3-dihydroquinoxalinyl and the like.

The term "heterocyclyl" (also referred to as "heterocycloalkyl") refers to 3-, 4-, 5-, 6- and 7-membered saturated or partially unsaturated carbocyclic rings, wherein one or more carbon atoms are replaced by heteroatoms such as nitrogen, oxygen and sulfur. Non-limiting examples of the heterocyclic group are, for example, pyranyl, pyrrolidinyl, pyrrolinyl, imidazolinyl, imidazolidinyl, pyrazolidinyl, pyrazolinyl, thiazolinyl, thiazolidinyl, dihydrofuryl, tetrahydrofuryl, 1,3-dioxolanyl, piperidinyl, piperazinyl, morpholine, morpholinyl, tetrahydropyrrolyl, thiomorpholinyl and the like.

The term "optionally substituted heterocyclyl" refers to that the above-mentioned "heterocyclyl" is substituted by one or more "C1-C6 alkyl", "C1-C3 alkyl", "C3-C6 cycloalkyl", "C1-C6 amido", "C1-C6 amido C1-C6 alkyl", "halogen atom", hydroxy, amino, nitro, cyano and the like, or not substituted.

The term "optionally substituted XX group" refers to that the "XX group" is substituted by one or more "C1-C6 alkyl", "optionally substituted C1-C6 alkyl", "C1-C3 alkyl", "C3-C6 cycloalkyl", "C1-C6 amido", "C1-C6 amido C1-C6 alkyl", "heterocyclyl", "halogen atom", hydroxy, amino, nitro, cyano and the like, or unsubstituted.

According to the present invention and unless otherwise provided, any of the above groups being "optionally substituted" also refers to that it may optionally be substituted at any of its free positions by one or more groups, for example by 1 to 6 groups, the groups being independently selected from: halogen atom, nitro, oxo (═O), cyano, C1-C6 alkyl, polyfluorinated alkyl, polyfluorinated alkoxy, alkenyl, alkynyl, hydroxyalkyl, hydroxyalkylamino, hydroxyheterocyclyl, aryl, aryl-alkyl, heteroaryl, heteroaryl-alkyl, heterocyclyl, heterocyclyl-alkyl, C3-C7 cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxy, alkoxy, aryloxy, heterocyclyloxy, alkyl-heterocyclyloxy, methylenedioxy, alkylcarbonyloxy, arylcarbonyloxy, cycloalkenyloxy, heterocyclylcarbonyloxy, alkyleneaminooxy, carboxy, alkoxycarbonyl, aryloxycarbonyl, cycloalkyloxycarbonyl, heterocyclyloxycarbonyl, amino, ureido, alkylamino, amino-alkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, formylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonyl-amino-alkylamino, alkoxycarbonylheterocyclyl-alkylamino, alkoxy-aryl-alkyl, hydroxyamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

Further, if appropriate, each of the above substituents may be further substituted by one or more of the above-exemplified groups.

The terms "alkoxy", "cycloalkoxy", "aryloxy", "heterocyclyloxy" "tri(C1-C6 alkyl) silyl C1-C6 alkoxy C1-C6 alkyl" and derivatives thereof refer to any of the above C1-C6 alkyl, C3-C7 cycloalkyl, aryl or heterocyclyl, which is attached to the remainder of molecules through oxygen atom (—O—). From all of the above description, it will be apparent to those skilled in the art that any group whose name is a compound name, for example, "arylamino" shall mean that it is conventionally constructed from the moiety that is derived, such as the amino substituted by the aryl, wherein the aryl is as defined above.

Similarly, any term such as alkylthio, alkylamino, heteroarylamino, dialkylamino, fluorine-containing alkoxy, polyfluorinated alkyl, polyfluorinated alkoxy, alkoxycarbonyl, alkoxycarbonylamino, heterocyclylcarbonyl, heterocyclylcarbonylamino, cycloalkyloxycarbonyl and the like includes groups, wherein alkyl, alkoxy, aryl, C3-C7 cycloalkyl and heterocyclyl moieties are as defined above.

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in 1 Burger's Medicinal Chemistry and Drug Discovery (1995) 172-178, 949-982 (Manfred E. Wolff, ed. $5^{th}$ edition).

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound, a stereoisomer thereof, a prodrug thereof, or a pharmaceutically acceptable salt thereof or pharmaceutically acceptable solvate thereof according to any one of the above embodiments, and a pharmaceutically acceptable carrier, diluent or excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprise incorporating a suitable pharmaceutically acceptable excipient, carrier, diluent and the like.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a tablet. For the treatment by oral administration, an active compound may be combined with one or more excipients, and be used in a form of a deglutible tablet, a buccal tablet, a troche, a capsule, an elixir, a suspension, a syrup, a wafer and the like. The composition and preparation shall comprise at least 0.1% of an active compound. The ratio of the composition to the preparation can be varied certainly, and the composition may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc.; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solution or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol and the like), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal and the like). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc.). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s). Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles) and the like.

EXPERIMENTAL SECTION

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhihuangwu Silica Gel Development Reagent Factory) under medium pressure or by a pre-packed silica gel cartridge (ISCO or Welch) with the use of an ISCO Combiflash Rf200 rapid purification system. The ingredient was developed by UV light ($\lambda$: 254 nm) or iodine vapor. When necessary, the compound was prepared by preparative HPLC and purified by a Waters Symmetry C18 (19×50 mm, 5 μm) column or a Waters X Terra RP 18 (30×150 mm, 5 μm) column, wherein a Waters preparative HPLC 600 equipped with a 996 Waters PDA detector and Micromass mod. ZMD single quadrupole mass spectrometry (electrospray ionization, cationic mode) were used. Method 1: Phase A: 0.1% TFA/MeOH 95/5; Phase B: MeOH/$H_2O$ 95/5. Gradient: proceeding at 10 to 90% B for 8 min, keeping at 90% B for 2 min; flow rate 20 mL/min. Method 2: Phase A: 0.05% $NH_4OH$/MeOH 95/5; Phase B: MeOH/$H_2O$ 95/5. Gradient: proceeding at 10 to 100% B for 8 min, keeping at 100% B for 2 min. Flow rate 20 mL/min.

¹H-NMR spectra were recorded in DMSO-de or CDCl₃ via a Bruker Avance 600 spectrometer (for ¹H) operated at 600 MHz. The residual solvent signal was used as a reference (δ=2.50 or 7.27 ppm). Chemical shift (δ) was reported in parts per million (ppm) and coupling constant (J) in Hz. The following abbreviations were used for peak splitting: s=single; br. s.=wide signal; d=double; t=triple; m=multiple; dd=double double.

Electrospray (ESI) mass spectra were obtained via Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters X Terra RP 18 column (4.6×50 mm; 3.5 μm).

Mobile phase A was ammonium acetate 5 mM buffer (pH 5.5 with acetic acid): acetonitrile 90:10, mobile phase B was ammonium acetate 5 mM buffer (pH 5.5 with acetic acid): acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol, dichloromethane were all analytically pure.

MODE OF CARRYING OUT THE INVENTION

The embodiments of the present invention are described in detail below by way of specific examples, but in any case they cannot be construed as limiting the present invention.

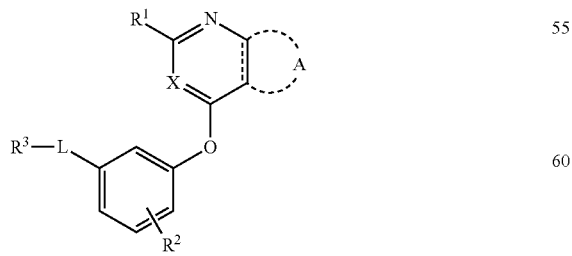

The above compound of formula was divided into several types for preparation.

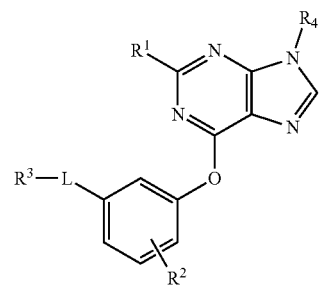

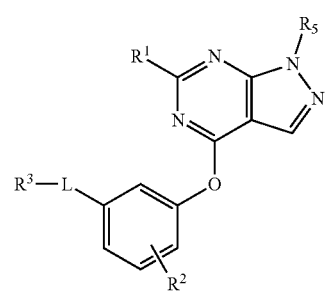

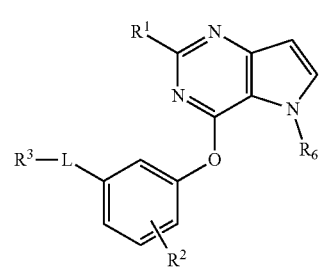

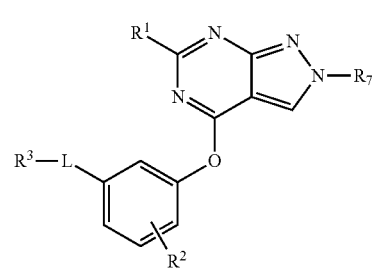

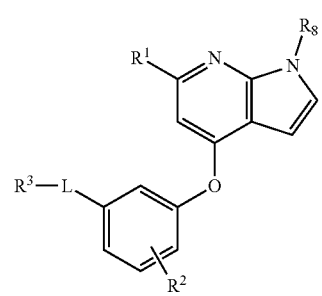

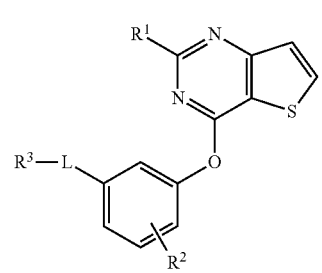

The compounds of formula I:
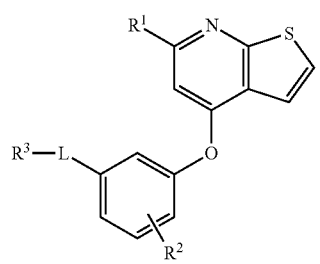
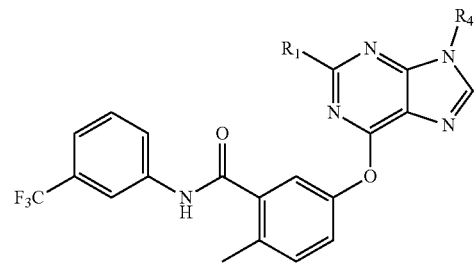
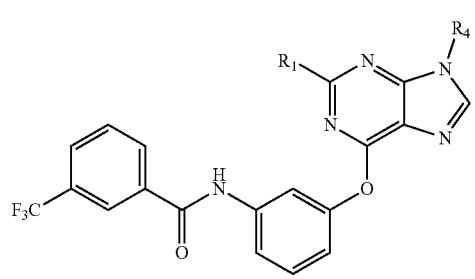
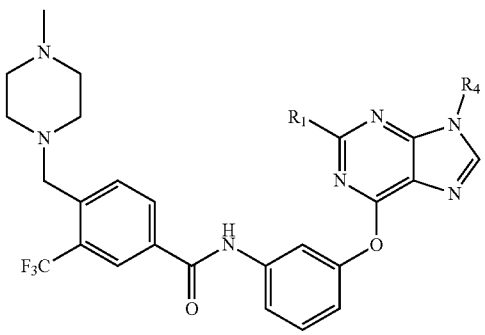
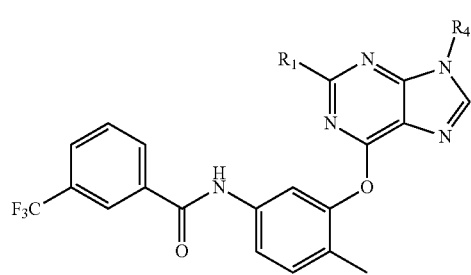
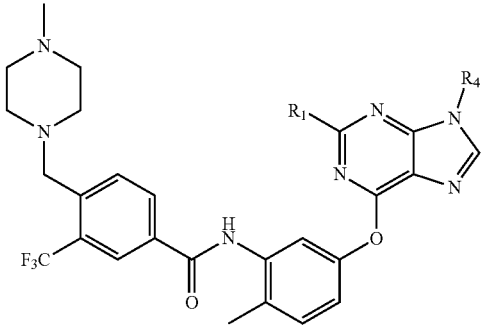
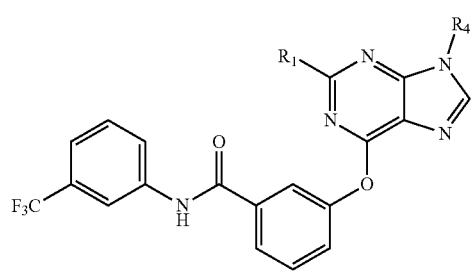
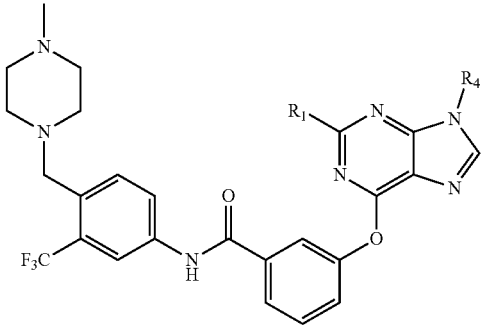
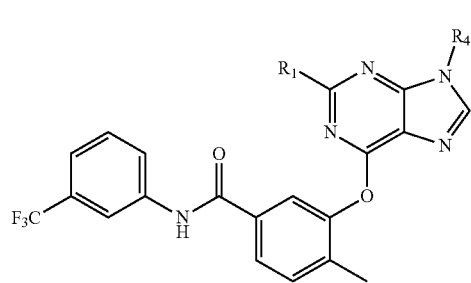
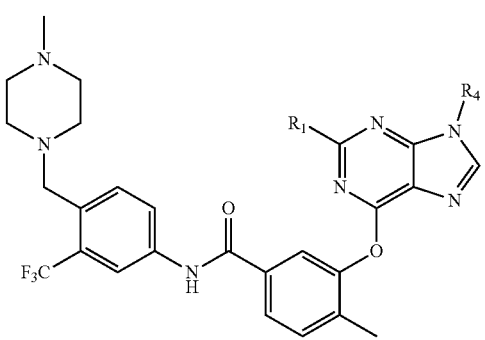

-continued

I-n

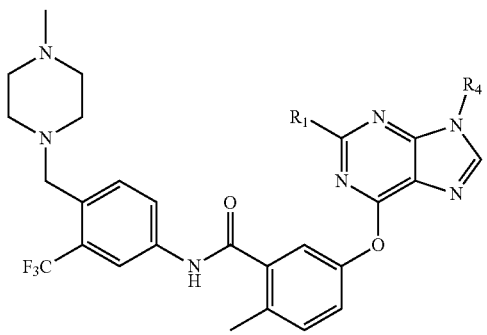

I-r

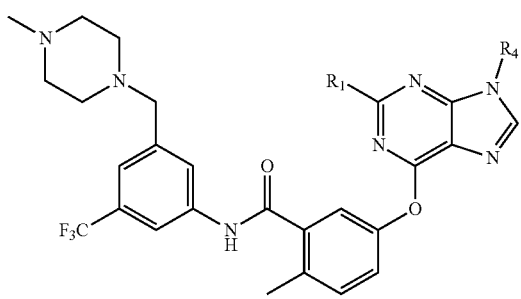

I-s wherein,
Synthetic scheme of compound I-a:

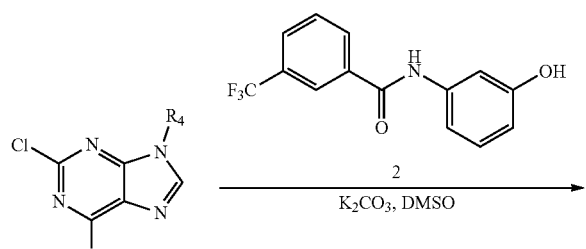

-continued

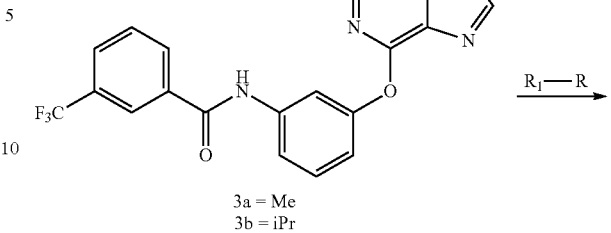

3a = Me
3b = iPr

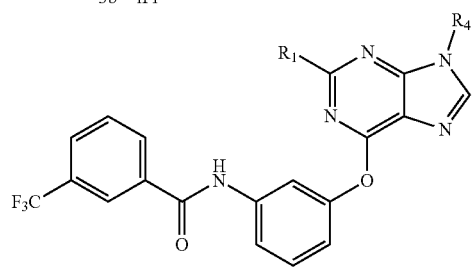

I-a

Preparation of Compound 3a

Compound 2 (281.2 mg, 1 mmol) was dissolved in dimethyl sulfoxide, to which was added $K_2CO_3$ at room temperature, followed by stirring for half an hour. Then, compound 1a (223.3 mg, 1.1 mmol) was added, and reaction was carried out at room temperature overnight. The reaction system was extracted with water/ethyl acetate (3×15 mL), then the organic phase was washed with saturated sodium chloride solution, dried with anhydrous sodium sulfate, concentrated, and separated by silica gel column chromatography (dichloromethane/methanol) to obtain compound 3a (white solid, 441.5 mg, 93.3%). MS (ESI) m/z 448 $[M+H]^+$.

Preparation of compound I-a

Method A:

Compound 3 (0.1 mmol), aryl boric acid (0.15 mmol), $PdCl_2(dppf)\text{-}CH_2Cl_2$ (20% m %), $Na_2CO_3$ (0.4 mmol) were added to 1 mL of 1,4-dioxane and 0.33 mL of $H_2O$, the system was purged with nitrogen, and placed in an oil bath preheated to 100° C. and stirred with heating overnight. The reaction system was filtered to remove solids and concentrated, followed by separation with silica gel column chromatography to obtain compound I-a.

Method B:

Compound 3 (0.1 mmol), aryl boric acid (0.15 mmol), $PdCl_2(dppf)\text{-}CH_2Cl_2$ (20% m %), $Na_2CO_3$ (0.4 mmol) were added to 1 mL of 1,4-dioxane and 0.33 mL of $H_2O$, the system was purged with nitrogen, and placed in an oil bath preheated to 100° C. and stirred with heating overnight. The reaction system was filtered and concentrated, followed by separation with preparative thin layer chromatography to obtain compound I-a.

Method C:

Compound 3 (0.1 mmol), aryl boric acid (0.15 mmol), $PdCl_2(dppf)\text{-}CH_2Cl_2$ (20% m %), $Na_2CO_3$ (0.4 mmol) were added to 1 mL of 1,4-dioxane and 0.33 mL of $H_2O$, the system was purged with nitrogen, and placed in an oil bath preheated to 100° C. and stirred with heating overnight. The reaction system was filtered and concentrated, followed by purification with reverse phase preparative HPLC (using 0.35% trifluoroacetic acid-containing aqueous solution and methanol as mobile phase), and vacuum concentration to obtain compound I-a.

Method D:

Compound 3 (0.1 mmol) was dissolved in 1 mL of t-BuOH, to which was added compounds 5a-5c (0.2 mmol). The reaction was carried out at room temperature, until complete reaction of compound 3 (TLC tracking). The reaction system was concentrated, followed by separation with silica gel column chromatography (dichloromethane/ammonia in methanol) to obtain compound I-a.

Method E:

Compound 3 (0.1 mmol), aryl boric acid (0.15 mmol), PdCl₂(dppf).CH₂Cl₂ (20% m %), Na₂CO₃ (0.4 mmol) were added to 1 mL of 1,4-dioxane and 0.33 mL of H₂O, the system was purged with nitrogen, and placed in an oil bath preheated to 100° C. and stirred with heating overnight. The reaction system was filtered to remove solids and concentrated, followed by separation with silica gel column chromatography to obtain a compound. The obtained compound was dissolved in 1 mL of dichloromethane, to which was added trifluoroacetic acid (10 eq). The reaction was carried out at room temperature overnight. The reaction system was concentrated and dried, to which was then added 1 mL of methanol, 0.5 mL of 7.0 N NH₃ solution in methanol, followed by reacting overnight. The resulting product was concentrated, and separated with silica gel column chromatography (dichloromethane/ammonia in methanol to obtain compound I-a.

Compounds II, III, IV, V, VI, VII all could be synthesized by a similar method.

Some raw materials and intermediates involved in the specific synthetic processes are given as follows:

1.

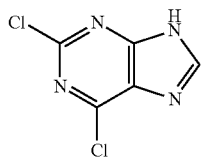 [SMILES: Clc1nc(Cl)c2nc[nH]c2n1]

CAS:5451-40-1, Bide, Shanghai;

2.

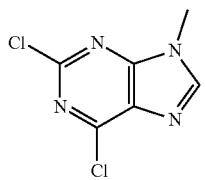

obtained from the reaction of 1 and methyl iodide (CAS: 74-88-4, Xiya Reagent, Shandong);

3.

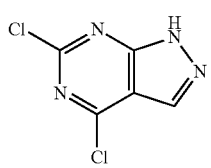 [SMILES: Clc1nc(Cl)c2cn[nH]c2n1]

obtained from the reaction of 2,4,6-trichloro-5-pyrimidine formaldehyde (CAS: 50270-27-4, Bide, Shanghai) and hydrazine hydrate (CAS: 7803-57-8, Energy, Shanghai);

4.

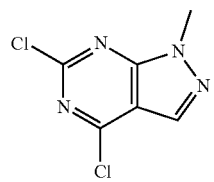

obtained from the reaction of 2,4,6-trichloro-5-pyrimidine formaldehyde and methyl hydrazine (CAS:60-34-4, Xiya Reagent, Shandong);

5.

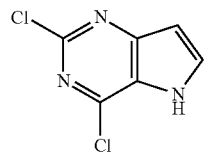 [SMILES: Clc1nc(Cl)c2[nH]ccc2n1]

CAS: 63200-54-4, PharmaBlock, Nanjing, Jiangsu;

6.

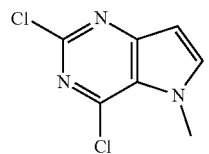

obtained from the reaction of 5 and dimethyl sulfate (CAS: 77-78-1 Xiya Reagent, Shandong);

7.

CAS: 959432-77-0, Sundia, Shanghai;

8.

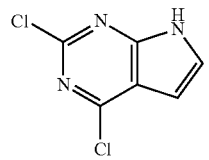 [SMILES: Clc1nc(Cl)c2cc[nH]c2n1]

CAS: 5912-18-5, Efe, Shanghai;

9.

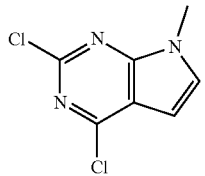

obtained from the reaction of 8 and methyl iodide (CAS: 74-88-4, Xiya Reagent, Shandong);

10.

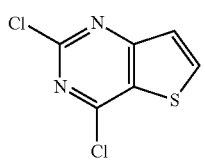 [SMILES: Clc1nc(Cl)c2sccc2n1]

CAS: 16234-14-3, PharmaBlock, Nanjing, Jiangsu;

11.

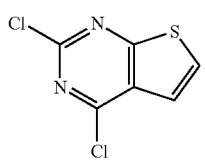 [SMILES: Clc1nc(Cl)c2ccsc2n1]

CAS: 18740-39-1, Chemlin, Jiangsu;

12.

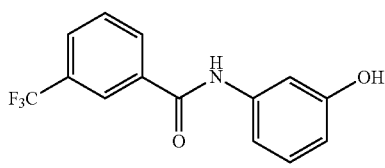 [SMILES: O=C(Nc1cccc(O)c1)c1cccc(C(F)(F)F)c1]

obtained from the condensation of 3-trifluoromethylbenzoic acid (CAS: 454-92-2, Energy, Shanghai) and 3-aminophenol (CAS: 591-27-5, Energy, Shanghai);

13

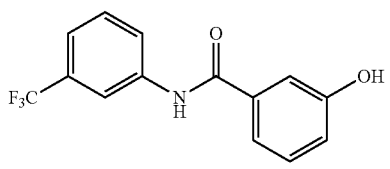 [SMILES: O=C(Nc1cccc(C(F)(F)F)c1)c1cccc(O)c1]

obtained by the reaction including the following steps: protecting phenolic hydroxy of m-hydroxybenzoic acid (CAS: 99-06-9, Efe, Shanghai) with acetyl, then reacting the above product with thionyl chloride (CAS: 7719-09-7, Aladdin, Shanghai) to obtain

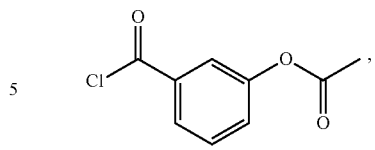

and further reacting the product in the previous step with m-aminotrifluorotoluene (CAS: 98-16-8, Energy, Shanghai) while removing the acetyl;

14.

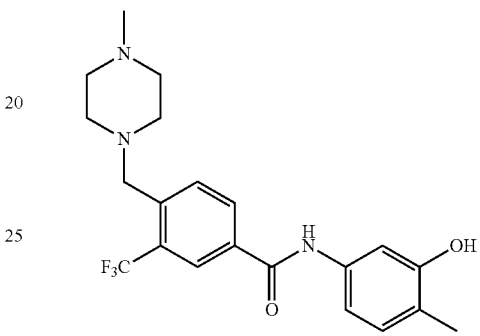

obtained by the reaction including the following steps: condensing

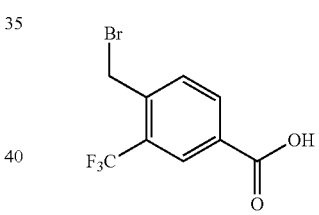

(CAS: 859213-39-1, J&K, Beijing) and

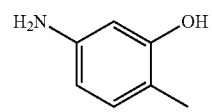

(CAS: 2835-95-2, Bide, Shanghai) to obtain

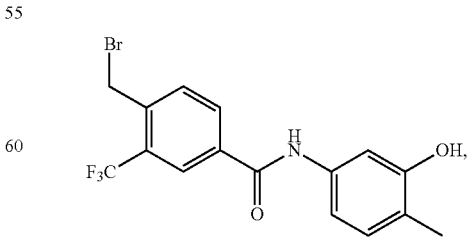

and then reacting the above product with N-methylpiperazine (CAS: 109-01-3, Energy, Shanghai);

15.

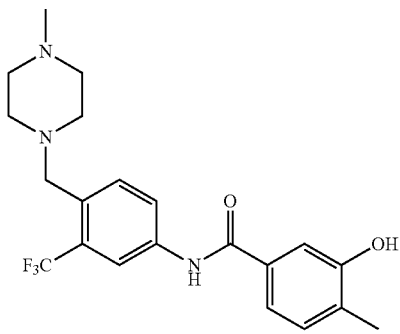 [SMILES: Cc1ccc(C(=O)Nc2ccc(CN3CCN(C)CC3)c(C(F)(F)F)c2)cc1O]

obtained by the reaction including the following steps: protecting phenolic hydroxy of 3-hydroxy-4-methylbenzoic acid (CAS: 586-30-1, Accela ChemBio, Shanghai) with acetyl, then reacting the above product with thionyl chloride to obtain

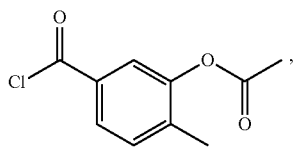

and further reacting the product in the previous step with

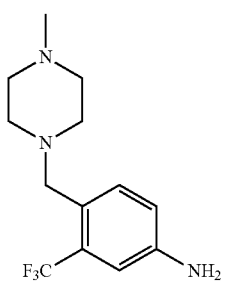 [SMILES: CN1CCN(Cc2ccc(N)cc2C(F)(F)F)CC1]

(CAS: 694499-26-8, Shuya, Shanghai) while removing the acetyl;

16.

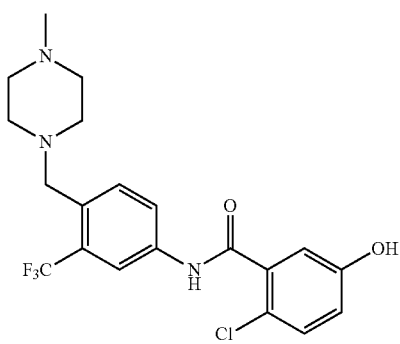 [SMILES: CN1CCN(Cc2ccc(NC(=O)c3cc(O)ccc3Cl)cc2C(F)(F)F)CC1]

obtained using 2-chloro-5-hydroxybenzoic acid (CAS: 56961-30-9, Shuya, Shanghai) as starting raw material, by a method similar to that for the synthesis of 15;

17.

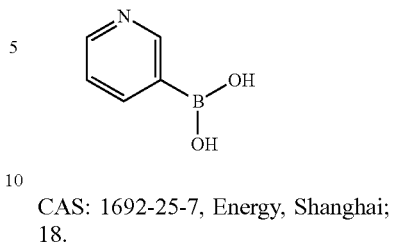

CAS: 1692-25-7, Energy, Shanghai;

18.

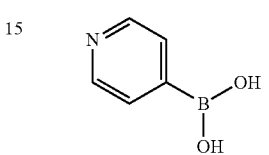

CAS: 1692-15-5, Energy, Shanghai;

19.

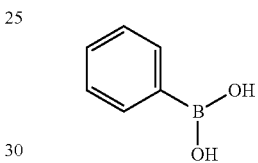

CAS: 98-80-6, Adamas, Switzerland;

20.

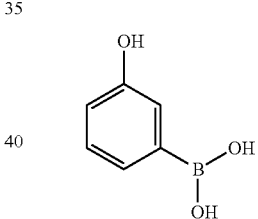

CAS: 87199-18-6, Energy, Shanghai;

21.

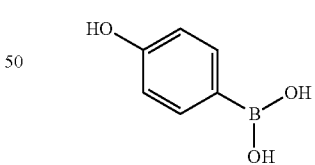

CAS: 71597-85-8, Bide, Shanghai;

22.

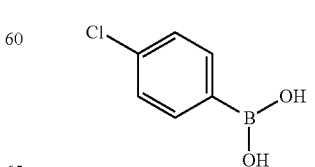

CAS: 1679-18-1, Energy, Shanghai;

23.
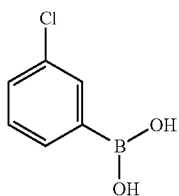
CAS: 63503-60-6, Energy, Shanghai;
24.
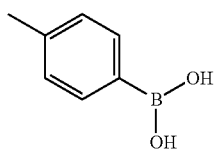
CAS: 5720-05-8, Energy, Shanghai;
25.
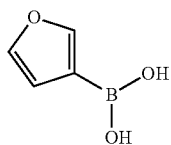
CAS: 55552-70-0, Energy, Shanghai;
26.
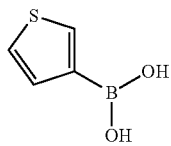
CAS: 6165-69-1, Energy, Shanghai;
27.
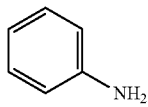
CAS: 62-53-3, Adamas, Switzerland;
28.
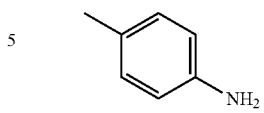
CAS: 106-49-0, Adamas, Switzerland;
29.
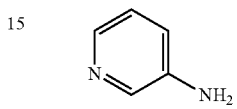
CAS: 462-08-8, Energy, Shanghai;
30
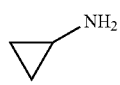
CAS: 765-30-0, Energy, Shanghai;
31.
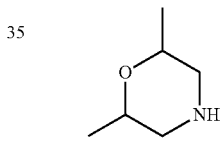
CAS: 141-91-3, Energy, Shanghai;
32.
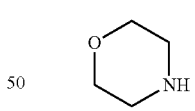
CAS: 110-91-8, Aladdin, Shanghai;
33.
CAS: 124-40-3, Meryer, Shanghai.
The table below lists the specific compounds and structure identification data.

TABLE 1

| No. | Structure | ¹H NMR and/or MS data |
|---|---|---|
| I-a-1 | 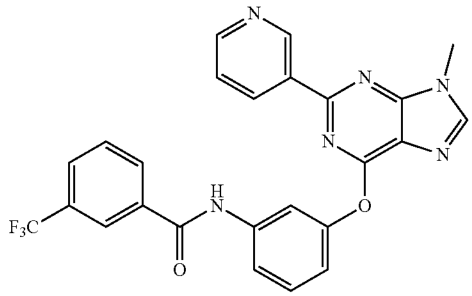 [SMILES: Cn1cnc2c(Oc3cccc(NC(=O)c4cccc(C(F)(F)F)c4)c3)nc(-c3cccnc3)nc21] | ¹H NMR (600 MHz, DMSO-$d_6$) δ 10.63 (s, 1H), 9.28 (s, 1H), 8.59 (d, J = 3.8 Hz, 1H), 8.49 (s, 1H), 8.46 (d, J = 7.9 Hz, 1H), 8.27 (s, 1H), 8.24 (d, J = 7.8 Hz, 1H), 7.94 (d, J = 7.7 Hz, 1H), 7.90 (s, 1H), 7.76 (t, J = 7.8 Hz, 1H), 7.72 (d, J = 8.2 Hz, 1H), 7.51 (t, J = 8.1 Hz, 1H), 7.45 (dd, J = 7.8, 4.8 Hz, 1H), 7.17 (d, J = 7.9 Hz, 1H), 3.91 (s, 1H). MS (ESI) m/z 491 [M + H]⁺. |
| I-a-2 | 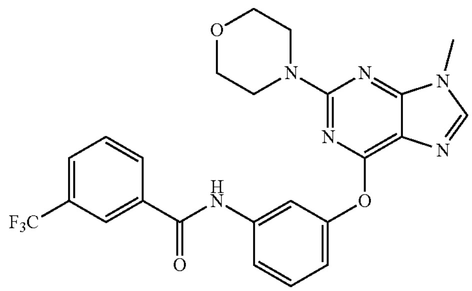 [SMILES: Cn1cnc2c(Oc3cccc(NC(=O)c4cccc(C(F)(F)F)c4)c3)nc(N3CCOCC3)nc21] | ¹H NMR (600 MHz, DMSO-$d_6$) δ 10.58 (s, 1H), 8.29 (s, 1H), 8.26 (d, J = 7.9 Hz, 1H), 8.05 (s, 1H), 7.98 (d, J = 7.8 Hz, 1H), 7.82 (t, J = 2.1 Hz, 1H), 7.80 (t, J = 7.8 Hz, 1H), 7.64 (ddd, J = 8.2, 1.9, 0.8 Hz, 1H), 7.45 (t, J = 8.2 Hz, 1H), 7.06 (ddd, J = 8.2, 2.3, 0.9 Hz, 1H), 3.68 (s, 3H), 3.60-3.58 (m, 4H), 3.55 (d, J = 4.9 Hz, 4H). MS (ESI) m/z 499 [M + H]⁺. |
| I-a-3 | 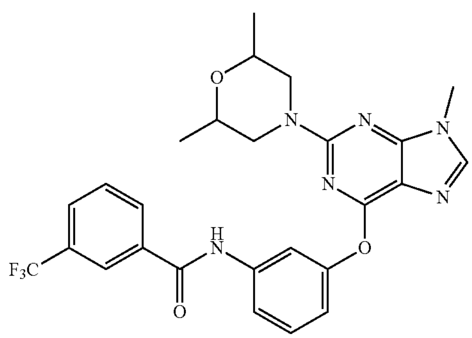 [SMILES: CC1CN(c2nc(Oc3cccc(NC(=O)c4cccc(C(F)(F)F)c4)c3)c3ncn(C)c3n2)CC(C)O1] | ¹H NMR (600 MHz, DMSO-$d_6$) δ 10.60 (s, 1H), 8.29 (s, 1H), 8.26 (d, J = 7.9 Hz, 1H), 8.04 (s, 1H), 7.98 (d, J = 7.8 Hz, 1H), 7.91 (t, J = 2.1 Hz, 1H), 7.80 (dd, J = 9.9, 5.7 Hz, 1H), 7.62 (dd, J = 8.1, 1.1 Hz, 1H), 7.45 (t, J = 8.1 Hz, 1H), 7.06 (dd, J = 8.1, 1.7 Hz, 1H), 3.68 (s, 3H), 3.53-3.46 (m, 2H), 2.44 (dd, J = 12.7, 10.9 Hz, 2H), 1.24 (d, J = 22.2 Hz, 2H), 1.05 (d, J = 5.8 Hz, 6H). MS (ESI) m/z 527 [M + H]⁺. |
| I-b-1 | 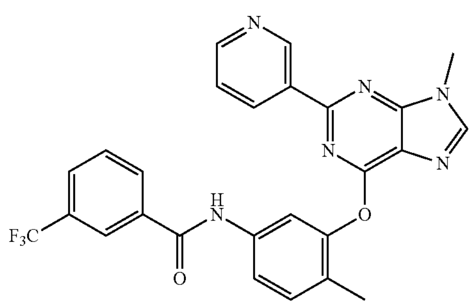 [SMILES: Cc1ccc(NC(=O)c2cccc(C(F)(F)F)c2)cc1Oc1nc(-c2cccnc2)nc2c1ncn2C] | ¹H NMR (600 MHz, DMSO-$d_6$) δ 10.57 (s, 1H), 9.25 (dd, J = 2.2, 0.8 Hz, 1H), 8.62 (dd, J = 4.7, 1.7 Hz, 1H), 8.53 (s, 1H), 8.46-8.44 (m, 1H), 8.28 (s, 1H), 8.25 (d, J = 7.9 Hz, 1H), 7.96 (d, J = 7.8 Hz, 1H), 7.81 (d, J = 2.1 Hz, 1H), 7.78 (t, J = 7.8 Hz, 1H), 7.68 (dd, J = 8.3, 2.1 Hz, 1H), 7.49 (ddd, J = 8.0, 4.8, 0.8 Hz, 1H), 7.43 (d, J = 8.4 Hz, 1H), 5.76 (s, 1H), 3.94 (s, 3H), 2.14 (s, 3H). MS (ESI) m/z 505 [M + H]⁺. |
| I-b-2 | 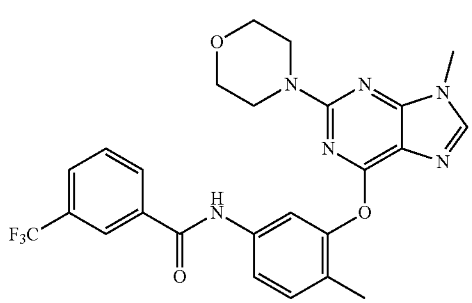 | MS (ESI) m/z 541 [M + H]⁺. |

TABLE 1-continued

Structure and characterization of compounds I

| No. | Structure | $^1$H NMR and/or MS data |
|---|---|---|
| I-b-3 | 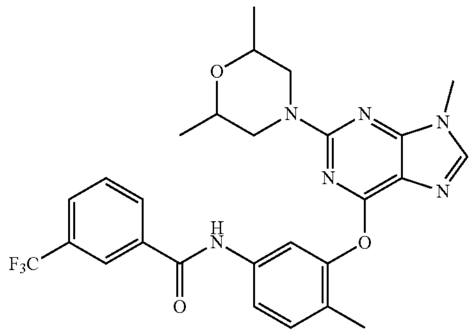 [SMILES: Cc1ccc(NC(=O)c2cccc(C(F)(F)F)c2)cc1Oc1nc(N2CC(C)OC(C)C2)nc2c1ncn2C] | $^1$H NMR (600 MHz, DMSO-$d_6$) δ 10.52 (s, 1H), 8.28 (s, 1H), 8.25 (d, J = 7.9 Hz, 1H), 8.03 (s, 1H), 7.96 (d, J = 7.8 Hz, 1H), 7.78 (q, J = 7.0 Hz, 2H), 7.56 (dd, J = 8.2, 2.1 Hz, 1H), 7.33 (d, J = 8.7 Hz, 1H), 3.68 (s, 3H), 3.50-3.43 (m, 2H), 2.41 (dd, J = 12.6, 11.0 Hz, 2H), 2.12 (s, 3H), 1.22 (d, J = 4.7 Hz, 2H), 1.02 (dd, J = 10.1, 5.2 Hz, 6H). MS (ESI) m/z 541 [M + H]$^+$. |
| I-d-1 | 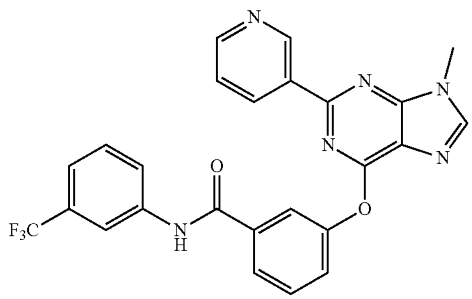 [SMILES: Cn1cnc2c(Oc3cccc(C(=O)Nc4cccc(C(F)(F)F)c4)c3)nc(-c3cccnc3)nc21] | $^1$H NMR (600 MHz, DMSO-$d_6$) δ 10.63 (s, 1H), 9.26 (s, 1H), 8.62 (d, J = 3.4 Hz, 1H), 8.54 (s, 1H), 8.45 (d, J = 7.7 Hz, 1H), 8.25 (s, 1H), 8.07 (d, J = 8.1 Hz, 1H), 8.03 (s, 1H), 8.00 (d, J = 7.0 Hz, 1H), 7.76-7.69 (m, 2H), 7.60 (t, J = 7.8 Hz, 1H), 7.46 (d, J = 7.2 Hz, 2H), 3.94 (s, 3H). MS (ESI) m/z 491 [M + H]$^+$. |
| I-d-2 | | $^1$H NMR (600 MHz, DMSO-$d_6$)) δ 10.63 (s, 1H), 8.66 (d, J = 5.9 Hz, 2H), 8.58 (s, 1H), 8.25 (s, 1H), 8.06 (d, J = 8.4 Hz, 1H), 8.04-7.98 (m, 4H), 7.72 (ddd, J = 11.3, 8.2, 5.1 Hz, 2H), 7.60 (t, J = 8.0 Hz, 1H), 7.46 (d, J = 7.8 Hz, 1H), 3.95 (s, 3H). MS (ESI) m/z 491 [M + H]$^+$. |
| I-d-3 | 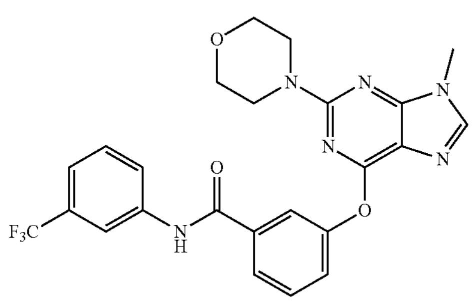 [SMILES: Cn1cnc2c(Oc3cccc(C(=O)Nc4cccc(C(F)(F)F)c4)c3)nc(N3CCOCC3)nc21] | $^1$H NMR (600 MHz, DMSO-$d_6$) δ 10.58 (s, 1H), 8.25 (s, 1H), 8.06 (d, J = 9.5 Hz, 2H), 7.93 (d, J = 1.7 Hz, 1H), 7.91 (d, J = 7.7 Hz, 1H), 7.64 (t, J = 7.9 Hz, 1H), 7.61 (t, J = 8.0 Hz, 1H), 7.57 (dd, J = 8.1, 1.3 Hz, 1H), 7.47 (d, J = 7.7 Hz, 1H), 3.69 (s, 3H), 3.59-3.56 (m, 4H), 3.52 (d, J = 3.9 Hz, 4H). MS (ESI) m/z 499 [M + H]$^+$. |
| I-d-4 | 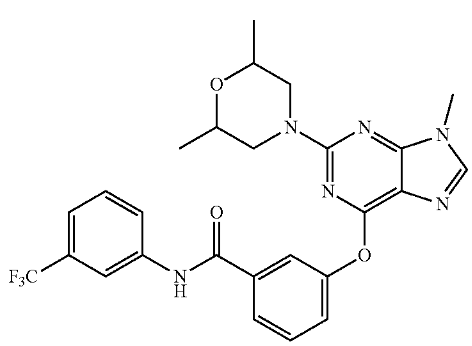 [SMILES: CC1CN(c2nc(Oc3cccc(C(=O)Nc4cccc(C(F)(F)F)c4)c3)c3ncn(C)c3n2)CC(C)O1] | MS (ESI) m/z 527 [M + H]$^+$. |

TABLE 1-continued

Structure and characterization of compounds I

| No. | Structure | $^1$H NMR and/or MS data |
|---|---|---|
| I-e-1 | 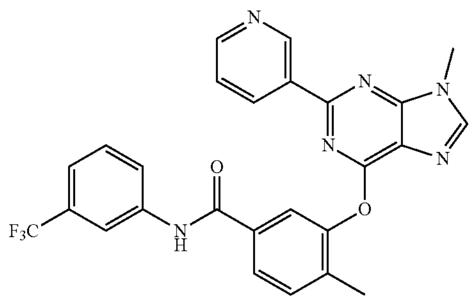 [SMILES: Cc1ccc(C(=O)Nc2cccc(C(F)(F)F)c2)cc1Oc1nc(-c2cccnc2)nc2c1ncn2C] | $^1$H NMR (600 MHz, DMSO-d$_6$) δ 10.51 (s, 1H), 9.18 (s, 1H), 8.59 (d, J = 3.4 Hz, 1H), 8.52 (s, 1H), 8.38 (d, J = 8.1 Hz, 1H), 8.20 (s, 1H), 8.03 (d, J = 8.5 Hz, 1H), 7.94 (m, J = 10.1 Hz, 2H), 7.61 (d, J = 7.8 Hz, 1H), 7.56 (t, J = 7.9 Hz, 1H), 7.45 (dd, J = 7.9, 4.9 Hz, 1H), 7.42 (d, J = 7.8 Hz, 1H), 3.92 (s, 3H), 2.22 (s, 3H). MS (ESI) m/z 505 [M + H]$^+$. |
| I-e-2 | 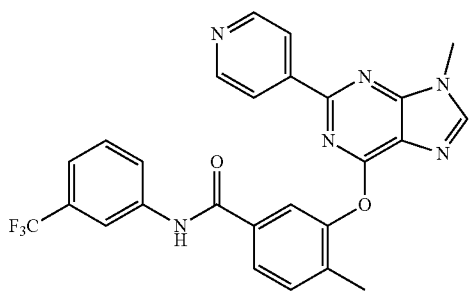 [SMILES: Cc1ccc(C(=O)Nc2cccc(C(F)(F)F)c2)cc1Oc1nc(-c2ccncc2)nc2c1ncn2C] | $^1$H NMR (600 MHz, DMSO-d$_6$) δ 10.52 (s, 1H), 8.65 (dd, J = 4.5, 1.6 Hz, 2H), 8.58 (s, 1H), 8.22 (s, 1H), 8.05 (d, J = 8.3 Hz, 1H), 7.99-7.95 (m, 4H), 7.63 (d, J = 7.8 Hz, 1H), 7.58 (t, J = 8.0 Hz, 1H), 7.44 (d, J = 7.7 Hz, 1H), 3.95 (s, 3H), 2.24 (s, 3H). MS (ESI) m/z 505 [M + H]$^+$. |
| I-e-3 | 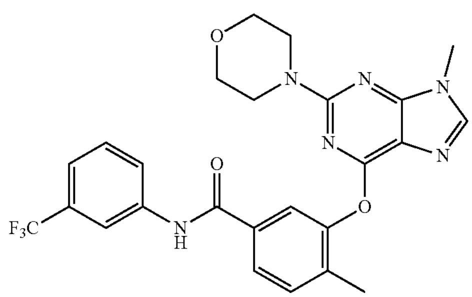 [SMILES: Cc1ccc(C(=O)Nc2cccc(C(F)(F)F)c2)cc1Oc1nc(N2CCOCC2)nc2c1ncn2C] | $^1$H NMR (600 MHz, DMSO-d$_6$) δ 10.49 (s, 1H), 8.23 (s, 1H), 8.06 (s, 2H), 7.89-7.86 (m, 2H), 7.59 (t, J = 8.0 Hz, 1H), 7.53 (d, J = 7.7 Hz, 1H), 7.45 (d, J = 7.7 Hz, 1H), 3.69 (s, 3H), 3.56-3.53 (m, 4H), 3.46 (s, 4H), 2.21 (s, 3H). MS (ESI) m/z: 513 [M + H]$^+$. |
| I-e-4 | 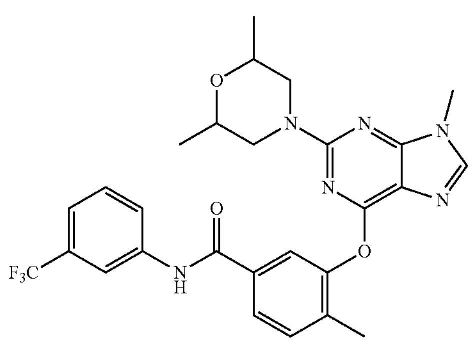 [SMILES: Cc1ccc(C(=O)Nc2cccc(C(F)(F)F)c2)cc1Oc1nc(N2CC(C)OC(C)C2)nc2c1ncn2C] | $^1$H NMR (600 MHz, DMSO-d$_6$)) δ 10.48 (s, 1H), 8.24 (s, 1H), 8.05 (d, J = 7.4 Hz, 2H), 7.97 (d, J = 1.7 Hz, 1H), 7.88 (dd, J = 7.9, 1.7 Hz, 1H), 7.59 (t, J = 8.0 Hz, 1H), 7.54 (d, J = 8.1 Hz, 1H), 7.45 (d, J = 7.8 Hz, 1H), 3.69 (s, 3H), 3.48-3.41 (m, 2H), 3.18 (d, J = 5.2 Hz, 2H), 2.44-2.37 (m, 2H), 2.24 (s, 3H), 1.04-0.99 (m, 6H), MS (ESI) m/z 541 [M + H]$^+$. |
| I-f-1 | 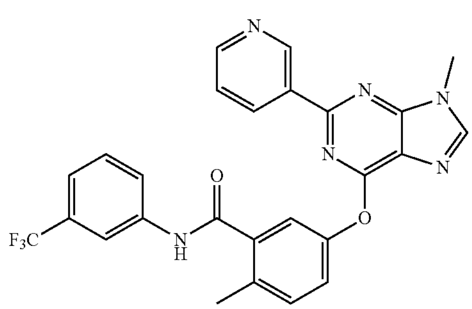 [SMILES: Cc1ccc(Oc2nc(-c3cccnc3)nc3c2ncn3C)cc1C(=O)Nc1cccc(C(F)(F)F)c1] | $^1$H NMR (600 MHz, DMSO-d$_6$) δ 10.73 (s, 1H), 9.31 (d, J = 2.3 Hz, 1H), 8.67-8.62 (m, 1H), 8.52 (s, 1H), 8.49 (dt, J = 8.0, 2.0 Hz, 1H), 8.24 (d, J = 2.0 Hz, 1H), 8.00-7.91 (m, 1H), 7.61-7.54 (m, 2H), 7.55-7.46 (m, 3H), 7.46-7.40 (m, 1H), 3.92 (s, 3H), 2.48 (s, 3H). MS (ESI) m/z 505 [M + H]$^+$. |

TABLE 1-continued

Structure and characterization of compounds I

| No. | Structure | ¹H NMR and/or MS data |
| --- | --- | --- |
| I-f-2 | 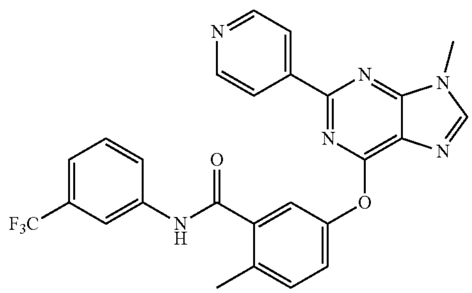 [SMILES: Cc1ccc(Oc2nc(-c3ccncc3)nc3c2ncn3C)cc1C(=O)Nc1cccc(C(F)(F)F)c1] | ¹H NMR (600 MHz, DMSO-$d_6$) δ 10.74 (s, 1H), 8.68 (s, 2H), 8.55 (s, 1H), 8.25 (s, 1H), 8.06 (s, 2H), 7.96 (d, J = 8.3 Hz, 1H), 7.61-7.55 (m, 2H), 7.53-7.46 (m, 2H), 7.44 (d, J = 7.7 Hz, 1H), 3.92 (s, 3H), 2.48 (s, 3H). MS (ESI) m/z 505 [M + H]⁺. |
| I-f-3 | 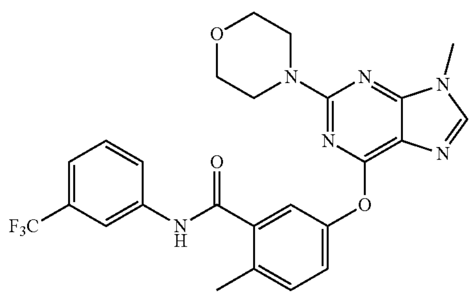 [SMILES: Cc1ccc(Oc2nc(N3CCOCC3)nc3c2ncn3C)cc1C(=O)Nc1cccc(C(F)(F)F)c1] | ¹H NMR (600 MHz, DMSO-$d_6$) δ 10.68 (s, 1H), 8.23 (s, 1H), 8.06 (s, 1H), 7.95 (d, J = 8.1 Hz, 1H), 7.59 (t, J = 8.0 Hz, 1H), 7.48 (d, J = 2.3 Hz, 1H), 7.46 (d, J = 8.0 Hz, 1H), 7.40-7.37 (m, 1H), 3.68 (s, 3H), 3.59 (s, 4H), 3.55 (s, 4H), 2.42 (s, 3H). MS (ESI) m/z 513 [M + H]⁺. |
| I-h-1 | 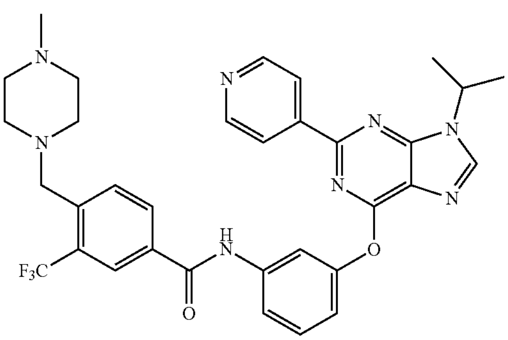 [SMILES: CC(C)n1cnc2c(Oc3cccc(NC(=O)c4ccc(CN5CCN(C)CC5)c(C(F)(F)F)c4)c3)nc(-c3ccncc3)nc21] | ¹H NMR (600 MHz, DMSO-$d_6$) δ 10.62 (s, 1H), 8.72 (s, 1H), 8.71-8.63 (m, 2H), 8.24 (s, 1H), 8.22 (dd, J = 8.2, 1.9 Hz, 1H), 8.10-8.05 (m, 2H), 7.92 (d, J = 8.0 Hz, 1H), 7.90 (t, J = 2.2 Hz, 1H), 7.72 (dd, J = 8.2, 2.0 Hz, 1H), 7.53 (t, J = 8.1 Hz, 1H), 7.18 (dd, J = 8.1, 2.5 Hz, 1H), 5.48-4.64 (m, 1H), 3.67 (s, 2H), 2.41 (s, 8H), 2.45-2.32 (m, 8H), 1.65 (d, J = 6.8 Hz, 6H). MS (ESI) m/z 631 [M + H]⁺. |
| I-j-1 | 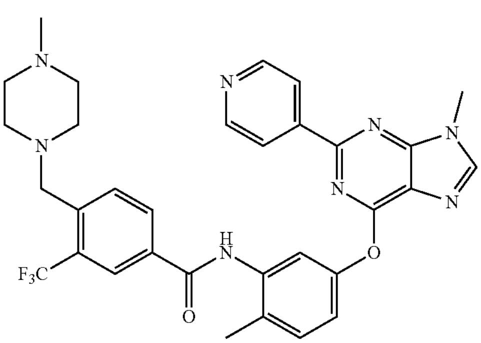 [SMILES: Cc1ccc(Oc2nc(-c3ccncc3)nc3c2ncn3C)cc1NC(=O)c1ccc(CN2CCN(C)CC2)c(C(F)(F)F)c1] | ¹H NMR (600 MHz, Methanol-$d_4$) δ 8.49-8.44 (m, 2H), 8.31 (s, 1H), 8.25 (d, J = 1.8 Hz, 1H), 8.15 (dd, J = 8.1, 1.8 Hz, 1H), 8.13-8.09 (m, 2H), 7.92 (d, J = 8.2 Hz, 1H), 7.47 (d, J = 2.5 Hz, 1H), 7.38 (d, J = 8.3 Hz, 1H), 7.18 (dd, J = 8.3, 2.5 Hz, 1H), 3.90 (s, 3H), 3.69 (s, 2H), 2.34 (s, 3H), 2.26 (s, 3H). MS (ESI) m/z 617 [M + H]⁺. |

TABLE 1-continued
Structure and characterization of compounds I
| No. | Structure | $^1$H NMR and/or MS data |
|---|---|---|
| I-j-2 | 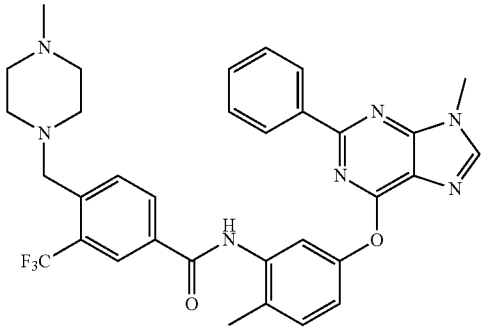 [SMILES: Cc1ccc(Oc2nc(-c3ccccc3)nc3c2ncn3C)cc1NC(=O)c1ccc(CN2CCN(C)CC2)c(C(F)(F)F)c1]<br>TFA Salt | MS (ESI) m/z 615 [M + H]$^+$. |
| I-j-3 | 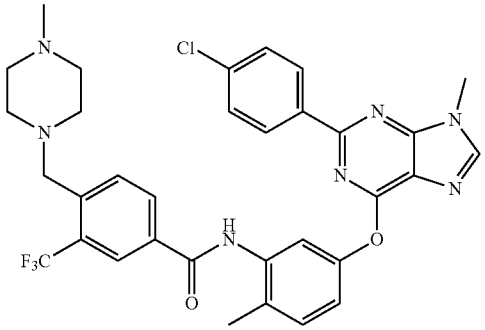 [SMILES: Cc1ccc(Oc2nc(-c3ccc(Cl)cc3)nc3c2ncn3C)cc1NC(=O)c1ccc(CN2CCN(C)CC2)c(C(F)(F)F)c1]<br>TFA Salt | MS (ESI) m/z 650 [M + H]$^+$. |
| I-j-4 | 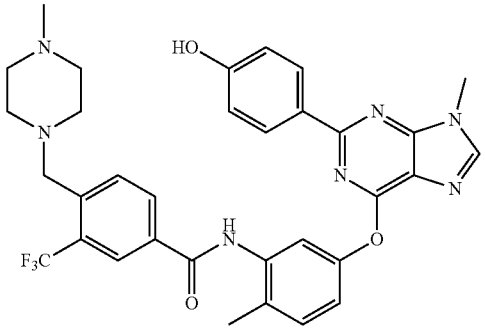 [SMILES: Cc1ccc(Oc2nc(-c3ccc(O)cc3)nc3c2ncn3C)cc1NC(=O)c1ccc(CN2CCN(C)CC2)c(C(F)(F)F)c1]<br>TFA Salt | MS (ESI) m/z 631 [M + H]$^+$. |
| I-j-5 | 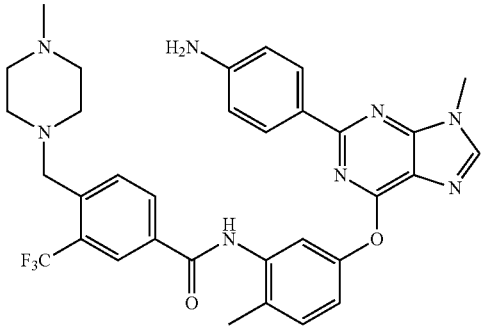 [SMILES: Cc1ccc(Oc2nc(-c3ccc(N)cc3)nc3c2ncn3C)cc1NC(=O)c1ccc(CN2CCN(C)CC2)c(C(F)(F)F)c1]<br>TFA salt | MS (ESI) m/z 630 [M + H]$^+$. |

TABLE 1-continued

Structure and characterization of compounds I

| No. | Structure | ¹H NMR and/or MS data |
|---|---|---|
| I-j-6 | TFA salt | MS (ESI) m/z 605 [M + H]⁺. |
| I-j-7 | TFA Salt | MS (ESI) m/z 621 [M + H]⁺. |
| I-l-1 | 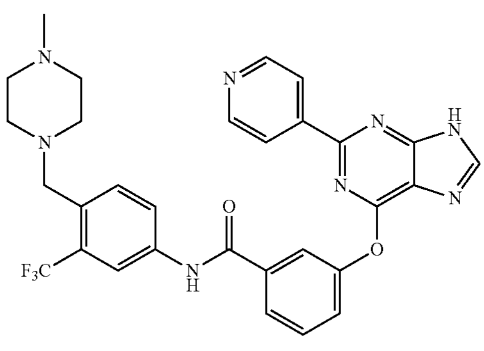 [SMILES: CN1CCN(Cc2ccc(NC(=O)c3cccc(Oc4nc(-c5ccncc5)nc5[nH]cnc45)c3)cc2C(F)(F)F)CC1] | ¹H NMR (600 MHz, DMSO-$d_6$) δ 10.64 (s, 1H), 8.78 (s, 2H), 8.69 (s, 1H), 8.22 (d, J = 2.1 Hz, 1H), 8.18 (d, J = 5.2 Hz, 2H), 8.12-8.08 (m, 1H), 8.04 (s, 1H), 8.02-8.00 (m, 1H), 7.75-7.73 (m, 2H), 7.71 (d, J = 8.6 Hz, 1H), 7.24-7.03 (m, 1H), 3.41 (d, J = 10.5 Hz, 2H), 3.04 (s, 2H), 2.91 (s, 2H), 2.81 (s, 3H), 2.39 (s, 2H). MS (ESI) m/z 589 [M + H]⁺. |
| I-l-2 | 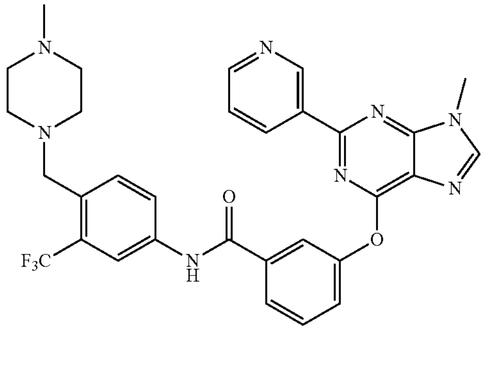 [SMILES: CN1CCN(Cc2ccc(NC(=O)c3cccc(Oc4nc(-c5cccnc5)nc5c4ncn5C)c3)cc2C(F)(F)F)CC1] | ¹H NMR (600 MHz, DMSO-$d_6$) δ 10.58 (s, 1H), 9.27 (d, J = 1.5 Hz, 1H), 8.62 (dd, J = 4.7, 1.7 Hz, 1H), 8.54 (s, 1H), 8.47-8.44 (m, 1H), 8.20 (d, J = 2.1 Hz, 1H), 8.04 (dd, J = 8.5, 1.9 Hz, 1H), 8.02 (t, J = 1.8 Hz, 1H), 7.99 (dt, J = 7.5, 1.4 Hz, 1H), 7.73 (t, J = 7.8 Hz, 1H), 7.71-7.68 (m, 2H), 7.48 (ddd, J = 8.0, 4.8, 0.7 Hz, 1H), 3.94 (s, 3H), 3.56 (s, 2H), 2.16 (s, 3H). MS (ESI) m/z 603 [M + H]⁺. |

TABLE 1-continued

Structure and characterization of compounds I

| No. | Structure | ¹H NMR and/or MS data |
|---|---|---|
| I-l-3 | (structure, TFA Salt) | MS (ESI) m/z 603 [M + H]⁺. |
| I-l-4 | (structure with SEM group) | MS (ESI) m/z 719 [M + H]⁺. |
| I-m-1 | (structure) | ¹H NMR (600 MHz, DMSO) δ 10.49 (s, 1H), 8.64 (d, J = 5.7 Hz, 3H), 8.18 (d, J = 1.9 Hz, 1H), 8.05 (d, J = 8.6 Hz, 1H), 7.99 (s, 1H), 7.98-7.96 (m, 1H), 7.93 (dd, J = 4.6, 1.4 Hz, 2H), 7.68 (d, J = 8.6 Hz, 1H), 7.63 (d, J = 8.1 Hz, 1H), 3.56 (s, 2H), 2.46-2.35 (m, 8H), 2.26 (s, 3H), 2.23 (s, 3H). MS (ESI) m/z 603 [M + H]⁺. |
| I-m-2 | (structure, TFA Salt) | ¹H NMR (600 MHz, DMSO-d₆) δ 10.54 (s, 1H), 9.21 (s, 1H), 8.67 (s, 1H), 8.56 (s, 1H), 8.51 (d, J = 7.9 Hz, 1H), 8.19 (d, J = 2.0 Hz, 1H), 8.10-8.07 (m, 1H), 7.98-7.95 (m, 2H), 7.69 (d, J = 8.6 Hz, 1H), 7.63 (d, J = 7.9 Hz, 1H), 7.58 (s, 1H), 3.95 (s, 3H), 3.39 (s, 2H), 2.98 (d, J = 73.2 Hz, 4H), 2.80 (s, 3H), 2.39 (s, 2H), 2.25 (s, 3H). MS (ESI) m/z: 617 [M + H]⁺. |

TABLE 1-continued

Structure and characterization of compounds I

| No. | Structure | ¹H NMR and/or MS data |
|---|---|---|
| I-m-3 | 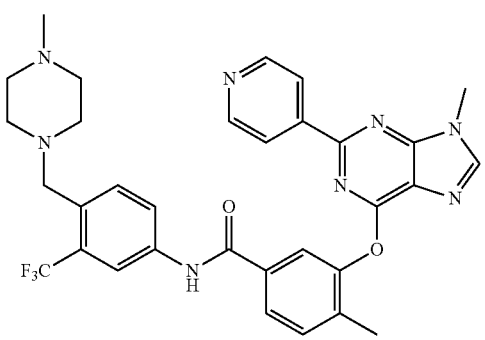 [SMILES: Cc1ccc(C(=O)Nc2ccc(CN3CCN(C)CC3)c(C(F)(F)F)c2)cc1Oc1nc(-c2ccncc2)nc2c1ncn2C] TFA Salt | ¹H NMR (600 MHz, DMSO-d$_6$) δ 10.49 (s, 1H), 8.65 (dd, J = 4.5, 1.6 Hz, 2H), 8.58 (s, 1H), 8.18 (d, J = 2.2 Hz, 1H), 8.04 (dd, J = 8.5, 2.0 Hz, 1H), 7.99-7.94 (m, 4H), 7.68 (d, J = 8.6 Hz, 1H), 7.62 (d, J = 8.0 Hz, 1H), 3.95 (s, 3H), 3.55 (s, 2H), 2.24 (s, 3H), 2.17 (s, 3H). MS (ESI) m/z 617 [M + H]⁺. |
| I-m-4 | 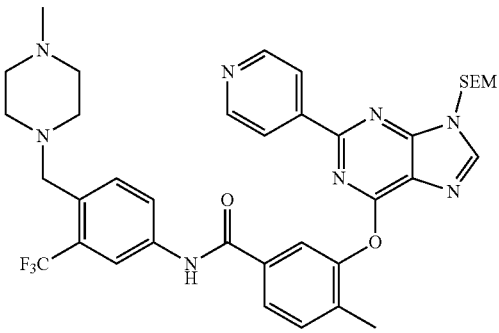 [SMILES: Cc1ccc(C(=O)Nc2ccc(CN3CCN(C)CC3)c(C(F)(F)F)c2)cc1Oc1nc(-c2ccncc2)nc2c1ncn2COCC[Si](C)(C)C] | MS (ESI) m/z 733 [M + H]⁺. |
| I-n-1 | 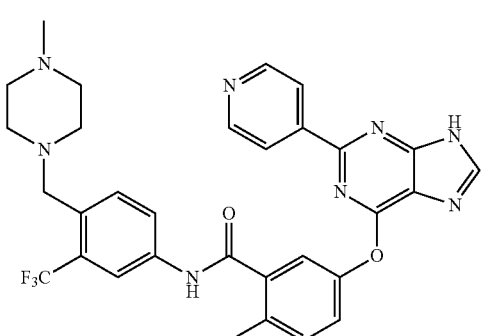 | ¹H NMR (600 MHz, DMSO) δ 10.69 (s, 1H), 8.68 (d, J = 5.8 Hz, 2H), 8.62 (s, 1H), 8.19 (s, 1H), 8.04 (d, J = 5.9 Hz, 2H), 7.99 (d, J = 8.1 Hz, 1H), 7.69 (d, J = 8.4 Hz, 1H), 7.59 (d, J = 2.1 Hz, 1H), 7.53 (dd, J = 8.3, 2.3 Hz, 1H), 7.49 (d, J = 8.4 Hz, 1H), 3.60 (s, 2H), 3.53-3.14 (m, 8H), 2.48 (s, 3H), 1.22 (s, 3H). MS (ESI) m/z 603 [M + H]⁺. |
| I-n-2 | 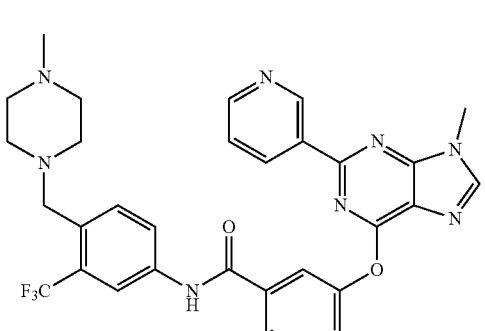 TFA Salt | ¹H NMR (600 MHz, DMSO-d$_6$) δ 10.70 (s, 1H), 9.32 (s, 1H), 8.68 (d, J = 3.6 Hz, 1H), 8.56 (dt, J = 8.0, 1.8 Hz, 1H), 8.54 (s, 1H), 8.20 (d, J = 1.6 Hz, 1H), 8.01 (d, J = 8.3 Hz, 1H), 7.70 (d, J = 8.5 Hz, 1H), 7.59-7.55 (m, 2H), 7.52 (dd, J = 8.3, 2.4 Hz, 1H), 7.49 (d, J = 8.4 Hz, 1H), 3.94 (s, 4H), 3.42-3.37 (m, 2H), 3.06-2.88 (m, 4H), 2.80 (s, 3H), 2.48 (s, 3H), 2.38 (s, 2H). MS (ESI) m/z 617 [M + H]⁺. |

TABLE 1-continued
Structure and characterization of compounds I
| No. | Structure | ¹H NMR and/or MS data |
|---|---|---|
| I-n-3 | 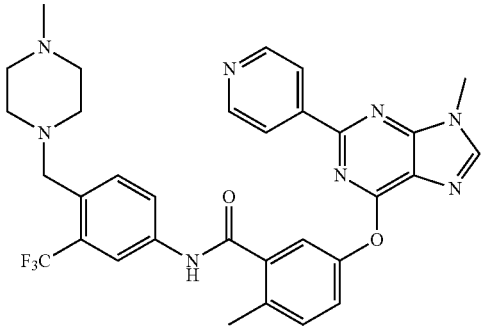 [SMILES: Cc1ccc(Oc2nc(-c3ccncc3)nc3c2ncn3C)cc1C(=O)Nc1ccc(CN2CCN(C)CC2)c(C(F)(F)F)c1] TFA Salt | ¹H NMR (600 MHz, Methanol-$d_4$) δ 8.83 (d, J = 5.9 Hz, 2H), 8.68 (d, J = 5.9 Hz, 2H), 8.51 (d, J = 2.9 Hz, 1H), 8.11 (d, J = 2.4 Hz, 1H), 7.90-7.82 (m, 1H), 7.71 (d, J = 8.2 Hz, 1H), 7.51 (d, J = 3.0 Hz, 1H), 7.44 (d, J = 8.2 Hz, 1H), 7.41-7.37 (m, 1H), 4.01 (d, J = 3.2 Hz, 3H), 3.74 (s, 2H), 2.86 (d, J = 2.8 Hz, 3H), 2.90-2.55 (m, 8H), 2.50 (d, J = 2.9 Hz, 3H). MS (ESI) m/z 617 [M + H]⁺. |
| I-n-4 | 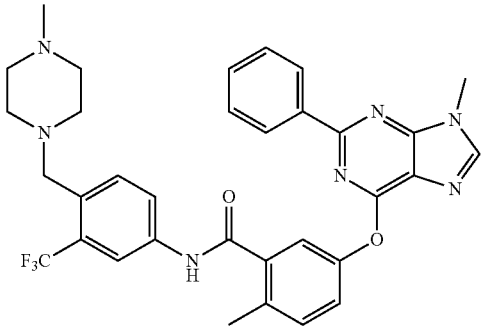 [SMILES: Cc1ccc(Oc2nc(-c3ccccc3)nc3c2ncn3C)cc1C(=O)Nc1ccc(CN2CCN(C)CC2)c(C(F)(F)F)c1] TFA Salt | MS (ESI) m/z 615 [M + H]⁺. |
| I-n-5 | 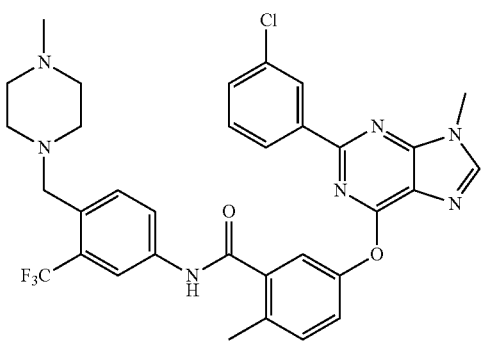 [SMILES: Cc1ccc(Oc2nc(-c3cccc(Cl)c3)nc3c2ncn3C)cc1C(=O)Nc1ccc(CN2CCN(C)CC2)c(C(F)(F)F)c1] TFA Salt | MS (ESI) m/z: 650 [M + H]⁺. |
| I-n-6 | 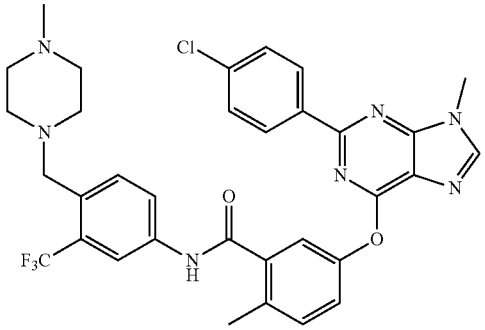 [SMILES: Cc1ccc(Oc2nc(-c3ccc(Cl)cc3)nc3c2ncn3C)cc1C(=O)Nc1ccc(CN2CCN(C)CC2)c(C(F)(F)F)c1] TFA Salt | MS (ESI) m/z 650 [M + H]⁺. |

TABLE 1-continued
Structure and characterization of compounds I
| No. | Structure | ¹H NMR and/or MS data |
|---|---|---|
| I-n-7 | 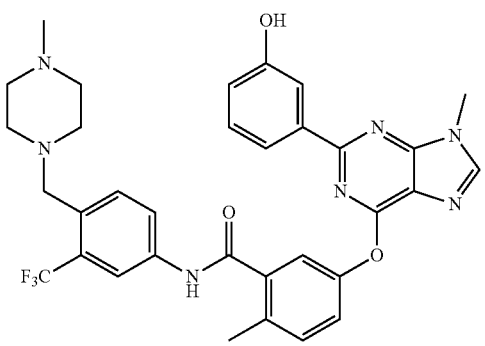 [SMILES: Cc1ccc(Oc2nc(-c3cccc(O)c3)nc3c2ncn3C)cc1C(=O)Nc1ccc(CN2CCN(C)CC2)c(C(F)(F)F)c1] TFA Salt | MS (ESI) m/z 631.25 [M + H]⁺. |
| I-n-8 | 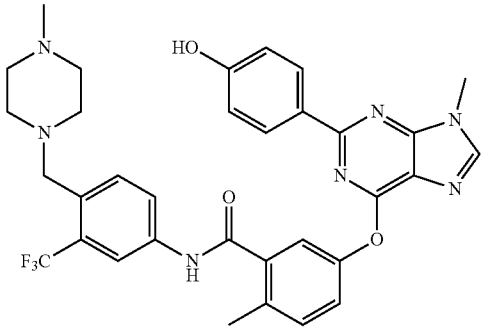 TFA Salt | MS (ESI) m/z 631 [M + H]⁺. |
| I-n-9 | 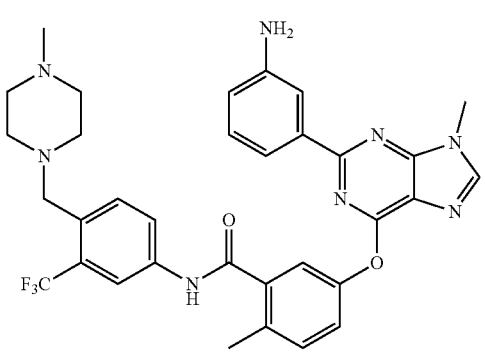 [SMILES: Cc1ccc(Oc2nc(-c3cccc(N)c3)nc3c2ncn3C)cc1C(=O)Nc1ccc(CN2CCN(C)CC2)c(C(F)(F)F)c1] | MS (ESI) m/z 630 [M + H]⁺. |
| I-n-10 | 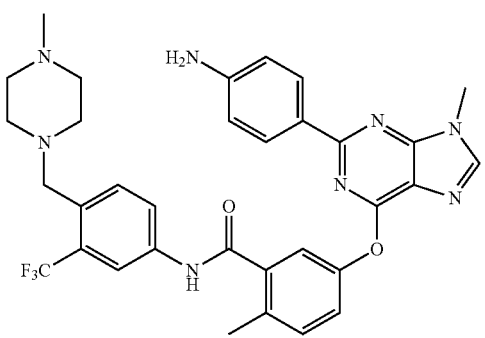 | MS (ESI) m/z 630 [M + H]⁺. |

TABLE 1-continued

Structure and characterization of compounds I

| No. | Structure | ¹H NMR and/or MS data |
|---|---|---|
| I-n-11 | TFA Salt | MS (ESI) m/z 605 [M + H]⁺. |
| I-n-12 | TFA Salt | MS (ESI) m/z 621 [M + H]⁺. |
| I-n-13 | TFA Salt | MS (ESI) m/z 539 [M + H]⁺. |
| I-n-14 | 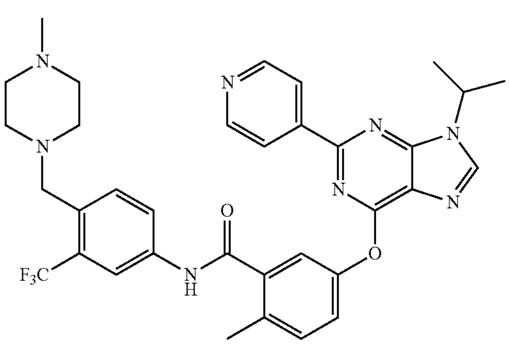 [SMILES: Cc1ccc(Oc2nc(-c3ccncc3)nc3c2ncn3C(C)C)cc1C(=O)Nc1ccc(CN2CCN(C)CC2)c(C(F)(F)F)c1] | ¹H NMR (600 MHz, Methanol-$d_4$) δ 8.62-8.58 (m, 2H), 8.58 (s, 1H), 8.26-8.18 (m, 2H), 8.11 (d, J = 2.2 Hz, 1H), 7.92-7.84 (m, 1H), 7.76 (d, J = 8.6 Hz, 1H), 7.56 (d, J = 2.5 Hz, 1H), 7.49 (d, J = 8.4 Hz, 1H), 7.45 (dd, J = 8.3, 2.5 Hz, 1H), 5.09 (p, J = 6.7 Hz, 1H), 3.65 (s, 2H), 2.67-2.45 (m, 11H), 2.31 (s, 3H), 1.75 (d, J = 6.8 Hz, 6H). MS (ESI) m/z 645 [M + H]⁺. |

TABLE 1-continued

Structure and characterization of compounds I

| No. | Structure | ¹H NMR and/or MS data |
|---|---|---|
| I-n-15 | 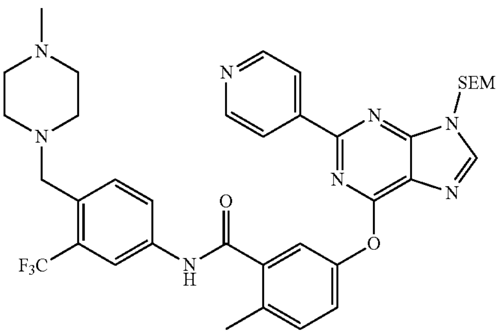 [SMILES: Cc1ccc(Oc2nc(-c3ccncc3)nc3c2ncn3COCC[Si](C)(C)C)cc1C(=O)Nc1ccc(CN2CCN(C)CC2)c(C(F)(F)F)c1] | MS (ESI) m/z 733 [M + H]⁺. |
| I-o-1 | 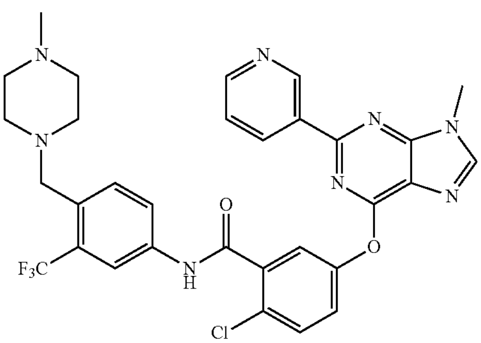 [SMILES: CN1CCN(Cc2ccc(NC(=O)c3cc(Oc4nc(-c5cccnc5)nc5c4ncn5C)ccc3Cl)cc2C(F)(F)F)CC1] | ¹H NMR (600 MHz, Methanol-d₄) δ 9.21 (d, J = 2.0 Hz, 1H), 8.51 (dd, J = 4.9, 1.7 Hz, 1H), 8.47 (dt, J = 8.1, 2.0 Hz, 1H), 8.33 (s, 1H), 8.09 (d, J = 2.2 Hz, 1H), 7.88 (dd, J = 8.7, 2.3 Hz, 1H), 7.73 (d, J = 8.5 Hz, 1H), 7.66-7.63 (m, 1H), 7.62 (s, 1H), 7.50 (dd, J = 8.7, 2.8 Hz, 1H), 7.41 (dd, J = 8.0, 4.8 Hz, 1H), 3.91 (s, 3H), 3.62 (s, 2H), 2.65-2.40 m, 8H), 2.30 (s, 3H). MS (ESI) m/z 638 [M + H]⁺. |
| I-o-2 | 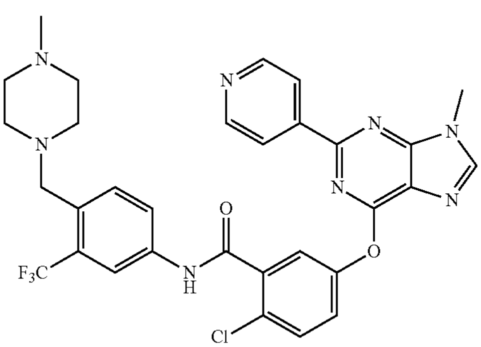 [SMILES: CN1CCN(Cc2ccc(NC(=O)c3cc(Oc4nc(-c5ccncc5)nc5c4ncn5C)ccc3Cl)cc2C(F)(F)F)CC1] | ¹H NMR (600 MHz, Methanol-d₄) δ 8.62-8.58 (m, 2H), 8.44 (s, 1H), 8.24-8.16 (m, 2H), 8.09 (d, J = 2.2 Hz, 1H), 7.88 (dd, J = 8.6, 2.2 Hz, 1H), 7.77 (d, J = 8.5 Hz, 1H), 7.70-7.69 (m, 2H), 7.55 (dd, J = 8.7, 2.8 Hz, 1H), 4.01 (s, 3H), 3.65 (s, 2H), 2.67-2.42 (m, 8H), 2.31 (s, 3H). MS (ESI) m/z: 638 [M + H]⁺. |
| I-o-3 | 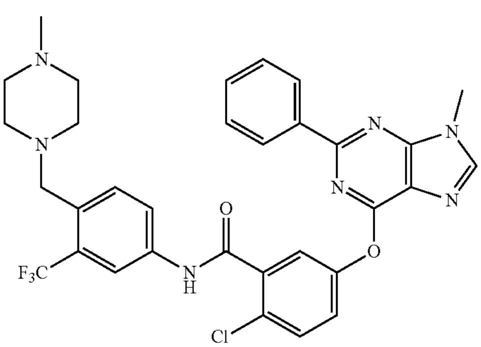 [SMILES: CN1CCN(Cc2ccc(NC(=O)c3cc(Oc4nc(-c5ccccc5)nc5c4ncn5C)ccc3Cl)cc2C(F)(F)F)CC1] | ¹H NMR (600 MHz, DMSO-d₆) δ 10.91 (s, 1H), 8.49 (s, 1H), 8.28-8.23 (m, 2H), 8.16 (d, J = 2.2 Hz, 1H), 7.92 (dd, J = 8.5, 2.1 Hz, 1H), 7.77-7.68 (m, 3H), 7.62 (dd, J = 8.8, 2.8 Hz, 1H), 7.49-7.41 (m, 3H), 3.92 (s, 3H), 3.55 (s, 2H), 2.15 (s, 3H). MS (ESI) m/z 637 [M + H]⁺. |

TABLE 1-continued
Structure and characterization of compounds I
| No. | Structure | ¹H NMR and/or MS data |
|---|---|---|
| I-o-4 | 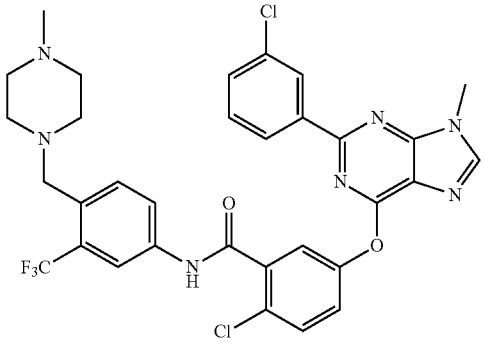 | MS (ESI) m/z 670 [M + H]⁺. |
| I-o-5 | 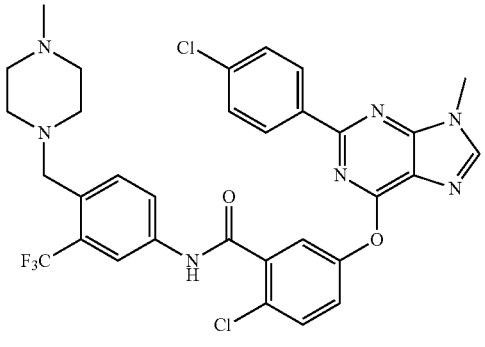 [SMILES: CN1CCN(Cc2ccc(NC(=O)c3cc(Oc4nc(-c5ccc(Cl)cc5)nc5c4ncn5C)ccc3Cl)cc2C(F)(F)F)CC1] | MS (ESI) m/z 670 [M + H]⁺. |
| I-o-6 | 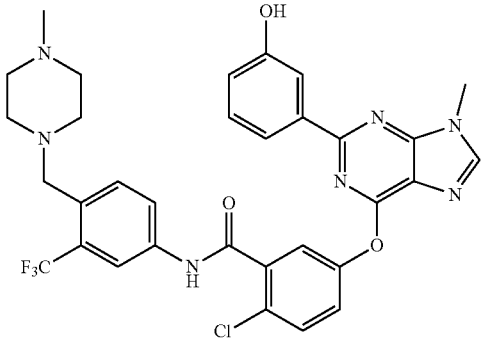 [SMILES: CN1CCN(Cc2ccc(NC(=O)c3cc(Oc4nc(-c5cccc(O)c5)nc5c4ncn5C)ccc3Cl)cc2C(F)(F)F)CC1] | MS (ESI) m/z 652 [M + H]⁺. |
| I-o-7 | 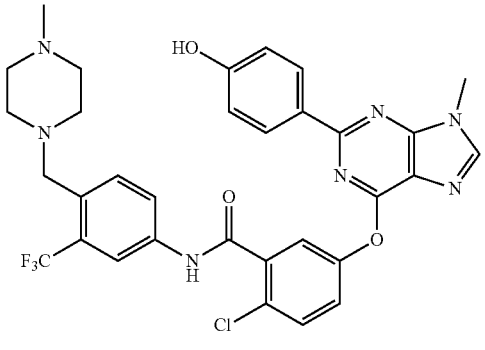 [SMILES: CN1CCN(Cc2ccc(NC(=O)c3cc(Oc4nc(-c5ccc(O)cc5)nc5c4ncn5C)ccc3Cl)cc2C(F)(F)F)CC1] | MS (ESI) m/z 652 [M + H]⁺. |

TABLE 1-continued

Structure and characterization of compounds I

| No. | Structure | ¹H NMR and/or MS data |
|---|---|---|
| I-o-8 | 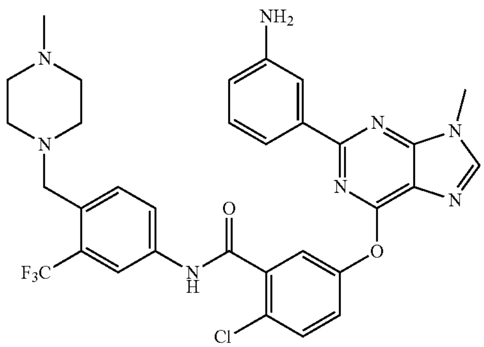 [SMILES: CN1CCN(Cc2ccc(NC(=O)c3cc(Oc4nc(-c5cccc(N)c5)nc5c4ncn5C)ccc3Cl)cc2C(F)(F)F)CC1] | MS (ESI) m/z 651 [M + H]⁺. |
| I-o-9 | 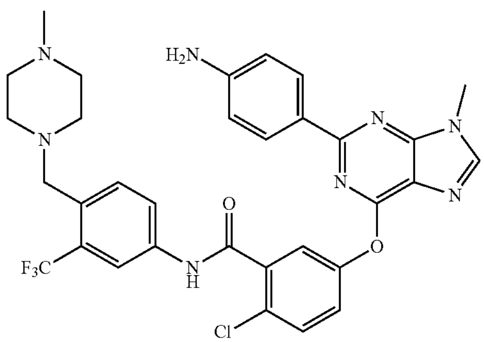 [SMILES: CN1CCN(Cc2ccc(NC(=O)c3cc(Oc4nc(-c5ccc(N)cc5)nc5c4ncn5C)ccc3Cl)cc2C(F)(F)F)CC1] | MS (ESI) m/z 651 [M + H]⁺. |
| I-o-10 | TFA Salt | MS (ESI) m/z 626 [M + H]⁺. |
| I-o-11 | TFA Salt | MS (ESI) m/z 642 [M + H]+ |

TABLE 1-continued

Structure and characterization of compounds I

| No. | Structure | $^1$H NMR and/or MS data |
|---|---|---|
| I-o-12 | 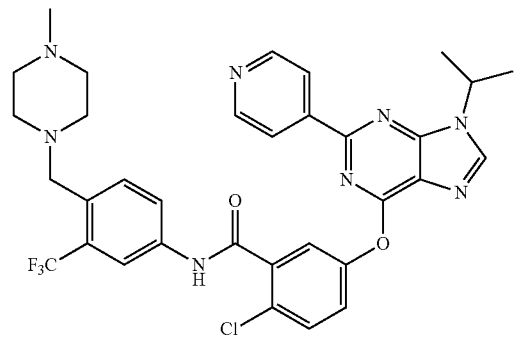 [SMILES: CC(C)n1cnc2c(Oc3ccc(Cl)c(C(=O)Nc4ccc(CN5CCN(C)CC5)c(C(F)(F)F)c4)c3)nc(-c3ccncc3)nc21] | $^1$H NMR (600 MHz, Methanol-d$_4$) δ 8.52 (t, J = 3.1 Hz, 3H), 8.14-8.09 (m, 2H), 8.03 (d, J = 2.2 Hz, 1H), 7.81 (dd, J = 8.5, 2.2 Hz, 1H), 7.68 (d, J = 8.5 Hz, 1H), 7.65-7.58 (m, 2H), 7.47 (dd, J = 8.8, 2.8 Hz, 1H), 5.02-4.93 (m, 1H), 3.56 (s, 2H), 2.52-2.29 (m, 8H), 2.21 (s, 3H), 1.66 (d, J = 6.8 Hz, 6H). MS (ESI) m/z: 666 [M + H]$^+$. |
| I-r-1 | 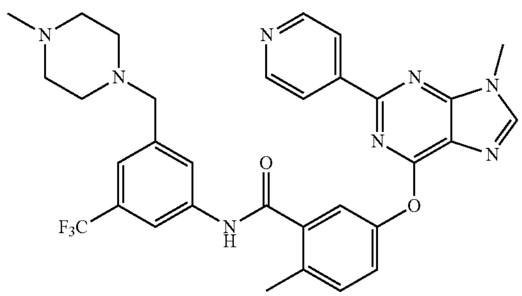 [SMILES: Cc1ccc(Oc2nc(-c3ccncc3)nc3c2ncn3C)cc1C(=O)Nc1cc(CN2CCN(C)CC2)cc(C(F)(F)F)c1] | $^1$H NMR (600 MHz, Methanol-d$_4$) δ 8.62-8.49 (m, 2H), 8.42 (s, 1H), 8.23-8.14 (m, 2H), 8.07 (s, 1H), 7.88 (s, 1H), 7.58 (d, J = 2.5 Hz, 1H), 7.48 (d, J = 8.4 Hz, 1H), 7.43 (dd, J = 8.4, 2.4 Hz, 2H), 4.00 (s, 3H), 3.60 (s, 2H), 2.65-2.40 (m, 8H), 2.56 (s, 3H), 2.29 (s, 3H). MS (ESI) m/z 617 [M + H]$^+$. |
| I-r-2 | 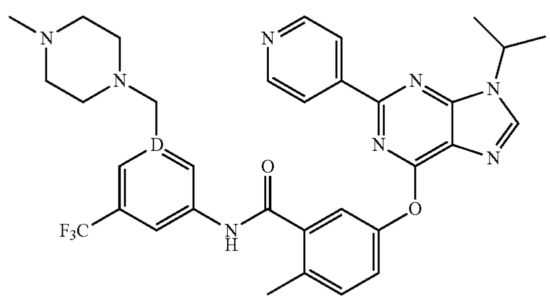 | MS (ESI) m/z 645 [M + H]$^+$. |
| I-r-3 | TFA salt | $^1$H NMR (600 MHz, DMSO-d$_6$) δ 10.74 (s, 1H), 9.48 (s, 1H), 9.27 (s, 1H), 8.66 (s, 1H), 8.59 (s, 1H), 8.48 (d, J = 7.9 Hz, 1H), 8.06 (s, 1H), 8.03 (s, 1H), 7.58 (s, 1H), 7.56-7.49 (m, 3H), 7.42 (s, 1H), 3.68 (s, 2H), 3.03 (s, 2H), 2.96 (d, J = 10.5 Hz, 2H), 2.78 (s, 3H), 2.49 (s, 3H). MS (ESI) m/z: 603 [M + H]$^+$. |

TABLE 1-continued

Structure and characterization of compounds I

| No. | Structure | ¹H NMR and/or MS data |
|---|---|---|
| I-s-1 | 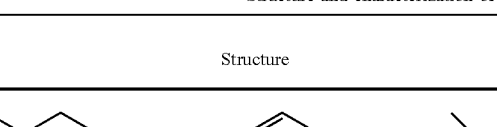 | MS (ESI) m/z 666 [M + H]⁺. |

TABLE 2

Structure and characterization of compounds II

| No. | Structure | 1H NMR and/or MS data |
|---|---|---|
| II-b-1 | 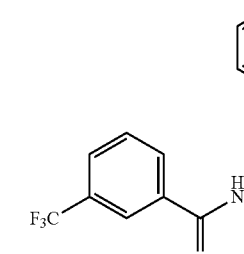 | ¹H NMR (600 MHz, Chloroform-d) δ 9.61 (s, 1H), 8.94-8.43 (m, 2H), 8.15 (s, 1H), 8.08 (s, 1H), 7.84-7.70 (m, 3H), 7.63-7.36 (m, 4H), 7.29 (d, J = 7.6 Hz, 1H), 4.15 (d, J = 2.8 Hz, 3H), 2.17 (d, J = 2.8 Hz, 3H). MS(ESI) m/z 505[M + H]⁺. |
| II-b-2 | 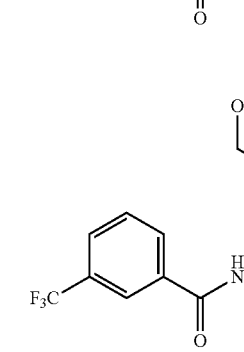 | ¹H NMR (600 MHz, Chloroform-d) δ 8.15-8.10 (m, 2H), 8.07-8.04 (m, 1H), 7.83-7.79 (m, 1H), 7.64 (d, J = 2.2 Hz, 1H), 7.62 (t, J = 7.8 Hz, 1H), 7.46 (dd, J = 8.2, 2.3 Hz, 1H), 7.35 (s, 1H), 7.28 (d, J = 2.8 Hz, 1H), 3.89 (s, 3H), 3.77-3.70 (m, 8H), 2.18 (s, 3H). MS(ESI) m/z 513[M + H]⁺. |
| II-b-3 | 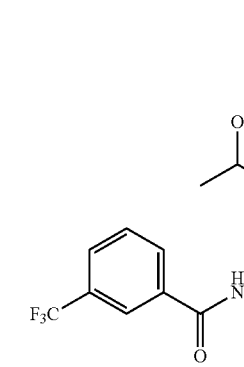 | MS(ESI) m/z 541[M + H]⁺. |

TABLE 2-continued

Structure and characterization of compounds II

| No. | Structure | 1H NMR and/or MS data |
|---|---|---|
| II-e-1 | 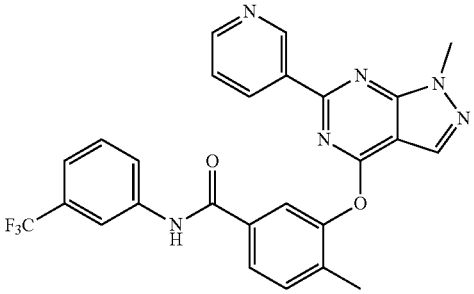 [SMILES: Cc1ccc(C(=O)Nc2cccc(C(F)(F)F)c2)cc1Oc1nc(-c2cccnc2)nc2c1cnn2C] | ¹H NMR (600 MHz, Chloroform-d) δ 9.42 (s, 1H), 8.80-8.46 (m, 3H), 7.99 (s, 1H), 7.96 (s, 1H), 7.93 (s, 1H), 7.83 (d, J = 9.3 Hz, 2H), 7.46 (s, 2H), 7.39 (d, J = 7.2 Hz, 1H), 4.17 (s, 3H), 2.25 (s, 3H). MS(ESI) m/z 505[M + H]⁺. |
| II-e-2 | 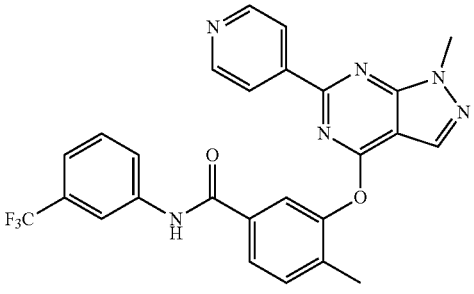 [SMILES: Cc1ccc(C(=O)Nc2cccc(C(F)(F)F)c2)cc1Oc1nc(-c2ccncc2)nc2c1cnn2C] | H NMR (600 MHz, Chloroform-d) δ 8.74 (s, 1H), 8.65 (s, 2H), 8.09 (d, J = 4.9 Hz, 2H), 7.97 (s, 1H), 7.96 (d, J = 1.8 Hz, 1H), 7.89 (ddd, J = 13.8, 8.4, 1.9 Hz, 2H), 7.84 (d, J = 1.7 Hz, 1H), 7.49 (d, J = 7.9 Hz, 2H), 7.45 (t, J = 8.0 Hz, 1H), 7.38 (dd, J = 7.8, 1.7 Hz, 1H), 4.20 (s, 3H), 2.26 (s, 3H). MS(ESI) m/z 505[M + H]⁺. |
| II-e-3 | 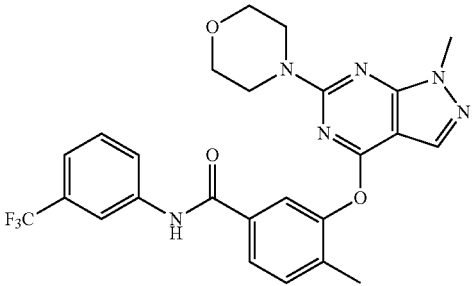 [SMILES: Cc1ccc(C(=O)Nc2cccc(C(F)(F)F)c2)cc1Oc1nc(N2CCOCC2)nc2c1cnn2C] | ¹H NMR (600 MHz, Chloroform-d) δ 8.17 (s, 1H), 7.95 (d, J = 1.9 Hz, 1H), 7.92-7.87 (m, 1H), 7.78 (dd, J = 7.9, 1.9 Hz, 1H), 7.74 (d, J = 1.9 Hz, 1H), 7.57 (s, 1H), 7.50 (t, J = 8.0 Hz, 1H), 7.43 (dd, J = 12.1, 7.8 Hz, 2H), 3.90 (s, 3H), 3.69 (s, 8H), 2.27 (s, 3H). MSI(ESI) m/z 513[M + H]⁺. |
| II-e-4 | 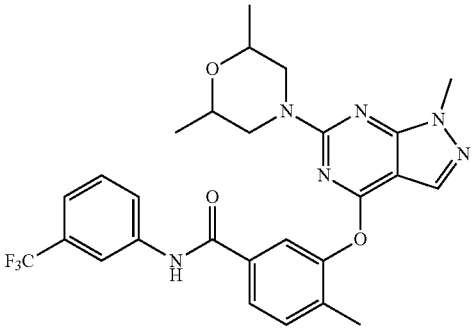 [SMILES: Cc1ccc(C(=O)Nc2cccc(C(F)(F)F)c2)cc1Oc1nc(N2CC(C)OC(C)C2)nc2c1cnn2C] | MS(ESI) m/z 541[M + H]⁺. |

TABLE 2-continued

Structure and characterization of compounds II

| No. | Structure | 1H NMR and/or MS data |
|---|---|---|
| II-h-1 | 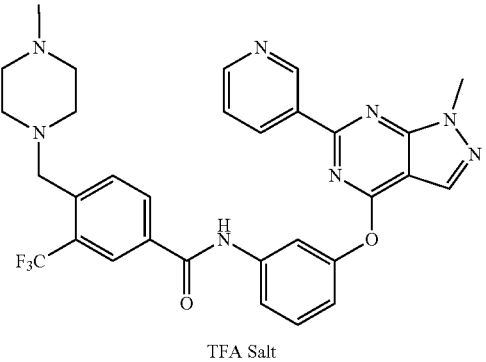 [SMILES: CN1CCN(Cc2ccc(C(=O)Nc3cccc(Oc4nc(-c5cccnc5)nc5c4cnn5C)c3)cc2C(F)(F)F)CC1] TFA Salt | ¹H NMR (600 MHz, Chloroform-d) δ 9.49 (d, J = 2.3 Hz, 1H), 8.77 (s, 1H), 8.63-8.56 (m, 2H), 8.14 (d, J = 1.8 Hz, 1H), 8.03 (dd, J = 8.2, 1.8 Hz, 1H), 7.91 (d, J = 8.2 Hz, 1H), 7.89 (t, J = 2.2 Hz, 1H), 7.87 (s, 1H), 7.55 (dd, J = 7.6, 1.9 Hz, 1H), 7.46 (t, J = 8.1 Hz, 1H), 7.36-7.30 (m, 1H), 7.18-7.09 (m, 1H), 4.15 (s, 3H), 3.68 (s, 2H), 2.50 (s, 8H), 2.30 (s, 3H). MS(ESI) m/z 603[M + H]⁺. |
| II-h-2 | 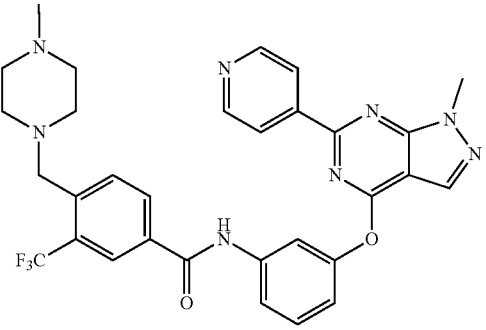 [SMILES: CN1CCN(Cc2ccc(C(=O)Nc3cccc(Oc4nc(-c5ccncc5)nc5c4cnn5C)c3)cc2C(F)(F)F)CC1] | ¹H NMR (600 MHz, Chloroform-d) δ 8.80 (s, 1H), 8.68-8.62 (m, 2H), 8.22-8.17 (m, 2H), 8.14 (d, J = 1.8 Hz, 1H), 8.04 (dd, J = 8.2, 1.8 Hz, 1H), 7.92 (d, J = 8.2 Hz, 1H), 7.90 (t, J = 2.2 Hz, 1H), 7.88 (s, 1H), 7.61-7.55 (m, 1H), 7.49 (t, J = 8.1 Hz, 1H), 7.13 (dd, J = 7.9, 2.3 Hz, 1H), 4.19 (s, 3H), 3.69 (s, 2H), 2.31 (s, 3H). MS(ESI) m/z 603[M + H]⁺. |
| II-h-3 | 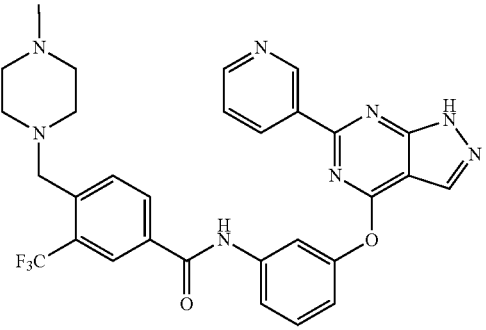 TFA salt | ¹H NMR (600 MHz, DMSO-d₆) δ 10.72 (s, 1H), 9.81 (s, 1H), 9.37-9.28 (m, 1H), 8.73-8.63 (m, 1H), 8.53 (dt, J = 8.0, 1.9 Hz, 1H), 8.30 (d, J = 1.7 Hz, 1H), 8.26 (dd, J = 8.2, 1.8 Hz, 1H), 8.12 (s, 1H), 7.96 (t, J = 2.2 Hz, 1H), 7.93 (d, J = 8.2 Hz, 1H), 7.77 (dd, J = 8.1, 1.9 Hz, 1H), 7.58 (t, J = 8.2 Hz, 1H), 7.54 (dd, J = 8.0, 4.7 Hz, 1H), 7.25 (dd, J = 8.0, 2.3 Hz, 1H), 3.79 (s, 2H), 3.41 (d, J = 12.2 Hz, 2H), 3.07 (s, 2H), 2.92 (d, J = 12.6 Hz, 2H), 2.81 (s, 3H), 2.42 (t, J = 12.2 Hz, 2H). MS(ESI) m/z: 589[M + H]⁺. |
| II-h-4 | 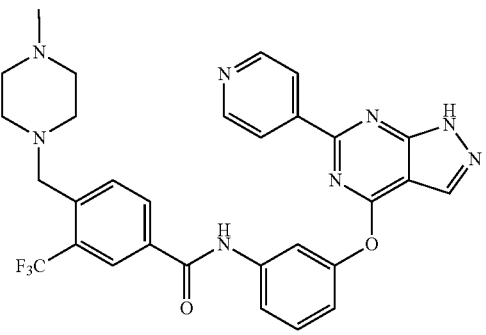 TFA salt | ¹H NMR (600 MHz, DMSO-d₆) δ 10.73 (s, 1H), 9.79 (s, 1H), 8.75 (d, J = 5.2 Hz, 2H), 8.30 (d, J = 1.8 Hz, 1H), 8.27 (dd, J = 8.1, 1.8 Hz, 1H), 8.17-8.09 (m, 2H), 7.96 (t, J = 2.2 Hz, 1H), 7.93 (d, J = 8.1 Hz, 1H), 7.77 (dd, J = 8.4, 1.9 Hz, 1H), 7.58 (t, J = 8.2 Hz, 1H), 7.25 (dd, J = 7.8, 2.2 Hz, 1H), 3.79 (s, 2H), 3.44-3.38 (m, 2H), 3.07 (s, 2H), 2.92 (d, J = 12.7 Hz, 2H), 2.81 (s, 3H), 2.42 (t, J = 12.2 Hz, 2H). MS(ESI) m/z: 589[M + H]⁺. |

TABLE 2-continued

Structure and characterization of compounds II

| No. | Structure | 1H NMR and/or MS data |
| --- | --- | --- |
| II-i-1 | 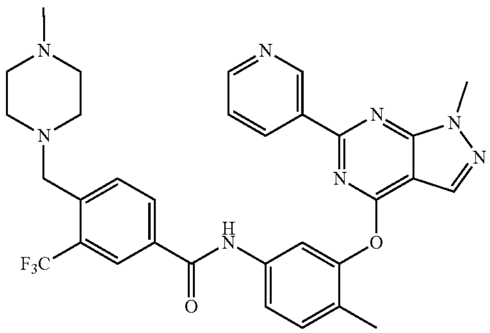 [SMILES: Cc1ccc(NC(=O)c2ccc(CN3CCN(C)CC3)c(C(F)(F)F)c2)cc1Oc1nc(-c2cccnc2)nc2c1cnn2C] | ¹H NMR (600 MHz, Chloroform-d) δ 9.42 (d, J = 2.1 Hz, 1H), 9.28 (s, 1H), 8.53 (ddd, J = 7.9, 4.4, 1.8 Hz, 2H), 8.13 (d, J = 1.8 Hz, 1H), 8.01 (dd, J = 8.2, 1.8 Hz, 1H), 7.83 (d, J = 8.2 Hz, 1H), 7.75 (d, J = 2.2 Hz, 1H), 7.69 (s, 1H), 7.47 (dd, J = 8.3, 2.2 Hz, 1H), 7.27 (dt, J = 8.0, 3.5 Hz, 1H), 7.23 (d, J = 8.3 Hz, 1H), 4.10 (s, 3H), 3.62 (s, 2H), 2.45 (s, 8H), 2.25 (s, 3H), 2.12 (s, 3H). MS(ESI) m/z 617[M + H]⁺. |
| II-i-2 | TFA Salt | ¹H NMR (600 MHz, Chloroform-d) δ 9.01 (s, 1H), 8.64-8.59 (m, 2H), 8.19-8.14 (m, 2H), 8.11 (d, J = 1.9 Hz, 1H), 8.01 (dd, J = 8.1, 1.9 Hz, 1H), 7.88 (d, J = 8.2 Hz, 1H), 7.78 (d, J = 2.2 Hz, 1H), 7.74 (s, 1H), 7.51 (dd, J = 8.4, 2.2 Hz, 1H), 7.30 (d, J = 8.3 Hz, 1H), 4.17 (s, 3H), 3.65 (s, 2H), 2.48 (s, 8H), 2.27 (s, 3H), 2.16 (s, 3H). MS(ESI) m/z 617[M + H]⁺. |
| II-i-3 | 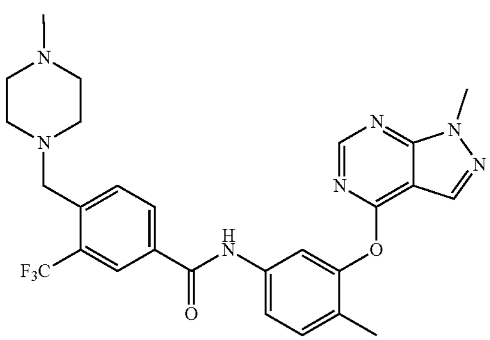 [SMILES: Cc1ccc(NC(=O)c2ccc(CN3CCN(C)CC3)c(C(F)(F)F)c2)cc1Oc1ncnc2c1cnn2C] | ¹H NMR (600 MHz, Chloroform-d₆) δ 10.54 (s, 1H), 8.56 (s, 1H), 8.23 (d, J = 1.8 Hz, 1H), 8.21 (d, J = 8.1 Hz, 1H), 8.13 (s, 1H), 7.92 (d, J = 8.2 Hz, 1H), 7.74 (d, J = 2.1 Hz, 1H), 7.63 (dd, J = 8.3, 2.2 Hz, 1H), 7.38 (d, J = 8.4 Hz, 1H), 4.06 (s, 3H), 3.67 (s, 2H), 2.42 (s, 8H), 2.17 (s, 3H), 2.07 (s, 3H). MS(ESI) m/z 540[M + H]⁺ |
| II-j-1 | 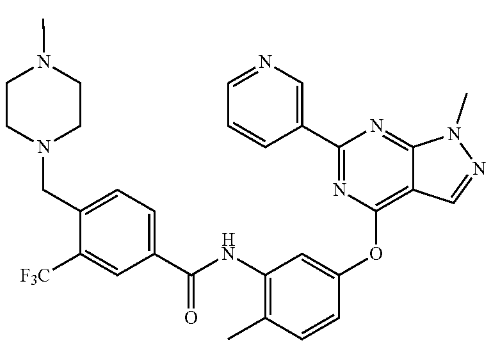 [SMILES: Cc1ccc(Oc2nc(-c3cccnc3)nc3c2cnn3C)cc1NC(=O)c1ccc(CN2CCN(C)CC2)c(C(F)(F)F)c1] | ¹H NMR (600 MHz, Chloroform-d) δ 9.45 (d, J = 2.2 Hz, 1H), 8.60 (dd, J = 13.0, 6.4 Hz, 2H), 8.33 (s, 1H), 8.19 (s, 1H), 8.05 (d, J = 8.1 Hz, 1H), 7.97 (dd, J = 11.0, 5.3 Hz, 2H), 7.85 (s, 1H), 7.35-7.27 (m, 2H), 7.07 (dd, J = 8.2, 2.5 Hz, 1H), 4.14 (s, 3H), 3.71 (s, 2H), 2.41 (s, 3H), 2.30 (s, 3H). MS(ESI) m/z [M + H]⁺. |

TABLE 2-continued

Structure and characterization of compounds II

| No. | Structure | 1H NMR and/or MS data |
|---|---|---|
| II-j-2 | 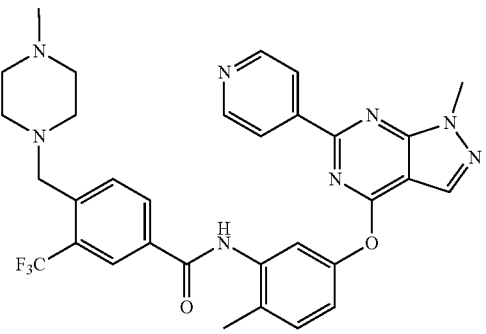 [SMILES: Cc1ccc(Oc2nc(-c3ccncc3)nc3c2cnn3C)cc1NC(=O)c1ccc(CN2CCN(C)CC2)c(C(F)(F)F)c1] | ¹H NMR (600 MHz, Chloroform-d) δ 8.64 (d, J = 5.0 Hz, 2H), 8.37 (s, 1H), 8.20 (d, J = 5.0 Hz, 2H), 8.16 (s, 1H), 8.04 (d, J = 8.2 Hz, 1H), 8.00 (s, 1H), 7.96 (d, J = 8.2 Hz, 1H), 7.84 (s, 1H), 7.34 (d, J = 8.2 Hz, 1H), 7.11 (dd, J = 8.3, 2.3 Hz, 1H), 4.15 (s, 3H), 3.70 (s, 2H), 2.57-2.47 (m, 8H), 2.42 (s, 3H), 2.29 (s, 3H). MS(ESI) m/z 617[M + H]⁺. |
| II-j-3 | 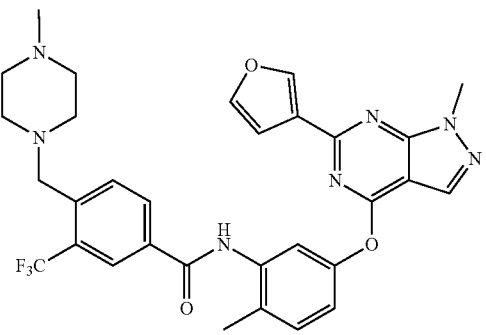<br>TFA Salt | MS(ESI) m/z 606[M + H]⁺. |
| II-j-4 | 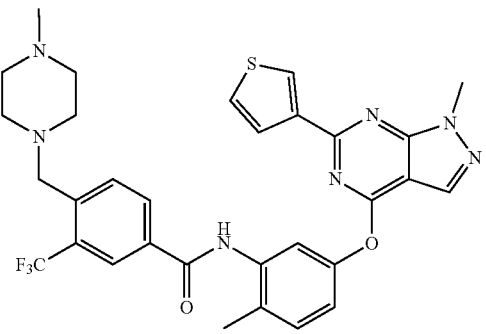 | ¹H NMR (600 MHz, DMSO-d₆) δ 10.25 (s, 1H), 8.35-8.28 (m, 2H), 8.27-8.21 (m, 1H), 7.93 (d, J = 8.1 Hz, 1H), 7.89 (s, 1H), 7.75 (d, J = 5.1 Hz, 1H), 7.63 (dd, J = 5.1, 3.0 Hz, 1H), 7.49 (d, J = 2.5 Hz, 1H), 7.45 (d, J = 8.4 Hz, 1H), 7.27 (dd, J = 8.3, 2.5 Hz, 1H), 4.07 (s, 3H), 3.69 (s, 2H), 2.46 (s, 8H), 2.33 (s, 3H). MS(ESI) m/z 622[M + H]⁺. |
| II-j-5 | 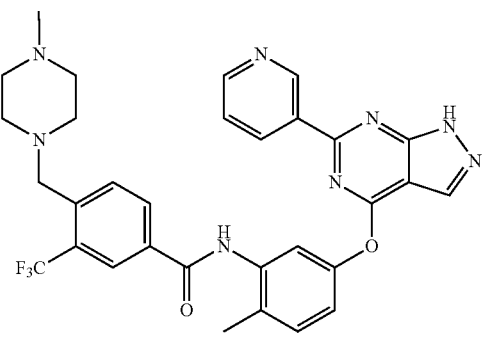<br>TFA salt | ¹H NMR (600 MHz, DMSO-d₆) δ 10.31 (s, 1H), 9.88 (s, 1H), 9.41 (d, J = 2.2 Hz, 1H), 8.78 (dd, J = 5.1, 1.6 Hz, 1H), 8.74 (dt, J = 8.2, 1.9 Hz, 1H), 8.34 (d, J = 1.8 Hz, 1H), 8.29 (dd, J = 8.1, 1.8 Hz, 1H), 8.06 (s, 1H), 7.93 (d, J = 8.2 Hz, 1H), 7.70 (dd, J = 8.1, 5.0 Hz, 1H), 7.51 (d, J = 2.5 Hz, 1H), 7.48 (d, J = 8.4 Hz, 1H), 7.31 (dd, J = 8.3, 2.5 Hz, 1H), 3.80 (s, 2H), 3.43 (dd, J = 11.9, 9.0 Hz, 2H), 3.11-3.02 (m, 2H), 2.94 (d, J = 12.5 Hz, 2H), 2.82 (s, 3H), 2.44 (t, J = 12.2 Hz, 2H), 2.35 (s, 3H). MS(ESI) m/z: 603[M + H]⁺. |

TABLE 2-continued

Structure and characterization of compounds II

| No. | Structure | 1H NMR and/or MS data |
|---|---|---|
| II-j-6 | 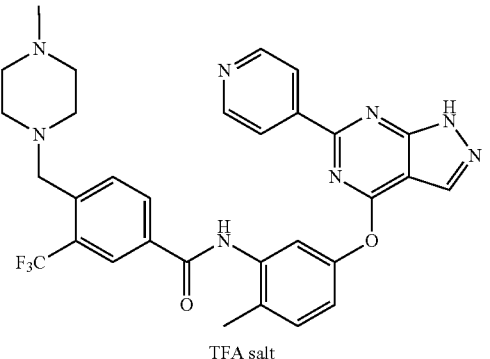 [SMILES: Cc1ccc(Oc2nc(-c3ccncc3)nc3[nH]ncc23)cc1NC(=O)c1ccc(CN2CCN(C)CC2)c(C(F)(F)F)c1] TFA salt | $^1$H NMR (600 MHz, DMSO-d$_6$) δ 10.31 (s, 1H), 9.68 (s, 1H), 8.84-8.75 (m, 2H), 8.34 (d, J = 1.8 Hz, 1H), 8.29 (dd, J = 8.1, 1.8 Hz, 1H), 8.26-8.19 (m, 2H), 8.08 (s, 1H), 7.93 (d, J = 8.2 Hz, 1H), 7.52 (d, J = 2.5 Hz, 1H), 7.49 (d, J = 8.4 Hz, 1H), 7.32 (dd, J = 8.3, 2.6 Hz, 1H), 3.79 (s, 2H), 3.45-3.38 (m, 2H), 3.07 (s, 2H), 2.93 (d, J = 12.2 Hz, 2H), 2.82 (s, 3H), 2.45-2.37 (m, 2H), 2.35 (s, 3H). MS(ESI) m/z: 603[M + H]$^+$. |
| II-k-1 | 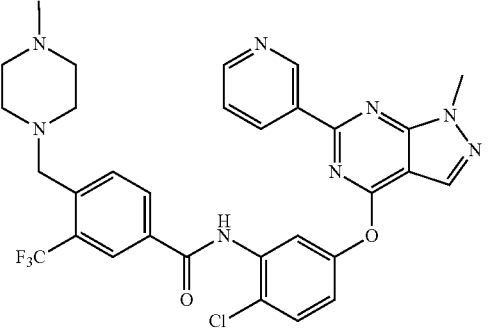 [SMILES: CN1CCN(Cc2ccc(C(=O)Nc3cc(Oc4nc(-c5cccnc5)nc5c4cnn5C)ccc3Cl)cc2C(F)(F)F)CC1] | $^1$H NMR (600 MHz, Chloroform-d) δ 9.51 (d, J = 2.1 Hz, 1H), 8.70-8.61 (m, 3H), 8.57 (s, 1H), 8.20 (d, J = 1.7 Hz, 1H), 8.08-8.00 (m, 3H), 7.56 (d, J = 8.6 Hz, 1H), 7.36 (ddd, J = 7.2, 4.3, 0.9 Hz, 1H), 7.14 (dd, J = 8.7, 2.8 Hz, 1H), 4.20 (s, 3H), 3.75 (s, 2H), 2.57 (s, 8H), 2.34 (s, 3H). MS(ESI) m/z: 638[M + H]$^+$. |
| II-k-2 | 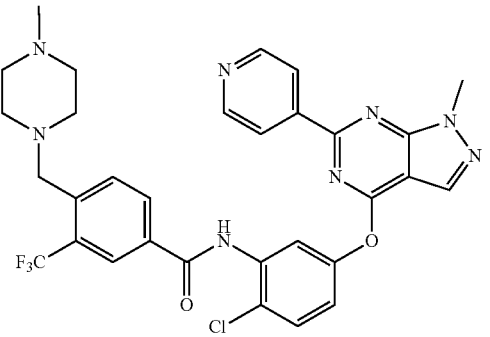 [SMILES: CN1CCN(Cc2ccc(C(=O)Nc3cc(Oc4nc(-c5ccncc5)nc5c4cnn5C)ccc3Cl)cc2C(F)(F)F)CC1] | $^1$H NMR (600 MHz, Chloroform-d) δ 8.77-8.67 (m, 3H), 8.57 (s, 1H), 8.24-8.21 (m, 2H), 8.20 (d, J = 1.7 Hz, 1H), 8.08-8.01 (m, 3H), 7.59 (d, J = 8.7 Hz, 1H), 7.16 (dd, J = 8.7, 2.8 Hz, 1H), 4.23 (s, 3H), 3.76 (s, 2H), 2.59 (s, 8H), 2.35 (s, 3H). MS(ESI) m/z: 638[M + H]$^+$. |
| II-k-3 | 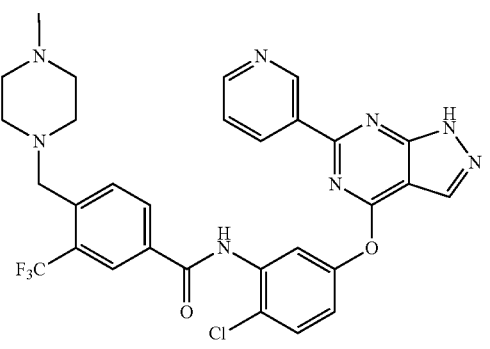 TFA salt | $^1$H NMR (600 MHz, DMSO-d$_6$) δ 10.55 (s, 1H), 9.77 (s, 1H), 9.39 (d, J = 2.3 Hz, 1H), 8.78 (dd, J = 5.0, 1.7 Hz, 1H), 8.71 (dt, J = 8.1, 1.9 Hz, 1H), 8.35 (d, J = 1.9 Hz, 1H), 8.30 (d, J = 9.3 Hz, 2H), 7.95 (d, J = 8.2 Hz, 1H), 7.78 (d, J = 5.9 Hz, 1H), 7.77 (s, 1H), 7.70 (dd, J = 8.1, 5.0 Hz, 1H), 7.48 (dd, J = 8.8, 2.8 Hz, 1H), 3.80 (s, 2H), 3.45-3.38 (m, 2H), 3.07 (t, J = 11.9 Hz, 2H), 2.94 (d, J = 12.6 Hz, 2H), 2.82 (s, 3H), 2.43 (t, J = 12.3 Hz, 2H). MS(ESI) m/z: 624[M + H]$^+$. |

TABLE 2-continued

Structure and characterization of compounds II

| No. | Structure | 1H NMR and/or MS data |
|---|---|---|
| II-k-4 | 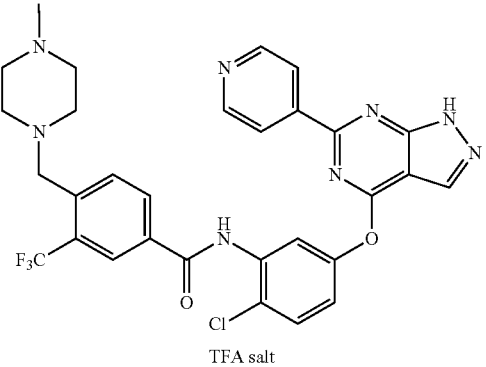 [SMILES: CN1CCN(Cc2ccc(C(=O)Nc3cc(Oc4nc(-c5ccncc5)nc5[nH]ncc45)ccc3Cl)cc2C(F)(F)F)CC1] TFA salt | ¹H NMR (600 MHz, DMSO-d₆) δ 10.57 (s, 1H), 9.84 (s, 1H), 8.91-8.83 (m, 2H), 8.36 (dd, J = 6.5, 1.8 Hz, 3H), 8.34 (s, 1H), 8.31 (dd, J = 8.1, 1.8 Hz, 1H), 7.95 (d, J = 8.3 Hz, 1H), 7.80-7.76 (m, 2H), 7.49 (dd, J = 8.8, 2.8 Hz, 1H), 3.80 (s, 2H), 3.42 (d, J = 12.0 Hz, 2H), 3.13-3.03 (m, 2H), 2.94 (d, J = 12.5 Hz, 2H), 2.82 (s, 3H), 2.44 (t, J = 12.3 Hz, 2H). MS(ESI) m/z: 624[M + H]⁺. |
| II-l-1 | 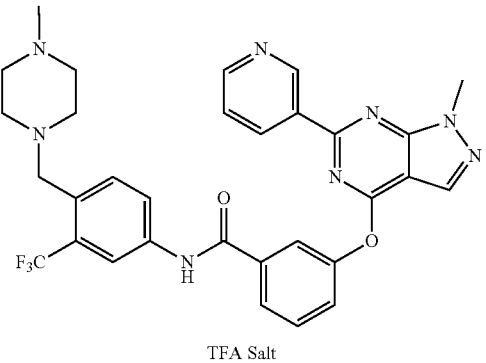 [SMILES: CN1CCN(Cc2ccc(NC(=O)c3cccc(Oc4nc(-c5cccnc5)nc5c4cnn5C)c3)cc2C(F)(F)F)CC1] TFA Salt | MS(ESI) m/z 603[M + H]⁺. |
| II-l-2 | 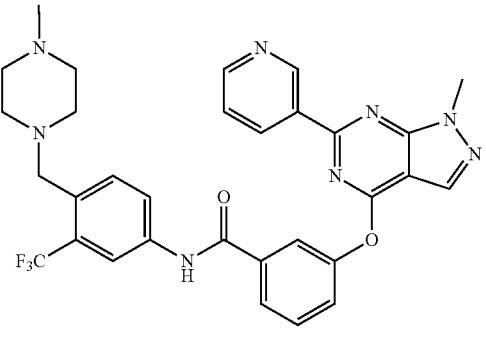 [SMILES: CN1CCN(Cc2ccc(NC(=O)c3cccc(Oc4nc(-c5cccnc5)nc5c4cnn5C)c3)cc2C(F)(F)F)CC1] | MS(ESI) m/z 603[M + H]⁺. |
| II-m-1 | 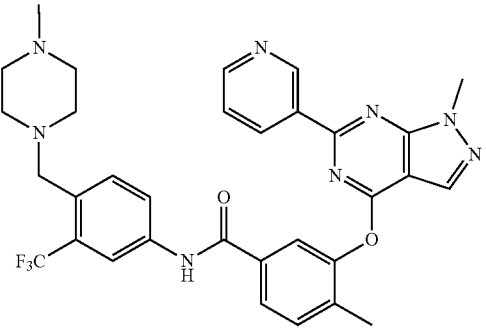 [SMILES: Cc1ccc(C(=O)Nc2ccc(CN3CCN(C)CC3)c(C(F)(F)F)c2)cc1Oc1nc(-c2cccnc2)nc2c1cnn2C] | ¹H NMR (600 MHz, Chloroform-d) δ 9.37 (d, J = 2.1 Hz, 1H), 8.95 (s, 1H), 8.56 (dd, J = 4.8, 1.7 Hz, 1H), 8.43 (dt, J = 8.0, 2.0 Hz, 1H), 7.91 (dd, J = 8.6, 2.2 Hz, 1H), 7.88 (s, 2H), 7.84 (d, J = 8.5 Hz, 2H), 7.71 (d, J = 8.5 Hz, 1H), 7.42 (d, J = 7.8 Hz, 1H), 7.25 (dd, J = 8.0, 4.8 Hz, 1H), 4.12 (s, 3H), 3.61 (s, 2H), 2.51 (s, 8H), 2.31 (s, 3H), 2.23 (s, 3H). MS(ESI) m/z 617[M + H]⁺. |

TABLE 2-continued

Structure and characterization of compounds II

| No. | Structure | 1H NMR and/or MS data |
|---|---|---|
| II-m-2 | 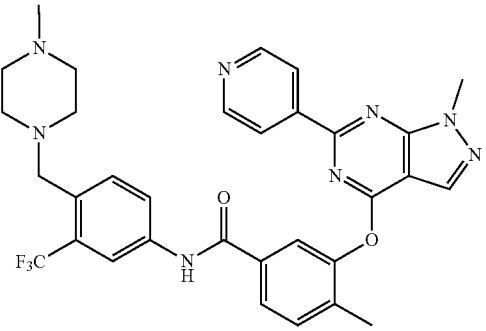 | ¹H NMR (600 MHz, Chloroform-d) δ 8.67 (d, J = 6.8 Hz, 1H), 8.64-8.60 (m, 2H), 8.07-8.02 (m, 2H), 7.95 (s, 1H), 7.91 (dd, J = 8.5, 2.3 Hz, 1H), 7.87 (dt, J = 4.4, 2.2 Hz, 2H), 7.83 (d, J = 1.7 Hz, 1H), 7.71 (d, J = 8.5 Hz, 1H), 7.49 (d, J = 8.0 Hz, 1H), 4.20 (s, 3H), 3.63 (s, 2H), 2.57 (s, 8H), 2.37 (s, 3H), 2.26 (s, 3H). MS(ESI) m/z 617[M + H]⁺. |
| II-m-3 | 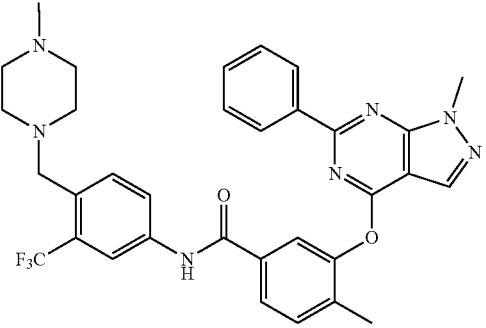 [SMILES: Cc1ccc(C(=O)Nc2ccc(CN3CCN(C)CC3)c(C(F)(F)F)c2)cc1Oc1nc(-c2ccncc2)nc2c1cnn2C]<br>TFA Salt | ¹H NMR (600 MHz, DMSO-d₆) δ 10.56 (s, 1H), 8.22-8.19 (m, 3H), 8.13 (s, 1H), 8.10 (dd, J = 8.6, 2.1 Hz, 1H), 8.01 (d, J = 1.6 Hz, 1H), 8.01-7.97 (m, 1H), 7.70 (d, J = 8.6 Hz, 1H), 7.65 (d, J = 7.9 Hz, 1H), 7.48 (d, J = 7.0 Hz, 1H), 7.45 (t, J = 7.4 Hz, 2H), 4.13 (s, 3H), 3.71 (s, 2H), 2.81 (s, 3H), 2.24 (s, 3H). MS(ESI) m/z 616[M + H]⁺. |
| II-m-4 | 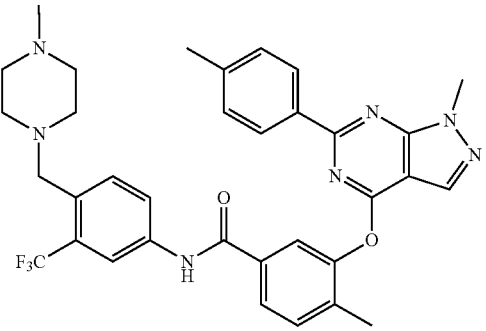<br>TFA Salt | ¹H NMR (600 MHz, DMSO-d₆) δ 10.55 (s, 1H), 8.21 (d, J = 2.1 Hz, 1H), 8.13-8.08 (m, 4H), 8.01 (d, J = 1.7 Hz, 1H), 7.99 (dd, J = 7.9, 1.8 Hz, 1H), 7.71 (d, J = 8.6 Hz, 1H), 7.64 (d, J = 7.9 Hz, 1H), 7.25 (d, J = 8.0 Hz, 1H), 4.11 (s, 3H), 3.71 (s, 2H), 3.41 (s, 2H), 3.06 (s, 2H), 2.95 (s, 2H), 2.81 (s, 3H), 2.44 (s, 2H), 2.33 (s, 3H), 2.24 (s, 3H). MS(ESI) m/z 630[M + H]⁺. |
| II-m-5 | 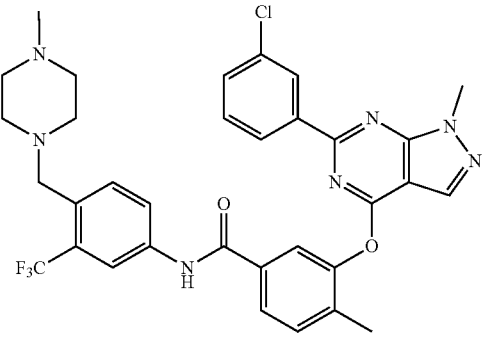<br>TFA Salt | ¹H NMR (600 MHz, DMSO-d₆) δ 10.56 (s, 1H), 8.20 (d, J = 2.2 Hz, 1H), 8.19 (t, J = 1.9 Hz, 1H), 8.15-8.12 (m, 2H), 8.09 (dd, J = 8.6, 2.2 Hz, 1H), 8.04 (d, J = 1.7 Hz, 1H), 8.00 (dd, J = 7.9, 1.8 Hz, 1H), 7.70 (d, J = 8.6 Hz, 1H), 7.65 (d, J = 8.0 Hz, 1H), 7.56 (ddd, J = 8.0, 2.3, 1.1 Hz, 1H), 7.49 (t, J = 7.9 Hz, 1H), 4.13 (s, 3H), 3.69 (s, 2H), 3.40 (s, 2H), 3.04 (s, 2H), 2.92 (s, 2H), 2.81 (s, 3H), 2.41 (s, 2H), 2.25 (s, 3H). MS(ESI) m/z 650[M + H]⁺. |

TABLE 2-continued

Structure and characterization of compounds II

| No. | Structure | 1H NMR and/or MS data |
|---|---|---|
| II-m-6 | 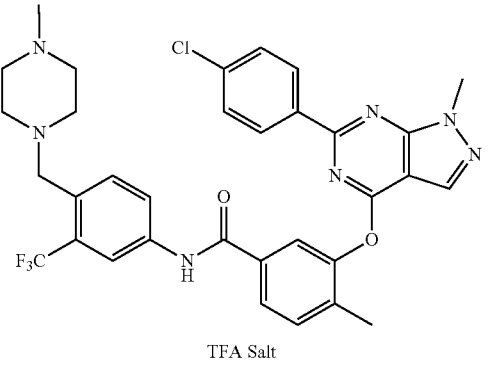 [SMILES: Cc1ccc(C(=O)Nc2ccc(CN3CCN(C)CC3)c(C(F)(F)F)c2)cc1Oc1nc(-c2ccc(Cl)cc2)nc2c1cnn2C]<br>TFA Salt | ¹H NMR (600 MHz, DMSO-d₆) δ 10.55 (s, 1H), 8.19 (d, J = 8.0 Hz, 3H), 8.11 (s, 1H), 8.10-8.07 (m, 1H), 8.02-7.97 (m, 2H), 7.70 (d, J = 8.6 Hz, 1H), 7.64 (d, J = 8.0 Hz, 1H), 7.52 (d, J = 8.3 Hz, 2H), 4.12 (s, 3H), 3.70 (s, 2H), 3.40 (s, 2H), 3.05 (s, 2H), 2.93 (s, 2H), 2.81 (s, 3H), 2.42 (s, 2H), 2.24 (s, 3H). MS(ESI) m/z 650[M + H]⁺. |
| II-m-7 | 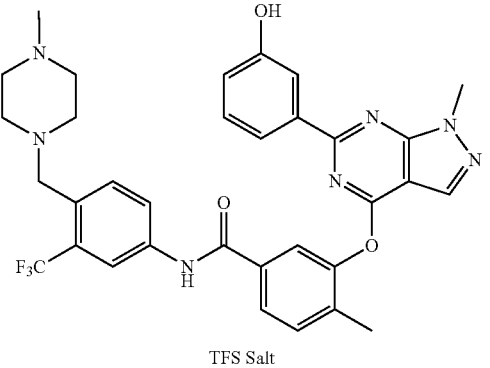 [SMILES: Cc1ccc(C(=O)Nc2ccc(CN3CCN(C)CC3)c(C(F)(F)F)c2)cc1Oc1nc(-c2cccc(O)c2)nc2c1cnn2C]<br>TFS Salt | ¹H NMR (600 MHz, DMSO-d₆) δ 10.54 (s, 1H), 8.20 (d, J = 2.1 Hz, 1H), 8.09 (d, J = 7.3 Hz, 2H), 8.04-7.97 (m, 2H), 7.70 (d, J = 8.6 Hz, 1H), 7.68-7.61 (m, 3H), 7.22 (t, J = 7.9 Hz, 1H), 6.88 (dd, J = 8.0, 2.4 Hz, 1H), 4.11 (s, 3H), 3.70 (s, 2H), 3.04 (s, 2H), 3.05 (s, 2H), 2.93 (s, 2H), 2.80 (s, 3H), 2.40 (d, J = 13.5 Hz, 2H), 2.24 (s, 3H). MS(ESI) m/z 632 [M + H]⁺. |
| II-m-8 | 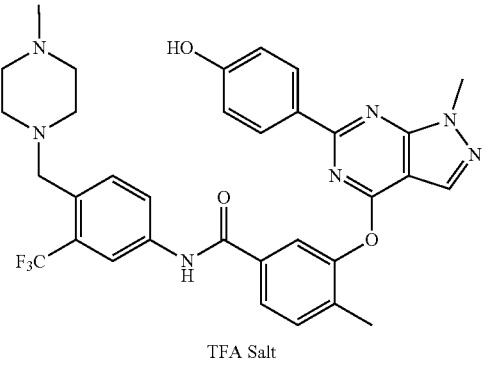 [SMILES: Cc1ccc(C(=O)Nc2ccc(CN3CCN(C)CC3)c(C(F)(F)F)c2)cc1Oc1nc(-c2ccc(O)cc2)nc2c1cnn2C]<br>TFA Salt | ¹H NMR (600 MHz, DMSO-d₆) δ 10.55 (s, 1H), 8.21 (d, J = 2.2 Hz, 1H), 8.10 (dd, J = 8.6, 2.2 Hz, 1H), 8.06 (d, J = 1.9 Hz, 1H), 8.05 (d, J = 2.8 Hz, 2H), 7.98 (d, J = 8.0 Hz, 2H), 7.71 (d, J = 8.6 Hz, 1H), 7.64 (d, J = 7.8 Hz, 1H), 6.94-6.71 (m, 2H), 4.08 (s, 3H), 3.70 (s, 2H), 3.41 (s, 2H), 3.05 (s, 2H), 2.93 (s, 2H), 2.81 (s, 3H), 2.42 (s, 2H), 2.23 (s, 3H). MS(ESI) m/z 632 [M + H]⁺. |
| II-m-9 | 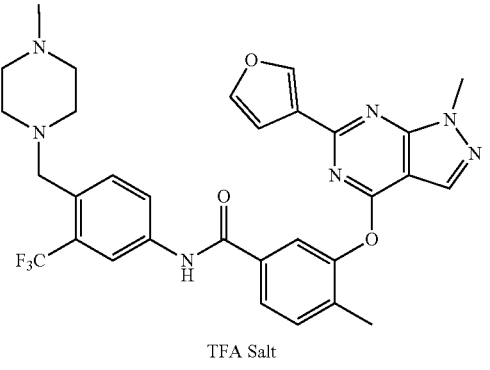 [SMILES: Cc1ccc(C(=O)Nc2ccc(CN3CCN(C)CC3)c(C(F)(F)F)c2)cc1Oc1nc(-c2ccoc2)nc2c1cnn2C]<br>TFA Salt | ¹H NMR (600 MHz, DMSO-d₆) δ 10.55 (s, 1H), 8.21 (d, J = 2.1 Hz, 1H), 8.15 (d, J = 1.4 Hz, 1H), 8.10 (dd, J = 8.6, 2.1 Hz, 1H), 8.00 (d, J = 1.7 Hz, 1H), 7.99-7.95 (m, 1H), 7.91 (s, 1H), 7.76 (t, J = 1.7 Hz, 1H), 7.71 (d, J = 8.5 Hz, 1H), 7.62 (d, J = 8.0 Hz, 1H), 6.88 (d, J = 1.6 Hz, 1H), 4.06 (s, 3H), 3.73 (s, 2H), 3.42 (s, 2H), 3.12-3.01 (m, 2H), 2.96 (s, 2H), 2.81 (s, 3H), 2.46 (s, 2H), 2.23 (s, 3H). MS(ESI) m/z 606 [M + H]⁺. |

TABLE 2-continued

Structure and characterization of compounds II

| No. | Structure | 1H NMR and/or MS data |
|---|---|---|
| II-m-10 | 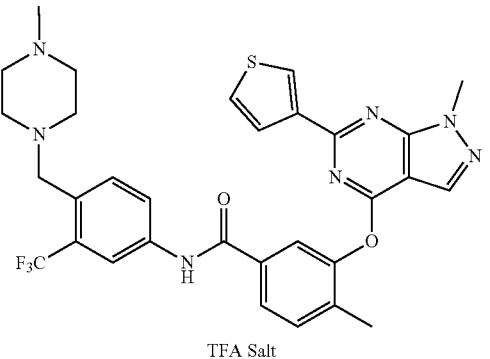 [SMILES: Cc1ccc(C(=O)Nc2ccc(CN3CCN(C)CC3)c(C(F)(F)F)c2)cc1Oc1nc(-c2ccsc2)nc2c1cnn2C] TFA Salt | $^1$H NMR (600 MHz, DMSO-d$_6$) δ 10.54 (s, 1H), 8.20 (d, J = 2.1 Hz, 1H), 8.13 (d, J = 2.9 Hz, 1H) 8.10 (dd, J = 8.6 2.1 Hz, 1H), 8.04 (s, 1H), 8.00 (d, J = 1.7 Hz, 1H), 7.99-7.96 (m, 1H), 7.71 (d, J = 8.6 Hz, 1H), 7.65-7.59 (m, 3H), 4.09 (s, 3H), 3.71 (s, 2H), 3.41 (s, 2H), 3.04 (d, J = 14.1 Hz, 2H), 2.94 (s, 2H), 2.81 (s, 3H), 2.42 (s, 2H), 2.24 (s, 3H). MS(ESI) m/z 622[M + H]$^+$. |
| II-m-11 | 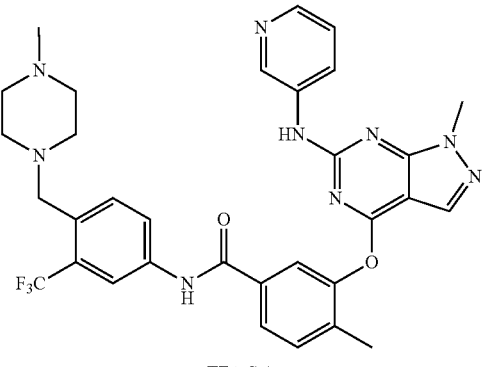 TFA Salt | $^1$H NMR (600 MHz, DMSO-d$_6$) δ 10.47 (s, 1H), 9.87 (s, 1H), 8.75 (s, 1H), 8.18 (d, J = 2.2 Hz, 1H), 8.09 (d, J = 4.6 Hz, 1H), 8.04 (dd, J = 8.5, 2.2 Hz, 1H), 7.96 (dd, J = 6.1, 2.0 Hz, 3H), 7.69 (d, J = 8.6 Hz, 1H), 7.60 (d, J = 8.5 Hz, 1H), 7.12 (d, J = 9.0 Hz, 1H), 3.93 (s, 3H), 3.55 (s, 2H), 2.37 (s, 8H), 2.22 (s, 3H), 2.16 (s, 3H). MS(ESI) m/z 632[M + H]$^+$. |
| II-m-12 | 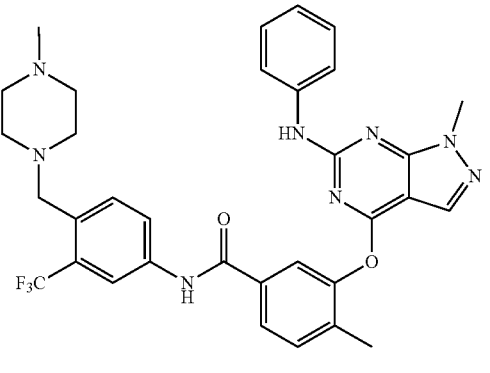 [SMILES: Cc1ccc(C(=O)Nc2ccc(CN3CCN(C)CC3)c(C(F)(F)F)c2)cc1Oc1nc(Nc2ccccc2)nc2c1cnn2C] | MS(ESI) m/z 631[M + H]$^+$. |
| II-m-13 | 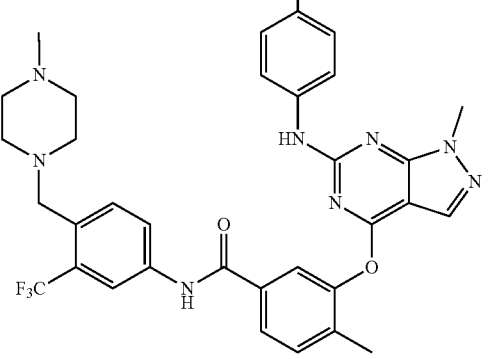 | $^1$H NMR (600 MHz, DMSO-d$_6$) δ 10.46 (s, 1H), 9.57 (s, 1H), 8.18 (d, J = 2.2 Hz, 1H), 8.04 (dd, J = 8.6, 2.2 Hz, 1H), 8.00-7.89 (m, 3H), 7.69 (d, J = 8.6 Hz, 1H), 7.59 (d, J = 7.9 Hz, 1H), 7.44 (s, 2H), 6.91 (s, 2H), 3.90 (s, 3H), 3.55 (s, 2H), 2.45-2.31 (m, 8H), 2.23 (s, 3H), 2.16 (s, 6H). MS(ESI) m/z 645[M + H]$^+$. |

TABLE 2-continued

Structure and characterization of compounds II

| No. | Structure | 1H NMR and/or MS data |
|---|---|---|
| II-m-14 | 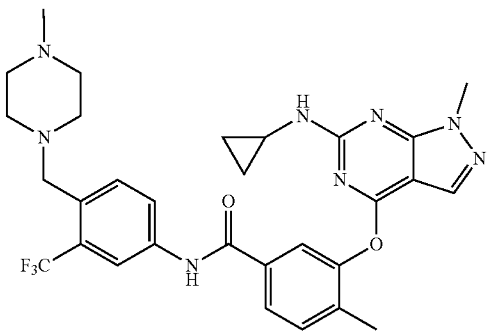 [SMILES: Cc1ccc(C(=O)Nc2ccc(CN3CCN(C)CC3)c(C(F)(F)F)c2)cc1Oc1nc(NC2CC2)nc2c1cnn2C] | MS(ESI) m/z 595[M + H]$^+$. |
| II-m-15 | 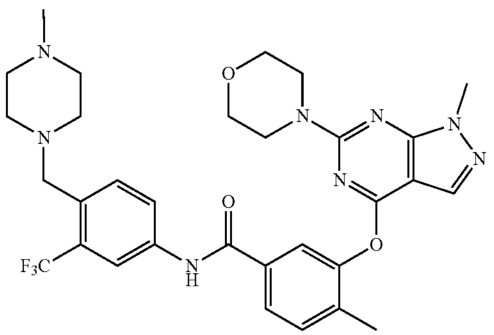 [SMILES: Cc1ccc(C(=O)Nc2ccc(CN3CCN(C)CC3)c(C(F)(F)F)c2)cc1Oc1nc(N2CCOCC2)nc2c1cnn2C] | $^1$H NMR (600 MHz, DMSO-d$_6$) δ 10.45 (s, 1H), 8.18 (d, J = 2.1 Hz, 1H), 8.04 (dd, J = 8.6, 2.1 Hz, 1H), 7.93-7.86 (m, 2H), 7.73-7.65 (m, 2H), 7.56 (d, J = 8.4 Hz, 1H), 3.84 (s, 3H), 3.57 (d, J = 5.9 Hz, 8H), 2.44-2.35 (m, 8H), 2.21 (s, 3H), 2.17 (s, 3H). MS(ESI) m/z 625[M + H]$^+$. |
| II-m-16 | TFA Salt | MS(ESI) m/z 653[M + H]$^+$. |
| II-m-17 | TFA Salt | MS(ESI) m/z 638[M + H]$^+$. |

TABLE 2-continued

Structure and characterization of compounds II

| No. | Structure | 1H NMR and/or MS data |
|---|---|---|
| II-m-18 | 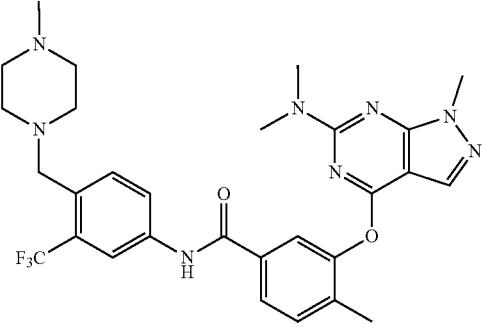 TFA Salt | MS(ESI) m/z 583[M + H]+. |
| II-m-19 | 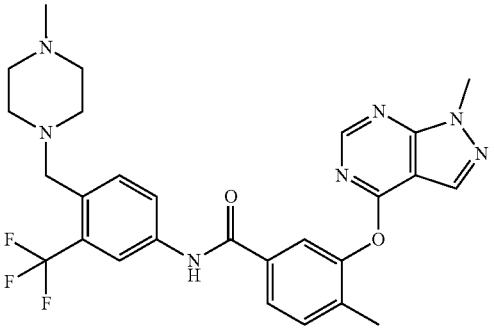 TFA Salt | $^1$H NMR (600 MHz, DMSO-d$_6$) δ 10.53 (s, 1H), 8.56 (s, 1H), 8.27 (s, 1H), 8.19 (d, J = 2.2 Hz, 1H), 8.09 (dd, J = 8.5, 2.3 Hz, 1H), 7.93 (dd, J = 7.9, 1.8 Hz, 1H), 7.90 (d, J = 1.8 Hz, 1H), 7.70 (d, J = 8.5 Hz, 1H), 7.59 (d, J = 8.1 Hz, 1H), 4.08 (s, 3H), 3.41 (d, J = 12.1 Hz, 2H), 3.10-2.99 (m, 2H), 2.93 (d, J = 12.3 Hz, 2H), 2.80 (s, 3H), 2.45-2.34 (m, 2H), 2.18 (s, 3H). MS(ESI) m/z 540[M + H]+. |
| II-m-20 | 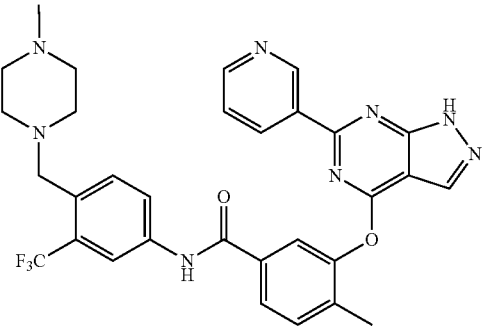 TFA salt | $^1$H NMR (600 MHz, DMSO-d$_6$) δ 10.57 (s, 1H), 9.74 (s, 1H), 9.25 (s, 1H), 8.78-8.66 (m, 1H), 8.56 (dt, J = 8.1, 2.0 Hz, 1H), 8.29-8.18 (m, 2H), 8.10 (dd, J = 8.6, 2.1 Hz, 1H), 8.02 (d, J = 1.7 Hz, 1H), 8.00 (dd, J = 7.9, 1.8 Hz, 1H), 7.71 (d, J = 8.6 Hz, 1H), 7.68-7.61 (m, 2H), 3.71 (s, 2H), 3.45-3.37 (m, 2H), 3.05 (s, 2H), 2.94 (s, 2H), 2.81 (s, 3H), 2.41 (d, J = 15.1 Hz, 2H), 2.26 (s, 3H). MS(ESI) m/z: 603[M + H]+. |
| II-m-21 | 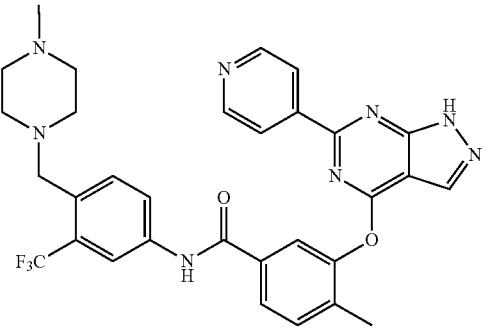 TFA salt | $^1$H NMR (600 MHz, DMSO-d$_6$) δ 10.55 (s, 1H), 9.62 (s, 1H), 8.78 (d, J = 5.3 Hz, 2H), 8.22 (s, 1H), 8.20 (d, J = 2.1 Hz, 1H), 8.13 (d, J = 5.4 Hz, 2H), 8.09 (dd, J = 8.6, 2.1 Hz, 1H), 8.02 (d, J = 1.7 Hz, 1H), 8.00 (dd, J = 7.9, 1.8 Hz, 1H), 3.68 (s, 2H), 3.40 (d, J = 12.1 Hz, 2H), 3.05 (d, J = 12.3 Hz, 2H), 2.92 (d, J = 12.4 Hz, 2H), 2.80 (s, 3H), 2.43-2.33 (m, 2H), 2.26 (s, 3H), MS(ESI) m/z: 603[M + H]+. |

TABLE 2-continued

Structure and characterization of compounds II

| No. | Structure | 1H NMR and/or MS data |
|---|---|---|
| II-m-22 | 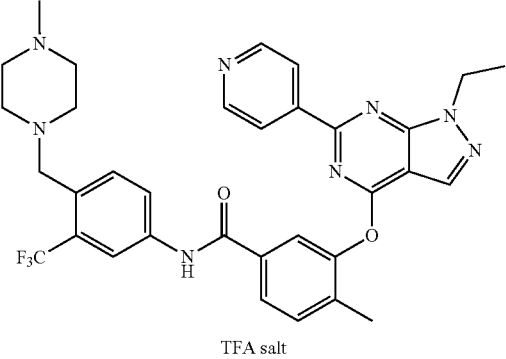 [SMILES: CCn1ncc2c(Oc3cc(C(=O)Nc4ccc(CN5CCN(C)CC5)c(C(F)(F)F)c4)ccc3C)nc(-c3ccncc3)nc21] TFA salt | $^1$H NMR (600 MHz, DMSO-d$_6$) δ 10.58 (s, 1H), 8.89-8.73 (m, 2H), 8.28-8.22 (m, 2H), 8.20 (d, J = 2.3 Hz, 2H), 8.09 (dd, J = 8.6, 2.2 Hz, 1H), 8.05-7.98 (m, 2H), 7.71 (d, J = 8.6 Hz), 1H), 7.66 (d, J = 7.9 Hz, 1H), 4.60 (q, J = 7.3 Hz, 2H), 3.70 (s 2H), 3.42 (d, J = 15.7 Hz, 2H), 3.05 (s, 2H), 2.93 (s, 2H), 2.81 (s, 3H), 2.43 (s, 2H), 2.26 (s, 3H), 1.52 (t, J = 7.2 Hz, 3H). MS(ESI) m/z: 632 [M + H]$^+$. |
| II-m-23 | 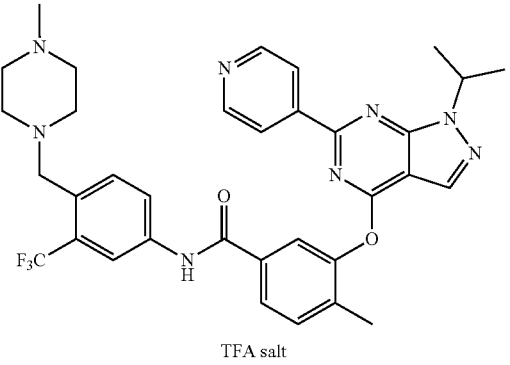 TFA salt | $^1$H NMR (600 MHz, DMSO-d$_6$) δ 10.58 (s, 1H), 8.82 (d, J = 5.4 Hz, 2H), 8.25 (d, J = 5.4 Hz, 2H), 8.20 (d, J = 2.6 Hz, 2H), 8.09 (dd, J = 8.6, 2.1 Hz, 1H), 8.01 (d, J = 7.0 Hz, 2H), 7.70 (d, J = 8.6 Hz, 1H), 7.66 (d, J = 8.1 Hz, 1H), 5.32 (p, J = 6.7 Hz, 1H), 3.70 (s, 2H), 3.41 (s, 2H), 3.05 (s, 2H), 2.93 (s, 2H), 2.81 (s, 3H), 2.41 (d, J = 17.3 Hz, 2H), 2.27 (s, 3H), 1.59 (d, J = 6.7 Hz, 6H). ME (ESI) m/z: 631 [M + H]$^+$. |
| II-n-1 | 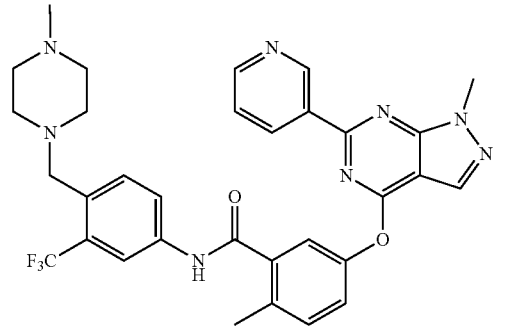 [SMILES: Cc1ccc(Oc2nc(-c3cccnc3)nc3c2cnn3C)cc1C(=O)Nc1ccc(CN2CCN(C)CC2)c(C(F)(F)F)c1] | MS(ESI) m/z 617[M + H]$^+$. |
| II-n-2 | 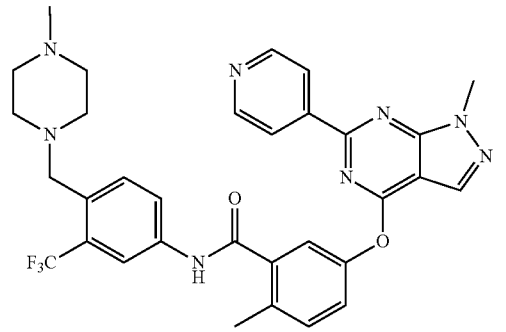 [SMILES: Cc1ccc(Oc2nc(-c3ccncc3)nc3c2cnn3C)cc1C(=O)Nc1ccc(CN2CCN(C)CC2)c(C(F)(F)F)c1] | $^1$H NMR (600 MHz, DMSO-d$_6$) δ 10.67 (s, 1H), 8.78-8.71 (m, 2H), 8.19-8.13 (m, 4H), 7.96 (dd, J = 8.5, 2.1 Hz, 1H), 7.69 (d, J = 8.6 Hz, 1H), 7.61 (d, J = 2.4 Hz, 1H), 7.55 (dd, J = 8.3, 2.5 Hz, 1H), 7.51 (d, J = 8.4 Hz, 1H), 4.15 (s, 3H), 3.56 (s, 2H), 2.49 (s, 3H), 2.42-2.36 (m, 8H), 2.19 (s, 3H). MS(ESI) m/z 617[M + H]$^+$. |

TABLE 2-continued

Structure and characterization of compounds II

| No. | Structure | 1H NMR and/or MS data |
|---|---|---|
| II-o-1 | 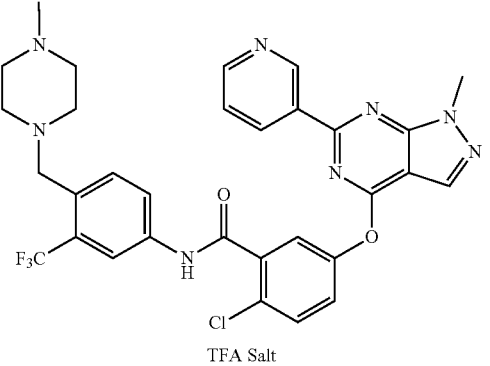 [SMILES: CN1CCN(Cc2ccc(NC(=O)c3cc(Oc4nc(-c5cccnc5)nc5c4cnn5C)ccc3Cl)cc2C(F)(F)F)CC1]<br>TFA Salt | ¹H NMR (600 MHz, DMSO-d$_6$) δ 10.98 (s, 1H), 9.40 (s, 1H), 8.76 (d, J = 4.8 Hz, 1H), 8.66 (dt, J = 8.0, 2.0 Hz, 1H), 8.31 (s, 1H), 8.17 (d, J = 2.1 Hz, 1H), 7.97 (dd, J = 8.5, 2.1 Hz, 1H), 7.83-7.76 (m, 2H), 7.73 (d, J = 8.6 Hz, 1H), 7.69 (dd, J = 8.8, 2.9 Hz, 1H), 7.64 (dd, J = 8.1, 4.8 Hz, 1H), 4.15 (s, 3H), 3.69 (s, 2H), 3.41 (d, J = 12.1 Hz, 2H), 3.04 (s, 2H), 2.93 (d, J = 13.1 Hz, 2H), 2.81 (s, 3H), 2.40 (s, 2H). MS(ESI) m/z 638[M + H]⁺. |
| II-o-2 | 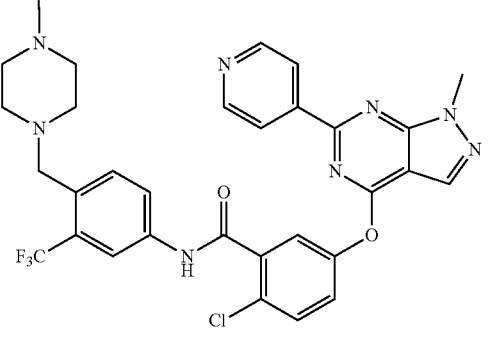 [SMILES: CN1CCN(Cc2ccc(NC(=O)c3cc(Oc4nc(-c5ccncc5)nc5c4cnn5C)ccc3Cl)cc2C(F)(F)F)CC1] | ¹H NMR (600 MHz, DMSO-d$_6$) δ 10.94 (s, 1H), 8.77-8.70 (m, 2H), 8.32 (s, 1H), 8.17-8.13 (m, 3H), 7.93 (dd, J = 8.5, 2.2 Hz, 1H), 7.80 (d J = 2.8 Hz, 1H), 7.78 (d, J = 8.7 Hz, 1H), 7.72 (d, J = 8.5 Hz, 1H), 7.68 (dd, J = 8.7, 2.9 Hz, 1H), 4.15 (s, 3H), 3.56 (s, 2H), 2.38 (s, 8H), 2.18 (s, 3H). MS(ESI) m/z 638[M + H]⁺. |
| II-p-1 | 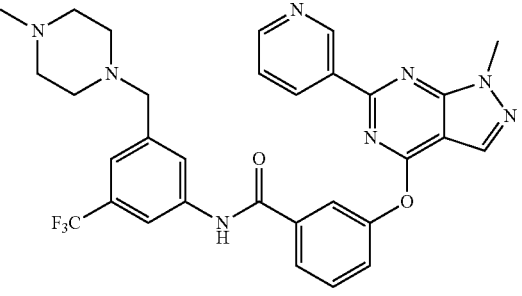 [SMILES: CN1CCN(Cc2cc(NC(=O)c3cccc(Oc4nc(-c5cccnc5)nc5c4cnn5C)c3)cc(C(F)(F)F)c2)CC1] | ¹H NMR (600 MHz, DMSO-d$_6$) δ 7.75 (d, J = 6.6 Hz, 2H), 7.37 (d, J = 5.2 Hz, 2H). 7.79 (d, J = 3.9 Hz, 2H), 7.20 (t, J = 5.9 Hz, 2H), 7.13 (s, 2H), 6.93-6.85 (m, 1H), 6.84-679 (m, 1H), 6.62 (s, 1H), 3.35 (d, J = 4.7 Hz, 3H), 2.79 (d, J = 4.9 Hz, 3H), 1.73 (s, 8H). MS (ESI m/z 603[M + H]⁺. |
| II-p-2 | 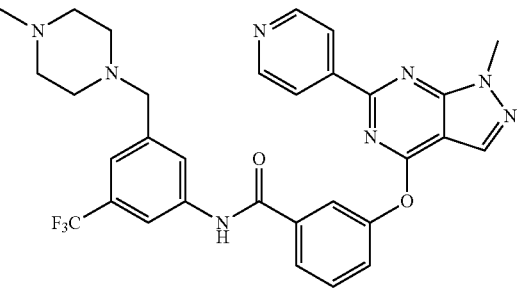 [SMILES: CN1CCN(Cc2cc(NC(=O)c3cccc(Oc4nc(-c5ccncc5)nc5c4cnn5C)c3)cc(C(F)(F)F)c2)CC1] | MS(ESI) m/z 603[M + H]⁺. |

TABLE 2-continued

Structure and characterization of compounds II

| No. | Structure | 1H NMR and/or MS data |
|---|---|---|
| II-s-1 | 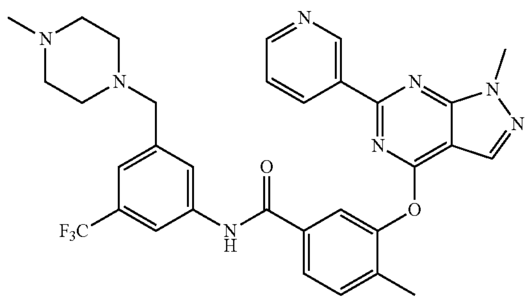 [SMILES: Cc1ccc(C(=O)Nc2cc(CN3CCN(C)CC3)cc(C(F)(F)F)c2)cc1Oc1nc(-c2cccnc2)nc2c1cnn2C] | $^1$H NMR (600 MHz, DMSO-d$_6$) δ 10.54 (s, 1H), 9.27 (d, J = 2.2 Hz, 1H), 8.66 (dd, J = 4.7, 1.8 Hz, 1H), 8.49 (dt, J = 8.0, 2.0 Hz, 1H), 8.19 (s, 1H), 8.16 (s, 1H), 8.05-7.97 (m, 3H), 7.65 (d, J = 8.0 Hz, 1H), 7.51 (dd, J = 8.0, 4.7 Hz, 1H), 7.34 (s, 1H), 4.14 (s, 3H), 3.52 (s, 2H), 2.36 (s, 9H), 2.24 (s, 3H), 2.16 (s, 3H), MS(ESI) m/z 617[M + H]$^+$. |
| II-s-2 | 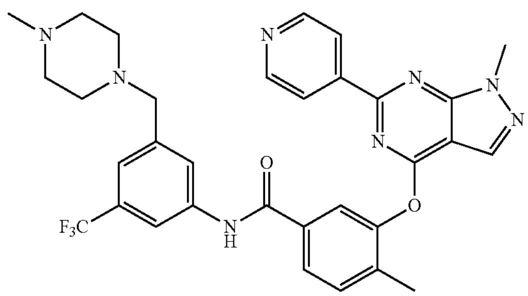 [SMILES: Cc1ccc(C(=O)Nc2cc(CN3CCN(C)CC3)cc(C(F)(F)F)c2)cc1Oc1nc(-c2ccncc2)nc2c1cnn2C] | $^1$H NMR (600 MHz, DMSO-d$_6$) δ 10.54 (s, 1H), 8.73-8.67 (m, 2H), 8.19 (s, 1H), 8.16 (d, J = 1.9 Hz, 1H), 8.06-8.04 (m, 2H), 8.03 (d, J = 1.8 Hz, 1H), 8.02-7.99 (m, 2H), 7.66 (d, J = 8.0 Hz, 1H), 7.35 (s, 1H), 4.16 (s, 3H), 3.53 (s, 2H), 2.45-2.33 (m, 8H), 2.24 (s, 3H), 2.19 (s, 3H). MS(ESI) m/z: 617[M + H]$^+$ |
| II-t-1 | 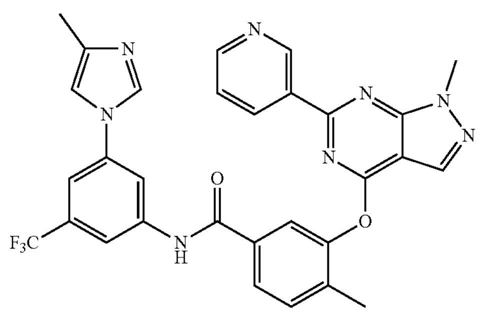 [SMILES: Cc1cn(-c2cc(NC(=O)c3ccc(C)c(Oc4nc(-c5ccncc5)nc5c4cnn5C)c3)cc(C(F)(F)F)c2)cn1] | $^1$H NMR (600 MHz, DMSO-d$_6$) δ 10.86 (s, 1H), 9.38 (s, 1H), 8.69 (d, J = 4.8 Hz, 1H), 8.57 (dt, J = 8.0, 2.0 Hz, 1H), 8.21-8.16 (m, 3H), 8.10 (s, 1H), 7.72 (d, J = 1.8 Hz, 1H), 7.66 (d, J = 2.5 Hz, 1H), 7.57 (dd, J = 8.4, 2.5 Hz, 1H), 7.55-7.51 (m, 2H), 7.47 (s, 1H), 4.13 (s, 3H), 2.52 (s, 3H), 2.17 (s, 3H). MS(ESI) m/z 585[M + H]$^+$. |
| II-t-2 | 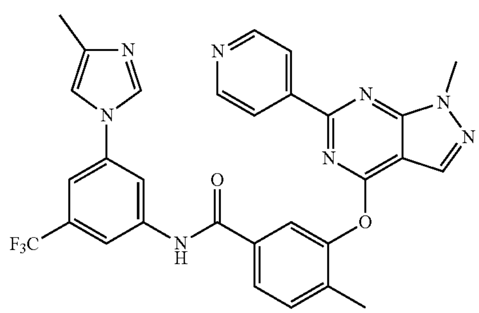 | $^1$H NMR (600 MHz, DMSO-d$_6$) δ 10.87 (s, 1H), 8.75-8.70 (m, 2H), 8.18 (d, J = 1.6 Hz, 2H), 8.15 (s, 1H), 8.14-8.11 (m, 2H), 8.10 (s, 1H), 7.72 (t, J = 1.7 Hz, 1H), 7.66 (d, J = 2.5 Hz, 1H), 7.57 (dd, J = 8.3, 2.5 Hz, 1H), 7.53 (d, J = 8.4 Hz, 1H), 7.45 (t, J = 1.3 Hz, 1H), 4.13 (s, 3H), 2.55 (s, 2H), 2.52 (s, 3H), 2.17 (d, J = 1.0 Hz, 3H). MS(ESI) m/z 585[M + H]$^+$. |
| II-v-1 | 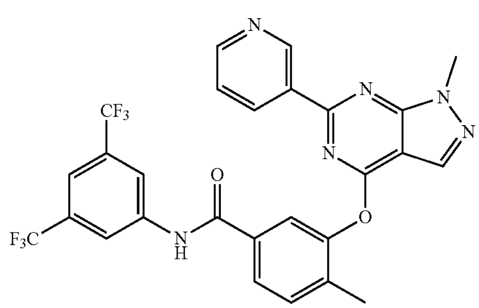 [SMILES: Cc1ccc(C(=O)Nc2cc(C(F)(F)F)cc(C(F)(F)F)c2)cc1Oc1nc(-c2cccnc2)nc2c1cnn2C] | $^1$H NMR (600 MHz, DMSO-d$_6$) δ 10.84 (s, 1H), 9.27 (d, J = 2.1 Hz, 1H), 8.68 (dd, J = 4.8, 1.7 Hz, 1H), 8.53-8.47 (m, 3H), 8.23 (s, 1H), 8.04 (d, J = 1.8 Hz, 1H), 8.02 (dd, J = 7.9, 1.8 Hz, 1H), 7.82 (s, 1H), 7.69 (d, J = 7.9 Hz, 1H), 7.53 (dd, J = 8.0, 4.8 Hz, 1H), 4.15 (s, 3H), 2.26 (s, 3H), ES(ESI) m/z 573[M + H]$^+$. |

TABLE 2-continued

Structure and characterization of compounds II

| No. | Structure | 1H NMR and/or MS data |
|---|---|---|
| II-v-2 | 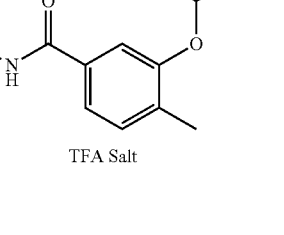 TFA Salt | $^1$H NMR (600 MHz, DMSO-d$_6$) δ 10.28 (s, 1H), 9.29 (s, 1H), 8.71 (s, 1H), 8.56 (d, J = 8.0 Hz, 1H), 8.19 (s, 1H), 7.98 (d, J = 9.0 Hz, 2H), 7.76 (d, J = 8.1 Hz, 2H), 7.64 (d, J = 7.8 Hz, 1H), 7.59 (d, J = 7.0 Hz, 1H), 7.34 (t, J = 7.8 Hz, 2H), 7.10 (t, J = 7.4 Hz, 1H), 4.15 (s, 3H), 2.24 (d, s 3H). MS(ESI) m/z 437 [M + H]$^+$. |
| II-v-3 | 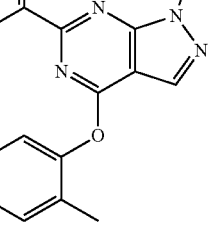 TFA Salt | $^1$H NMR (600 MHz, DMSO-d$_6$) δ 9.27 (d, J = 2.0 Hz, 1H), 8.92-8.84 (m, 1H), 8.73 (dd, J = 5.0, 1.6 Hz, 1H), 8.58 (dt, J = 8.1, 2.0 Hz, 1H), 7.63 (dd, J = 8.0, 4.9 Hz, 1H), 7.53 (d, J = 7.8 Hz, 1H), 7.44 (d, J = 1.5 Hz, 1H), 7.38 (dd, J = 7.8, 1.6 Hz, 1H), 4.12 (s, 3H), 3.60 (s, 8H), 2.20 (s, 3H). MS (ESI) m/z 431[M + H]$^+$. |
| II-v-4 | 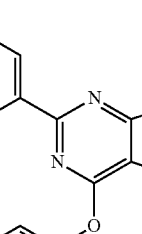 | $^1$H NMR (600 MHz, DMSO-d$_6$) δ 9.27 (dd, J = 2.2 0.8 Hz, 1H), 8.68 (dd, J = 4.8, 1.7 Hz, 1H), 8.50--8.47 (m, 1H), 8.46 (t, J = 5.7 Hz, 1H), 8.15 (s, 1H), 7.85-7.80 (m, 2H), 7.56 (dd, J = 8.4, 0.8 Hz, 1H), 7.52 (ddd, J = 8.0, 4.8, 0.9 Hz, 1H), 4.14 (s, 3H), 3.54 (t, J = 4.6 Hz, 4H), 3.37 (q, J = 6.8 Hz, 2H), 2.45 (t, J = 7.0 Hz, 2H), 2.39 (s, 4H), 2.21 (s, 3H). MS(ESI) m/z 474[M + H]$^+$. |
| II-v-5 | 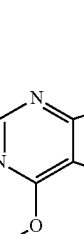 | MS(ESI) m/z 444 [M + H]$^+$. |

TABLE 2-continued

Structure and characterization of compounds II

| No. | Structure | 1H NMR and/or MS data |
|---|---|---|
| II-v-6 | 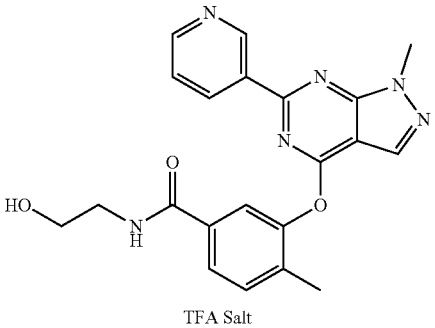 [SMILES: Cc1ccc(C(=O)NCCO)cc1Oc1nc(-c2cccnc2)nc2c1cnn2C] TFA Salt | $^1$H NMR (600 MHz, DMSO-d$_6$) δ 9.29 (d, J = 2 Hz, 1H), 8.75 (dd, J = 5.1, 1.7 Hz, 1H), 8.62 (dt, J = 8.0, 1.9 Hz, 1H), 8.49 (t, J = 5.7 Hz, 1H), 8.11 (s, 1H), 7.86 (dq, J = 2.9, 1.8 Hz, 2H), 7.66 (dd, J = 8.1, 4.9 Hz, 1H), 7.58-7.53 (m, 1H), 4.14 (s, 3H), 3.51 (t, J = 6.2 Hz, 2H), 3.32 (q, J = 6.0 Hz, 2H), 2.21 (s, 3H), MS(ESI) m/z 405[M + H]$^+$. |
| II-v-7 | 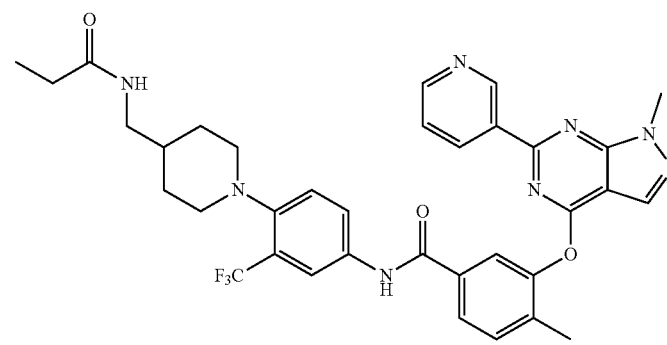 | $^1$H NMR (600 MHz, DMSO-d$_6$) δ 10.43 (s, 1H), 9.28 (s, 1H), 8.67 (s, 1H), 8.48 (dd, J = 7.9, 2.0 Hz, 1H), 8.18 (s, 1H), 8.11 (d, J = 2.4 Hz, 1H), 8.05-7.94 (m, 3H), 7.78 (t, J = 5.9 Hz, 1H), 7.64 (d, J = 8.0 Hz, 1H), 7.51 (d, J = 8.8 Hz, 2H), 4.13 (s, 3H), 2.99 (t, J = 6.4 Hz, 2H), 2.90 (dt, J = 11.8, 3.5 Hz, 2H), 2.67 (td, J = 11.5, 2.4 Hz, 2H), 2.24 (s, 3H), 2.09 (q, J = 7.6 Hz, 2H), 1.74-1.63 (m, 2H), 1.51 (ddq, J = 11.0, 7.4, 3.7 Hz, 1H), 1.22 (td, J = 12.1, 3.9 Hz, 2H), 1.00 (t, J = 7.6 Hz, 3H). MS(ESI) m/z: 673 [M + H]$^+$. |
| II-v-8 | 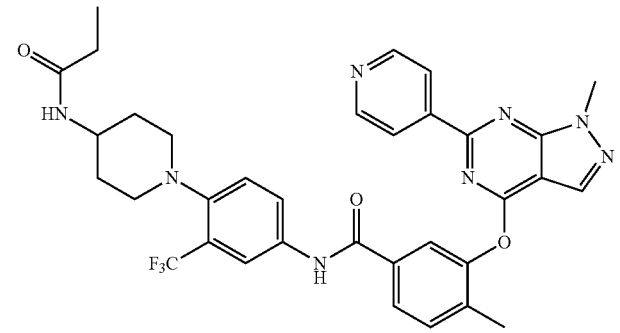 [SMILES: CCC(=O)NC1CCN(c2ccc(NC(=O)c3ccc(C)c(Oc4nc(-c5ccncc5)nc5c4cnn5C)c3)cc2C(F)(F)F)CC1] | $^1$H NMR (600 MHz, Chloroform-d) δ 9.38 (s, 1H), 8.64-8.54 (m, 2H), 8.05 (d, J = 5.2 Hz, 2H), 7.95-7.81 (m, 5H), 7.43 (d, J = 7.9 Hz, 1H), 7.22 (d, J = 8.5 Hz, 1H), 4.16 (s, 3H), 3.83 (dtd, J = 11.5, 7.6, 4.4 Hz, 1H), 2.91 (d, J = 10.5 Hz, 2H), 2.68 (t, J = 11.2 Hz, 2H), 2.33 (s, 3H), 2.18 (q, J = 7.6 Hz, 2H), 1.88 (dd, J = 12.8, 4.1 Hz, 2H), 1.55 (tt, J = 11.6, 6.0 Hz, 2H), 1.12 (t, J = 7.6 Hz, 3H). MS (ESI) m/z: 659 [M + H]$^+$. |
| II-v-9 | 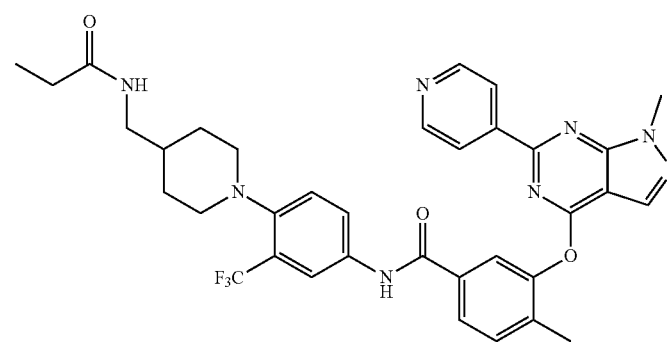 TFA Salt | $^1$H NMR (600 MHz, Methanol-d$_4$) δ 8.58 (d, J = 5.2 Hz, 2H), 8.21-8.16 (m, 2H), 8.10 (s, 1H), 8.02 (d, J = 2.5 Hz, 1H), 7.96-7.91 (m, 2H), 7.89 (dd, J = 8.7, 2.6 Hz, 1H), 7.57 (d, J = 7.9 Hz, 1H), 7.44 (d, J = 8.8 Hz, 1H), 4.19 (s, 3H), 3.13 (t, J = 6.3 Hz, 2H), 3.04-2.96 (m, 2H), 2.73 (td, J = 11.5, 2.3 Hz, 2H), 2.28 (s, 3H), 2.23 (q, J = 7.6 Hz, 2H), 1.80-1.73 (m, 2H), 1.63 (td, J = 7.3, 3.7 Hz, 1H), 1.28 (s, 2H), 1.17-1.14 (m, 3H). MS (ESI) m/z: 673 [M + H]+. |

TABLE 2-continued

Structure and characterization of compounds II

| No. | Structure | 1H NMR and/or MS data |
|---|---|---|
| II-v-10 | 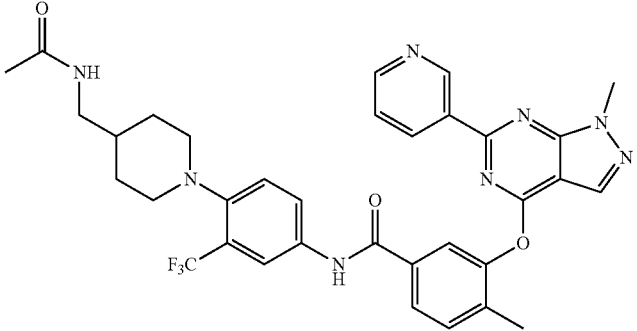 TFA Salt | ¹H NMR (600 MHz, DMSO-d₆) δ 10.43 (s, 1H), 9.29 (s, 1H), 8.76-8.69 (m, 1H), 8.59 (dt, J = 8.1, 1.9 Hz, 1H), 8.18 (s, 1H), 8.11 (d, J = 2.4 Hz, 1H), 8.04-7.95 (m, 3H), 7.88 (t, J = 5.9 Hz, 1H), 7.63 (dd, J = 16.7, 7.8 Hz, 2H), 7.52 (d, J = 8.8 Hz, 1H), 4.15 (s, 3H), 2.98 (t, J = 6.3 Hz, 2H), 2.93-2.87 (m, 2H), 2.67 (td, J = 11.4, 2.3 Hz, 2H), 2.24 (s, 3H), 1.82 (s, 3H), 1.70 (dd, J = 13.4, 3.5 Hz, 2H), 1.50 (ddq, J = 11.3, 7.8, 3.9 Hz, 1H), 1.23 (qd, J = 11.7, 3.8 Hz, 2H). MS (ESI) m/z: 659 [M + H]⁺. |
| II-v-11 | 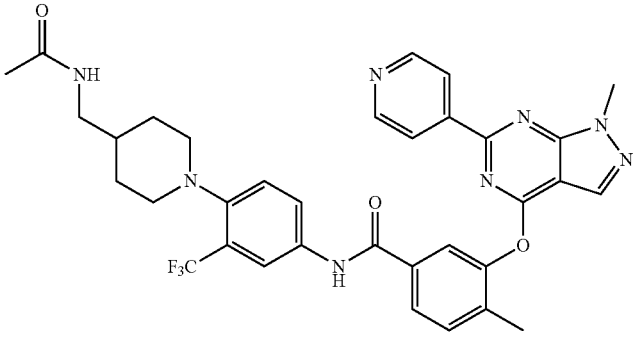 TFA Salt | ¹H NMR (600 MHz, DMSO-d₆) δ 10.44 (s, 1H), 8.81 (s, 2H), 8.22 (s, 2H), 8.20 (s, 1H), 8.11 (d, J = 2.5 Hz, 1H), 8.05-7.96 (m, 3H), 7.88 (t, J = 5.9 Hz, 1H), 7.64 (d, J = 8.0 Hz, 1H), 7.51 (d, J = 8.8 Hz, 1H), 4.17 (s, 3H), 2.98 (t, J = 6.4 Hz, 2H), 2.93-2.84 (m, 2H), 2.67 (td, J = 11.5, 2.3 Hz, 2H), 2.24 (s, 3H), 1.82 (s, 3H), 1.73-1.63 (m, 2H), 11.50 (ddd, J = 11.2, 7.4, 3.9 Hz, 1H), 1.28-1.13 (m, 2H). MS (ESI) m/z: 659 [M + H]⁺. |
| II-v-12 | 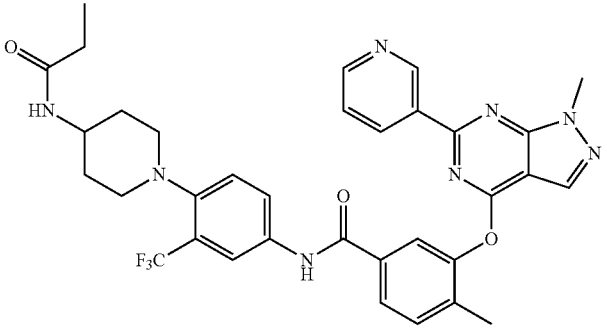 TFA Salt | ¹H NMR (600 MHz, DMSO-d₆) δ 10.45 (s, 1H), 9.35 (d, J = 2.0 Hz, 1H), 8.91-8.83 (m, 2H), 8.18 (s, 1H), 8.12 (d, J = 2.5 Hz, 1H), 8.01 (td, J = 10.7, 2.2 Hz, 3H), 7.90 (dd, J = 8.1, 5.3 Hz, 1H), 7.76 (d, J = 7.8 Hz, 1H), 7.65 (d, J = 7.9 Hz, 1H), 7.56 (d, J = 8.9 Hz, 1H), 4.17 (s, 3H), 3.69 (dtd, J = 11.2, 7.1, 3.8 Hz, 1H), 2.95-2.84 (m, 2H), 2.78 (td, J = 11.6, 2.5 Hz, 2H), 2.25 (s, 3H), 2.07 (q, J = 7.6 Hz, 2H), 1.84-1.74 (m, 2H), 1.52 (qd, J = 11.4, 3.9 Hz, 2H), 0.99 (t, J = 7.6 Hz, 3H). MS (ESI) m/z: 659 [M + H]⁺. |
| II-v-13 | 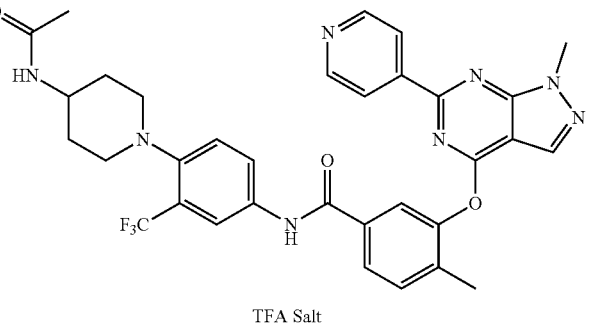 TFA Salt | ¹H NMR (600 MHz, DMSO-d₆) δ 10.44 (s, 1H), 8.79 (d, J = 5.4 Hz, 2H), 8.21 (s, 1H), 8.19-8.17 (m, 2H), 8.13 (d, J = 2.5 Hz, 1H), 8.01 (td, J = 10.9, 5.3 Hz, 3H), 7.85 (d, J = 7.8 Hz, 1H), 7.65 (d, J = 8.0 Hz, 1H), 7.56 (d, J = 9.0 Hz, 1H), 4.17 (s, 3H), 3.69 (dt, J = 7.7, 5.4 Hz, 1H), 2.95-2.86 (m, 2H), 2.78 (td, J = 11.5, 2.5 Hz, 2H), 2.25 (s, 3H), 1.81 (s, 5H), 1.51 (qd, J = 11.4, 3.9 Hz, 2H). MS (ESI) m/z: 645 [M + H]⁺ |

TABLE 2-continued

Structure and characterization of compounds II

| No. | Structure | 1H NMR and/or MS data |
|---|---|---|
| II-v-14 | 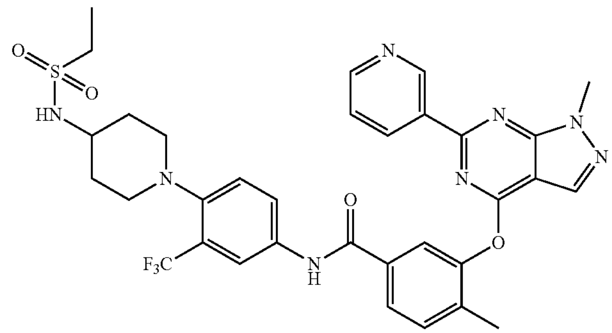 [SMILES: CCS(=O)(=O)NC1CCN(c2ccc(NC(=O)c3ccc(C)c(Oc4nc(-c5cccnc5)nc5c4cnn5C)c3)cc2C(F)(F)F)CC1] | ¹H NMR (600 MHz, Chloroform-d) δ 9.40 (s, 1H), 9.04 (s, 1H), 8.61 (s, 1H), 8.50 (d, J = 7.9 Hz, 1H), 7.88 (s, 2H), 7.87-7.80 (m, 3H), 7.40 (d, J = 7.8 Hz, 1H), 7.31 (d, J = 11.6 Hz, 1H), 7.25 (d, J = 8.6 Hz, 1H), 4.78 (d, J = 7.9 Hz, 1H), 4.13 (s, 3H), 3.40 (dt, J = 8.5, 4.2 Hz, 1H), 3.06 (q, J = 7.4 Hz, 2H), 2.97 (dt, J = 12.5, 3.9 Hz, 2H), 2.77-2.67 (m, 2H), 2.22 (s, 3H), 2.01 (dd, J = 13.0, 3.8 Hz, 2H), 1.77-1.62 (m, 2H), 1.38 (t, J = 7.3 Hz, 3H). MS (ESI) m/z: 695 [M + H]⁺ |
| II-v-15 | 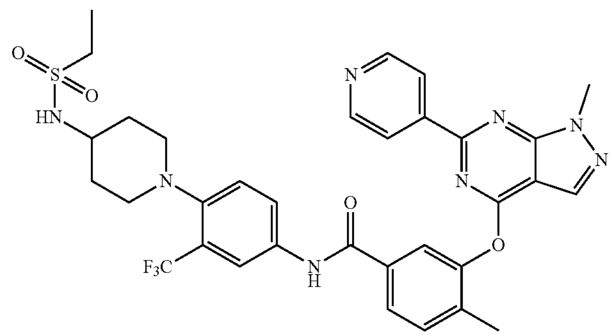 [SMILES: CCS(=O)(=O)NC1CCN(c2ccc(NC(=O)c3ccc(C)c(Oc4nc(-c5ccncc5)nc5c4cnn5C)c3)cc2C(F)(F)F)CC1] | ¹H NMR (600 MHz, Chloroform-d) δ 9.04 (s, 1H), 8.60 (s, 2H), 8.06 (s, 2H), 7.91 (s, 1H), 7.90-7.86 (m, 2H), 7.84 (d, J = 1.7 Hz, 1H), 7.81 (d, J = 2.5 Hz, 1H), 7.44 (d, J = 8.0 Hz, 1H), 7.24 (d, J = 8.8 Hz, 1H), 4.92 (d, J = 7.9 Hz, 1H), 4.16 (s, 3H), 3.39 (ddt, J = 14.7, 10.6, 5.4 Hz, 1H), 3.05 (q, J = 7.4 Hz, 2H), 2.96 (dd, J = 11.0, 5.4 Hz, 2H), 2.77-2.67 (m, 2H), 2.23 (s, 3H), 2.04-1.93 (m, 2H), 1.75-1.64 (m, 2H), 1.36 (t, J = 7.4 Hz, 3H). MS (ESI) m/z: 695 [M + H]⁺ |
| II-v-16 | TFA Salt | ¹H NMR (600 MHz, DMSO-d₆) δ 10.44 (s, 1H), 9.25 (d, J = 2.1 Hz, 1H), 8.74 (dd, J = 5.0, 1.6 Hz, 1H), 8.58 (dt, J = 8.1, 1.8 Hz, 1H), 8.19 (s, 1H), 8.11 (d, J = 2.6 Hz, 1H), 8.02 (dd, J = 8.5, 2.2 Hz, 2H), 7.99 (dd, J = 7.9, 1.8 Hz, 1H), 7.80 (t, J = 5.9 Hz, 1H), 7.69-7.65 (m, 1H), 7.64 (d, J = 8.2 Hz, 1H), 7.51 (d, J = 8.8 Hz, 1H), 2.98 (t, J = 6.3 Hz, 2H), 2.94-2.87 (m, 2H), 2.67 (td, J = 11.6, 2.3 Hz, 2H), 2.25 (s, 3H), 2.09 (q, J = 7.6 Hz, 2H), 1.72-1.64 (m, 2H), 1.55-1.45 (m, 1H), 1.23 (qd, J = 12.1, 3.8 Hz, 2H), 1.00 (t, J = 7.6 Hz, 3H). MS (ESI) m/z: 659 [M + H]⁺ |
| II-v-17 | TFA Salt | ¹H NMR (600 MHz, DMSO-d₆) δ 10.43 (s, 1H), 8.87-8.75 (m, 2H), 8.23 (s, 1H), 8.20-8.15 (m, 2H), 8.11 (d, J = 2.5 Hz, 1H), 8.02 (dd, J = 8.0, 2.1 Hz, 2H), 8.00 (dd, J = 7.9, 1.8 Hz, 1H), 7.79 (t, J = 5.9 Hz, 1H), 7.65 (d, J = 8.0 Hz, 1H), 7.52 (d, J = 8.8 Hz, 1H), 2.99 (t, J = 6.4 Hz, 2H), 2.94-2.86 (m, 2H), 2.67 (td, J = 11.6, 2.4 Hz, 2H), 2.25 (s, 3H), 2.09 (q, J = 7.6 Hz, 2H), 1.69 (dd, J = 13.4, 3.6 Hz, 2H), 1.51 (ddd, J = 11.2, 7.3, 3.9 Hz, 1H), 1.24 (qd, J = 11.9, 3.9 Hz, 2H), 1.00 (t, J = 7.6 Hz, 3H). MS (ESI) m/z: 659 [M + H]⁺ |

TABLE 3

Structure and characterization of compounds III

| No. | Structure | $^1$H NMR and/or MS data |
|---|---|---|
| III-b-1 | 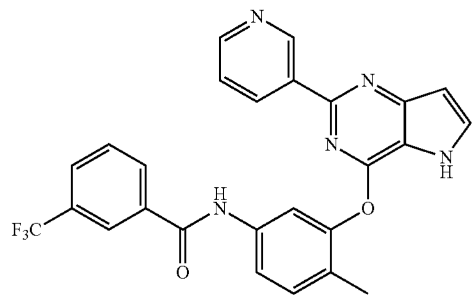 | $^1$H NMR (600 MHz, Chloroform-d) δ 9.29 (d, J = 2.0 Hz, 1H), 8.97 (s, 1H), 8.51-8.42 (m, 2H), 8.16 (s, 1H), 8.07 (d, J = 7.9 Hz, 1H), 7.82 (d, J = 2.1 Hz, 1H), 7.72 (d, J = 7.8 Hz, 1H), 7.52 (t, J = 7.8 Hz, 1H), 7.37 (dd, J = 8.3, 2.1 Hz, 1H), 7.33 (d, J = 3.1 Hz, 1H), 7.27-7.20 (m, 2H), 6.68 (d, J = 3.1 Hz, 1H), 4.17 (s, 3H), 2.19 (s, 3H). MS(ESI) m/z 504[M + H]$^+$. |
| III-b-2 | 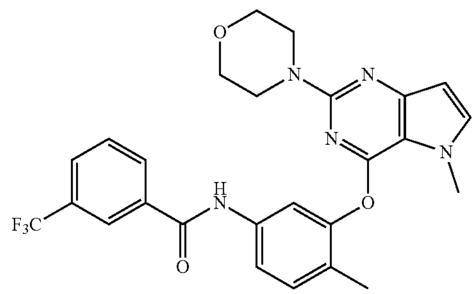 [SMILES: Cc1ccc(NC(=O)c2cccc(C(F)(F)F)c2)cc1Oc1nc(N2CCOCC2)nc2ccn(C)c12] | $^1$H NMR (600 MHz, Chloroform-d) δ 8.34 (s, 1H), 8.15 (s, 1H), 8.10 (d, J = 7.9 Hz, 1H), 7.80 (d, J = 7.8 Hz, 1H), 7.71 (d, J = 2.2 Hz, 1H), 7.62 (t, J = 7.8 Hz, 1H), 7.44 (dd, J = 8.3, 2.2 Hz, 1H), 7.28 (d, J = 8.5 Hz, 1H), 7.15 (d, J = 3.0 Hz, 1H), 6.40 (d, J = 3.1 Hz, 1H), 4.05 (s, 3H), 2.21 (s, 3H). MS(ESI) m/z 512[M + H]$^+$. |
| III-b-3 | 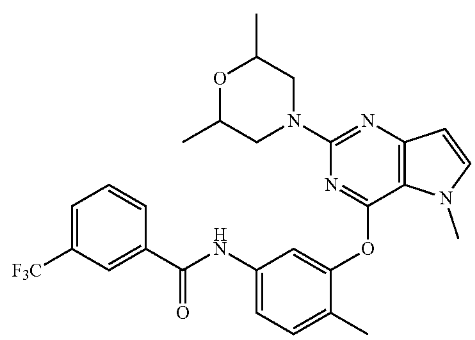 [SMILES: Cc1ccc(NC(=O)c2cccc(C(F)(F)F)c2)cc1Oc1nc(N2CC(C)OC(C)C2)nc2ccn(C)c12] | $^1$H NMR (600 MHz, Chloroform-d) δ 8.22 (s, 1H), 8.14 (s, 1H), 8.08 (d, J = 7.9 Hz, 1H), 7.81 (d, J = 7.8 Hz, 1H), 7.76 (d, J = 2.2 Hz, 1H), 7.62 (t, J = 7.8 Hz, 1H), 7.40 (dd, J = 8.2, 2.2 Hz, 1H), 7.29 (d, J = 1.8 Hz, 1H), 7.13 (d, J = 3.1 Hz, 1H), 6.37 (d, J = 3.0 Hz, 1H), 4.24 (d, J = 13.0 Hz, 2H), 4.05 (s, 3H), 3.56 (dtt, J = 12.6, 6.1, 3.0 Hz, 2H), 2.44 (dd, J = 13.0, 10.6 Hz, 2H), 2.22 (s, 3H), 1.13 (d, J = 6.2 Hz, 6H). MS(ESI) m/z 540[M + H]$^+$. |
| III-e-1 | 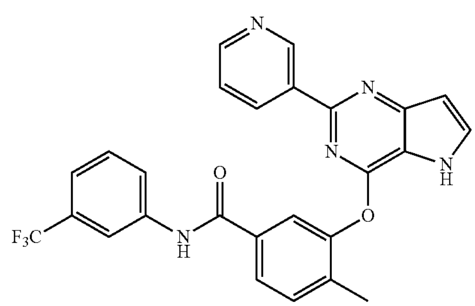 [SMILES: Cc1ccc(C(=O)Nc2cccc(C(F)(F)F)c2)cc1Oc1nc(-c2cccnc2)nc2cc[nH]c12] | $^1$H NMR (600 MHz, DMSO-d$_6$) δ 12.54 (t, J = 2.4 Hz, 1H), 10.54 (s, 1H), 9.17 (s, 1H), 8.61-8.45 (m, 1H), 8.38 (dt, J = 8.1, 2.0 Hz, 1H), 8.22 (d, J = 1.9 Hz, 1H), 8.08-8.04 (m, 1H), 8.03 (d, J = 1.8 Hz, 1H), 7.97 (dd, J = 7.9, 1.8 Hz, 1H), 7.91 (t, J = 3.0 Hz, 1H), 7.64 (d, J = 8.0 Hz, 1H), 7.59 (t, J = 8.0 Hz, 1H), 7.48-7.43 (m, 1H), 7.41 (dd, J = 8.0, 4.7 Hz, 1H), 6.77 (dd, J = 3.0, 1.8 Hz, 1H), 2.28 (s, 3H). MS(ESI) m/z 490[M + H]$^+$. |
| III-e-2 | 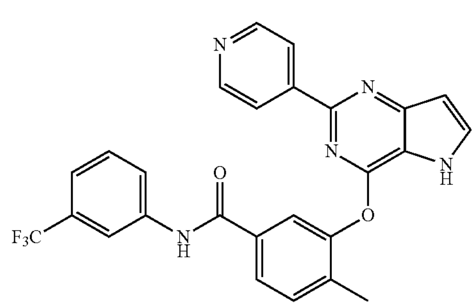 [SMILES: Cc1ccc(C(=O)Nc2cccc(C(F)(F)F)c2)cc1Oc1nc(-c2ccncc2)nc2cc[nH]c12] | $^1$H NMR (600 MHz, DMSO-d$_6$) δ 12.61 (t, J = 2.3 Hz, 1H), 10.54 (s, 1H), 8.60 (s, 2H), 8.22 (d, J = 1.9 Hz, 1H), 8.10-8.05 (m, 1H), 8.04 (d, J = 1.8 Hz, 1H), 7.98 (dd, J = 8.0, 1.9 Hz, 1H), 7.95 (q, J = 3.3 Hz, 3H), 7.64 (d, J = 8.0 Hz, 1H), 7.59 (t, J = 8.0 Hz, 1H), 7.48-7.42 (m, 1H), 6.81 (dd, J = 3.0, 1.8 Hz, 1H), 2.28 (s, 3H). MS(ESI) m/z 490[M + H]$^+$. |

TABLE 3-continued

Structure and characterization of compounds III

| No. | Structure | ¹H NMR and/or MS data |
|---|---|---|
| III-e-3 | 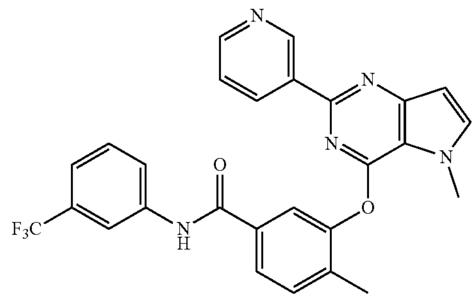 [SMILES: Cc1ccc(C(=O)Nc2cccc(C(F)(F)F)c2)cc1Oc1nc(-c2cccnc2)nc2ccn(C)c12] | ¹H NMR (600 MHz, DMSO-d$_6$) δ 10.56 (s, 1H), 9.15 (dd, J = 2.2, 0.8 Hz, 1H), 8.56 (dd, J = 4.8, 1.7 Hz, 1H), 8.38 (dt, J = 8.0, 1.9 Hz, 1H), 8.23 (d, J = 1.9 Hz, 1H), 8.12-8.03 (m, 2H), 7.97 (dd, J = 7.9, 1.8 Hz, 1H), 7.89 (d, J = 3.0 Hz, 1H), 7.63 (dd, J = 7.9, 0.8 Hz, 1H), 7.59 (t, J = 8.0 Hz, 1H), 7.47-7.41 (m, 2H), 6.73 (d, J = 3.2 Hz, 1H), 4.21 (s, 3H), 2.31 (s, 3H). MS(ESI) m/z 504[M + H]⁺. |
| III-e-4 | 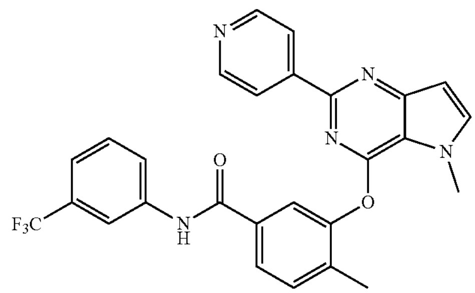 [SMILES: Cc1ccc(C(=O)Nc2cccc(C(F)(F)F)c2)cc1Oc1nc(-c2ccncc2)nc2ccn(C)c12] | ¹H NMR (600 MHz, Chloroform-d) δ 8.67 (s, 1H), 8.54 (d, J = 5.2 Hz, 2H), 8.01 (s, 1H), 7.98 (d, J = 5.0 Hz, 2H), 7.90-7.84 (m, 3H), 7.50 (d, J = 7.9 Hz, 1H), 7.47 (t, J = 8.0 Hz, 1H), 7.42 (d, J = 3.1 Hz, 1H), 7.40 (dd, J = 8.0, 1.4 Hz, 1H), 6.76 (d, J = 3.1 Hz, 1H), 4.19 (s, 3H), 2.31 (s, 3H). MS(ESI) m/z 504[M + H]⁺. |
| III-e-5 | 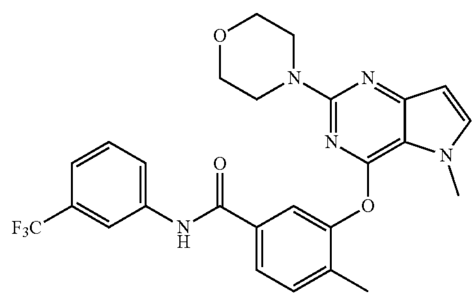 [SMILES: Cc1ccc(C(=O)Nc2cccc(C(F)(F)F)c2)cc1Oc1nc(N2CCOCC2)nc2ccn(C)c12] | ¹H NMR (600 MHz, Chloroform-d) δ 8.34-8.28 (m, 1H), 7.97 (d, J = 2.0 Hz, 1H), 7.90 (dd, J = 8.3, 2.0 Hz, 1H), 7.78 (d, J = 1.8 Hz, 1H), 7.75 (dd, J = 7.9, 1.9 Hz, 1H), 7.48 (t, J = 8.0 Hz, 1H), 7.42 (dd, J = 12.7, 7.8 Hz, 2H), 7.16 (d, J = 3.0 Hz, 1H), 6.36 (d, J = 3.0 Hz, 1H), 4.05 (s, 3H), 3.65 (t, J = 4.8 Hz, 4H), 3.48 (t, J = 4.8 Hz, 4H), 2.30 (s, 3H). MS(ESI) m/z 512[M + H]⁺. |
| III-e-6 | 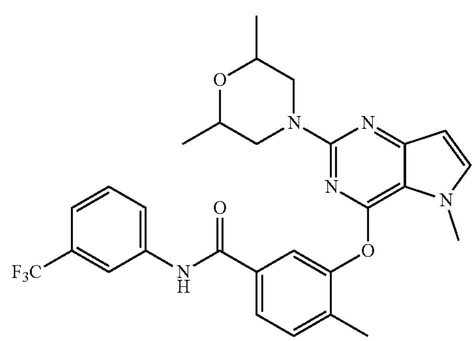 | ¹H NMR (600 MHz, Chloroform-d) δ 8.34 (s, 1H), 8.15 (s, 1H), 8.10 (d, J = 7.9 Hz, 1H), 7.80 (d, J = 7.8 Hz, 1H), 7.71 (d, J = 2.2 Hz, 1H), 7.62 (t, J = 7.8 Hz, 1H), 7.44 (dd, J = 8.3, 2.2 Hz, 1H), 7.28 (d, J = 8.5 Hz, 1H), 7.15 (d, J = 3.0 Hz, 1H), 6.40 (d, J = 3.1 Hz, 1H), 4.05 (s, 3H), 2.21 (s, 3H). MS(ESI) m/z 512[M + H]⁺. |
| III-h-1 | 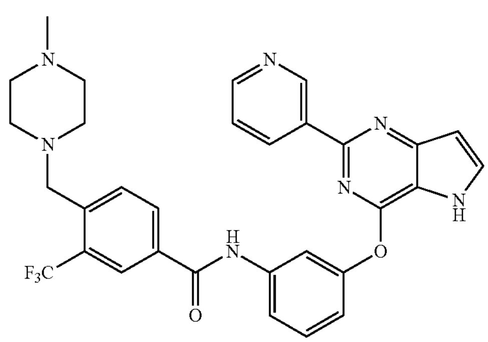 [SMILES: CN1CCN(Cc2ccc(C(=O)Nc3cccc(Oc4nc(-c5cccnc5)nc5cc[nH]c45)c3)cc2C(F)(F)F)CC1] | ¹H NMR (600 MHz, DMSO-d$_6$) δ 12.62 (s, 1H), 10.70 (s, 1H), 9.35 (d, J = 2.0 Hz, 1H), 8.84-8.81 (m, 1H), 8.77 (dd, J = 5.2, 1.5 Hz, 1H), 8.30 (d, J = 1.8 Hz, 1H), 8.27 (dd, J = 8.2, 1.8 Hz, 1H), 7.97 (t, J = 2.2 Hz, 1H), 7.95-7.92 (m, 2H), 7.80 (dd, J = 8.1, 5.2 Hz, 1H), 7.72 (dd, J = 8.3, 1.9 Hz, 1H), 7.55 (t, J = 8.2 Hz, 1H), 7.25-7.23 (m, 1H), 6.80 (dd, J = 3.0, 1.8 Hz, 1H), 3.80 (s, 2H), 3.42 (d, J = 12.0 Hz, 2H), 3.07 (t, J = 12.1 Hz, 2H), 2.93 (d, J = 12.5 Hz, 2H), 2.82 (s, 3H), 2.44 (t, J = 12.5 Hz, 2H). MS (ESI) m/z 588 [M + H]⁺. |

TABLE 3-continued

Structure and characterization of compounds III

| No. | Structure | ¹H NMR and/or MS data |
|---|---|---|
| III-h-2 | (structure, TFA Salt) | ¹H NMR (600 MHz, DMSO-$d_6$) δ 12.79 (s, 1H), 10.74 (s, 1H), 8.86 (d, J = 5.9 Hz, 2H), 8.43 (d, J = 5.9 Hz, 2H), 8.30 (d, J = 1.7 Hz, 1H), 8.27 (dd, J = 8.1, 1.8 Hz, 1H), 8.01 (t, J = 2.9 Hz, 1H), 7.97 (t, J = 2.2 Hz, 1H), 7.93 (d, J = 8.1 Hz, 1H), 7.74 (dd, J = 8.2, 1.8 Hz, 1H), 7.56 (t, J = 8.2 Hz, 1H), 7.28-7.23 (m, 1H), 6.87 (q, J = 3.1, 1.8 Hz, 1H), 3.79 (s, 3H), 3.42 (d, J = 11.7 Hz, 2H), 3.07 (t, J = 12.1 Hz, 2H), 2.92 (d, J = 12.7 Hz, 2H), 2.81 (s, 3H), 2.43 (t, J = 12.3 Hz, 2H). MS (ESI) m/z 588 [M + H]⁺. |
| III-h-3 | (structure, TFA Salt) | ¹H NMR (600 MHz, DMSO-$d_6$) δ 10.70 (s, 1H), 9.33 (s, 1H), 8.79 (d, J = 8.3 Hz, 1H), 8.76 (d, J = 5.1 Hz, 1H), 8.31 (s, 1H), 8.27 (d, J = 8.6 Hz, 1H), 8.00 (t, J = 2.2 Hz, 1H), 7.94-7.91 (m, 2H), 7.78 (dd, J = 8.1, 5.2 Hz, 1H), 7.71 (dd, J = 8.5, 1.9 Hz, 1H), 7.55 (t, J = 8.1 Hz, 1H), 7.27-7.24 (m, 1H), 6.76 (d, J = 3.1 Hz, 1H), 4.17 (s, 3H), 3.80 (s, 2H), 3.42 (d, J = 12.1 Hz, 2H), 3.07 (t, J = 11.9 Hz, 2H), 2.93 (d, J = 12.5 Hz, 2H), 2.82 (s, 3H), 2.43 (t, J = 12.2 Hz, 2H). MS (ESI) m/z 602 [M + H]⁺. |
| III-h-4 | (structure, TFA Salt) | ¹H NMR (600 MHz, DMSO-$d_6$) δ 10.72 (s, 1H), 8.85-8.82 (m, 2H), 8.41-8.39 (m, 2H), 8.31 (d, J = 1.8 Hz, 1H), 8.27 (dd, J = 8.1, 1.8 Hz, 1H), 8.00 (t, J = 2.2 Hz, 1H), 7.97 (d, J = 3.1 Hz, 1H), 7.93 (d, J = 8.2 Hz, 1H), 7.73 (dd, J = 7.8, 1.9 Hz, 1H), 7.55 (t, J = 8.1 Hz, 1H), 7.27-7.24 (m, 1H), 6.83 (d, J = 3.1 Hz, 1H), 4.19 (s, 3H), 3.79 (s, 2H), 3.42 (d, J = 12.1 Hz, 2H), 3.07 (t, J = 12.0 Hz, 2H), 2.92 (d, J = 12.6 Hz, 2H), 2.82 (s, 3H), 2.44 (t, J = 12.3 Hz, 2H). MS (ESI) m/z 602 [M + H]⁺. |
| III-i-1 | (structure, TFA Salt) | ¹H NMR (600 MHz, DMSO-$d_6$) δ 12.68 (s, 1H), 10.64 (s, 1H), 9.30 (d, J = 2.0 Hz, 1H), 8.77 (t, 2H), 8.29 (s, 1H), 8.25 (d, J = 8.7 Hz, 1H), 7.96 (t, J = 3.0 Hz, 1H), 7.92 (d, J = 8.2 Hz, 1H), 7.89 (d, J = 2.1 Hz, 1H), 7.81 (dd, J = 8.1, 5.2 Hz, 1H), 7.66 (dd, J = 8.4, 2.2 Hz, 1H), 7.44 (d, J = 8.4 Hz, 1H), 6.81 (dd, J = 3.0, 1.9 Hz, 1H), 3.79 (s, 2H), 3.42 (d, J = 12.0 Hz, 2H), 3.06 (t, J = 11.9 Hz, 2H), 2.92 (d, J = 12.3 Hz, 2H), 2.81 (s, 3H), 2.43 (t, J = 12.4 Hz, 2H), 2.18 (s, 3H). MS (ESI) m/z 602 [M + H]⁺. |

TABLE 3-continued

Structure and characterization of compounds III

| No. | Structure | ¹H NMR and/or MS data |
|---|---|---|
| III-i-2 | 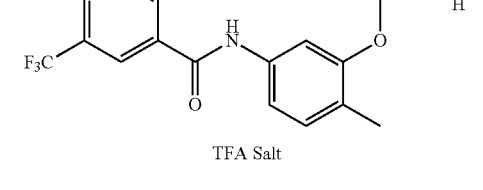 TFA Salt | ¹H NMR (600 MHz, DMSO-d$_6$) δ 12.83 (s, 1H), 10.65 (s, 1H), 8.86 (d, J = 6.7 Hz, 2H), 8.40 (d, J = 6.8 Hz, 2H), 8.29 (s, 1H), 8.25 (dd, J = 8.1, 1.8 Hz, 1H), 8.02 (t, J = 3.0 Hz, 1H), 7.92 (d, J = 8.2 Hz, 1H), 7.88 (d, J = 2.0 Hz, 1H), 7.68 (dd, J = 8.3, 2.1 Hz, 1H), 7.44 (d, J = 8.4 Hz, 1H), 6.88-6.87 (m, 1H), 3.78 (s, 2H), 3.42 (d, J = 12.0 Hz, 2H), 3.06 (t, J = 12.1 Hz, 2H), 2.92 (d, J = 12.8 Hz, 2H), 2.81 (s, 3H), 2.42 (t, J = 12.2 Hz, 2H), 2.17 (s, 3H). MS (ESI) m/z 602 [M + H]⁺. |
| III-i-3 | 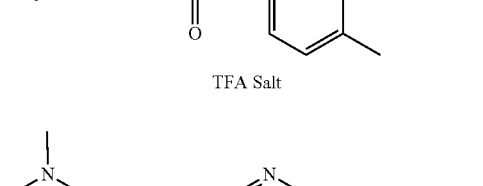 TFA Salt | ¹H NMR (600 MHz, DMSO-d$_6$) δ 10.62 (s, 1H), 9.26 (d, J = 1.9 Hz, 1H), 8.75-8.68 (m, 2H), 8.29 (d, J = 1.8 Hz, 1H), 8.25 (dd, J = 8.1, 1.8 Hz, 1H), 7.94-7.90 (m, 3H), 7.73 (dd, J = 8.1, 5.1 Hz, 1H), 7.64 (dd, J = 8.3, 2.2 Hz, 1H), 7.43 (d, J = 8.5 Hz, 1H), 6.76 (d, J = 3.1 Hz, 1H), 4.20 (s, 3H), 3.79 (s, 2H), 3.42 (d, J = 12.0 Hz, 2H), 3.07 (t, J = 11.9 Hz, 2H), 2.92 (d, J = 12.6 Hz, 2H), 2.81 (s, 3H), 2.43 (t, J = 12.5 Hz, 2H), 2.20 (s, 3H). MS (ESI) m/z 616 [M + H]⁺. |
| III-i-4 | 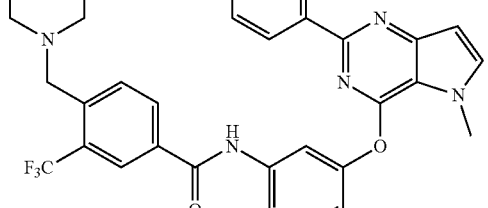 TFA Salt | ¹H NMR (600 MHz, DMSO-d$_6$) δ 10.64 (s, 1H), 8.80 (d, J = 6.6 Hz, 2H), 8.30 (d, J = 6.6 Hz, 3H), 8.25 (dd, J = 8.0, 1.9 Hz, 1H), 7.97 (d, J = 3.0 Hz, 1H), 7.93-7.91 (m, 2H), 7.66 (dd, J = 8.3, 2.1 Hz, 1H), 7.43 (d, J = 8.4 Hz, 1H), 6.82 (d, J = 3.0 Hz, 1H), 4.21 (s, 3H), 3.78 (s, 2H), 3.42 (d, J = 12.0 Hz, 2H), 3.06 (t, J = 11.9 Hz, 2H), 2.92 (d, J = 12.8 Hz, 2H), 2.81 (s, 3H), 2.43 (t, J = 12.2 Hz, 2H), 2.20 (s, 3H). MS (ESI) m/z 616 [M + H]⁺. |
| III-j-1 | 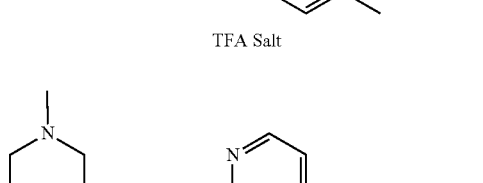 TFA Salt | ¹H NMR (600 MHz, DMSO-d$_6$) δ 12.63 (s, 1H), 10.30 (s, 1H), 9.40 (s, 1H), 8.89 (d, J = 8.1 Hz, 1H), 8.79 (d, J = 5.2 Hz, 1H), 8.34 (s, 1H), 8.30 (d, J = 8.7 Hz, 1H), 7.94-7.92 (m, 2H), 7.83 (t, 1H), 7.51 (d, J = 2.5 Hz, 1H), 7.45 (d, J = 8.4 Hz, 1H), 7.31 (q, J = 8.3, 2.5 Hz, 1H), 6.79 (dd, J = 3.0 1.8 Hz, 1H), 3.80 (s, 2H), 3.42 (d, J = 12.1 Hz, 2H), 3.07 (s, 2H), 2.93 (d, J = 12.5 Hz, 2H), 2.82 (s, 3H), 2.46-2.41 (m, 2H), 2.34 (s, 3H). MS (ESI) m/z 602 [M + H]⁺. |

TABLE 3-continued

Structure and characterization of compounds III

| No. | Structure | ¹H NMR and/or MS data |
|---|---|---|
| III-j-2 | 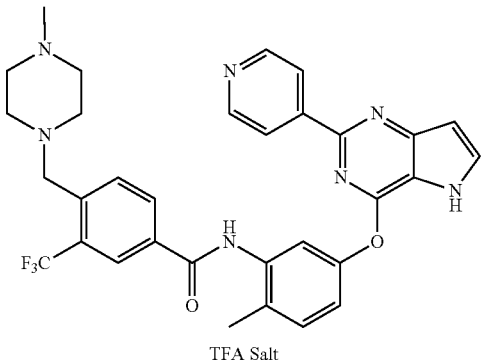 [SMILES: Cc1ccc(Oc2nc(-c3ccncc3)nc3cc[nH]c23)cc1NC(=O)c1ccc(CN2CCN(C)CC2)c(C(F)(F)F)c1] TFA Salt | ¹H NMR (600 MHz, DMSO-$d_6$) δ 12.80 (s, 1H), 10.32 (s, 1H), 8.90 (d, J = 5.9 Hz, 2H), 8.55 (d, J = 6.4 Hz, 2H), 8.33 (s, 1H), 8.30 (d, J = 8.6 Hz, 1H), 8.00 (t, J = 2.9 Hz, 1H), 7.94 (d, J = 8.2 Hz, 1H), 7.51 (d, J = 2.4 Hz, 1H), 7.46 (d, J = 8.4 Hz, 1H), 7.32 (dd, J = 8.3, 2.5 Hz, 1H), 6.86 (dd, J = 3.0, 1.8 Hz, 1H), 3.80 (s, 2H), 3.42 (d, J = 12.0 Hz, 2H), 3.08 (t, 2H), 2.93 (d, J = 12.5 Hz, 2H), 2.81 (s, 3H), 2.44 (t, J = 12.2 Hz, 2H), 2.34 (s, 3H). MS (ESI) m/z 602 [M + H]⁺. |
| III-j-3 | 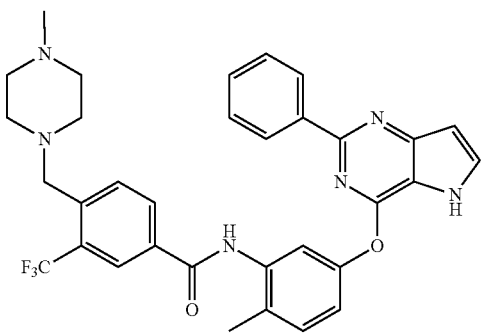 [SMILES: Cc1ccc(Oc2nc(-c3ccccc3)nc3cc[nH]c23)cc1NC(=O)c1ccc(CN2CCN(C)CC2)c(C(F)(F)F)c1] | ¹H NMR (600 MHz, DMSO-$d_6$) δ 12.35 (s, 1H), 10.28 (s, 1H), 8.32 (s, 1H), 8.30 (d, J = 8.2 Hz, 1H), 8.22-8.20 (m, 2H), 7.93 (d, J = 8.3 Hz, 1H), 7.83 (t, J = 2.8 Hz, 1H), 7.45 (dd, J = 8.4, 5.6 Hz, 2H), 7.39 (dd, J = 5.3, 3.4 Hz, 3H), 7.29 (d, J = 2.5 Hz, 1H), 6.70 (dd, J = 3.0, 1.5 Hz, 1H), 3.77 (s, 2H), 2.65 (s, 3H), 2.33 (s, 3H). MS (ESI) m/z 601[M + H]⁺. |
| III-j-4 | 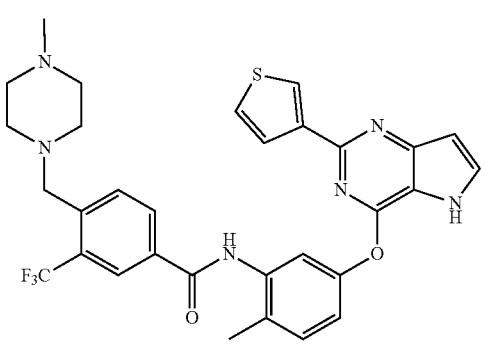 TFA Salt | ¹H NMR (600 MHz, DMSO-$d_6$) δ 12.30 (s, 1H), 10.21 (s, 1H), 8.29 (s, 1H), 8.26 (d, J = 8.2 Hz, 1H), 8.01 (dd, J = 3.1, 1.2 Hz, 1H), 7.93 (d, J = 8.2 Hz, 1H), 7.80 (t, J = 2.9 Hz, 1H), 7.64 (dd, J = 5.0, 1.2 Hz, 1H), 7.53 (dd, J = 5.0, 3.1 Hz, 1H), 7.46 (d, J = 2.5 Hz, 1H), 7.42 (d, J = 8.7 Hz, 1H), 7.25 (dd, J = 8.3, 2.5 Hz, 1H), 6.66 (dd, J = 3.0, 1.8 Hz, 1H), 3.68 (s, 2H), 2.32 (s, 3H), 2.19 (s, 3H). MS (ESI) m/z 607[M + H]⁺. |
| III-j-5 | 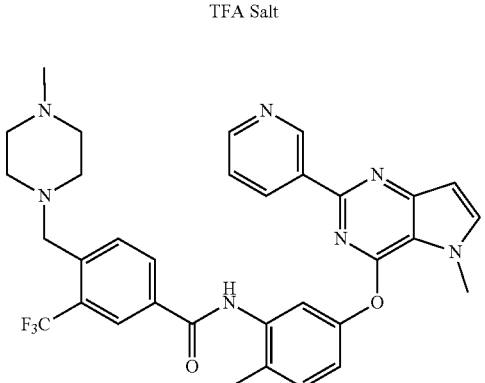 TFA Salt | MS (ESI) m/z 616 [M + H]⁺. |

TABLE 3-continued

Structure and characterization of compounds III

| No. | Structure | $^1$H NMR and/or MS data |
|---|---|---|
| III-j-6 | TFA Salt | $^1$H NMR (600 MHz, DMSO-d$_6$) δ 10.33 (s, 1H), 8.89 (d, J = 6.8 Hz, 2H), 8.51 (d, J = 6.7 Hz, 2H), 8.34 (s, 1H), 8.31 (dd, J = 8.2, 1.8 Hz, 1H), 7.97-7.92 (m, 2H), 7.54 (d, J = 2.6 Hz, 1H), 7.46 (d, J = 8.4 Hz, 1H), 7.34 (dd, J = 8.3, 2.5 Hz, 1H), 6.82 (d, J = 3.1 Hz, 1H), 4.18 (s, 3H), 3.80 (s, 2H), 3.43 (d, J = 11.9 Hz, 2H), 3.07 (s, 2H), 2.93 (d, J = 12.2 Hz, 2H), 2.82 (s, 3H), 2.45 (s, 2H), 2.34 (s, 3H). MS (ESI) m/z 616 [M + H]$^+$. |
| III-j-7 | 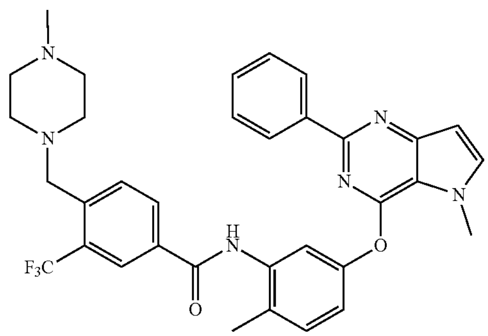 [SMILES: Cc1ccc(Oc2nc(-c3ccccc3)nc3ccn(C)c23)cc1NC(=O)c1ccc(CN2CCN(C)CC2)c(C(F)(F)F)c1] | $^1$H NMR (600 MHz, DMSO-d$_6$) δ 10.24 (s, 1H), 8.30 (s, 1H), 8.27 (d, J = 7.8 Hz, 1H), 8.20 (d, J = 5.0 Hz, 2H), 7.93 (d, J = 7.8 Hz, 1H), 7.79 (s, 1H), 7.50 (s, 1H), 7.44 (d, J = 7.9 Hz, 1H), 7.39 (s, 3H), 7.30 (d, J = 7.0 Hz, 1H), 6.66 (s, 1H), 4.13 (s, 3H), 3.68 (s, 2H), 2.33 (s, 3H), 2.18 (s, 3H). MS (ESI) m/z 615[M + H]$^+$. |
| III-j-8 | 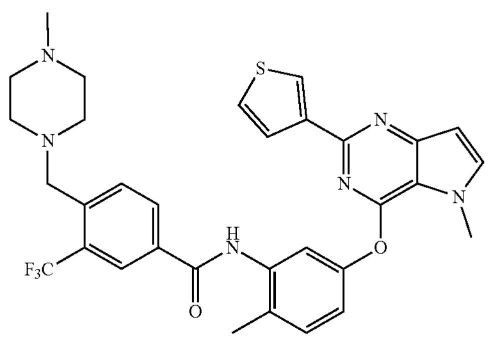 [SMILES: Cc1ccc(Oc2nc(-c3ccsc3)nc3ccn(C)c23)cc1NC(=O)c1ccc(CN2CCN(C)CC2)c(C(F)(F)F)c1] | $^1$H NMR (600 MHz, DMSO-d$_6$) δ 10.23 (s, 1H), 8.29 (s, 1H), 8.26 (d, J = 8.1 Hz, 1H), 8.01 (dd, J = 3.1, 1.1 Hz, 1H), 7.93 (d, J = 8.2 Hz, 1H), 7.77 (d, J = 3.0 Hz, 1H), 7.63 (dd, J = 5.0, 1.1 Hz, 1H), 7.53 (dd, J = 5.0, 3.1 Hz, 1H), 7.49 (d, J = 2.4 Hz, 1H), 7.42 (d, J = 8.4 Hz, 1H), 7.28 (dd, J = 8.3, 2.5 Hz, 1H), 6.62 (d, J = 3.0 Hz, 1H), 4.12 (s, 3H), 3.68 (s, 2H), 2.32 (s, 3H), 2.17 (s, 3H). MS (ESI) m/z 621[M + H]$^+$. |
| III-j-9 | 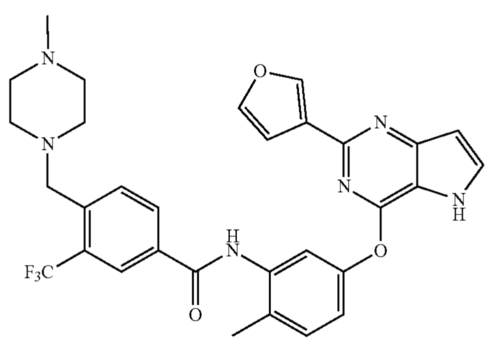 [SMILES: Cc1ccc(Oc2nc(-c3ccoc3)nc3cc[nH]c23)cc1NC(=O)c1ccc(CN2CCN(C)CC2)c(C(F)(F)F)c1] | $^1$H NMR (600 MHz, DMSO-d$_6$) δ 12.28 (s, 1H), 10.20 (s, 1H), 8.28 (s, 1H), 8.26 (d, J = 8.2 Hz, 1H), 8.09-8.07 (m, 1H), 7.93 (d, J = 8.1 Hz, 1H), 7.78 (t, J = 2.9 Hz, 1H), 7.68 (t, J = 1.7 Hz, 1H), 7.46 (d, J = 2.4 Hz, 1H), 7.41 (d, J = 8.4 Hz, 1H), 7.23 (dd, J = 8.3, 2.5 Hz, 1H), 6.89=6.87 (m, 1H), 6.63 (dd, J = 2.9, 1.8 Hz, 1H), 3.68 (s, 2H), 2.31 (s, 3H), 2.18 (s, 3H). MS (ESI) m/z: 589[M + H]$^+$ |

TABLE 3-continued

Structure and characterization of compounds III

| No. | Structure | ¹H NMR and/or MS data |
|---|---|---|
| III-j-10 | 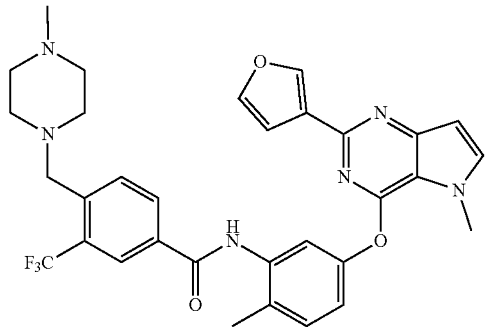 [SMILES: Cc1ccc(Oc2nc(-c3ccoc3)nc3ccn(C)c23)cc1NC(=O)c1ccc(CN2CCN(C)CC2)c(C(F)(F)F)c1] | ¹H NMR (600 MHz, DMSO-d$_6$) δ 10.22 (s, 1H), 8.29 (s, 1H), 8.26 (d, J = 8.1 Hz, 1H), 8.08 (d, J = 0.7 Hz, 1H), 7.93 (d, J = 8.1 Hz, 1H), 7.76 (d, J = 3.0 Hz, 1H), 7.68 (d, J = 1.6 Hz, 1H), 7.49 (d, J = 2.4 Hz, 1H), 7.41 (d, J = 8.4 Hz, 1H), 7.26 (dd, J = 8.3, 2.4 Hz, 1H), 6.87 (d, J = 1.0 Hz, 1H), 6.58 (d, J = 3.0 Hz, 1H), 4.11 (s, 3H), 3.68 (s, 2H), 2.31 (s, 3H). 2.18 (s, 3H). MS (ESI) m/z: 605[M + H]⁺ |
| III-j-11 | 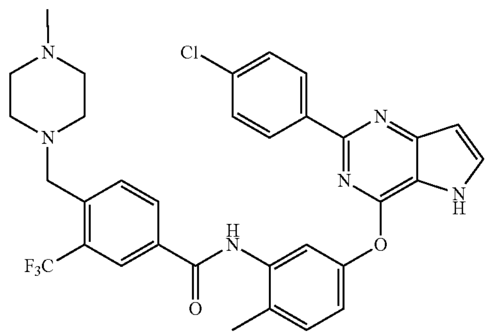 [SMILES: Cc1ccc(Oc2nc(-c3ccc(Cl)cc3)nc3cc[nH]c23)cc1NC(=O)c1ccc(CN2CCN(C)CC2)c(C(F)(F)F)c1] | ¹H NMR (600 MHz, DMSO-d$_6$) δ 12.39 (s, 1H), 10.20 (s, 1H), 8.29 (s, 1H), 8.26 (d, J = 8.1 Hz, 1H), 8.21 (d, J = 8.5 Hz, 2H), 7.93 (d, J = 8.2 Hz, 1H), 7.84 (s, 1H), 7.48 (d, J = 2.3 Hz, 1H), 7.46 (d, J = 8.5 Hz, 2H), 7.43 (d, J = 8.4 Hz, 1H), 7.27 (dd, J = 8.3, 2.4 Hz, 1H), 6.71 (d, J = 2.7 Hz, 1H), 3.68 (s, 2H), 2.33 (s, 3H), 2.16 (s, 3H). MS (ESI) m/z: 636[M + H]⁺ |
| III-j-12 | 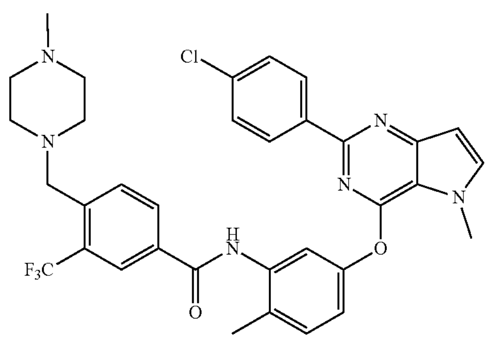 [SMILES: Cc1ccc(Oc2nc(-c3ccc(Cl)cc3)nc3ccn(C)c23)cc1NC(=O)c1ccc(CN2CCN(C)CC2)c(C(F)(F)F)c1] | ¹H NMR (600 MHz, DMSO-d$_6$) δ 10.23 (s, 1H), 8.30 (s, 1H), 8.27 (d, J = 8.6 Hz, 1H), 8.21-8.18 (m, 2H), 7.93 (d, J = 8.1 Hz, 1H), 7.81 (d, J = 3.0 Hz, 1H), 7.49 (d, J = 2.4 Hz, 1H), 7.46-7.44 (m, 2H), 7.43 (d, J = 8.5 Hz, 1H), 7.29 (dd, J = 8.3, 2.5 Hz, 1H), 2.32 (s, 3H), 2.19 (s, 3H). MS (ESI) m/z: 650[M + H]⁺ |
| III-j-13 | TFA Salt | ¹H NMR (600 MHz, DMSO-d$_6$) δ 12.75 (d, J = 14.7 Hz, 1H), 10.27 (d, J = 9.5 Hz, 1H), 8.30 (d, J = 6.4 Hz, 1H), 8.26 (d, 1H), 8.02-7.98 (m, 2H), 7.93 (dd, J = 7.3, 4.4 Hz, 2H), 7.48-7.44 (m, 2H), 7.28 (dd, J = 8.3, 2.5 Hz, 1H), 6.85-6.81 (m, 2H), 6.70 (dt, J = 7.8, 3.9 Hz, 1H), 3.79 (s, 2H), 3.40 (s, 2H), 3.04 (d, J = 27.6 Hz, 2H), 2.89 (m, 2H), 2.80 (s, 3H), 2.39 (t, 2H), 2.32 (s, 3H). MS (ESI) m/z: 617[M + H]⁺ |

TABLE 3-continued

Structure and characterization of compounds III

| No. | Structure | ¹H NMR and/or MS data |
|---|---|---|
| III-j-14 | 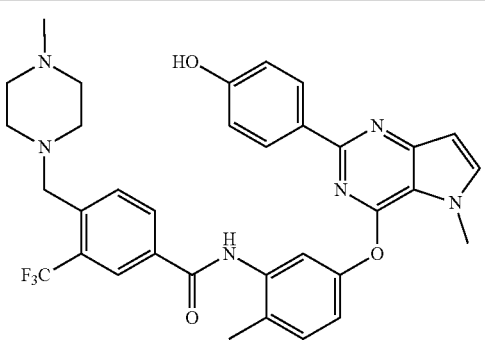 [SMILES: Cc1ccc(Oc2nc(-c3ccc(O)cc3)nc3ccn(C)c23)cc1NC(=O)c1ccc(CN2CCN(C)CC2)c(C(F)(F)F)c1] | ¹H NMR (600 MHz, DMSO-d₆) δ 10.23 (s, 1H), 9.70 (s, 1H), 8.30 (s, 1H), 8.26 (d, J = 8.1 Hz, 1H), 8.02 (t, J = 5.7 Hz, 2H), 7.93 (d, J = 8.2 Hz, 1H), 7.73 (d, J = 3.0 Hz, 1H), 7.46 (d, J = 2.4 Hz, 1H), 7.42 (d, J = 8.4 Hz, 1H), 7.28 (dd, J = 8.3, 2.5 Hz, 1H), 6.76 (d, J = 8.7 Hz, 2H), 6.58 (d, J = 3.0 Hz, 1H), 4.10 (s, 3H), 3.68 (s, 2H), 2.32 (s, 3H), 2.19 (s, 3H). MS (ESI) m/z: 631[M + H]⁺ |
| III-j-15 | 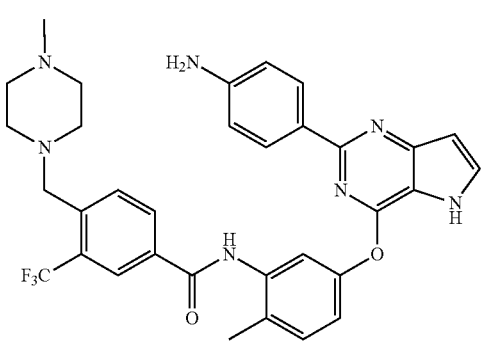 | ¹H NMR (600 MHz, DMSO-d₆) δ 12.07 (d, J = 25.0 Hz, 1H), 10.22 (s, 1H), 8.27 (s, 1H), 8.24 (d, J = 8.0 Hz, 1H), 7.91 (d, J = 8.1 Hz, 1H), 7.88 (d, J = 8.7 Hz, 2H), 7.70 (t, J = 2.8 Hz, 1H), 7.43-7.40 (m, 2H), 7.23 (dd, J = 8.3, 2.5 Hz, 1H), 6.57 (dd, J = 2.9, 1.6 Hz, 1H), 6.53 (d, J = 8.7 Hz, 2H), 3.80-3.75 (m, 2H), 3.67 (s, 2H), 2.31 (s, 3H), 2.18 (s, 3H). MS (ESI) m/z: 616[M + H]⁺ |
| III-j-16 | 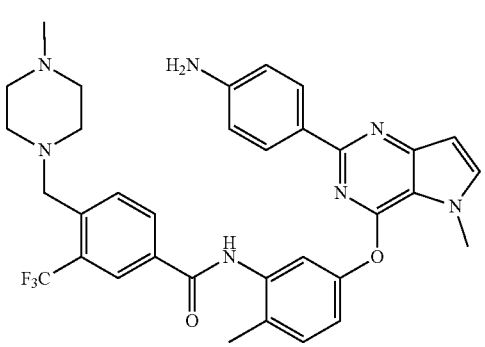TFA Salt | ¹H NMR (600 MHz, DMSO-d₆) δ 10.31 (s, 1H), 8.31 (s, 1H), 8.27 (d, J = 8.0 Hz, 1H), 7.93 (t, J = 6.3 Hz, 1H), 7.91 (d, J = 8.8 Hz, 2H), 7.88 (d, J = 3.0 Hz, 1H), 7.48 (d, J = 2.5 Hz, 1H), 7.46 (d, J = 8.6 Hz, 1H), 7.31 (dd, J = 8.3, 2.5 Hz, 1H), 6.74 (d, J = 8.8 Hz, 2H), 6.63 (d, J = 3.0 Hz, 1H), 4.13 (s, 3H), 3.79 (s, 2H), 3.40 (s, 2H), 3.06 (s, 2H), 2.92 (s, 2H), 2.80 (s, 3H), 2.43 (s, 2H), 2.32 (s, 3H). MS (ESI) m/z: 631[M + H]⁺ |
| III-j-17 | 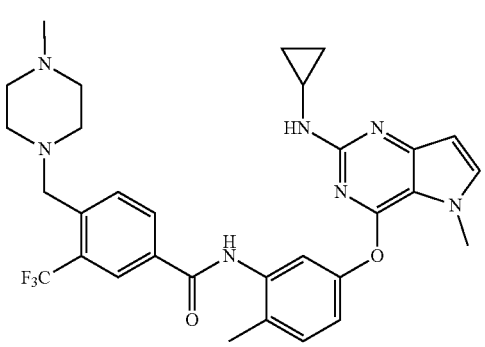TFA Salt | ¹H NMR (600 MHz, DMSO-d₆) δ 10.28 (s, 1H), 8.31 (s, 1H), 8.27 (d, J = 8.1 Hz, 1H), 8.25 (d, J = 2.9 Hz, 1H), 7.94 (d, J = 8.2 Hz, 1H), 7.49 (d, J = 2.2 Hz, 1H), 7.47 (d, J = 8.6 Hz, 1H), 7.26 (dd, J = 8.3, 2.3 Hz, 1H), 7.00 (d, J = 2.9 Hz, 1H), 6.52 (s, 1H), 4.23 (s, 3H), 3.79 (s, 2H), 3.17 (s, 1H), 3.07 (s, 2H), 2.93 (d, J = 12.3 Hz, 2H), 2.82 (s, 3H), 2.46-2.38 (m, 4H), 2.31 (s, 3H). MS (ESI) m/z: 594 [M + H]⁺ |

TABLE 3-continued

Structure and characterization of compounds III

| No. | Structure | ¹H NMR and/or MS data |
|---|---|---|
| III-j-18 | 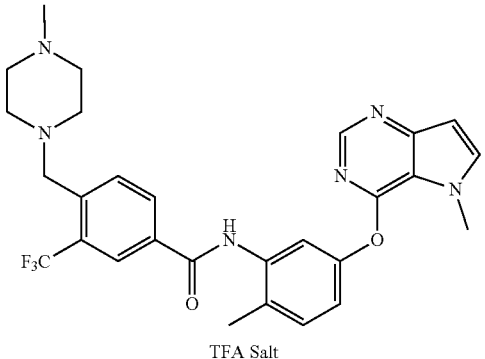 [SMILES: Cc1ccc(Oc2ncnc3ccn(C)c23)cc1NC(=O)c1ccc(CN2CCN(C)CC2)c(C(F)(F)F)c1] TFA Salt | ¹H NMR (600 MHz, DMSO-d₆) δ 10.22 (d, J = 6.8 Hz, 1H), 8.27 (s, 1H), 8.25 (d, J = 6.7 Hz, 1H), 8.22 (t, J = 7.2 Hz, 1H), 7.91 (t, J = 7.4 Hz, 1H), 7.75 (t, J = 5.4 Hz, 1H), 7.38 (d, J = 8.4 Hz, 1H), 7.32 (d, J = 2.4 Hz, 1H), 7.15 (dd, 1H), 6.59 (d, J = 3.1 Hz, 1H), 4.10 (s, 3H), 3.67 (s, 2H), 2.26 (s, 3H), 2.18 (s, 3H). MS (ESI) m/z: 539 [M + H]⁺ |
| III-k-1 | 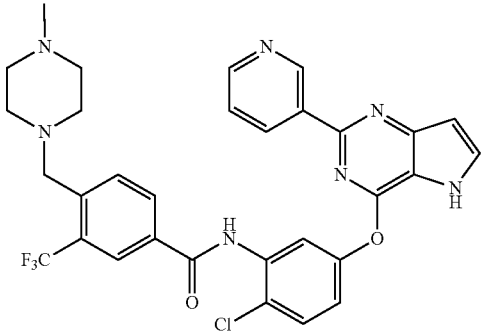 [SMILES: CN1CCN(Cc2ccc(C(=O)Nc3cc(Oc4nc(-c5cccnc5)nc5cc[nH]c45)ccc3Cl)cc2C(F)(F)F)CC1] | ¹H NMR (600 MHz, DMSO-d₆) δ 12.50 (s, 1H), 10.47 (s, 1H), 9.30 (d, J = 1.5 Hz, 1H), 8.59 (dd, J = 4.7, 1.7 Hz, 1H), 8.50 (dt, J = 8.0, 1.9 Hz, 1H), 8.32 (s, 1H), 8.27 (d, J = 8.1 Hz, 1H), 7.94 (d, J = 8.2 Hz, 1H), 7.90 (t, J = 2.9 Hz, 1H), 7.74 (t, J = 5.3 Hz, 2H), 7.48-7.44 (m, 2H), 6.76 (dd, J = 2.9, 1.8 Hz, 1H), 3.71 (s, 2H), 2.36 (s, 3H). MS (ESI) m/z: 623[M + H]⁺ |
| III-k-2 | 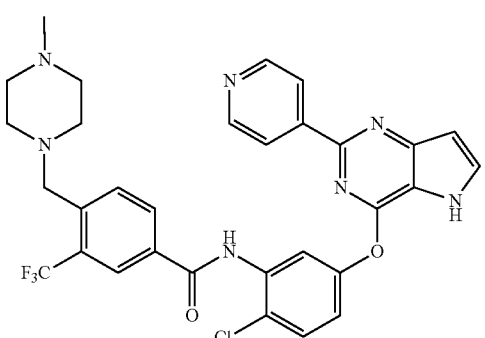 | ¹H NMR (600 MHz, DMSO-d₆) δ 12.72 (s, 1H), 10.52 (s, 1H), 8.80 (d, J = 4.8 Hz, 2H), 8.37 (d, J = 6.0 Hz, 2H), 8.35 (d, J = 1.5 Hz, 1H), 8.32-8.29 (m, 1H), 7.99 (t, J = 2.9 Hz, 1H), 7.95 (d, J = 8.2 Hz, 1H), 7.76 (dd, J = 7.5, 5.8 Hz, 2H), 7.48 (dd, J = 8.8, 2.8 Hz, 1H), 6.85 (dd, J = 3.0, 1.8 Hz, 1H), 3.80 (s, 2H), 3.42 (d, J = 11.6 Hz, 2H), 3.07 (t, J = 11.2 Hz, 2H), 2.93 (d, J = 12.4 Hz, 2H), 2.82 (s, 3H), 2.47-2.38 (m, 2H). MS (ESI) m/z: 623[M + H]⁺ |
| III-k-3 | 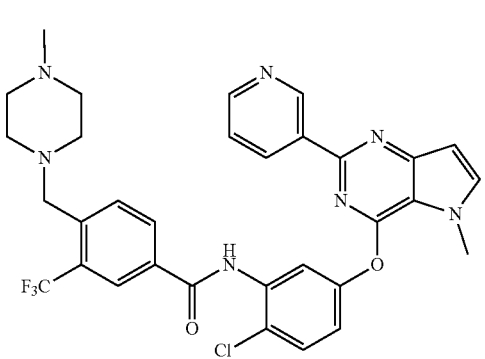 [SMILES: CN1CCN(Cc2ccc(C(=O)Nc3cc(Oc4nc(-c5cccnc5)nc5ccn(C)c45)ccc3Cl)cc2C(F)(F)F)CC1] | ¹H NMR (600 MHz, DMSO-d₆) δ 10.52 (s, 1H), 9.33 (s, 1H), 8.70-8.65 (m, 2H), 8.36 (d, J = 1.5 Hz, 1H), 8.30 (dd, J = 8.1, 1.5 Hz, 1H), 7.95 (d, J = 8.2 Hz, 1H), 7.89 (d, J = 3.1 Hz, 1H), 7.78-7.74 (m, 2H), 7.63 (dd, J = 7.6, 5.2 Hz, 1H), 7.49 (dd, J = 8.8, 2.8 Hz, 1H), 6.74 (d, J = 3.1 Hz, 1H), 4.16 (s, 3H), 3.42 (d, J = 12.2 Hz, 2H), 3.07 (t, J = 11.2 Hz, 2H), 2.93 (d, J = 12.5 Hz, 2H), 2.82 (s, 3H), 2.42 (t, J = 22.0, 10.4 Hz, 2H). MS (ESI) m/z: 637[M + H]⁺ |

TABLE 3-continued

Structure and characterization of compounds III

| No. | Structure | $^1$H NMR and/or MS data |
|---|---|---|
| III-k-4 | (TFA salt) | $^1$H NMR (600 MHz, DMSO-$d_6$) δ 10.56 (s, 1H), 8.82 (d, J = 5.0 Hz, 2H), 8.39 (d, J = 5.9 Hz, 2H), 8.36 (d, J = 1.5 Hz, 1H), 8.31 (dd, J = 8.1, 1.5 Hz, 1H), 7.97-7.94 (m, 2H), 7.80 (d, J = 2.8 Hz, 1H), 7.76 (d, J = 8.8 Hz, 1H), 7.50 (dd, J = 8.8, 2.8 Hz, 1H), 6.81 (d, J = 3.1 Hz, 1H), 4.18 (s, 3H), 3.42 (d, J = 11.2 Hz, 2H), 3.07 (t, J = 11.1 Hz, 2H), 2.93 (d, J = 11.8 Hz, 2), 2.82 (s, 3H), 2.44 (t, J = 11.5 Hz, 2H). MS (ESI) m/z: 637[M + H]$^+$ |
| III-k-5 | (TFA salt) | $^1$H NMR (600 MHz, DMSO-$d_6$) δ 12.38 (s, 1H), 10.49 (s, 1H), 8.34 (d, J = 1.3 Hz, 1H), 8.31-8.27 (m, 1H), 8.12 (dd, J = 1.5, 0.6 Hz, 1H), 7.95 (d, J = 8.2 Hz, 1H), 7.83 (t, J = 2.9 Hz, 1H), 7.72-7.69 (m, 3H), 7.40 (dd, 1H), 6.90 (dd, J = 1.8, 0.6 Hz, 1H), 6.65 (dd, J = 3.0, 1.9 Hz, 1H), 3.80 (s, 2H), 3.42 (d, J = 11.9 Hz, 2H), 3.07 (t, J = 11.1 Hz, 2H), 2.93 (d, J = 12.5 Hz, 2H), 2.82 (s, 3H), 2.43 (t, J = 11.8 Hz, 2H), MS (ESI) m/z: 612[M + H]$^+$ |
| III-k-6 | 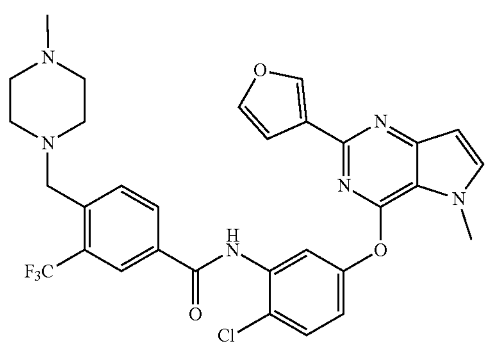 [SMILES: CN1CCN(Cc2ccc(C(=O)Nc3cc(Oc4nc(-c5ccoc5)nc5ccn(C)c45)ccc3Cl)cc2C(F)(F)F)CC1] | $^1$H NMR (600 MHz, DMSO-$d_6$) δ 10.46 (s, 1H), 8.31 (d, J = 1.2 Hz, 1H), 8.26 (d, J = 8.1 Hz, 1H), 8.11-8.09 (m, 1H), 7.95 (d, J = 8.2 Hz, 1H), 7.78 (d, J = 3.0 Hz, 1H), 7.74 (d, J = 2.8 Hz, 1H), 7.72-7.69 (m, 2H), 7.43 (dd, 1H), 6.88-6.87 (m, 1H), 6.60 (d, J = 3.0 Hz, 1H), 4.11 (s, 3H), 3.69 (s, 2H), 2.17 (s, 3H). MS (ESI) m/z: 626[M + H]$^+$ |
| III-k-7 | 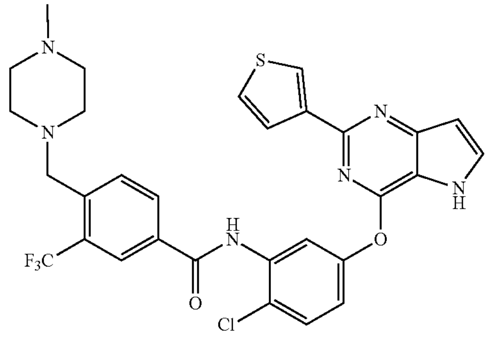 [SMILES: CN1CCN(Cc2ccc(C(=O)Nc3cc(Oc4nc(-c5ccsc5)nc5cc[nH]c45)ccc3Cl)cc2C(F)(F)F)CC1] | $^1$H NMR (600 MHz, DMSO-$d_6$) δ 12.34 (s, 1H), 10.45 (s, 1H), 8.30 (d, J = 1.3 Hz, 1H), 8.28-8.25 (m, 1H), 8.03 (dd, J = 3.1, 1.2 Hz, 1H), 7.95 (d, J = 8.2 Hz, 1H), 7.82 (t, J = 2.9 Hz, 1H), 7.74-7.70 (m, 2H), 7.66 (dd, J = 5.0, 1.1 Hz, 1H), 7.54 (dd, J = 5.0, 3.1 Hz, 1H), 7.42 (dd, J = 8.8, 2.8 Hz, 1H), 6.68 (dd, J = 3.0, 1.7 Hz, 1H), 3.69 (s, 2H), 2.18 (s, 3H). MS (ESI) m/z: 628 [M + H]$^+$ |

TABLE 3-continued

Structure and characterization of compounds III

| No. | Structure | ¹H NMR and/or MS data |
|---|---|---|
| III-k-8 | (TFA salt) | ¹H NMR (600 MHz, MeOH) δ 8.35 (s, 2H), 8.26 (d, J = 8.2 Hz, 1H), 8.05-8.01 (m, 2H), 7.91 (d, J = 3.0 Hz, 1H), 7.76-7.72 (m, 2H), 7.58 (dt, J = 8.0, 4.0 Hz, 1H), 7.41 (dd, J = 8.8, 2.7 Hz, 1H), 6.75 (d, J = 3.0 Hz, 1H), 4.27 (s, 3H), 3.90 (s, 2H), 3.51 (s, 2H), 3.21 (s, 2H), 3.06 (d, J = 7.9 Hz, 2H), 2.93 (s, 3H), 2.56 (s, 2H). MS (ESI) m/z: 642[M + H]⁺ |
| III-k-9 | (TFA salt) | ¹H NMR (600 MHz, MeOH) δ 8.35 (d, J = 1.4 Hz, 1H), 8.26 (dd, J = 8.1, 1.5 Hz, 1H), 8.05-8.01 (m, 5H), 7.74 (d, 1H), 7.41 (dd, J = 8.8, 2.8 Hz, 1H), 6.94-6.90 (m, 2H), 6.83 (d, J = 3.0 Hz, 1H), 3.89 (s, 2H), 3.51 (s, 2H), 3.21 (d J = 5.7 Hz, 2H), 3.05 (s, 2H), 2.93 (s, 3H), 2.57 (s, 2H). MS (ESI) m/z: 638[M + H]⁺ |
| III-k-10 | 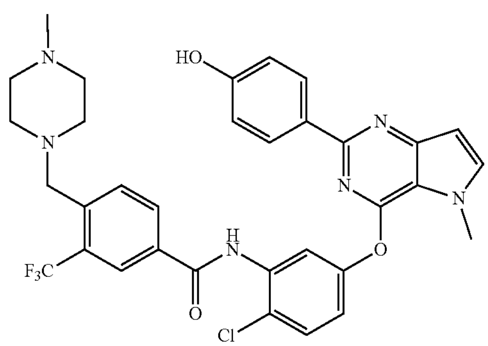 | ¹H NMR (600 MHz, DMSO-d₆) δ 10.47 (s, 1H), 9.73 (s, 1H), 8.31 (d, J = 1.2 Hz, 1H), 8.27 (d, J = 8.1 Hz, 1H), 8.05-8.00 (m, 2H), 7.95 (d, J = 8.2 Hz, 1H), 7.76 (d, J = 3.0 Hz, 1H), 7.72 (dd, J = 5.8, 2.9 Hz, 2H), 7.44 (dd, J = 8.8, 2.8 Hz, 1H), 6.79-6.75 (m, 2H), 6.60 (d, J = 3.0 Hz, 1H), 4.11 (s, 3H), 3.70 (s, 2H), 2.23 (s, 3H). MS (ESI) m/z: 662[M + H]⁺ |
| III-k-11 | 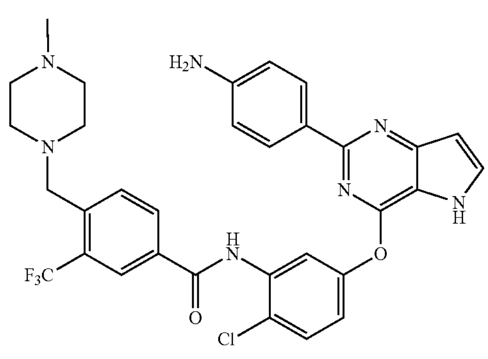 [SMILES: CN1CCN(Cc2ccc(C(=O)Nc3cc(Oc4nc(-c5ccc(N)cc5)nc5cc[nH]c45)ccc3Cl)cc2C(F)(F)F)CC1] | ¹H NMR (600 MHz, DMSO-d₆) δ 12.15 (s, 1H), 10.44 (s, 1H), 8.30 (s, 1H), 8.26 (d, J = 8.1 Hz, 1H), 7.94 (d, J = 8.2 Hz, 1H), 7.89 (d, J = 8.6 Hz, 2H), 7.74 (t, J = 2.9 Hz, 1H), 7.71 (d, J = 8.8 Hz, 1H), 7.68 (d, J = 2.8 Hz, 1H), 7.40 (dd, J = 8.8, 2.8 Hz, 1H), 6.59 (dd, J = 2.8, 1.8 Hz, 1H), 6.54 (d, J = 8.6 Hz, 2H), 5.38 (s, 2H), 3.68 (s, 2H), 2.17 (s, 3H). MS (ESI) m/z: 637[M + H]⁺ |

TABLE 3-continued

Structure and characterization of compounds III

| No. | Structure | ¹H NMR and/or MS data |
|---|---|---|
| III-k-12 | 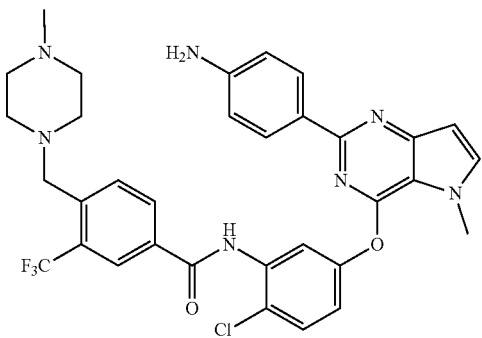 [SMILES: CN1CCN(Cc2ccc(C(=O)Nc3cc(Oc4nc(-c5ccc(N)cc5)nc5ccn(C)c45)ccc3Cl)cc2C(F)(F)F)CC1] | ¹H NMR (600 MHz, DMSO-d$_6$) δ 10.44 (s, 1H), 8.26 (d, J = 28.6 Hz, 2H), 7.96-7.83 (m, 3H), 7.73-7.65 (m, 3H), 7.52 (d, J = 33.2 Hz, 1H), 7.41 (s, 1H), 4.07 (s, 2H), 2.51 (s, 3H), 2.15 (s, 3H). MS (ESI) m/z: 651[M + H]$^+$ |
| III-k-13 | 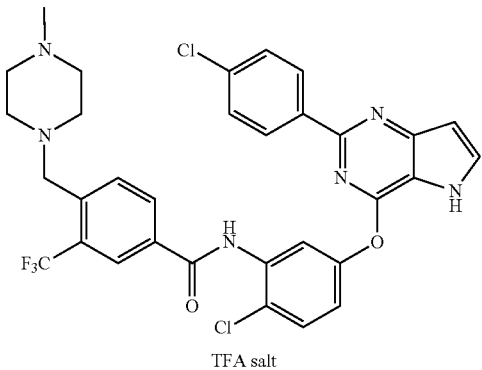 [SMILES: CN1CCN(Cc2ccc(C(=O)Nc3cc(Oc4nc(-c5ccc(Cl)cc5)nc5cc[nH]c45)ccc3Cl)cc2C(F)(F)F)CC1]<br>TFA salt | ¹H NMR (600 MHz, DMSO-d$_6$) δ 12.45 (s, 1H), 10.50 (s, 1H), 8.35 (s, 1H), 8.29 (d, J = 8.1 Hz, 1H), 8.22 (d, J = 8.6 Hz, 2H), 7.95 (d, J = 8.2 Hz, 1H), 7.87 (t, J = 2.9 Hz, 1H), 7.74-7.71 (m, 2H), 7.47 (d, J = 8.6 Hz, 2H), 7.44 (dd, J = 8.8, 2.8 Hz, 1H), 6.72 (dd, J = 2.9, 1.9 Hz, 1H), 3.80 (s, 2H), 3.42 (d, J = 11.6 Hz, 2H), 3.07 (t, J = 11.0 Hz, 2H), 2.93 (d, J = 12.3 Hz, 2H), 2.81 (s, 3H), 2.43 (t, J = 11.8 Hz, 2H). MS (ESI) m/z: 656[M + H]$^+$ |
| III-k-14 | 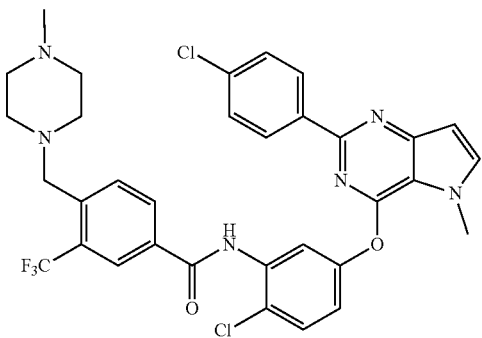 [SMILES: CN1CCN(Cc2ccc(C(=O)Nc3cc(Oc4nc(-c5ccc(Cl)cc5)nc5ccn(C)c45)ccc3Cl)cc2C(F)(F)F)CC1] | ¹H NMR (600 MHz, DMSO-d$_6$) δ 10.47 (s, 1H), 8.32 (s, 1H), 8.27 (d, J = 8.1 Hz, 1H), 8.22-8.18 (m, 2H), 7.95 (d, J = 8.2 Hz, 1H), 7.83 (d, J = 3.0 Hz, 1H), 7.76 (d, J = 2.7 Hz, 1H), 7.73 (d, J = 8.8 Hz, 1H), 7.48-7.44 (m, 3H), 6.68 (d, J = 3.0 Hz, 1H), 4.13 (s, 3H), 3.70 (s, 2H), 2.26 (s, 3H). MS (ESI) m/z: 670[M + H]$^+$ |
| III-k-15 | 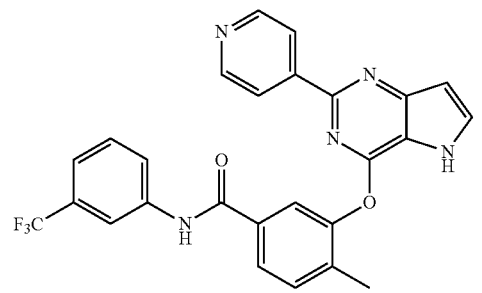 | ¹H NMR (600 MHz, DMSO-d$_6$) δ 12.45 (s, 1H), 10.51 (s, 1H), 8.32 (s, 1H), 8.27 (d, J = 8.1 Hz, 1H), 8.07 (d, J = 8.1 Hz, 2H), 7.94 (d, J = 8.2 Hz, 1H), 7.85 (t, J = 2.8 Hz, 1H), 7.72 (t, J = 5.9 Hz, 2H), 7.42 (dd, J = 8.7, 2.8 Hz, 1H), 7.22 (d, J = 8.1 Hz, 2H), 6.70 (t, 1H), 3.79 (s, 2H), 3.39 (s, 2H), 3.06 (s, 2H), 2.91 (s, 2H), 2.80 (s, 3H), 2.43 (s, 2H), 2.32 (s, 3H). MS (ESI) m/z: 636[M + H]$^+$ |

TABLE 3-continued

Structure and characterization of compounds III

| No. | Structure | ¹H NMR and/or MS data |
|---|---|---|
| III-k-16 | 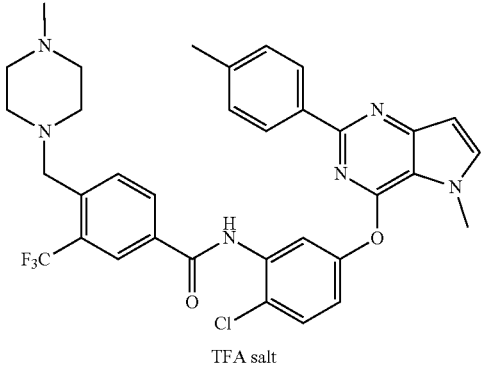 [SMILES: Cc1ccc(-c2nc(Oc3ccc(Cl)c(NC(=O)c4ccc(CN5CCN(C)CC5)c(C(F)(F)F)c4)c3)c3c(ccn3C)n2)cc1] TFA salt | ¹H NMR (600 MHz, DMSO-d₆) δ 10.51 (s, 1H), 8.36 (d, J = 1.3 Hz, 1H), 8.31-8.28 (m, 1H), 8.08 (d, J = 8.2 Hz, 2H), 7.95 (d, J = 8.2 Hz, 1H), 7.82 (d, J = 3.0 Hz, 1H), 7.75-7.72 (m, 2H), 7.46 (dd, J = 8.8, 2.8 Hz, 1H), 7.22 (d, J = 8.0 Hz, 2H), 6.65 (d, J = 3.0 Hz, 1H), 4.13 (s, 3H), 3.80 (s, 2H), 3.42 (d, J = 11.9 Hz, 2H), 3.07 (t, J = 11.2 Hz, 2H), 2.94 (d, J = 12.4 Hz, 2H), 2.82 (s, 3H), 2.43 (t, J = 11.8 Hz, 2H), 2.32 (s, 3H). MS (ESI) m/z: 650[M + H]⁺ |
| III-k-17 | 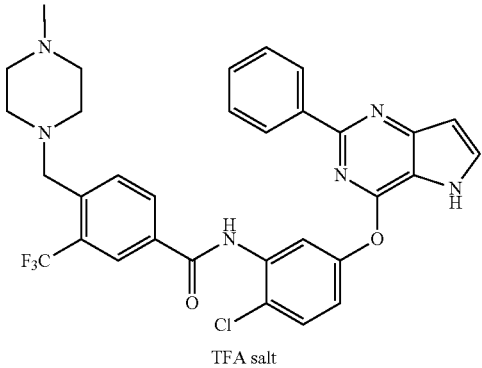 [SMILES: CN1CCN(Cc2ccc(C(=O)Nc3cc(Oc4nc(-c5ccccc5)nc5cc[nH]c45)ccc3Cl)cc2C(F)(F)F)CC1] TFA salt | ¹H NMR (600 MHz, DMSO-d₆) δ 12.40 (s, 1H), 10.50 (s, 1H), 8.32 (s, 1H), 8.27 (d, J = 8.1 Hz, 1H), 8.21-8.18 (m, 2H), 7.94 (d, J = 8.2 Hz, 1H), 7.84 (t, J = 2.9 Hz, 1H), 7.73 (d, J = 8.8 Hz, 1H), 7.70 (d, J = 2.8 Hz, 1H), 7.44-7.39 (m, 4H), 6.72 (dd, J = 2.9, 1.9 Hz, 1H), 3.78 (s, 2H), 3.39 (d, J = 11.4 Hz, 2H), 3.05 (d, J = 10.5 Hz, 2H), 2.92 (d, J = 10.9 Hz, 2H), 2.80 (s, 3H), 2.42 (t, J = 11.8 Hz, 2H). MS (ESI) m/z: 622[M + H]⁺ |
| III-k-18 | 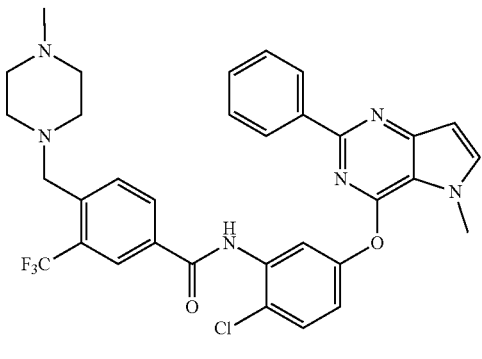 [SMILES: CN1CCN(Cc2ccc(C(=O)Nc3cc(Oc4nc(-c5ccccc5)nc5ccn(C)c45)ccc3Cl)cc2C(F)(F)F)CC1] | ¹H NMR (600 MHz, DMSO-d₆) δ 12.40 (s, 1H), 8.29 (s, 1H), 8.24 (d, J = 8.1 Hz, 1H), 8.18 (dd, J = 7.6, 1.9 Hz, 2H), 7.92 (d, J = 8.1 Hz, 1H), 7.77 (d, J = 3.0 Hz, 1H), 7.74 (d, J = 2.7 Hz, 1H), 7.71 (d, J = 8.8 Hz, 1H), 7.44 (dd, J = 8.8, 2.8 Hz, 1H), 7.41-7.37 (m, 3H), 6.66 (d, J = 3.0 Hz, 1H), 4.11 (s, 3H), 3.66 (s, 2H), 2.15 (d, J = 7.1 Hz, 3H). MS (ESI) m/z: 636[M + H]⁺ |
| III-l-1 | 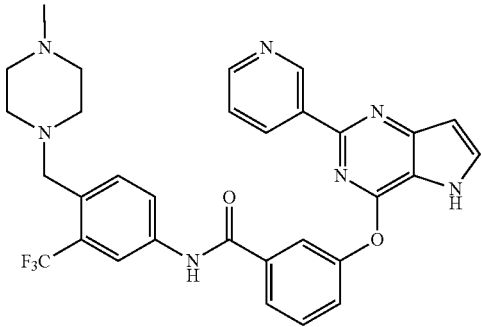 [SMILES: CN1CCN(Cc2ccc(NC(=O)c3cccc(Oc4nc(-c5cccnc5)nc5cc[nH]c45)c3)cc2C(F)(F)F)CC1] | ¹H NMR (600 MHz, DMSO-d₆) δ 12.51 (s, 1H), 10.60 (s, 1H), 9.23 (d, J = 2.0 Hz, 1H), 8.55 (dd, J = 4.7, 1.7 Hz, 1H), 8.42 (dt, J = 7.9, 1.9 Hz, 1H), 8.20 (d, J = 2.2 Hz, 1H), 8.04 (dq, J = 4.5, 2.2 Hz, 2H), 8.02-7.96 (m, 1H), 7.90 (d, J = 3.1 Hz, 1H), 7.75-7.71 (m, 2H), 7.69 (d, J = 8.6 Hz, 1H), 7.42 (dd, J = 7.9, 4.7 Hz, 1H), 6.77 (d, J = 3.0 Hz, 1H), 3.55 (s, 2H), 2.38 (s, 8H), 2.17 (s, 3H). MS(ESI) m/z: 588[M + H]⁺. |

TABLE 3-continued

Structure and characterization of compounds III

| No. | Structure | $^1$H NMR and/or MS data |
|---|---|---|
| III-l-2 | 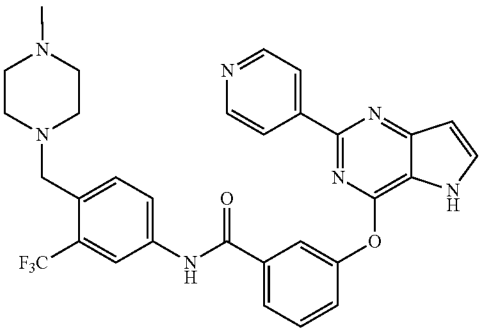 [SMILES: CN1CCN(Cc2ccc(NC(=O)c3cccc(Oc4nc(-c5ccncc5)nc5cc[nH]c45)c3)cc2C(F)(F)F)CC1] | $^1$H NMR (600 MHz, DMSO-$d_6$) δ 12.59 (s, 1H), 10.60 (s, 1H), 8.60 (d, J = 5.4 Hz, 2H), 8.21 (d, J = 2.1 Hz, 1H), 8.08-8.04 (m, 2H), 8.03-7.99 (m, 3H), 7.94 (d, J = 3.0 Hz, 1H), 7.73 (d, J = 7.2 Hz, 2H), 7.70 (d, J = 8.6 Hz, 1H), 6.80 (d, J = 3.0 Hz, 1H), 3.56 (s, 2H), 2.44-2.35 (m, 8H), 2.19 (s, 3H). MS(ESI) m/z: 588[M + H]$^+$. |
| III-l-3 | TFA Salt | $^1$H NMR (600 MHz, DMSO-$d_6$) δ 10.67 (s, 1H), 9.24 (s, 1H), 8.69 (d, J = 4.2 Hz, 1H), 8.64-8.60 (m, 1H), 8.23 (d, J = 2.1 Hz, 1H), 8.11 (dd, J = 8.6, 1.9 Hz, 1H), 8.07 (d, J = 2.0 Hz, 1H), 8.01 (dt, J = 6.5, 1.8 Hz, 1H), 7.92 (d, J = 3.1 Hz, 1H), 7.75 (dd, J = 5.5, 3.5 Hz, 2H), 7.72 (d, J = 8.6 Hz, 1H), 6.76 (d, J = 3.1 Hz, 1H), 4.19 (s, 3H), 3.70 (s, 2H), 3.05 (s, 2H), 2.93 (s, 2H), 2.81 (s, 3H), 2.40 (s, 2H). MS (ESI) m/z: 602[M + H]$^+$. |
| III-l-4 | TFA Salt | $^1$H NMR (600 MHz, DMSO-$d_6$) δ 10.71 (s, 1H), 8.84 (s, 2H), 8.35 (s, 2H), 8.24 (d, J = 1.6 Hz, 1H), 8.12 (d, J = 8.4 Hz, 1H), 8.09 (s, 1H), 8.03 (d, J = 6.8 Hz, 1H), 7.99 (d, J = 3.0 Hz, 1H), 4.21 (s, 3H), 3.71 (s, 2H), 3.06 (s, 2H), 2.93 (s, 2H), 2.81 (s, 3H). MS (ESI) m/z: 602[M + H]$^+$. |
| III-m-1 | 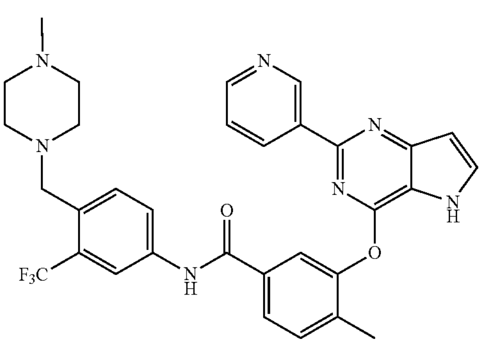 [SMILES: Cc1ccc(C(=O)Nc2ccc(CN3CCN(C)CC3)c(C(F)(F)F)c2)cc1Oc1nc(-c2cccnc2)nc2cc[nH]c12] | $^1$H NMR (600 MHz, DMSO-$d_6$) δ 12.54 (d, J = 2.9 Hz, 1H), 10.50 (s, 1H), 9.16 (d, J = 2.1 Hz, 1H), 8.54 (dd, J = 4.8, 1.7 Hz, 1H), 8.37 (dt, J = 8.0, 2.0 Hz, 1H), 8.18 (d, J = 2.2 Hz, 1H), 8.04 (dd, J = 8.6, 2.2 Hz, 1H), 8.02 (d, J = 1.8 Hz, 1H), 7.97 (dd, J = 7.9, 1.8 Hz, 1H), 7.91 (t, J = 2.8 Hz, 1H), 7.69 (d, J = 8.6 Hz, 1H), 7.63 (d, J = 8.0 Hz, 1H), 7.41 (dd, J = 8.0, 4.7 Hz, 1H), 6.77 (d, J = 2.8 Hz, 1H), 3.56 (s, 2H), 2.39 (s, 8H), 2.28 (s, 3H), 2.18 (s, 3H). MS(ESI) m/z: 602[M + H]$^+$. |

TABLE 3-continued

Structure and characterization of compounds III

| No. | Structure | $^1$H NMR and/or MS data |
|---|---|---|
| III-m-2 | 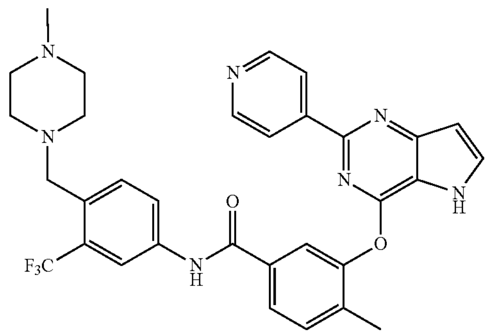 [SMILES: Cc1ccc(C(=O)Nc2ccc(CN3CCN(C)CC3)c(C(F)(F)F)c2)cc1Oc1nc(-c2ccncc2)nc2cc[nH]c12] | $^1$H NMR (600 MHz, DMSO-d$_6$) δ 12.62 (s, 1H), 10.51 (s, 1H), 8.59 (d, J = 5.4 Hz, 2H), 8.19 (d, J = 2.1 Hz, 1H), 8.13-8.01 (m, 2H), 7.98 (dd, J = 7.9, 1.8 Hz, 1H), 7.95 (q, J = 2.8, 2.3 Hz, 3H), 7.69 (d, J = 8.6 Hz, 1H), 7.63 (d, J = 8.0 Hz, 1H), 6.81 (d, J = 3.0 Hz, 1H), 3.57 (s, 2H), 2.43 (s, 8H), 2.27 (s, 3H), 2.25 (s, 3H). MS(ESI) m/z: 602[M + H]$^+$. |
| III-m-3 | TFA Salt | $^1$H NMR (600 MHz, Methanol-d$_4$) δ 8.11 (s, 1H), 8.09-8.06 (m, 2H), 7.94 (s, 1H), 7.90 (d, J = 8.0 Hz, 2H), 7.72 (t, J = 6.8 Hz, 2H), 7.55 (d, J = 8.0 Hz, 1H), 7.32 (d, J = 6.4 Hz, 3H), 6.73 (d, J = 3.0 Hz, 1H), 3.63 (s, 2H), 2.31 (s, 3H), 2.29 (s, 3H). MS (ESI) m/z: 601[M + H]$^+$. |
| III-m-4 | TFA Salt | $^1$H NMR (600 MHz, DMSO-d$_6$) δ 12.56 (s, 1H), 10.57 (s, 1H), 8.21 (d, J = 1.9 Hz, 1H), 8.11 (d, J = 8.5 Hz, 1H), 8.03 (d, J = 1.4 Hz, 1H), 7.96 (d, J = 8.2 Hz, 3H), 7.91 (t, J = 2.9 Hz, 1H), 7.71 (d, J = 8.6 Hz, 1H), 7.63 (d, J = 8.1 Hz, 1H), 7.18 (d, J = 8.1 Hz, 2H), 6.73 (dd, J = 2.8, 1.9 Hz, 1H), 3.72 (s, 2H), 3.05 (s, 2H), 2.95 (s, 2H), 2.81 (s, 3H), 2.29 (d, J = 6.7 Hz, 6H). MS (ESI) m/z: 615[M + H]$^+$. |
| III-m-5 | TFA Salt | $^1$H NMR (600 MHz, DMSO-d$_6$) δ 12.57 (s, 1H), 10.56 (s, 1H), 8.21 (s, 1H), 8.10 (d, J = 8.2 Hz, 1H), 8.06 (d, J = 6.6 Hz, 2H), 8.02 (d, J = 6.8 Hz, 1H), 7.97 (d, J = 7.9 Hz, 1H), 7.92 (s, 1H), 7.70 (d, J = 8.4 Hz, 1H), 7.64 (d, J = 8.0 Hz, 1H), 7.41 (d, J = 7.7 Hz, 2H), 6.77 (s, 1H), 3.69 (s, 2H), 3.04 (s, 2H), 2.92 (s, 2H), 2.81 (s, 3H), 2.40 (s, 2H), 2.29 (s, 3H). MS (ESI) m/z: 635[M + H]$^+$. |

TABLE 3-continued

Structure and characterization of compounds III

| No. | Structure | ¹H NMR and/or MS data |
|---|---|---|
| III-m-6 | 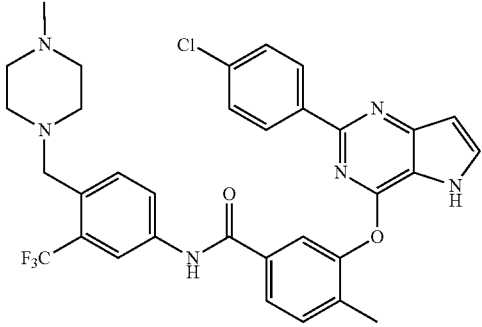 [SMILES: Cc1ccc(C(=O)Nc2ccc(CN3CCN(C)CC3)c(C(F)(F)F)c2)cc1Oc1nc(-c2ccc(Cl)cc2)nc2cc[nH]c12] | ¹H NMR (600 MHz, DMSO-d$_6$) δ 12.50 (s, 1H), 10.49 (s, 1H), 8.18 (s, 1H), 8.10-8.01 (m, 4H), 7.96 (d, J = 8.2 Hz, 1H), 7.90 (s, 1H), 7.71-7.66 (m, 2H), 7.62 (d, J = 8.2 Hz, 1H), 7.43 (d, J = 8.5 Hz, 2H), 6.74 (s, 1H), 3.55 (s, 2H), 2.27 (s, 3H), 2.15 (s, 3H). MS (ESI) m/z: 635[M + H]⁺. |
| III-m-7 | 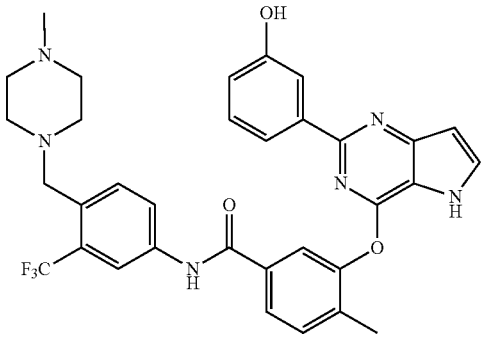<br>TFA Salt | ¹H NMR (600 MHz, DMSO-d$_6$) δ 12.46 (s, 1H), 10.54 (s, 1H), 8.20 (d, J = 2.1 Hz, 1H), 8.10 (dd, J = 8.6, 1.9 Hz, 1H), 7.99 (d, J = 1.6 Hz, 1H), 7.97 (dd, J = 7.9, 1.7 Hz, 1H), 7.88 (t, J = 2.9 Hz, 1H), 7.70 (d, J = 8.6 Hz, 1H), 7.63 (d, J = 8.1 Hz, 1H), 7.56-7.54 (m, 1H), 7.49 (d, J = 7.8 Hz, 1H), 7.13 (t, J = 7.9 Hz, 1H), 6.78-6.74 (m, 1H), 6.72 (dd, J = 3.0, 1.9 Hz, 1H), 3.68 (s, 2H), 3.40 (d, J = 9.5 Hz, 2H), 3.04 (s, 2H), 2.92 (d, J = 10.5 Hz, 2H), 2.80 (s, 3H), 2.39 (s, 2H), 2.27 (s, 3H). MS (ESI) m/z: 617[M + H]⁺. |
| III-m-8 | 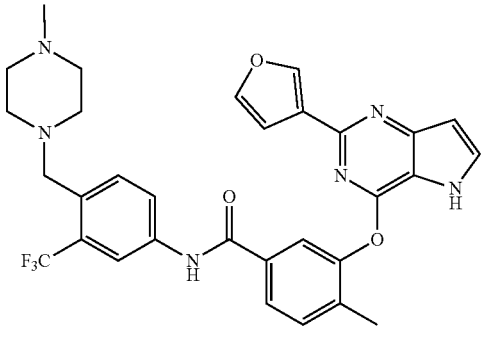 | ¹H NMR (600 MHz, DMSO-d$_6$) δ 12.38 (s, 1H), 10.49 (s, 1H), 8.19 (s, 1H), 8.05 (d, J = 8.2 Hz, 1H), 8.01 (s, 1H), 7.93 (d, J = 13.7 Hz, 2H), 7.83 (s, 1H), 7.69 (d, J = 8.0 Hz, 1H), 7.65 (s, 1H), 7.59 (d, J = 7.6 Hz, 1H), 6.75 (s, 1H), 6.66 (s, 1H), 3.55 (s, 2H), 2.26 (s, 3H), 2.15 (s, 3H). MS (ESI) m/z: 591 [M + H]⁺. |
| III-m-9 | 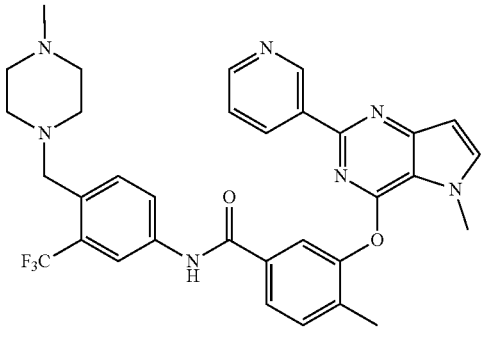 [SMILES: Cc1ccc(C(=O)Nc2ccc(CN3CCN(C)CC3)c(C(F)(F)F)c2)cc1Oc1nc(-c2cccnc2)nc2ccn(C)c12] | ¹H NMR (600 MHz, Chloroform-d) δ 9.44 (s, 1H), 9.12 (d, J = 2.0 Hz, 1H), 8.42 (dd, J = 4.8, 1.6 Hz, 1H), 8.22 (dt, J = 8.1, 1.9 Hz, 1H), 7.93 (d, J = 2.1 Hz, 1H), 7.88-7.85 (m, 2H), 7.82 (dd, J = 7.9, 1.7 Hz, 1H), 7.65 (d, J = 8.5 Hz, 1H), 7.35 (d, J = 7.9 Hz, 1H), 7.31-7.28 (m, 1H), 7.09 (dd, J = 8.0, 4.8 Hz, 1H), 6.63 (d, J = 3.0 Hz, 1H), 4.09 (s, 3H), 3.58 (s, 2H), 2.31 (s, 3H), 2.21 (s, 3H). MS(ESI) m/z: 616[M + H]⁺. |

TABLE 3-continued

Structure and characterization of compounds III

| No. | Structure | ¹H NMR and/or MS data |
|---|---|---|
| III-m-10 | 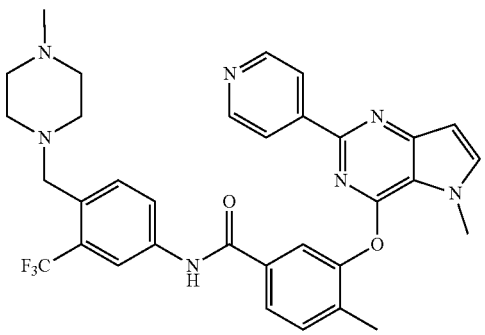 [SMILES: Cc1ccc(C(=O)Nc2ccc(CN3CCN(C)CC3)c(C(F)(F)F)c2)cc1Oc1nc(-c2ccncc2)nc2ccn(C)c12] | ¹H NMR (600 MHz, Chloroform-d) δ 9.21 (s, 1H), 8.52-8.46 (m, 2H), 7.95 (d, J = 2.2 Hz, 1H), 7.87 (td, J = 4.7, 3.9, 1.8 Hz, 3H), 7.85-7.82 (m, 2H), 7.70 (d, J = 8.5 Hz, 1H), 7.45 (d, J = 7.8 Hz, 1H), 7.36 (d, J = 3.1 Hz, 1H), 6.70 (d, J = 3.1 Hz, 1H), 4.11 (s, 3H), 3.61 (s, 2H), 2.51 (s, 8H), 2.30 (s, 3H), 2.26 (s, 3H). MS (ESI) m/z: 616[M + H]⁺. |
| III-m-11 | 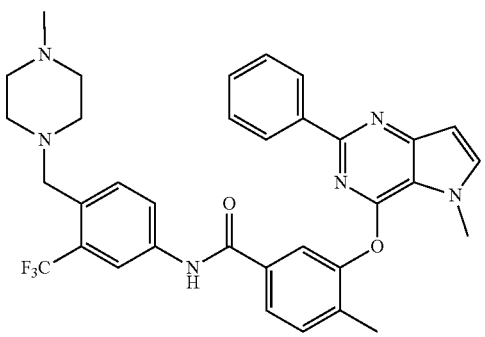 [SMILES: Cc1ccc(C(=O)Nc2ccc(CN3CCN(C)CC3)c(C(F)(F)F)c2)cc1Oc1nc(-c2ccccc2)nc2ccn(C)c12] | ¹H NMR (600 MHz, DMSO-d₆) δ 10.52 (s, 1H), 8.19 (s, 1H), 8.07 (dd, J = 13.2, 7.9 Hz, 4H), 7.95 (d, J = 8.0 Hz, 1H), 7.84 (d, J = 2.9 Hz, 1H), 7.69 (d, J = 8.6 Hz, 1H), 7.62 (d, J = 8.0 Hz, 1H), 7.37-7.33 (m, 3H), 6.69 (d, J = 3.0 Hz, 1H), 4.19 (s, 3H), 3.55 (s, 2H), 2.30 (s, 3H), 2.15 (s, 3H). MS (ESI) m/z: 615[M + H]⁺. |
| III-m-12 | 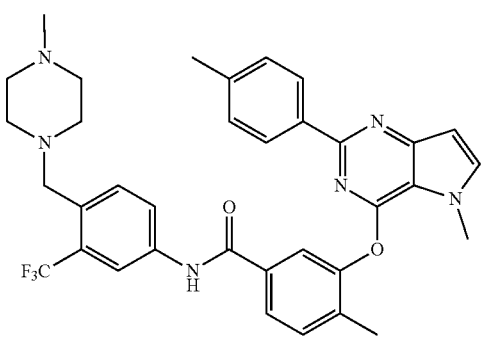 [SMILES: Cc1ccc(-c2nc(Oc3cc(C(=O)Nc4ccc(CN5CCN(C)CC5)c(C(F)(F)F)c4)ccc3C)c3c(ccn3C)n2)cc1] | ¹H NMR (600 MHz, DMSO-d₆) δ 10.52 (s, 1H), 8.18 (d, J = 2.1 Hz, 1H), 8.05 (dd, J = 10.5, 1.6 Hz, 2H), 7.94 (dd, J = 11.2, 4.9 Hz, 3H), 7.82 (d, J = 3.1 Hz, 1H), 7.69 (d, J = 8.6 Hz, 1H), 7.61 (d, J = 8.1 Hz, 1H), 7.14 (d, J = 8.0 Hz, 2H), 6.66 (d, J = 3.1 Hz, 1H), 4.17 (s, 3H), 3.55 (s, 2H), 2.29 (s, 3H), 2.27 (s, 3H), 2.16 (s, 3H). MS (ESI) m/z: 629[M + H]⁺. |
| III-m-13 | 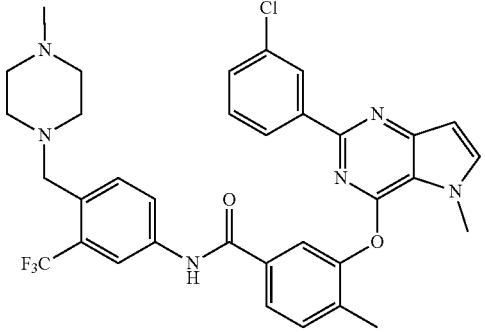 [SMILES: Cc1ccc(C(=O)Nc2ccc(CN3CCN(C)CC3)c(C(F)(F)F)c2)cc1Oc1nc(-c2cccc(Cl)c2)nc2ccn(C)c12] | ¹H NMR (600 MHz, DMSO-d₆) δ 10.52 (s, 1H), 8.19 (s, 1H), 8.08 (s, 1H), 8.05 (d, J = 7.8 Hz, 2H), 8.00 (d, J = 7.3 Hz, 1H), 7.96 (d, J = 7.9 Hz, 1H), 7.88 (d, J = 2.8 Hz, 1H), 7.69 (d, J = 8.6 Hz, 1H), 7.62 (d, J = 8.0 Hz, 1H), 7.43-7.37 (m, 2H), 6.72 (d, J = 2.7 Hz, 1H), 4.20 (s, 3H), 3.55 (s, 2H), 2.51 (s, 2H), 2.31 (s, 3H), 2.16 (s, 3H). MS (ESI) m/z: 650[M + H]⁺. |

TABLE 3-continued

Structure and characterization of compounds III

| No. | Structure | ¹H NMR and/or MS data |
|---|---|---|
| III-m-14 | 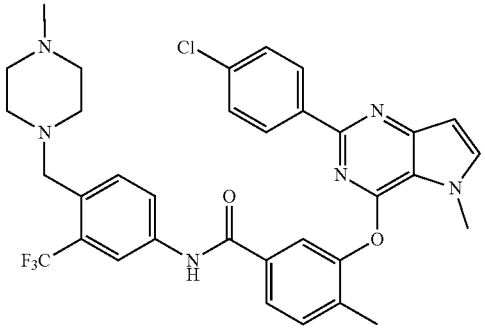 | ¹H NMR (600 MHz, DMSO-d$_6$) δ 10.52 (s, 1H), 8.18 (s, 1H), 8.05 (d, J = 8.5 Hz, 4H), 7.95 (d, J = 8.0 Hz, 1H), 7.86 (d, J = 2.7 Hz, 1H), 7.69 (d, J = 8.4 Hz, 1H), 7.61 (d, J = 8.0 Hz, 2H), 7.42 (d, J = 8.5 Hz, 1H), 6.70 (d, J = 2.9 Hz, 3H), 4.19 (d, J = 7.0 Hz, 2H), 2.29 (s, 3H), 2.15 (s, 3H). MS (ESI) m/z: 650[M + H]⁺. |
| III-m-15 | 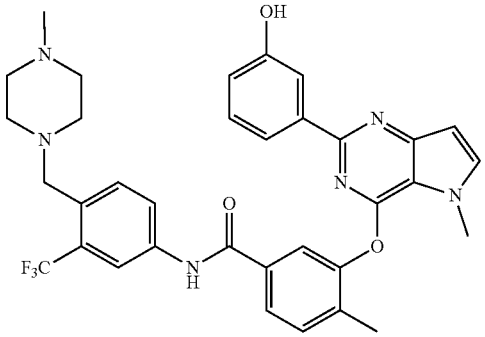<br>TFA Slat | ¹H NMR (600 MHz, DMSO-d$_6$) δ 10.59 (s, 1H), 8.22 (s, 1H), 8.11 (d, J = 8.6 Hz, 1H), 8.01 (s, 1H), 7.96 (d, J = 7.8 Hz, 1H), 7.85 (d, J = 2.7 Hz, 1H), 7.71 (d, J = 8.5 Hz, 1H), 7.62 (d, J = 8.0 Hz, 1H), 7.53 (s, 1H), 7.47 (d, J = 7.8 Hz, 1H), 7.13 (t, J = 7.9 Hz, 1H), 6.77 (d, J = 8.0 Hz, 1H), 6.68 (d, J = 2.8 Hz, 1H), 4.19 (s, 3H), 3.73 (s, 2H), 3.42 (s, 2H), 3.01 (d, J = 62.2 Hz, 4H), 2.81 (s, 3H), 2.45 (s, 2H), 2.30 (s, 3H). MS (ESI) m/z: 631[M + H]⁺. |
| III-m-16 | 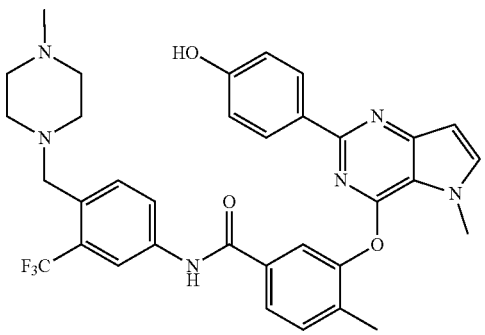 [SMILES: Cc1ccc(C(=O)Nc2ccc(CN3CCN(C)CC3)c(C(F)(F)F)c2)cc1Oc1nc(-c2ccc(Cl)cc2)nc2ccn(C)c12]<br>TFA Salt | ¹H NMR (600 MHz, DMSO-d$_6$) δ 10.60 (s, 1H), 8.22 (s, 1H), 8.11 (d, J = 8.2 Hz, 1H), 8.02 (s, 1H), 7.95 (d, J = 8.0 Hz, 1H), 7.89 (d, J = 8.3 Hz, 2H), 7.84 (s, 1H), 7.71 (d, J = 8.5 Hz, 1H), 7.62 (d, J = 8.0 Hz, 1H), 6.74 (d, J = 8.4 Hz, 2H), 6.64 (d, J = 2.1 Hz, 1H), 4.18 (s, 3H), 3.70 (s, 2H), 2.99 (d, J = 69.4 Hz, 4H), 2.81 (s, 3H), 2.42 (s, 2H), 2.30 (s, 3H). MS (ESI) m/z: 631[M + H]⁺. |
| III-m-17 | 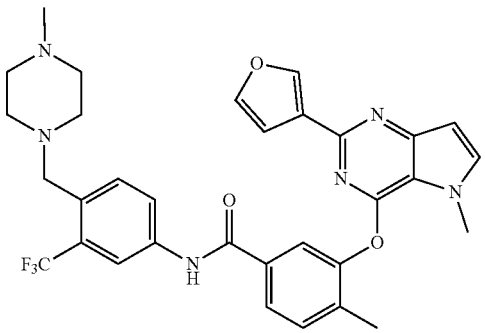 [SMILES: Cc1ccc(C(=O)Nc2ccc(CN3CCN(C)CC3)c(C(F)(F)F)c2)cc1Oc1nc(-c2ccoc2)nc2ccn(C)c12] | ¹H NMR (600 MHz, DMSO-d$_6$) δ 10.51 (s, 1H), 8.19 (s, 1H), 8.06 (d, J = 8.4 Hz, 1H), 8.03 (s, 1H), 7.94-7.90 (m, 2H), 7.80 (d, J = 2.0 Hz, 1H), 7.69 (d, J = 8.6 Hz, 1H), 7.66 (s, 1H), 7.58 (d, J = 7.9 Hz, 1H), 6.74 (s, 1H), 6.62 (d, J = 2.0 Hz, 1H), 4.17 (s, 3H), 3.55 (s, 2H), 2.29 (s, 3H), 2.17 (s, 3H). MS (ESI) m/z: 605[M + H]⁺. |

TABLE 3-continued

Structure and characterization of compounds III

| No. | Structure | ¹H NMR and/or MS data |
|---|---|---|
| III-m-18 | 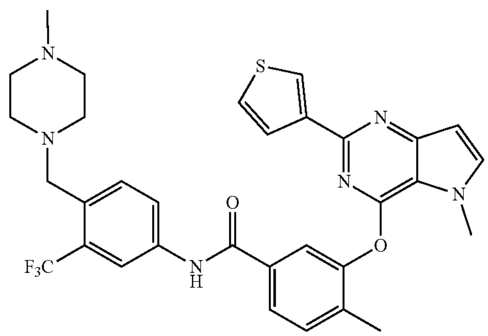 [SMILES: Cc1ccc(C(=O)Nc2ccc(CN3CCN(C)CC3)c(C(F)(F)F)c2)cc1Oc1nc(-c2ccsc2)nc2ccn(C)c12] | ¹H NMR (600 MHz, DMSO-d$_6$) δ 10.51 (s, 1H), 8.19 (s, 1H), 8.06 (d, J = 8.3 Hz, 1H), 8.03 (s, 1H), 7.94 (d, J = 7.9 Hz, 1H), 7.84 (s, 1H), 7.82 (s, 1H), 7.69 (d, J = 8.4 Hz, 1H), 7.60 (d, J = 7.8 Hz, 1H), 7.50 (s, 2H), 6.65 (d, J = 2.9 Hz, 1H), 4.17 (s, 3H), 3.55 (s, 2H), 2.29 (s, 3H), 2.15 (s, 3H). MS (ESI) m/z: 621[M + H]⁺. |
| III-m-19 | 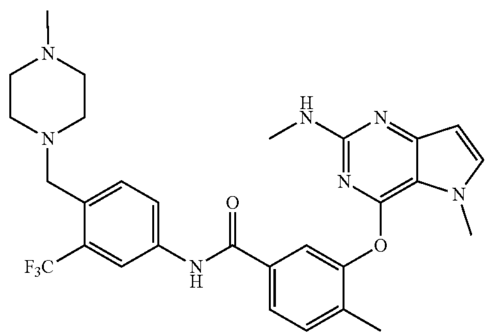 [SMILES: CNc1nc(Oc2cc(C(=O)Nc3ccc(CN4CCN(C)CC4)c(C(F)(F)F)c3)ccc2C)c2c(ccn2C)n1] | ¹H NMR (600 MHz, DMSO-d$_6$) δ 10.47 (s, 1H), 8.19 (d, J = 2.2 Hz, 1H), 8.07-8.04 (m, 1H), 7.89 (d, J = 1.7 Hz, 1H), 7.86 (dd, J = 7.9, 1.8 Hz, 1H), 7.70 (d, J = 8.5 Hz, 1H), 7.52 (d, J = 8.0 Hz, 1H), 7.46 (d, J = 3.0 Hz, 1H), 6.18 (d, J = 3.0 Hz, 2H), 3.99 (s, 3H), 3.56 (s, 2H), 2.64 (d, J = 4.8 Hz, 3H), 2.25 (s, 3H), 2.15 (s, 3H). MS (ESI) m/z: 568[M + H]⁺. |
| III-m-20 | TFA Salt | ¹H NMR (600 MHz, DMSO-d$_6$) δ 10.64 (s, 1H), 8.22 (s, 1H), 8.11 (d, J = 8.6 Hz, 1H), 8.00 (s, 1H), 7.93 (d, J = 7.9 Hz, 1H), 7.79 (s, 1H), 7.72 (d, J = 8.5 Hz, 1H), 7.58 (d, J = 8.0 Hz, 1H), 6.40 (s, 1H), 4.10 (s, 3H), 3.72 (s, 2H), 3.59 (s, 4H), 3.46 (s, 4H), 3.06 (s, 2H), 2.95 (s, 2H), 2.81 (s, 3H), 2.45 (s, 2H), 2.29 (s, 3H). MS (ESI) m/z: 624[M + H]⁺. |
| III-m-21 | TFA Salt | ¹H NMR (600 MHz, DMSO-d$_6$) δ 10.62 (s, 1H), 8.23 (s, 1H), 8.08 (d, J = 11.1 Hz, 2H), 7.93 (d, J = 7.8 Hz, 1H), 7.77 (d, J = 2.6 Hz, 1H), 7.72 (d, J = 8.5 Hz, 1H), 7.58 (d, J = 7.9 Hz, 1H), 6.39 (d, J = 2.6 Hz, 1H), 4.10 (s, 3H), 3.70 (s, 2H), 3.47 (d, J = 63.3 Hz, 4H), 2.99 (d, J = 74.8 Hz, 4H), 2.81 (s, 3H), 2.32 (s, 2H), 1.00 (d, J = 5.6 Hz, 6H). MS (ESI) m/z: 652[M + H]⁺. |

TABLE 3-continued

Structure and characterization of compounds III

| No. | Structure | ¹H NMR and/or MS data |
|---|---|---|
| III-m-22 | 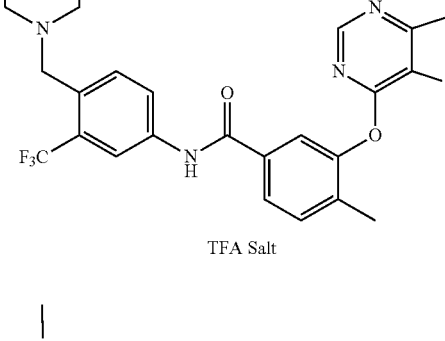<br>TFA Salt | ¹H NMR (600 MHz, DMSO-d$_6$) δ 10.57 (s, 1H), 8.41 (s, 1H), 8.21 (s, 1H), 8.11 (d, J = 7.8 Hz, 1H), 7.92 (s, 3H), 7.71 (d, J = 8.1 Hz, 1H), 7.57 (d, J = 8.2 Hz, 1H), 6.69 (s, 1H), 4.19 (s, 3H), 3.71 (s, 2H), 3.05 (s, 2H), 2.95 (s, 2H), 2.81 (s, 3H), 2.41 (d, J = 19.7 Hz, 2H), 2.24 (s, 3H). MS (ESI) m/z: 539[M + H]⁺. |
| III-m-23 | 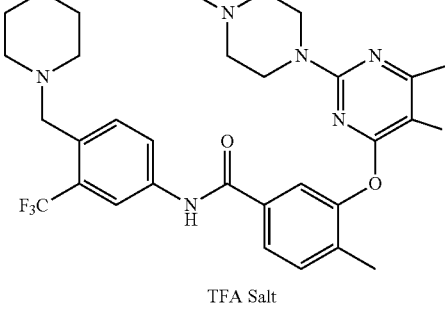<br>TFA Salt | ¹H NMR (600 MHz, DMSO-d$_6$) δ 10.49 (s, 1H), 8.19 (d, J = 1.8 Hz, 1H), 8.07 (d, J = 8.5 Hz, 1H), 7.97 (d, J = 1.3 Hz, 1H), 7.89-7.84 (m, 1H), 7.70 (d, J = 8.6 Hz, 1H), 7.55 (d, J = 2.9 Hz, 1H), 7.53 (d, J = 8.0 Hz, 1H), 6.23 (d, J = 2.9 Hz, 1H), 4.03 (s, 3H), 3.57 (s, 2H), 3.42 (s, 3H), 2.24 (s, 3H), 2.13 (s, 3H). MS (ESI) m/z: 637[M + H]⁺. |
| III-m-24 | 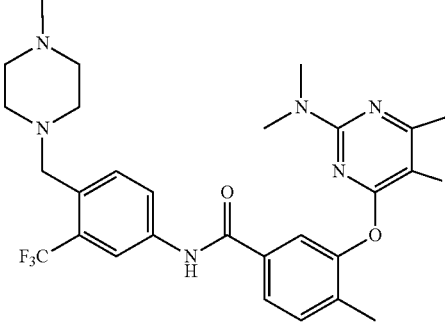<br>TFA Salt | ¹H NMR (600 MHz, Methanol-d$_4$) δ 8.19 (d, J = 2.2 Hz, 1H), 7.99 (dd, J = 8.5, 2.0 Hz, 1H), 7.94-7.92 (m, 2H), 7.78 (d, J = 8.5 Hz, 1H), 7.66 (d, J = 2.9 Hz, 1H), 7.57 (d, J = 8.5 Hz, 1H), 6.45 (d, J = 2.9 Hz, 1H), 4.19 (s, 3H), 3.79 (s, 2H), 3.08 (s, 6H), 2.92 (s, 3H), 2.37 (s, 3H). MS (ESI) m/z: 582[M + H]⁺. |
| III-m-25 | 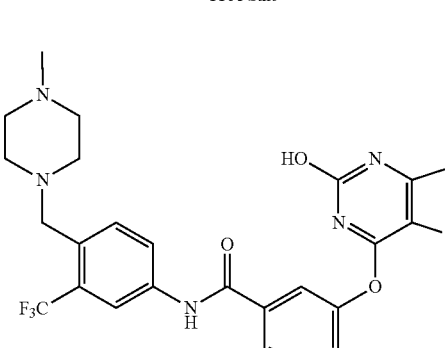 | ¹H NMR (600 MHz, DMSO-d$_6$) δ 11.31 (s, 1H), 10.50 (s, 1H), 8.19 (d, J = 2.1 Hz, 1H), 8.08-8.05 (m, 1H), 7.89 (dd, J = 7.9, 1.7 Hz, 1H), 7.84 (d, J = 1.7 Hz, 1H), 7.70 (d, J = 8.6 Hz, 1H), 7.53 (d, J = 8.1 Hz, 1H), 5.95 (d, J = 2.8 Hz, 1H), 3.98 (s, 3H), 3.57 (s, 2H), 2.23 (d, J = 12.8 Hz, 6H). MS (ESI) m/z: 555[M + H]⁺. |

TABLE 3-continued

Structure and characterization of compounds III

| No. | Structure | $^1$H NMR and/or MS data |
|---|---|---|
| III-m-26 | 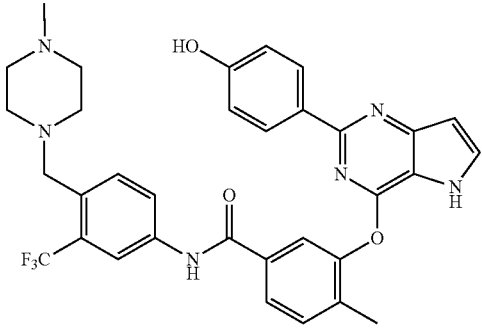 [SMILES: Cc1ccc(C(=O)Nc2ccc(CN3CCN(C)CC3)c(C(F)(F)F)c2)cc1Oc1nc(-c2ccc(O)cc2)nc2cc[nH]c12] | $^1$H NMR (600 MHz, DMSO-d$_6$) δ 12.30 (s, 1H), 10.49 (s, 1H), 9.70 (s, 1H), 8.19 (d, J = 1.7 Hz, 1H), 8.05 (d, J = 8.3 Hz, 1H), 8.00 (s, 1H), 7.95 (d, J = 7.9 Hz, 1H), 7.91 (d, J = 8.7 Hz, 2H), 7.81 (t, J = 2.8 Hz, 1H), 7.69 (d, J = 8.6 Hz, 1H), 7.62 (d, J = 8.1 Hz, 1H), 6.72 (d, J = 8.7 Hz, 2H), 6.66 (d, J = 1.7 Hz, 1H), 3.55 (s, 2H), 2.26 (s, 3H), 2.16 (s, 3H). MS (ESI) m/z: 617[M + H]$^+$ |
| III-m-27 | 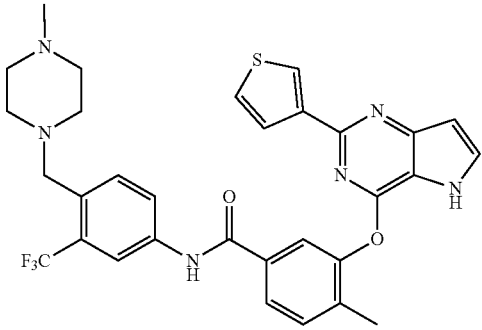<br>TFA salt | $^1$H NMR (600 MHz, DMSO-d$_6$) δ 12.50 (s, 1H), 10.54 (s, 1H), 8.21 (d, J = 2.0 Hz, 1H), 8.12-8.09 (m, 1H), 8.01 (d, J = 1.6 Hz, 1H), 7.95 (dd, J = 7.9, 1.7 Hz, 1H), 7.88 (t, J = 2.2 Hz, 2H), 7.70 (d, J = 8.6 Hz, 1H), 7.62 (d, J = 8.2 Hz, 1H), 7.54-7.50 (m, 2H), 6.71 (dd, J = 3.0, 1.9 Hz, 1H), 3.69 (s, 2H), 3.04 (s, 2H), 2.93 (d, J = 13.8 Hz, 2H), 2.81 (s, 3H), 2.39 (s, 2H), 2.28 (s, 3H). MS (ESI) m/z: 607[M + H]$^+$ |
| III-n-1 | 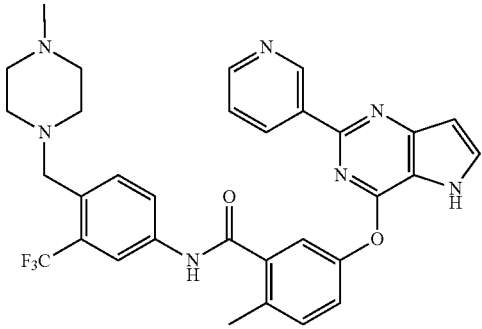 [SMILES: Cc1ccc(Oc2nc(-c3cccnc3)nc3cc[nH]c23)cc1C(=O)Nc1ccc(CN2CCN(C)CC2)c(C(F)(F)F)c1] | $^1$H NMR (600 MHz, DMSO-d$_6$) δ 12.45 (s, 1H), 10.67 (s, 1H), 9.28 (d, J = 2.1 Hz, 1H), 8.58 (dd, J = 4.8, 1.7 Hz, 1H), 8.47 (dt, J = 8.0, 2.0 Hz, 1H), 8.19 (d, J = 2.1 Hz, 1H), 7.96 (dd, J = 8.5, 2.1 Hz, 1H), 7.88 (t, J = 2.7 Hz, 1H), 7.69 (d, J = 8.5 Hz, 1H), 7.57 (d, J = 2.5 Hz, 1H), 7.54 (dd, J = 8.3, 2.6 Hz, 1H), 7.49 (d, J = 8.4 Hz, 1H), 7.45 (dd, J = 7.9, 4.7 Hz, 1H), 6.75 (d, J = 2.9 Hz, 1H), 3.56 (s, 2H), 2.48 (s, 3H), 2.20 (s, 3H). MS(ESI) m/z: 602[M + H]$^+$. |
| III-n-2 | 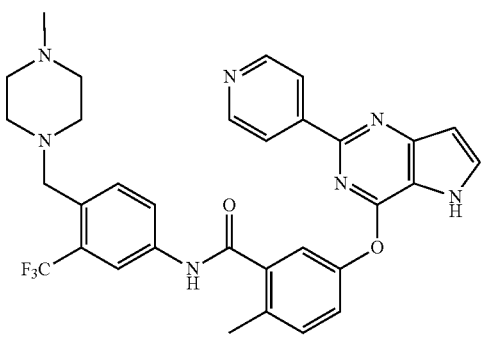 [SMILES: Cc1ccc(Oc2nc(-c3ccncc3)nc3cc[nH]c23)cc1C(=O)Nc1ccc(CN2CCN(C)CC2)c(C(F)(F)F)c1] | $^1$H NMR (600 MHz, DMSO-d$_6$) δ 10.69 (s, 1H), 8.68-8.57 (m, 2H), 8.19 (d, J = 2.2 Hz, 1H), 8.11-8.03 (m, 2H), 8.02-7.94 (m, 1H), 7.91 (d, J = 3.1 Hz, 1H), 7.69 (d, J = 8.5 Hz, 1H), 7.59 (d, J = 2.5 Hz, 1H), 7.54 (dd, J = 8.3, 2.5 Hz, 1H), 7.49 (d, J = 8.4 Hz, 1H), 6.78 (d, J = 3.1 Hz, 1H), 5.75 (s, 1H), 3.56 (s, 2H), 2.48 (s, 3H), 2.23 (s, 3H). MS (ESI) m/z: 602[M + H]$^+$. |

TABLE 3-continued

Structure and characterization of compounds III

| No. | Structure | $^1$H NMR and/or MS data |
|---|---|---|
| III-n-3 | 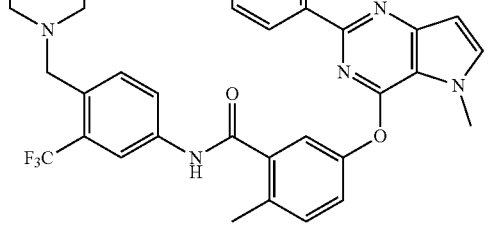 | $^1$H NMR (600 MHz, Chloroform-d) δ 9.30 (t, J = 2.7 Hz, 1H), 8.96 (d, J = 36.4 Hz, 1H), 8.50 (dt, J = 4.8, 2.3 Hz, 1H), 8.36-8.25 (m, 1H), 7.90 (d, J = 11.8 Hz, 2H), 7.71 (d, J = 8.4 Hz, 1H), 7.51 (d, J = 2.4 Hz, 1H), 7.32 (dtd, J = 17.9, 7.9, 7.4, 2.7 Hz, 3H), 7.21 (dd, J = 8.0, 4.4 Hz, 1H), 6.64-6.62 (m, 1H), 4.13 (d, J = 2.3 Hz, 3H), 3.64 (s, 2H), 2.59 (s, 3H), 2.37 (d, J = 2.2 Hz, 3H). MS(ESI) m/z: 616[M + H]$^+$. |
| III-n-4 | 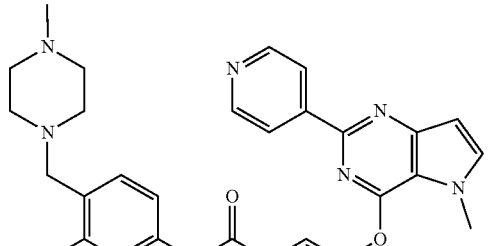 | $^1$H NMR (600 MHz, Chloroform-d) δ 9.00 (s, 1H), 8.53-8.45 (m, 2H), 7.99-7.92 (m, 2H), 7.92-7.83 (m, 2H), 7.72 (d, J = 8.4 Hz, 1H), 7.50 (d, J = 1.7 Hz, 1H), 7.40-7.34 (m, 3H), 6.71 (d, J = 3.0 Hz, 1H), 4.13 (s, 3H), 3.63 (s, 2H), 2.59 (s, 3H), 2.33 (s, 3H). MS(ESI) m/z: 616[M + H]$^+$. |
| III-o-1 | 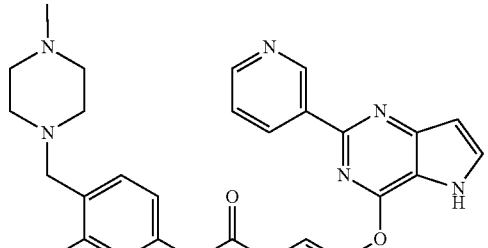 | $^1$H NMR (600 MHz, DMSO-d$_6$) δ 12.49 (s, 1H), 10.93 (s, 1H), 9.31 (s, 1H), 8.60 (d, J = 3.7 Hz, 1H), 8.48 (dt, J = 8.0, 1.9 Hz, 1H), 8.17 (d, J = 2.1 Hz, 1H), 7.93 (dd, J = 8.5, 1.8 Hz, 1H), 7.90 (d, J = 3.0 Hz, 1H), 7.75 (dd, J = 5.8, 2.9 Hz, 2H), 7.71 (d, J = 8.6 Hz, 1H), 7.67 (dd, J = 8.8, 2.8 Hz, 1H), 7.46 (dd, J = 7.9, 4.8 Hz, 1H), 6.76 (t, J = 3.8 Hz, 1H), 3.55 (s, 2H), 2.15 (s, 3H). MS (ESI) m/z: 623[M + H]$^+$. |
| III-o-2 | 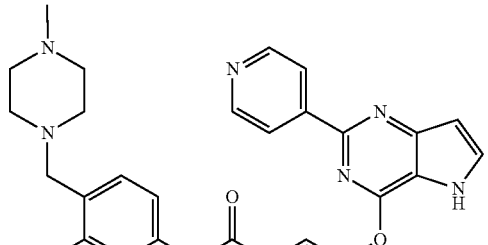<br>TFA Salt | $^1$H NMR (600 MHz, DMSO-d$_6$) δ 12.78 (s, 1H), 10.99 (s, 1H), 8.87 (s, 2H), 8.45 (s, 2H), 8.18 (d, J = 2.0 Hz, 1H), 8.01 (t, J = 2.9 Hz, 1H), 7.98-7.95 (m, 1H), 7.78-7.75 (m, 2H), 7.73 (d, J = 8.6 Hz, 1H), 7.70 (dd, J = 8.8, 2.8 Hz, 1H), 6.87 (dd, J = 2.9, 1.8 Hz, 1H), 3.69 (s, 2H), 3.04 (s, 2H), 2.92 (s, 2H), 2.81 (s, 3H), 2.39 (s, 2H). MS (ESI) m/z: 623[M + H]$^+$ |

TABLE 3-continued

Structure and characterization of compounds III

| No. | Structure | ¹H NMR and/or MS data |
|---|---|---|
| III-o-3 | 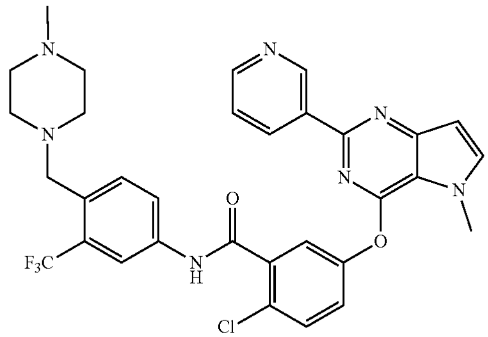 [SMILES: CN1CCN(Cc2ccc(NC(=O)c3cc(Oc4nc(-c5cccnc5)nc5ccn(C)c45)ccc3Cl)cc2C(F)(F)F)CC1] | ¹H NMR (600 MHz, DMSO-d$_6$) δ 10.93 (s, 1H), 9.28 (d, J = 1.8 Hz, 1H), 8.59 (dd, J = 4.7, 1.6 Hz, 1H), 8.46 (dt, J = 8.0, 1.9 Hz, 1H), 8.16 (d, J = 2.1 Hz, 1H), 7.93 (dd, J = 8.5, 1.9 Hz, 1H), 7.86 (d, J = 3.0 Hz, 1H), 7.79 (d, J = 2.8 Hz, 1H), 7.76 (d, J = 8.7 Hz, 1H), 7.73-7.70 (m, 2H), 7.46 (dd, J = 7.9, 4.7 Hz, 1H), 6.72 (d, J = 3.0 Hz, 1H), 4.14 (s, 3H), 3.56 (s, 2H), 2.17 (s, 3H). MS (ESI) m/z: 637[M + H]⁺. |
| III-o-4 | 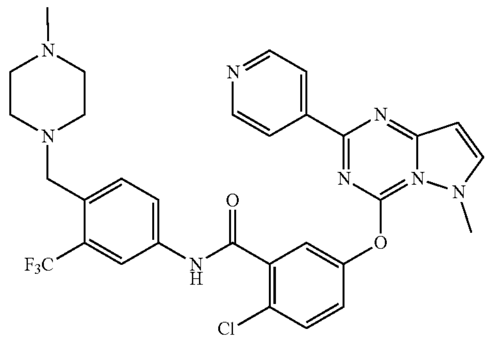 | ¹H NMR (600 MHz, DMSO-d$_6$) δ 10.94 (s, 1H), 8.63 (dd, J = 4.5, 1.5 Hz, 2H), 8.17 (d, J = 2.1 Hz, 1H), 8.05 (dd, J = 4.5, 1.5 Hz, 2H), 7.94 (dd, J = 8.5, 1.9 Hz, 1H), 7.89 (d, J = 3.1 Hz, 1H), 7.81 (d, J = 2.8 Hz, 1H), 7.76 (d, J = 8.7 Hz, 1H), 7.73-7.69 (m, 2H), 6.75 (d, J = 3.0 Hz, 1H), 4.14 (s, 3H), 3,56 (s, 2H), 2.15 (s, 3H). MS (ESI) m/z: 637[M + H]⁺. |
| III-p-1 | 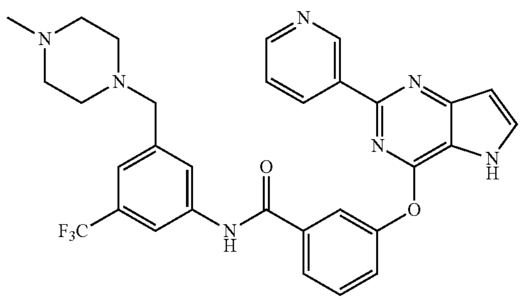 [SMILES: CN1CCN(Cc2cc(NC(=O)c3cccc(Oc4nc(-c5cccnc5)nc5cc[nH]c45)c3)cc(C(F)(F)F)c2)CC1] | ¹H NMR (600 MHz, DMSO-d$_6$) δ 12.51 (s, 1H), 10.61 (s, 1H), 9.23 (d, J = 2.0 Hz, 1H), 8.56 (dd, J = 4.7, 1.6 Hz, 1H), 8.42 (dt, J = 8.0, 1.9 Hz, 1h), 8.19 (s, 1H), 8.07 (s, 1H), 8.03-8.00 (m, 2H), 7.91 (d, J = 3.0 Hz, 1H), 7.77-7.70 (m, 2H), 7.43 (dd, J = 8.0, 4.7 Hz, 1H), 7.36 (s, 1H), 6.77 (d, J = 3.0 Hz, 1H), 3.54 (s, 2H), 3.18 (s, 4H), 2.16 (s, 3H). MS (ESI) m/z: 588[M + H]⁺. |
| III-p-2 | 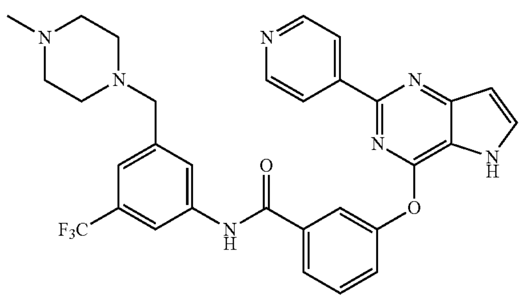 [SMILES: CN1CCN(Cc2cc(NC(=O)c3cccc(Oc4nc(-c5ccncc5)nc5cc[nH]c45)c3)cc(C(F)(F)F)c2)CC1] | ¹H NMR (600 MHz, DMSO-d$_6$) δ 12.59 (s, 1H), 10.61 (s, 1H), 8.61 (dd, J = 4.5, 1.6 Hz, 2H), 8.19 (s, 1H), 8.08 (d, J = 2.1 Hz, 1H), 8.04-8.00 (m, 4H), 7.95 (d, J = 2.9 Hz, 1H), 7.77-7.70 (m, 2H), 7.36 (s, 1H), 6.81 (d, J = 3.0 Hz, 1H), 3.53 (s, 2H), 2.15 (s, 3H). MS (ESI) m/z: 588[M + H]⁺. |
| III-p-3 | 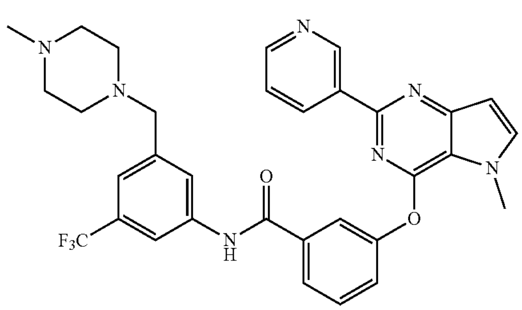 [SMILES: CN1CCN(Cc2cc(NC(=O)c3cccc(Oc4nc(-c5cccnc5)nc5ccn(C)c45)c3)cc(C(F)(F)F)c2)CC1] | ¹H NMR (600 MHz, DMSO-d$_6$) δ 10.63 (s, 1H), 9.21 (d, J = 2.1 Hz, 1H), 8.56 (dd, J = 4.7, 1.6 Hz, 1H), 8.40 (dt, J = 8.0, 1.9 Hz, 1H), 8.19 (s, 1H), 8.08 (s, 1H), 8.04-7.99 (m, 2H), 7.88 (d, J = 3.1 Hz, 1H), 7.76-7.72 (m, 2H), 7.42 (dd, J = 8.0, 4.7 Hz, 1H), 7.36 (s, 1H), 6.73 (d, J = 3.1 Hz, 1H), 4.18 (s, 3H), 3.53 (s, 2H), 2.15 (s, 3H). MS (ESI) m/z: 602[M + H]⁺. |

TABLE 3-continued

Structure and characterization of compounds III

| No. | Structure | $^1$H NMR and/or MS data |
|---|---|---|
| III-p-4 | 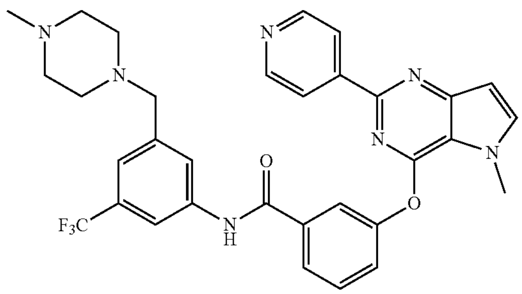 [SMILES: CN1CCN(Cc2cc(NC(=O)c3cccc(Oc4nc(-c5ccncc5)nc5ccn(C)c45)c3)cc(C(F)(F)F)c2)CC1] | $^1$H NMR (600 MHz, DMSO-$d_6$) δ 10.63 (s, 1H), 8.61 (dd, J = 4.5, 1.6 Hz, 2H), 8.19 (s, 1H), 8.08 (s, 1H), 8.03-8.00 (m, 2H), 7.98 (dd, J = 4.5, 1.6 Hz, 2H), 7.92 (d, J = 3.1 Hz, 1H),7.74 (dd, J = 3.4, 1.8 Hz, 2H), 7.36 (s, 1H), 6.77 (d, J = 3.1 Hz, 1H), 4.19 (s, 3H), 3.54 (s, 2H), 2.16 (s, 3H). MS (ESI) m/z: 602[M + H]$^+$. |
| III-q-1 | 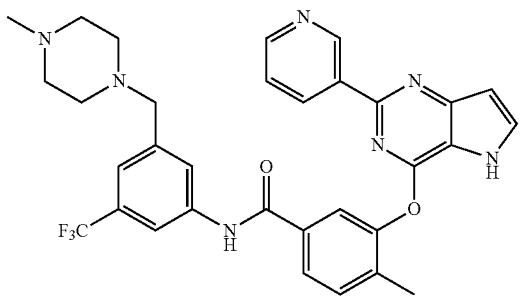 [SMILES: Cc1ccc(C(=O)Nc2cc(CN3CCN(C)CC3)cc(C(F)(F)F)c2)cc1Oc1nc(-c2cccnc2)nc2cc[nH]c12] | $^1$H NMR (600 MHz, DMSO-$d_6$) δ 12.54 (s, 1H), 10.51 (s, 1H), 9.17 (d, J = 1.9 Hz, 1H), 8.55 (dd, J = 4.7, 1.6 Hz, 1H), 8.38 (dt, J = 8.0, 1.9 Hz, 1H), 8.17 (s, 1H), 8.05 (d, J = 1.6 Hz, 1H), 8.01-7.97 (m, 2H), 7.92 (d, J = 2.9 Hz, 1H), 7.64 (d, J = 8.1 Hz, 1H), 7.41 (dd, J = 8.0, 4.7 Hz, 1H), 7.34 (s, 1H), 6.78 (d, J = 3.0 Hz, 1H), 3.52 (s, 2H), 2.28 (s, 3H), 2.15 (s, 3H). MS (ESI) m/z: 602[M + H]$^+$. |
| III-q-2 | 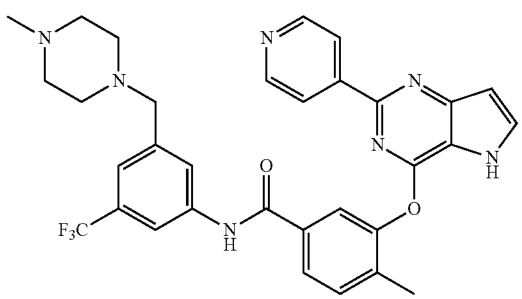 [SMILES: Cc1ccc(C(=O)Nc2cc(CN3CCN(C)CC3)cc(C(F)(F)F)c2)cc1Oc1nc(-c2ccncc2)nc2cc[nH]c12] | $^1$H NMR (600 MHz, DMSO-$d_6$) δ 12.62 (s, 1H), 10.52 (s, 1H), 8.59 (dd, J = 4.6, 1.4 Hz, 2H), 8.18 (s, 1H), 8.18 (s, 1H), 8.06 (d, J = 1.5 Hz, 1H), 8.02-7.97 (m, 2H), 7.97-7.93 (m, 3H), 7.64 (d, J = 8.1 Hz, 1H), 7.34 (s, 1H), 6.81 (d, J = 3.0 Hz, 1H), 3.52 (s, 2H), 2.28 (s, 3H), 2.15 (s, 3H). MS (ESI) m/z: 602[M + H]$^+$. |
| III-q-3 | 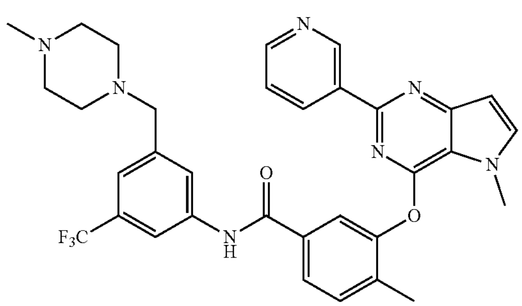 [SMILES: Cc1ccc(C(=O)Nc2cc(CN3CCN(C)CC3)cc(C(F)(F)F)c2)cc1Oc1nc(-c2cccnc2)nc2ccn(C)c12] | $^1$H NMR (600 MHz, DMSO-$d_6$) δ 10.53 (s, 1H), 9.14 (d, J = 1.5 Hz, 1H), 8.54 (dd, J = 4.7, 1.6 Hz, 1H), 8.38-8.34 (m, 1H), 8.17 (s, 1H), 8.06 (d, J = 1.5 Hz, 1H), 8.00 (s, 1H), 7.97 (dd, J = 7.9, 1.6 Hz, 1H), 7.89 (d, J = 3.0 Hz, 1H), 7.63 (d, J = 8.0 Hz, 1H), 7.41 (d, J = 7.9, 4.8 Hz, 1H), 7.34 (s, 1H), 6.73 (d, J = 3.1 Hz, 1H), 4.21 (s, 3H), 3.52 (s, 2H), 2.31 (s, 3H), 2.15 (s, 3H). MS (ESI) m/z: 616[M + H]$^+$. |
| III-q-4 | 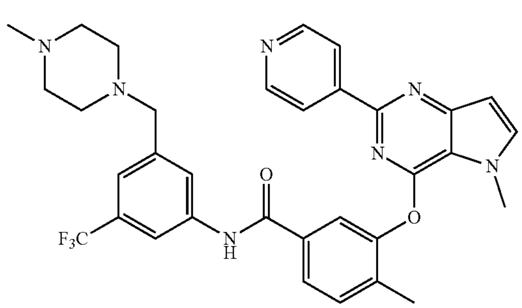 [SMILES: Cc1ccc(C(=O)Nc2cc(CN3CCN(C)CC3)cc(C(F)(F)F)c2)cc1Oc1nc(-c2ccncc2)nc2ccn(C)c12] | $^1$H NMR (600 MHz, DMSO-$d_6$) δ 10.53 (s, 1H), 8.58 (dd, J = 4.6, 1.5 Hz, 2H), 8.17 (s, 1H), 8.07 (d, J = 1.7 Hz, 1H), 8.01 (s, 1H), 7.98 (dd, J = 7.9, 1.7 Hz, 1H), 7.94-7.90 (m, 3H), 7.63 (d, J = 8.1 Hz, 1H), 7.34 (s, 1H), 6.77 (d, J = 3.1 Hz, 1H), 4.21 (s, 3H), 3.52 (s, 2H), 3.18 (s, 4H), 2.30 (s, 3H), 2.14 (s, 3H). MS (ESI) m/z: 616[M + H]$^+$. |

TABLE 3-continued

Structure and characterization of compounds III

| No. | Structure | ¹H NMR and/or MS data |
|---|---|---|
| III-r-1 | 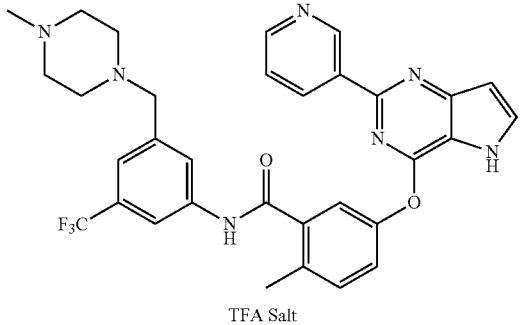 [SMILES: Cc1ccc(Oc2nc(-c3cccnc3)nc3cc[nH]c23)cc1C(=O)Nc1cc(CN2CCN(C)CC2)cc(C(F)(F)F)c1] TFA Salt | ¹H NMR (600 MHz, DMSO-d$_6$) δ 12.58 (s, 1H), 10.77 (s, 1H), 9.33 (s, 1H), 8.73 (s, 2H), 8.10 (s, 1H), 8.06 (s, 1H), 7.93 (s, 1H), 7.73 (s, 1H), 7.57 (d, J = 15.2 Hz, 2H), 7.53-7.44 (m, 2H), 6.79 (s, 1H), 3.86 (s, 2H), 2.80 (s, 3H). MS (ESI) m/z: 602[M + H]$^+$. |
| III-r-2 | 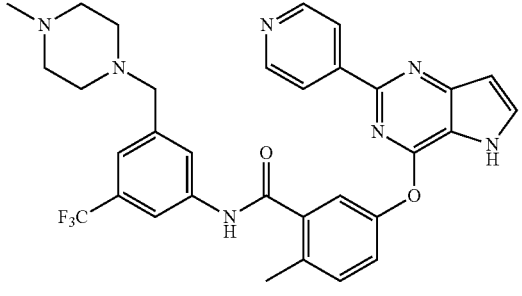 [SMILES: Cc1ccc(Oc2nc(-c3ccncc3)nc3cc[nH]c23)cc1C(=O)Nc1cc(CN2CCN(C)CC2)cc(C(F)(F)F)c1] | ¹H NMR (600 MHz, DMSO-d$_6$) δ 12.53 (s, 1H), 10.72 (s, 1H), 8.63 (dd, J = 4.5, 1.6 Hz, 2H), 8.16 (s, 1H), 8.07 (dd, J = 4.5, 1.6 Hz, 2H), 7.94 (s, 1H), 7.91 (d, J = 3.0 Hz, 1H), 7.62 (d, J = 2.5 Hz, 1H), 7.54 (dd, J = 8.3, 2.5 Hz, 1H), 7.49 (d, J = 8.5 Hz, 1H), 7.35 (s, 1H), 6.79 (d, J = 3.0 Hz, 1H), 3.53 (s, 2H), 2.49 (s, 3H), 2.18 (s, 3H). MS (ESI) m/z: 602[M + H]$^+$. |
| III-r-3 | 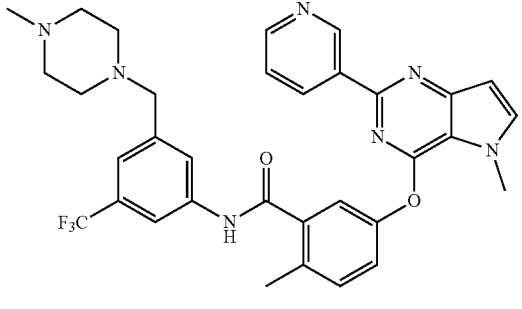 [SMILES: Cc1ccc(Oc2nc(-c3cccnc3)nc3ccn(C)c23)cc1C(=O)Nc1cc(CN2CCN(C)CC2)cc(C(F)(F)F)c1] | ¹H NMR (600 MHz, DMSO-d$_6$) δ 10.72 (s, 1H), 9.26 (dd, J = 2.2, 0.7 Hz, 1H), 8.58 (dd, J = 4.7, 1.7 Hz, 1H), 8.46-8.43 (m, 1H), 8.14 (s, 1H), 7.92 (s, 1H), 7.85 (d, J = 3.1 Hz, 1H), 7.63 (d, J = 2.5 Hz, 1H), 7.63 (d, J = 2.5 Hz, 1H), 7.57 (dd, J = 8.3, 2.5 Hz, 1H), 7.49 (d, J = 8.5 Hz, 1H), 7.44 (ddd, J = 8.0, 4.8, 0.8 Hz, 1H), 7.35 (s, 1H), 6.71 (d, J = 3.0 Hz, 1H), 4.15 (s, 3H), 3.52 (s, 2H), 2.48 (s, 3H), 2.14 (s, 3H). MS (ESI) m/z: 616[M + H]$^+$. |
| III-r-4 | 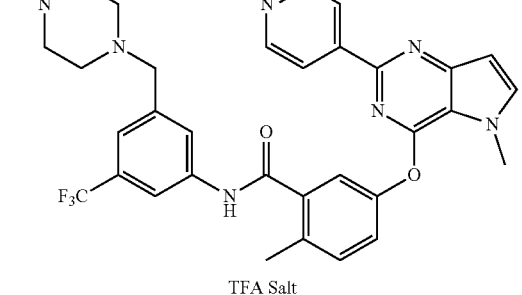 TFA Salt | ¹H NMR (600 MHz, DMSO-d$_6$) δ 10.84 (s, 1H), 8.90 (s, 2H), 8.45 (s, 2H), 8.10 (d, J = 21.8 Hz, 2H), 7.98 (s, 1H), 7.66-7.59 (m, 2H), 7.52 (d, J = 8.3 Hz, 2H), 6.83 (s, 1H), 4.19 (s, 3H), 3.96 (s, 2H), 2.82 (s, 3H). MS (ESI) m/z: 616[M + H]$^+$. |

TABLE 3-continued

Structure and characterization of compounds III

| No. | Structure | $^1$H NMR and/or MS data |
|---|---|---|
| III-u-1 | 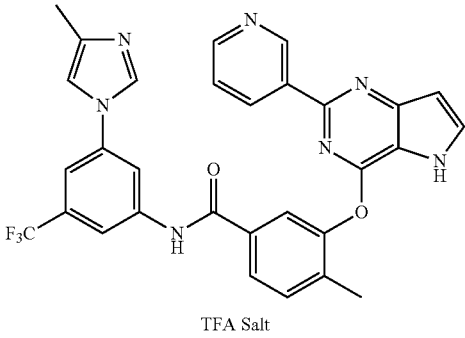 [SMILES: Cc1cn(-c2cc(NC(=O)c3ccc(C)c(Oc4nc(-c5cccnc5)nc5cc[nH]c45)c3)cc(C(F)(F)F)c2)cn1] TFA Salt | $^1$H NMR (600 MHz, DMSO-$d_6$) δ 12.69 (s, 1H), 10.89 (s, 1H), 9.63 (d, J = 1.7 Hz, 1H), 9.22 (d, J = 2.1 Hz, 1H), 8.72 (dd, J = 5.2, 1.6 Hz, 1H), 8.67-8.64 (m, 1H), 8.58 (s, 1H), 8.24 (s, 1H), 8.07 (d, J = 1.8 Hz, 1H), 8.04-8.01 (m, 2H), 7.98 (t, J = 3.0 Hz, 1H), 7.94 (s, 1H), 7.73 (q, J = 8.1, 5.1 Hz, 1H), 7.68 (d, J = 8.0 Hz, 1H), 6.82 (q, J = 3.1, 1.8 Hz, 1H), 2.36 (d, J = 1.2 Hz, 3H), 2.30 (s, 3H). MS (ESI) m/z: 570 [M + H]$^+$. |
| III-u-2 | 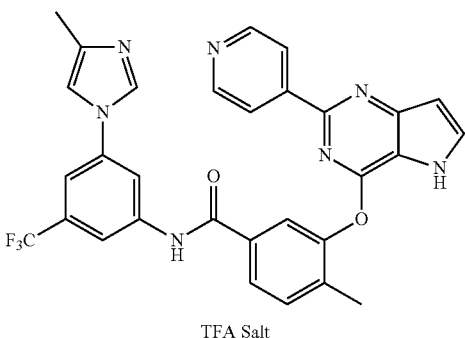 [SMILES: Cc1cn(-c2cc(NC(=O)c3ccc(C)c(Oc4nc(-c5ccncc5)nc5cc[nH]c45)c3)cc(C(F)(F)F)c2)cn1] TFA Salt | $^1$H NMR (600 MHz, DMSO-$d_6$) δ 12.81 (s, 1H), 10.91 (s, 1H), 9.55 (s, 1H), 8.77 (d, J = 5.7 Hz, 2H), 8.56 (s, 1H), 8.23 (t, 3H), 8.08 (d, J = 1.8 Hz, 1H), 8.05-7.99 (m, 3H), 7.93 (s, 1H), 7.68 (d, J = 8.01 Hz, 1H), 6.87 (s, 3H), 2.35 (s, 5H), 2.30 (s, 3H). MS (ESI) m/z: 570 [M + H]$^+$. |
| III-u-3 | 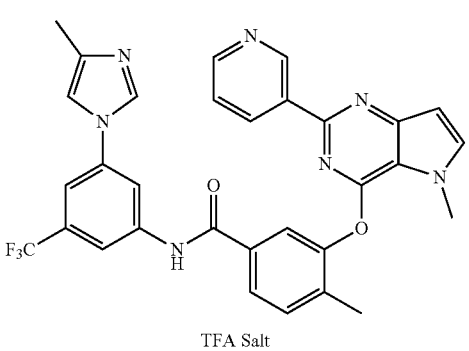 [SMILES: Cc1cn(-c2cc(NC(=O)c3ccc(C)c(Oc4nc(-c5cccnc5)nc5ccn(C)c45)c3)cc(C(F)(F)F)c2)cn1] TFA Salt | $^1$H NMR (600 MHz, DMSO-$d_6$) δ 10.93 (s, 1H), 9.61 (d, J = 1.7 Hz, 1H), 9.17 (d, J = 2.1 Hz, 1H), 8.66 (d, J = 4.9 Hz, 1H), 8.58-8.54 (m, 2H), 8.25 (s, 1H), 8.09 (d, J = 1.8 Hz, 1H), 8.03-8.00 (m, 2H), 7.94-7.91 (m, 2H), 7.67 (d, J = 8.1 Hz, 1H), 7.67-7.61 (m, 1H), 6.76 (d, J = 3.1 Hz, 1H), 4.22 (s, 3H), 2.36 (d, J = 1.1 Hz, 3H), 2.33 (s, 3H). MS (ESI) m/z: 584 [M + H]$^+$. |
| III-u-4 | 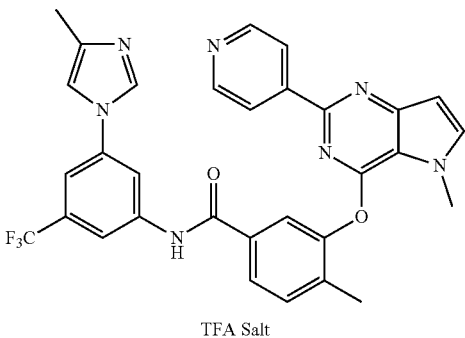 [SMILES: Cc1cn(-c2cc(NC(=O)c3ccc(C)c(Oc4nc(-c5ccncc5)nc5ccn(C)c45)c3)cc(C(F)(F)F)c2)cn1] TFA Salt | $^1$H NMR (600 MHz, DMSO-$d_6$) δ 10.95 (s, 1H), 9.58 (d, J = 1.7 Hz, 1H), 8.78 (d, J = 6.6 Hz, 2H), 8.57 (s, 1H), 8.26 (s, 1H), 8.23-8.21 (m, 2H), 8.10 (d, J = 1.8 Hz, 1H), 8.04-8.01 (m, 2H), 7.99 (d, J = 3.1 Hz, 1H), 7.93 (s, 1H), 7.67 (d, J = 8.5 Hz, 1H), 6.84 (d, J = 3.1 Hz, 1H), 4.24 (s, 3H), 2.36 (d, J = 1.2 Hz, 3H), 2.32 (s, 3H). MS (ESI) m/z: 584 [M + H]$^+$. |

TABLE 3-continued

Structure and characterization of compounds III

| No. | Structure | $^1$H NMR and/or MS data |
|---|---|---|
| III-v-1 | 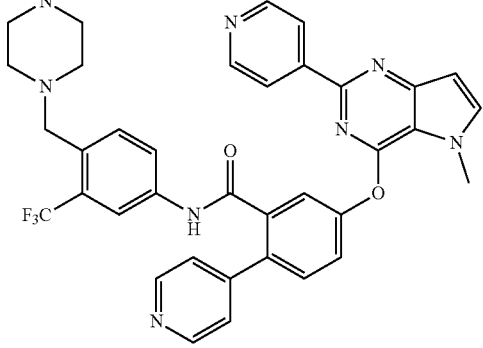 TFA Salt | $^1$H NMR (600 MHz, DMSO-d$_6$) δ 11.04 (s, 1H), 8.86 (s, 4H), 8.43 (d, J = 5.2 Hz, 2H), 8.02 (d, J = 1.8 Hz, 1H), 8.01 (d, J = 3.1 Hz, 1H), 7.97 (d, J = 2.4 Hz, 1H), 7.93 (dd, J = 8.5, 2.3 Hz, 2H), 7.85 (t, J = 10.2 Hz, 2H), 7.68 (d, J = 8.6 Hz, 1H), 6.86 (d, J = 3.1 Hz, 1H), 4.21 (s, 3H), 3.67 (s, 2H), 3.03 (s, 2H), 2.89 (s, 2H), 2.81 (s, 3H), 2.41 (s, 2H). MS (ESI) m/z: 679[M + H]$^+$. |
| II-v-2 | 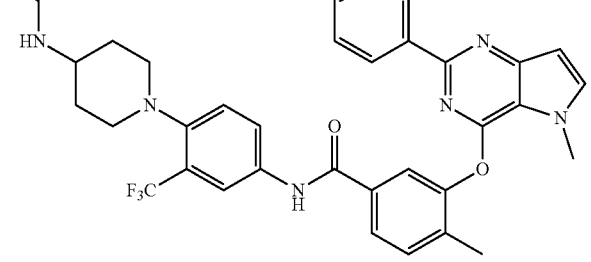 | $^1$H NMR (600 MHz, DMSO-d$_6$) δ 10.46 (s, 1H), 9.14 (d, J = 2.0 Hz, 1H), 8.57 (dd, J = 4.8, 1.7 Hz, 1H), 8.40 (dt, J = 8.0, 2.0 Hz, 1H), 8.13 (d, J = 2.5 Hz, 1H), 8.06-8.01 (m, 2H), 7.95 (dd, J = 7.9, 1.8 Hz, 1H), 7.89 (d, J = 3.1 Hz, 1H), 7.85 (d, J = 7.8 Hz, 1H), 7.62 (d, J = 8.0 Hz, 1H), 7.55 (d, J = 7.8 Hz, 1H), 7.62 (d J = 8.0 Hz, 1H), 7.55 (d, J = 8.8 Hz, 1H), 7.45 (dd, J = 8.0, 4.8 Hz, 1H), 6.73 (d, J = 3.0 Hz, 1H), 4.20 (s, 3H), 3.69 (dtd, J = 11.0, 6.9, 3.8 Hz, 1H), 2.90 (dd, J = 11.8, 3.9 Hz, 2H), 2.78 (td, J = 11.6, 2.5 Hz, 2H), 2.30 (s, 3H), 1.81 (s, 5H), 1.58-1.45 (m, 2H). MS (ESI) m/z: 644 [M + H]$^+$. |
| III-v-3 | 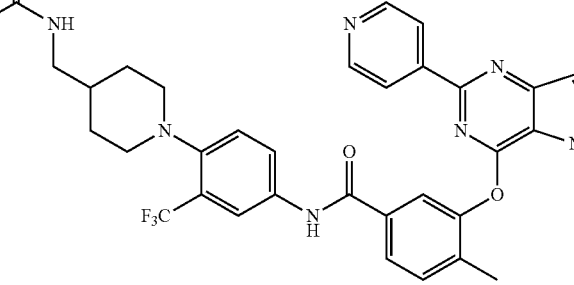 | $^1$H NMR (600 MHz, DMSO-d$_6$) δ 10.45 (s, 1H), 8.82-8.75 (m, 2H), 8.29-8.20 (m, 2H), 8.12 (d, J = 2.5 Hz, 1H), 8.06-8.20 (m, 2H), 8.12 (d, J = 2.5 Hz, 1H), 8.06-8.00 (m, 2H), 8.01-7.95 (m, 2H), 7.88 (t, J = 5.9 Hz, 1H), 7.63 (d, J = 8.1 Hz, 1H), 7.52 (d, J = 8.8 Hz, 1H), 6.83 (d, J = 3.1 Hz, 1H), 4.23 (s, 3H), 2.98 (t, J = 6.4 Hz, 2H), 2.94-2.88 (m, 2H), 2.68 (td, J = 11.5, 2.3 Hz, 2H), 2.31 (s, 3H), 1.82 (s, 3H), 1.73-1.66 (m, 2H), 1.50 (ddt, J = 11.2, 7.7, 3.9 Hz, 1H), 1.24 (qd, J = 11.9, 3.9 Hz, 2H). MS (ESI) m/z: 658 [M + H]$^+$. |
| III-v-4 | 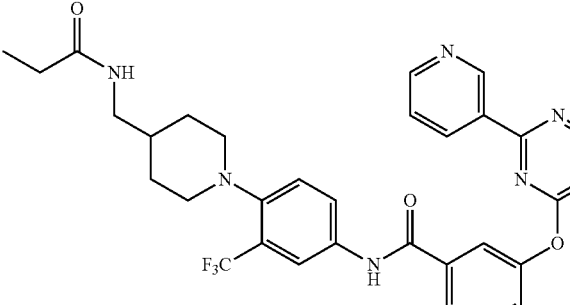 TFA Salt | $^1$H NMR (600 MHz, DMSO-d$_6$) δ 10.45 (d, J = 1.9 Hz, 1H), 9.20 (s, 1H), 8.73 (s, 1H), 8.66 (d, J = 8.0 Hz, 1H), 8.11 (d, J = 2.2 Hz, 1H), 8.05 (s, 1H), 8.03 (d, J = 9.2 Hz, 1H), 7.96 (d, J = 7.9 Hz, 1H), 7.92 (d, J = 2.5 Hz, 1H), 7.82-7.78 (m, 1H), 7.76-7.73 (m, 1H), 7.61 (d, J = 7.9 Hz, 1H), 7.51 (d, J = 8.9 Hz, 1H), 6.76 (t, J = 2.4 Hz, 1H), 4.21 (d, J = 1.9 Hz, 3H), 2.99 (t, J = 6.4 Hz, 2H), 2.90 (d, J = 10.8 Hz, 2H), 2.67 (t, J = 11.3 Hz, 2H), 2.30 (d, J = 1.8 Hz, 3H), 2.09 (qd, J = 7.6, 1.9 Hz, 2H), 1.69 (d, J = 12.4 Hz, 2H), 1.50 (d, J = 9.4 Hz, 1H), 1.24 (q, J = 11.6 Hz, 2H), 1.00 (td, J = 7.6, 1.9 Hz, 3H). MS (ESI) m/z: 672 [M + H]$^+$ |

TABLE 3-continued

Structure and characterization of compounds III

| No. | Structure | ¹H NMR and/or MS data |
|---|---|---|
| III-v-5 | 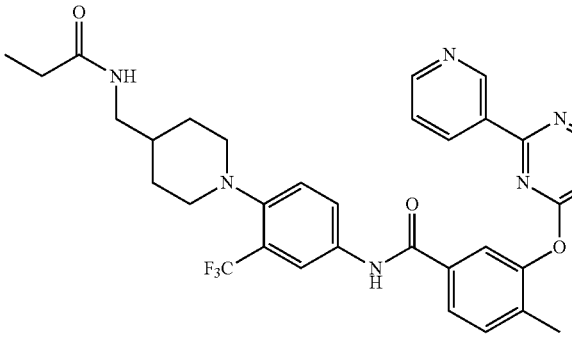<br>TFA Salt | ¹H NMR (600 MHz, DMSO-d₆) δ 10.46 (s, 1H), 8.80 (d, J = 5.7 Hz, 2H), 8.29-8.21 (m, 2H), 8.12 (d, J = 2.5 Hz, 1H), 8.05 (d, J = 1.7 Hz, 1H), 8.03 (dd, J = 8.8, 2.5 Hz, 1H), 7.99 (d, J = 3.2 Hz, 1H), 7.97 (dd, J = 7.9, 1.8 Hz, 1H), 7.81 (t, J = 5.9 Hz, 1H), 7.63 (d, J = 8.1 Hz, 1H), 7.52 (d, J = 8.8 Hz, 1H), 6.84 (d, J = 3.0 Hz, 1H), 4.23 (s, 3H), 2.99 (t, J = 6.4 Hz, 2H), 2.93-2.86 (m, 2H), 2.67 (td, J = 11.6, 2.4 Hz, 2H), 2.30 (s, 3H), 2.09 (q, J = 7.6 Hz, 2H), 1.69 (dd, J = 13.3, 3.6 Hz, 2H), 1.51 (ddd, J = 11.2, 7.4, 4.0 Hz, 1H), 1.29-1.18 (m, 2H), 1.00 (t, J = 7.6 Hz, 3H). MS (ESI) m/z: 672 [M + H]⁺ |
| III-v-6 | 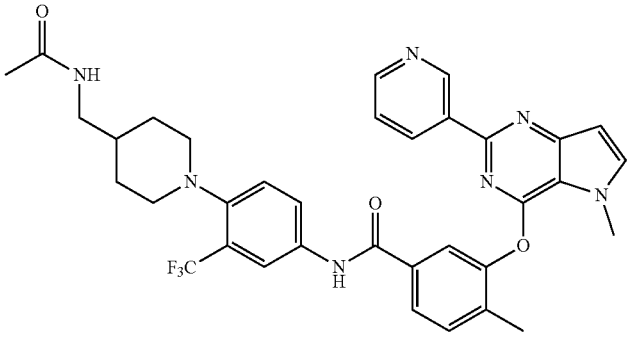 [SMILES: CC(=O)NCC1CCN(c2ccc(NC(=O)c3ccc(C)c(Oc4nc(-c5cccnc5)nc5ccn(C)c45)c3)cc2C(F)(F)F)CC1] | ¹H NMR (600 MHz, DMSO-d₆) δ 10.44 (s, 1H), 9.13 (d, J = 2.1 Hz, 1H), 8.54 (dd, J = 4.7, 1.7 Hz, 1H), 8.35 (dt, J = 8.1, 2.0 Hz, 1H), 8.10 (d, J = 2.5 Hz, 1H), 8.02 (dd, J = 7.0, 2.1 Hz, 2H), 7.94 (dd, J = 7.9, 1.8 Hz, 1H), 7.89 (t, J = 6.1 Hz, 1H), 7.87 (d, J = 3.1 Hz, 1H), 7.61 (d, J = 8.0 Hz, 1H), 7.51 (d, J = 8.8 Hz, 1H), 7.40 (dd, J = 8.0, 4.7 Hz, 1H), 6.72 (d, J = 3.1 Hz, 1H), 4.20 (s, 3H), 2.98 (t, J = 6.4 Hz, 2H), 2.94-2.87 (m, 2H), 2.67 (td, J = 11.6, 2.3 Hz, 2H), 2.29 (s, 3H), 1.82 (s, 3H), 1.75-1.65 (m, 2H), 1.50 (qd, J = 7.5, 3.9 Hz, 1H), 1.23 (qd, J = 12.1, 3.9 Hz, 2H). MS (ESI) m/z: 658 [M + H]⁺ |
| III-v-7 | 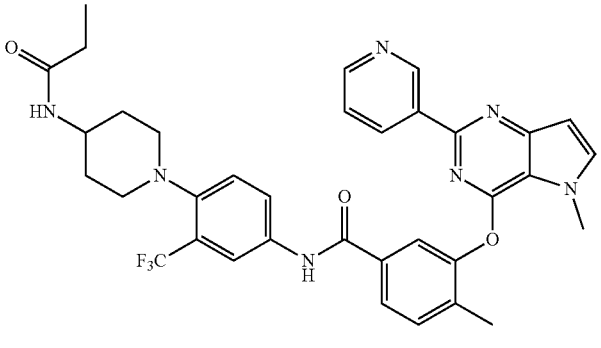 [SMILES: CCC(=O)NC1CCN(c2ccc(NC(=O)c3ccc(C)c(Oc4nc(-c5cccnc5)nc5ccn(C)c45)c3)cc2C(F)(F)F)CC1] | ¹H NMR (600 MHz, DMSO-d₆) δ 10.44 (s, 1H), 9.15 (s, 1H), 8.54 (s, 1H), 8.35 (dt, J = 8.1, 1.9 Hz, 1H), 8.13 (d, J = 2.5 Hz, 1H), 8.03 (q, J = 4.2, 3.3 Hz, 2H), 7.95 (d, J = 7.8 Hz, 1H), 7.88 (t, J = 2.2 Hz, 1H), 7.74 (d, J = 7.8 Hz, 1H), 7.62 (d, J = 8.0 Hz, 1H), 7.55 (t, J = 8.8 Hz, 1H), 7.41 (dd, J = 7.9, 4.8 Hz, 1H), 6.73 (t, J = 2.3 Hz, 1H), 4.35 (t, J = 5.1 Hz, 2H), 4.20 (d, J = 1.7 Hz, 3H), 3.69 (d, J = 10.5 Hz, 1H), 2.90 (d, J = 11.2 Hz, 2H), 2.78 (t, J = 11.2 Hz, 2H), 2.30 (s, 3H), 1.80 (d, J = 12.1 Hz, 2H), 1.60-1.47 (m, 2H), 1.00 (td, J = 7.6, 1.7 Hz, 3H). MS (ESI) m/z: 658 [M + H]⁺ |
| III-v-8 | 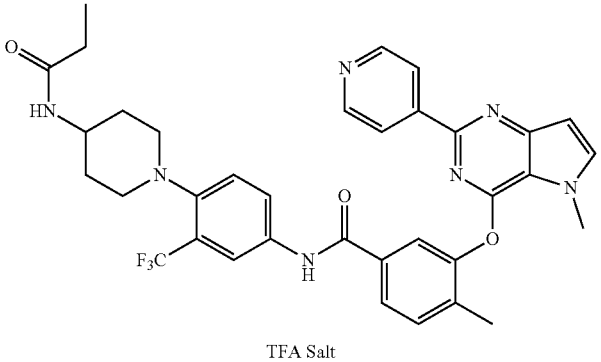 [SMILES: CCC(=O)NC1CCN(c2ccc(NC(=O)c3ccc(C)c(Oc4nc(-c5ccncc5)nc5ccn(C)c45)c3)cc2C(F)(F)F)CC1]<br>TFA Salt | ¹H NMR (600 MHz, DMSO-d₆) δ 10.46 (s, 1H), 8.79 (d, J = 5.6 Hz, 2H), 8.29-8.20 (m, 2H), 8.13 (d, J = 2.5 Hz, 1H), 8.05 (d, J = 1.7 Hz, 1H), 8.03 (dd, J = 8.8, 2.6 Hz, 1H), 7.99 (d, J = 3.2 Hz, 1H), 7.97 (dd, J = 8.0, 1.9 Hz, 1H), 7.76 (d, J = 3.2 Hz, 1H), 7.97 (dd, J = 8.0, 1.9 Hz, 1H), 7.76 (d, J = 7.8 Hz, 1H), 7.63 (d, J = 8.0 Hz, 1H), 7.56 (d, J = 8.8 Hz, 1H), 6.84 (d, J = 3.1 Hz, 1H), 4.23 (s, 3H), 3.69 (ddd, J = 11.0, 7.6, 4.1 Hz, 1H), 2.94-2.85 (m, 2H), 2.78 (td, J = 11.5, 2.4 Hz, 2H), 2.31 (s, 3H), 2.07 (q, J = 7.6 Hz, 2H), 1.80 (dd, J = 12.9, 4.3 Hz, 2H), 1.59-1.43 (m, 2H), 1.00 (t, J = 7.6 Hz, 3H). MS (ESI) m/z: 658 [M + H]⁺ |

TABLE 3-continued

Structure and characterization of compounds III

| No. | Structure | $^1$H NMR and/or MS data |
|---|---|---|
| III-v-9 | 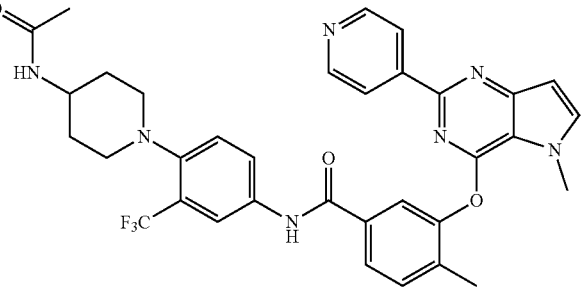 TFA Salt | $^1$H NMR (600 MHz, DMSO-d$_6$) δ 10.47 (s, 1H), 8.92-8.78 (m, 2H), 8.38-8.28 (m, 2H), 8.13 (d, J = 2.5 Hz, 1H), 8.06 (d, J = 1.7 Hz, 1H), 8.04 (dd, J = 8.8, 2.5 Hz, 1H), 8.00 (d, J = 3.1 Hz, 1H), 7.98 (dd, J = 7.9, 1.8 Hz, 1H), 7.86 (d, J = 7.8 Hz, 1H), 7.63 (d, J = 8.0 Hz, 1H), 7.55 (d, J = 8.8 Hz, 1H), 6.85 (d, J = 3.1 Hz, 1H), 4.24 (s, 3H), 3.69 (ddt, J = 14.7, 11.1, 6.2 Hz, 1H), 2.90 (dt, J = 11.7, 4.0 Hz, 2H), 2.78 (td, J = 11.4, 2.4 Hz, 2H), 2.31 (s, 3H), 1.81 (s, 5H), 1.56-1.45 (m, 2H). MS (ESI) m/z: 644 [M + H]$^+$ |
| III-v-10 | 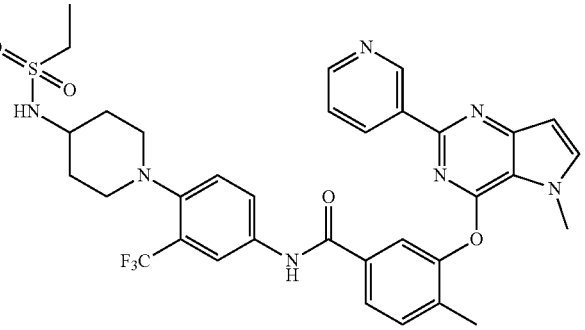 | $^1$H NMR (600 MHz, Chloroform-d) δ 9.70 (s, 1H), 9.23 (d, J = 7.9 Hz, 1H), 9.10 (d, J = 1.8 Hz, 1H), 8.61 (d, J = 5.3 Hz, 1H), 7.96 (t, J = 2.6 Hz, 1H), 7.89 (dd, J = 8.7, 2.6 Hz, 1H), 7.86-7.78 (m, 1H), 7.72 (d, J = 8.0 Hz, 1H), 7.70 (s, 1H), 7.47 (d, J = 3.1 Hz, 1H), 7.43 (d, J = 7.8 Hz, 1H), 7.26 (d, J = 8.6 Hz, 1H), 6.75 (d, J = 3.0 Hz, 1H), 4.66 (s, 1H), 4.25 (s, 3H), 3.40 (s, 1H), 3.07 (q, J = 7.4 Hz, 2H), 2.97 (dd, J = 11.7, 4.1 Hz, 2H), 2.81-2.65 (m, 2H), 2.25 (s, 3H), 2.00 (dd, J = 12.7, 3.9 Hz, 2H), 1.70 (qd, J = 11.0, 3.8 Hz, 2H), 1.38 (t, J = 7.2 Hz, 3H). MS (ESI) m/z: 694 [M + H]$^+$ |
| III-v-11 | 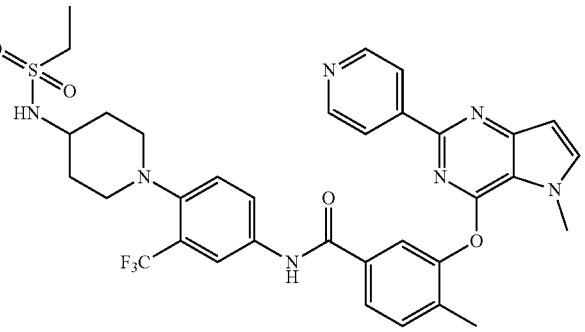 | $^1$H NMR (600 MHz, Chloroform-d) δ 9.38 (s, 1H), 8.47 (d, J = 5.4 Hz, 2H), 7.94-7.83 (m, 6H), 7.42 (d, J = 7.9 Hz, 1H), 7.36 (d, J = 3.1 Hz, 1H), 7.22 (d, J = 8.7 Hz, 1H), 6.69 (d, J = 3.1 Hz, 1H), 4.85 (d, J = 7.9 Hz, 1H), 4.11 (s, 3H), 3.38 (dtd, J = 11.0, 6.9, 4.1 Hz, 1H), 3.03 (q, J = 7.3 Hz, 2H), 2.98-2.91 (m, 2H), 2.77-2.67 (m, 2H), 2.25 (s, 3H), 1.99 (dd, J = 12.6, 4.1 Hz, 2H), 1.76-1.63 (m, 2H), 1.36 (t, J = 7.4 Hz, 3H). MS (ESI) m/z: 694 [M + H]$^+$ |
| III-v-12 | 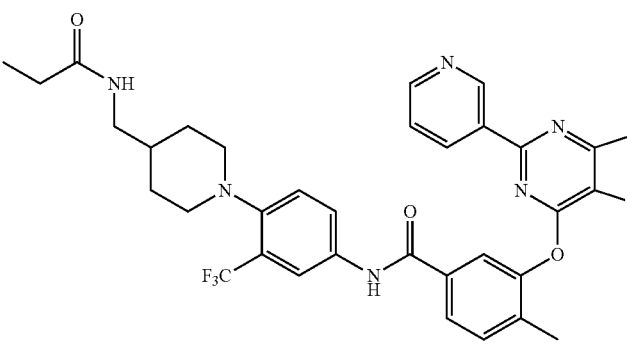 TFA Salt | $^1$H NMR (600 MHz, DMSO-d$_6$) δ 12.70 (t, J = 2.3 Hz, 1H), 10.44 (s, 1H), 9.23 (s, 1H), 8.74 (d, J = 5.1 Hz, 1H), 8.70 (dt, J = 8.1, 1.8 Hz, 1H), 8.12 (d, J = 2.5 Hz, 1H), 8.07-8.00 (m, 2H), 8.01-7.91 (m, 2H), 7.81 (t, J = 5.9 Hz, 1H), 7.77 (dd, J = 8.2, 5.2 Hz, 1H), 7.62 (d, J = 8.1 Hz, 1H), 7.51 (d, J = 8.8 Hz, 1H), 6.81 (dd, J = 3.0, 1.8 Hz, 1H), 2.99 (t, J = 6.4 Hz, 2H), 2.94-2.86 (m, 2H), 2.73-2.63 (m, 2H), 2.28 (s, 3H), 2.09 (q, J = 7.6 Hz, 2H), 1.72-1.63 (m, 2H), 1.51 (ddd, J = 11.2, 7.3, 3.9 Hz, 1H), 1.24 (qd, J = 12.2, 4.0 Hz, 2H), 1.00 (t, J = 7.6 Hz, 3H). MS (ESI) m/z: 658 [M + H]$^+$ |

TABLE 3-continued

Structure and characterization of compounds III

| No. | Structure | ¹H NMR and/or MS data |
|---|---|---|
| III-v-13 | 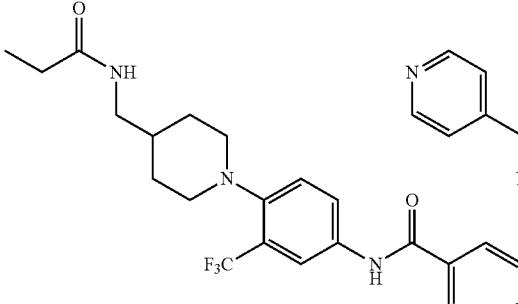 TFA Salt | ¹H NMR (600 MHz, DMSO-d₆) δ 12.83 (t, J = 2.4 Hz, 1H), 10.42 (s, 1H), 8.82 (d, J = 5.8 Hz, 2H), 8.34-8.29 (m, 2H), 8.11 (d, J = 2.5 Hz, 1H), 8.06-8.01 (m, 3H), 7.98 (dd, J = 7.9, 1.8 Hz, 1H), 7.80 (t, J = 5.9 Hz, 1H), 7.64 (d, J = 8.1 Hz, 1H), 7.52 (d, J = 8.9 Hz, 1H), 6.88 (dd, J = 3.1, 1.8 Hz, 1H), 2.99 (t, J = 6.4 Hz, 2H), 2.90 (dt, J = 11.7, 3.6 Hz, 2H), 2.67 (td, J = 11.6, 2.4 Hz, 2H), 2.28 (s, 3H), 2.09 (q, J = 7.6 Hz, 2H), 1.74-1.63 (m, 2H), 1.51 (ddq, J = 11.0, 7.6, 3.8 Hz, 1H), 1.29-1.18 (m, 2H), 1.00 (t, J = 7.6 Hz, 3H). MS (ESI) m/z: 658 [M + H]⁺ |

TABLE 4

Structure and characterization of compounds IV

| No. | Structure | ¹H NMR and/or MS data |
|---|---|---|
| IV-a-1 | 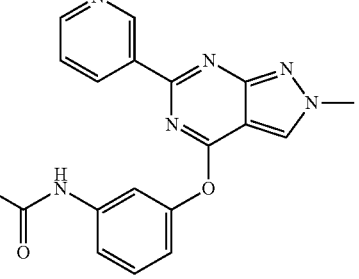 | ¹H NMR (600 MHz, DMSO-d₆) δ 10.63 (s, 1H), 9.25 (d, J = 1.5 Hz, 1H), 8.67 (d, J = 0.5 Hz, 1H), 8.62-8.57 (m, 1H), 8.48 (dt, J = 8.0, 1.9 Hz, 1H), 8.25 (s, 1H), 8.22 (d, J = 7.9 Hz, 1H), 7.92 (d, J = 7.8 Hz, 1H), 7.90 (t, J = 2.1 Hz, 1H), 7.74 (t, J = 7.8 Hz, 1H), 7.71 (dd, J = 8.2, 1.1 Hz, 1H), 7.51 (t, J = 8.2 Hz, 1H), 7.47 (dd, J = 7.9, 4.8 Hz, 1H), 7.18 (ddd, J = 8.1, 2.3, 0.8 Hz, 1H), 4.18 (s, 3H). MS (ESI) m/z 491 [M + H]⁺. |
| IV-a-2 | 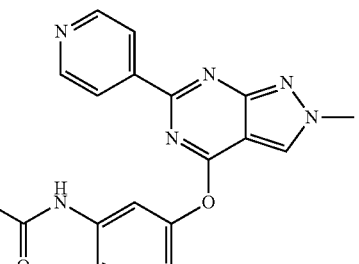 | ¹H NMR (600 MHz, DMSO-d₆) δ 10.69 (s, 1H), 8.75 (d, J = 0.8 Hz, 1H), 8.68 (d, J = 5.1 Hz, 2H), 8.30 (s, 1H), 8.27 (d, J = 8.2 Hz, 1H), 8.10-8.04 (m, 2H), 8.00-7.97 (m, 1H), 7.94 (t, J = 2.2 Hz, 1H), 7.80 (t, J = 7.8 Hz, 1H), 7.76 (ddd, J = 8.2, 2.0, 0.9 Hz, 1H), 7.56 (t, J = 8.2 Hz, 1H), 7.23 (ddd, J = 8.1, 2.3, 0.9 Hz, 1H), 4.24 (s, 3H). MS (ESI) m/z: 4.91 [M + H]⁺. |
| IV-a-3 | 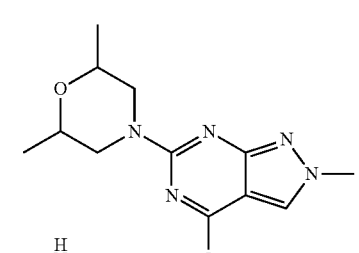 | ¹H NMR (600 MHz, DMSO-d₆) δ 10.65 (s, 1H), 8.29 (s, 1H), 8.29 (d, J = 0.4 Hz, 1H), 8.27 (d, J = 7.8 Hz, 1H), 7.99 (d, J = 7.8 Hz, 1H), 7.94 (t, J = 2.1 Hz, 1H), 7.81 (t, J = 7.7 Hz, 1H), 7.67-7.64 (m, 1H), 7.48 (t, J = 8.2 Hz, 1H), 7.09 (ddd, J = 8.1, 2.3, 0.9 Hz, 1H), 4.00 (s, 3H), 1.24 (s, 4H), 1.05 (s, 6H). MS (ESI) m/z: 527[M + H]⁺. |

TABLE 4-continued

Structure and characterization of compounds IV

| No. | Structure | $^1$H NMR and/or MS data |
|---|---|---|
| IV-b-1 | 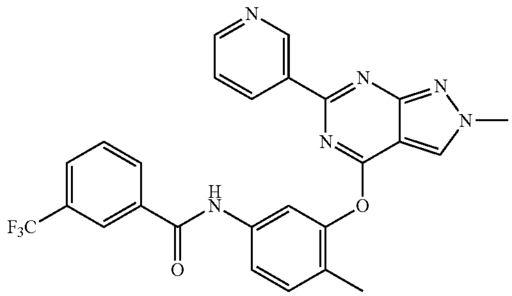 [SMILES: Cc1ccc(NC(=O)c2cccc(C(F)(F)F)c2)cc1Oc1nc(-c2cccnc2)nc2nn(C)cc12] | $^1$H NMR (600 MHz, DMSO-d$_6$) δ 10.60 (s, 1H), 9.25 (d, J = 1.6 Hz, 1H), 8.73 (s, 1H), 8.63 (dd, J = 4.7, 1.7 Hz, 1H), 8.47 (dt, J = 8.0, 1.9 Hz, 1H), 8.29 (s, 1H), 8.26 (d, J = 7.9 Hz, 1H), 7.95 (d, J = 7.8 Hz, 1H), 7.87 (d, J = 2.0 Hz, 1H), 7.78 (t, J = 7.8 Hz, 1H), 7.70 (dd, J = 8.3, 2.1 Hz, 1H), 7.48 (ddd, J = 8.0, 4.8, 0.6 Hz, 1H), 7.44 (d, J = 8.5 Hz, 1H), 5.75 (s, 1H), 4.24 (s, 3H), 2.14 (s, 3H). MS (ESI) m/z: 505 [M + H]$^+$. |
| IV-b-2 | 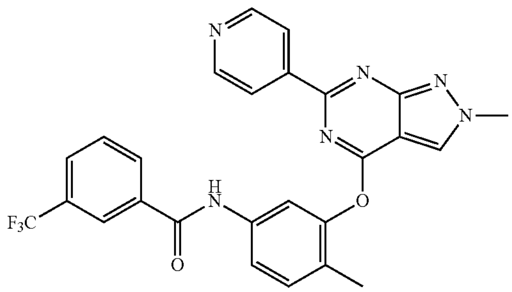 [SMILES: Cc1ccc(NC(=O)c2cccc(C(F)(F)F)c2)cc1Oc1nc(-c2ccncc2)nc2nn(C)cc12] | $^1$H NMR (600 MHz, DMSO-d$_6$) δ 10.59 (s, 1H), 8.73 (s, 1H), 8.67 (s, 2H), 8.28 (s, 1H), 8.25 (d, J = 7.9 Hz, 1H), 8.03 (d, J = 5.0 Hz, 2H), 7.96 (d, J = 7.8 Hz, 1H), 7.85 (d, J = 2.1 Hz, 1H), 7.78 (t, J = 7.8 Hz, 1H), 7.69 (dd, J = 8.3, 2.2 Hz, 1H), 7.44 (d, J = 8.4 Hz, 1H), 4.24 (s, 3H), 2.12 (s, 3H). MS (ESI) m/z: 505 [M + H]$^+$. |
| IV-b-3 | 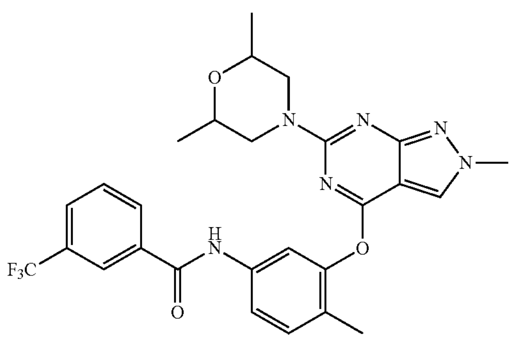 [SMILES: Cc1ccc(NC(=O)c2cccc(C(F)(F)F)c2)cc1Oc1nc(N2CC(C)OC(C)C2)nc2nn(C)cc12] | $^1$H NMR (600 MHz, DMSO-d$_6$) δ 10.55 (s, 1H), 8.28 (s, 1H), 8.27-8.24 (m, 2H), 7.97 (d, J = 7.8 Hz, 1H), 7.83 (d, J = 2.1 Hz, 1H), 7.79 (t, J = 7.8 Hz, 1H), 7.59 (dd, J = 8.3, 2.1 Hz, 1H), 7.36 (d, J = 8.6 Hz, 1H), 4.00 (s, 3H), 3.50-3.41 (m, 3H), 2.45-2.38 (m, 2H), 2.12 (s, 4H), 1.03 (d, J = 3.9 Hz, 6H). MS (ESI) m/z: 541[M + H]$^+$. |
| IV-c-1 | 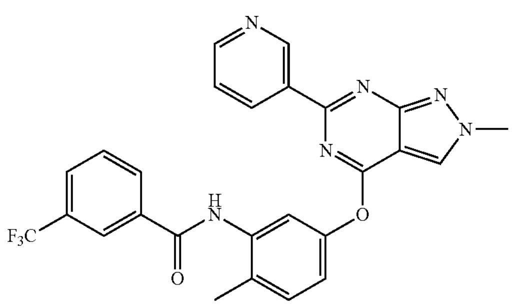 [SMILES: Cc1ccc(Oc2nc(-c3cccnc3)nc3nn(C)cc23)cc1NC(=O)c1cccc(C(F)(F)F)c1] | $^1$H NMR (600 MHz, Methanol-d$_4$) δ 9.27 (s, 1H), 8.81 (s, 1H), 8.58 (s, 1H), 8.50 (s, 1H), 8.36-8.15 (m, 3H), 7.85 (s, 1H), 7.68 (s, 1H), 7.53 (s, 1H), 7.41 (s, 2H), 7.20 (s, 1H), 4.17 (s, 3H), 2.35 (s, 3H). MS (ESI) m/z: 505 [M + H]$^+$. |
| IV-c-2 | 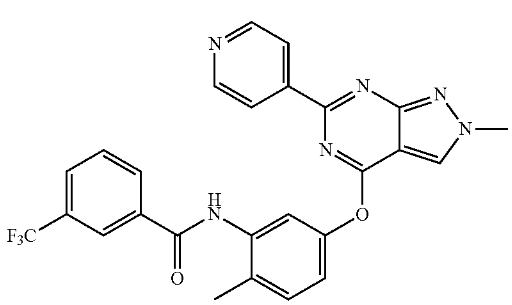 [SMILES: Cc1ccc(Oc2nc(-c3ccncc3)nc3nn(C)cc23)cc1NC(=O)c1cccc(C(F)(F)F)c1] | $^1$H NMR (600 MHz, DMSO-d$_6$) δ 10.29 (s, 1H), 8.72 (d, J = 0.7 Hz, 1H), 8.69-8.67 (m, 2H), 8.32 (d, J = 1.7 Hz, 1H), 8.29 (d, J = 7.9 Hz, 1H), 8.12-8.07 (m, 2H), 7.99-7.96 (m, 1H), 7.82-7.76 (m, 1H), 7.51 (d, J = 2.5 Hz, 1H), 7.46 (dd, J = 8.3, 0.9 Hz, 1H), 7.29 (dd, J = 8.3, 2.6 Hz, 1H), 4.23 (d, J = 0.7 Hz, 3H), 2.34 (s, 3H). MS (ESI) m/z: 505 [M + H]$^+$. |

TABLE 4-continued

Structure and characterization of compounds IV

| No. | Structure | ¹H NMR and/or MS data |
|---|---|---|
| IV-d-1 | 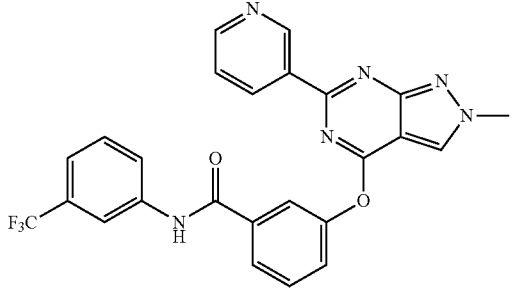 | ¹H NMR (600 MHz, DMSO-d₆) δ 10.64 (s, 1H), 9.24 (dd, J = 2.3, 0.9 Hz, 1H), 8.77 (d, J = 0.8 Hz, 1H), 8.63 (dd, J = 4.8, 1.8 Hz, 1H), 8.46 (dt, J = 8.0, 2.0 Hz, 1H), 8.25 (d, J = 2.0 Hz, 1H), 8.09-8.01 (m, 3H), 7.79-7.72 (m, 2H), 7.60 (t, J = 8.0 Hz, 1H), 7.55-7.40 (m, 2H), 4.24 (s, 3H). MS (ESI) m/z: 491 [M + H]⁺. |
| IV-d-2 | 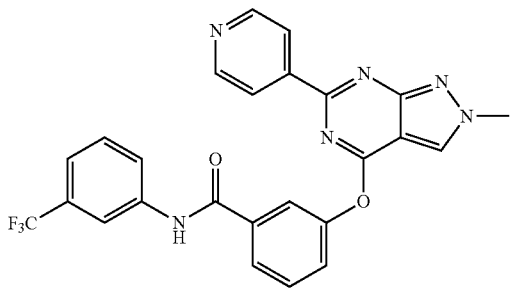 | ¹H NMR (600 MHz, DMSO-d₆) δ 10.67 (s, 1H), 8.80 (s, 1H), 8.71 (s, 1H), 8.26 (s, 1H), 8.06 (td, J = 11.2, 10.0, 6.4 Hz, 5H), 7.76 (d, J = 6.1 Hz, 2H), 7.61 (t, J = 8.0 Hz, 1H), 7.47 (d, J = 7.7 Hz, 1H), 4.26 (s, 3H). MS (ESI) m/z: 491[M + H]⁺. |
| IV-e-1 | 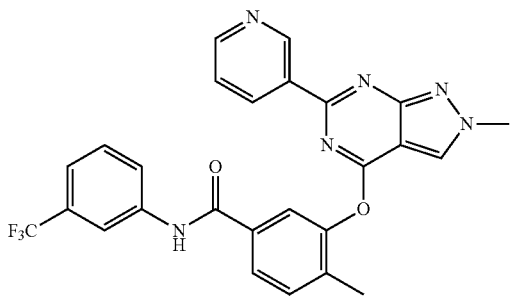 | ¹H NMR (600 MHz, DMSO-d₆) δ 10.55 (s, 1H), 9.19 (s, 1H), 8.79 (s, 1H), 8.63 (s, 1H), 8.42 (dt, J = 8.0, 2.0 Hz, 1H), 8.23 (d, J = 2.0 Hz, 1H), 8.06 (dd, J = 8.1, 2.0 Hz, 1H), 8.02 (d, J = 1.8 Hz, 1H), 7.99 (dd, J = 7.9, 1.9 Hz, 1H), 7.67-7.62 (m, 1H), 7.59 (t, J = 8.0 Hz, 1H), 7.52-7.39 (m, 2H), 4.25 (s, 3H), 2.25 (s, 3H). MS (ESI) m/z: 505 [M + H]⁺. |
| IV-e-2 | 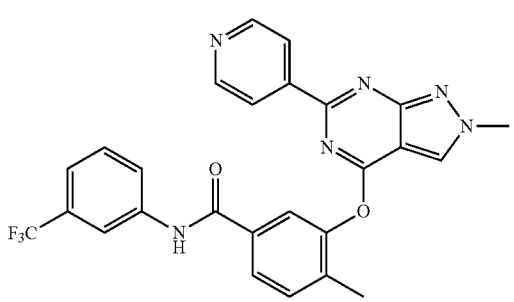 | ¹H NMR (600 MHz, DMSO-d₆) δ 10.54 (s, 1H), 8.79 (s, 1H), 8.71-8.60 (m, 2H), 8.23 (d, J = 1.9 Hz, 1H), 8.07 (dt, J = 8.3, 1.3 Hz, 1H), 8.03 (d, J = 1.8 Hz, 1H), 8.00 (dd, J = 8.0, 1.8 Hz, 1H), 7.99-7.97 (m, 2H), 7.66-7.63 (m, 1H), 7.59 (t, J = 8.0 Hz, 1H), 7.49-7.35 (m, 1H), 4.27 (s, 3H), 2.25 (s, 3H). MS (ESI) m/z: 505 [M + H]⁺. |
| IV-e-3 | 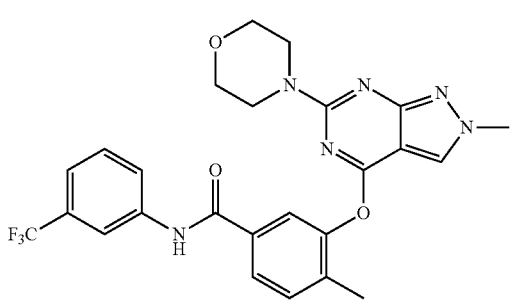 | ¹H NMR (600 MHz, DMSO-d₆) δ 10.50 (s, 0H), 8.36 (d, J = 0.7 Hz, 1H), 8.26-8.19 (m, 1H), 8.10-8.00 (m, 1H), 7.95-7.84 (m, 1H), 7.60 (t, J = 8.0 Hz, 1H), 7.55 (dd, J = 7.9, 1.0 Hz, 1H), 7.46 (ddd, J = 7.8, 1.8, 0.9 Hz, 1H), 4.03 (d, J = 0.6 Hz, 3H), 3.54 (t, J = 4.7 Hz, 4H), 3.47 (s, 4H), 2.21 (s, 3H). MS (ESI) m/z: 513 [M + H]⁺. |

TABLE 4-continued

Structure and characterization of compounds IV

| No. | Structure | ¹H NMR and/or MS data |
|---|---|---|
| IV-e-4 | 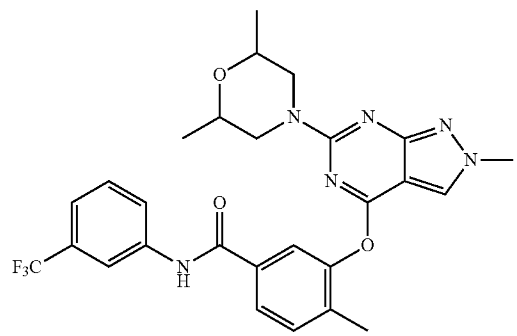 | ¹H NMR (600 MHz, DMSO-d$_6$) δ 10.49 (s, 1H), 8.35 (s, 1H), 8.24 (d, J = 2.0 Hz, 1H), 8.08-8.03 (m, 1H), 8.01 (d, J = 1.9 Hz, 1H), 7.92 (dd, J = 7.9, 1.9 Hz, 1H), 7.60 (t, J = 8.0 Hz, 1H), 7.56 (d, J = 8.0 Hz, 1H), 7.46 (d, J = 7.8 Hz, 1H), 4.21 (s, 0H), 4.02 (s, 3H), 3.44 (s, 2H), 3.34 (s, 2H), 2.41 (t, J = 11.8 Hz, 2H), 2.23 (s, 3H), 1.01 (s, 6H). MS (ESI) m/z: 541 [M + H]$^+$. |
| IV-f-1 | 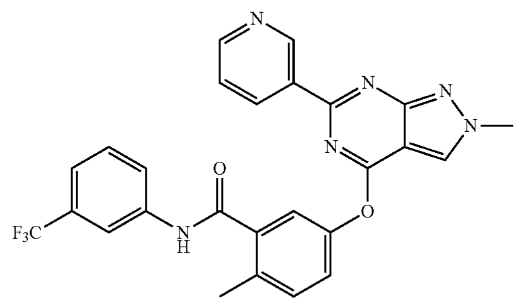 | ¹H NMR (600 MHz, DMSO-d$_6$) δ 10.70 (s, 1H), 9.29 (dd, J = 2.3, 0.8 Hz, 1H), 8.74 (d, J = 0.7 Hz, 1H), 8.65 (dd, J = 4.8, 1.7 Hz, 1H), 8.50 (dt, J = 8.0, 1.9 Hz, 1H), 8.22 (s, 1H), 7.95 (d, J = 8.4 Hz, 1H), 7.61-7.52 (m, 3H), 7.53-7.47 (m, 2H), 4.23 (d, J = 0.6 Hz, 3H), 2.48 (s, 3H). MS (ESI) m/z: 505[M + H]$^+$. |
| IV-f-2 | 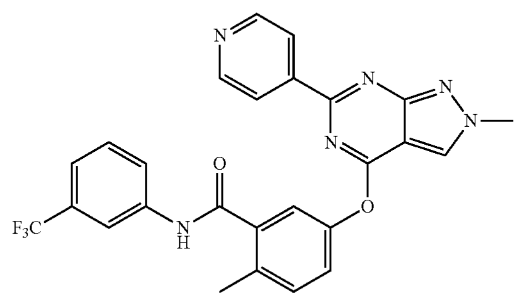 | ¹H NMR (600 MHz, DMSO-d$_6$) δ 10.71 (s, 1H), 8.75 (s, 1H), 8.71-8.64 (m, 2H), 8.22 (s, 1H), 8.10-8.04 (m, 2H), 7.95 (d, J = 8.4 Hz, 1H), 7.64-7.41 (m, 5H), 4.24 (s, 3), 2.48 (s, 3H). MS (ESI) m/z: 505[M + H]$^+$. |
| IV-g-1 | 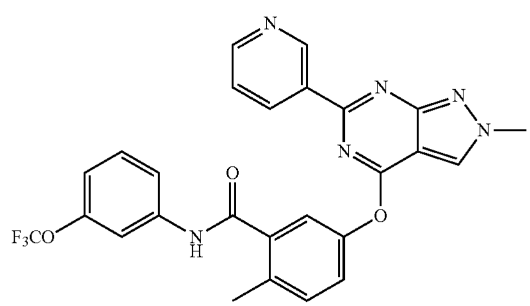 | ¹H NMR (600 MHz, DMSO-d$_6$) δ 10.67 (s, 1H), 9.30 (d, J = 2.2 Hz, 1H), 8.75 (s, 1H), 8.66 (d, J = 4.8 Hz, 1H), 8.50 (d, J = 8.0 Hz, 1H), 7.91 (s, 1H), 7.70 (d, J = 8.3 Hz, 1H), 7.59 (d, J = 2.5 Hz, 1H), 7.56 (dd, J = 8.3, 2.5 Hz, 1H), 7.50 (t, 2H), 7.47 (d, J = 8.2 Hz, 1H), 7.09 (d, J = 8.5 Hz, 1H), 4.24 (s, 3H), 2.49 (s, 3H). MS (ESI) m/z: 521 [M + H]$^+$. |
| IV-g-2 | 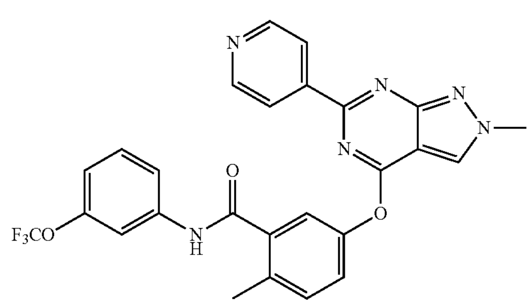 | ¹H NMR (600 MHz, DMSO-d$_6$) δ 10.68 (s, 1H), 8.77 (s, 1H), 8.69 (d, J = 6.1 Hz, 2H), 8.08 (d, J = 6.1 Hz, 2H), 7.91 (s, 1H), 7.71-7.68 (m, 1H), 7.61 (d, J = 2.5 Hz, 1H), 7.56 (dd, J = 8.3, 2.6 Hz, 1H), 7.52 (s, 1H), 7.50 (d, J = 4.2 Hz, 1H), 7.47 (d, J = 8.2 Hz, 1H), 4.25 (s, 3H), 2.49 (s, 3H). MS (ESI) m/z: 521 [M + H]$^+$. |

TABLE 4-continued

Structure and characterization of compounds IV

| No. | Structure | $^1$H NMR and/or MS data |
|---|---|---|
| IV-h-1 | 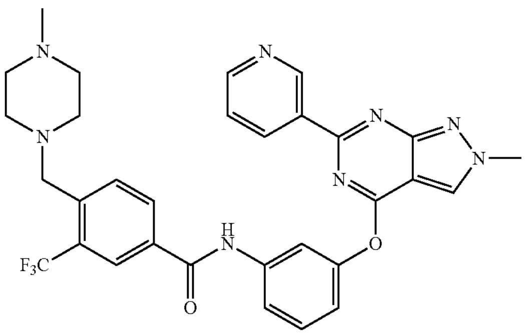 [SMILES: CN1CCN(Cc2ccc(C(=O)Nc3cccc(Oc4nc(-c5cccnc5)nc5nn(C)cc45)c3)cc2C(F)(F)F)CC1] | $^1$H NMR (600 MHz, DMSO-d$_6$) δ 10.67 (s, 1H), 9.29 (d, J = 1.7 Hz, 1H), 8.73 (s, 1H), 8.64 (dd, J = 4.7, 1.7 Hz, 1H), 8.50 (s, 1H), 8.26 (s, 1H), 8.24 (d, J = 8.2 Hz, 1H), 7.95 (t, J = 2.1 Hz, 1H), 7.92 (d, J = 8.1 Hz, 1H), 7.81-772 (m, 1H), 7.56 (s, 1H), 7.49 (dd, J = 8.0, 4.8 Hz, 1H), 7.22 (dd, J = 8.1, 1.7 Hz, 1H), 4.23 (s, 3H), 3.69 (s, 2H), 2.49-2.41 (m, 8H), 2.25 (s, 3H). MS (ESI) m/z: 603[M + H]$^+$. |
| IV-h-2 | 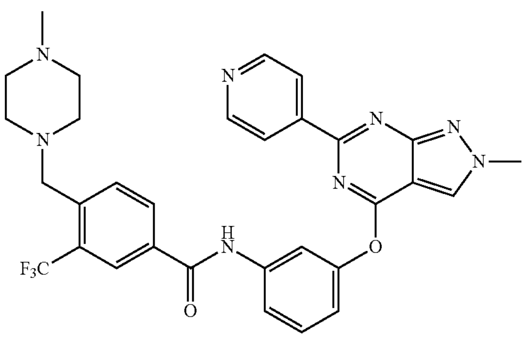 [SMILES: CN1CCN(Cc2ccc(C(=O)Nc3cccc(Oc4nc(-c5ccncc5)nc5nn(C)cc45)c3)cc2C(F)(F)F)CC1] | $^1$H NMR (600 MHz, DMSO-d$_6$) δ 10.66 (s, 1H), 8.73 (s, 1H), 8.68 (dd, J = 4.5, 1.5 Hz, 2H), 8.25 (s, 1H), 8.24 (d, J = 8.2 Hz, 1H), 8.08 (dd, J = 4.5, 1.6 Hz, 2H), 7.95 (t, J = 2.1 Hz, 1H), 7.92 (d, J = 8.1 Hz, 1H), 7.79-7.73 (m, 1H), 7.56 (t, J = 8.2 Hz, 1H), 7.22 (dd, J = 8.1, 1.6 Hz, 1H), 4.24 (s, 3H), 3.67 (s, 2H), 2.47-2.34 (m, 8 H), 2.19 (s, 3H). MS (ESI) m/z: 603[M + H]$^+$. |
| IV-i-1 | 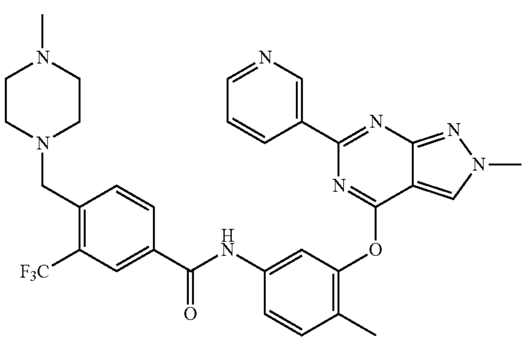 [SMILES: Cc1ccc(NC(=O)c2ccc(CN3CCN(C)CC3)c(C(F)(F)F)c2)cc1Oc1nc(-c2cccnc2)nc2nn(C)cc12] | $^1$H NMR (600 MHz, DMSO-d$_6$) δ 10.57 (s, 1H), 9.24 (d, J = 1.5 Hz, 1H), 8.73 (s, 1H), 8.63 (dd, J = 4.7, 1.6 Hz, 1H), 8.47 (dt, J = 8.0, 1.9 Hz, 1H), 8.24 (s, 1H), 8.21 (d, J = 8.1 Hz, 1H), 7.91 (d, J = 8.2 Hz, 1H), 7.85 (d, J = 1.9 Hz, 1H), 7.68 (dd, J = 8.3, 2.0 Hz, 1H), 7.52-7.46 (m, 1H), 7.43 (d, J = 8.6 Hz, 1H), 4.23 (s, 3H), 3.66 (s, 2H), 2.45-2.28 (m, 8H), 2.16 (s, 3H), 2.13 (s, 3H). MS (ESI) m/z: 617 [M + H]$^+$. |
| IV-i-2 | 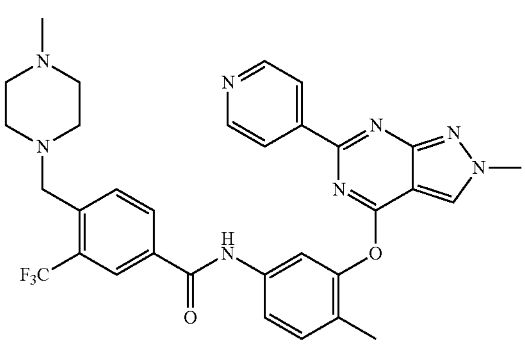 [SMILES: Cc1ccc(NC(=O)c2ccc(CN3CCN(C)CC3)c(C(F)(F)F)c2)cc1Oc1nc(-c2ccncc2)nc2nn(C)cc12] | $^1$H NMR (600 MHz, DMSO-d$_6$) δ 10.56 (s, 1H), 8.72 (s, 1H), 8.69-8.63 (m, 2H), 8.24 (d, J = 1.8 Hz, 1H), 8.21 (dd, J = 8.2, 1.8 Hz, 1H), 8.06-7.99 (m, 2H), 7.90 (d, J = 8.1 Hz, 1H), 7.86 (d, J = 2.1 Hz, 1H), 7.68 (dd, J = 8.3, 2.2 Hz, 1H), 7.43 (d, J = 8.4 Hz, 1H), 4.24 (s, 3H), 3.65 (s, 2H), 2.43-2.22 (m, 8H), 2.14 (s, 3H), 2.13 (s, 3H). MS (ESI) m/z: 617 [M + H]$^+$. |

TABLE 4-continued

Structure and characterization of compounds IV

| No. | Structure | ¹H NMR and/or MS data |
|---|---|---|
| IV-l-1 | 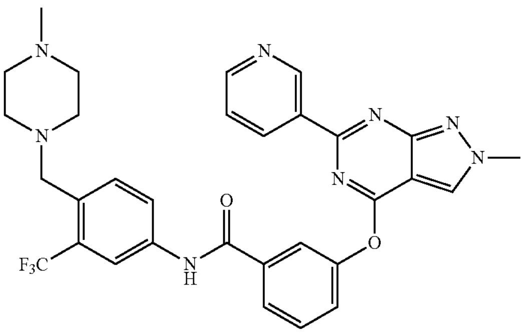 [SMILES: CN1CCN(Cc2ccc(NC(=O)c3cccc(Oc4nc(-c5cccnc5)nc5nn(C)cc45)c3)cc2C(F)(F)F)CC1] | ¹H NMR (600 MHz, DMSO-d$_6$) δ 10.57 (s, 1H), 9.23 (d, J = 2.1 Hz, 1H), 8.77 (s, 1H), 8.62 (dd, J = 4.8, 1.7 Hz, 1H), 8.51-8.44 (m, 1H), 8.19 (d, J = 2.2 Hz, 1H), 8.06-7.99 (m, 3H), 7.77-7.67 (m, 3H), 7.47 (dd, J = 7.9, 4.6 Hz, 1H), 4.24 (s, 3H), 3.55 (s, 2H), 2.42-2.31(m, 8H), 2.15 (s, 3H) MS (ESI) m/z: 603 [M + H]⁺. |
| IV-l-2 | 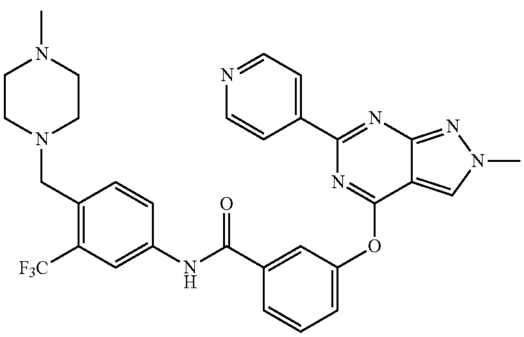 [SMILES: CN1CCN(Cc2ccc(NC(=O)c3cccc(Oc4nc(-c5ccncc5)nc5nn(C)cc45)c3)cc2C(F)(F)F)CC1] | ¹H NMR (600 MHz, DMSO-d$_6$) δ 10.60 (s, 1H), 8.78 (s, 1H), 8.69-8.64 (m, 2H), 8.21 (d, J = 2.2 Hz, 1H), 8.07-8.00 (m, 5H), 7.79-7.72 (m, 2H), 7.70 (d, J = 8.6 Hz, 1H), 4.26 (s, 3H), 3.56 (s, 2H), 2.45-2.34 (m, 8H), (s, 8H), 2.18 (s, 3H). MS (ESI) m/z: 603 [M + H]⁺. |
| IV-m-1 | 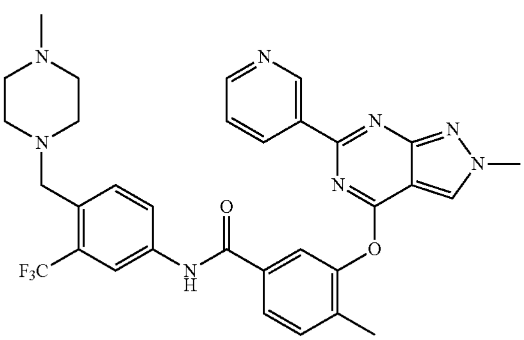 [SMILES: Cc1ccc(C(=O)Nc2ccc(CN3CCN(C)CC3)c(C(F)(F)F)c2)cc1Oc1nc(-c2cccnc2)nc2nn(C)cc12] | ¹H NMR (600 MHz, DMSO-d$_6$) δ 10.50 (s, 1H), 9.19 (d, J = 2.1 Hz, 1H), 8.79 (s, 1H), 8.62 (dd, J = 4.8, 1.7 Hz, 1H), 8.42 (dt, J = 8.0, 2.0 Hz, 1H), 8.18 (d, J = 2.2 Hz, 1H), 8.06-7.96 (m, 3H), 7.69 (d, J = 8.6 Hz, 1H), 7.64 (d, J = 8.0 Hz, 1H), 7.47 (dd, J = 8.0, 4.7 Hz, 1H), 4.25 (s, 3H), 3.56 (s, 2H), 2.44-2.29 (s, 8H), 2.25 (s, 3H), 2.17 (s, 3H). MS (ESI) m/z: 617 [M + H]⁺. |
| IV-m-2 | 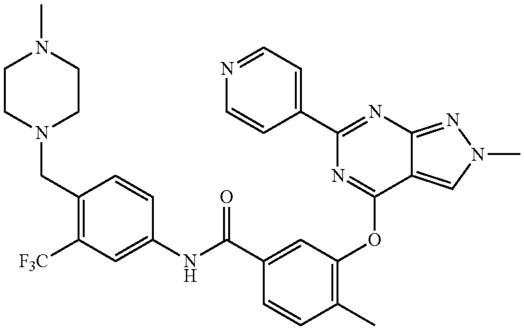 [SMILES: Cc1ccc(C(=O)Nc2ccc(CN3CCN(C)CC3)c(C(F)(F)F)c2)cc1Oc1nc(-c2ccncc2)nc2nn(C)cc12] | ¹H NMR (600 MHz, DMSO-d$_6$) δ 10.51 (s, 1H), 8.79 (s, 1H), 8.67-8.63 (m, 2H), 8.18 (d, J = 2.2 Hz, 1H), 8.05 (dd, J = 8.6, 2.2 Hz, 1H), 8.02 (d, J = 1.8 Hz, 1H), 7.99 (dd, J = 7.9, 1.8 Hz, 1H), 7.98-7.96 (m, 2H), 7.68 (d, J = 8.6 Hz, 1H), 7.63 (d, J = 8.1 Hz, 1H), 4.26 (s, 3H), 3.55 (s, 2H), 2.42-2.33 (m, 8H), , 2.24 (s, 3H), 2.16 (s, 3H). MS (ESI) m/z: 617 [M + H]⁺. |

TABLE 4-continued

Structure and characterization of compounds IV

| No. | Structure | $^1$H NMR and/or MS data |
|---|---|---|
| IV-n-1 | 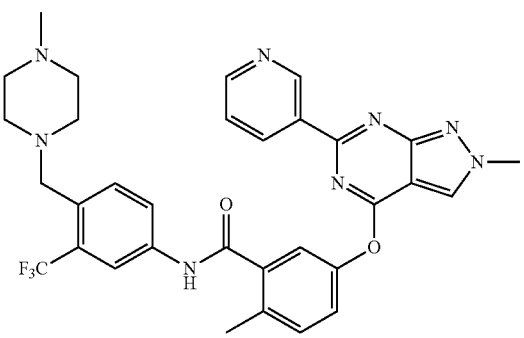 [SMILES: Cc1ccc(Oc2nc(-c3cccnc3)nc3nn(C)cc23)cc1C(=O)Nc1ccc(CN2CCN(C)CC2)c(C(F)(F)F)c1] | $^1$H NMR (600 MHz, DMSO-d$_6$) δ 10.69 (s, 1H), 9.30 (s, 1H), 8.75 (s, 1H), 8.66 (s, 1H), 8.50 (d, J = 7.0 Hz, 1H), 8.19 (s, 1H), 7.97 (d, J = 8.0 Hz, 1H), 7.69 (d, J = 8.1 Hz, 1H), 7.58 (s, 1H), 7.55 (d, J = 8.1 Hz, 1H), 7.51 (s, 1H), 7.50 (s, 1H), 4.24 (s, 3H), 3.56 (s, 2H), 3.35 (s, 2H), 2.49 (s, 3H), 2.44-2.37 (m, 6H), 2.22 (s, 3H). MS (ESI) m/z: 617[M + H]$^+$. |
| IV-n-2 | 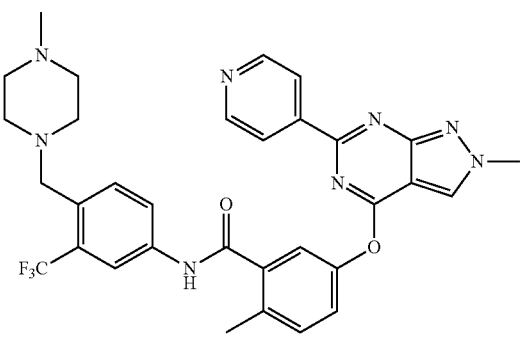 [SMILES: Cc1ccc(Oc2nc(-c3ccncc3)nc3nn(C)cc23)cc1C(=O)Nc1ccc(CN2CCN(C)CC2)c(C(F)(F)F)c1] | $^1$H NMR (600 MHz, DMSO-d$_6$) δ 10.71 (s, 1H), 8.75 (s, 1H), 8.68 (d, J = 5.5 Hz, 2H), 8.19 (s, 1H), 8.07 (d, J = 5.8 Hz, 2H), 7.97 (d, J = 8.4 Hz, 1H), 7.68 (d, J = 8.5 Hz, 1H), 7.59 (d, J = 2.3 Hz, 1H), 7.54 (dd, J = 8.3, 2.3 Hz, 1H), 7.49 (d, J = 8.4 Hz, 1H), 4.24 (s, 3H), 3.55 (s, 2H), 3.36 (s, 2H), 2.48 (s, 3H), 2.43-2.29 (m, 6H), 2.19 (s, 3H). MS (ESI) m/z: 617[M + H]$^+$. |
| IV-n-3 | 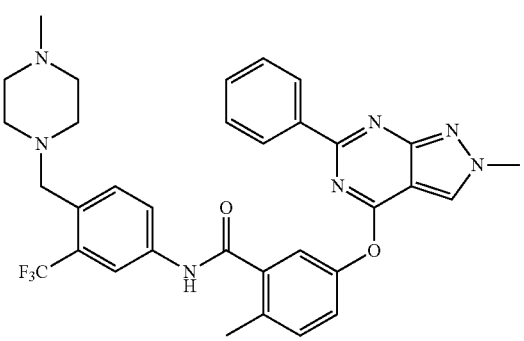<br>TFA Salt | MS (ESI) m/z: 615[M + H]$^+$. |
| IV-n-4 | 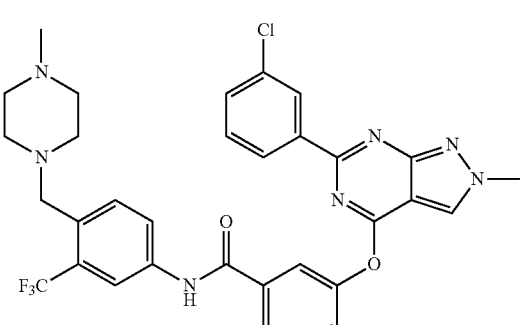<br>TFA Salt | MS (ESI) m/z: 651 [M + H]$^+$. |

TABLE 4-continued
Structure and characterization of compounds IV
| No. | Structure | ¹H NMR and/or MS data |
|---|---|---|
| IV-n-5 | 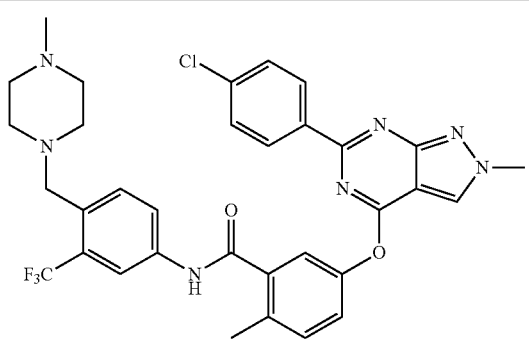 TFA Salt | MS (ESI) m/z: 651 [M + H]⁺. |
| IV-n-6 | 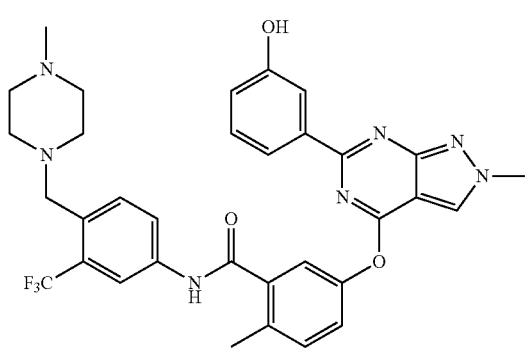 TFA Salt | MS (ESI) m/z: 631 [M + H]⁺. |
| IV-n-7 | 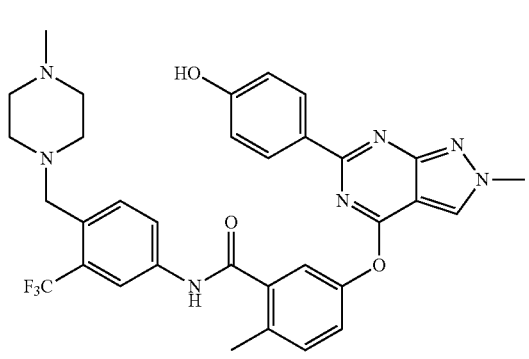 TFA Salt | MS (ESI) m/z: 631 [M + H]⁺. |
| IV-n-8 | 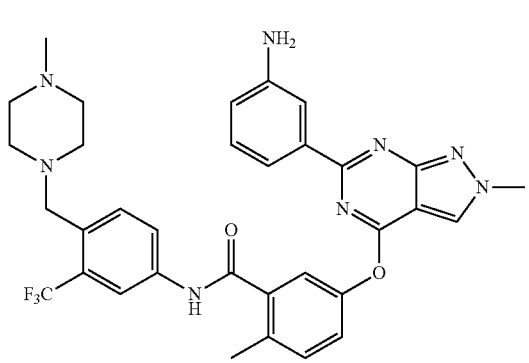 [SMILES: Cc1ccc(Oc2nc(-c3cccc(N)c3)nc3nn(C)cc23)cc1C(=O)Nc1ccc(CN2CCN(C)CC2)c(C(F)(F)F)c1] | MS (ESI) m/z: 630 [M + H]⁺. |

TABLE 4-continued
Structure and characterization of compounds IV
| No. | Structure | ¹H NMR and/or MS data |
|---|---|---|
| IV-n-9 | 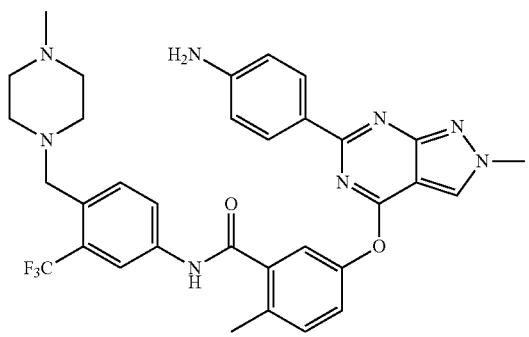 [SMILES: Cc1ccc(Oc2nc(-c3ccc(N)cc3)nc3nn(C)cc23)cc1C(=O)Nc1ccc(CN2CCN(C)CC2)c(C(F)(F)F)c1] | MS (ESI) m/z: 630 [M + H]⁺. |
| IV-n-10 | 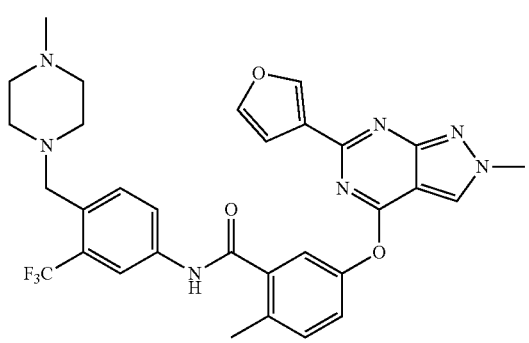 [SMILES: Cc1ccc(Oc2nc(-c3ccoc3)nc3nn(C)cc23)cc1C(=O)Nc1ccc(CN2CCN(C)CC2)c(C(F)(F)F)c1] | MS (ESI) m/z: 605[M + H]⁺. |
| IV-n-11 | 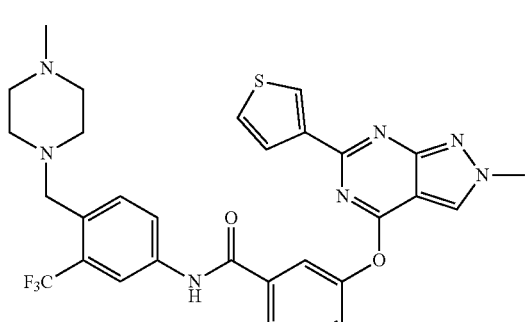 TFA Salt | MS (ESI) m/z: 621[M + H]⁺. |
| IV-o-1 | 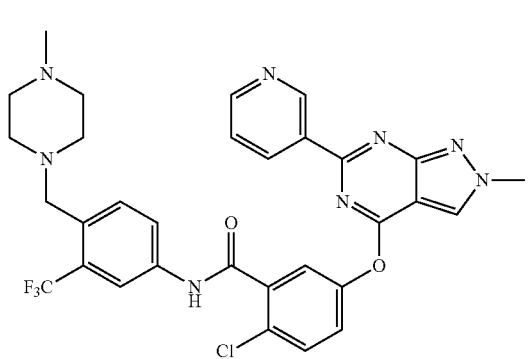 [SMILES: CN1CCN(Cc2ccc(NC(=O)c3cc(Oc4nc(-c5cccnc5)nc5nn(C)cc45)ccc3Cl)cc2C(F)(F)F)CC1] | ¹H NMR (600 MHz, Methanol-$d_4$) δ 9.29 (d, J = 2.1 Hz, 1H), 8.61-8.55 (m, 2H), 8.51 (s, 1H), 8.10 (d, J = 2.2 Hz, 1H), 7.88 (dd, J = 8.5, 2.2 Hz, 1H), 7.76 (d, J = 8.5 Hz, 1H), 7.71-7.66 (m, 2H), 7.57 (dd, J = 8.7, 2.8 Hz, 1H), 7.48 (dd, J = 8.0, 4.9 Hz, 1H), 4.26 (s, 3H), 3.65 (s, 2H), 2.59-2.49(m, 8H), 2.34 (s, 3H). MS (ESI) m/z: 638 [M + H]⁺. |

TABLE 4-continued

Structure and characterization of compounds IV

| No. | Structure | ¹H NMR and/or MS data |
|---|---|---|
| IV-o-2 | 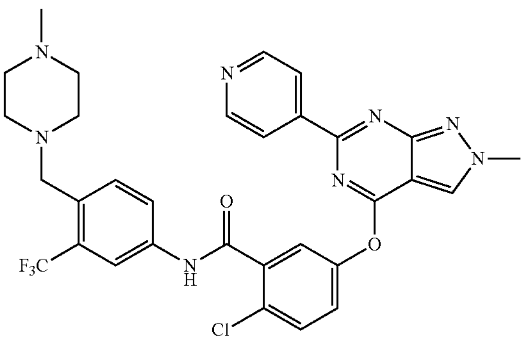 [SMILES: CN1CCN(Cc2ccc(NC(=O)c3cc(Oc4nc(-c5ccncc5)nc5nn(C)cc45)ccc3Cl)cc2C(F)(F)F)CC1] | ¹H NMR (600 MHz, DMSO-d$_6$) δ 10.92 (s, 1H), 8.82 (s, 1H), 8.76-8.64 (m, 2H), 8.16 (d, J = 2.2 Hz, 1H), 8.12-8.03 (m, 2H), 7.99-7.83 (m, 1H), 7.78 (d, J = 2.9 Hz, 1H), 7.77 (d, J = 8.7 Hz, 1H), 7.72 (d, J = 8.5 Hz, 1H), 7.68 (dd, J = 8.8, 2.8 Hz, 1H), 4.25 (s, 3H), 3.56 (s, 2H), 2.43-2.35 (m, 8H), 2.19 (s, 3H). MS (ESI) m/z: 638[M + H]⁺. |
| IV-o-3 | 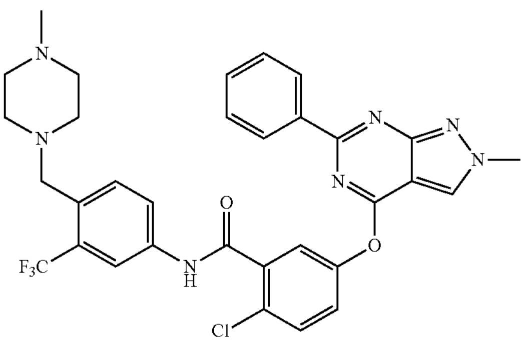 [SMILES: CN1CCN(Cc2ccc(NC(=O)c3cc(Oc4nc(-c5ccccc5)nc5nn(C)cc45)ccc3Cl)cc2C(F)(F)F)CC1] | MS (ESI) m/z: 635 [M + H]⁺. |
| IV-o-4 | 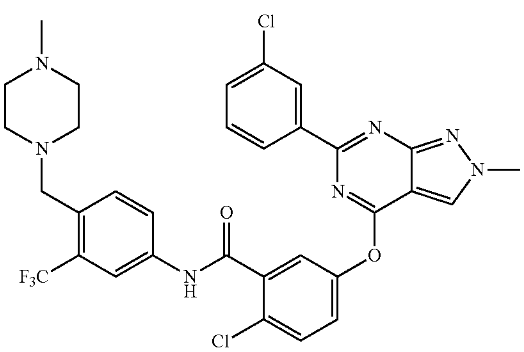 [SMILES: CN1CCN(Cc2ccc(NC(=O)c3cc(Oc4nc(-c5cccc(Cl)c5)nc5nn(C)cc45)ccc3Cl)cc2C(F)(F)F)CC1] | ¹H NMR (600 MHz, DMSO-d$_6$) δ 10.95 (s, 1H), 9.53 (s, 1H), 8.79 (s, 1H), 8.19 (t, J = 1.9 Hz, 1H), 8.18-8.13 (m, 2H), 7.97 (dd, J = 8.5, 2.2 Hz, 1H), 7.79 (d, J = 2.8 Hz, 1H), 7.77 (d, J = 8.7 Hz, 1H), 7.71 (d, J = 8.7 Hz, 1H), 7.68 (dd, J = 8.8, 2.8 Hz, 1H), 7.55 (ddd, J = 7.9, 2.3, 1.1 Hz, 1H), 7.50 (t, J = 7.8 Hz, 1H), 4.24 (s, 3H), 3.67 (s, 2H), 3.43-3.36 (m, 2H), 3.07-2.98 (m, 2H), 2.94-2.87 (m, 2H), 2.80 (s, 3H), 2.45-2.23 (m, 2H). MS (ESI) m/z: 670 [M + H]⁺. |
| IV-o-5 | 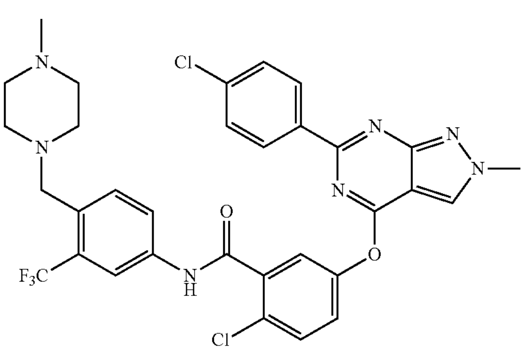 [SMILES: CN1CCN(Cc2ccc(NC(=O)c3cc(Oc4nc(-c5ccc(Cl)cc5)nc5nn(C)cc45)ccc3Cl)cc2C(F)(F)F)CC1] | ¹H NMR (600 MHz, DMSO-d$_6$) δ 10.94 (s, 1H), 9.55 (s, 1H), 8.77 (s, 1H), 8.22 (d, J = 8.6 Hz, 2H), 8.14 (d, J = 2.2 Hz, 1H), 7.99 (dd, J = 8.5, 2.2 Hz, 1H), 7.78 (d, J = 2.8 Hz, 1H), 7.76 (d, J = 8.8 Hz, 1H), 7.72 (d, J = 8.6 Hz, 1H), 7.66 (dd, J = 8.8, 2.8 Hz, 1H), 4.23 (s, 3H), 3.67 (s, 2H), 3.44-3.32 (m, 2H), 3.06-2.97 (m, 2H), 2.94-2.85 (m, 2H), 2.80 (s, 3H), 2.41-2.30 (m, 2H). MS (ESI) m/z: 671 [M + H]⁺. |

TABLE 4-continued

Structure and characterization of compounds IV

| No. | Structure | ¹H NMR and/or MS data |
|---|---|---|
| IV-o-6 | 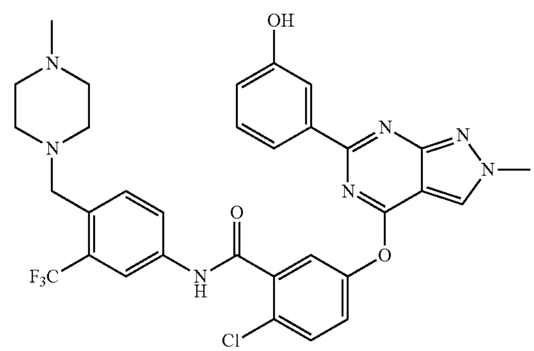 | ¹H NMR (600 MHz, DMSO-d$_6$) δ 10.90 (s, 1H), 9.59 (s, 1H), 8.73 (s, 1H), 8.15 (d, J = 2.2 Hz, 1H), 7.92 (dd, J = 8.6 2.2 Hz, 1H), 7.79-7.61 (m, 6H), 7.23 (t, J = 7.9 Hz, 1H), 6.86 (dd, J = 7.9, 2.5 Hz, 1H), 4.21 (s, 3H), 3.55 (s, 2H), 3.17 (s, 3H), 2.45-2.24(m, 8H) MS (ESI) m/z: 652 [M + H]⁺. |
| IV-o-7 | 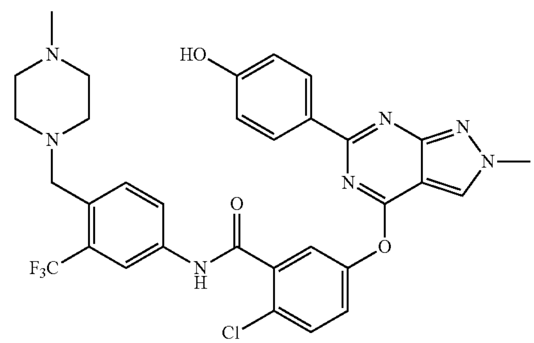 [SMILES: CN1CCN(Cc2ccc(NC(=O)c3cc(Oc4nc(-c5ccc(O)cc5)nc5nn(C)cc45)ccc3Cl)cc2C(F)(F)F)CC1] | ¹H NMR (600 MHz, DMSO-d$_6$) δ 10.90 (s, 1H), 9.92 (s, 1H), 8.68 (s, 1H), 8.16 (d, J = 2.3 Hz, 1H), 8.08-8.04 (m, 2H), 7.92 (dd, J = 8.5, 2.2 Hz, 1H), 7.75 (d, J = 1.7 Hz, 1H) 7.74 (d, J = 4.2 Hz, 1H), 7.72 (d, J = 8.5 Hz, 1H), 7.64 (dd, J = 8.8, 2.8 Hz, 1H), 6.92-6.63 (m, 2H), 4.19 (s, 3H), 3.56 (d, J = 2.8 Hz, 2H), 2.44-2.30(m, 8H), 2.17 (s, 3H). MS (ESI) m/z: 652 [M + H]⁺. |
| IV-o-8 | 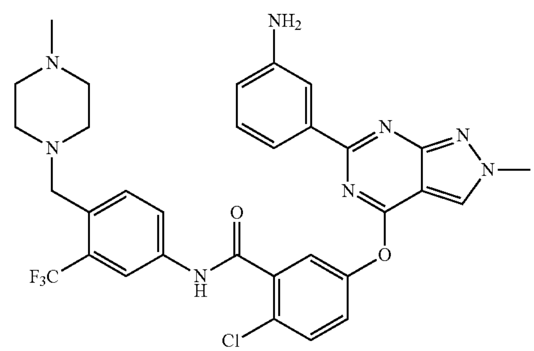 [SMILES: CN1CCN(Cc2ccc(NC(=O)c3cc(Oc4nc(-c5cccc(N)c5)nc5nn(C)cc45)ccc3Cl)cc2C(F)(F)F)CC1] | MS (ESI) m/z: 650 [M + H]⁺. |
| IV-o-9 | TFA Salt | MS (ESI) m/z: 650[M + H]⁺. |

TABLE 4-continued
Structure and characterization of compounds IV
| No. | Structure | ¹H NMR and/or MS data |
|---|---|---|
| IV-o-10 | 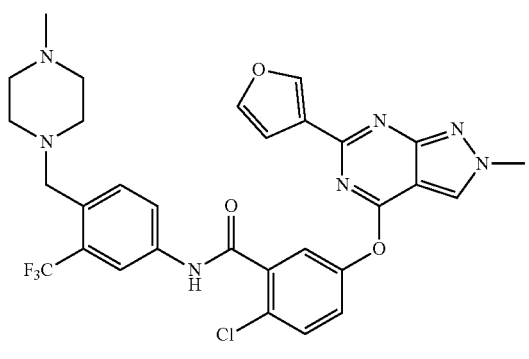 TFA Salt | MS (ESI) m/z: 626[M + H]⁺. |
| IV-o-11 | 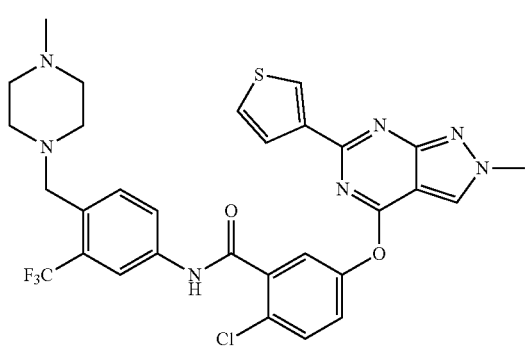 [SMILES: CN1CCN(Cc2ccc(NC(=O)c3cc(Oc4nc(-c5ccsc5)nc5nn(C)cc45)ccc3Cl)cc2C(F)(F)F)CC1] | ¹H NMR (600 MHz, DMSO-d₆) δ 10.91 (s, 1H), 8.72 (s, 1H), 8.15 (d, J = 2.2 Hz, 1H), 8.12 (dd, J = 3.1, 1.2 Hz, 1H), 7.94 (dd, J = 8.5, 2.2 Hz, 1H), 7.76 (d, J = 2.8 Hz, 1H), 7.74 (d, J = 8.8 Hz, 1H), 7.72 (d, J = 8.5 Hz, 1H), 7.68 (dd, J = 5.0, 1.2 Hz, 1H), 7.64 (dd, J = 8.7, 2.8 Hz, 1H), 7.60 (dd, J = 5.0, 3.1 Hz, 1H), 4.21 (s, 3H), 3.58 (s, 2H), 2.48-2.36(m, 8H), 2.28 (s, 3H). MS (ESI) m/z: 643 [M + H]⁺. |
| IV-o-12 | 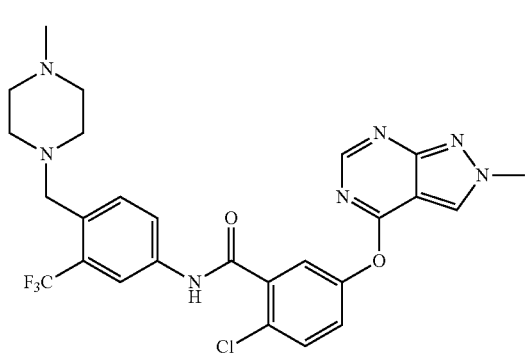 | MS (ESI) m/z: 539 [M + H]+. |
| IV-r-1 | 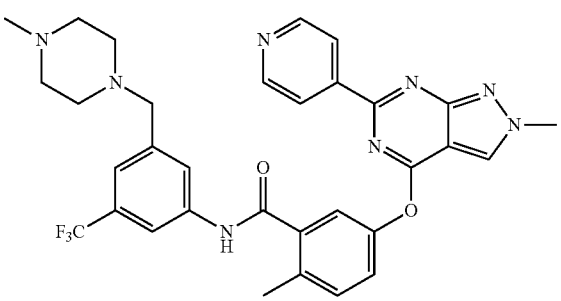 | ¹H NMR (600 MHz, DMSO-d₆) δ 10.70 (s, 1H), 8.76 (s, 1H), 8.70-8.65 (m, 2H), 8.14 (s, 1H), 8.10-8.03 (m, 2H), 7.92 (s, 1H), 7.62 (d, J = 2.5 Hz, 1H), 7.54 (dd, J = 8.3, 2.5 Hz, 1H), 7.50 (d, J = 8.4 Hz, 1H), 7.35 (s, 1H), 4.24 (s, 3H), 3.53 (s, 2H), 2.49 (s, 3H), 2.45-2.29 (m, 8H), 2.19 (s, 3H). MS (ESI) m/z: 617[M + H]⁺. |

TABLE 4-continued

Structure and characterization of compounds IV

| No. | Structure | ¹H NMR and/or MS data |
|---|---|---|
| IV-t-1 | 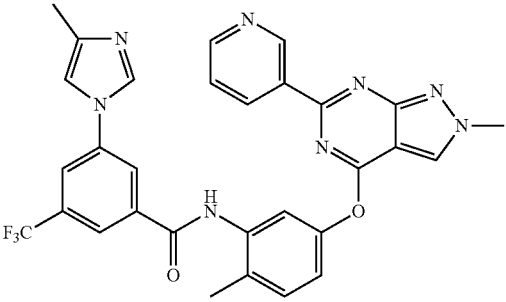 [SMILES: Cc1cn(-c2cc(C(=O)Nc3cc(Oc4nc(-c5cccnc5)nc5nn(C)cc45)ccc3C)cc(C(F)(F)F)c2)cn1] | ¹H NMR (600 MHz, DMSO-d$_6$) δ 10.87 (s, 1H), 9.38 (s, 1H), 8.77 (s, 2H), 8.52 (d, J = 8.0 Hz, 1H), 8.22 (s, 1H), 8.19 (s, 1H), 8.11 (s, 1H), 7.73 (s, 1H), 7.64 (d, J = 2.5 Hz, 1H), 7.58 (dd, J = 8.3, 2.5 Hz, 1H), 7.54 (s, 1H), 7.52 (s, 1H), 7.49 (s, 1H), 4.24 (s, 3H), 2.17 (s, 3H), 1.34 (s, 3H). MS (ESI) m/z: 585[M + H]⁺. |

TABLE 5

Structure and characterization of compounds V

| No. | Structure | ¹H NMR and/or MS data |
|---|---|---|
| V-a-1 | 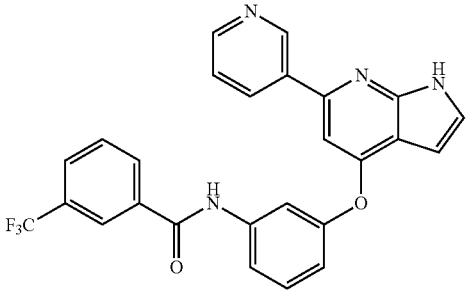  TFA Salt | ¹H NMR (600 MHz, DMSO-d$_6$) δ 11.98 (s, 1H), 10.57 (s, 1H), 9.22 (s, 1H), 8.59 (d, J = 4.3 Hz, 1H), 8.36 (d, J = 7.6 Hz, 1H), 8.30-8.21 (m, 2H), 7.97 (d, J = 7.8 Hz, 1H), 7.78 (t, J = 7.9 Hz, 1H), 7.74-7.69 (m, 2H), 7.52-7.43 (m, 3H), 7.30 (s, 1H), 7.04 (d, J = 7.9 Hz, 1H), 6.12 (s, 1H), MS (ESI) m/z: 475 [M + H]⁺. |
| V-a-2 | 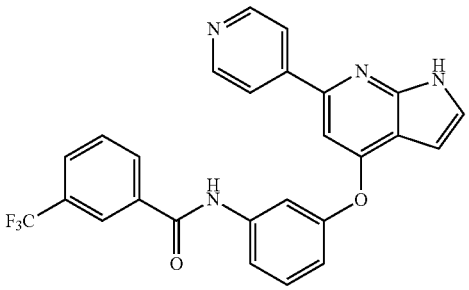 [SMILES: O=C(Nc1cccc(Oc2cc(-c3ccncc3)nc3[nH]ccc23)c1)c1cccc(C(F)(F)F)c1] | ¹H NMR (600 MHz, DMSO-d$_6$) δ 12.04 (s, 1H), 10.58 (s, 1H), 8.66 (d, J = 6.0 Hz, 2H), 8.27 (s, 1H), 8.24 (d, J = 7.9 Hz, 1H), 8.00 (d, J = 6.1 Hz, 2H), 7.97 (d, J = 7.8 Hz, 1H), 7.78 (t, J = 7.8 Hz, 1H), 7.75-7.69 (m, 2H), 7.52-7.46 (m, 2H), 7.37 (s, 1H), 7.04 (dd, J = 8.1, 2.3 Hz, 1H), 6.15 (dd, J = 3.3, 1.9 Hz, 1H). MS (ESI) m/z: 475 [M + H]⁺. |
| V-a-3 | 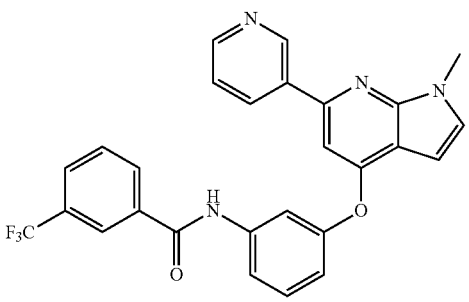 [SMILES: Cn1ccc2c(Oc3cccc(NC(=O)c4cccc(C(F)(F)F)c4)c3)cc(-c3cccnc3)nc21] | ¹H NMR (600 MHz, DMSO-d$_6$) δ 10.57 (s, 1H), 9.29 (d, J = 1.7 Hz, 1H), 8.60 (dd, J = 4.7, 1.6 Hz, 1H), 8.44 (ddd, J = 8.0, 2.2, 1.7 Hz, 1H), 8.27 (s, 1H), 8.24 (d, J = 7.8 Hz, 1H), 7.97 (d, J = 7.8 Hz, 1H), 7.78 (t, J = 7.8 Hz, 1H), 7.75-7.67 (m, 2H), 7.55-7.44 (m, 3H), 7.34 (s, 1H), 7.03 (ddd, J = 8.1, 2.4, 0.8 Hz, 1H), 6.11 (d, J = 3.5 Hz, 1H), 3.91 (s, 3H). MS (ESI) m/z: 489 [M + H]⁺. |

TABLE 5-continued

Structure and characterization of compounds V

| No. | Structure | ¹H NMR and/or MS data |
|---|---|---|
| V-a-4 | 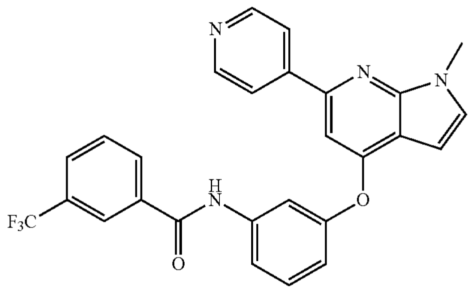 [SMILES: Cn1ccc2c(Oc3cccc(NC(=O)c4cccc(C(F)(F)F)c4)c3)cc(-c3ccncc3)nc21] | ¹H NMR (600 MHz, Chloroform-d) δ 9.02 (s, 1H), 8.55 (dd, J = 4.6, 1.6 Hz, 2H), 8.14 (s, 1H), 8.06 (d, J = 7.8 Hz, 1H), 7.90 (dd, J = 4.6, 1.6 Hz, 2H), 7.74 (d, J = 7.8 Hz, 1H), 7.68-7.57 (m, 2H), 7.54 (t, J = 7.8 Hz, 1H), 7.39 (t, J = 8.1 Hz, 1H), 7.14 (d, J = 3.5 Hz, 1H), 7.10 (s, 1H), 6.98 (ddd, J = 8.1, 2.3, 0.7 Hz, 1H), 6.30 (d, J = 3.4 Hz, 1H), 3.94 (s, 3H). MS (ESI) m/z: 489 [M + H]⁺. |
| V-b-1 | 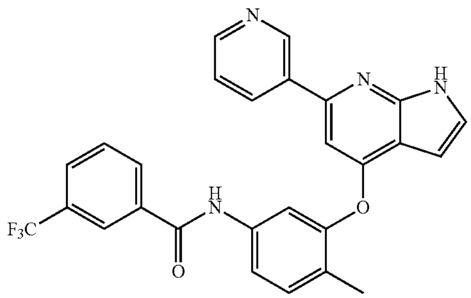 [SMILES: Cc1ccc(NC(=O)c2cccc(C(F)(F)F)c2)cc1Oc1cc(-c2cccnc2)nc2[nH]ccc12] | ¹H NMR (600 MHz, Chloroform-d) δ 9.18 (d, J = 1.6 Hz, 1H), 8.57 (d, J = 4.6 Hz, 1H), 8.29 (d, J = 8.0 Hz, 1H), 8.18 (s, 1H), 8.12 (s, 1H), 8.05 (d, J = 7.8 Hz, 1H), 7.79 (d, J = 7.8 Hz, 1H), 7.60 (t, J = 7.8 Hz, 1H), 7.56 (d, J = 1.6 Hz, 1H), 7.50 (dd, J = 8.3, 1.8 Hz, 1H), 7.37-7.32 (m, 2H), 7.27 (d, J = 3.6 Hz, 1H), 6.93 (s, 1H), 6.41 (d, J = 3.6 Hz, 1H), 2.27 (s, 3H). MS (ESI) m/z: 489 [M + H]⁺. |
| V-b-2 | 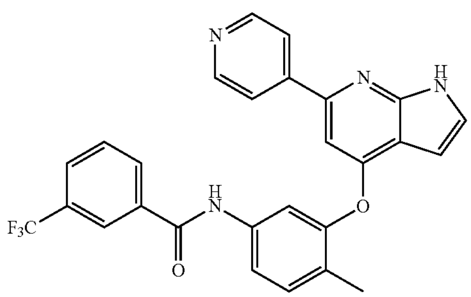 [SMILES: Cc1ccc(NC(=O)c2cccc(C(F)(F)F)c2)cc1Oc1cc(-c2ccncc2)nc2[nH]ccc12] | ¹H NMR (600 MHz, DMSO-d₆) δ 12.01 (s, 1H), 10.50 (s, 1H), 8.65 (dd, J = 4.6, 1.5 Hz, 2H), 8.25 (s, 1H), 8.22 (d, J = 8.0 Hz, 1H), 7.98-7.93 (m, 3H), 7.76 (t, J = 7.8 Hz, 1H), 7.69 (dd, J = 8.3, 2.0 Hz, 1H), 7.62 (d, J = 2.0 Hz, 1H), 7.48-7.46 (m, 1H), 7.42 (d, J = 8.4 Hz, 1H), 7.22 (s, 1H), 6.08 (dd, J = 3.4, 1.9 Hz, 1H), 2.22 (s, 3H). MS (ESI) m/z: 489 [M + H]⁺. |
| V-b-3 | 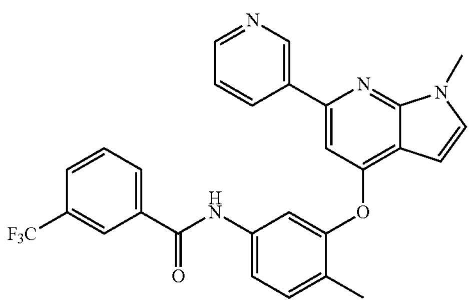 [SMILES: Cc1ccc(NC(=O)c2cccc(C(F)(F)F)c2)cc1Oc1cc(-c2cccnc2)nc2c1ccn2C] | ¹H NMR (600 MHz, DMSO-d₆) δ 10.50 (s, 1H), 9.26 (d, J = 2.0 Hz, 1H), 8.60 (dd, J = 4.7, 1.3 Hz, 1H), 8.41 (d, J = 8.0 Hz, 1H), 8.25 (s, 1H), 8.22 (d, J = 7.9 Hz, 1H), 7.95 (d, J = 7.8 Hz, 1H), 7.76 (t, J = 7.8 Hz, 1H), 7.72-7.67 (m, 1H), 7.63 (d, J = 2.1 Hz, 1H), 7.50 (dd, J = 7.9, 4.8 Hz, 1H), 7.47 (d, J = 3.5 Hz, 1H), 7.41 (d, J = 8.4 Hz, 1H), 7.19 (s, 1H), 6.04 (d, J = 3.5 Hz, 1H), 3.90 (s, 3H), 2.21 (s, 3H). MS (ESI) m/z: 503 [M + H]⁺. |
| V-b-4 | 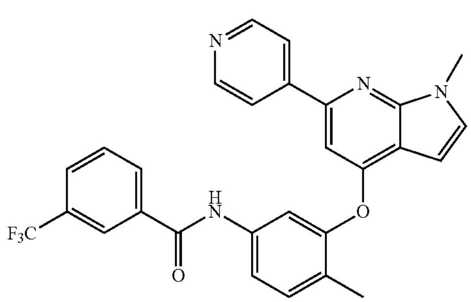 [SMILES: Cc1ccc(NC(=O)c2cccc(C(F)(F)F)c2)cc1Oc1cc(-c2ccncc2)nc2c1ccn2C] | ¹H NMR (600 MHz, Chloroform-d) δ 8.88 (s, 1H), 8.52 (d, J = 3.7 Hz, 2H), 8.10 (s, 1H), 8.02 (d, J = 7.8 Hz, 1H), 7.82 (d, J = 5.6 Hz, 2H), 7.71 (d, J = 7.8 Hz, 1H), 7.55 (dd, J = 8.2, 1.7 Hz, 1H), 7.50 (t, J = 7.8 Hz, 1H), 7.45 (d, J = 1.6 Hz, 1H), 7.28 (d, J = 8.3 Hz, 1H), 7.11 (d, J = 3.5 Hz, 1H), 6.92 (s, 1H), 6.26 (d, J = 3.4 Hz, 1H), 3.92 (s, 3H), 2.22 (s, 3H). MS (ESI) m/z: 503 [M + H]⁺. |

TABLE 5-continued

Structure and characterization of compounds V

| No. | Structure | ¹H NMR and/or MS data |
|---|---|---|
| V-c-1 | 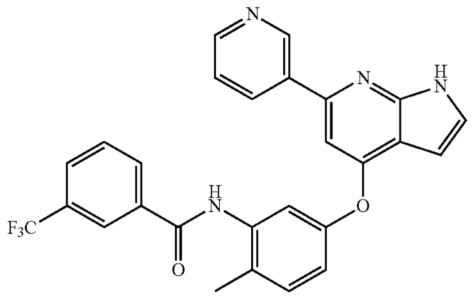 [SMILES: Cc1ccc(Oc2cc(-c3cccnc3)nc3[nH]ccc23)cc1NC(=O)c1cccc(C(F)(F)F)c1] | ¹H NMR (600 MHz, DMSO-d₆) δ 11.95 (s, 1H), 10.21 (s, 1H), 9.19 (s, 1H), 8.59 (d, J = 4.5 Hz, 1H), 8.37-8.33 (m, 1H), 8.30 (s, 1H), 8.27 (d, J = 7.9 Hz, 1H), 7.97 (d, J = 7.7 Hz, 1H), 7.78 (t, J = 7.8 Hz, 1H), 7.49 (dd, J = 7.9, 4.7 Hz, 1H), 7.45-7.42 (m, 1H), 7.40 (d, J = 8.4 Hz, 1H), 7.33 (d, J = 2.4 Hz, 1H), 7.21 (s, 1H), 7.11 (dd, J = 8.3, 2.6 Hz, 1H), 6.16 (dd, J = 3.4, 2.0 Hz, 1H), 2.30 (s, 3H). MS (ESI) m/z: 489 [M + H]⁺. |
| V-c-2 | 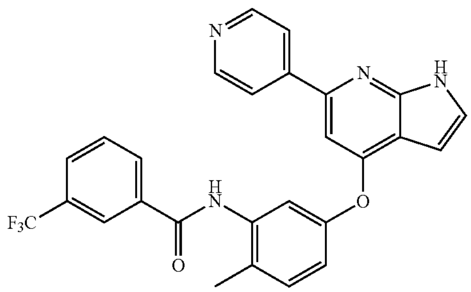 [SMILES: Cc1ccc(Oc2cc(-c3ccncc3)nc3[nH]ccc23)cc1NC(=O)c1cccc(C(F)(F)F)c1] | ¹H NMR (600 MHz, Methanol-d₄) δ 8.59 (d, J = 5.7 Hz, 2H), 8.31 (s, 1H), 8.25 (d, J = 7.9 Hz, 1H), 8.04 (d, J = 6.2 Hz, 2H), 7.92 (d, J = 7.7 Hz, 1H), 7.75 (t, J = 7.9 Hz, 1H), 7.43 (d, J = 8.4 Hz, 1H), 7.38 (d, J = 3.5 Hz, 1H), 7.35 (d, J = 2.3 Hz, 1H), 7.22 (s, 1H), 7.11 (dd, J = 8.3, 2.5 Hz, 1H), 6.38 (d, J = 3.5 Hz, 1H), 2.39 (s, 3H). MS (ESI) m/z: 489 [M + H]⁺. |
| V-c-3 | 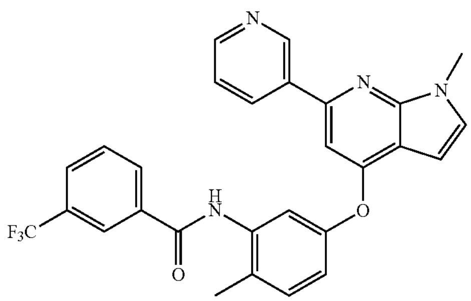 [SMILES: Cc1ccc(Oc2cc(-c3cccnc3)nc3c2ccn3C)cc1NC(=O)c1cccc(C(F)(F)F)c1] | ¹H NMR (600 MHz, Chloroform-d) δ 9.47 (s, 1H), 9.08 (d, J = 7.0 Hz, 1H), 8.76 (s, 1H), 8.40 (s, 1H), 8.20 (s, 1H), 8.15 (d, J = 7.4 Hz, 1H), 7.89 (s, 1H), 7.85-7.77 (m, 2H), 7.65 (t, J = 7.8 Hz, 1H), 7.35 (d, J = 8.2 Hz, 1H), 7.22 (d, J = 3.4 Hz, 1H), 7.09 (s, 1H), 7.04 (dd, J = 8.2, 2.3 Hz, 1H), 6.53 (d, J = 3.4 Hz, 1H), 3.96 (s, 3H), 2.42 (s, 3H). MS (ESI) m/z: 503 [M + H]⁺. |
| V-c-4 | TFA Salt | ¹H NMR (600 MHz, Chloroform-d) δ 8.78 (s, 2H), 8.54 (s, 2H), 8.16 (s, 1H), 8.12-8.07 (m, 2H), 7.92 (d, J = 1.7 Hz, 1H), 7.84 (d, J = 7.7 Hz, 1H), 7.67 (t, J = 7.8 Hz, 1H), 7.35 (d, J = 8.3 Hz, 1H), 7.29 (d, J = 4.8 Hz, 2H), 7.02 (dd, J = 8.2, 2.3 Hz, 1H), 6.48 (d, J = 3.3 Hz, 1H), 3.99 (s, 3H), 2.44 (s, 3H). MS (ESI) m/z: 503 [M + H]⁺. |
| V-d-1 | 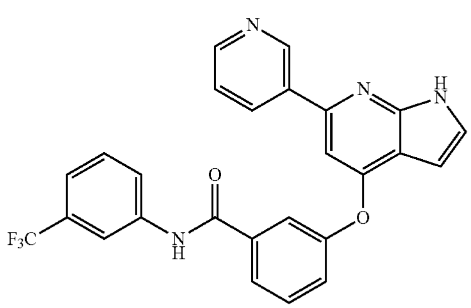 [SMILES: O=C(Nc1cccc(C(F)(F)F)c1)c1cccc(Oc2cc(-c3cccnc3)nc3[nH]ccc23)c1] | ¹H NMR (600 MHz, Methanol-d₄) δ 9.11 (d, J = 1.7 Hz, 1H), 8.49 (dd, J = 4.8, 1.4 Hz, 1H), 8.33-8.28 (m, 1H), 8.13 (s, 1H), 7.91 (d, J = 8.1 Hz, 1H), 7.86 (d, J = 8.2 Hz, 1H), 7.83-7.81 (m, 1H), 7.58 (t, J = 7.9 Hz, 1H), 7.50 (t, J = 8.0 Hz, 1H), 7.45 (dd, J = 8.0, 4.9 Hz, 1H), 7.42-7.39 (m, 2H), 7.31 (d, J = 3.5 Hz, 1H), 7.31 (d, J = 3.5 Hz, 1H), 7.08 (s, 1H), 7.08 (s, 1H), 6.20 (d, J = 3.5 Hz, 1H). MS (ESI) m/z: 475 [M + H]⁺. |

TABLE 5-continued

Structure and characterization of compounds V

| No. | Structure | ¹H NMR and/or MS data |
|---|---|---|
| V-d-2 | 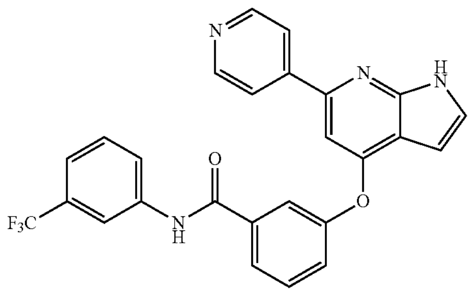 [SMILES: O=C(Nc1cccc(C(F)(F)F)c1)c1cccc(Oc2cc(-c3ccncc3)nc3[nH]ccc23)c1] | ¹H NMR (600 MHz, DMSO-d₆) δ 12.08 (s, 1H), 10.60 (s, 1H), 8.65 (dd, J = 4.6, 1.6 Hz, 2H), 8.24 (s, 1H), 8.05 (d, J = 8.5 Hz, 1H), 7.99 (dd, J = 4.6, 1.6 Hz, 2H), 7.93 (d, J = 7.8 Hz, 1H), 7.87 (s, 1H), 7.67 (t, J = 7.9 Hz, 1H), 7.60 (t, J = 8.0 Hz, 1H), 7.52-7.48 (m, 2H), 7.46 (d, J = 7.8 Hz, 1H), 7.35 (s, 1H), 6.12 (dd, J = 3.1, 1.4 Hz, 1H). MS (ESI) m/z: 475 [M + H]⁺. |
| V-d-3 | 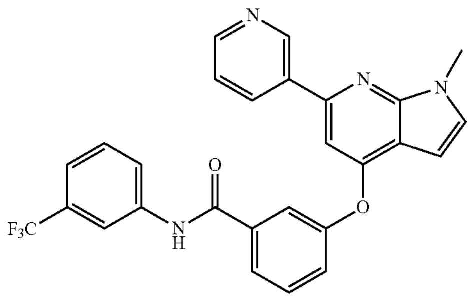 [SMILES: Cn1ccc2c(Oc3cccc(C(=O)Nc4cccc(C(F)(F)F)c4)c3)cc(-c3cccnc3)nc21] | ¹H NMR (600 MHz, Chloroform-d) δ 9.16 (d, J = 2.0 Hz, 1H), 8.96 (s, 1H), 8.50 (dd, J = 4.8, 1.4 Hz, 1H), 8.23 (dt, J = 8.0, 1.9 Hz, 1H), 7.96 (s, 1H), 7.86 (d, J = 8.2 Hz, 1H), 7.79-7.77 (m, 1H), 7.76-7.74 (m, 1H), 7.50 (t, J = 7.9 Hz, 1H), 7.43 (t, J = 8.0 Hz, 1H), 7.37 (d, J = 7.8 Hz, 1H), 7.36-7.33 (m, 1H), 7.31-7.29 (m, 1H), 7.08 (d, J = 3.5 Hz, 1H), 6.96 (s, 1H), 6.17 (d, J = 3.5 Hz, 1H), 3.91 (s, 3H). MS (ESI) m/z: 489 [M + H]⁺. |
| V-d-4 | 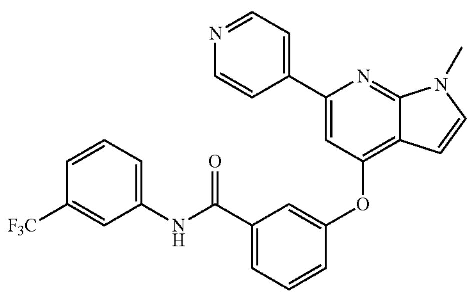 [SMILES: Cn1ccc2c(Oc3cccc(C(=O)Nc4cccc(C(F)(F)F)c4)c3)cc(-c3ccncc3)nc21] | ¹H NMR (600 MHz, Chloroform-d) δ 8.81 (s, 1H), 8.57 (dd, J = 4.7, 1.4 Hz, 2H), 7.96 (s, 1H), 7.88-7.85 (m, 3H), 1.6 Hz, 3H), 7.80 (ddd, J = 7.7, 1.5, 0.9 Hz, 1H), 7.75-7.73 (m, 1H), 7.55 (t, J = 7.9 Hz, 1H), 7.46 (t, J = 8.0 Hz, 1H), 7.38 (ddd, J = 7.0, 5.0, 3.2 Hz, 2H), 7.16 (d, J = 3.5 Hz, 1H), 7.06 (s, 1H), 6.20 (d, J = 3.5 Hz, 1H), 3.97 (s, 3H). MS (ESI) m/z: 489 [M + H]⁺. |
| V-e-1 | 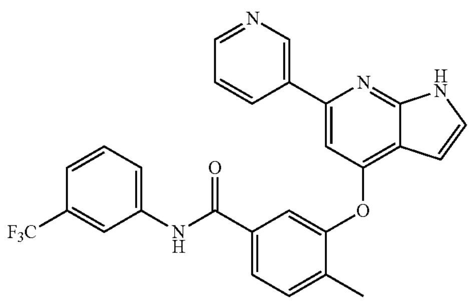 | ¹H NMR (600 MHz, DMSO-d₆) δ 11.98 (s, 1H), 10.49 (s, 1H), 9.17 (d, J = 2.2 Hz, 1H), 8.58 (dd, J = 4.7, 1.6 Hz, 1H), 8.33-8.29 (m, 1H), 8.20 (s, 1H), 8.03 (d, J = 8.1 Hz, 1H), 7.93 (dd, J = 7.9, 1.7 Hz, 1H), 7.82 (d, J = 1.6 Hz, 1H), 7.64-7.55 (m, 2H), 7.48 (dd, J = 8.0, 4.7 Hz, 1H), 7.45-7.41 (m, 2H), 7.08 (s, 1H), 6.03 (dd, J = 3.4, 2.0 Hz, 1H), 2.31 (s, 3H). MS (ESI) m/z: 489 [M + H]⁺. |
| V-e-2 | 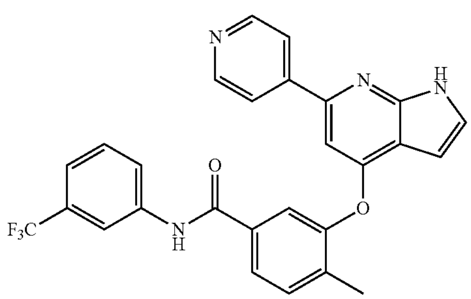 | ¹H NMR (600 MHz, DMSO-d₆) δ 12.05 (s, 1H), 10.49 (s, 1H), 8.64 (dd, J = 4.5, 1.6 Hz, 2H), 8.20 (s, 1H), 8.03 (d, J = 8.9 Hz, 1H), 7.97-7.90 (m, 3H), 7.82 (d, J = 1.7 Hz, 1H), 7.62 (d, J = 8.3 Hz, 1H), 7.58 (t, J = 8.0 Hz, 1H), 7.48 (dd, J = 3.4, 2.6 Hz, 1H), 7.44 (d, J = 7.9 Hz, 1H), 7.16 (s, 1H), 6.05 (dd, J = 3.4, 1.9 Hz, 1H), 2.31 (s, 3H). MS (ESI) m/z: 489 [M + H]⁺. |

TFA Salt

TABLE 5-continued

Structure and characterization of compounds V

| No. | Structure | ¹H NMR and/or MS data |
|---|---|---|
| V-e-3 | 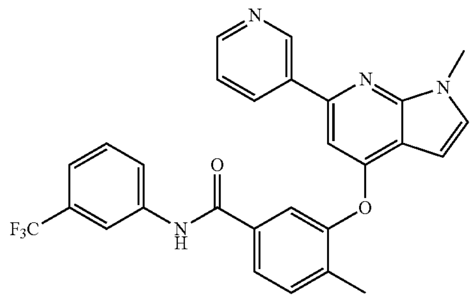 [SMILES: Cc1ccc(C(=O)Nc2cccc(C(F)(F)F)c2)cc1Oc1cc(-c2cccnc2)nc2c1ccn2C] | ¹H NMR (600 MHz, Chloroform-d) δ 9.18 (s, 1H), 9.13 (dd, J = 2.3, 0.7 Hz, 1H), 8.45 (dd, J = 4.8, 1.6 Hz, 1H), 8.17-8.13 (m, 1H), 7.95 (s, 1H), 7.82 (d, J = 8.2 Hz, 1H), 7.78 (dd, J = 7.9, 1.8 Hz, 1H), 7.72 (d, J = 1.8 Hz, 1H), 7.41-7.35 (m, 2H), 7.33 (d, J = 7.8 Hz, 1H), 7.22 (ddd, J = 8.0, 4.8, 0.7 Hz, 1H), 7.05 (d, J = 3.5 Hz, 1H), 6.78 (s, 1H), 6.11 (d, J = 3.5 Hz, 1H), 3.89 (s, 3H), 2.31 (s, 3H). MS (ESI) m/z: 503 [M + H]⁺. |
| V-e-4 | 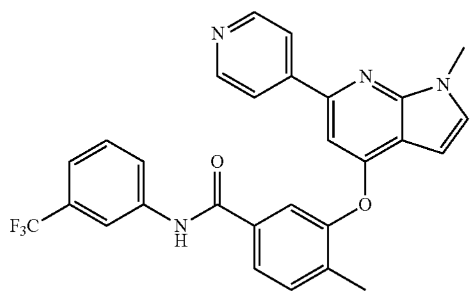 [SMILES: Cc1ccc(C(=O)Nc2cccc(C(F)(F)F)c2)cc1Oc1cc(-c2ccncc2)nc2c1ccn2C] | ¹H NMR (600 MHz, Chloroform-d) δ 9.41 (s, 1H), 8.46 (dd, J = 4.6, 1.5 Hz, 2H), 7.95 (s, 1H), 7.84-7.79 (m, 2H), 7.77 (dd, J = 4.6, 1.6 Hz, 2H), 7.73 (d, J = 1.6 Hz, 1H), 7.41-7.35 (m, 2H), 7.32 (d, J = 7.8 Hz, 1H), 7.11 (d, J = 3.5 Hz, 1H), 6.85 (s, 1H), 6.12 (d, J = 3.5 Hz, 1H), 3.93 (s, 3H), 2.32 (s, 3H). MS (ESI) m/z: 503 [M + H]⁺. |
| V-f-1 | 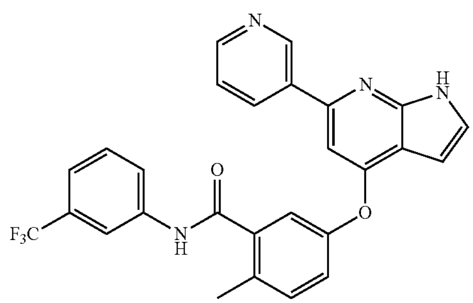 | ¹H NMR (600 MHz, DMSO-d₆) δ 11.98 (s, 1H), 10.66 (s, 1H), 9.19 (d, J = 1.9 Hz, 1H), 8.59 (dd, J = 4.7, 1.5 Hz, 1H), 8.36-8.31 (m, 1H), 8.23 (s, 1H), 7.94 (d, J = 8.3 Hz, 1H), 7.59 (t, J = 8.0 Hz, 1H), 7.49 (dd, J = 7.7, 5.0 Hz, 1H), 7.47-7.40 (m, 4H), 7.29 (dd, J = 8.3, 2.6 Hz, 1H), 7.21 (s, 1H), 6.16 (dd, J = 3.3, 1.9 Hz, 1H), 2.44 (s, 3H). MS (ESI) m/z: 489 [M + H]⁺. |
| V-f-2 | 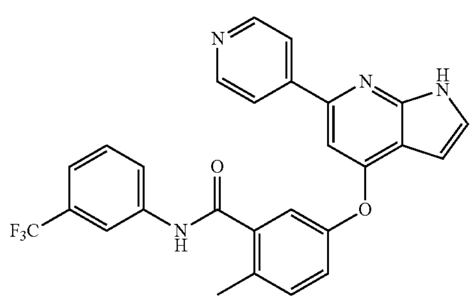 [SMILES: Cc1ccc(Oc2cc(-c3ccncc3)nc3[nH]ccc23)cc1C(=O)Nc1cccc(C(F)(F)F)c1] | ¹H NMR (600 MHz, DMSO-d₆) 12.04 (s, 1H), 10.66 (s, 1H), 8.66 (d, J = 6.0 Hz, 2H), 8.23 (s, 1H), 7.97 (d, J = 6.1 Hz, 2H), 7.94 (d, J = 8.2 Hz, 1H), 7.59 (t, J = 8.0 Hz, 1H), 7.52-7.48 (m, 1H), 7.47-7.40 (m, 3H), 7.33-7.27 (m, 2H), 6.18 (dd, J = 3.1, 1.8 Hz, 1H), 2.45 (s, 3H). MS (ESI) m/z: 489 [M + H]⁺. |
| V-f-3 | 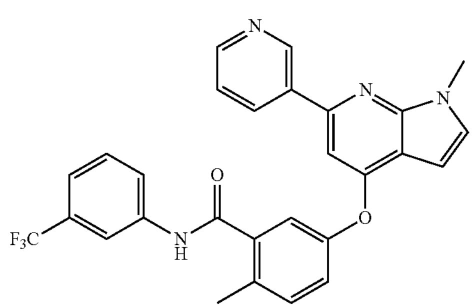 [SMILES: Cc1ccc(Oc2cc(-c3cccnc3)nc3c2ccn3C)cc1C(=O)Nc1cccc(C(F)(F)F)c1] | ¹H NMR (600 MHz, Chloroform-d) δ 9.17 (d, J = 2.0 Hz, 1H), 8.74 (s, 1H), 8.56 (dd, J = 4.7, 1.2 Hz, 1H), 8.27 (d, J = 8.0 Hz, 1H), 7.97 (s, 1H), 7.90 (d, J = 7.9 Hz, 1H), 7.46 (t, J = 8.0 Hz, 1H), 7.40-7.36 (m, 2H), 7.36-7.34 (m, 1H), 7.33-7.30 (m, 1H), 7.18 (dd, J = 8.3, 2.5 Hz, 1H), 7.10 (d, J = 3.5 Hz, 1H), 6.95 (s, 1H), 6.24 (d, J = 3.4 Hz, 1H), 3.93 (s, 3H), 2.56 (d, J = 8.9 Hz, 3H). MS (ESI) m/z: 503 [M + H]⁺. |

TABLE 5-continued

Structure and characterization of compounds V

| No. | Structure | ¹H NMR and/or MS data |
|---|---|---|
| V-f-4 | 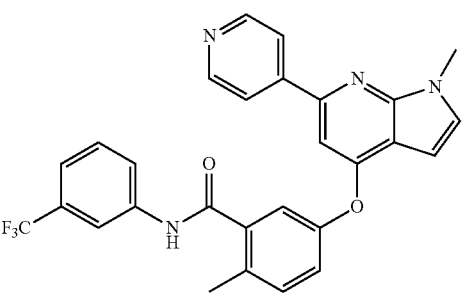 [SMILES: Cc1ccc(Oc2cc(-c3ccncc3)nc3c2ccn3C)cc1C(=O)Nc1cccc(C(F)(F)F)c1] | ¹H NMR (600 MHz, Chloroform-d) δ 8.73 (s, 1H), 8.53 (d, J = 6.0 Hz, 2H), 7.94 (s, 1H), 7.88-7.82 (m, 3H), 7.46 (t, J = 8.0 Hz, 1H), 7.40 (d, J = 7.8 Hz, 1H), 7.34 (dd, J = 6.7, 5.8 Hz, 2H), 7.20 (dd, J = 8.3, 2.6 Hz, 1H), 7.16 (d, J = 3.5 Hz, 1H), 7.01 (s, 1H), 6.27 (d, J = 3.5 Hz, 1H), 3.95 (s, 3H), 2.57 (s, 3H). MS (ESI) m/z: 503 [M + H]⁺. |
| V-h-1 | 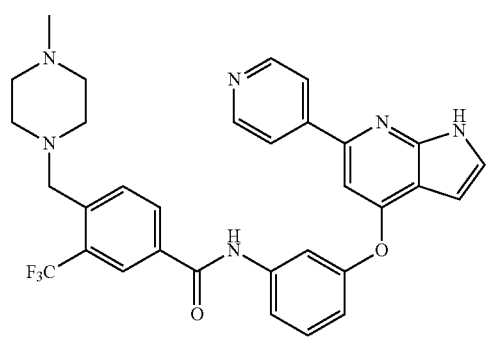 [SMILES: CN1CCN(Cc2ccc(C(=O)Nc3cccc(Oc4cc(-c5ccncc5)nc5[nH]ccc45)c3)cc2C(F)(F)F)CC1] | ¹H NMR (600 MHz, DMSO-d₆) δ 12.04 (s, 1H), 10.55 (s, 1H), 8.65 (dd, J = 4.6, 1.5 Hz, 2H), 8.21 (s, 1H), 8.21-8.18 (m, 1H), 7.99 (dd, J = 4.6, 1.6 Hz, 2H), 7.90 (d, J = 8.1 Hz, 1H), 7.73-7.69 (m, 2H), 7.48 (dt, J = 14.3, 5.3 Hz, 2H), 7.36 (s, 1H), 7.09-6.95 (m, 1H), 6.15 (dd, J = 3.4, 1.9 Hz, 1H), 3.66 (s, 2H), 2.41 (s, 8H), 2.18 (s, 3H). MS (ESI) m/z: 587 [M + H]⁺. |
| V-l-1 | 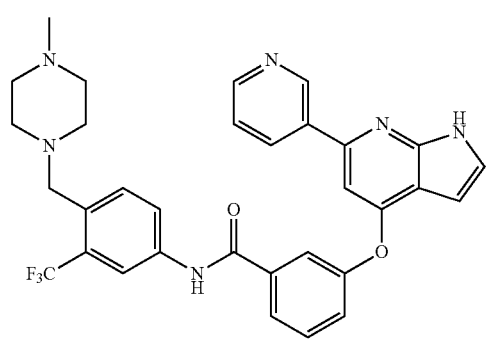 [SMILES: CN1CCN(Cc2ccc(NC(=O)c3cccc(Oc4cc(-c5cccnc5)nc5[nH]ccc45)c3)cc2C(F)(F)F)CC1] | ¹H NMR (600 MHz, Chloroform-d) δ 11.51 (s. 1H), 9.19 (d, J = 1.9 Hz, 1H), 8.78 (s, 1H), 8.58 (dd, J = 4.8, 1.5 Hz, 1H), 8.14-8.08 (m, 1H),, 7.90-7.84 (m, 2H), 7.81-7.76 (m, 2H), 7.72 (d, J = 8.2 Hz, 1H), 7.52 (t, J = 7.9 Hz, 1H), 7.39-7.30 (m, 2H), 7.09 (dd, J = 3.3, 2.4 Hz, 1H), 6.93 (s, 1H), 6.18 (dd, J = 3.4, 1.9 Hz, 1H), 3.61 (s, 2H), 2.51 (s, 8H), 2.31 (s, 3H). MS (ESI) m/z: 588 [M + H]⁺. |
| V-l-2 | 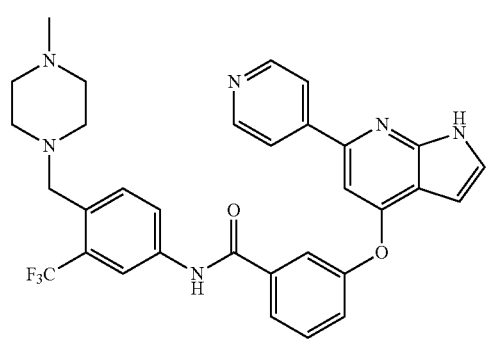 [SMILES: CN1CCN(Cc2ccc(NC(=O)c3cccc(Oc4cc(-c5ccncc5)nc5[nH]ccc45)c3)cc2C(F)(F)F)CC1] | ¹H NMR (600 MHz, DMSO-d₆) δ 12.08 (s, 1H), 10.55 (s, 1H), 8.65 (d, J = 6.0 Hz, 2H), 8.19 (d, J = 2.1 Hz, 1H), 8.03 (d, J = 8.7 Hz, 1H), 7.99 (d, J = 6.1 Hz, 2H), 7.92 (d, J = 7.5 Hz, 1H), 7.86 (s, 1H), 7.70 (d, J = 8.4 Hz, 1H), 7.66 (t, J = 8.0 Hz, 1H), 7.52-7.47 (m, 2H), 7.35 (s, 1H), 6.11 (dd, J = 3.3, 1.9 Hz, 1H), 3.57 (s, 2H), 2.40 (m, 8H), 2.19 (s, 3H). MS (ESI) m/z: 588 [M + H]⁺. |

TABLE 5-continued

Structure and characterization of compounds V

| No. | Structure | ¹H NMR and/or MS data |
|---|---|---|
| V-l-3 | 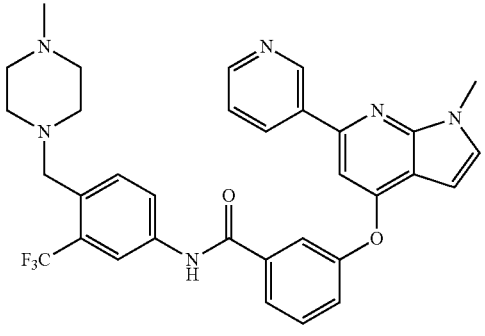 [SMILES: CN1CCN(Cc2ccc(NC(=O)c3cccc(Oc4cc(-c5cccnc5)nc5c4ccn5C)c3)cc2C(F)(F)F)CC1] | ¹H NMR (600 MHz, Chloroform-d) δ 9.19 (d, J = 1.7 Hz, 1H), 8.56 (d, J = 4.7 Hz, 1H), 8.44 (s, 1H), 8.29 (d, J = 8.0 Hz, 1H), 7.90-7.84 (m, 2H), 7.79-7.74 (m, 2H), 7.73 (s, 1H), 7.54 (t, J = 7.9 Hz, 1H), 7.40-7.32 (m, 2H), 7.12 (d, J = 3.4 Hz, 1H), 7.01 (s, 1H), 6.21 (d, J = 3.4 Hz, 1H), 3.95 (s, 3H), 3.63 (s, 2H), 2.51 (s, 8H), 2.30 (s, 3H). MS (ESI) m/z: 601 [M + H]⁺. |
| V-l-4 | 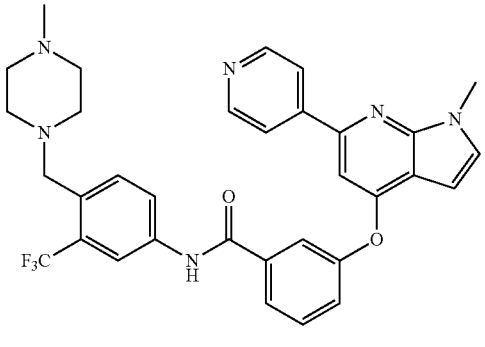 [SMILES: CN1CCN(Cc2ccc(NC(=O)c3cccc(Oc4cc(-c5ccncc5)nc5c4ccn5C)c3)cc2C(F)(F)F)CC1] | ¹H NMR (600 MHz, Chloroform-d) δ 8.87 (s, 1H), 8.55 (dd, J = 4.6, 1.5 Hz, 2H), 7.89-7.83 (m, 4H), 7.82-7.78 (m, 1H), 7.74 (dd, J = 4.7, 2.6 Hz, 2H), 7.54 (t, J = 7.9 Hz, 1H), 7.37 (ddd, J = 8.1, 2.3, 0.8 Hz, 1H), 7.15 (d, J = 3.5 Hz, 1H), 7.04 (s, 1H), 6.19 (d, J = 3.5 Hz, 1H), 3.96 (s, 3H), 3.62 (s, 2H), 2.45 (m, J = 58.3 Hz, 8H), 2.30 (s, 3H). MS (ESI) m/z: 601 [M + H]⁺. |
| V-m-1 | 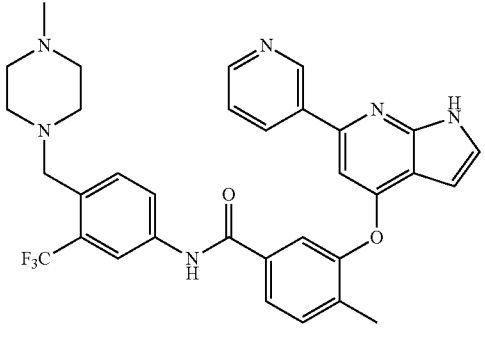 | ¹H NMR (600 MHz, DMSO-d₆) δ 11.98 (s, 1H), 10.44 (s, 1H), 9.19-9.15 (m, 1H), 8.58 (dd, J = 4.7, 1.6 Hz, 1H), 8.33-8.28 (m, 1H), 8.16 (d, J = 2.1 Hz, 1H), 8.01 (dd, J = 8.6, 2.0 Hz, 1H), 7.92 (dd, J = 7.9, 1.7 Hz, 1H), 7.81 (d, J = 1.7 Hz, 1H), 7.68 (d, J = 8.7 Hz, 1H), 7.61 (d, J = 8.1 Hz, 1H), 7.48 (ddd, J = 8.0, 4.8, 0.8 Hz, 1H), 7.43 (dd, J = 3.4, 2.5 Hz, 1H), 7.08 (s, 1H), 6.03 (dd, J = 3.4, 2.0 Hz, 1H), 3.55 (s, 2H), 2.47-2.27 (m, 11H), 2.18 (s, 3H). MS (ESI) m/z: 602 [M + H]⁺. |
| V-m-2 | 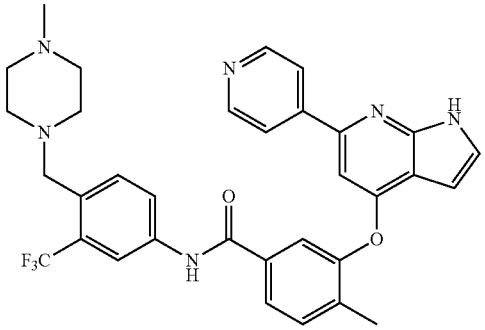 [SMILES: Cc1ccc(C(=O)Nc2ccc(CN3CCN(C)CC3)c(C(F)(F)F)c2)cc1Oc1cc(-c2ccncc2)nc2[nH]ccc12] | ¹H NMR (600 MHz, DMSO-d₆) δ 12.05 (s, 1H), 10.45 (s, 1H), 8.64 (dd, J = 4.5, 1.6 Hz, 2H), 8.16 (d, J = 2.1 Hz, 1H), 8.01 (dd, J = 8.5, 2.0 Hz, 1H), 7.97-7.91 (m, 3H), 7.82 (d, J = 1.5 Hz, 1H), 7.68 (d, J = 8.6 Hz, 1H), 7.61 (d, J = 8.1 Hz, 1H), 7.49-7.46 (m, 1H), 7.16 (s, 1H), 6.05 (dd, J = 3.4, 1.8 Hz, 1H), 3.54 (s, 2H), 2.30 (m, 11H), 2.16 (s, 3H). MS (ESI) m/z: 602 [M + H]⁺. |

TABLE 5-continued

Structure and characterization of compounds V

| No. | Structure | ¹H NMR and/or MS data |
|---|---|---|
| V-m-3 | 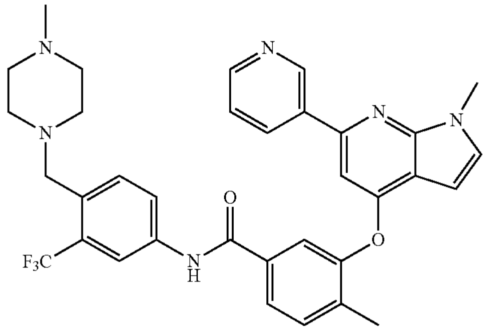 [SMILES: Cc1ccc(C(=O)Nc2ccc(CN3CCN(C)CC3)c(C(F)(F)F)c2)cc1Oc1cc(-c2cccnc2)nc2c1ccn2C] | ¹H NMR (600 MHz, Chloroform-d) δ 9.15 (s, 1H), 8.57-8.50 (m, 2H), 8.23 (d, J = 7.9 Hz, 1H), 7.87-7.82 (m, 2H), 7.76 (dd, J = 7.9, 1.3 Hz, 1H), 7.72 (d, J = 8.2 Hz, 1H), 7.68 (s, 1H), 7.44 (d, J = 7.9 Hz, 1H), 7.31 (d, J = 5.0 Hz, 1H), 7.09 (d, J = 3.4 Hz, 1H), 6.83 (s, 1H), 6.17 (d, J = 3.2 Hz, 1H), 3.93 (s, 3H), 3.61 (s, 2H), 2.50 (m, 8H), 2.34 (s, 3H), 2.30 (s, 3H). MS (ESI) m/z: 615 [M + H]⁺. |
| V-m-4 | 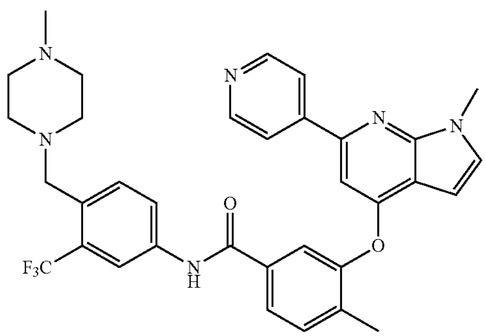 [SMILES: Cc1ccc(C(=O)Nc2ccc(CN3CCN(C)CC3)c(C(F)(F)F)c2)cc1Oc1cc(-c2ccncc2)nc2c1ccn2C] | ¹H NMR (600 MHz, Chloroform-d) δ 8.60 (d, J = 5.6 Hz, 2H), 8.41 (s, 1H), 7.89-7.82 (m, 4H), 7.78 (d, J = 8.0 Hz, 1H), 7.72 (d, J = 8.5 Hz, 1H), 7.67 (s, 1H), 7.48 (d, J = 7.9 Hz, 1H), 7.16 (d, J = 3.4 Hz, 1H), 6.93 (s, 1H), 6.19 (d, J = 3.4 Hz, 1H), 3.98 (s, 3H), 3.63 (s, 2H), 2.54 (m, 8H), 2.36 (s, 3H), 2.35 (s, 3H). MS (ESI) m/z: 615 [M + H]⁺. |
| V-n-1 | 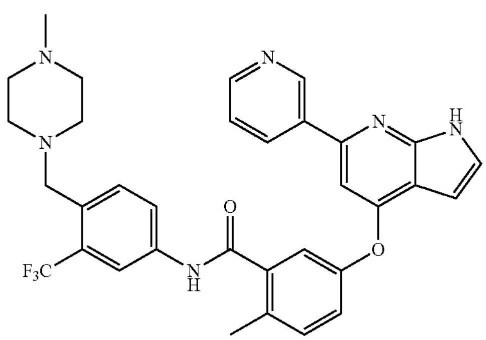 | ¹H NMR (600 MHz, Chloroform-d) δ 11.42 (s, 1H), 9.15 (d, J = 1.9 Hz, 1H), 8.59 (dd, J = 4.7, 1.4 Hz, 1H), 8.54 (s, 1H), 8.10 (d, J = 8.0 Hz, 1H), 7.89-7.81 (m, 2H), 7.75 (d, J = 8.5 Hz, 1H), 7.39-7.33 (m, 2H), 7.31 (d, J = 8.4 Hz, 1H), 7.18 (dd, J = 8.3, 2.5 Hz, 1H), 7.08-7.05 (m, 1H), 6.90 (s, 1H), 6.19 (d, J = 2.2 Hz, 1H), 3.62 (s, 2H), 2.59-2.36 (m, 11H), 2.31 (s, 3H). MS (ESI) m/z: 602 [M + H]⁺. |
| V-n-2 | 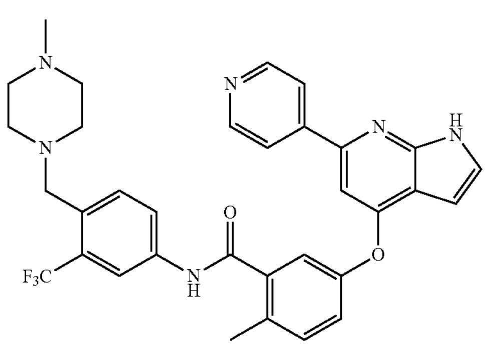 [SMILES: Cc1ccc(Oc2cc(-c3ccncc3)nc3[nH]ccc23)cc1C(=O)Nc1ccc(CN2CCN(C)CC2)c(C(F)(F)F)c1] | ¹H NMR (600 MHz, Chloroform-d) δ 11.27 (s, 1H), 8.96 (s, 1H), 8.56 (d, J = 5.9 Hz, 2H), 7.91 (d, J = 8.2 Hz, 1H), 7.86 (s, 1H), 7.76 (d, J = 8.5 Hz, 1H), 7.67 (d, J = 5.8 Hz, 2H), 7.40 (d, J = 2.2 Hz, 1H), 7.34 (d, J = 8.4 Hz, 1H), 7.20 (dd, J = 8.3, 2.5 Hz, 1H), 7.09-7.05 (m, 1H), 6.88 (s, 1H), 6.32 (dd, J = 3.2, 2.0 Hz, 1H), 3.62 (s, 2H), 2.65-2.40 (m, 11H), 2.30 (s, 3H). MS (ESI) m/z: 602 [M + H]⁺. |

TABLE 5-continued

Structure and characterization of compounds V

| No. | Structure | ¹H NMR and/or MS data |
|---|---|---|
| V-n-3 | 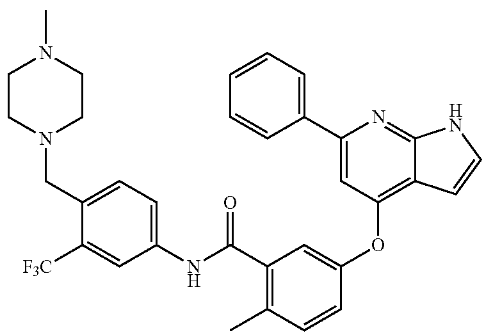 [SMILES: Cc1ccc(Oc2cc(-c3ccccc3)nc3[nH]ccc23)cc1C(=O)Nc1ccc(CN2CCN(C)CC2)c(C(F)(F)F)c1] | ¹H NMR (600 MHz, DMSO-d$_6$) δ 11.89 (s, 1H), 10.66 (s, 1H), 8.18 (d, J = 1.8 Hz, 1H), 7.98 (dt, J = 10.0, 2.6 Hz, 2H), 7.68 (d, J = 8.5 Hz, 1H), 7.48-7.44 (m, 2H), 7.43-7.39 (m, 3H), 7.38 (t, J = 4.6 Hz, 1H), 7.29 (dd, J = 8.3, 2.6 Hz, 1H), 7.10 (s, 1H), 6.17 (dd, J = 3.4, 2.0 Hz, 1H), 3.63 (s, 2H), 3.36 (s, 6H), 3.18 (s, 2H), 2.71 (s, 3H), 2.43 (s, 3H). MS (ESI) m/z: 600 [M + H]⁺. |
| V-n-4 | 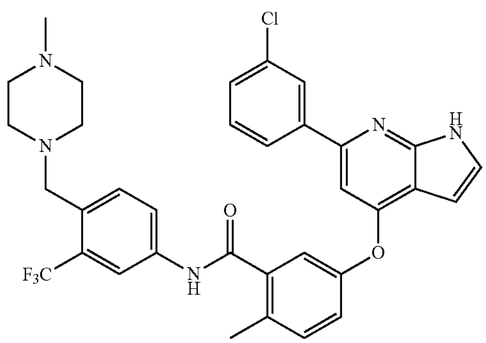 [SMILES: Cc1ccc(Oc2cc(-c3cccc(Cl)c3)nc3[nH]ccc23)cc1C(=O)Nc1ccc(CN2CCN(C)CC2)c(C(F)(F)F)c1] | ¹H NMR (600 MHz, DMSO-d$_6$) δ 11.92 (d, J = 33.9 Hz, 1H), 10.67 (s, 1H), 8.18 (d, J = 1.7 Hz, 1H), 8.08 (t, J = 1.8 Hz, 1H), 7.96 (d, J = 7.1 Hz, 1H), 7.94-7.90 (m, 1H), 7.68 (d, J = 8.6 Hz, 1H), 7.48 (t, J = 7.8 Hz, 1H), 7.44 (ddd, J = 5.9, 2.7, 1.8 Hz, 2H), 7.40 (dd, J = 9.3, 5.5 Hz, 2H), 7.28 (dd, J = 8.3, 2.6 Hz, 1H), 7.19 (s, 1H), 6.14 (dt, J = 27.9, 13.9 Hz, 1H), 3.64 (s, 2H), 3.40 (s, 6H), 3.17 (s, 2H), 2.75 (s, 3H), 2.41 (d, J = 11.0 Hz, 3H). MS (ESI) m/z: 635 [M + H]⁺. |
| V-n-5 | 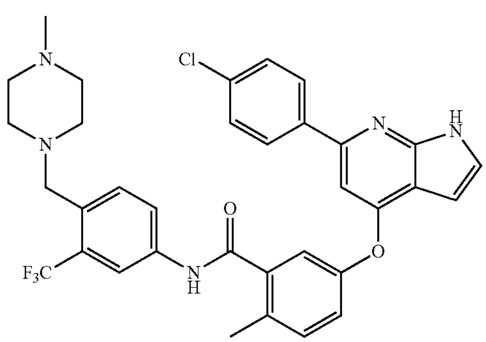 [SMILES: Cc1ccc(Oc2cc(-c3ccc(Cl)cc3)nc3[nH]ccc23)cc1C(=O)Nc1ccc(CN2CCN(C)CC2)c(C(F)(F)F)c1] | ¹H NMR (600 MHz, DMSO-d$_6$) δ 11.92 (s, 1H), 10.66 (s, 1H), 8.18 (s, 1H), 8.02 (d, J = 8.5 Hz, 2H), 7.98 (d, J = 8.2 Hz, 1H), 7.69 (d, J = 8.5 Hz, 1H), 7.51 (d, J = 8.5 Hz, 2H), 7.45-7.39 (m, 3H), 7.29 (dd, J = 8.3, 2.3 Hz, 1H), 7.13 (s, 1H), 6.17 (s, 1H), 3.65 (s, 2H), 3.02 (s, 2H), 2.89 (d, J = 10.5 Hz, 2H), 2.79 (s, 3H), 2.51 (s, 2H), 2.43 (s, 3H), 2.39 (d, J = 14.6 Hz, 2H). MS (ESI) m/z: 635 [M + H]⁺. |
| V-n-6 | 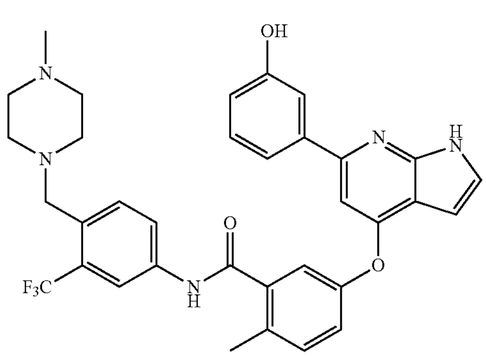 [SMILES: Cc1ccc(Oc2cc(-c3cccc(N)c3)nc3[nH]ccc23)cc1C(=O)Nc1ccc(CN2CCN(C)CC2)c(C(F)(F)F)c1] | ¹H NMR (600 MHz, DMSO-d$_6$) δ 11.87 (s, 1H), 10.69 (s, 1H), 8.19 (d, J = 1.7 Hz, 1H), 7.96 (d, J = 8.4 Hz, 1H), 7.68 (d, J = 8.6 Hz, 1H), 7.40 (dd, J = 4.7, 2.6 Hz, 2H), 7.38 (d, J = 2.6 Hz, 2H), 7.36-7.35 (m, 1H), 7.35-7.33 (m, 1H), 7.28 (d, J = 2.6 Hz, 1H), 7.26 (d, J = 2.6 Hz, 1H), 6.98 (s, 1H), 6.78 (ddd, J = 8.0, 2.5, 0.9 Hz, 1H), 6.19 (dd, J = 3.4, 2.0 Hz, 1H), 3.64 (s, 2H), 3.43-3.33 (m, 2H), 3.03 (d, J = 21.5 Hz, 2H), 2.87 (d, J = 10.6 Hz, 2H), 2.78 (s, 3H), 2.42 (s, 3H), 2.40-2.36 (m, 2H). MS (ESI) m/z: 616 [M + H]⁺. |

TABLE 5-continued

Structure and characterization of compounds V

| No. | Structure | $^1$H NMR and/or MS data |
|---|---|---|
| V-n-7 | 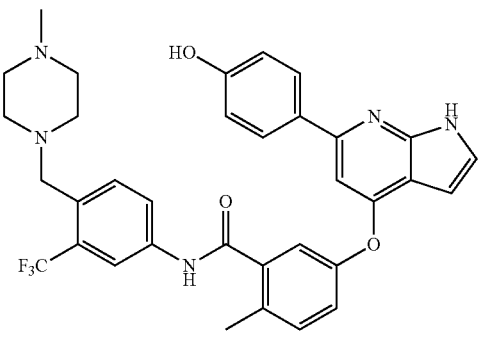 | $^1$H NMR (600 MHz, DMSO-d$_6$) δ 11.78 (s, 1H), 10.66 (s, 1H), 9.85 (s, 1H), 8.18 (d, J = 1.6 Hz, 1H), 7.98 (d, J = 8.5 Hz, 1H), 7.86-7.77 (m, 2H), 7.69 (d, J = 8.6 Hz, 1H), 7.41 (d, J = 8.5 Hz, 1H), 7.38 (d, J = 2.6 Hz, 1H), 7.34 (dd, J = 3.3, 2.6 Hz, 1H), 7.27 (s, 2H), 6.84 (m, 2H), 6.13 (dd, J = 3.4, 2.0 Hz, 1H), 3.66 (s, 2H), 3.40 (d, J = 10.8 Hz, 2H), 3.01 (d, J = 15.4 Hz, 2H), 2.90 (d, J = 11.1 Hz, 2H), 2.80 (s, 3H), 2.43 (s, 3H), 2.40-2.33 (m, 2H). MS (ESI) m/z: 616 [M + H]$^+$. |
| V-n-8 | 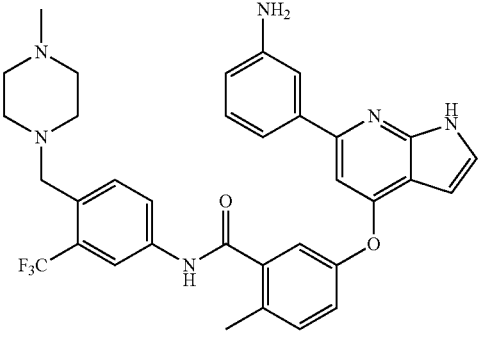 | $^1$H NMR (600 MHz, DMSO-d$_6$) δ 11.81 (s, 1H), 10.64 (s, 1H), 8.18 (d, J = 1.6 Hz, 1H), 7.95 (d, J = 8.3 Hz, 1H), 7.68 (d, J = 8.6 Hz, 1H), 7.44-7.36 (m, 1H), 7.27 (dd, J = 8.3, 2.6 Hz, 1H), 7.22 (d, J = 1.7 Hz, 1H), 7.11-7.03 (m, 1H), 6.95 (s, 1H), 6.65-6.52 (m, 1H), 6.28-6.10 (m, 1H), 5.15 (s, 2H), 3.58 (s, 2H), 3.43 (d, J = 5.2 Hz, 4H), 2.63 (s, 2H), 2.47 (s, 2H), 2.43 (s, 3H), 2.38 (s, 3H). MS (ESI) m/z: 615 [M + H]$^+$. |
| V-n-9 | 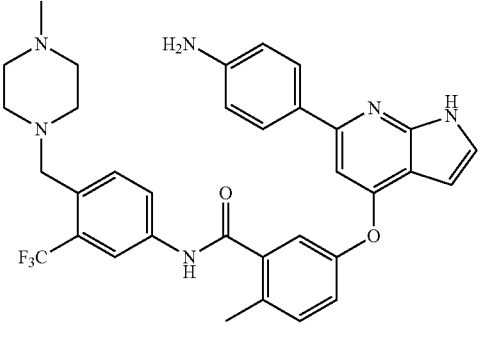 [SMILES: Cc1ccc(Oc2cc(-c3ccc(N)cc3)nc3[nH]ccc23)cc1C(=O)Nc1ccc(CN2CCN(C)CC2)c(C(F)(F)F)c1] | $^1$H NMR (600 MHz, DMSO-d$_6$) δ 11.97 (s, 1H), 10.68 (s, 1H), 8.19 (d, J = 1.6 Hz, 1H), 7.98 (d, J = 8.7 Hz, 1H), 7.90 (d, J = 8.6 Hz, 2H), 7.70 (d, J = 8.6 Hz, 1H), 7.45-7.39 (m, 3H), 7.30 (dd, J = 8.3, 2.6 Hz, 1H), 7.09 (d, J = 8.5 Hz, 2H), 7.06 (s, 1H), 6.17 (d, J = 2.1 Hz, 1H), 3.70 (s, 2H), 3.41 (s, 2H), 3.06 (s, 2H), 2.92 (s, 2H), 2.81 (s, 3H), 2.43 (s, 3H), 2.41-2.38 (m, 2H). MS (ESI) m/z: 615 [M + H]$^+$. |
| V-n-10 | 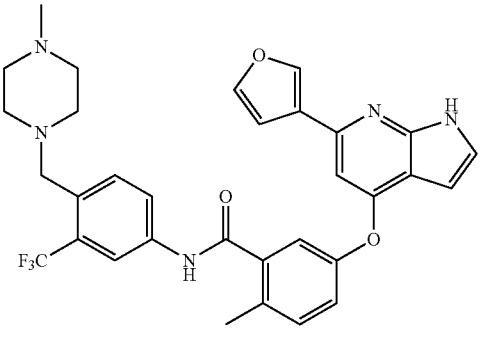 [SMILES: Cc1ccc(Oc2cc(-c3ccoc3)nc3[nH]ccc23)cc1C(=O)Nc1ccc(CN2CCN(C)CC2)c(C(F)(F)F)c1] | $^1$H NMR (600 MHz, DMSO-d$_6$) δ 11.81 (t, J = 2.3 Hz, 1H), 10.64 (s, 1H), 8.24 (dd, J = 1.6, 0.8 Hz, 1H), 8.18 (d, J = 2.2 Hz, 1H), 7.97 (dd, J = 8.3, 2.1 Hz, 1H), 7.74 (t, J = 1.7 Hz, 1H), 7.68 (d, J = 8.5 Hz, 1H), 7.41-7.36 (m, 1H), 7.35 (d, J = 2.7 Hz, 1H), 7.33 (dd, J = 3.5, 2.5 Hz, 1H), 7.23 (dd, J = 8.4, 2.7 Hz, 1H), 7.06-6.81 (m, 2H), 6.04 (dd, J = 3.5, 2.0 Hz, 1H), 3.66 (s, 2H), 3.39 (d, J = 12.1 Hz, 2H), 3.02 (t, J = 11.9 Hz, 2H), 2.90 (d, J = 12.7 Hz, 2H), 2.80 (s, 3H), 2.41 (s, 3H), 2.40-2.38 (m, 2H). MS (ESI) m/z: 590 [M + H]$^+$. |

TABLE 5-continued

Structure and characterization of compounds V

| No. | Structure | ¹H NMR and/or MS data |
|---|---|---|
| V-n-11 | 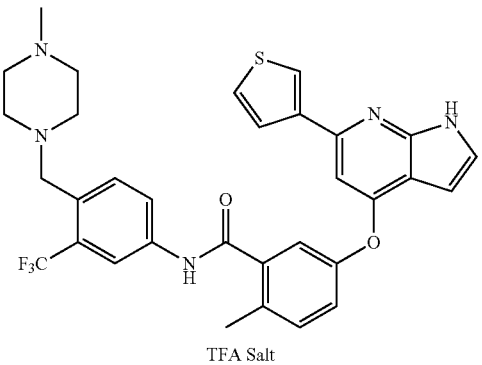 [SMILES: Cc1ccc(Oc2cc(-c3ccsc3)nc3[nH]ccc23)cc1C(=O)Nc1ccc(CN2CCN(C)CC2)c(C(F)(F)F)c1] TFA Salt | ¹H NMR (600 MHz, DMSO-d₆) δ 11.85 (s, 1H), 10.66 (s, 1H), 8.19 (d, J = 1.8 Hz, 1H), 8.03 (dd, J = 3.0, 1.3 Hz, 1H), 7.98 (d, J = 8.4 Hz, 1H), 7.72-7.67 (m, 2H), 7.61 (dd, J = 5.0, 3.0 Hz, 1H), 7.40 (d, J = 8.5 Hz, 1H), 7.39-7.35 (m, 2H), 7.25 (dd, J = 8.3, 2.6 Hz, 1H), 7.12 (s, 1H), 6.09 (dd, J = 3.4, 2.0 Hz, 1H), 3.67 (s, 2H), 3.41 (dd, J = 16.1, 3.8 Hz, 2H), 3.05 (d, J = 15.8 Hz, 2H), 2.91 (d, J = 10.2 Hz, 2H), 2.80 (s, 3H), 2.42 (s, 3H), 2.40-2.36 (m, 2H). MS (ESI) m/z: 606 [M + H]⁺. |
| V-n-12 | 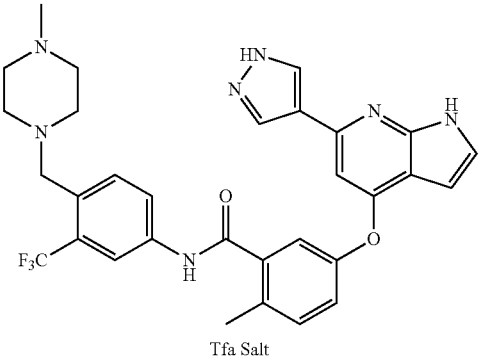 [SMILES: Cc1ccc(Oc2cc(-c3cn[nH]c3)nc3[nH]ccc23)cc1C(=O)Nc1ccc(CN2CCN(C)CC2)c(C(F)(F)F)c1] Tfa Salt | ¹H NMR (600 MHz, DMSO-d₆) δ 11.71 (s, 1H), 10.62 (s, 1H), 8.18 (d, J = 1.6 Hz, 1H), 7.95 (d, J = 8.4 Hz, 1H), 7.68 (d, J = 8.6 Hz, 1H), 7.38 (d, J = 8.5 Hz, 1H), 7.34 (d, J = 2.6 Hz, 1H), 7.28 (dd, J = 3.4, 2.5 Hz, 1H), 7.21 (dd, J = 8.3, 2.6 Hz, 1H), 6.98 (s, 1H), 6.02 (dd, J = 3.4, 2.0 Hz, 1H), 3.59 (s, 2H), 3.49-3.40 (s, 41H), 3.18 (s, 2H), 2.71 (s, 2H), 2.43 (s, 3H), 2.41 (s, 3H). MS (ESI) m/z: 590 [M + H]⁺. |
| V-n-13 | 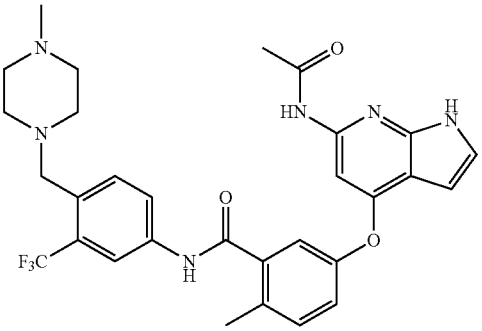 [SMILES: CC(=O)Nc1cc(Oc2ccc(C)c(C(=O)Nc3ccc(CN4CCN(C)CC4)c(C(F)(F)F)c3)c2)c2cc[nH]c2n1] | ¹H NMR (600 MHz, DMSO-d₆) δ 11.61 (s, 1H), 10.67 (s, 1H), 10.33 (s, 1H), 8.18 (d, J = 1.6 Hz, 1H), 7.95 (d, J = 8.2 Hz, 1H), 7.67 (d, J = 8.6 Hz, 1H), 7.36 (d, J = 8.5 Hz, 1H), 7.32 (d, J = 2.6 Hz, 1H), 7.22-7.18 (m, 2H), 6.15 (dd, J = 3.4, 2.0 Hz, 1H), 3.62 (s, 2H), 3.59 (s, 2H), 3.36 (s, 2H), 3.02 (s, 2H), 2.87 (d, J = 19.8 Hz, 2H), 2.77 (s, 3H), 2.40 (s, 3H), 2.02 (s, 3H). MS (ESI) m/z: 581 [M + H]⁺. |
| V-n-14 | 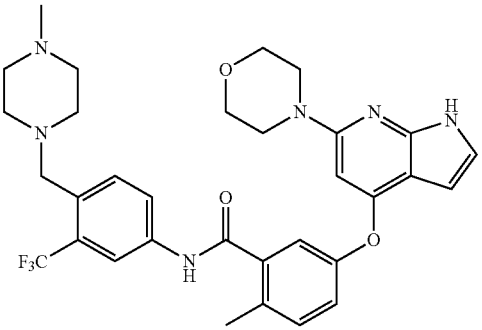 [SMILES: Cc1ccc(Oc2cc(N3CCOCC3)nc3[nH]ccc23)cc1C(=O)Nc1ccc(CN2CCN(C)CC2)c(C(F)(F)F)c1] | ¹H NMR (600 MHz, DMSO-d₆) δ 11.25 (s, 1H), 10.63 (s, 1H), 9.88 (s, 1H), 8.18 (s, 1H), 7.97 (d, J = 8.5 Hz, 1H), 7.68 (t, J = 6.6 Hz, 1H), 7.37 (t, J = 8.3 Hz, 1H), 7.11 (s, 1H), 6.99 (dd, J = 3.4, 2.4 Hz, 1H), 6.14 (s, 1H), 5.89 (dd, J = 3.4, 2.0 Hz, 1H), 3.65 (s, 2H), 3.39 (s, 8H), 3.36-3.33 (m, 2H), 3.02 (s, 2H), 2.89 (d, J = 11.4 Hz, 2H), 2.80 (s, 3H), 2.40 (s, 3H), 2.38-2.33 (m, 2H). MS (ESI) m/z: 609 [M + H]⁺. |

TABLE 5-continued

Structure and characterization of compounds V

| No. | Structure | ¹H NMR and/or MS data |
|---|---|---|
| V-n-15 | 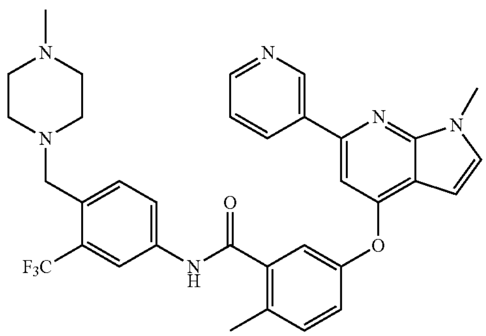 [SMILES: Cc1ccc(Oc2cc(-c3cccnc3)nc3c2ccn3C)cc1C(=O)Nc1ccc(CN2CCN(C)CC2)c(C(F)(F)F)c1] | ¹H NMR (600 MHz, Methanol-$d_4$) δ 9.54 (s, 1H), 9.18 (d, J = 8.2 Hz, 1H), 8.81 (d, J = 5.6 Hz, 1H), 8.16 (s, 1H), 8.12 (dd, J = 8.0, 5.9 Hz, 1H), 7.92 (d, J = 8.4 Hz, 1H), 7.77 (d, J = 8.5 Hz, 1H), 7.42 (d, J = 8.4 Hz, 1H), 7.39 (d, J = 3.4 Hz, 1H), 7.36 (d, J = 2.0 Hz, 1H), 7.29 (s, 1H), 7.24 (dd, J = 8.4, 2.3 Hz, 1H), 6.28 (d, J = 3.4 Hz, 1H), 3.96 (s, 3H), 3.85 (s, 2H), 3.35 (d, J = 11.7 Hz, 3H), 2.93 (s, 8H), 2.51 (s, 3H). MS (ESI) m/z: 615 [M + H]⁺. |
| V-n-16 | 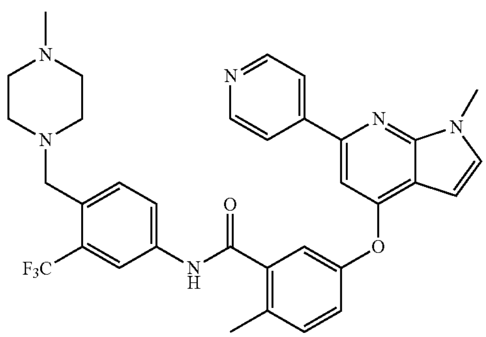 [SMILES: Cc1ccc(Oc2cc(-c3ccncc3)nc3c2ccn3C)cc1C(=O)Nc1ccc(CN2CCN(C)CC2)c(C(F)(F)F)c1] | ¹H NMR (600 MHz, Chloroform-d) δ 8.59 (d, J = 6.0 Hz, 2H), 8.25 (s, 1H), 7.89-7.80 (m, 4H), 7.76 (d, J = 8.5 Hz, 1H), 7.37-7.31 (m, 2H), 7.21 (dd, J = 8.3, 2.5 Hz, 1H), 7.17 (d, J = 3.5 Hz, 1H), 7.05 (s, 1H), 6.28 (d, J = 3.4 Hz, 1H), 3.97 (s, 3H), 3.63 (s, 2H), 2.56 (s, 3H), 2.54-2.47 (m, 8H), 2.32 (s, 3H). MS (ESI) m/z: 615 [M + H]⁺. |
| V-r-1 | 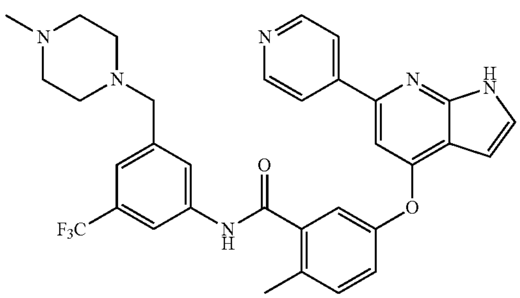 [SMILES: Cc1ccc(Oc2cc(-c3ccncc3)nc3[nH]ccc23)cc1C(=O)Nc1cc(CN2CCN(C)CC2)cc(C(F)(F)F)c1] | ¹H NMR (600 MHz, DMSO-$d_6$) δ 12.04 (s, 1H), 10.65 (s, 1H), 8.65 (dd, J = 4.5, 1.6 Hz, 2H), 8.14 (s, 1H), 7.97 (dd, J = 4.5, 1.6 Hz, 2H), 7.90 (s, 1H), 7.50 (dd, J = 3.4, 2.6 Hz, 1H), 7.44 (d, J = 2.6 Hz, 1H), 7.41 (d, J = 8.5 Hz, 1H), 7.34 (s, 1H), 7.30-7.27 (m, 2H), 6.18 (dd, J = 3.4, 1.9 Hz, 1H), 3.52 (s, 2H), 2.44 (s, 3H), 2.39 (s, 8H), 2.18 (s, 3H). MS (ESI) m/z: 601 [M + H]⁺. |

TABLE 6

Structure and characterization of compounds VI

| No. | Structure | ¹H NMR and/or MS data |
|---|---|---|
| VI-h-1 | TFA Salt | ¹H NMR (600 MHz, DMSO-$d_6$) δ 10.68 (s, 1H), 9.35 (s, 1H), 8.70 (d, J = 4.2 Hz, 1H), 8.63-8.58 (m, 1H), 8.56 (d, J = 5.3 Hz, 1H), 8.30 (d, J = 1.8 Hz, 1H), 8.26 (dd, J = 8.2, 1.7 Hz, 1H), 7.97 (t, J = 2.2 Hz, 1H), 7.93 (d, J = 8.1 Hz, 1H), 7.79 (d, J = 5.3 Hz, 1H), 7.75 (dd, J = 8.1, 1.9 Hz, 1H), 7.66-7.54 (m, 4H), 7.27 (dd, J = 8.0, 2.6 Hz, 1H), 3.79 (s, 2H), 3.42 (d, J = 18.8 Hz, 3H), 3.07 (s, 2H), 2.92 (d, J = 12.2 Hz, 2H), 2.82 (s, 3H), 2.45-2.37 (m, 2H). MS (ESI) m/z: 605 [M + H]⁺. |

TABLE 6-continued

Structure and characterization of compounds VI

| No. | Structure | ¹H NMR and/or MS data |
|---|---|---|
| VI-h-2 | (structure; TFA Salt) | ¹H NMR (600 MHz, DMSO-d$_6$) δ 10.68 (s, 1H), 8.83-8.76 (m, 2H), 8.60 (d, J = 5.4 Hz, 1H), 8.32-8.30 (m, 1H), 8.26 (dd, J = 8.2, 1.8 Hz, 1H), 8.24-8.19 (m, 2H), 7.98 (s, 1H), 7.93 (d, J = 8.2 Hz, 1H), 7.83 (d, J = 5.4 Hz, 1H), 7.76 (dd, J = 8.1, 1.9 Hz, 1H), 7.58 (t, J = 8.2 Hz, 1H), 7.28 (dd, 8.1, 2.3 Hz, 1H), 3.80 (s, 2H), 3.15 (s, 2H), 3.07 (s, 2H), 2.93 (d, J = 12.7 Hz, 2H), 2.82 (s, 3H), 2.46-2.37 (m, 2H). MS (ESI) m/z: 605 [M + H]⁺. |
| VI-i-1 | (structure; TFA Salt) | ¹H NMR (600 MHz, DMSO-d$_6$) δ 10.60 (s, 1H), 9.29 (d, J = 2.2 Hz, 1H), 8.68 (dd, J = 4.9, 1.7 Hz, 1H), 8.56 (d, J = 5.4 Hz, 1H), 8.56-8.53 (m, 1H), 8.29 (d, J = 1.8 Hz, 1H), 8.25 (dd, J = 8.1, 1.8 Hz, 1H), 7.92 (d, J = 8.2 Hz, 1H), 7.89 (d, J = 2.1 Hz, 1H), 7.79 (d, J = 5.3 Hz, 1H), 7.69 (dd, J = 8.4, 2.2 Hz, 1H), 7.56 (dd, J = 8.0, 4.9 Hz, 1H), 7.45 (d, J = 8.4 Hz, 1H), 3.78 (s, 2H), 3.41 (d, J = 12.1 Hz, 2H), 3.06 (s, 2H), 2.92 (d, J = 12.7 Hz, 2H), 2.81 (s, 3H), 2.45-2.37 (m, 2H), 2.16 (s, 3H). MS (ESI) m/z: 619 [M + H]⁺. |
| VI-i-2 | (structure; TFA Salt) | ¹H NMR (600 MHz, DMSO-d$_6$) δ 10.66 (s, 1H), 8.81-8.75 (m, 2H), 8.62 (d, J = 5.3 Hz, 1H), 8.20-8.15 (m, 2H), 8.14-8.11 (m, 2H), 8.09 (t, J = 2.0 Hz, 1H), 8.04 (dt, J = 7.3, 1.5 Hz, 1H), 7.85 (d, J = 5.4 Hz, 1H), 7.82-7.75 (m, 2H), 7.45 (s, 1H), 3.74 (s, 2H), 3.42 (s, 1H), 3.13 (s, 1H), 3.02 (d, J = 27.2 Hz, 4H), 2.80 (s, 3H), 2.39 (d, J = 1.9 Hz, 1H). MS (ESI) m/z: 619 [M + H]⁺. |
| VI-j-1 | (structure; TFA Salt) | ¹H NMR (600 MHz, DMSO-d$_6$) δ 10.27 (s, 1H), 9.37 (d, J = 2.1 Hz, 1H), 8.72 (dd, J = 4.8, 1.6 Hz, 1H), 8.65 (dt, J = 8.1, 2.0 Hz, 1H), 8.55 (d, J = 5.4 Hz, 1H), 8.33 (d, J = 1.8 Hz, 1H), 8.29 (d, J = 8.2 Hz, 1H), 7.93 (d, J = 8.2 Hz, 1H), 7.78 (d, J = 5.4 Hz, 1H), 7.61 (dd, J = 8.0, 4.9 Hz, 1H), 7.52 (d, J = 2.5 Hz, 1H), 7.48 (d, J = 8.4 Hz, 1H), 7.34 (dd, J = 8.3, 2.6 Hz, 1H), 3.41 (d, J = 12.2 Hz, 2H), 3.07 (s, 2H), 2.93 (d, J = 12.6 Hz, 2H), 2.82 (s, 3H), 2.46-2.38 (m, 2H), 2.34 (s, 3H). MS (ESI) m/z: 619 [M + H]⁺. |

TABLE 6-continued

Structure and characterization of compounds VI

| No. | Structure | ¹H NMR and/or MS data |
|---|---|---|
| VI-j-2 | 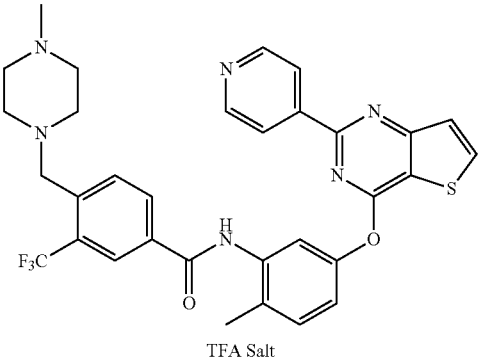 [SMILES: Cc1ccc(Oc2nc(-c3ccncc3)nc3ccsc23)cc1NC(=O)c1ccc(CN2CCN(C)CC2)c(C(F)(F)F)c1] TFA Salt | ¹H NMR (600 MHz, DMSO-d₆) δ 10.28 (s, 1H), 8.87-8.77 (m, 2H), 8.59 (d, J = 5.3 Hz, 1H), 8.35-8.31 (m, 3H), 8.29 (dd, J = 8.1, 1.8 Hz, 1H), 7.94 (d, J = 8.1 Hz, 1H), 7.82 (d, J = 5.4 Hz, 1H), 7.54 (d, J = 2.5 Hz, 1H), 7.48 (d, J = 8.4 Hz, 1H), 7.35 (dd, J = 8.3, 2.6 Hz, 1H), 3.42 (d, J = 12.1 Hz, 2H), 3.07 (t, J = 12.3 Hz, 2H), 2.93 (d, J = 12.6 Hz, 2H), 2.82 (s, 3H), 2.42 (t, J = 12.1 Hz, 2H), 2.35 (s, 3H). MS (ESI) m/z: 619 [M + H]⁺. |
| VI-l-1 | 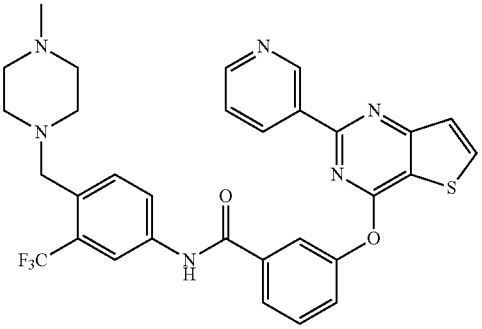 TFA Salt | ¹H NMR (600 MHz, DMSO-d₆) δ 10.63 (s, 1H), 9.29 (d, J = 2.2 Hz, 1H), 8.68 (d, J = 4.8 Hz, 1H), 8.58 (d, J = 5.4 Hz, 1H), 8.53 (dt, J = 8.0, 2.0 Hz, 1H), 8.21 (d, J = 2.2 Hz, 1H), 8.11 (dd, J = 8.6, 2.2 Hz, 1H), 8.08 (t, J = 1.9 Hz, 1H), 8.03 (d, J = 7.4 Hz, 1H), 7.83-7.75 (m, 3H), 7.71 (d, J = 8.6 Hz, 1H), 7.55 (dd, J = 8.0, 4.8 Hz, 1H), 3.68 (s, 2H), 3.40 (d, J = 12.2 Hz, 2H), 3.04 (s, 2H), 2.92 (d, J = 12.6 Hz, 2H), 2.81 (s, 3H), 2.37 (t, J = 12.0 Hz, 2H). MS (ESI) m/z: 605 [M + H]⁺. |
| VI-m-1 | 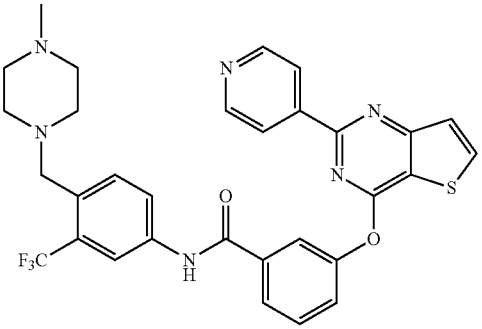 TFA Salt | ¹H NMR (600 MHz, DMSO-d₆) δ 10.54 (s, 1H), 9.23 (d, J = 2.1 Hz, 1H), 8.67 (dd, J = 4.8, 1.7 Hz, 1H), 8.58 (d, J = 5.4 Hz, 1H), 8.48 (dt, 8.0, 2.0 Hz, 1H), 8.19 (d, J = 2.2 Hz, 1H), 8.10 (dd, 8.6, 2.2 Hz, 1H), 8.05 (d, J = 1.7 Hz, 1H), 7.99 (dd, J = 7.9, 1.8 Hz, 1H), 7.81 (d, J = 5.3 Hz, 1H), 7.70 (d, J = 8.6 Hz, 1H), 7.66 (d, J = 8.1 Hz, 1H), 7.54 (dd, 8.0, 4.8 Hz, 1H), 3.67 (s, 2H), 3.40 (d, J = 12.1 Hz, 2H), 3.03 (s, 2H), 2.91 (d, J = 12.6 Hz, 2H), 2.80 (s, 3H), 2.42-2.33 (m, 2H), 2.27 (s, 3H). MS (ESI) m/z: 619 [M + H]⁺. |
| VI-n-1 | 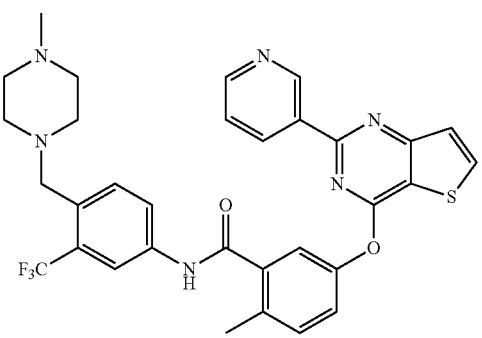 TFA Salt | ¹H NMR (600 MHz, DMSO-d₆) δ 10.70 (s, 1H), 9.34 (d, J = 2.1 Hz, 1H), 8.76-8.71 (m, 1H), 8.61 (dt, J = 8.0, 2.0 Hz, 1H), 8.56 (d, J = 5.3 Hz, 1H), 8.19 (d, J = 2.2 Hz, 1H), 8.04-7.97 (m, 1H), 7.79 (d, J = 5.4 Hz, 1H), 7.70 (d, J = 8.5 Hz, 1H), 7.65-7.58 (m, 3H), 7.52 (d, J = 8.5 Hz, 1H), 3.68 (s, 2H), 3.40 (d, J = 12.4 Hz, 2H), 3.03 (s, 2H), 2.92 (d, J = 12.4 Hz, 2H), 2.81 (s, 3H), 2.49 (s, 3H), 2.39 (d, J = 11.7 Hz, 2H). MS (ESI) m/z: 619 [M + H]⁺. |

TABLE 6-continued

Structure and characterization of compounds VI

| No. | Structure | ¹H NMR and/or MS data |
|---|---|---|
| VI-o-1 | 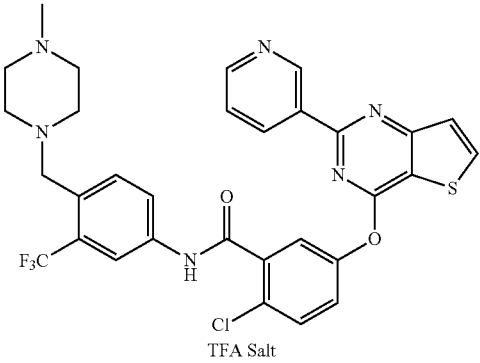 [SMILES: CN1CCN(Cc2ccc(NC(=O)c3cc(Oc4nc(-c5cccnc5)nc5ccsc45)ccc3Cl)cc2C(F)(F)F)CC1] TFA Salt | ¹H NMR (600 MHz, DMSO-$d_6$) δ 10.96 (s, 1H), 9.35 (d, J = 2.2 Hz, 1H), 8.71 (dd, J = 4.8, 1.7 Hz, 1H), 8.61-8.54 (m, 2H), 8.16 (d, J = 2.2 Hz, 1H), 7.98 (dd, J = 8.5, 2.2 Hz, 1H), 7.82 (d, J = 2.8 Hz, 1H), 7.81-7.77 (m, 2H), 7.75-7.70 (m, 2H), 7.58 (dd, J = 8.0, 4.8 Hz, 1H), 3.68 (s, 2H), 3.40 (d, J = 12.1 Hz, 2H), 3.03 (s, 2H), 2.91 (d, J = 12.7 Hz, 2H), 2.81 (s, 3H), 2.42-2.31 (m, 2H). MS (ESI) m/z: 640 [M + H]⁺. |
| VI-o-2 | 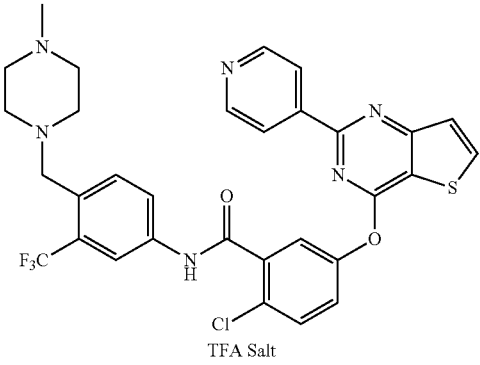 TFA Salt | ¹H NMR (600 MHz, DMSO-$d_6$) δ 10.65 (s, 1H), 9.29 (d, J = 2.1 Hz, 1H), 8.69 (dd, J = 4.8, 1.7 Hz, 1H), 8.59 (d, J = 5.4 Hz, 1H), 8.53 (dd, J = 8.0, 2.0 Hz, 1H), 8.13 (s, 1H), 8.12-8.07 (m, 2H), 8.03 (dt, J = 7.4, 1.6 Hz, 1H), 7.84-7.75 (m, 3H), 7.56 (dd, J = 8.0, 4.8 Hz, 1H), 7.44 (s, 1H), 3.41 (s, 3H), 3.02 (d, J = 33.1 Hz, 4H), 2.79 (s, 3H), 2.45-2.35 (m, 3H). MS (ESI) m/z: 605 [M + H]⁺. |
| VI-p-1 | 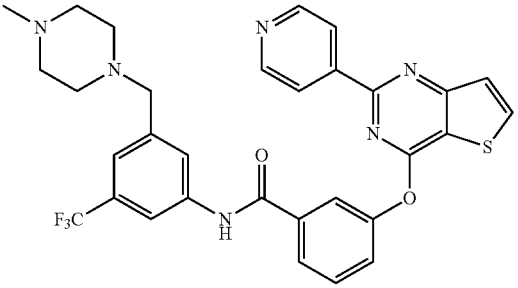 TFA Salt | ¹H NMR (600 MHz, DMSO-$d_6$) δ 10.65 (s, 1H), 9.29 (d, J = 2.1 Hz, 1H), 8.69 (dd, J = 4.8, 1.7 Hz, 1H), 8.59 (d, J = 5.4 Hz, 1H), 8.53 (dd, J = 8.0, 2.0 Hz, 1H), 8.13 (s, 1H), 8.12-8.07 (m, 2H), 8.03 (dt, J = 7.4, 1.6 Hz, 1H), 7.84-7.75 (m, 3H), 7.56 (dd, J = 8.0, 4.8 Hz, 1H), 7.44 (s, 1H), 3.41 (s, 3H), 3.02 (d, J = 33.1 Hz, 4H), 2.79 (s, 3H), 2.45-2.35 (m, 3H). MS (ESI) m/z: 605 [M + H]⁺. |
| VI-p-2 | 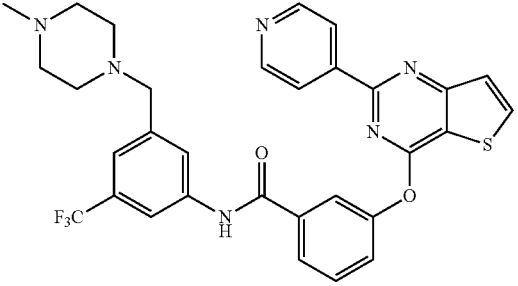 TFA Salt | ¹H NMR (600 MHz, DMSO-$d_6$) δ 10.66 (s, 1H), 6.81-8.73 (m, 2H), 8.62 (d, J = 5.4 Hz, 1H), 8.16-8.14 (m, 2H), 8.12 (d, J = 2.2 Hz, 2H), 8.09 (d, J = 2.0 Hz, 1H), 8.06-8.03 (m, 1H), 7.85 (d, J = 5.4 Hz, 1H), 7.82-7.75 (m, 2H), 7.45 (s, 1H), 3.73 (s, 2H), 3.43 (d, J = 10.3 Hz, 2H), 3.02 (d, J = 35.2 Hz, 4H), 2.79 (s, 3H), 2.47-2.35 (m, 2H). MS (ESI) m/z: 605 [M + H]⁺. |

TABLE 6-continued

Structure and characterization of compounds VI

| No. | Structure | ¹H NMR and/or MS data |
|---|---|---|
| VI-q-1 | 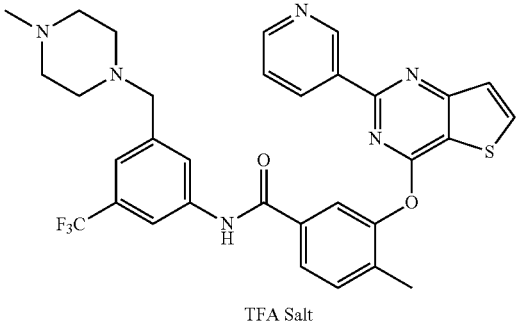 [SMILES: Cc1ccc(C(=O)Nc2cc(CN3CCN(C)CC3)cc(C(F)(F)F)c2)cc1Oc1nc(-c2cccnc2)nc2ccsc12] TFA Salt | ¹H NMR (600 MHz, DMSO-d₆) δ 10.58 (s, 1H), 9.24 (d, J = 2.2 Hz, 1H), 8.69 (dd, J = 4.9, 1.7 Hz, 1H), 8.59 (d, J = 5.4 Hz, 1H), 8.52 (dt, J = 8.0, 1.9 Hz, 1H), 8.13 (s, 1H), 8.10 (s, 1H), 8.06 (d, J = 1.8 Hz, 1H), 8.00 (dd, J = 8.0, 1.8 Hz, 1H), 7.81 (d, J = 5.4 Hz, 1H), 7.66 (d, J = 8.1 Hz, 1H), 7.57 (dd, J = 8.1, 4.9 Hz, 1H), 7.44 (s, 1H), 3.78 (s, 2H), 3.42 (s, 2H), 3.04 (s, 4H), 2.79 (s, 3H), 2.28 (s, 3H). MS (ESI) m/z: 619 [M + H]⁺. |
| VI-q-2 | 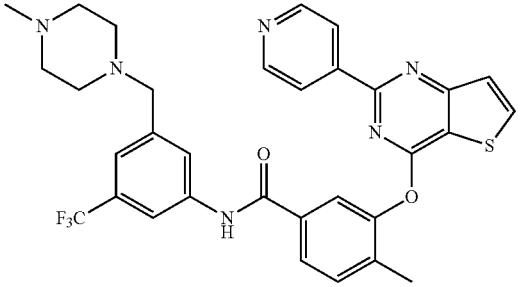 TFA Salt | ¹H NMR (600 MHz, DMSO-d₆) δ 10.57 (s, 1H), 8.76 (d, J = 5.4 Hz, 2H), 8.63 (d, J = 5.3 Hz, 1H), 8.15-8.09 (m, 4H), 8.07 (d, J = 1.8 Hz, 1H), 8.01 (dd, J = 7.9, 1.8 Hz, 1H), 7.86 (d, J = 5.4 Hz, 1H), 7.67 (d, J = 8.1 Hz, 1H), 7.43 (s, 1H), 3.74 (s, 2H), 3.42 (d, J = 5.9 Hz, 1H), 3.07 (d, J = 61.2 Hz, 3H), 2.79 (s, 3H), 2.47-2.36 (m, 2H), 2.28 (s, 3H). MS (ESI) m/z: 619 [M + H]⁺. |

TABLE 7

Structure and characterization of compounds VII

| No. | Structure | ¹H NMR and/or MS data |
|---|---|---|
| VII-h-1 | 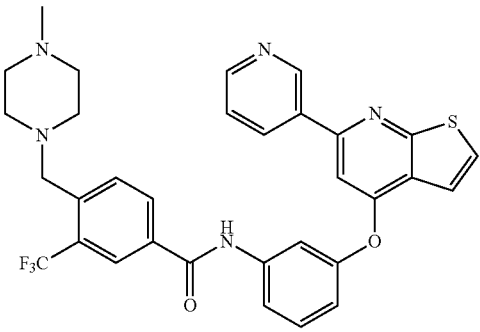 TFA Salt | ¹H NMR (600 MHz, DMSO-d₆) 10,64 (s, 1H), 9.36 (d, J = 2.3 Hz, 1H), 8.90-8.65 (m, 2H), 8.26 (d, J = 1.8 Hz, 1H), 8.23 (dd, J = 8.3, 1.7 Hz, 1H), 7.96 (d, J = 6.0 Hz, 1H), 7.91 (d, J = 8.2 Hz, 1H), 7.81 (dd, J = 8.1, 5.1 Hz, 1H), 7.77 (t, J = 2.2 Hz, 1H), 7.72 (dd, J = 8.3, 1.9 Hz, 1H), 7.58 (s, 1H), 7.52 (t, J = 8.2 Hz, 1H), 7.45 (d, J = 6.0 Hz, 1H), 7.09 (dd, J = 8.0, 2.4 Hz, 1H), 3.79 (s, 2H), 3.41 (d, J = 12.1 Hz, 2H), 3.06 (s, 2H), 2.91 (d, J = 12.7 Hz, 2H), 2.81 (s, 3H), 2.45-2.39 (m, 2H). MS (ESI) m/z: 604 [M + H]⁺. |

TABLE 7-continued

Structure and characterization of compounds VII

| No. | Structure | $^1$H NMR and/or MS data |
|---|---|---|
| VII-h-2 | 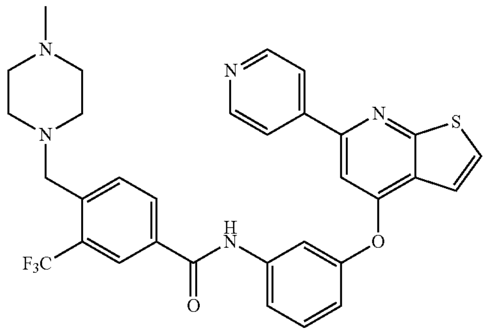 [SMILES: CN1CCN(Cc2ccc(C(=O)Nc3cccc(Oc4cc(-c5ccncc5)nc5sccc45)c3)cc2C(F)(F)F)CC1] | $^1$H NMR (600 MHz, DMSO-d$_6$) δ 10.58 (s, 1H), 8.73-8.60 (m, 2H), 8.21 (s, 1H), 8.19 (d, J = 8.1 Hz, 1H), 8.01-7.98 (m, 2H), 7.96 (d, J = 6.0 Hz, 1H), 7.91 (d, J = 8.2 Hz, 1H), 7.75-7.71 (m, 2H), 7.54-7.48 (m, 2H), 7.45 (d, J = 6.0 Hz, 1H), 7.08 (dd, J = 8.3, 2.4 Hz, 1H), 3.66 (s, 2H), 2.47-2.18 (m, 8H), 2.16 (s, 3H). MS (ESI) m/z: 604 [M + H]$^+$. |
| VII-i-1 | TFA Salt | $^1$H NMR (600 MHz, DMSO-d$_6$) δ 10.55 (s, 1H), 9.28 (d, J = 2.2 Hz, 1H), 8.74 (dd, J = 5.1, 1.4 Hz, 1H), 8.82 (dt, J = 8.1, 1.9 Hz, 1H), 8.24 (d, J = 1.8 Hz, 1H), 8.21 (dd, J = 8.1, 1.8 Hz, 1H), 7.95 (d, J = 6.0 Hz, 1H), 7.89 (d, J = 8.2 Hz, 1H), 7.72 (dd, J = 8.1, 5.0 Hz, 1H), 7.69-7.65 (m, 2H), 7.49 (d, J = 6.0 Hz, 1H), 7.44 (d, J = 8.7 Hz, 1H), 7.31 (s, 1H), 3.77 (s, 2H), 3.40 (d, J = 12.1 Hz, 2H), 3.05 (t, J = 12.2 Hz, 2H), 2.90 (d, J = 12.7 Hz, 2H), 2.80 (s, 3H), 2.42 (t, J = 11.9 Hz, 2H), 2.22 (s, 3H). MS (ESI) m/z: 618 [M + H]$^+$. |
| VII-i-2 | 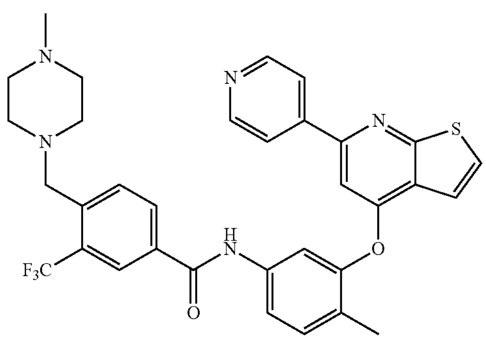 [SMILES: Cc1ccc(NC(=O)c2ccc(CN3CCN(C)CC3)c(C(F)(F)F)c2)cc1Oc1cc(-c2ccncc2)nc2sccc12] | $^1$H NMR (600 MHz, DMSO-d$_6$) δ 10.49 (s, 1H), 8.72-8.57 (m, 2H), 8.19 (s, 1H), 8.17 (d, J = 8.1 Hz, 1H), 7.96 (dd, J = 6.1, 1.3 Hz, 1H), 7.96-7.92 (m, 2H), 7.89 (d, J = 8.1 Hz, 1H), 7.68 (dd, J = 8.3, 2.0 Hz, 1H), 7.65 (d, J = 2.1 Hz, 1H), 7.50 (d, J = 6.1 Hz, 1H), 7.44 (d, J = 8.4 Hz, 1H), 7.28 (d, J = 1.2 Hz, 1H), 3.65 (s, 2H), 2.47-2.24 (m, 8H), 2.21 (s, 3H), 2.15 (d, J = 1.5 Hz, 3H). MS (ESI) m/z: 618 [M + H]$^+$. |
| VII-j-1 | 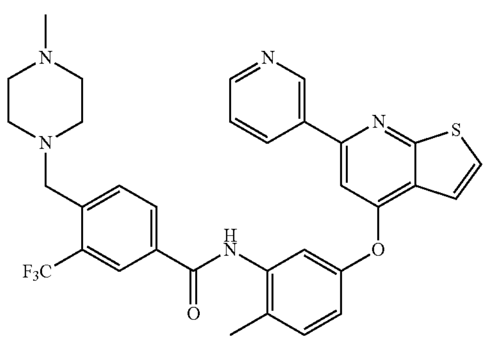 [SMILES: Cc1ccc(Oc2cc(-c3cccnc3)nc3sccc23)cc1NC(=O)c1ccc(CN2CCN(C)CC2)c(C(F)(F)F)c1] | $^1$H NMR (600 MHz, DMSO-d$_6$) δ 10.19 (s, 1H), 9.17 (d, J = 2.3 Hz, 1H), 8.63 (dd, J = 4.7, 1.6 Hz, 1H), 8.37 (dt, J = 8.1, 2.0 Hz, 1H), 8.25 (s, 1H), 8.22 (d, J = 8.1 Hz, 1H), 7.92-7.86 (m, 2H), 7.51 (dd, J = 8.0, 4.7 Hz, 1H), 7.46 (d, J = 6.1 Hz, 1H), 7.43 (d, J = 8.4 Hz, 1H), 7.39 (d, J = 2.6 Hz, 1H), 7.36 (s, 1H), 7.17 (dd, J = 8.3, 2.7 Hz, 1H), 3.66 (s, 2H), 2.47-2.28 (m, 8H), 2.30 (s, 3H), 2.16 (s, 3H). MS (ESI) m/z: 618 [M + H]$^+$. |

TABLE 7-continued

Structure and characterization of compounds VII

| No. | Structure | ¹H NMR and/or MS data |
|---|---|---|
| VII-j-2 | 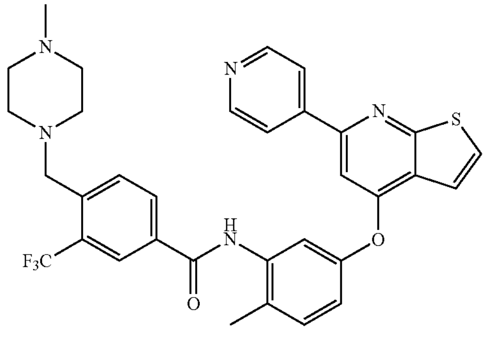 [SMILES: Cc1ccc(Oc2cc(-c3ccncc3)nc3sccc23)cc1NC(=O)c1ccc(CN2CCN(C)CC2)c(C(F)(F)F)c1] | ¹H NMR (600 MHz, DMSO-$d_6$) δ 10.19 (s, 1H), 8.77-8.55 (m, 2H), 8.26 (s, 1H), 8.23 (d, J = 7.4 Hz, 1H), 7.99-7.96 (m, 2H), 7.95 (d, J = 6.0 Hz, 1H), 7.91 (d, J = 8.1 Hz, 1H), 7.48 (d, J = 5.9 Hz, 1H), 7.44-7.40 (m, 2H), 7.39 (d, J = 2.6 Hz, 1H), 7.17 (dd, J = 8.3, 2.7 Hz, 1H), 3.66 (s, 2H), 2.47-2.27 (m, 8H), 2.31 (s, 3H), 2.16 (s, 3H). MS (ESI) m/z: 618 [M + H]⁺. |
| VII-l-1 | 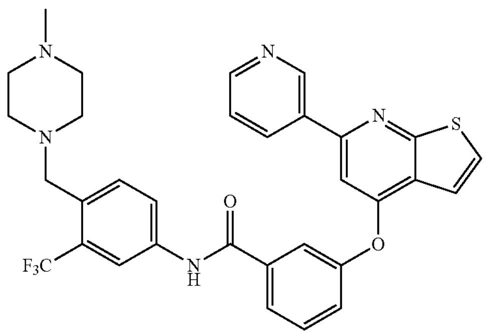 [SMILES: CN1CCN(Cc2ccc(NC(=O)c3cccc(Oc4cc(-c5cccnc5)nc5sccc45)c3)cc2C(F)(F)F)CC1] | ¹H NMR (600 MHz, DMSO-$d_6$) δ 10.56 (s, 1H), 9.18 (dd, J = 2.4, 0.8 Hz, 1H), 8.63 (dd, J = 4.8, 1.6 Hz, 1H), 8.37 (dt, J = 8.0, 2.0 Hz, 1H), 8.18 (d, J = 2.2 Hz, 1H), 8.04-8.00 (m, 1H), 7.95 (dd, J = 7.9, 1.3 Hz, 1H), 7.94-7.89 (m, 2H), 7.73-7.65 (m, 2H), 7.56 (ddd, J = 8.2, 2.5, 1.0 Hz, 1H), 7.50 (ddd, J = 8.0, 4.7, 0.8 Hz, 1H), 7.45 (d, J = 6.0 Hz, 1H), 7,40 (s, 1H), 3.55 (s, 2H), 2.47-2.17 (m, 8H), 2.15 (s, 3H). MS (ESI) m/z: 604 [M + H]⁺. |
| VII-l-2 | 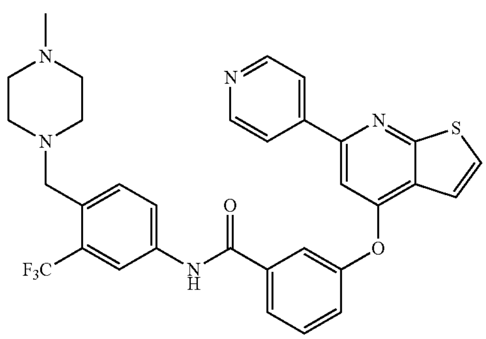 [SMILES: CN1CCN(Cc2ccc(NC(=O)c3cccc(Oc4cc(-c5ccncc5)nc5sccc45)c3)cc2C(F)(F)F)CC1] | ¹H NMR (600 MHz, DMSO-$d_6$) δ 10.56 (s, 1H), 8.73-8.54 (m, 2H), 8.19 (d, J = 2.2 Hz, 1H), 8.03 (dd, J = 8.5, 2.2 Hz, 1H), 8.01-7.95 (m, 4H), 7.94 (t, J = 2.1 Hz, 1H), 7.73-7.68 (m, 2H), 7.57 (ddd, J = 8.1, 2.5, 0.9 Hz, 1H), 7.49 (d, J = 6.0 Hz, 1H), 7.45 (s, 1H), 3.56 (s, 2H), 2.48-2.17 (m, 8H), 2.15 (s, 3H). MS (ESI) m/z: 604 [M + H]⁺. |
| VII-n-1 | 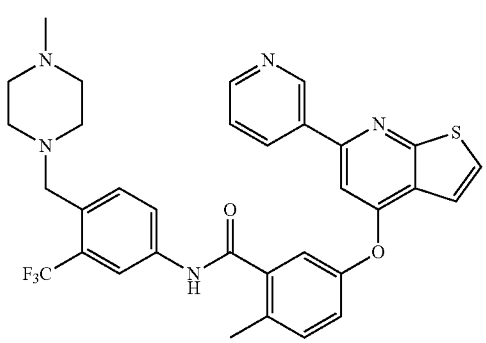 [SMILES: Cc1ccc(Oc2cc(-c3cccnc3)nc3sccc23)cc1C(=O)Nc1ccc(CN2CCN(C)CC2)c(C(F)(F)F)c1] | ¹H NMR (600 MHz, DMSO-$d_6$) δ 10.64 (s, 1H), 9.16 (d, J = 2.3 Hz, 1H), 8.63 (dd, J = 4.8, 1.6 Hz, 1H), 8.35 (dt, J = 8.0, 2.0 Hz, 1H), 8.16 (d, J = 2.2 Hz, 1H), 7.91 (t, J = 7.5 Hz, 2H), 7.67 (d, J = 8.5 Hz, 1H), 7.52-7.49 (m, 2H), 7.46 (s, 1H), 7.44 (d, J = 3.0 Hz, 1H), 7.36 (dd, J = 8.4, 2.6 Hz, 1H), 7.34 (s, 1H), 3.54 (s, 2H), 2.43 (s, 3H), 2.45-2.17 (m, 8H), 2.14 (s, 3H). MS (ESI) m/z: 618 [M + H]⁺. |

TABLE 7-continued

Structure and characterization of compounds VII

| No. | Structure | ¹H NMR and/or MS data |
|---|---|---|
| VII-n-2 | 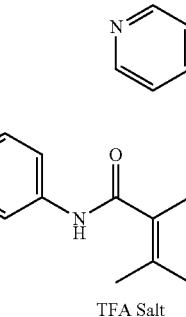 TFA Salt | ¹H NMR (600 MHz, DMSO-$d_6$) δ 10.66 (s, 1H), 8.76 (d, J = 5.4 Hz, 2H), 8.17 (d, J = 2.2 Hz, 1H), 8.15-8.12 (m, 2H), 8.00 (d, J = 6.0 Hz, 1H), 7.97 (dd, J = 8.4, 2.1 Hz, 1H), 7.68 (d, J = 8.5 Hz, 1H), 7.50 (d, J = 2.6 Hz, 1H), 7.49-7.44 (m, 3H), 7.39 (dd, J = 8.3, 2.7 Hz, 1H), 3.65 (s, 2H), 3.39 (d, J = 12.2 Hz, 2H), 3.02 (s, 2H), 2.89 (d, J = 12.6 Hz, 2H), 2.80 (s, 3H), 2.44 (s, 3H), 2.36 (t, J = 12.7 Hz, 2H). MS (ESI) m/z: 618 [M + H]⁺. |
| VII-o-1 | 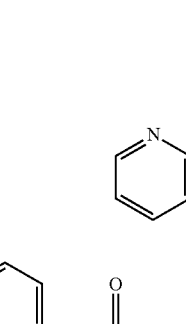 | ¹H NMR (600 MHz, DMSO-$d_6$) δ 10.85 (s, 1H), 9.22 (d, J = 2.4 Hz, 1H), 8.64 (dd, J = 4.7, 1.7 Hz, 1H), 8.42 (dt, J = 8.0, 2.1 Hz, 1H), 8.14 (d, J = 2.2 Hz, 1H), 7.93 (d, J = 6.0 Hz, 1H), 7.88 (dd, J = 8.5, 2.2 Hz, 1H), 7.69 (t, J = 8.9 Hz, 2H), 7.65 (d, J = 3.0 Hz, 1H), 7.52 (dd, J = 8.0, 4.8 Hz, 1H), 7.49 (s, 1H), 7.47 (dd, J = 8.8, 2.9 Hz, 1H), 7.44 (d, J = 6.0 Hz, 1H), 3.55 (s, 2H), 2.47-2.20 (m, 8H), 2.14 (s, 3H). MS (ESI) m/z: 638 [M + H]⁺. |
| VII-o-2 | 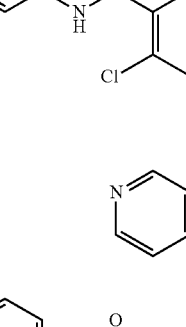 | ¹H NMR (600 MHz, DMSO-$d_6$) δ 10.83 (s, 1H), 8.74-8.54 (m, 2H), 8.14 (d, J = 2.3 Hz, 1H), 8.06-8.02 (m, 2H), 7.99 (d, J = 6.0 Hz, 1H), 7.89 (dd, J = 8.6, 2.2 Hz, 1H), 7.74-7.68 (m, 2H), 7.67 (d, J = 2.9 Hz, 1H), 7.55 (s, 1H), 7.49 (dd, J = 8.8, 3.0 Hz, 1H), 7.47 (d, J = 6.0 Hz, 1H), 3.56 (s, 2H), 2.48-2.20 (m, 8H), 2.16 (s, 3H). MS (ESI) m/z: 638 [M + H]⁺. |
| VII-p-1 | 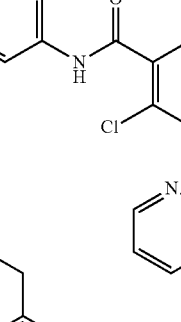 TFA Salt | ¹H NMR (600 MHz, DMSO-$d_6$) δ 10.65 (s, 1H), 9.29 (s, 1H), 8.73 (d, J = 5.0 Hz, 1H), 8.61 (dd, J = 8.3, 2.2 Hz, 1H), 8.12 (d, J = 2.1 Hz, 2H), 8.00-7.94 (m, 2H), 7.94-7.91 (m, 1H), 7.75-7.65 (m, 2H), 7.58 (ddd, J = 8.1, 2.5, 1.0 Hz, 1H), 7.51-7.42 (m, 3H), 3.83 (s, 2H), 3.65-2.83 (m, 8H), 2.80 (s, 3H). MS (ESI) m/z: 604 [M + H]⁺. |

TABLE 7-continued

Structure and characterization of compounds VII

| No. | Structure | ¹H NMR and/or MS data |
|---|---|---|
| VII-p-2 | 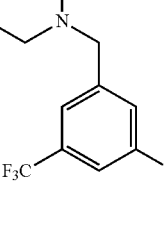 | ¹H NMR (600 MHz, DMSO-$d_6$) δ 10.58 (s, 1H), 8.81-8.61 (m, 2H), 8.16 (d, J = 1.9 Hz, 1H), 8.00-7.96 (m, 5H), 7.94 (t, J = 2.0 Hz, 1H), 7.70 (t, J = 7.9 Hz, 1H), 7.56 (dd, J = 8.1, 2.5 Hz, 1H), 7.48 (d, J = 6.0 Hz, 1H), 7.43 (s, 1H), 7.35 (s, 1H), 3.52 (s, 2H), 2.45-2.20 (m, 8H), 2.13 (s, 3H). MS (ESI) m/z: 604 [M + H]⁺. |
| VII-u-1 | 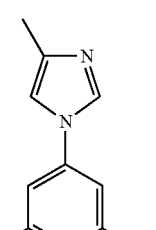 | ¹H NMR (600 MHz, DMSO-$d_6$) δ 10.83 (s, 1H), 9.62 (d, J = 1.7 Hz, 1H), 9.29 (s, 1H), 8.76 (d, J = 5.0 Hz, 1H), 8.68 (dt, J = 7.6, 1.7 Hz, 1H), 8.53 (t, J = 2.0 Hz, 1H), 8.20 (d, J = 1.8 Hz, 1H), 8.02 (t, J = 1.5 Hz, 1H), 8.00-7.96 (m, 2H), 7.92 (t, J = 1.7 Hz, 1H), 7.88 (d, J = 1.8 Hz, 1H), 7.77 (dd, J = 8.1, 5.1 Hz, 1H), 7.68 (d, J = 8.0 Hz, 1H), 7.55 (d, J = 6.1 Hz, 1H), 7.27 (s, 1H), 2.35 (d, J = 1.1 Hz, 3H), 2.33 (s, 3H). MS (ESI) m/z: 586 [M + H]⁺. |
| VII-u-2 | 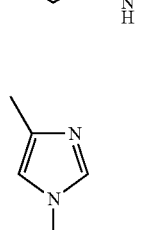 | ¹H NMR (600 MHz, DMSO-$d_6$) δ 10.62 (s, 1H), 6.82-8.44 (m, 2H), 8.24 (d, J = 2.0 Hz, 1H), 8.18 (d, J = 1.4 Hz, 1H), 8.10 (d, J = 1.9 Hz, 1H), 7.99 (d, J = 6.0 Hz, 1H), 7.97 (dd, J = 8.0, 1.8 Hz, 1H), 7.94-7.91 (m, 2H), 7.88 (d, J = 1.7 Hz, 1H), 7.71 (s, 1H), 7.67 (d, J = 8.1 Hz, 1H), 7.55 (d, J = 6.0 Hz, 1H), 7.45 (s, 1H), 7.18 (s, 1H), 2.31 (s, 3H), 2.16 (s, 3H). MS (ESI) m/z: 586 [M + H]⁺. |

Test Example

Biological Activity Assay:

Growth inhibitory activity of compounds on cell lines stably transfected with kinase The activity of compounds against kinase RET is evaluated by their effect of inhibiting growth of cell lines stably transfected with kinase CCDC6-RET-BaF3, KIF5B-RET-BaF3, and wild-type BaF3 (*Proc. Natl. Acad. Sci. USA.*, 2006, 103, 3153-8.). The growth of the cell lines stably transfected with kinase CCDC6-RET-BaF3, KIF5B-RET-BaF3 depends on their kinase activity. If a compound can inhibit the activity of the kinase RET per se or the activity of the RET signaling pathway, the compound can inhibit the growth of BaF3 cells stably transfected with kinase. While the growth of wild-type BaF3 cells does not depend on the activity of RET or RET signaling pathway, the effect of a compound on the growth of wild-type BaF3 cells can be used to evaluate its broad-spectrum toxicity. Therefore, a larger ratio between $IC_{50}$ of a compound to wild-type BaF3 and $IC_{50}$ of the compound to the cell lines stably transfected with kinase CCDC6-RET-BaF3, KIF5B-RET-BaF3 indicates better targeting.

The specific test method is given as follows:

1) Medium: DMEM (Dulbecco's modified eagle medium) or RPMI 1640 (containing 10% fetal bovine serum, 100 μg/mL ampicillin, 100 μg/mL streptomycin).

2) Reagents: MTS reaction solution (containing 2 mg/mL of MTS [3-(4,5-dimethylthiazol-2-yl)-5-(3-carboxymethoxyphenyl)-2-(4-sulfophenyl)-2H-tetrazolium, inner Salt]; 100 μg/mL PES (phenazine methosulfate)).

3) Compound test: cells stably transfected with kinase (CCDC6-RET-BaF3, KIF5B-RET-BaF3) or wild-type BaF3 cells (2×10⁴ cells/well) were incubated into a 96-well culture plate, the volume of cell culture fluid was 90 μL, and then 10 μL of the compound at each gradient concentration was added (the highest concentration was 10 μM, which was diluted stepwise by ⅓, and 8 concentration points were set in total; the system contained 0.1% DMSO (dimethyl sulfoxide)). The cell plate with uniformly mixed compound was cultured in a cell culture incubator (37° C.; 5% $CO_2$) for 48 h, then 20 μL of MTS reaction solution was added, uniformly mixed and incubated in the cell culture incubator (37° C.; 5% $CO_2$) for 1-4 hr, OD values at 490 nm were measured by a microplate reader (VARIOSKAN FLASH, Thermo). Three parallels were set in each group of experiments, with 0.1% (a final concentration) DMSO as a negative control, and a medium without cells or compounds as a blank control. The cell growth inhibition rate was calculated by the following formula:

Cell growth inhibition rate %=1−(OD$_{experimental\ group}$−OD$_{blank\ group}$)/(OD$_{negative\ group}$−OD$_{blank\ group}$)×100%

4) IC$_{50}$ calculation: The semi-inhibitory concentration of the compound acting on cell growth was calculated using GradPad Prism 5 software according to the measured cell growth inhibition rate.

TABLE 8

Growth inhibitory activity of compounds on cell lines stably transfected with kinase and wild-type Ba/F3 cells*

| Cmpd ID | CCDC6-RET (IC$_{50}$/nM) | KIF5B-RET (IC$_{50}$/nM) | WT Ba/F3 (IC$_{50}$/nM) |
|---|---|---|---|
| I-d-2 | 1541 | 5714 | >10000 |
| I-f-2 | 4845 | 8120 | n.d. |
| I-h-1 | 4934 | 2290 | n.d. |
| II-e-1 | 1974 | 2241 | n.d. |
| II-e-2 | 1428 | 1767 | >10000 |
| II-h-1 | 1112 | 952.7 | n.d. |
| II-h-2 | 140.2 | 106.2 | n.d. |
| II-h-3 | 342.8 | 820.3 | 4089 |
| II-h-4 | 78.58 | 299.6 | 3927 |
| II-i-1 | 476.6 | 411 | n.d. |
| II-i-2 | 616.6 | 469.2 | n.d. |
| II-i-3 | 880.8 | 1036 | n.d. |
| I-j-1 | 0.7407 | 2.739 | n.d. |
| I-j-2 | 2128 | 1578 | 2107 |
| I-j-3 | 1416 | 1431 | 1768 |
| I-j-4 | 1011 | 1611 | 1793 |
| I-j-5 | 1876 | 2369 | 4205 |
| I-j-6 | 221 | 1178 | 4220 |
| I-j-7 | 1027 | 1437 | 2412 |
| I-l-1 | 476.3 | 1947 | >10000 |
| I-l-2 | 3614 | 17751 | 1356 |
| I-l-3 | 25.22 | 5.882 | >10000 |
| I-m-1 | 504.4 | 810.4 | >10000 |
| I-m-2 | 710.2 | 1300 | n.d. |
| I-m-3 | 447.4 | 1046 | n.d. |
| I-n-1 | 297.5 | 899.9 | >10000 |
| I-n-2 | 3212 | 3636 | 1612 |
| I-n-3 | 8.378 | 40.5 | n.d. |
| I-n-4 | 2700 | 2373 | n.d. |
| I-n-5 | 1539 | 1505 | n.d. |
| I-n-6 | 1785 | 1380 | n.d. |
| I-n-7 | 1557 | 1454 | n.d. |
| I-n-8 | 1206 | 1328 | n.d. |
| I-n-9 | 1549 | 1476 | n.d. |
| I-n-10 | 1402 | 1403 | n.d. |
| I-n-11 | 1205 | 1962 | n.d. |
| I-n-12 | 2032 | 1864 | n.d. |
| I-n-13 | 3005 | 4845 | n.d. |
| I-n-14 | 163.2 | 46.98 | n.d. |
| I-o-1 | 1465 | 1392 | n.d. |
| I-o-2 | 20.6 | 3.146 | n.d. |
| I-o-3 | 1383 | 1383 | n.d. |
| I-o-4 | 1404 | 1407 | n.d. |
| I-o-5 | 1317 | 1387 | n.d. |
| I-o-6 | 1290 | 1358 | n.d. |
| I-o-7 | 903.3 | 1207 | n.d. |
| I-o-8 | 1586 | 1490 | n.d. |
| I-o-9 | 1392 | 1497 | n.d. |
| I-o-10 | 1367 | 1907 | n.d. |
| I-o-11 | 1676 | 1565 | n.d. |
| I-o-12 | 55.22 | 153.8 | n.d. |
| II-j-1 | 4166 | 4418 | n.d. |
| II-j-2 | 13.09 | 5,797 | n.d. |
| II-j-3 | 1417 | 3206 | n.d. |
| II-j-4 | 2070 | 2357 | n.d. |
| II-j-5 | 2371 | 3888 | 7402 |
| II-j-6 | 7.958 | 44.21 | 4230 |
| II-k-1 | 2068 | 1394 | n.d. |
| II-k-2 | 15.8 | 114 | n.d. |
| II-k-3 | 567 | 1347 | 1344 |
| II-k-4 | 37.68 | 103.8 | >10000 |
| II-m-1 | 35.21 | 8.282 | n.d. |
| II-m-2 | 30.23 | 17.82 | n.d. |
| II-m-3 | 348 | 97.74 | n.d. |
| II-m-4 | 847,6 | 152.3 | n.d. |
| II-m-5 | 807.3 | 319.6 | n.d. |
| II-m-6 | 696 | 114 | n.d. |
| II-m-7 | 178.1 | 28.31 | n.d. |
| II-m-8 | 165.7 | 56.89 | n.d. |
| II-m-9 | 75.14 | 14.61 | n.d. |
| II-m-10 | 449.3 | 36.38 | n.d. |
| II-m-11 | 31.78 | 14.94 | n.d. |
| II-m-12 | 123.2 | 69.66 | n.d. |
| II-m-13 | 253.4 | 172.2 | n.d. |
| II-m-14 | 9.31 | 21.64 | n.d. |
| II-m-15 | 110.6 | 18.03 | n.d. |
| II-m-16 | 383.5 | 84.55 | n.d. |
| II-m-17 | 1100 | 159.9 | n.d. |
| II-m-18 | 256.7 | 34.28 | n.d. |
| II-m-19 | 54.93 | 123.6 | n.d. |
| II-m-20 | 10.57 | 74.34 | >10000 |
| II-m-21 | 73.39 | 240.4 | 4779 |
| II-m-22 | >10000 | 442061 | n.d. |
| II-m-23 | 1104 | 915.8 | n.d. |
| II-n-2 | 1518 | 440.4 | n.d. |
| II-o-1 | 4167 | 4019 | n.d. |
| II-o-2 | 108 | 130.4 | n.d. |
| II-p-1 | 267.9 | 250.5 | n.d. |
| II-p-2 | 458.4 | 521.3 | n.d. |
| II-s-1 | 264.2 | 482.4 | n.d. |
| II-s-2 | 187.9 | 355.2 | n.d. |
| II-t-2 | 1569 | 2616 | n.d. |
| II-v-1 | 7228 | 7945 | n.d. |
| II-v-7 | 1201 | 1203 | n.d. |
| II-v-8 | 346 | 407.4 | n.d. |
| II-v-9 | 961.5 | 934.4 | n.d. |
| II-v-10 | 491.9 | 462.6 | n.d. |
| II-v-11 | 546.1 | 646.5 | n.d. |
| II-v-12 | 364.3 | 118.3 | n.d. |
| II-v-13 | 533.3 | 587.4 | n.d. |
| II-v-14 | 73.89 | 69.27 | n.d. |
| II-v-15 | 114.4 | 135 | n.d. |
| II-v-16 | 2487 | 3067 | n.d. |
| II-v-17 | 899.8 | 1044 | n.d. |
| III-h-1 | 2814 | 1539 | n.d. |
| III-h-2 | 16.78 | 16.4 | n.d. |
| III-h-3 | 4098 | 2139 | n.d. |
| III-h-4 | 194.8 | 179.9 | n.d. |
| III-i-1 | 4108 | 2846 | n.d. |
| III-i-2 | 1396 | 773.9 | n.d. |
| III-i-3 | 4343 | 3627 | n.d. |
| III-i-4 | 2020 | 1327 | n.d. |
| III-j-1 | 5943 | 3253 | n.d. |
| III-j-2 | 6.06 | 2.323 | n.d. |
| III-j-3 | 2482 | 2349 | 3776 |
| III-j-4 | 1363 | 1717 | 3409 |
| III-j-5 | 4264 | 3102 | n.d. |
| III-j-6 | 27.99 | 13.21 | n.d. |
| III-j-7 | 1268 | 1367 | 2564 |
| III-j-8 | 1135 | 1315 | 1881 |
| III-j-9 | 97.6 | 463.9 | 4258 |
| III-j-10 | 233.6 | 427.8 | 1456 |
| III-j-11 | 1529 | 1568 | 1365 |
| III-j-12 | 2662 | 2973 | 2151 |
| III-j-13 | 1715 | 2402 | 4153 |
| III-j-14 | 876.3 | 1379 | 1344 |
| III-j-15 | 744.6 | 619.9 | 1205 |
| III-j-16 | 2039 | 1468 | 2277 |
| III-j-18 | 477.1 | 1353 | >10000 |
| III-k-1 | 1862 | 1320 | 4155 |
| III-k-2 | 0.79 | 17.2 | 1342 |
| III-k-3 | 1248 | 1188 | 1167 |
| III-k-4 | 11.2 | 70.7 | 1622 |
| III-k-5 | 1488 | 1915 | 4365 |

TABLE 8-continued

Growth inhibitory activity of compounds on cell lines stably transfected with kinase and wild-type Ba/F3 cells*

| Cmpd ID | CCDC6-RET ($IC_{50}$/nM) | KIF5B-RET ($IC_{50}$/nM) | WT Ba/F3 ($IC_{50}$/nM) |
|---|---|---|---|
| III-k-6 | 989.7 | 1012 | 2474 |
| III-k-7 | 2961 | 1900 | 3715 |
| III-k-8 | 3458 | 3576 | 3990 |
| III-k-9 | 1188 | 1489 | 1650 |
| III-k-10 | 2297 | 2438 | 1439 |
| III-k-11 | 451.1 | 495.9 | 1289 |
| III-k-12 | 1813 | 2662 | n.d. |
| III-k-13 | 1447 | 1547 | 1603 |
| III-k-15 | 2201 | 2380 | n.d. |
| III-k-16 | 2087 | 3194 | 3631 |
| III-k-17 | 1411 | 2615 | 2633 |
| III-k-18 | 4125 | 3994 | 3887 |
| III-l-2 | 22.68 | 5.705 | n.d. |
| III-l-3 | 1403 | 1544 | n.d. |
| III-l-4 | 18.67 | 11.31 | n.d. |
| III-m-1 | 4503 | 2102 | n.d. |
| III-m-2 | 3626 | 1306 | n.d. |
| III-m-3 | 2706 | 2406 | 3100 |
| III-m-4 | 2723 | 3863 | 3459 |
| III-m-5 | 3758 | 4041 | 3919 |
| III-m-6 | 3772 | 3948 | 2786 |
| III-m-7 | 1412 | 2346 | 4328 |
| III-m-8 | 1238 | 1712 | 4097 |
| III-m-9 | 1254 | 3049 | 1444 |
| III-m-10 | 543.9 | 1049 | 622.9 |
| III-m-12 | 4021 | 4277 | 3576 |
| III-m-13 | 3510 | 2995 | 3394 |
| III-m-14 | 2919 | 2720 | 3192 |
| III-m-15 | 2958 | 3931 | 7206 |
| III-m-16 | 3672 | 4422 | 4362 |
| III-m-17 | 3153 | 2761 | n.d. |
| III-m-18 | 2965 | 2678 | 3511 |
| III-m-19 | 2512 | 3273 | 4023 |
| III-m-20 | 2961 | 2500 | 3554 |
| III-m-21 | 3491 | 3747 | 2921 |
| III-m-22 | 597.1 | 854.1 | >10000 |
| III-m-23 | 514.7 | 476.6 | 463.5 |
| III-m-24 | 3122 | 3232 | 3080 |
| III-m-26 | 1318 | 2898 | 4096 |
| III-m-27 | 1401 | 1501 | 34462 |
| III-n-2 | 53.72 | 21 | n.d. |
| III-n-4 | 43.12 | 17.18 | n.d. |
| III-o-1 | 2154 | 1547 | 1626 |
| III-o-2 | 17.4 | 13.43 | 1290 |
| III-o-3 | 1278 | 1334 | 1299 |
| III-o-4 | 6.046 | 13.31 | 1154 |
| III-p-1 | 4404 | 2917 | 3550 |
| III-p-2 | 449.3 | 672.5 | >10000 |
| III-p-3 | 4530 | 3379 | n.d. |
| III-p-4 | 3234 | 3652 | >10000 |
| III-q-1 | 1330 | 1537 | 1432 |
| III-q-2 | 351.2 | 593.7 | 843.2 |
| III-q-3 | 1403 | 1396 | 1380 |
| III-q-4 | 901.1 | 1268 | 1334 |
| III-r-1 | 4454 | 4770 | n.d. |
| III-r-2 | 385.6 | 535.3 | 4134 |
| III-r-3 | 3773 | 2721 | 3651 |
| III-r-4 | 186.8 | 324.9 | 1378 |
| III-v-1 | 431.3 | 834.5 | >10000 |
| III-v-2 | <4 | 35927 | n.d. |
| III-v-3 | 23766 | 21289 | n.d. |
| III-v-4 | <4 | 76095 | n.d. |
| III-v-5 | <4 | 304425 | n.d. |
| III-v-6 | <4 | 48058 | n.d. |
| III-v-7 | 147612 | 14159 | n.d. |
| III-v-8 | 10940 | 4339 | n.d. |
| III-v-9 | 4210 | 1750 | n.d. |
| III-v-10 | <4 | 34976 | n.d. |
| III-v-11 | 3334 | 1457 | n.d. |
| III-v-12 | 149.3 | 191 | n.d. |
| III-v-13 | 18303 | 13834 | n.d. |
| IV-b-2 | 5870 | 4166 | n.d. |
| IV-c-2 | 1683 | 2838 | n.d. |
| IV-e-2 | 2907 | 8445 | 2225 |
| IV-n-2 | 171.7 | 172.9 | n.d. |
| IV-n-3 | 4148 | 3543 | n.d. |
| IV-n-4 | 3904 | 1711 | n.d. |
| IV-n-5 | 2959 | 2317 | n.d. |
| IV-n-6 | 4307 | 4228 | n.d. |
| IV-n-7 | 2811 | 3938 | n.d. |
| IV-n-8 | 2087 | 1623 | n.d. |
| IV-n-9 | 1826 | 1569 | n.d. |
| IV-n-10 | 2163 | 1842 | n.d. |
| IV-n-11 | 5221 | 4212 | n.d. |
| IV-o-1 | 1981 | 1722 | n.d. |
| IV-o-2 | 88.63 | 12.13 | n.d. |
| IV-o-3 | 4313 | 4183 | n.d. |
| IV-o-4 | 4279 | 3106 | n.d. |
| IV-o-5 | 4090 | 3390 | n.d. |
| IV-o-6 | 4016 | 3403 | n.d. |
| IV-o-7 | 1505 | 1610 | n.d. |
| IV-o-8 | 172.1 | 151.7 | n.d. |
| IV-o-9 | 4815 | 4362 | n.d. |
| IV-o-10 | 4290 | 3760 | n.d. |
| IV-o-11 | 3030 | 1620 | n.d. |
| IV-o-12 | 990.2 | 2514 | n.d. |
| V-l-1 | 1462 | 1462 | 2073 |
| V-l-2 | 168.6 | 168.6 | 3395 |
| V-l-3 | 587.1 | 595.2 | 1245 |
| V-l-4 | 337.1 | 142.8 | 1416 |
| V-m-1 | 1023 | 473.3 | 1375 |
| V-m-2 | 1350 | 978.4 | 904.8 |
| V-m-3 | 1174 | 613.2 | 3366 |
| V-m-4 | 1240 | 811.2 | 1417 |
| V-n-1 | 2902 | 2117 | 2309 |
| V-n-2 | 579.7 | 616.1 | 2071 |
| V-n-12 | 565.7 | 672.8 | n.d. |
| V-n-16 | 471.8 | 388.4 | n.d. |
| V-r-1 | 2960 | 2806 | n.d. |
| VI-h-2 | 561.1 | 493.1 | 3904 |
| VI-i-1 | 1954 | 1472 | 1533 |
| VI-i-2 | 5702 | 7418 | n.d. |
| VI-j-1 | 2695 | 3957 | 3383 |
| VI-j-2 | 3.076 | 16.96 | 3942 |
| VI-l-1 | 2643 | 3218 | 4621 |
| VI-m-1 | 1236 | 1252 | 1583 |
| VI-n-1 | 3244 | 2836 | 4191 |
| VI-o-1 | 2171 | 2871 | 3990 |
| VI-o-2 | 39.84 | 99.42 | 1961 |
| VI-q-1 | 3568 | 3427 | 4357 |
| VI-q-2 | 1517 | 1470 | 1516 |
| VII-h-2 | 636.9 | 1078 | n.d. |
| VII-i-2 | 1357 | 1332 | n.d. |
| VII-j-1 | 810.5 | 1282 | n.d. |
| VII-j-2 | 95.61 | 189.4 | n.d. |
| VII-l-1 | 1017 | 1351 | n.d. |
| VII-l-2 | 215 | 314.6 | n.d. |
| VII-n-1 | 1688 | 1777 | n.d. |
| VII-n-2 | 221.4 | 404.9 | n.d. |
| VII-o-1 | 1568 | 1626 | n.d. |
| VII-o-2 | 326.2 | 498.8 | n.d. |
| Cabozantinib | 226.5 | 301.8 | n.d. |

*n.d. means not determined, Cabozantinib acts as a positive control.

Growth inhibitory activity of compounds on kinase RET-positive non-small cell lung cancer cells LC-2/AD The specific test method is given as follows:

1) Medium: DMEM (Dulbecco's modified eagle medium) or RPMI 1640 (containing 10% fetal bovine serum, 100 μg/mL ampicillin, 100 μg/mL streptomycin).

2) Reagents: MTS reaction solution (containing 2 mg/mL of MTS [3-(4,5-dimethylthiazol-2-yl)-5-(3-carboxymethoxyphenyl)-2-(4-sulfophenyl)-2H-tetrazolium, inner Salt]; 100 μg/mL PES (phenazine methosulfate)).

3) Compound test: LC-2/AD cells ($2 \times 10^4$ cells/well) were incubated into a 96-well culture plate, the volume of cell culture fluid was 90 μL, and then 10 μL of the compound at each gradient concentration was added (the highest concentration was 10 μM, which was diluted stepwise by ⅓, and 8 concentration points were set in total; the system contained 0.1% DMSO (dimethyl sulfoxide)). The cell plate with uniformly mixed compound was cultured in a cell culture incubator (37° C.; 5% $CO_2$) for 48 h, then 20 μL of MTS reaction solution was added, uniformly mixed and incubated in the cell culture incubator (37° C.; 5% $CO_2$) for 1-4 hr; OD values at 490 nm were measured by a microplate reader (VARIOSKAN FLASH, Thermo). Three parallels were set in each group of experiments, with 0.1% (a final concentration) DMSO as a negative control, and a medium without cells or compounds as a blank control. The cell growth inhibition rate was calculated by the following formula:

Cell growth inhibition rate %=1−
($OD_{experimental\ group}$−$OD_{blank\ group}$)/
($OD_{negative\ group}$−$OD_{blank\ group}$)×100%

4) $IC_{50}$ calculation: The semi-inhibitory concentration of the compound acting on cell growth was calculated using GradPad Prism 5 software according to the measured cell growth inhibition rate.

TABLE 9

Growth inhibitory activity of some compounds on non-small cell lung cancer cells LC-2/AD*

| Cmpd ID | LC-2/AD ($IC_{50}$/nM) |
| --- | --- |
| I-n-3 | 818.4 |
| II-m-1 | 300.7 |
| IV-n-2 | 1401 |
| Cabozantinib | 4148 |

*Cabozantinib acts as a positive control

What has been described above are only some embodiments of the invention. It will be apparent to those skilled in the art that various modifications and improvements can be made without departing from the spirit of the invention, all of which fall into the protection scope of the invention.

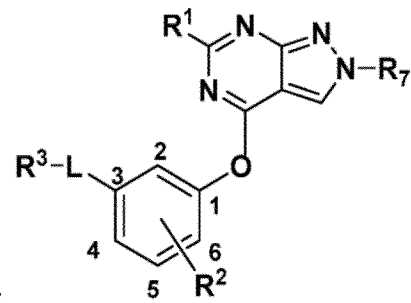

The invention claimed is:

1. A substituted aryl ether compound having the following formula, or a pharmaceutically acceptable salt thereof:

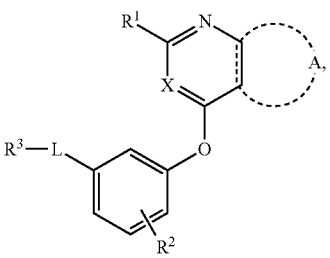

which is selected from:

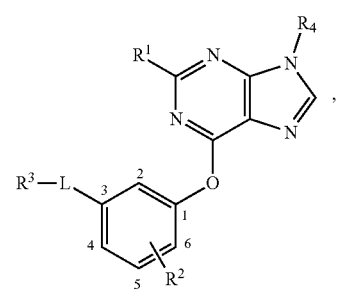

I

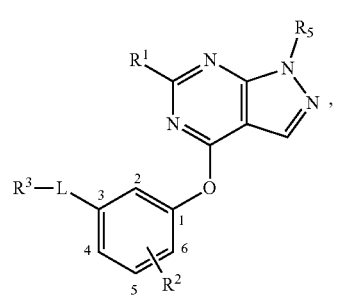

II

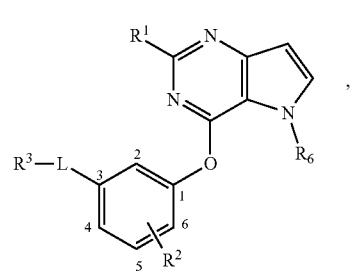

III

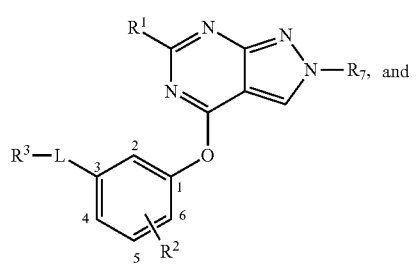

IV, and

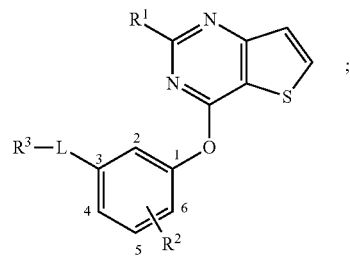

VI

;

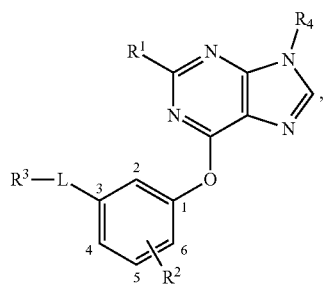

R¹ is selected from:

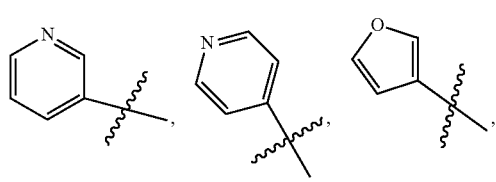

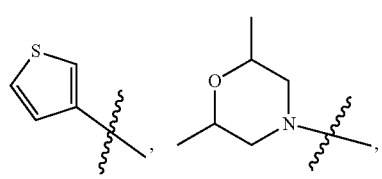

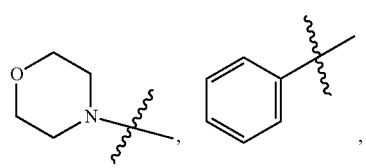

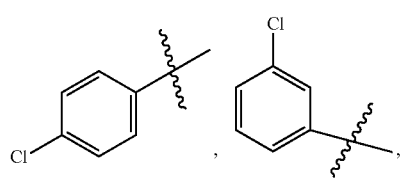

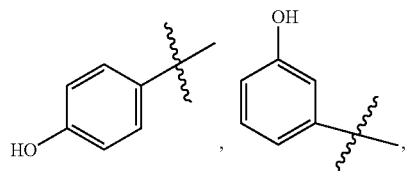

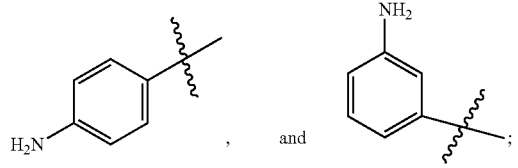

R² is selected from: hydrogen, halogen atom, C1-C6 alkyl, and C1-C6 fluorine-containing alkyl;

R³ is

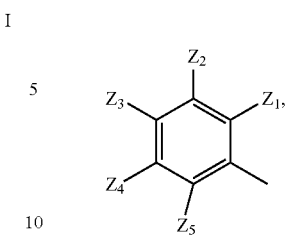

wherein one of $Z_1$-$Z_5$ is $CF_3$—, the rest being H; or any two of $Z_2$, $Z_3$, and $Z_4$ are each are independently selected from $CF_3$—,

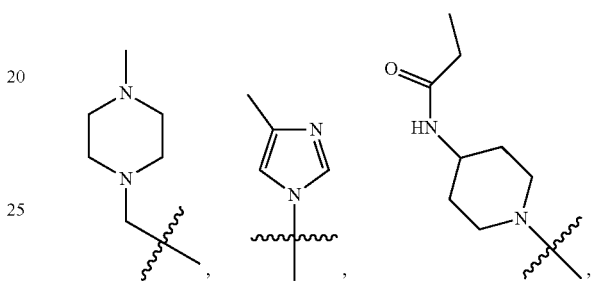

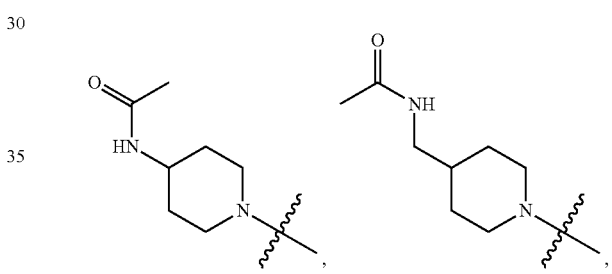

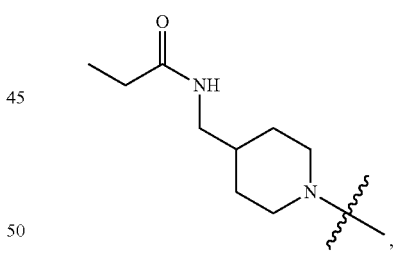

and

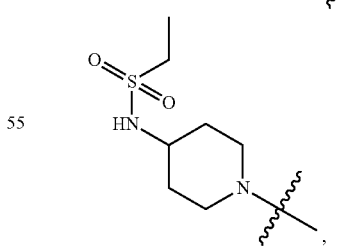

with the remaining one, $Z_1$, and $Z_5$ being H;

R₄ is selected from: hydrogen, methyl, ethyl, propyl, isopropyl, trifluoromethyl, and tri(C1-C6 alkyl) silyl C1-C6 alkoxy C1-C6 alkyl;

L is selected from: —NHCO—, and —CONH—;

for
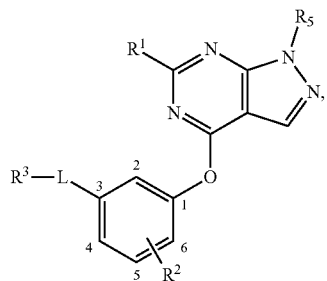
II
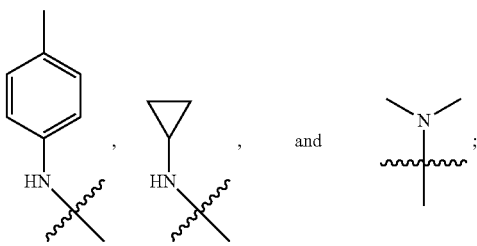
$R^2$ is selected from: hydrogen, halogen atom, $C_{1-6}$ alkyl, and C1-C6 fluorine-containing alkyl;
$R^3$ is selected from:
1)
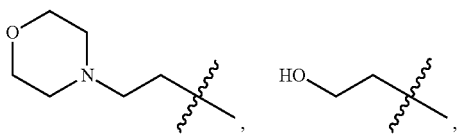
$R^1$ is selected from: —H,
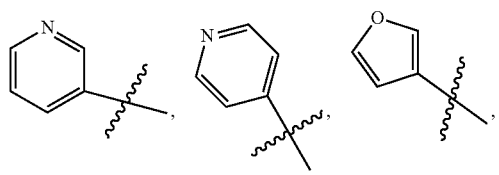
and
2)
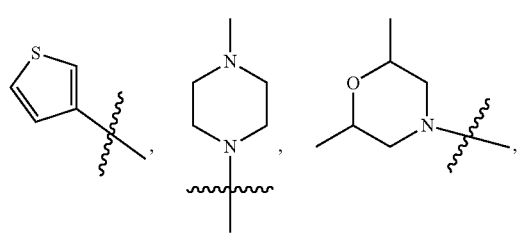
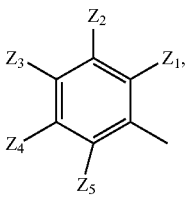
wherein $Z_1$, $Z_2$, $Z_3$, $Z_4$, $Z_5$ are all H; or $Z_4$ is $CF_3$—, one of $Z_2$ or $Z_3$ is selected from $CF_3$—
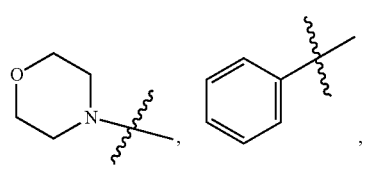
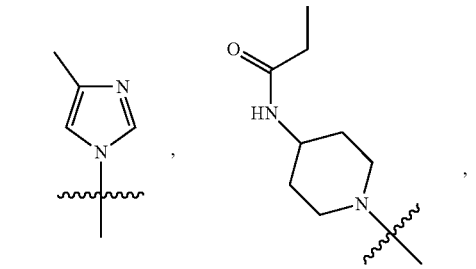
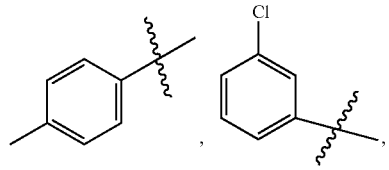
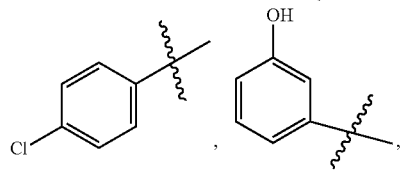
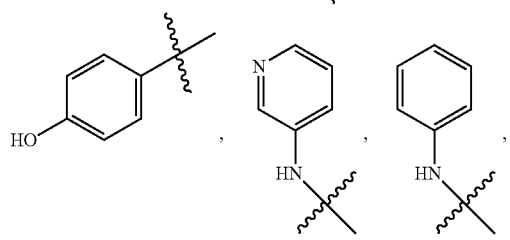
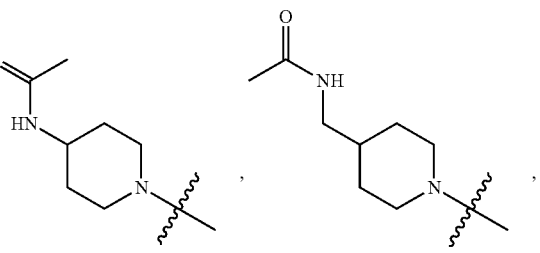

-continued

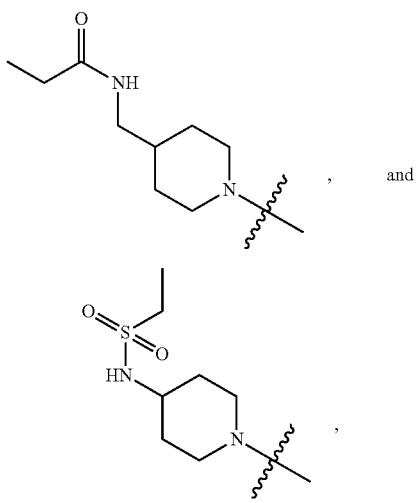, and

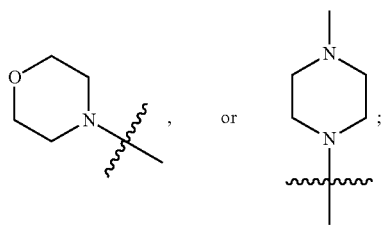, with the remaining one, $Z_1$, and $Z_5$ being H;
or, when L is —CO—, $R^3$ is

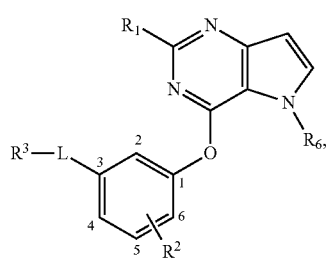 or 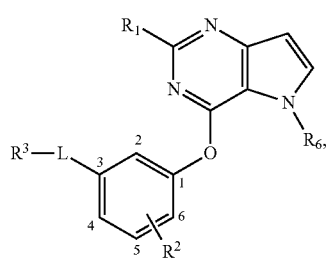;

$R_5$ is selected from: hydrogen, methyl, ethyl, propyl, isopropyl, and trifluoromethyl;

L is selected from: —NHCO—, —CONH—, and —CO—;

for

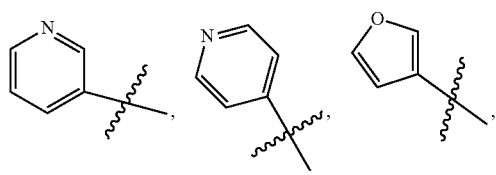

III $R^1$ is selected from: —H, —OH,

-continued

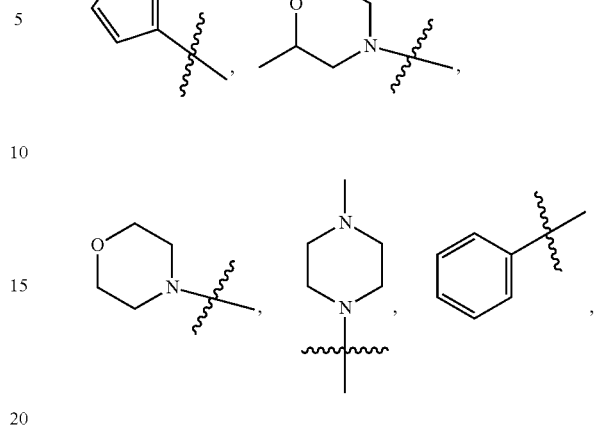,

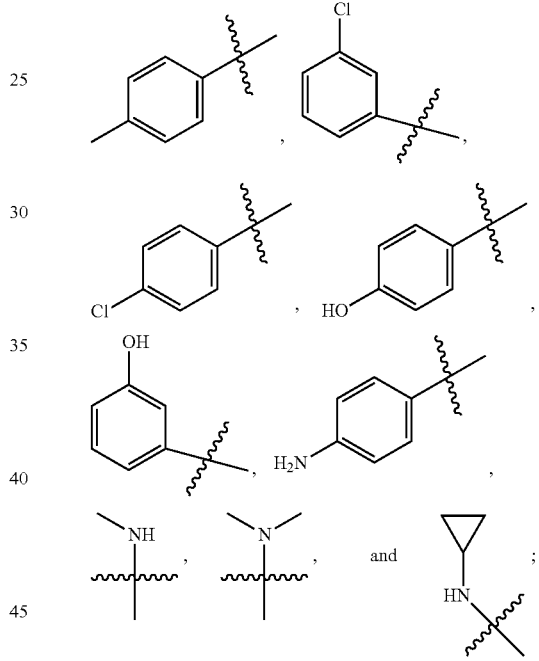

$R^2$ is selected from: hydrogen, halogen atom, optionally substituted C1-C6 alkyl, C1-C6 fluorine-containing alkyl, optionally substituted C6-C10 aryl and optionally substituted heteroaryl;

$R^3$ is

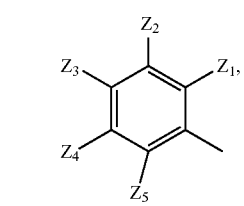

wherein $Z_4$ is $CF_3$—, the rest of $Z_1$, $Z_2$, $Z_3$, and $Z_5$ being H;
or $Z_4$ is $CF_3$—, one of $Z_2$ or $Z_3$ is selected from

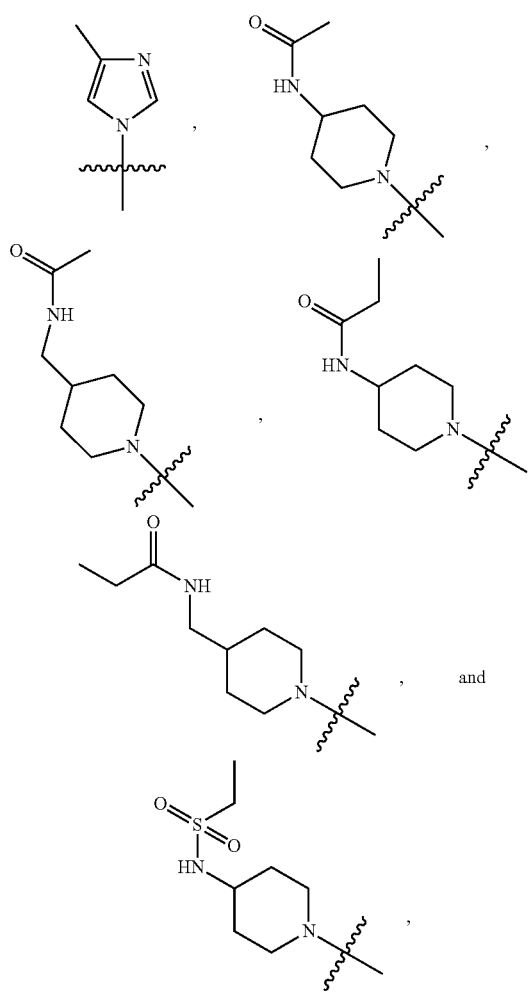

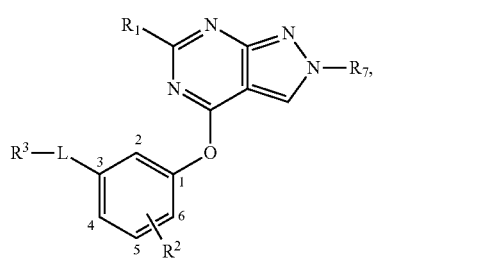

, and

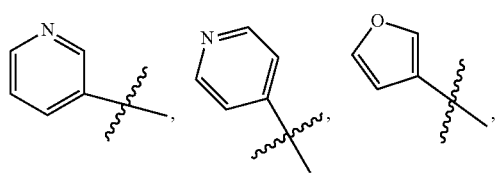

, with the remaining one, $Z_1$, and $Z_5$ being H;
$R_6$ is selected from: hydrogen, methyl, ethyl, propyl, isopropyl, and trifluoromethyl;
L is selected from: —NHCO—, and —CONH—;
for

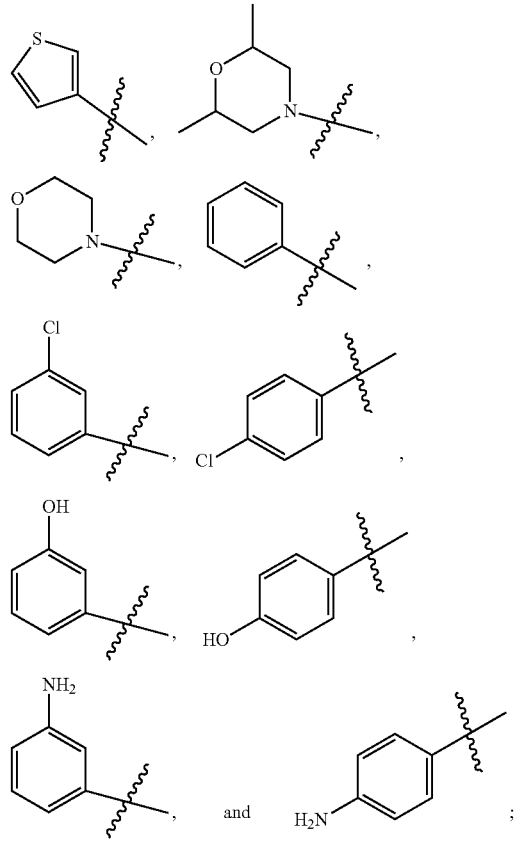

$R^1$ is selected from: —H,

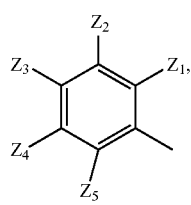

$R^2$ is selected from: hydrogen, halogen atom, $C_{1-6}$ alkyl, and C1-C6 fluorine-containing alkyl;
$R^3$ is

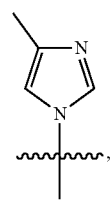

wherein $Z_4$ is $CF_3$— or $CF_3O$—, the rest of $Z_1$, $Z_2$, $Z_3$, and $Z_5$ being H; or $Z_4$ is $CF_3$—, one of $Z_2$ or $Z_3$ is with the remining one, $Z_1$, and $Z_5$ being H;
$R_7$ is selected from: methyl, ethyl, propyl, isopropyl, and trifluoromethyl;
L is selected from: —NHCO—, and —CONH—;

for

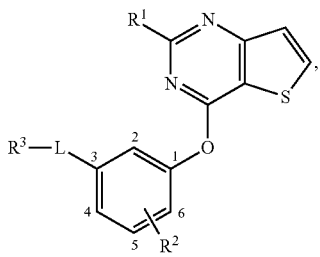

R¹ is selected from:

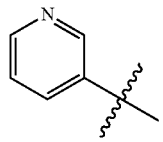 and 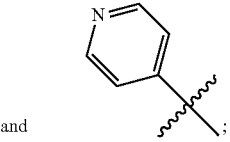 ;

R² is selected from: hydrogen, halogen atom, $C_{1-6}$ alkyl, and C1-C6 fluorine-containing alkyl;

R³ is

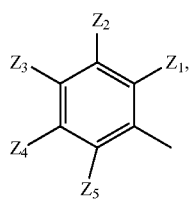

wherein any two of $Z_2$, $Z_3$, $Z_4$ each are independently selected from $CF_3$—,

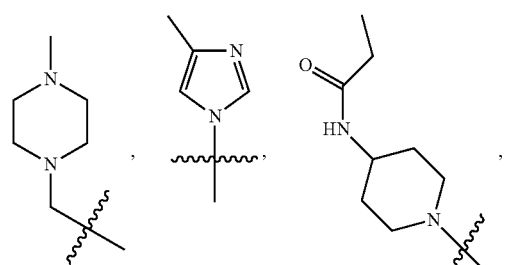

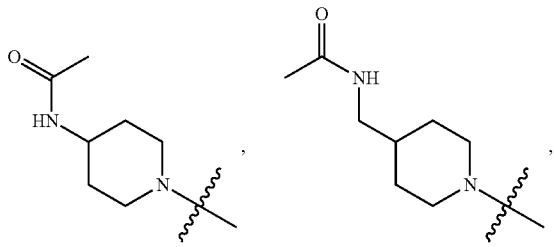

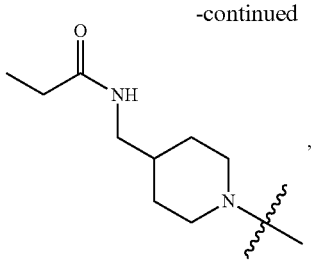

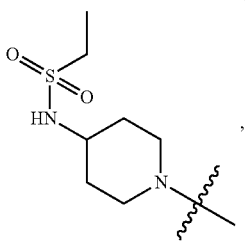

with the remaining one, $Z_1$, and $Z_5$ being H;
L is selected from: —NHCO—, and —CONH—; and
the pharmaceutically acceptable salt is an inorganic acid salt or an organic acid salt, wherein the inorganic acid salt is selected from hydrochloride, hydrobromide, nitrate, sulfate and phosphate;
the organic acid salt is selected from formate, acetate, propionate, benzoate, maleate, fumarate, succinate, tartrate, citrate, alkyl sulfonate and aryl sulfonate; preferably, said alkyl sulfonate is methyl sulfonate or ethyl sulfonate; and said aryl sulfonate is benzenesulfonate or p-toluenesulfonate.

2. A compound according to claim 1 or a pharmaceutically acceptable salt thereof, characterized in that the compound has the following structure:

I

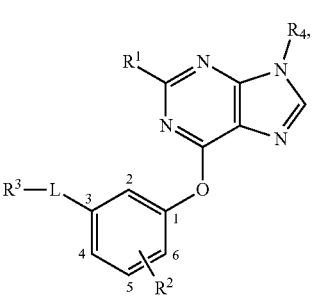

wherein, R¹ is selected from:

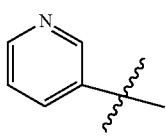 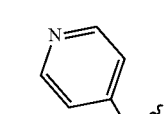 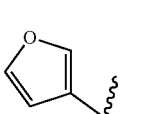

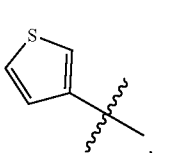 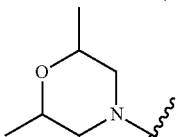 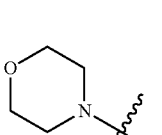

-continued

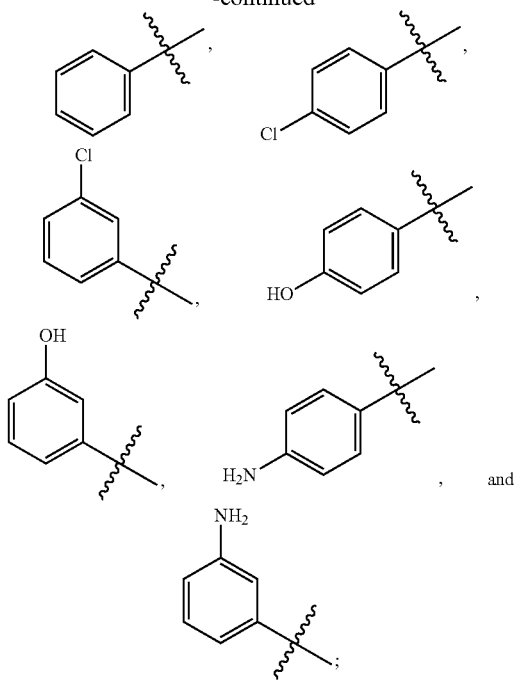

$R^2$ is selected from: hydrogen, halogen atom, C1-C6 alkyl, and C1-C6 fluorine-containing alkyl;
$R^3$ is

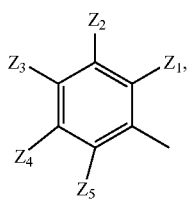

wherein one of $Z_1$-$Z_5$ is $CF_3$—, the rest being H; or any two of $Z_2$, $Z_3$, $Z_4$ each are independently selected from $CF_3$—, -continued

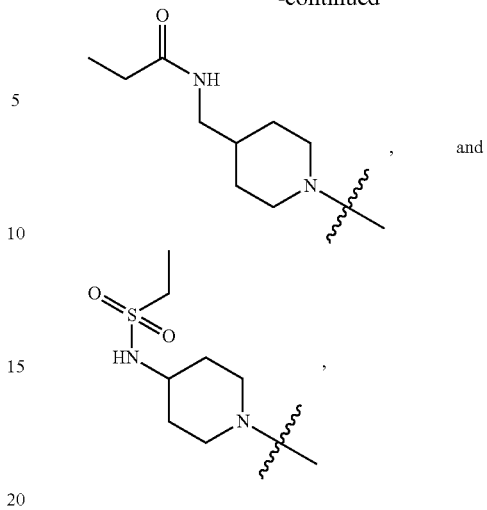

with the remaining one, $Z_1$, and $Z_5$ being H;
$R_4$ is selected from: hydrogen, methyl, ethyl, propyl, isopropyl, trifluoromethyl, and tri(C1-C6 alkyl) silyl C1-C6 alkoxy C1-C6 alkyl;
L is selected from: —NHCO—, and —CONH—.

3. A compound according to claim 1 or a pharmaceutically acceptable salt thereof, characterized in that the compound has the following structure:

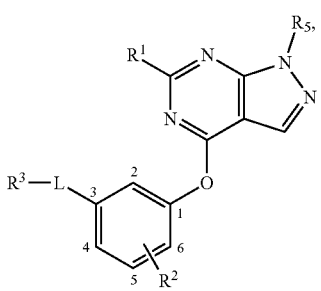

wherein, $R^1$ is selected from: —H,

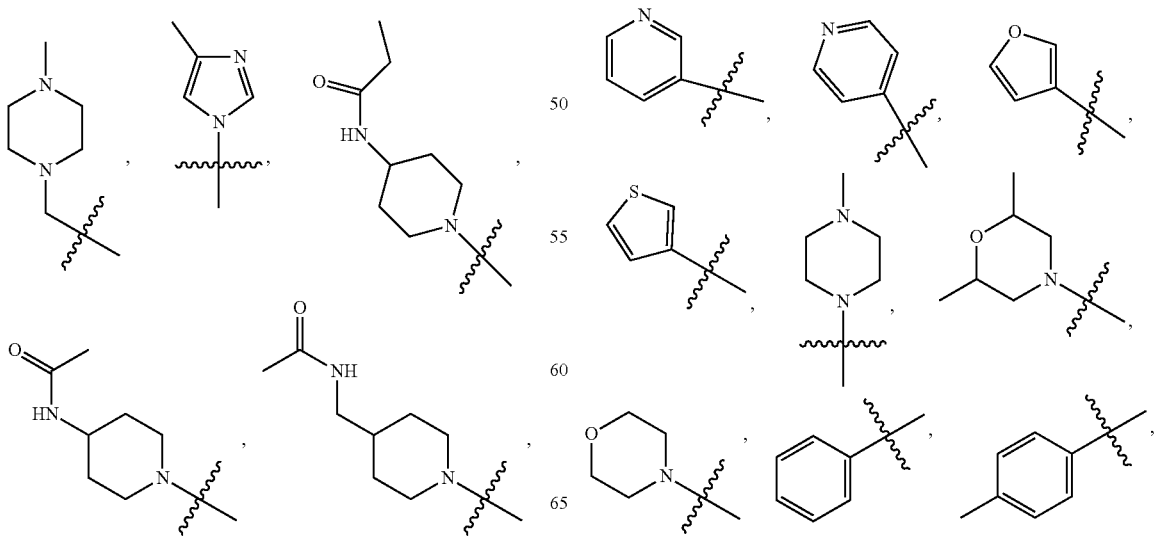

-continued

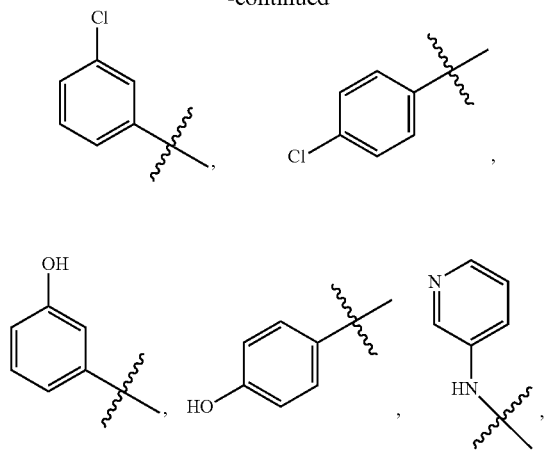

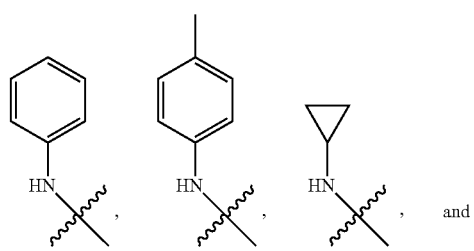

R² is selected from: hydrogen, halogen atom, C₁₋₆ alkyl, and C1-C6 fluorine-containing alkyl;

R³ is selected from:

1)

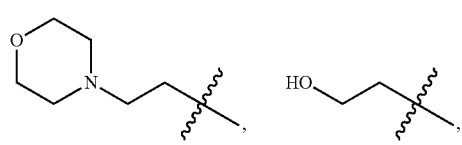

and

2)

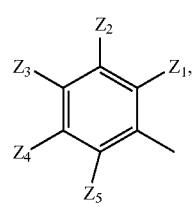

wherein $Z_1$, $Z_2$, $Z_3$, $Z_4$, $Z_5$ are all H; or $Z_4$ is CF₃—, one of $Z_2$ or $Z_3$ is selected from CF₃—,

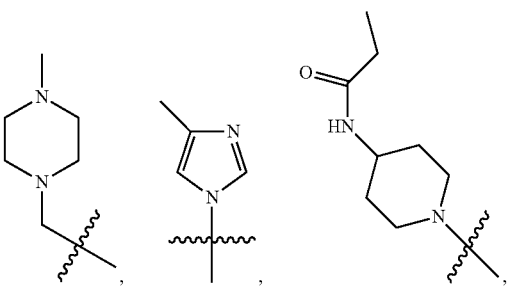

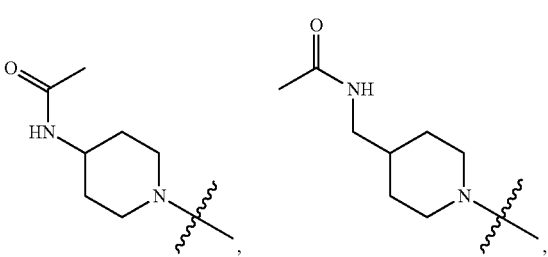

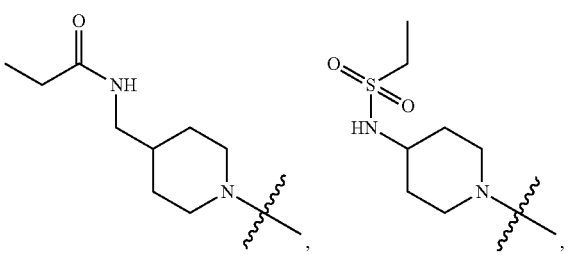

with the remaining one, $Z_1$, and $Z_5$ being H;

or, when L is —CO—, R³ is

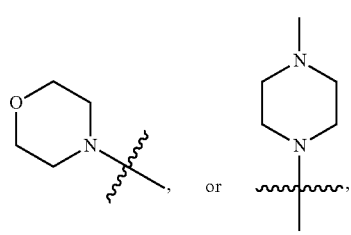

$R_5$ is selected from: hydrogen, methyl, ethyl, propyl, isopropyl, and trifluoromethyl;

L is selected from: —NHCO—, —CONH—, and —CO.

4. A compound according to claim 1 or a pharmaceutically acceptable salt thereof, characterized in that the compound has the following structure:

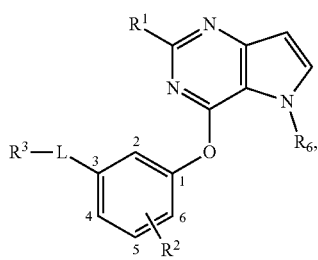

III wherein, R¹ is selected from: —H, —OH,

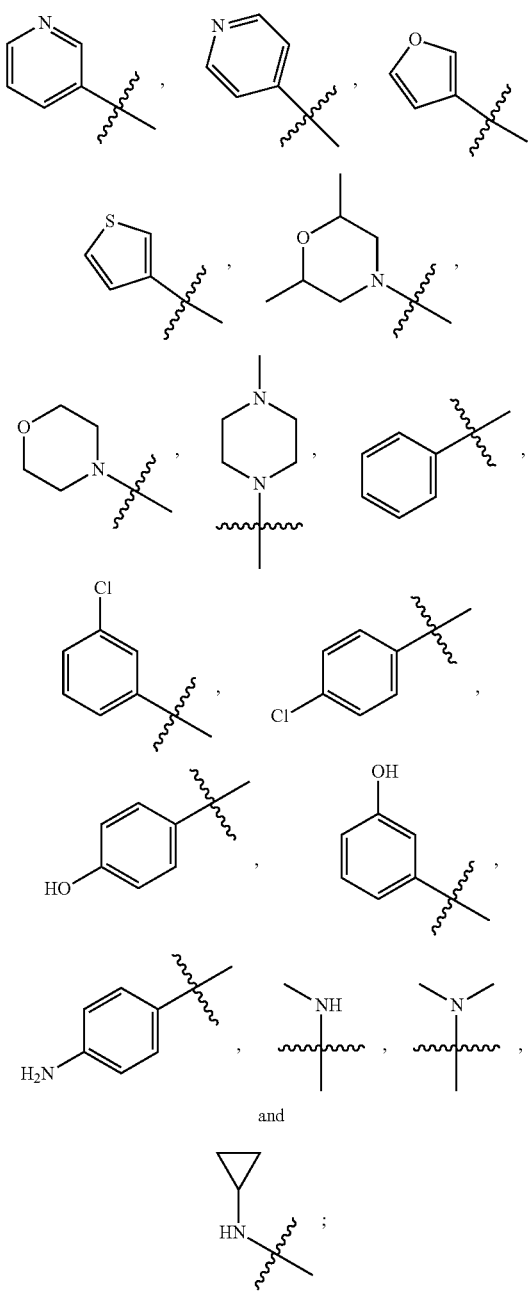

and

R² is selected from: hydrogen, halogen atom, optionally substituted C1-C6 alkyl, C1-C6 fluorine-containing alkyl, optionally substituted C6-C10 aryl and optionally substituted heteroaryl;

R³ is

wherein $Z_4$ is $CF_3$—, the rest of $Z_1$, $Z_2$, $Z_3$, and $Z_5$ being H; or $Z_4$ is $CF_3$—, one of $Z_2$ or $Z_3$ is selected from with the remaining one, $Z_1$, and $Z_5$ being H; $R_6$ is selected from: hydrogen, methyl, ethyl, propyl, isopropyl, and trifluoromethyl;

L is selected from: —NHCO—, and —CONH—.

5. A compound according to claim 1 or a pharmaceutically acceptable salt thereof, characterized in that the compound has the following structure:

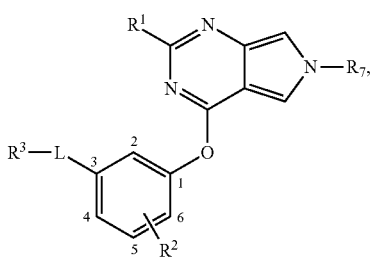

wherein, $R^1$ is selected from: —H

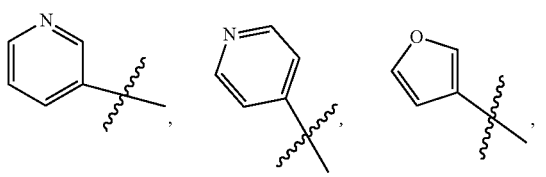

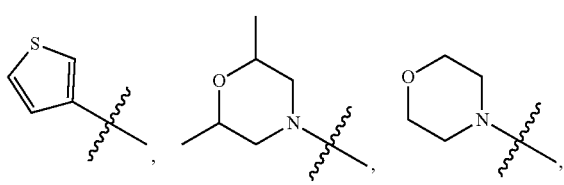

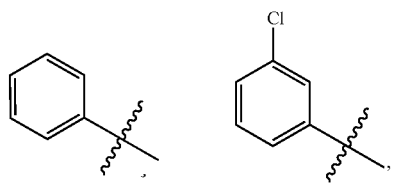

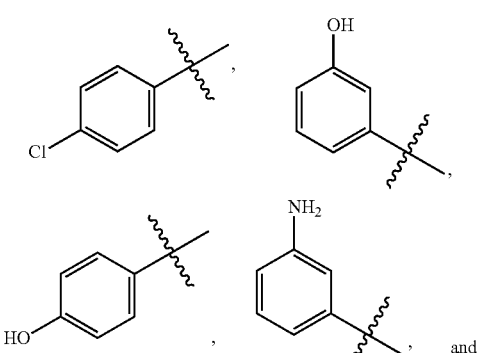

$R^2$ is selected from: hydrogen, halogen atom, $C_{1-6}$ alkyl, and C1-C6 fluorine-containing alkyl;

$R^3$ is

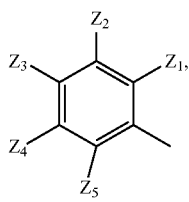

wherein $Z_4$ is $CF_3$— or $CF_3O$—, the rest of $Z_1$, $Z_2$, $Z_3$, and $Z_5$ being H; or $Z_4$ is $CF_3$—, one of $Z_2$ or $Z_3$ is

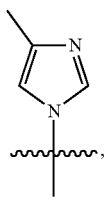

with the remaining one, $Z_1$, and $Z_5$ being H;

$R_7$ is selected from: methyl, ethyl, propyl, isopropyl, and trifluoromethyl;

L is selected from: —NHCO—, and —CONH—.

6. A compound according to claim 1 or a pharmaceutically acceptable salt thereof, characterized in that the compound has the following structure:

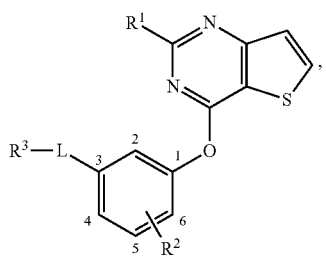

wherein, $R^1$ is selected from:

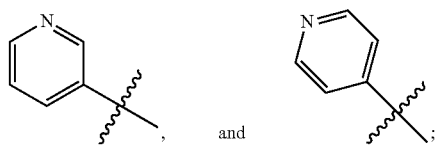 [SMILES: *c1cccnc1 ; *c1ccncc1]

$R^2$ is selected from: hydrogen, halogen atom, $C_{1-6}$ alkyl, C1-C6 fluorine-containing alkyl;

$R^3$ is

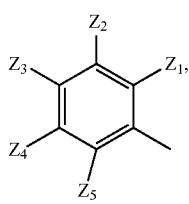

wherein any two of $Z_2$, $Z_3$, $Z_4$ each are independently selected from $CF_3$—
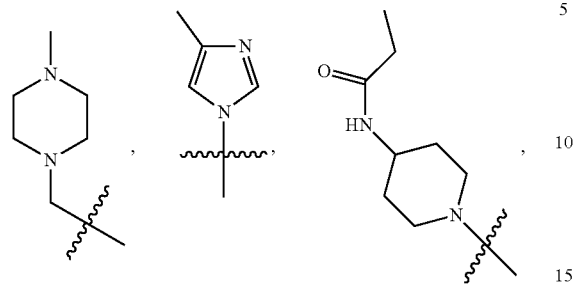
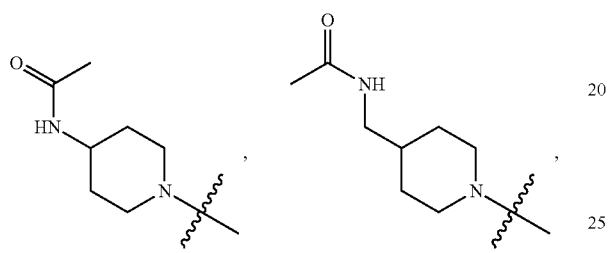
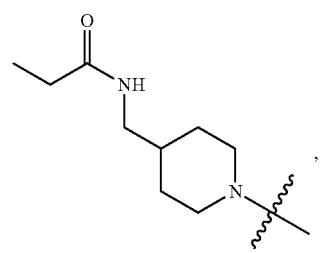
, and
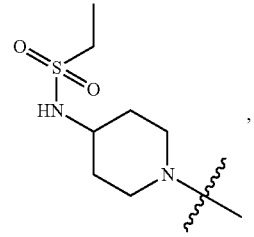
with the remaining one, $Z_1$, and $Z_5$ being H;
L is selected from: —NHCO—, and —CONH—.
7. A compound according to claim 1 or a pharmaceutically acceptable salt thereof, characterized in that the compound is selected from:
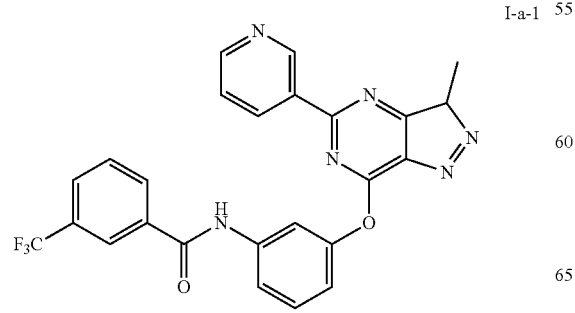
I-a-1
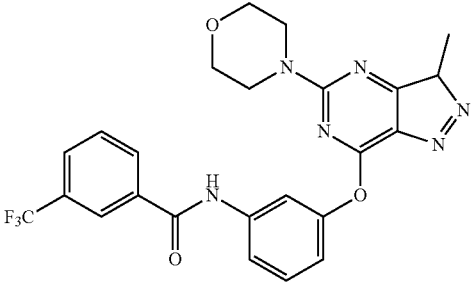
I-a-2
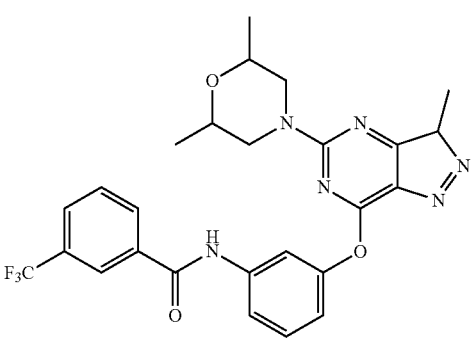
I-a-3
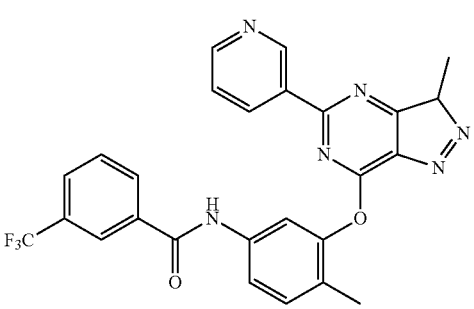
I-b-1
I-b-2
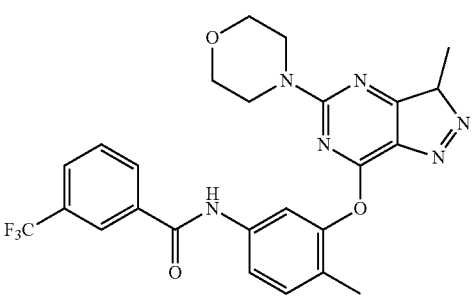
I-b-3

-continued
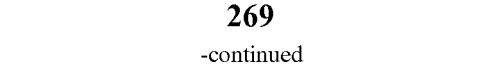
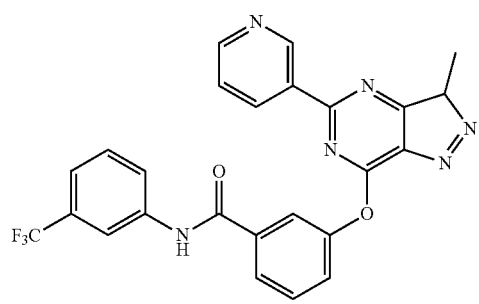
I-d-1
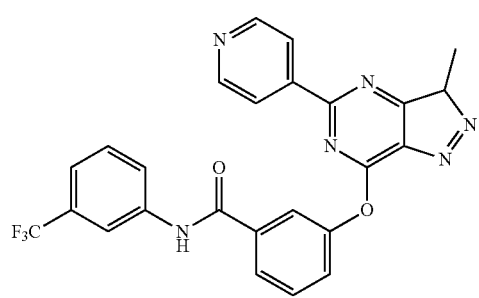
I-d-2
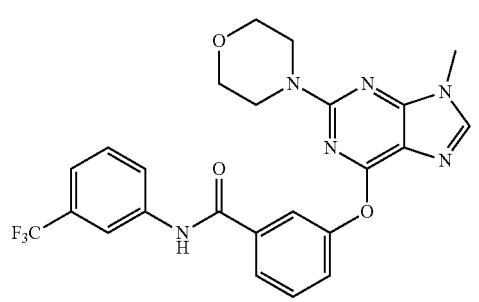
I-d-3
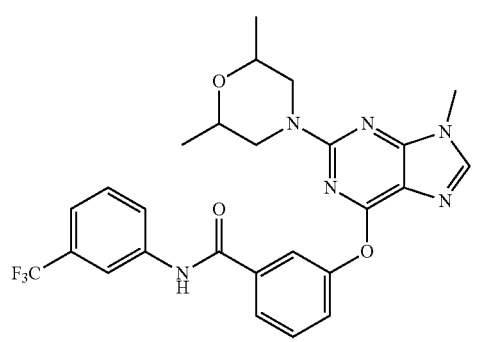
I-d-4
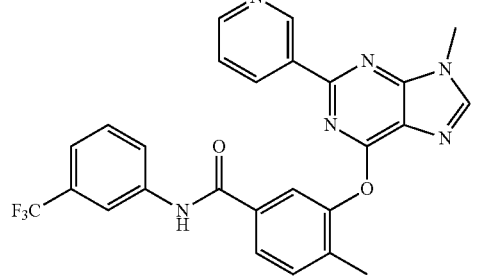
I-e-1
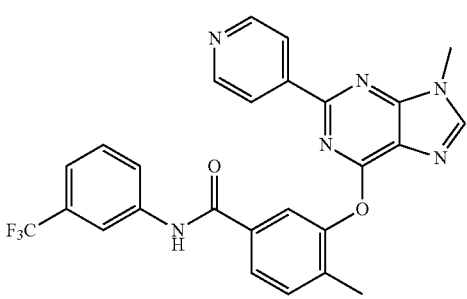
I-e-2
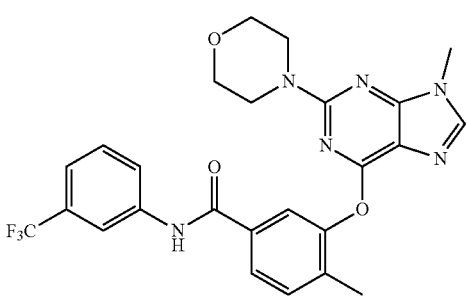
I-e-3
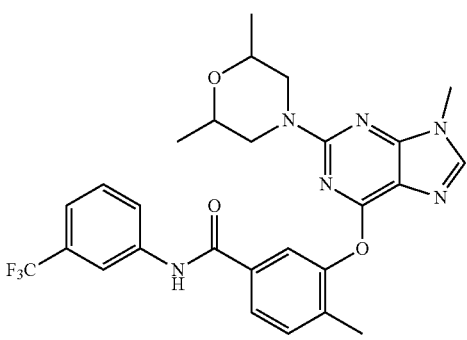
I-e-4
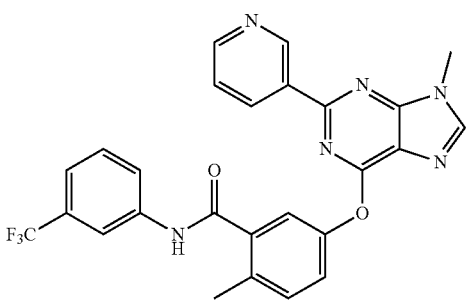
I-f-1
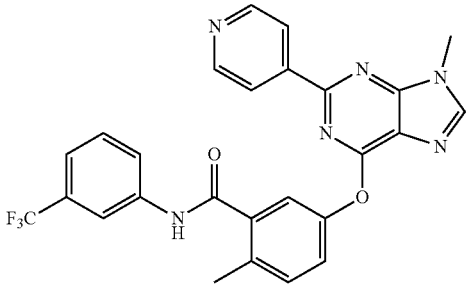
I-f-2

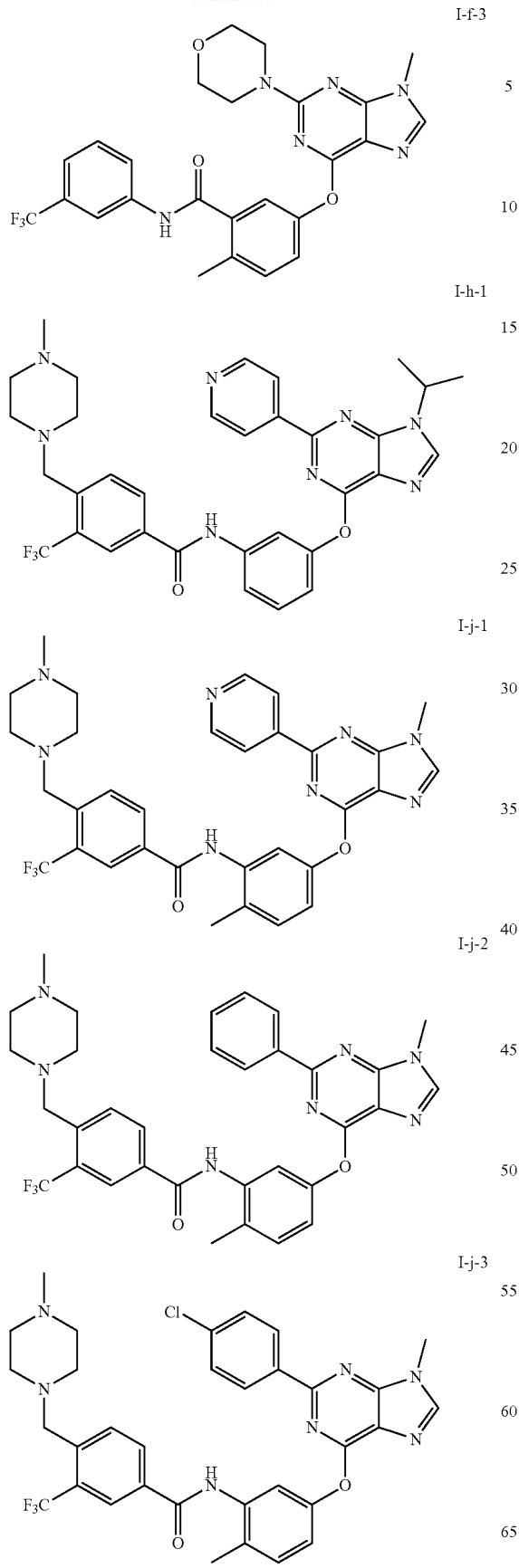
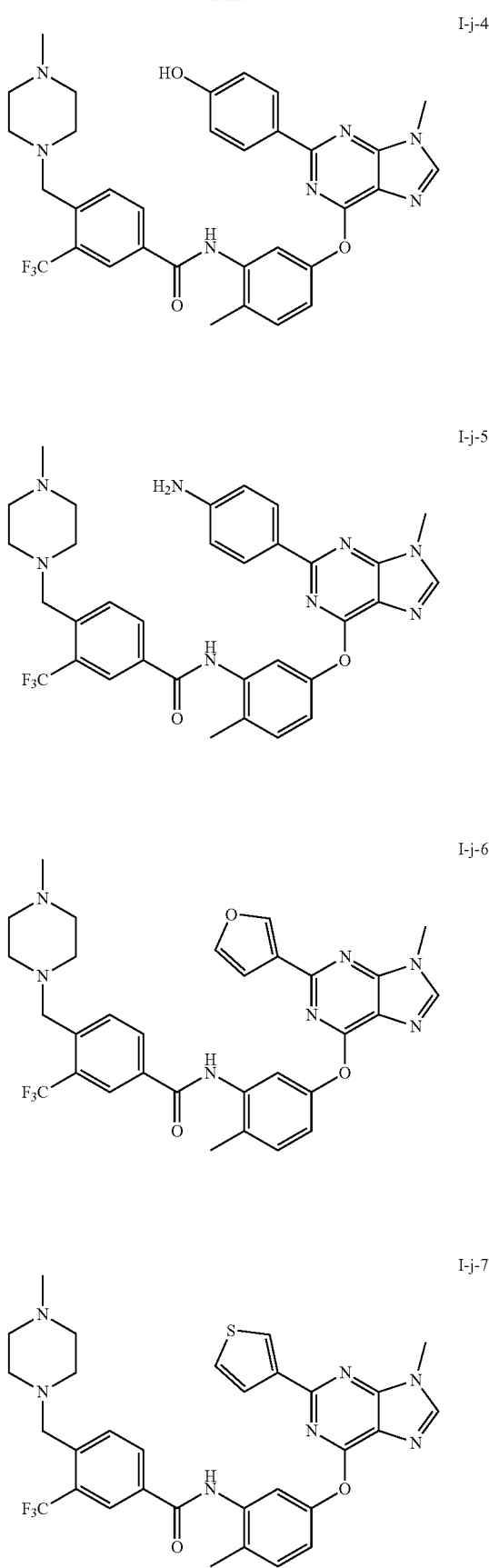

I-l-1
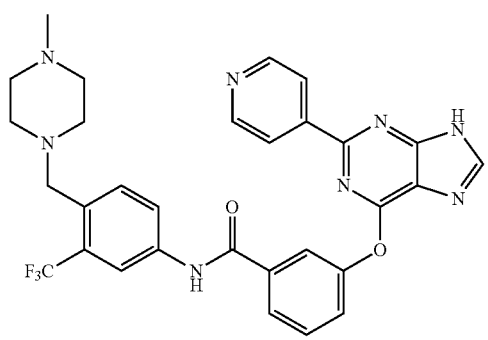
I-m-2
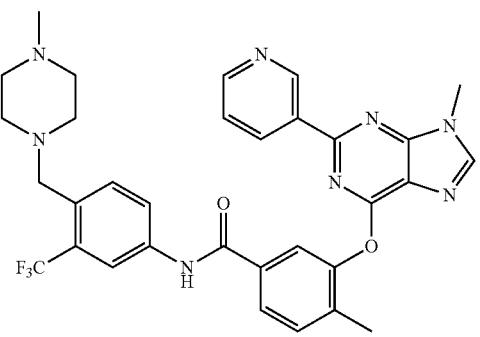
I-l-2
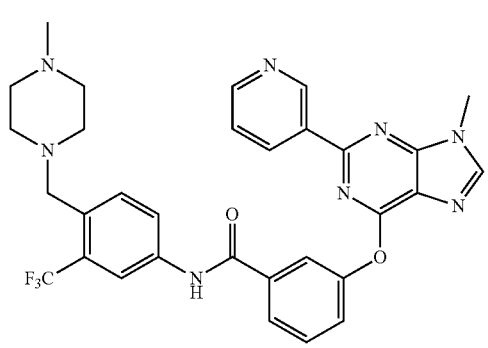
I-m-3
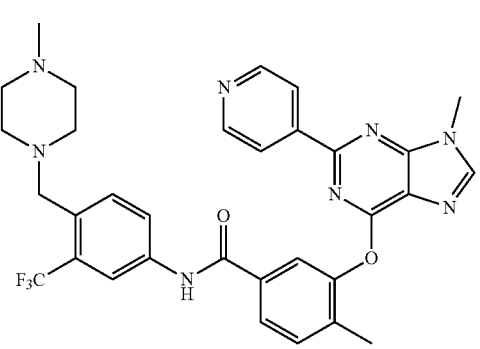
I-l-4
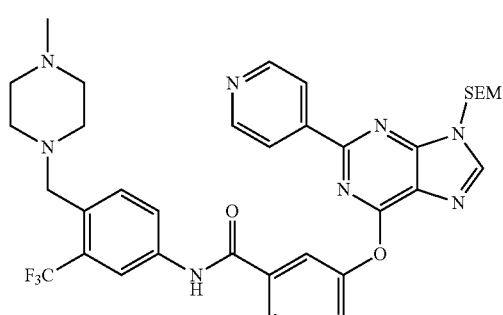
I-m-4
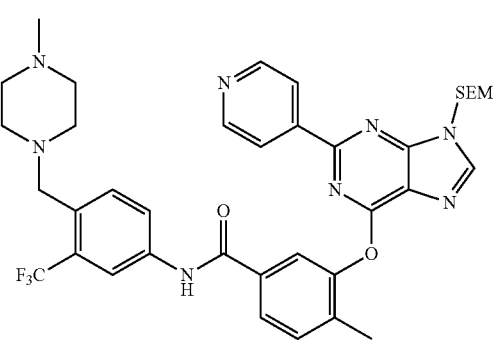
I-m-1
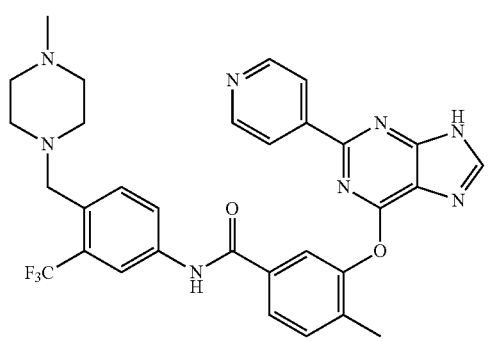
I-n-1
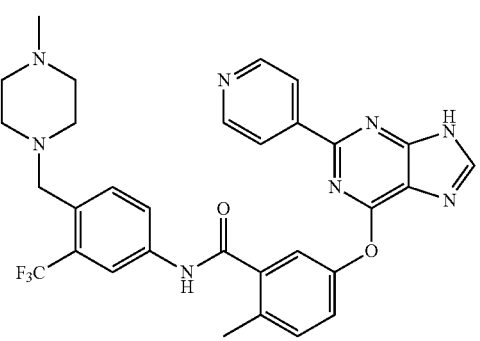

-continued
I-n-2
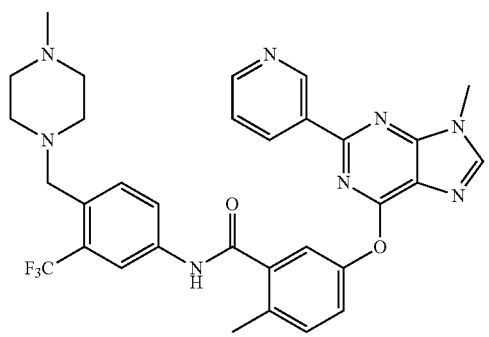
I-n-3
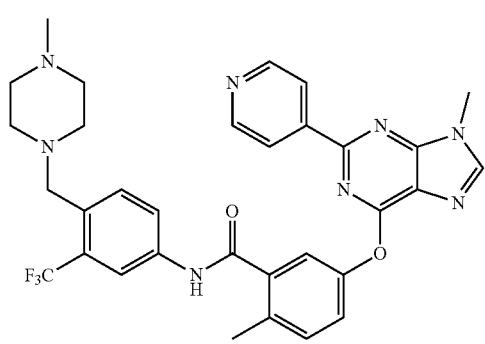
I-n-4
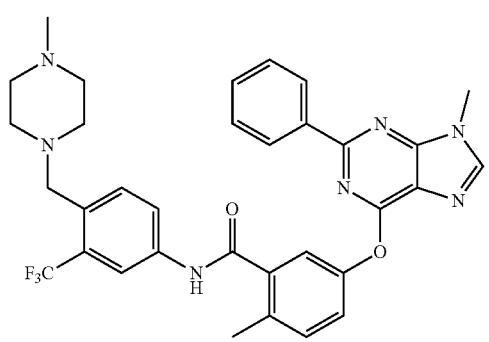
I-n-5
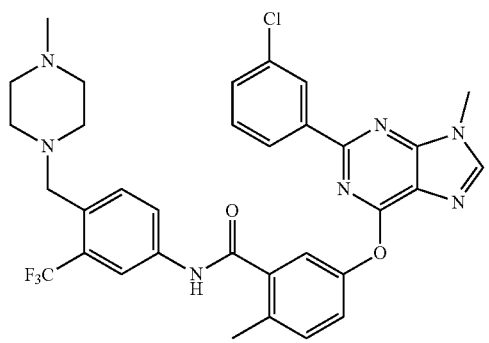
-continued
I-n-6
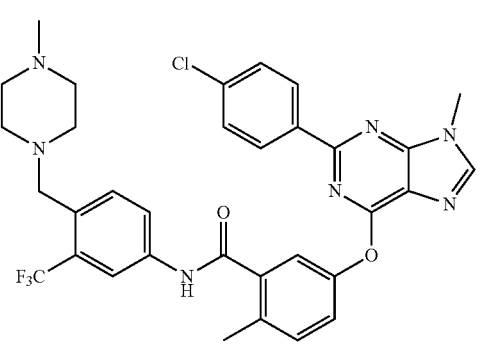
I-n-7
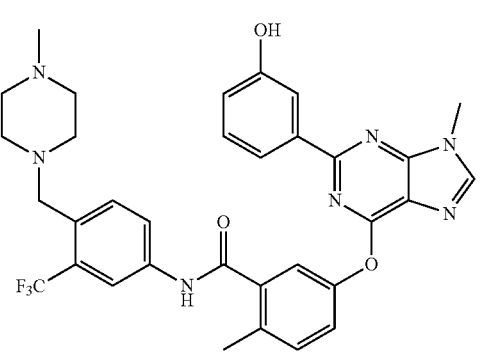
I-n-8
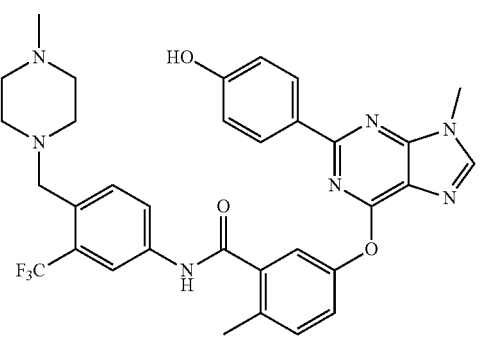
I-n-9
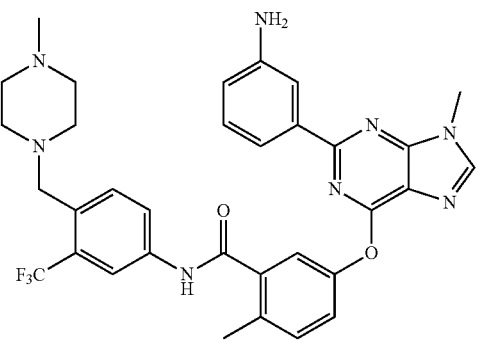

I-n-10
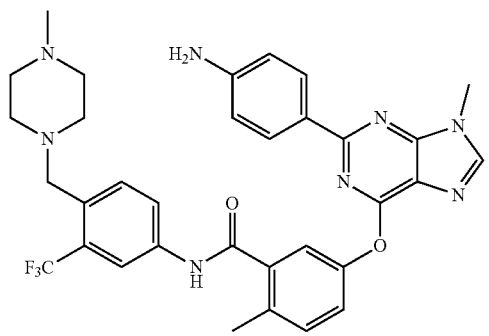
I-n-14
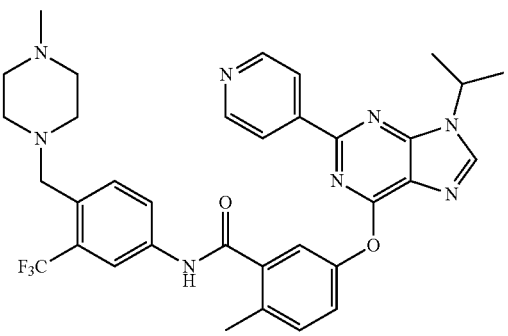
I-n-11
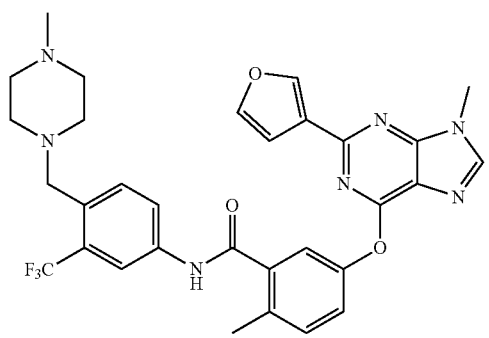
I-n-15
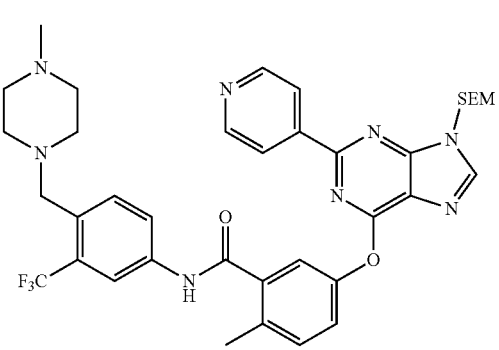
I-n-12
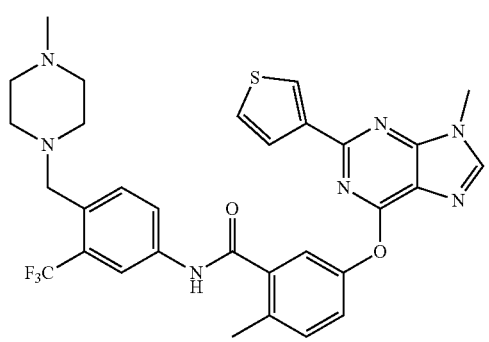
I-o-1
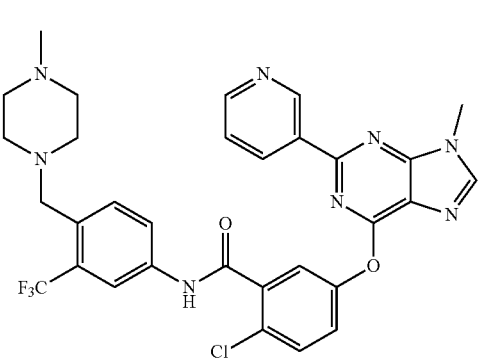
I-n-13
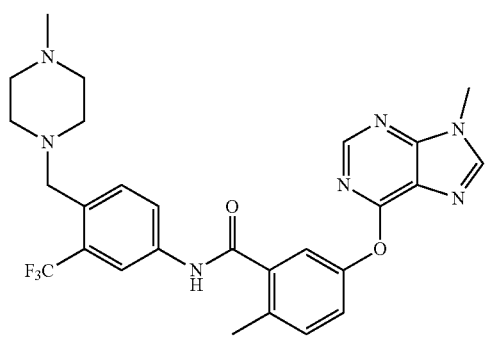
I-o-2
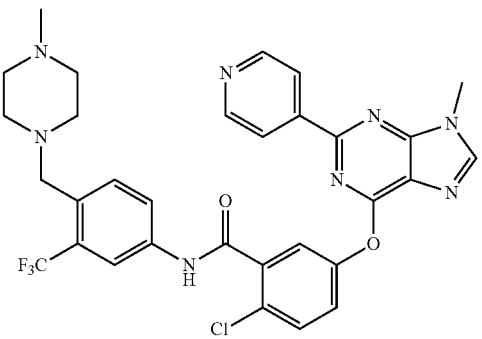

-continued
I-o-3
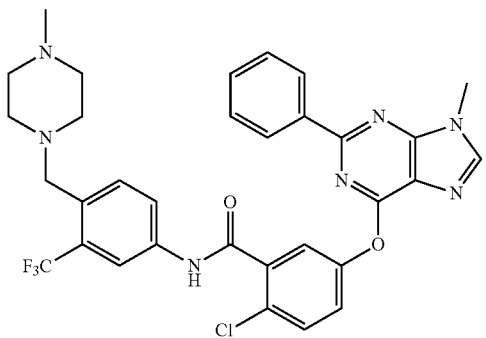
I-o-4
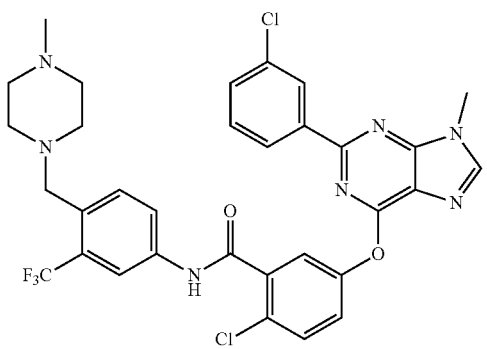
I-o-5
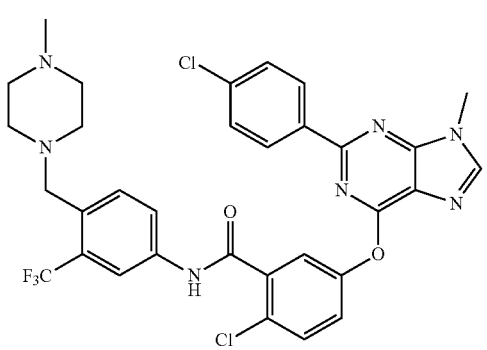
I-o-6
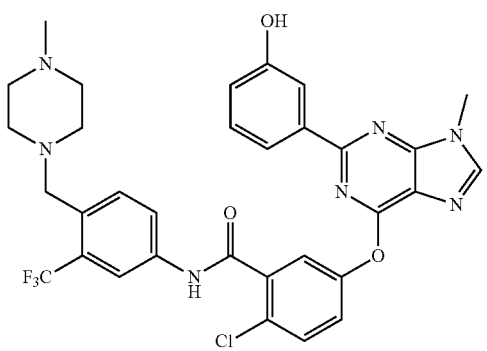
-continued
I-o-7
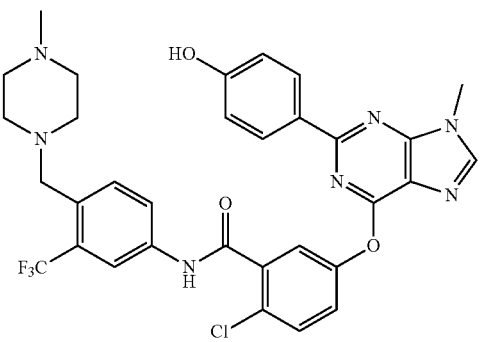
I-o-8
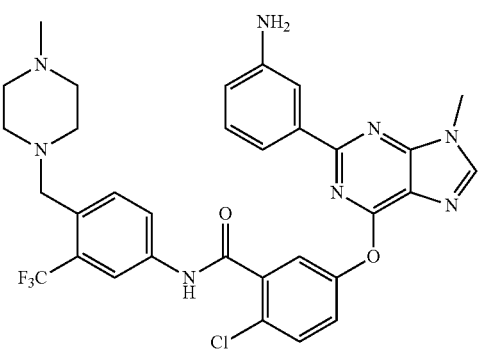
I-o-9
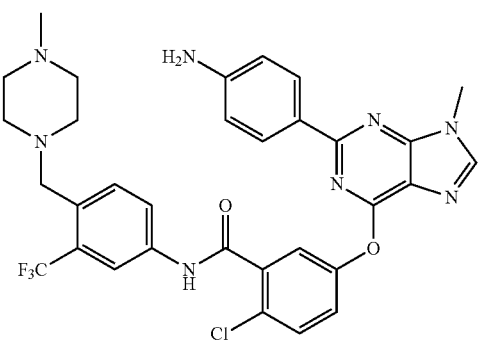
I-o-10
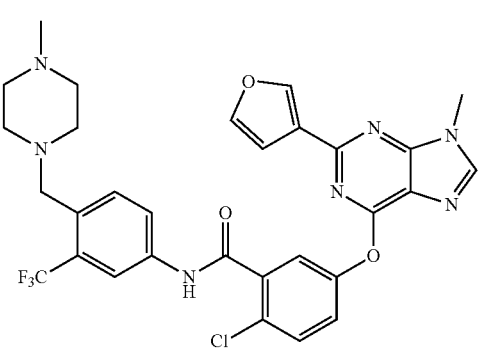

-continued
I-o-11
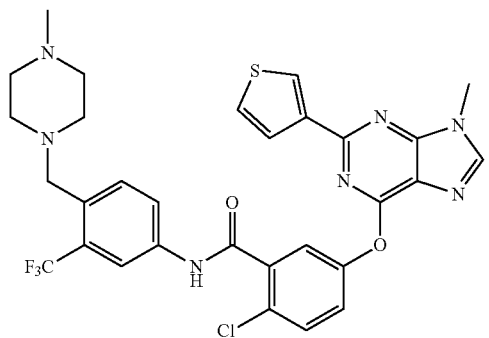
I-o-12
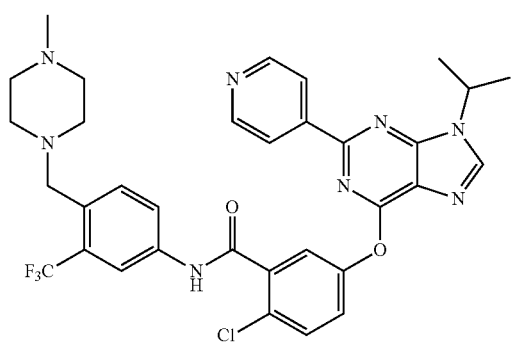
I-r-1
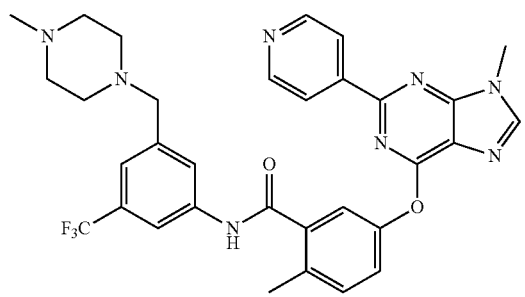
I-r-2
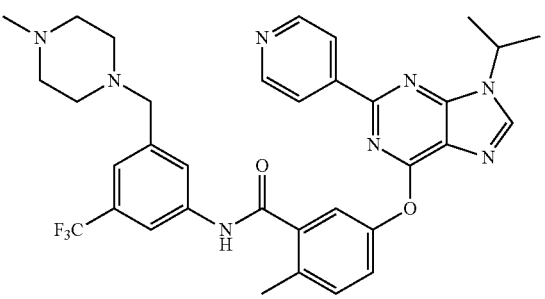
-continued
I-r-3
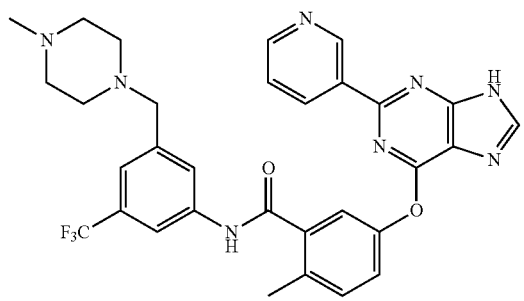
I-s-1
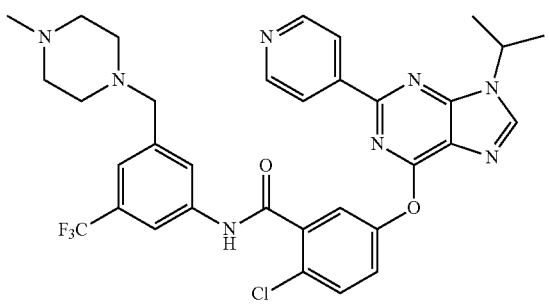
I-l-3
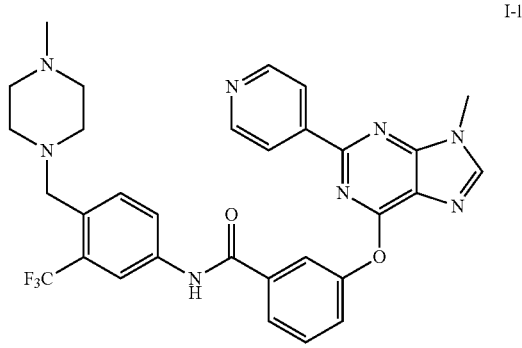
II-b-1
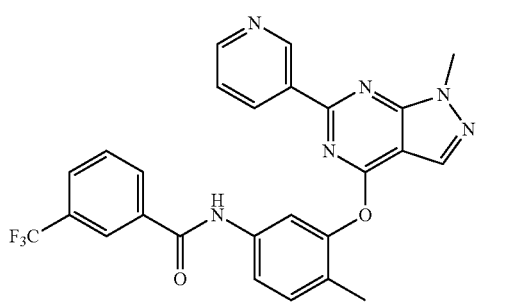
II-b-2
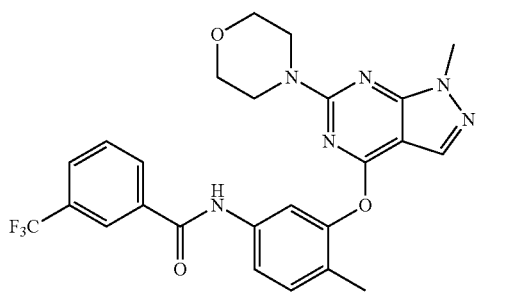

II-b-3
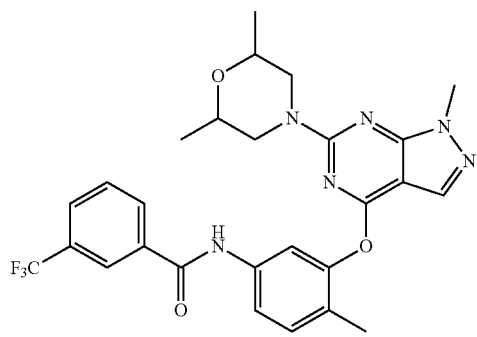
II-e-1
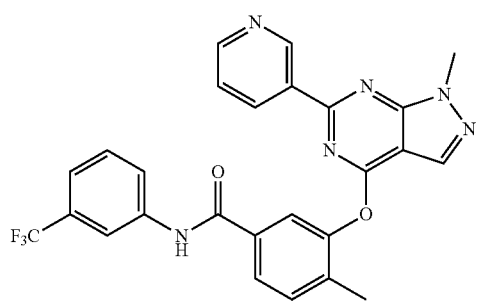
II-e-2
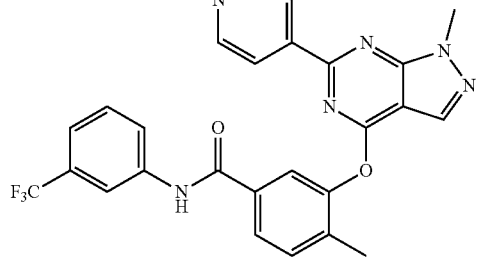
II-e-3
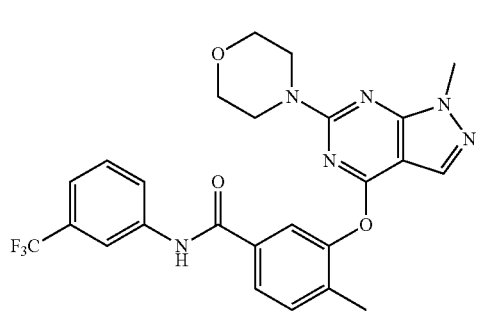
II-e-4
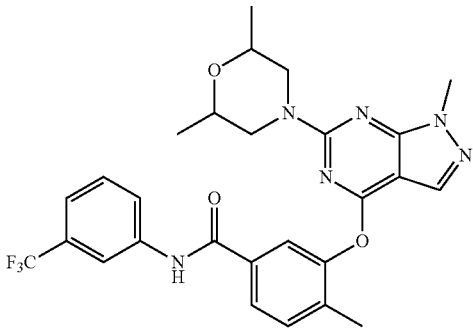
II-h-1
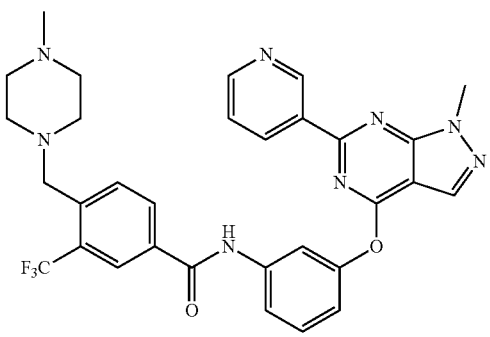
II-h-2
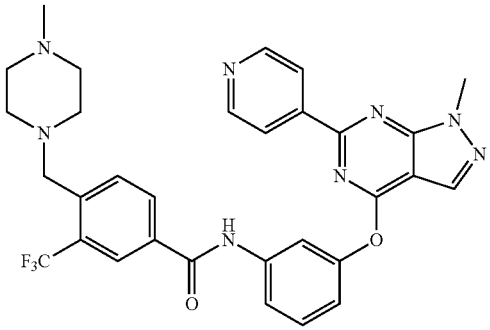
II-i-1
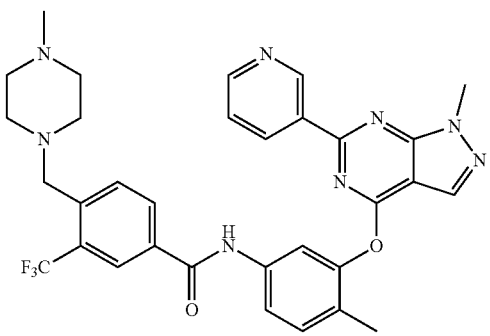

II-i-2
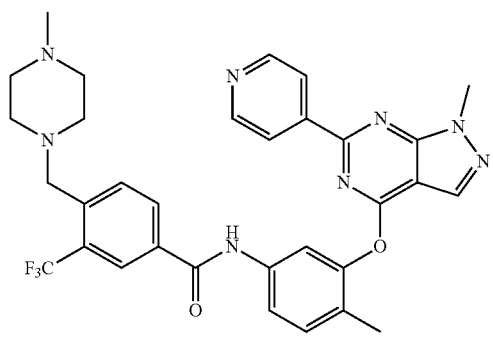
II-j-3
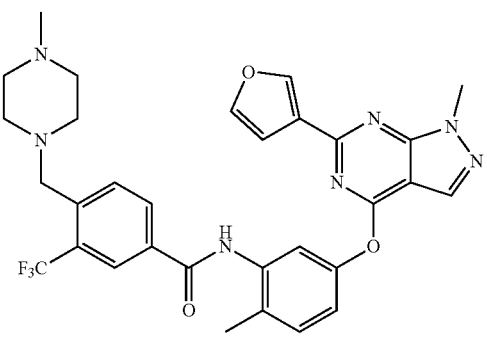
II-i-3
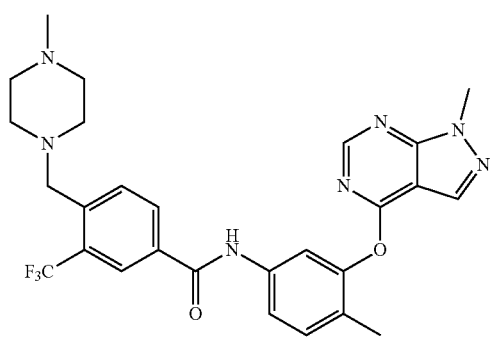
II-j-4
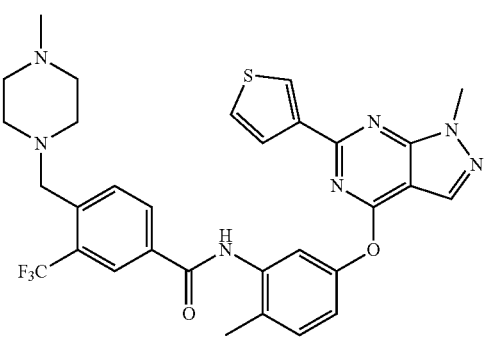
II-j-1
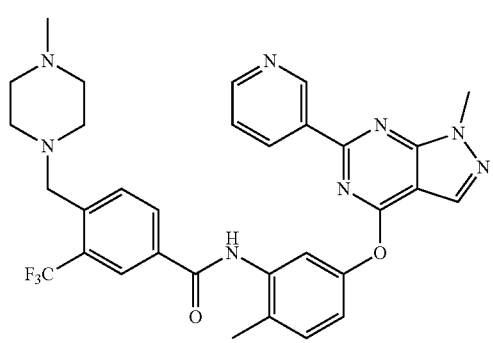
II-l-1
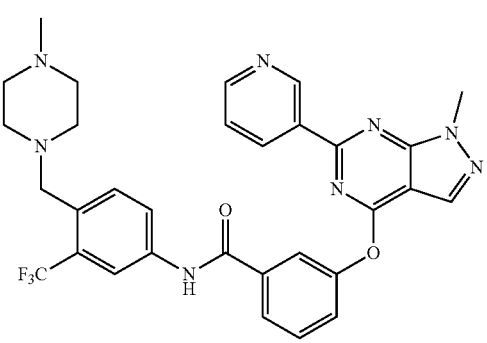
II-j-2
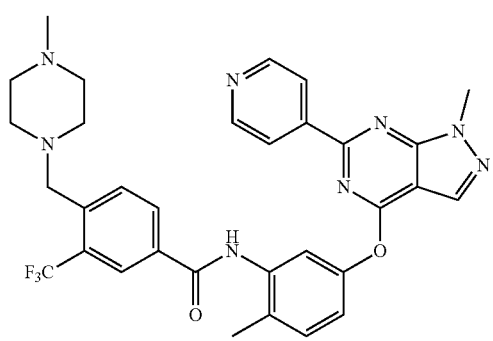
II-l-2
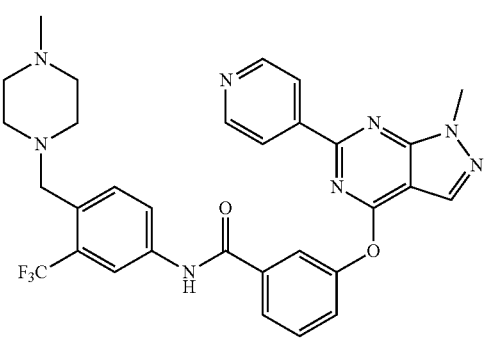

II-m-1
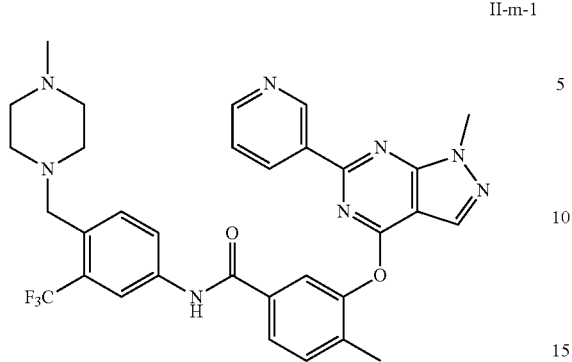
II-m-5
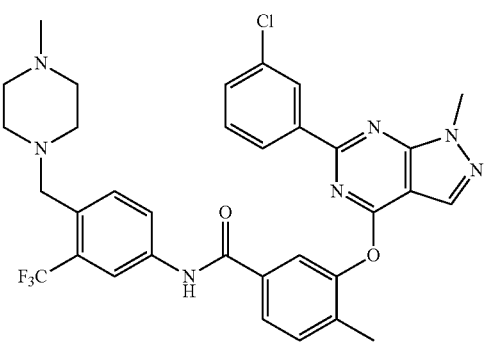
II-m-2
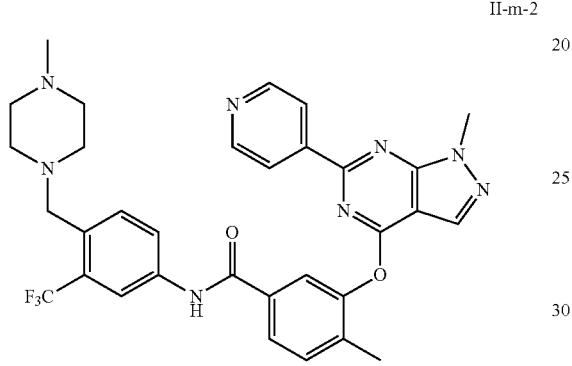
II-m-6
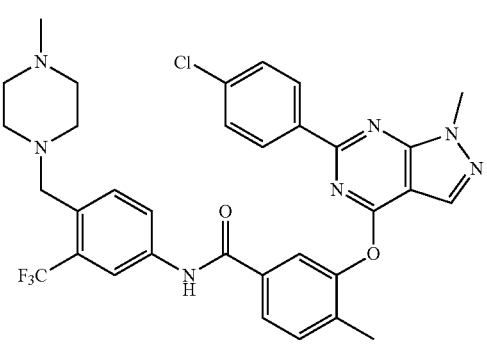
II-m-3
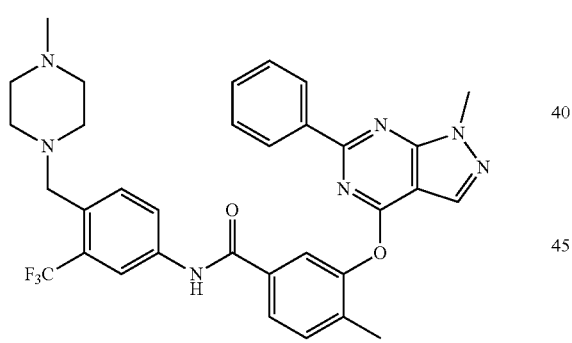
II-m-7
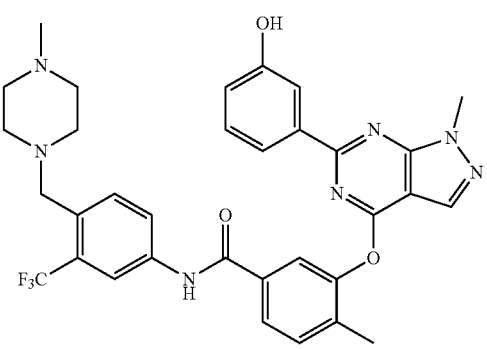
II-m-4
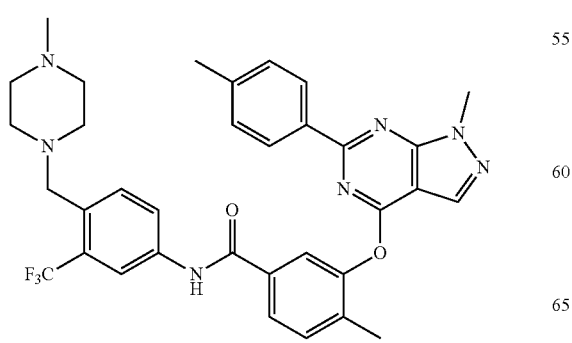
II-m-8
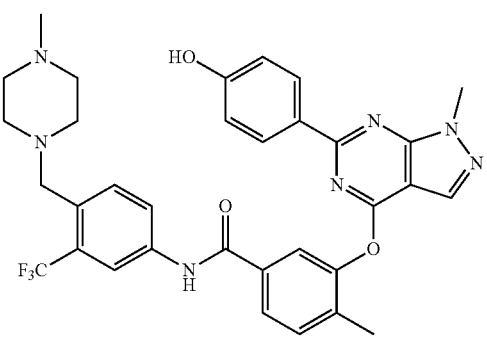

II-m-9
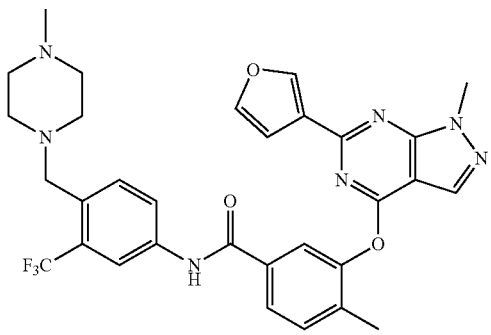
II-m-10
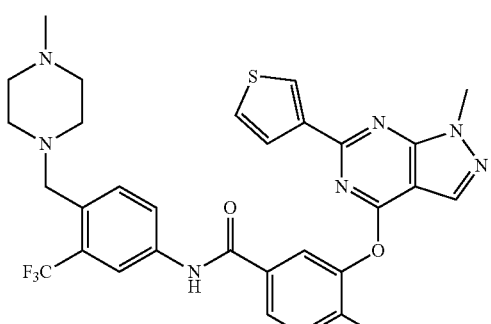
II-m-11
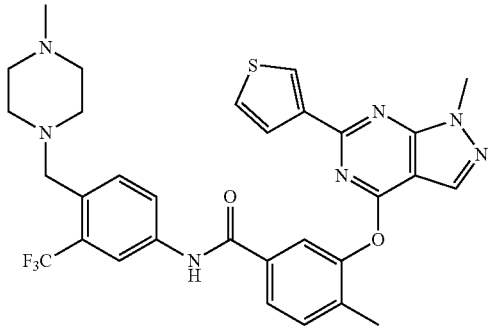
II-m-12
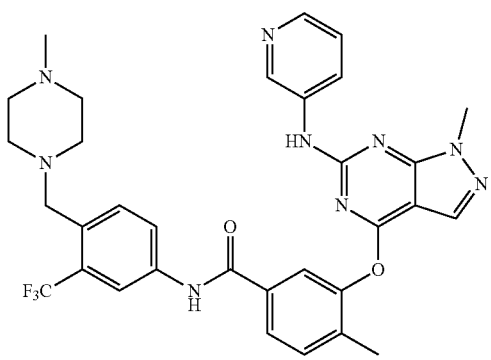
II-m-13
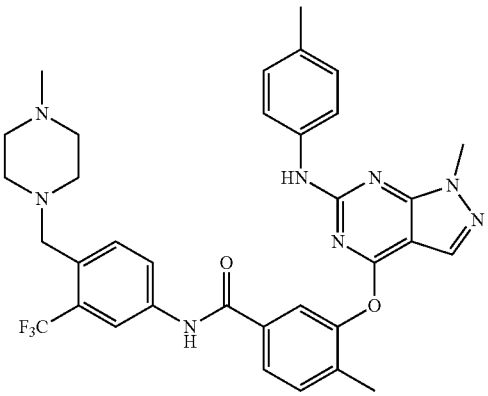
II-m-14
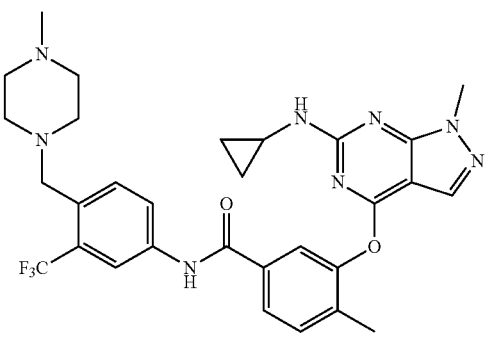
II-m-15
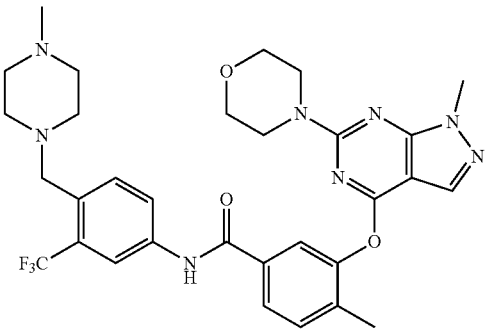
II-m-16
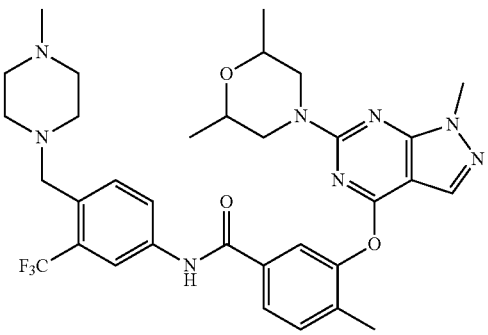

II-m-17
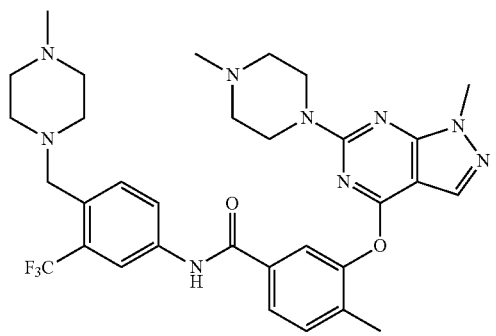
II-n-2
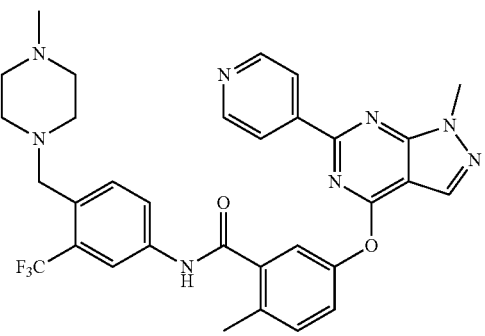
II-m-18
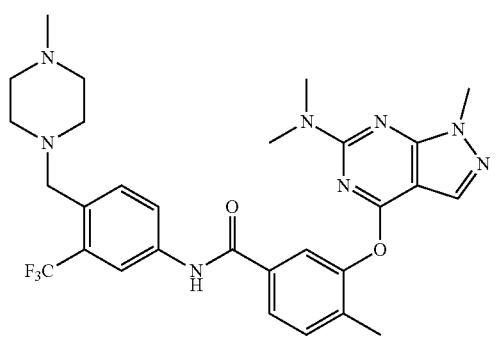
II-o-1
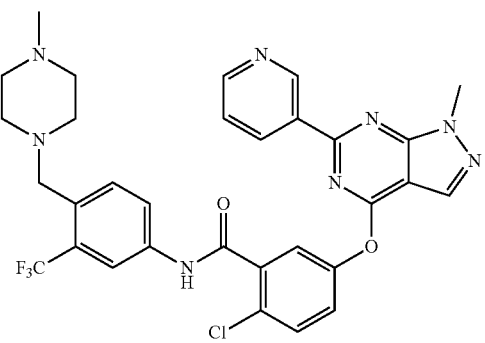
II-m-19
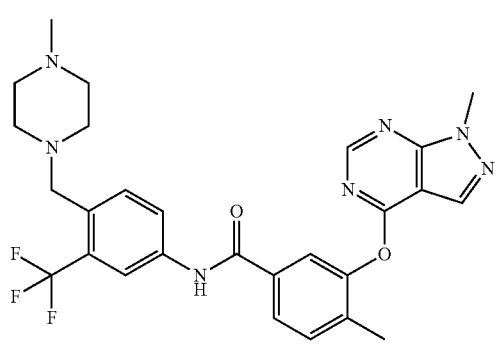
II-o-2
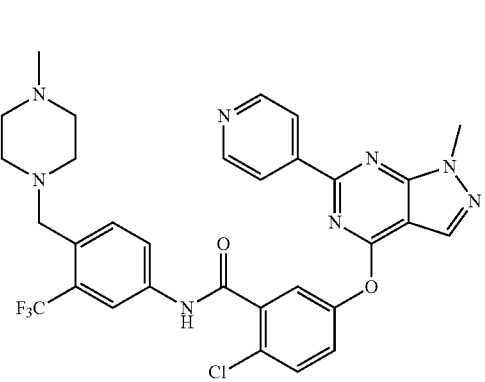
II-n-1
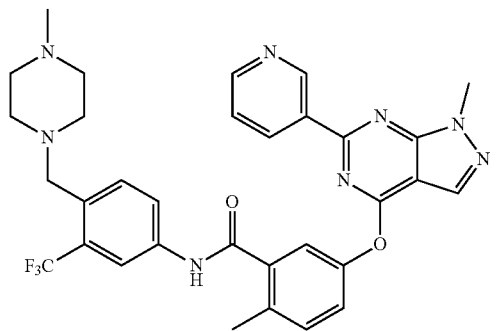
II-p-1
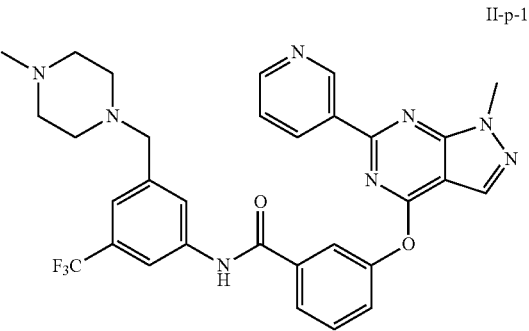

II-p-2
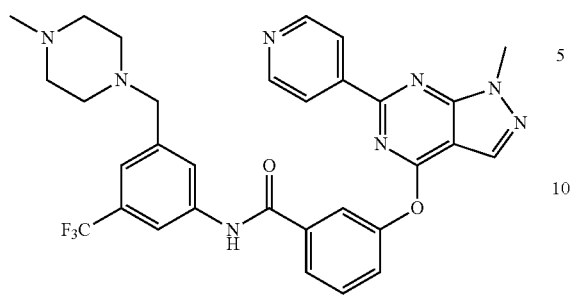
II-s-1
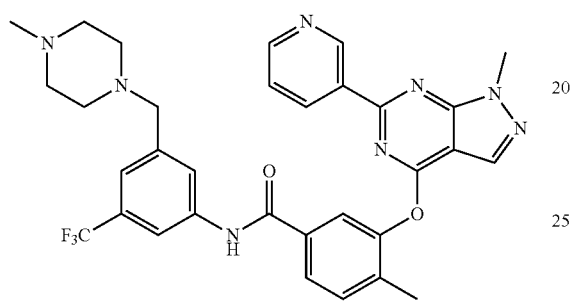
II-t-1
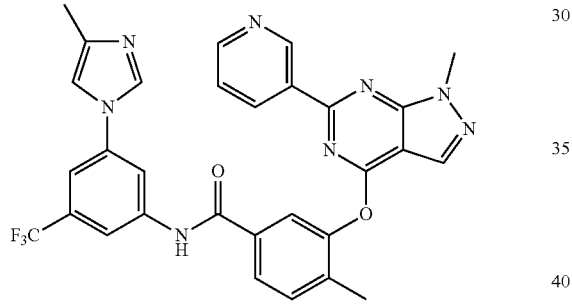
II-t-2
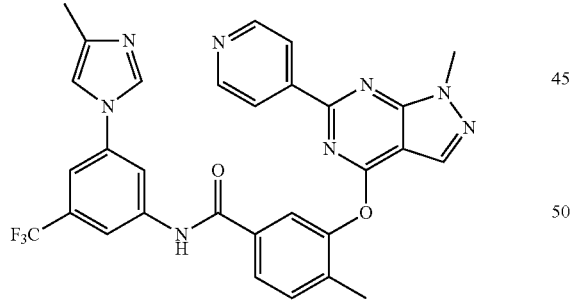
II-v-1
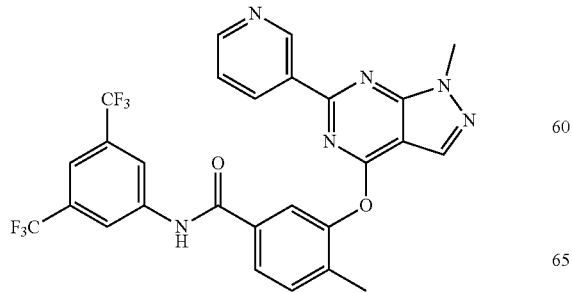
II-v-2
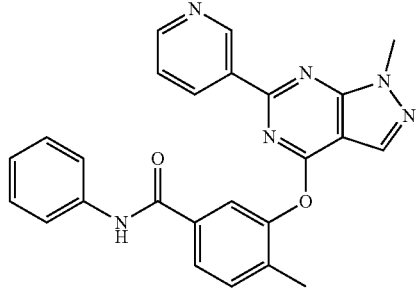
II-v-3
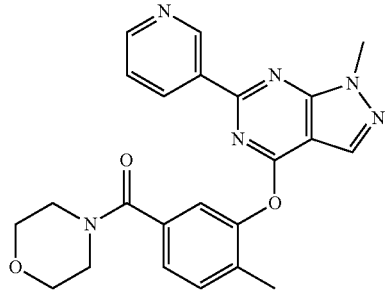
II-v-4
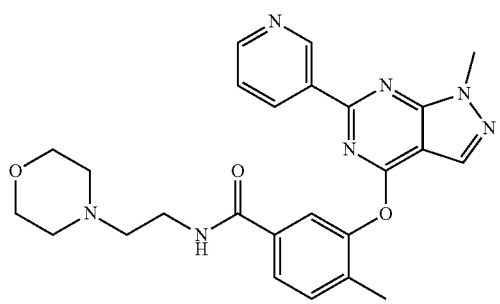
II-v-5
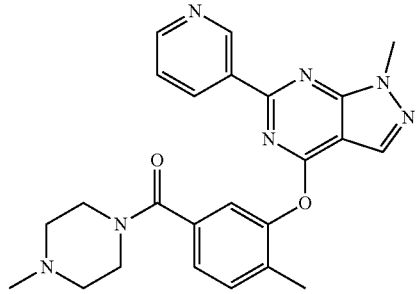
II-v-6
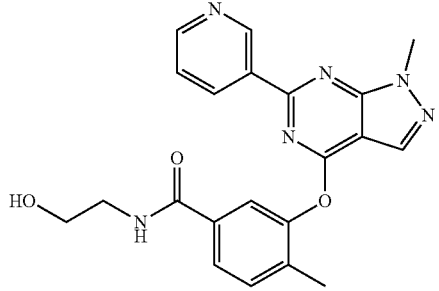

II-v-7
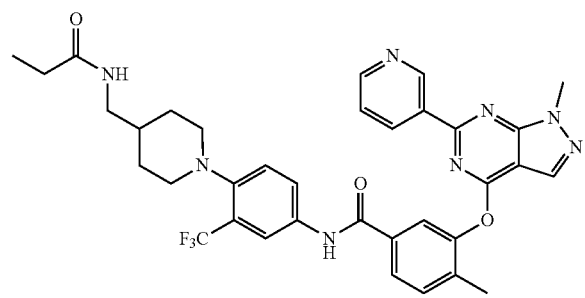
II-v-8
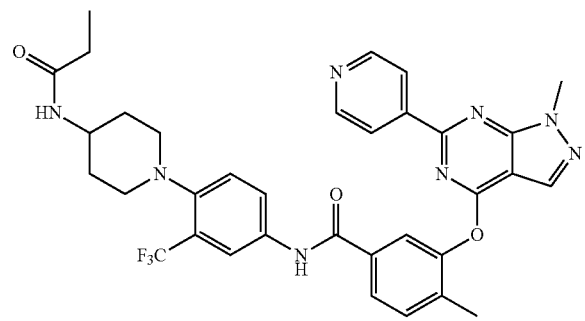
II-v-9
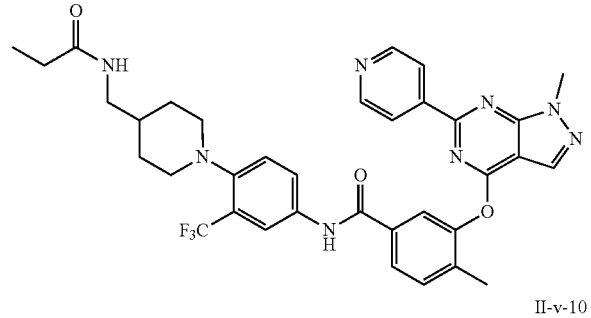
II-v-10
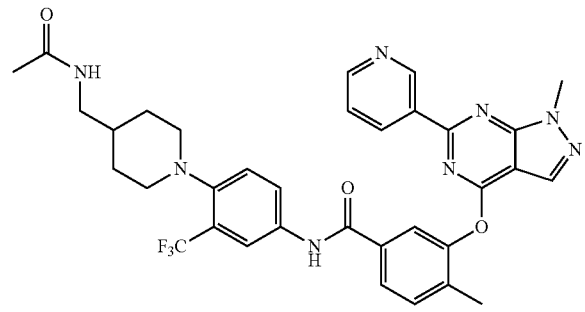
II-v-11
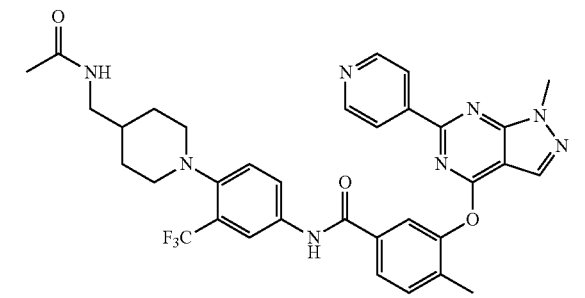
II-v-12
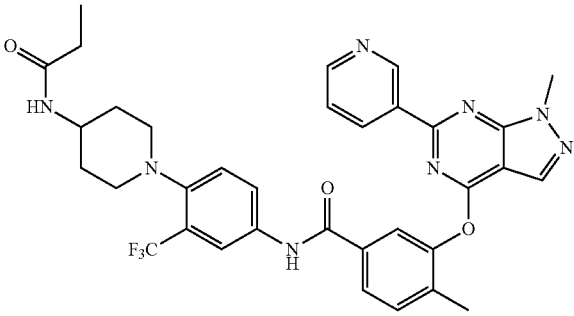
II-v-13
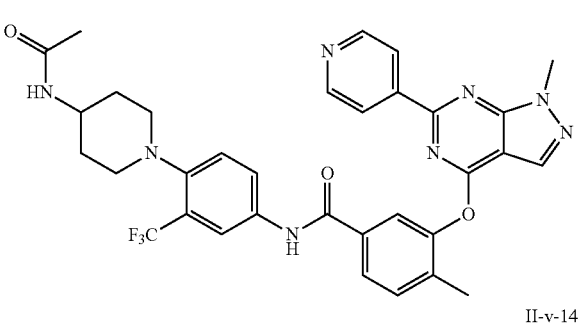
II-v-14
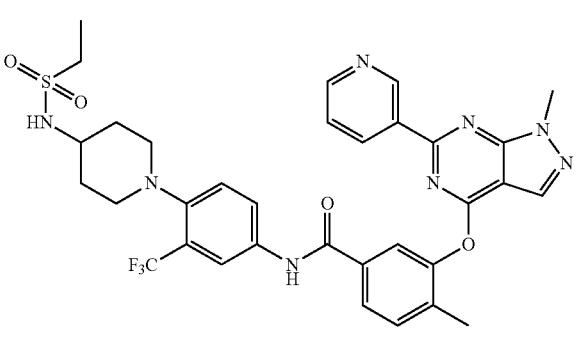
II-v-15
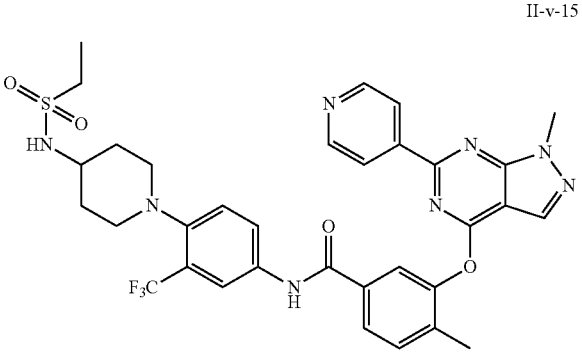
II-v-16
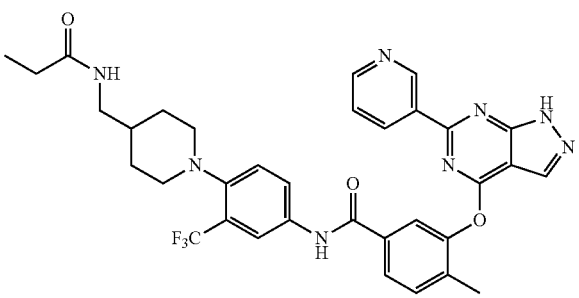

II-v-17
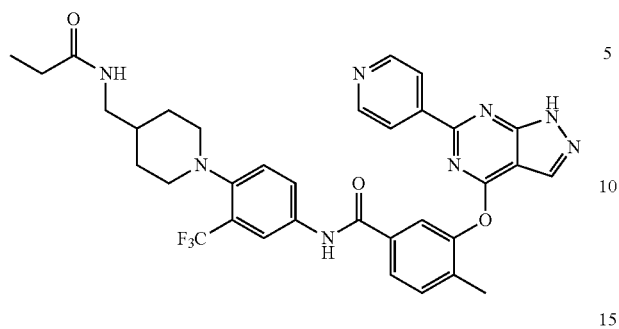
II-s-2
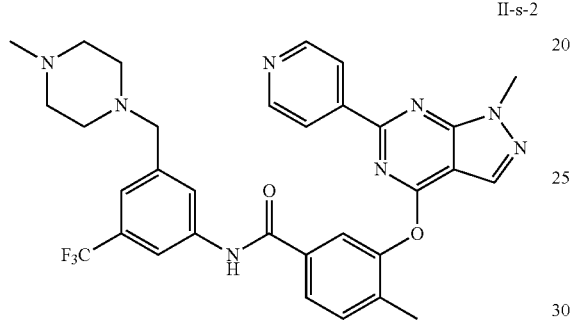
II-h-3
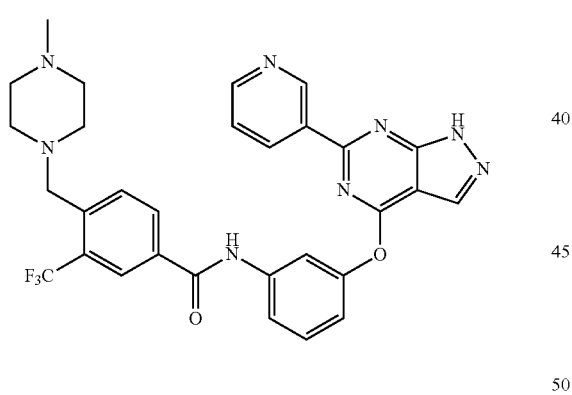
II-h-4
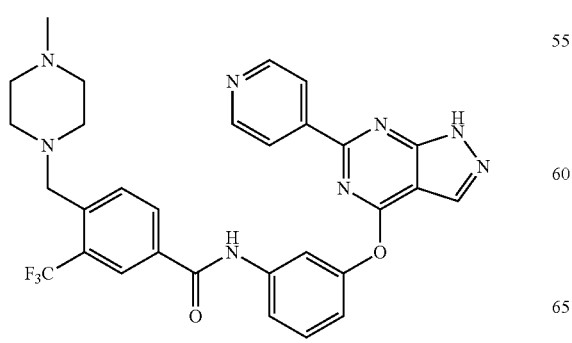
II-j-5
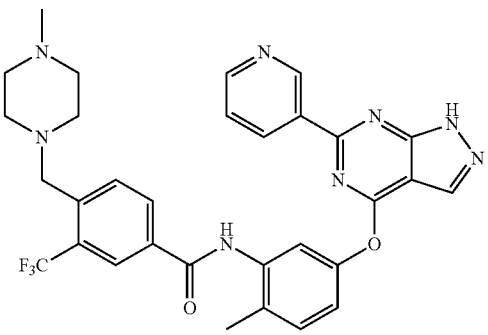
II-j-6
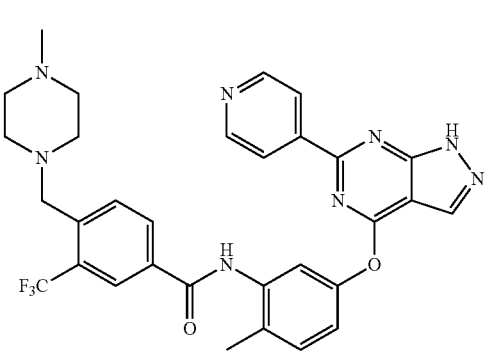
II-k-1
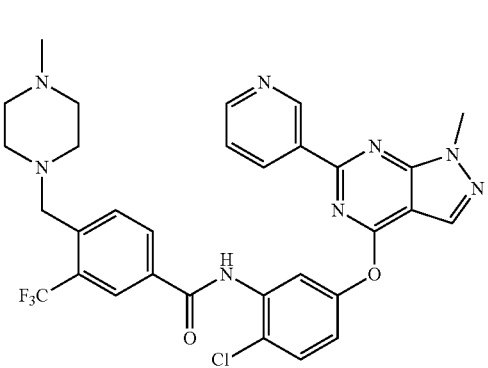
II-k-2
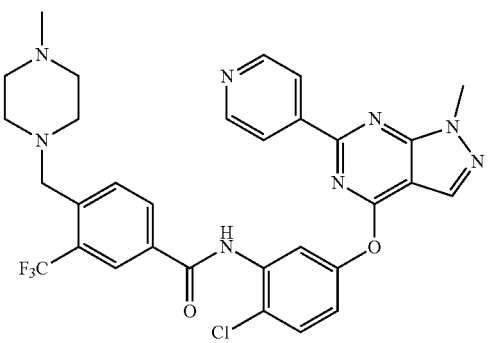

II-k-3
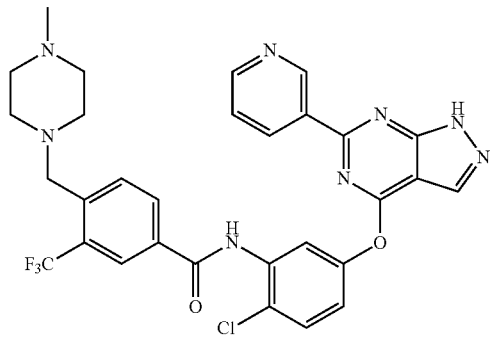
II-m-22
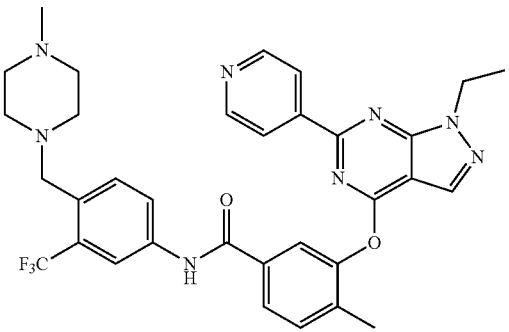
II-k-4
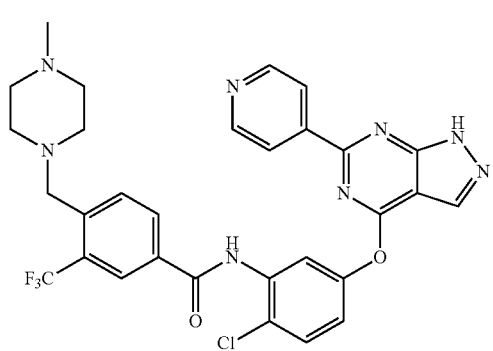
II-m-23
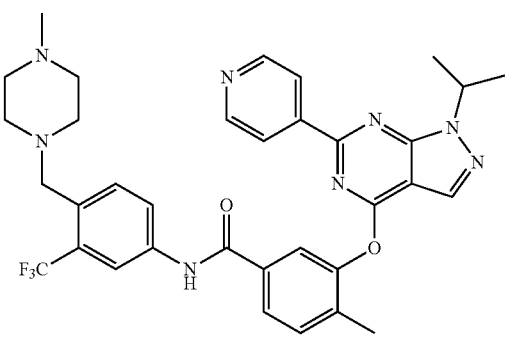
II-m-20
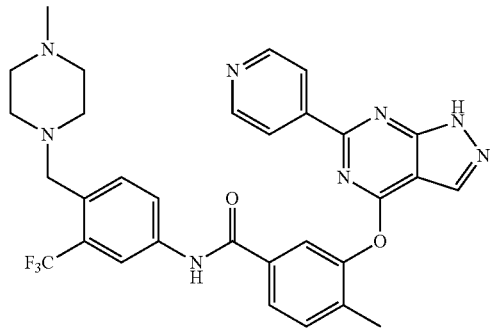
III-b-1
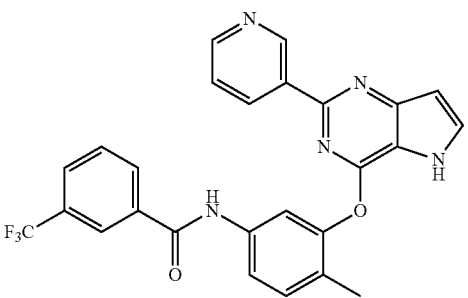
II-m-21
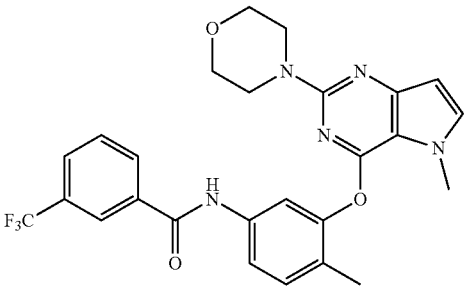
III-b-2

III-b-3
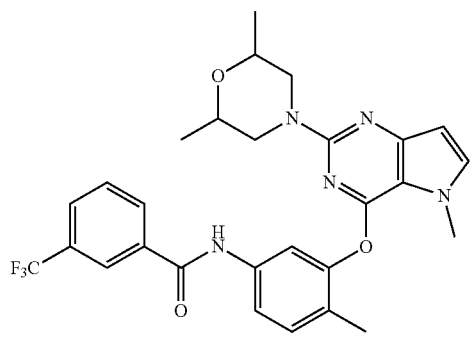
III-e-1
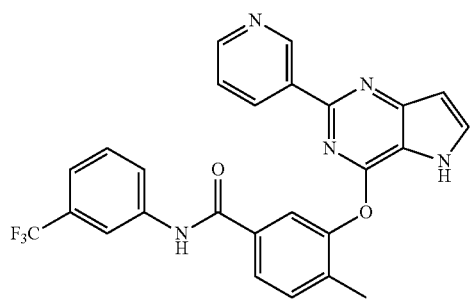
III-e-2
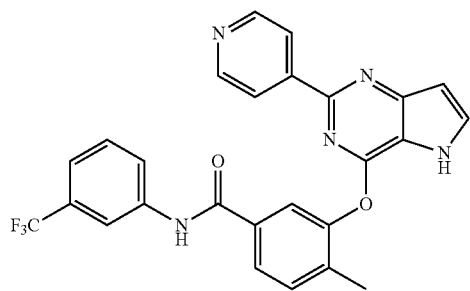
III-e-3
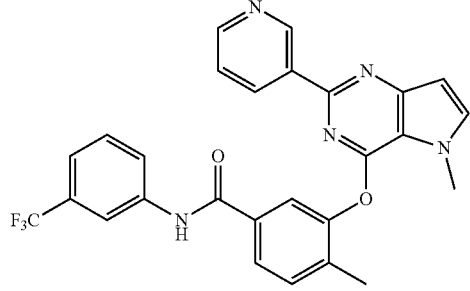
III-e-4
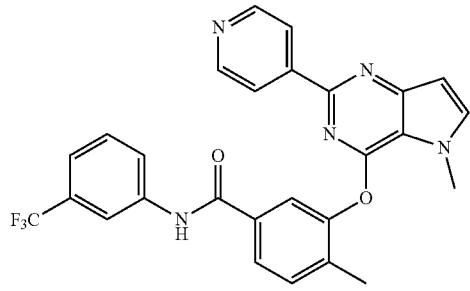
III-e-5
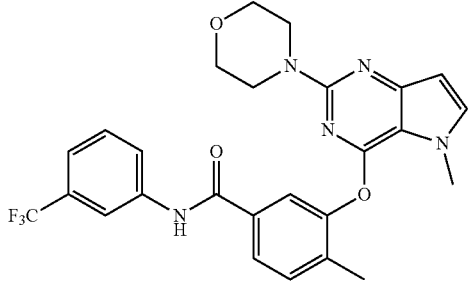
III-e-6
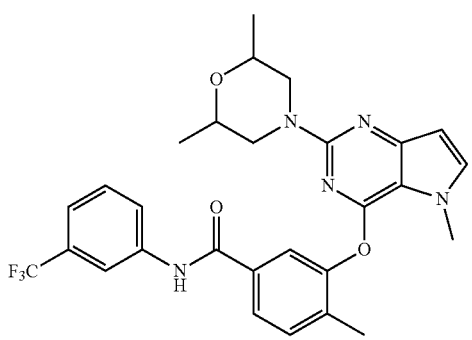
III-h-1
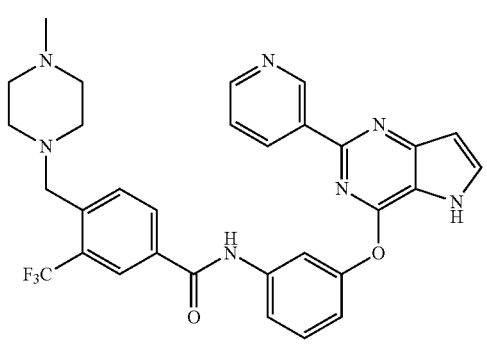
III-h-2
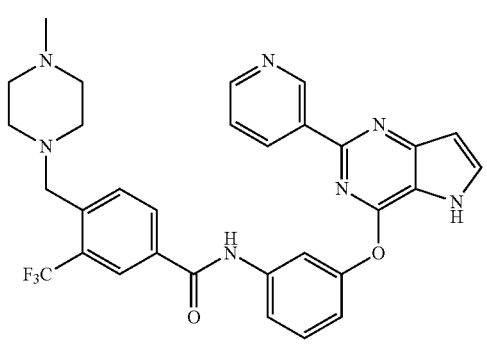

III-h-3
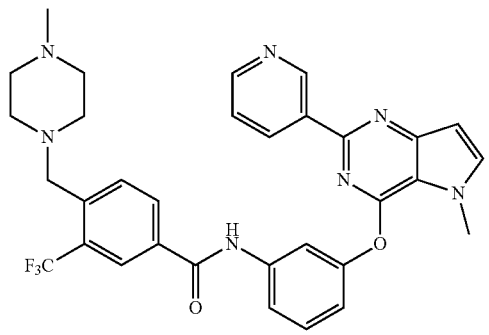
III-i-3
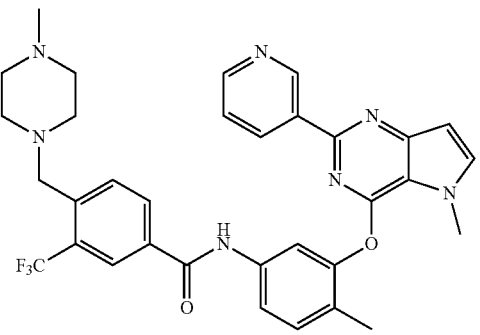
III-h-4
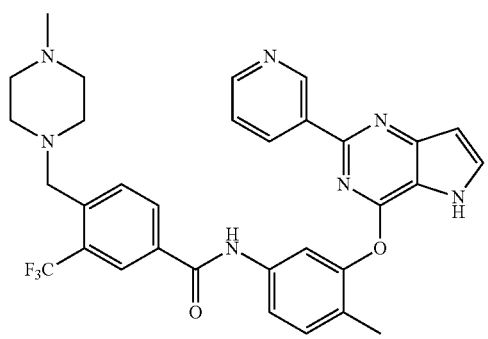
III-i-4
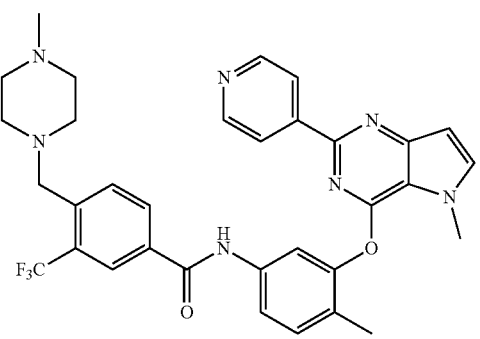
III-i-1
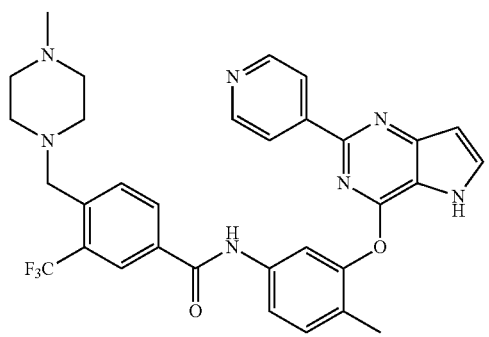
III-j-1
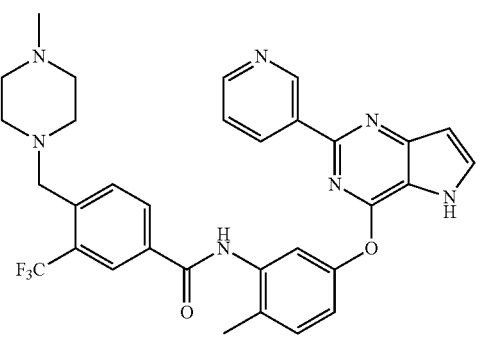
III-i-2
III-j-2
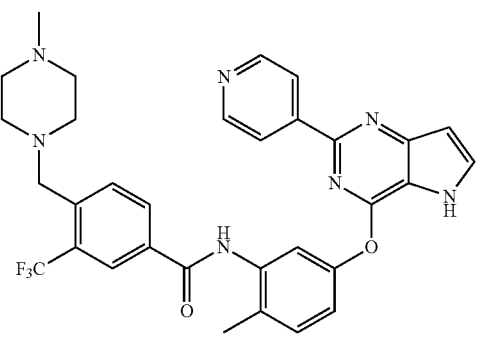

III-j-3
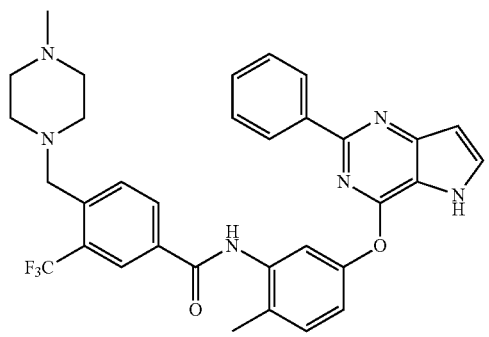
III-j-7
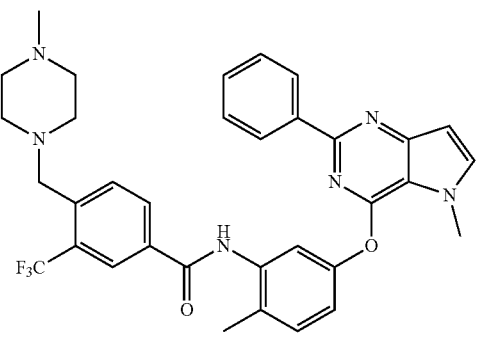
III-j-4
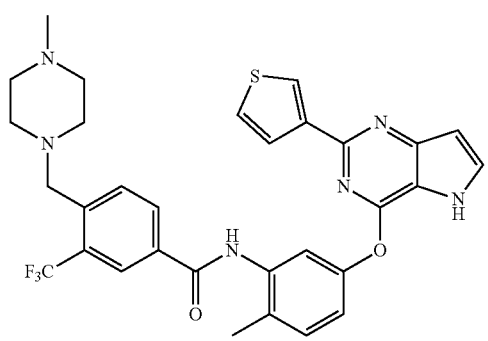
III-j-8
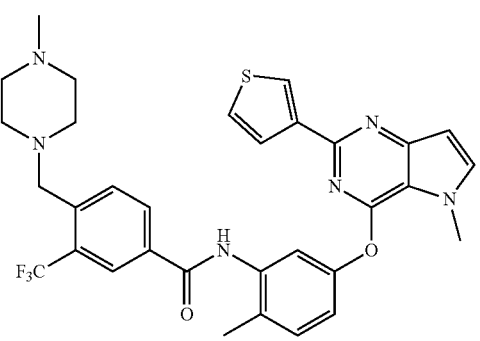
III-j-5
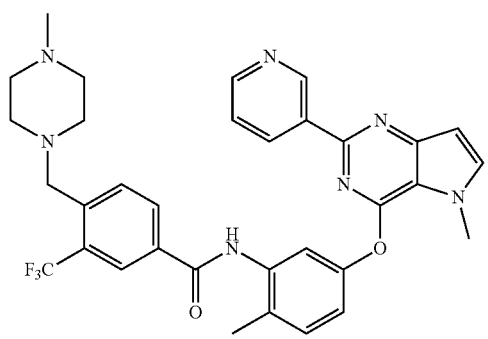
III-j-9
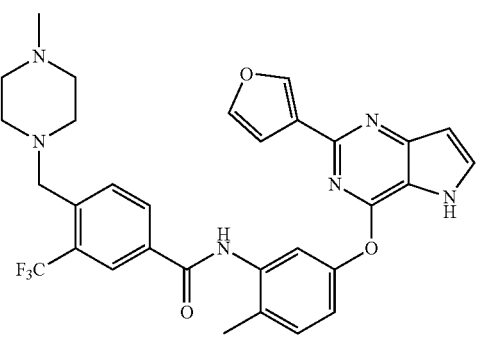
III-j-6
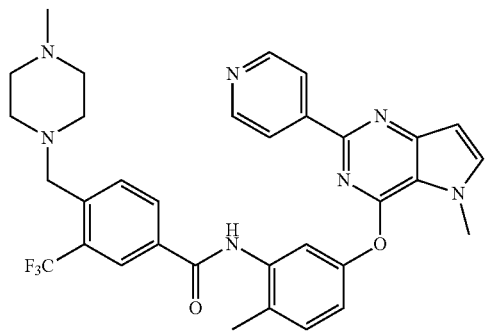
III-j-10
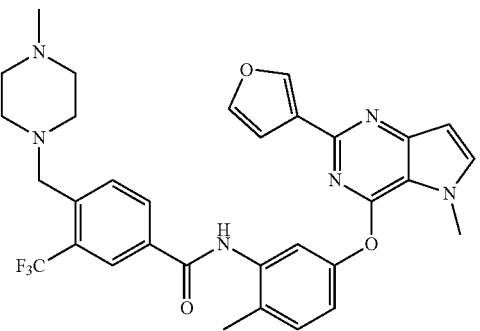

III-j-11
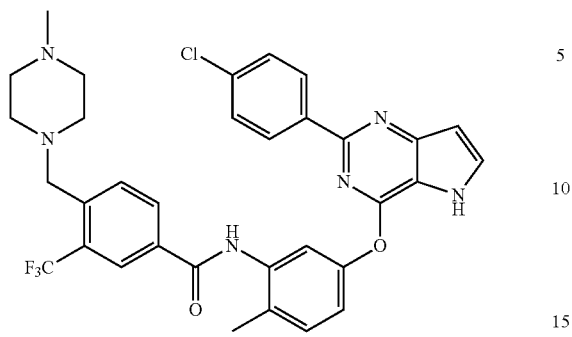
III-j-15
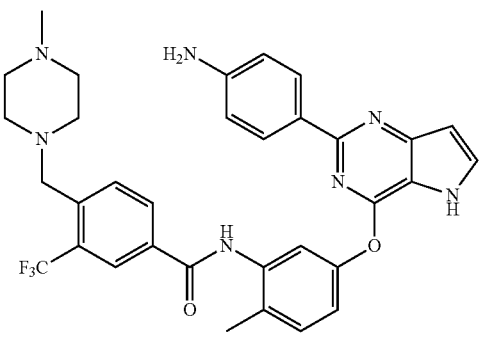
III-j-12
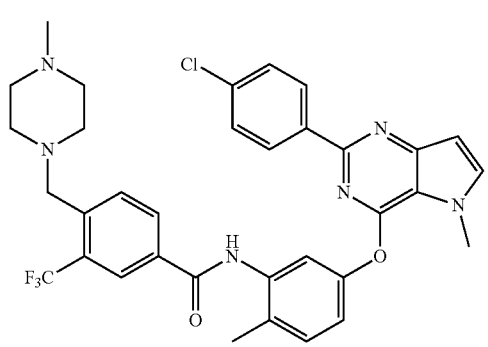
III-j-16
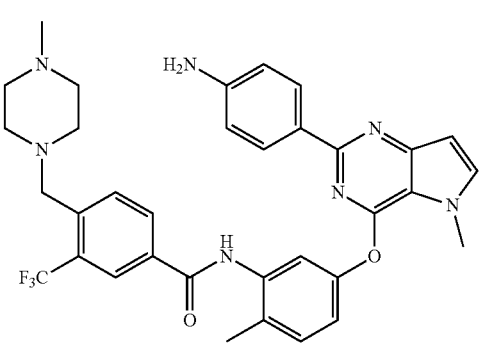
III-j-13
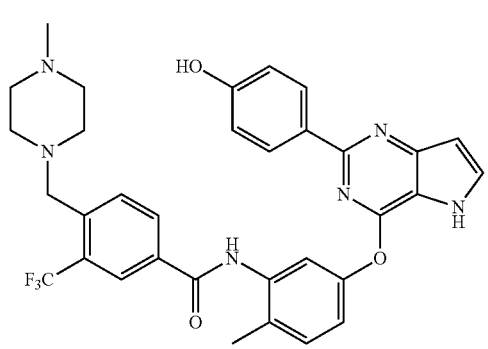
III-j-17
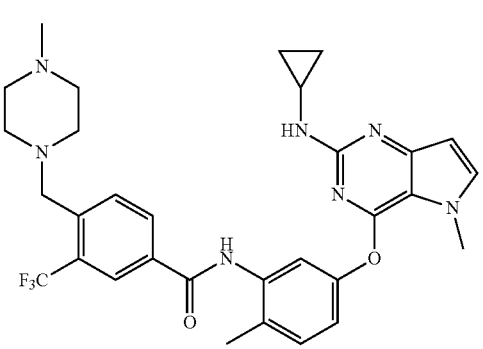
III-j-14
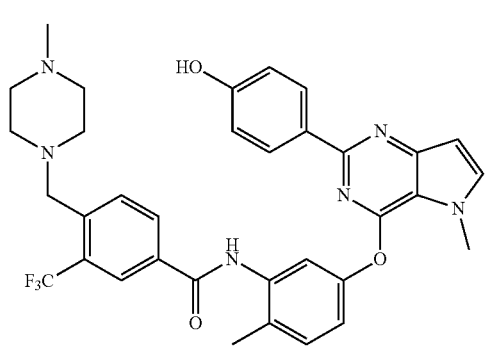
III-j-18
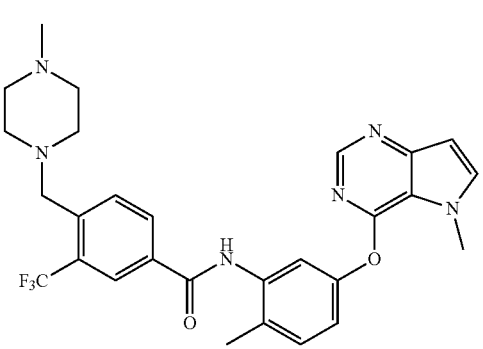

III-k-1
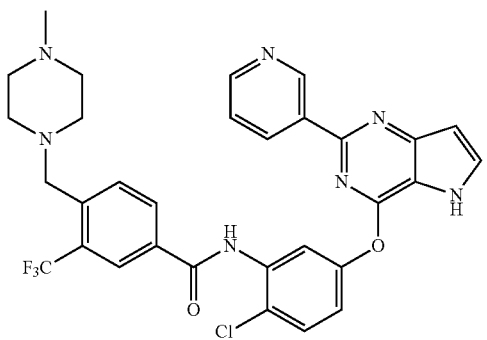
III-k-5
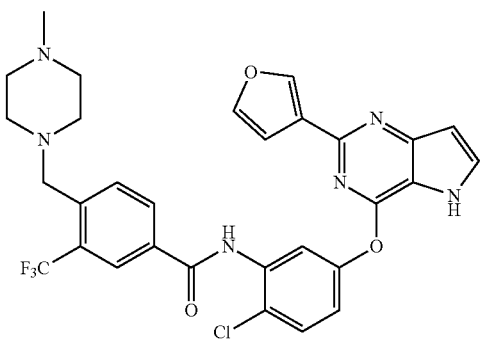
III-k-2
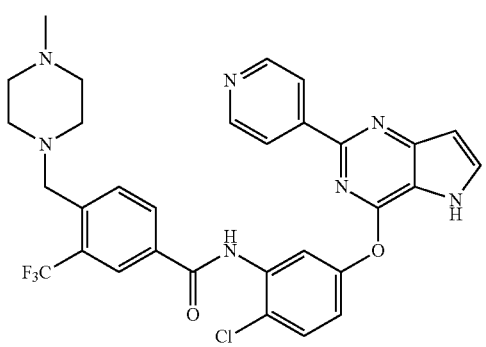
III-k-6
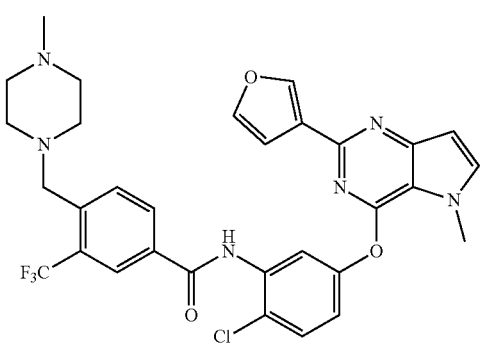
III-k-3
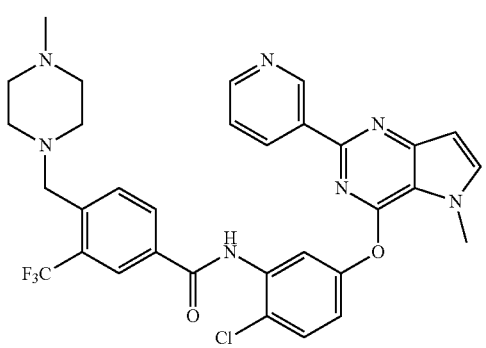
III-k-7
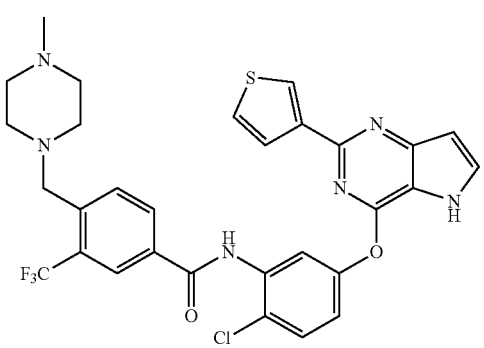
III-k-4
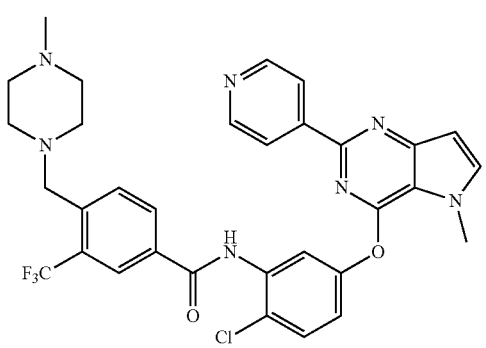
III-k-8
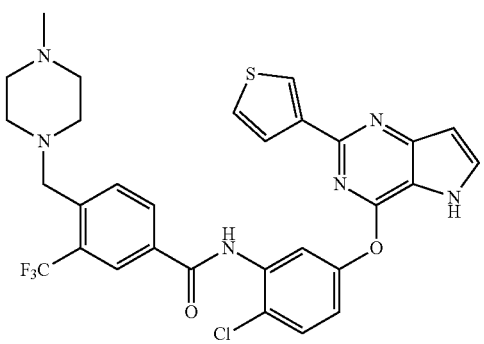

-continued
III-k-9
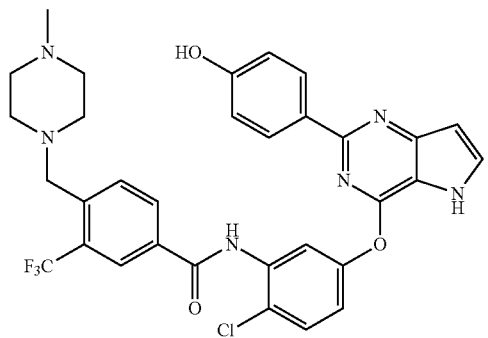
III-k-10
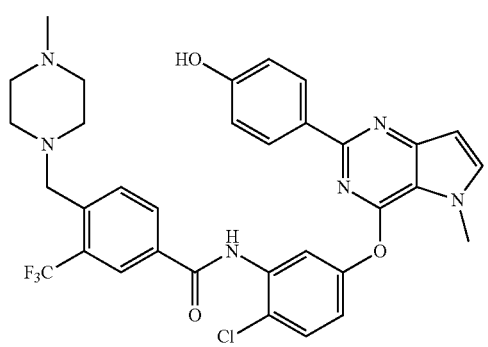
III-k-11
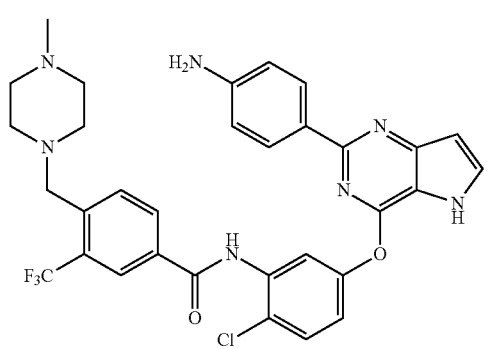
III-k-12
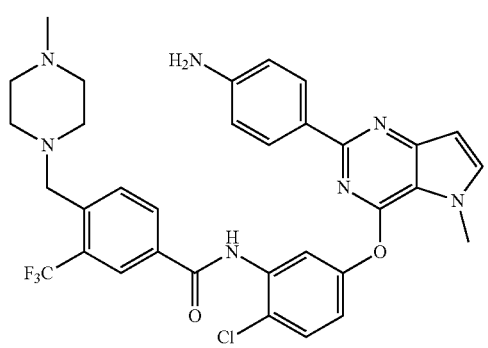
-continued
III-k-13
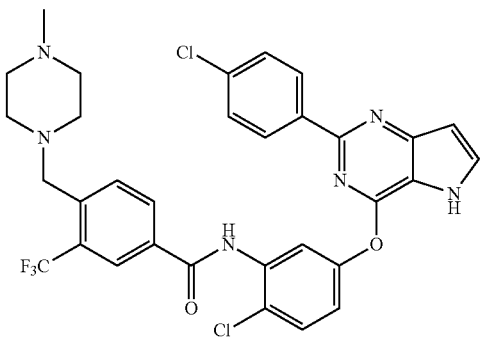
III-k-14
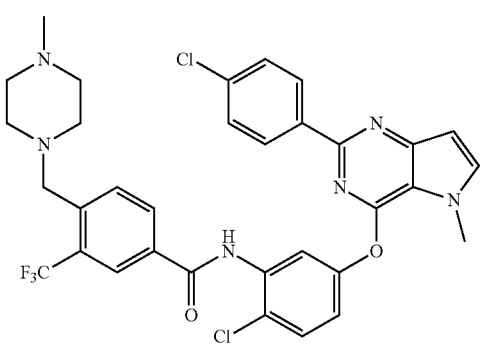
III-k-15
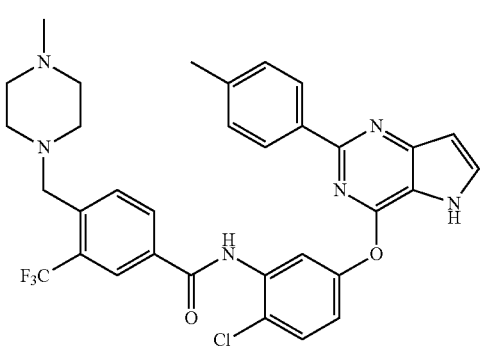
III-k-16
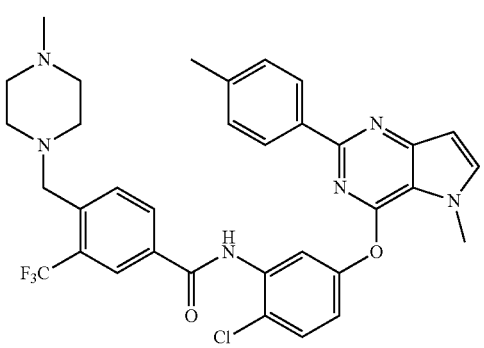

III-k-17
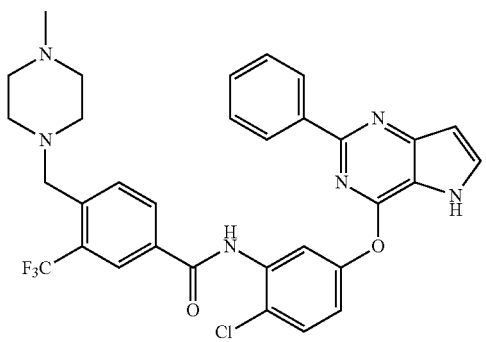
III-k-18
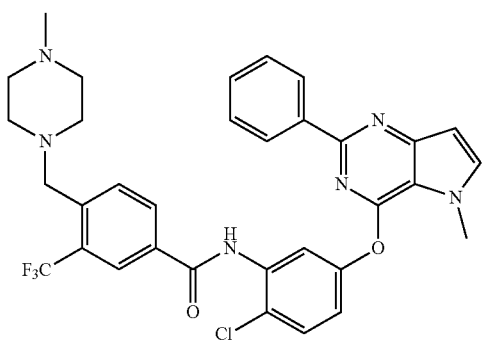
III-l-1
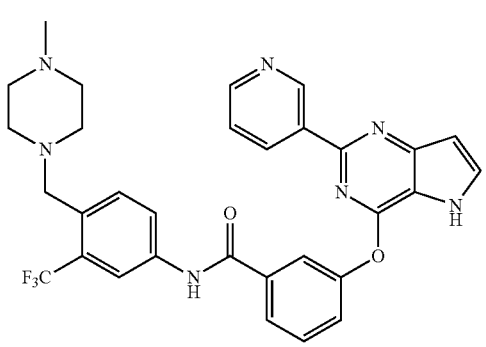
III-l-2
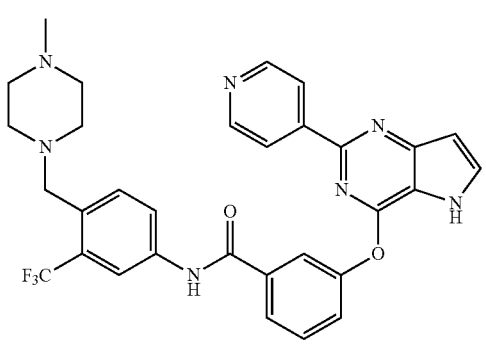
III-l-3
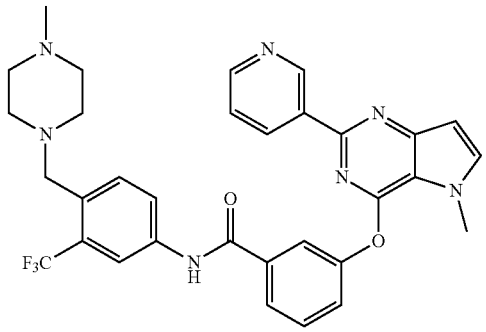
III-l-4
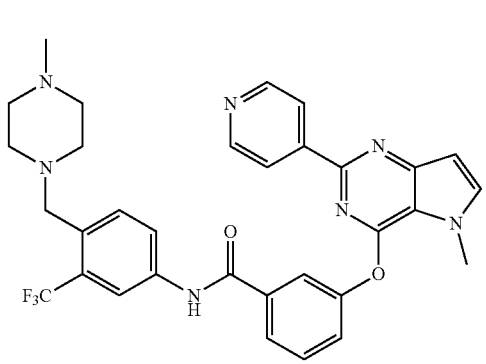
III-m-1
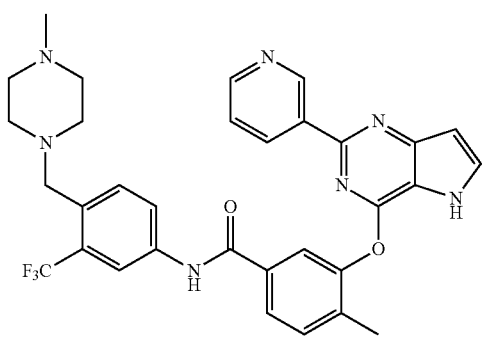
III-m-2
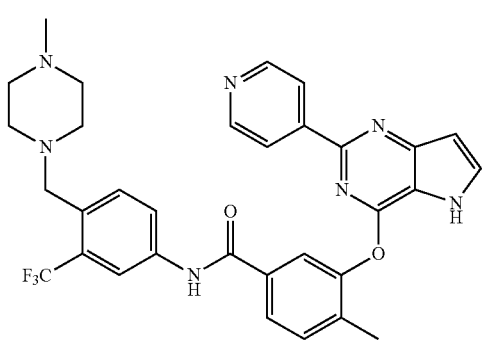

-continued
III-m-3
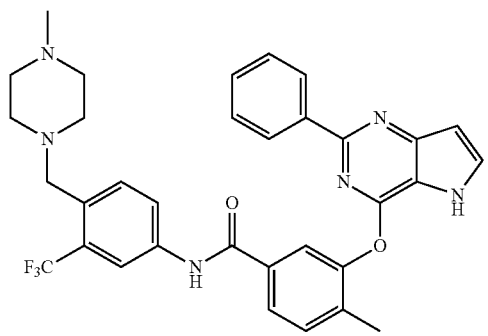
III-m-4
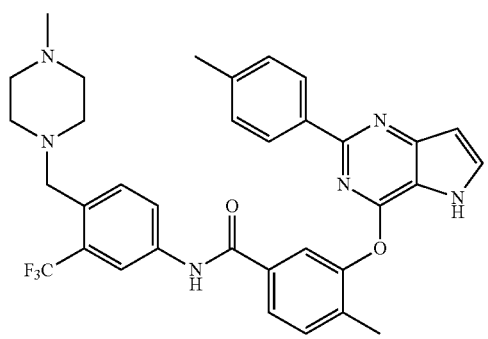
III-m-5
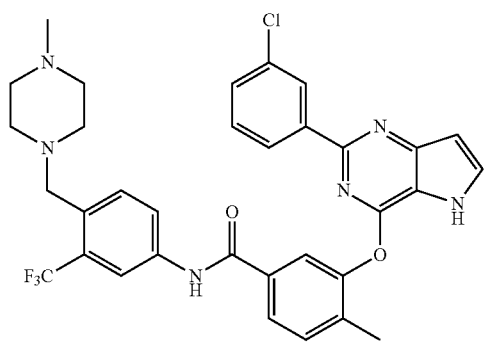
III-m-6
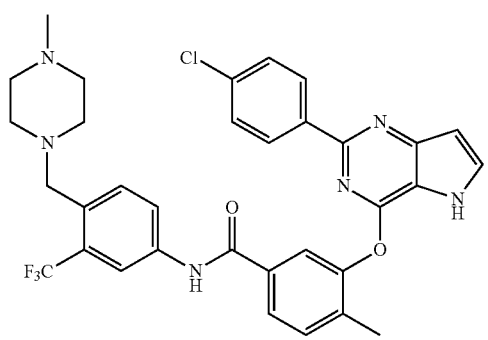
-continued
III-m-7
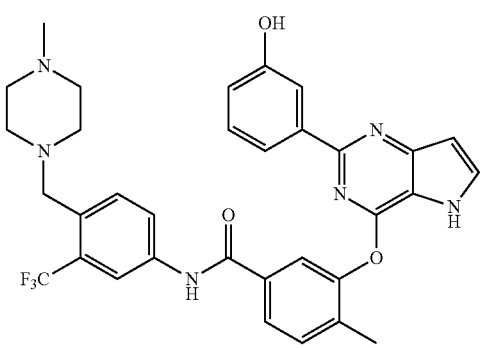
III-m-8
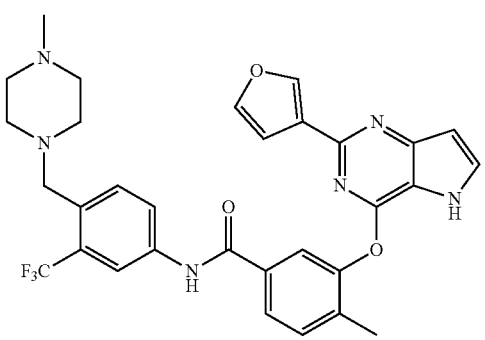
III-m-9
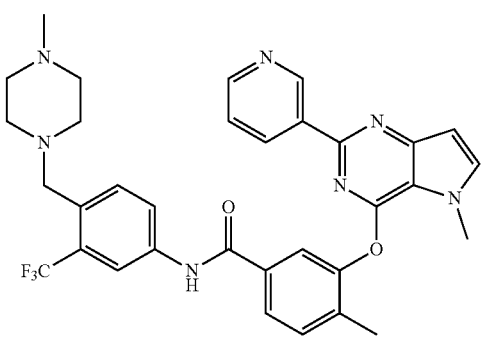
III-m-10
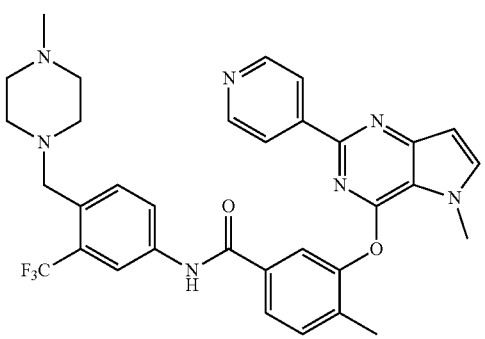

III-m-11
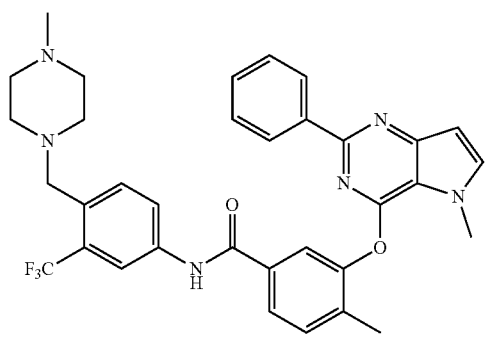
III-m-12
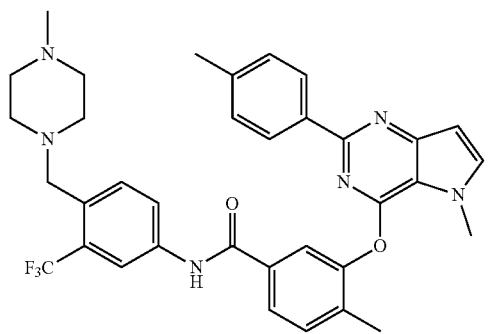
III-m-13
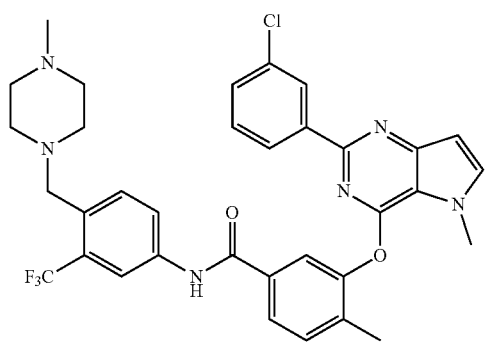
III-m-14
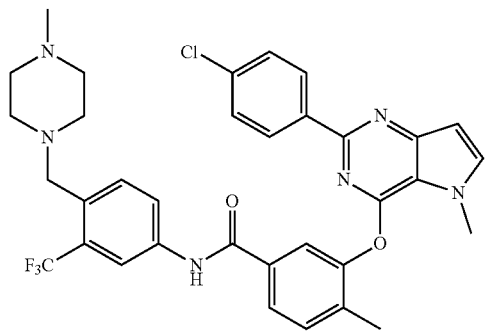
III-m-15
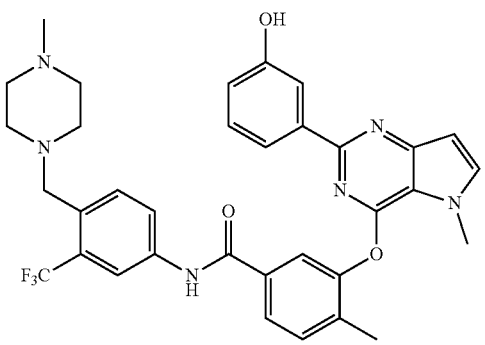
III-m-16
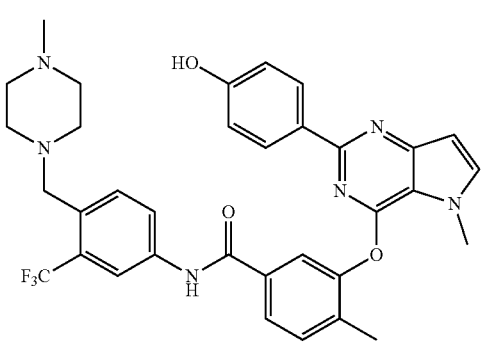
III-m-17
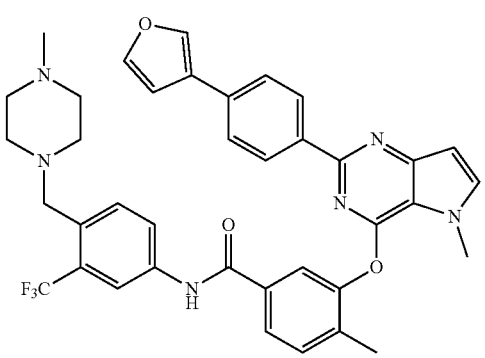
III-m-18
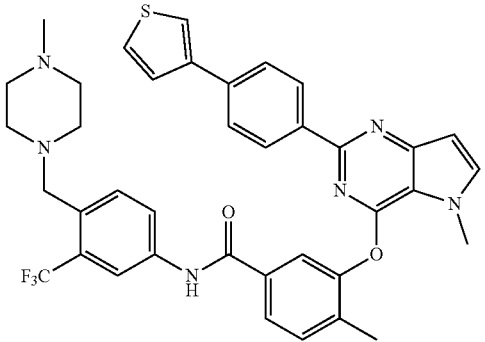

III-m-19
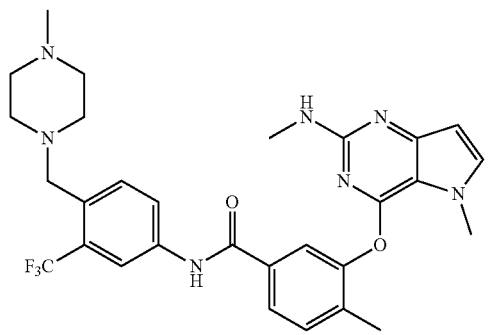
III-m-20
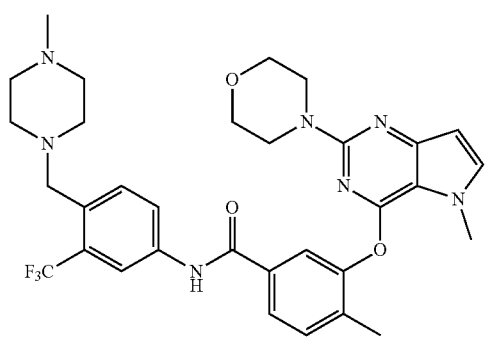
III-m-21
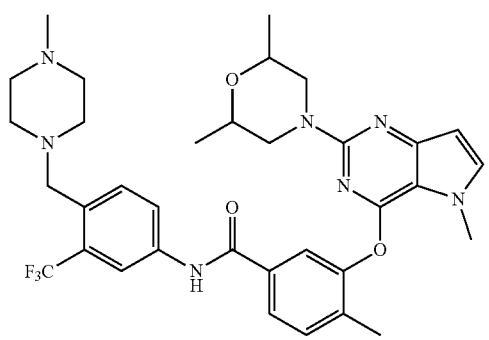
III-m-22
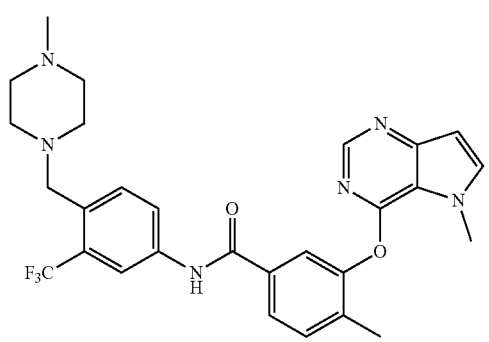
III-m-23
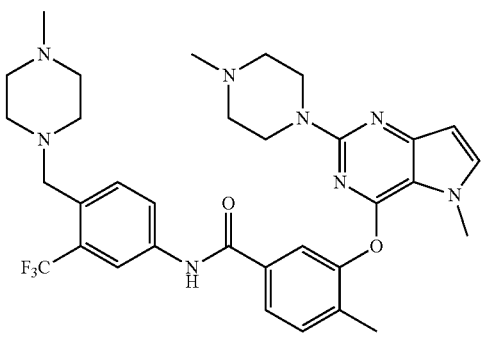
III-m-24
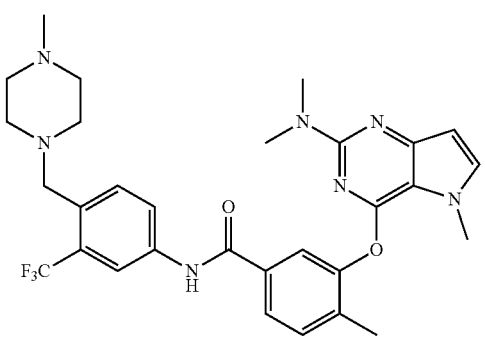
III-m-25
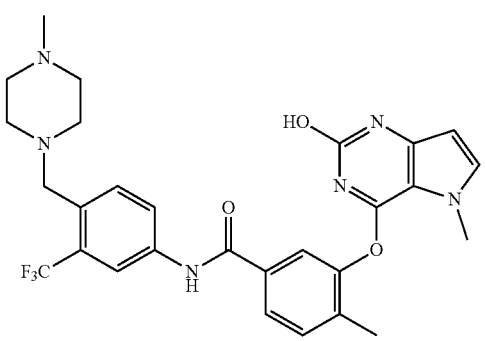
III-m-26
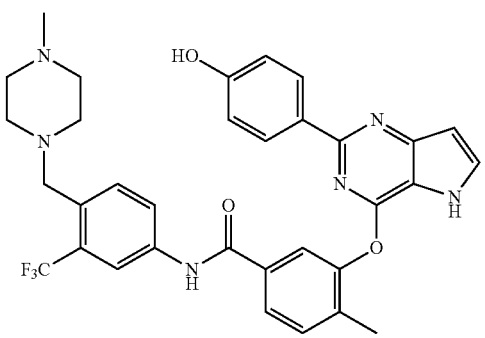

III-m-27
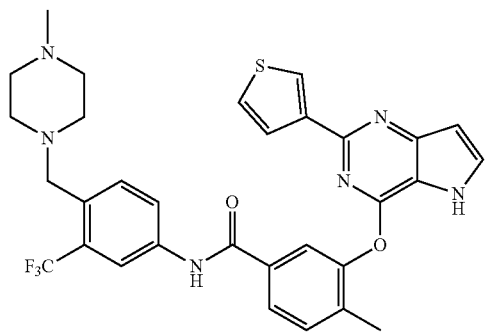
III-n-1
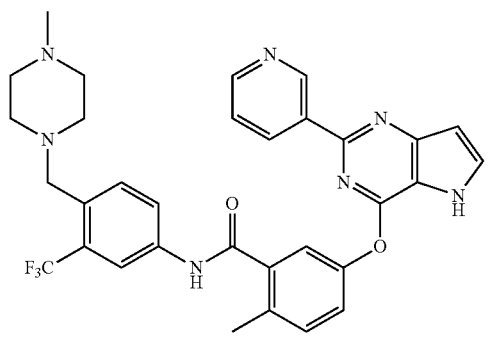
III-n-2
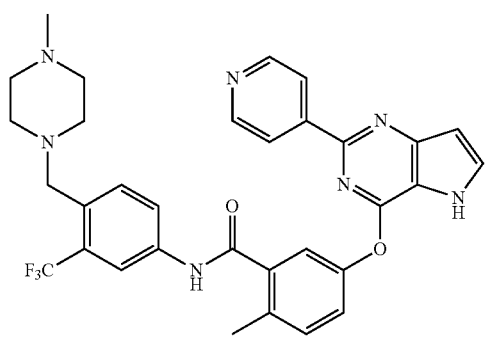
III-n-3
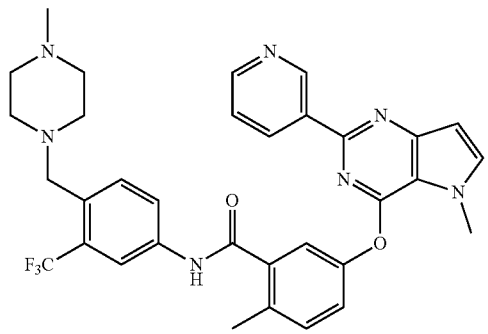
III-n-4
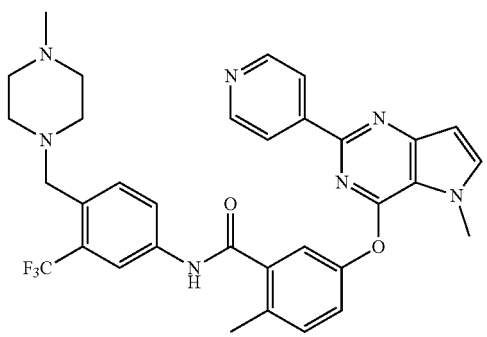
III-o-1
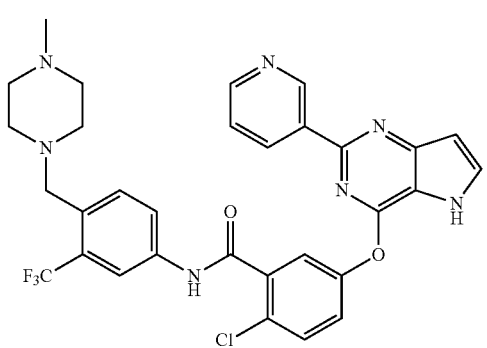
III-o-2
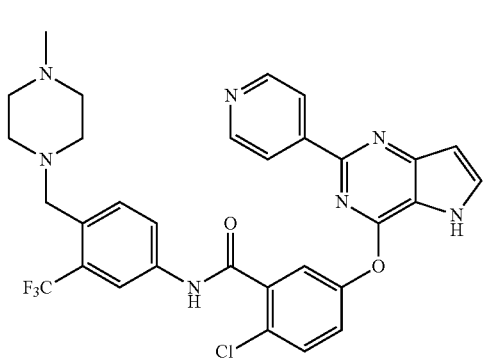
III-o-3
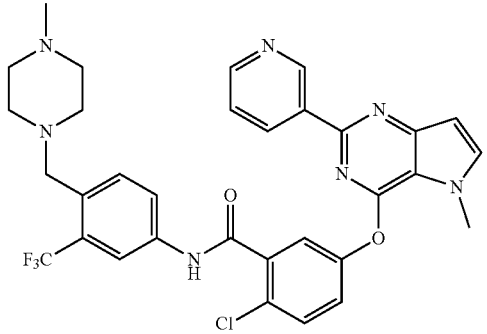

323
-continued
III-o-4
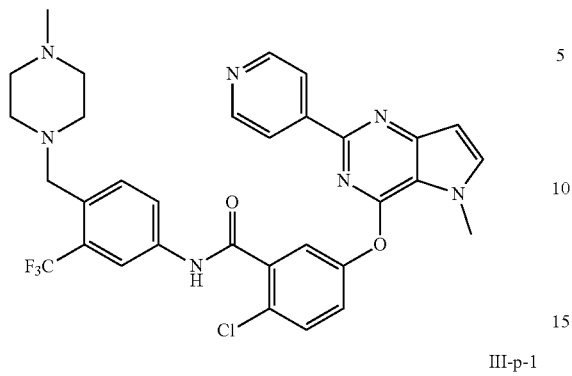
III-p-1
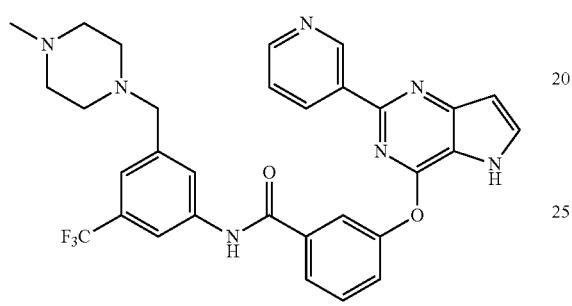
III-p-2
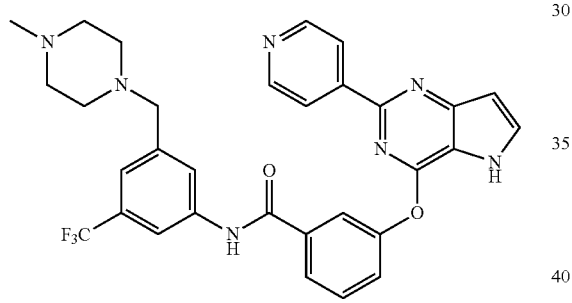
III-p-3
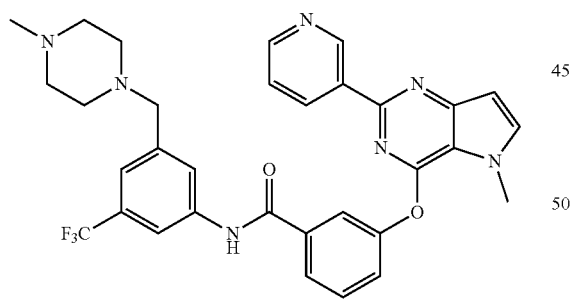
III-p-4
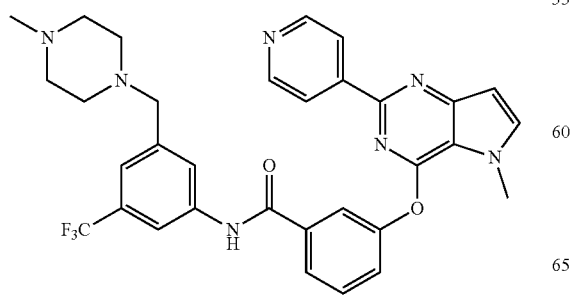
324
-continued
III-q-1
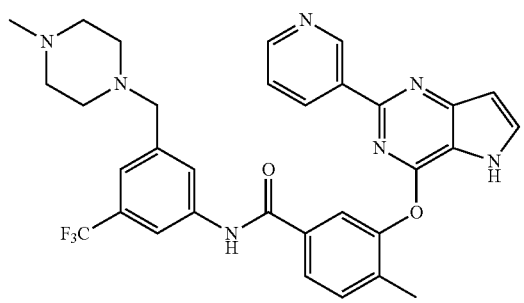
III-q-2
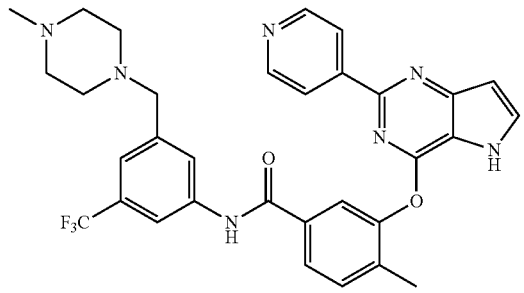
III-q-3
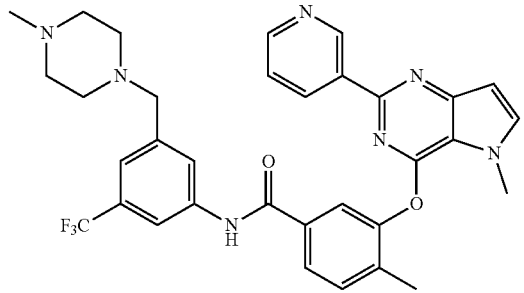
III-q-4
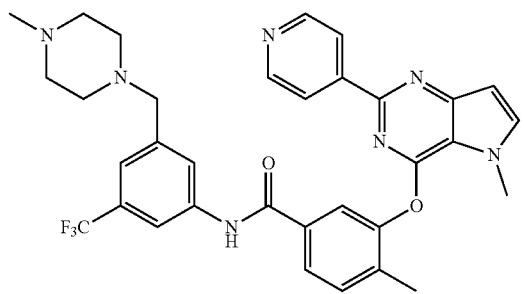
III-r-1
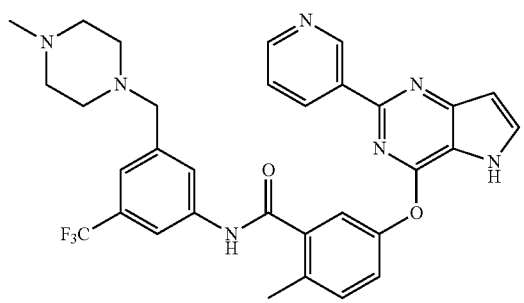

III-r-2
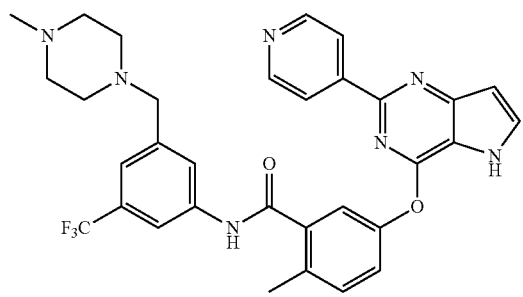
III-r-3
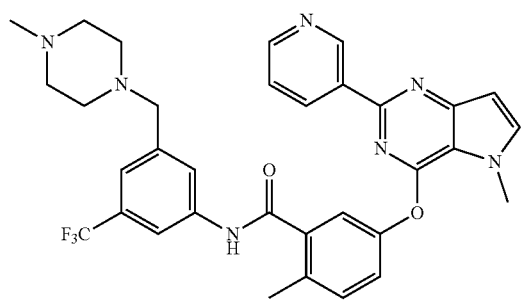
III-r-4
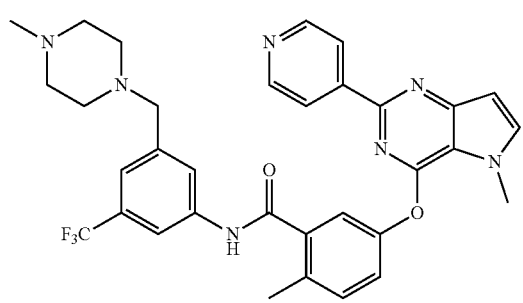
III-u-1
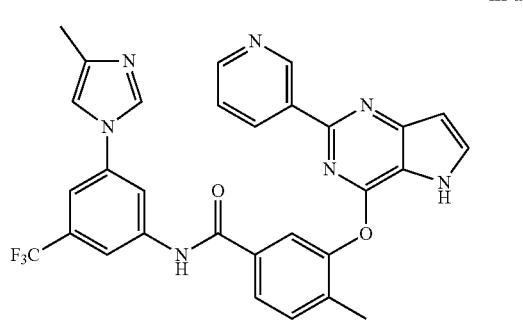
III-u-2
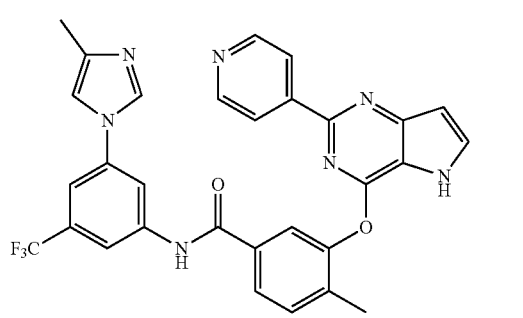
III-u-3
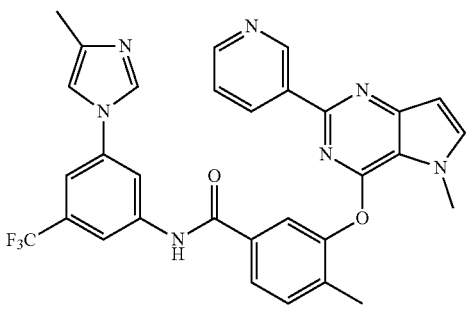
III-u-4
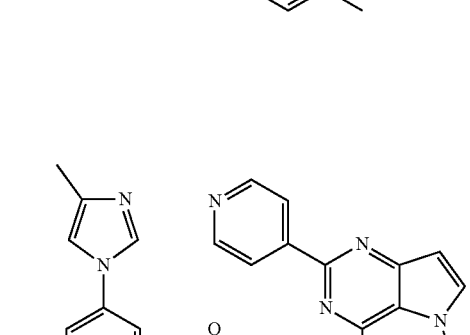
III-v-1
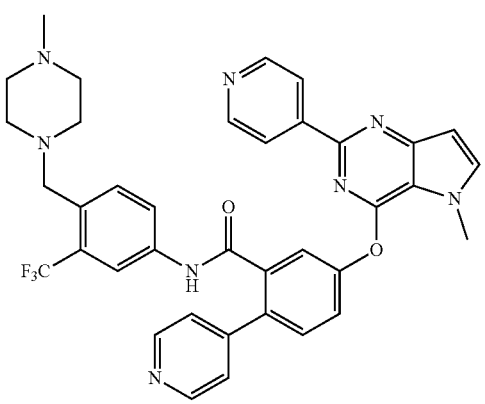
III-v-2
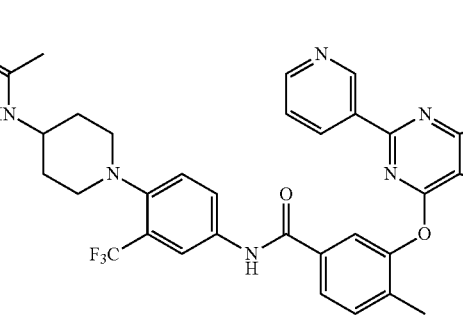

III-v-3
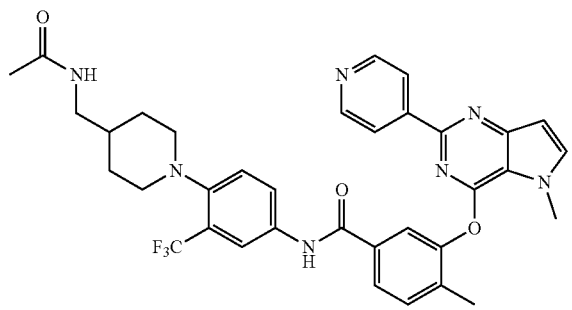
III-v-4
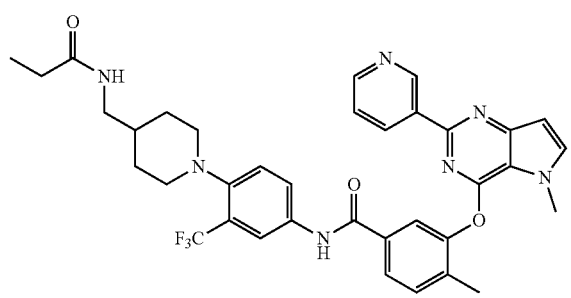
III-v-5
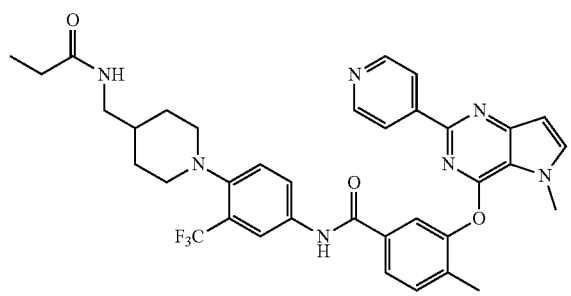
III-v-6
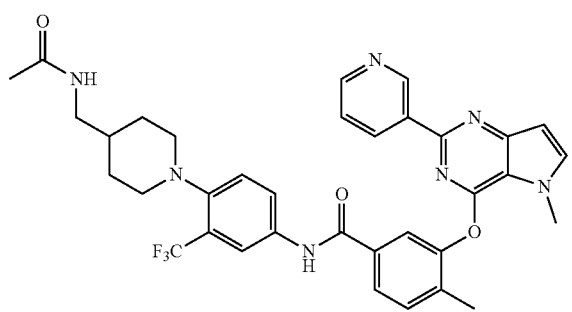
III-v-7
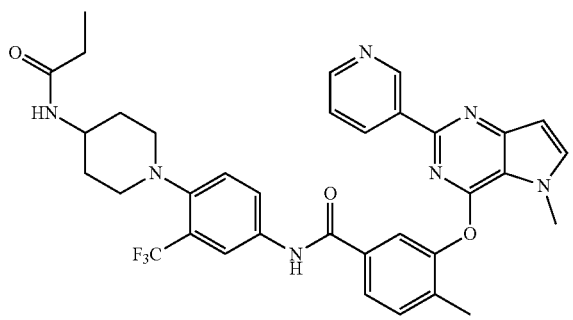
III-v-8
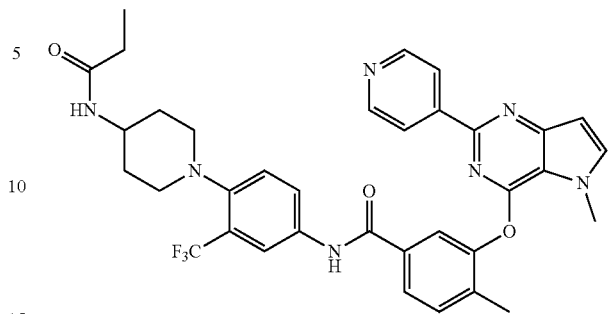
III-v-9
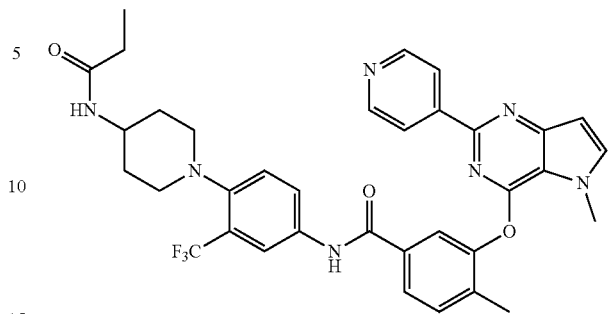
III-v-10
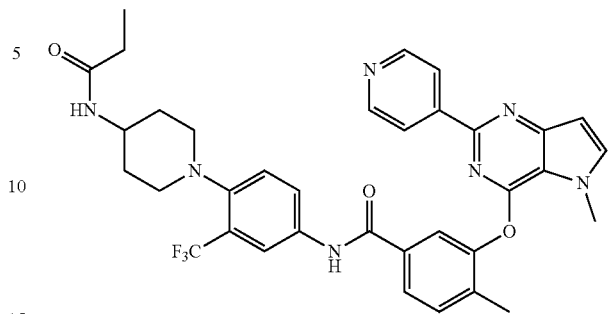
III-v-11
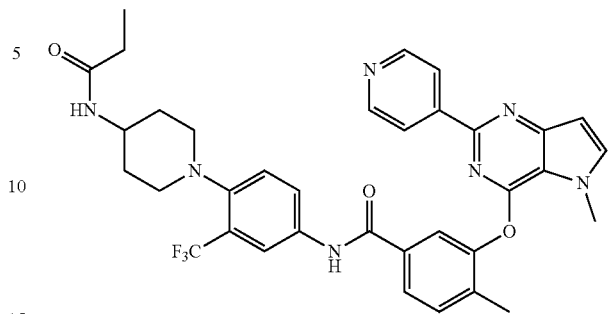
III-v-12

329
-continued
III-v-13
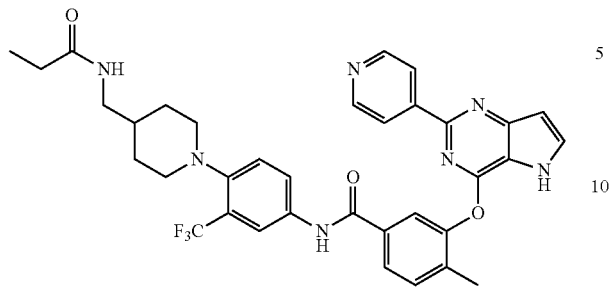
IV-a-1
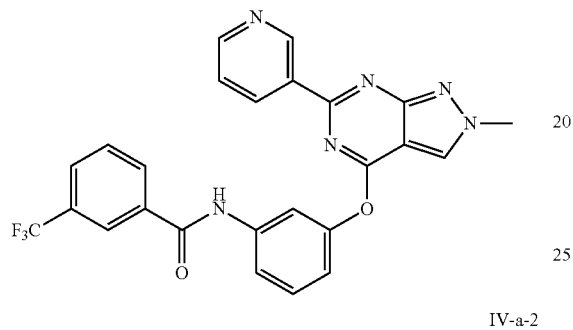
IV-a-2
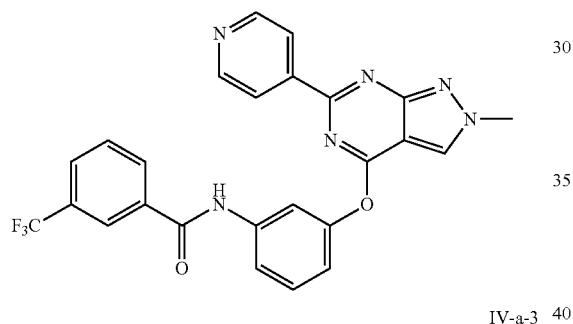
IV-a-3
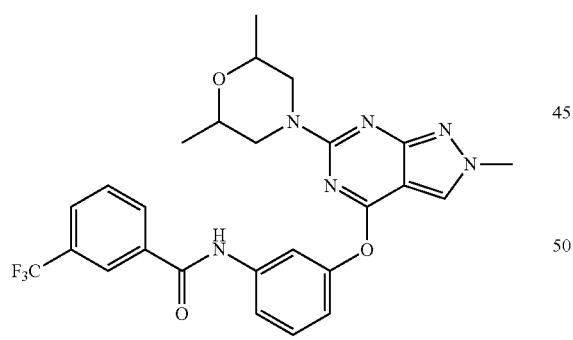
IV-b-1
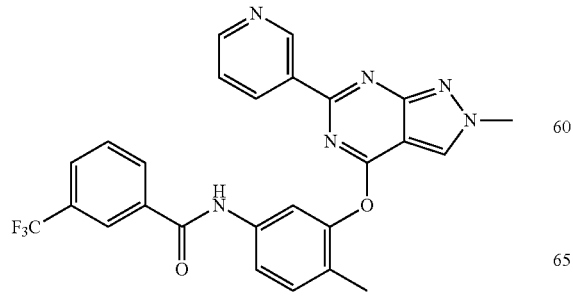
330
-continued
IV-b-2
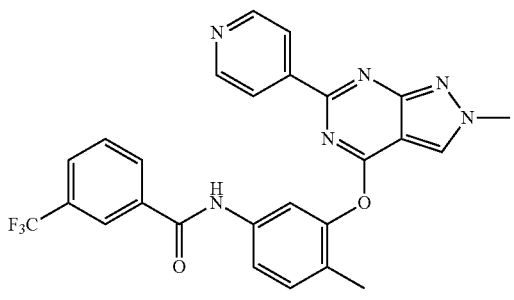
IV-b-3
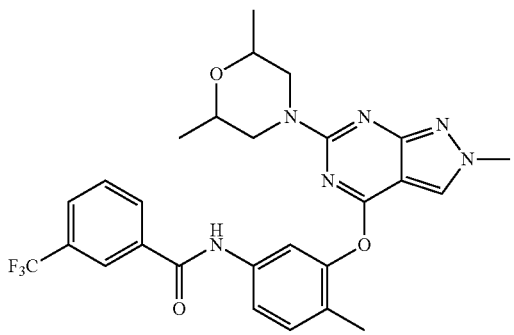
IV-c-1
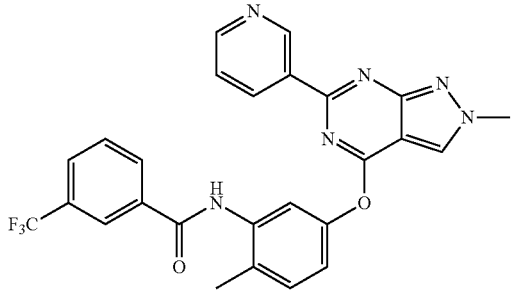
IV-c-2
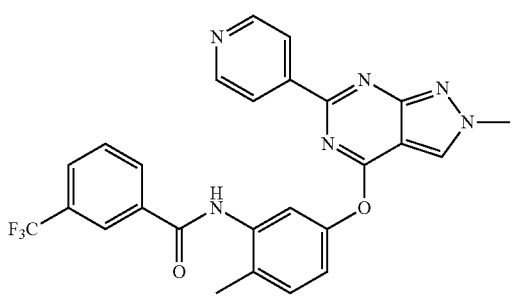
IV-d-1
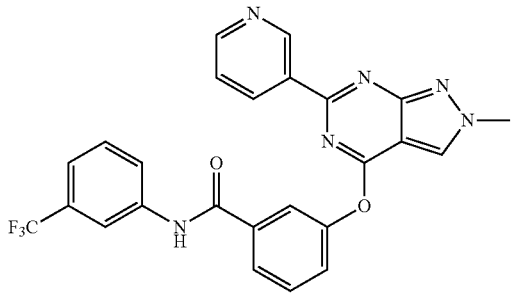

-continued
IV-d-2
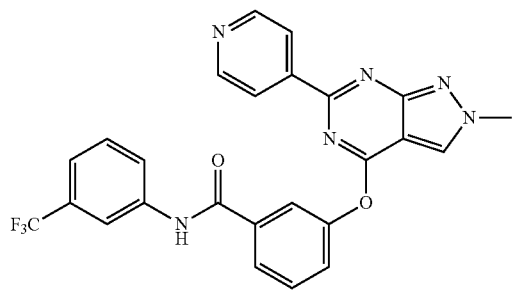
IV-e-1
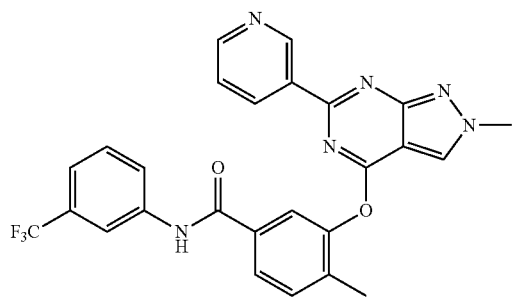
IV-e-2
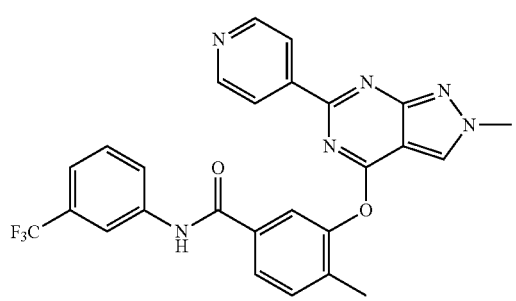
IV-e-3
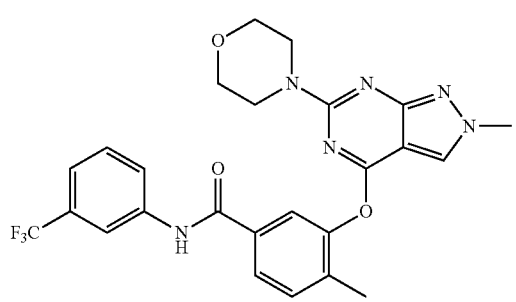
IV-e-4
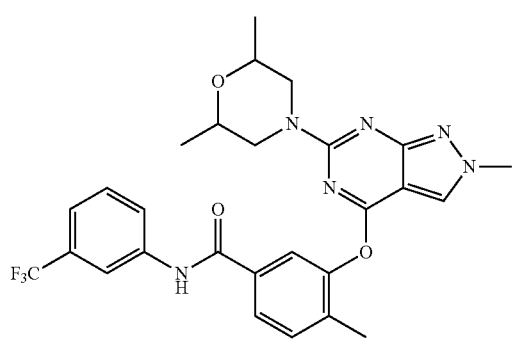
-continued
IV-f-1
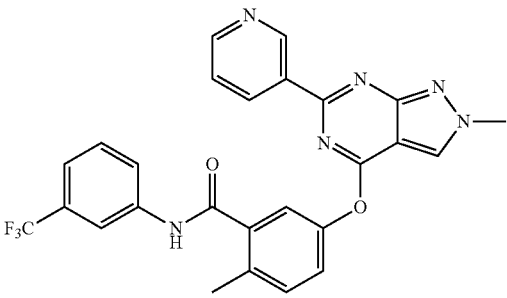
IV-f-2
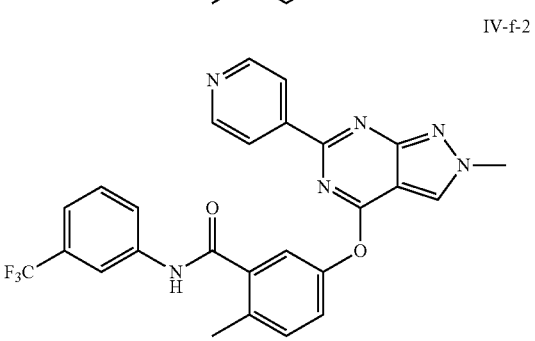
IV-g-1
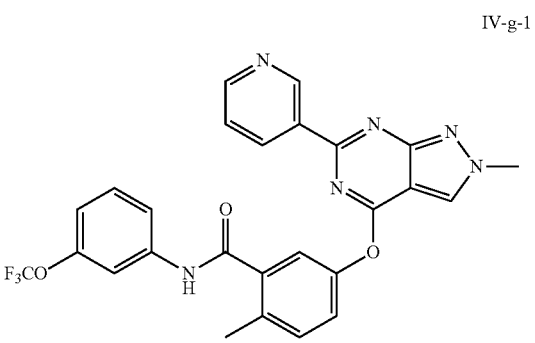
IV-g-2
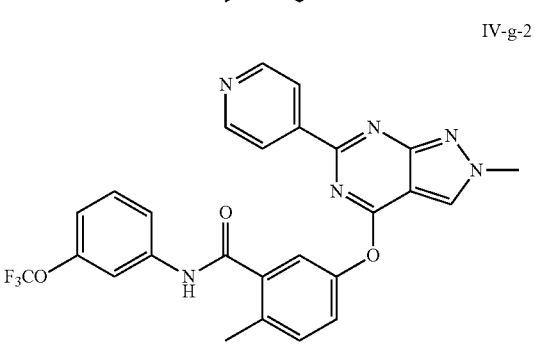
IV-h-1
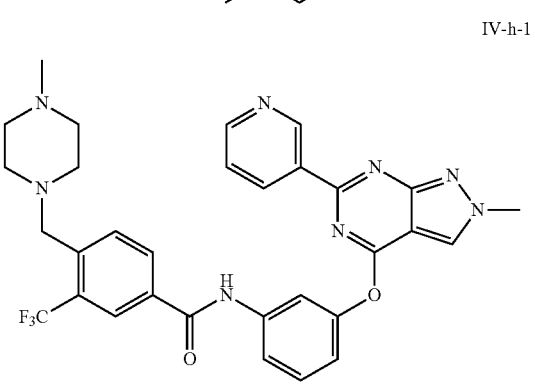

IV-h-2
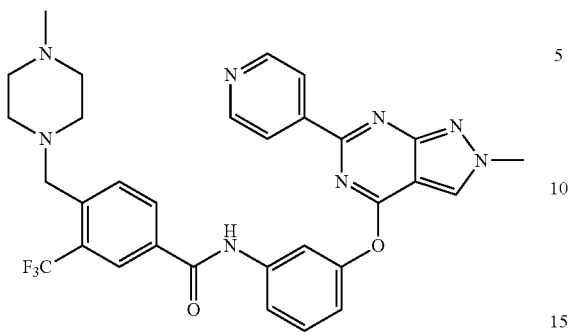
IV-l-2
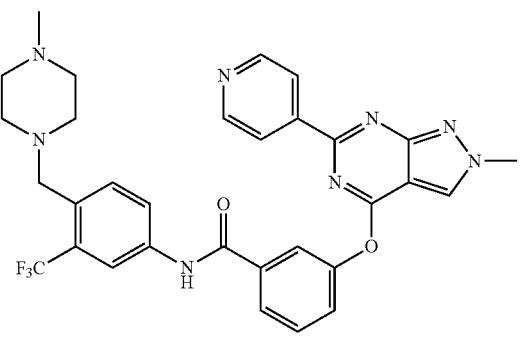
IV-i-1
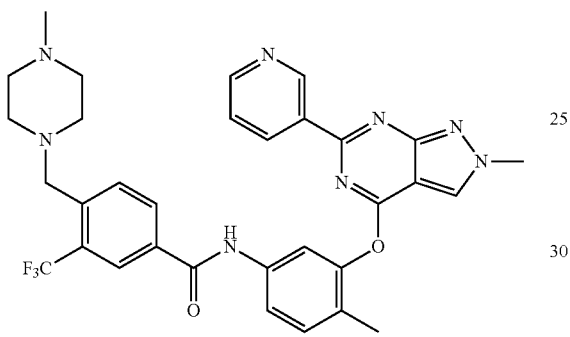
IV-m-1
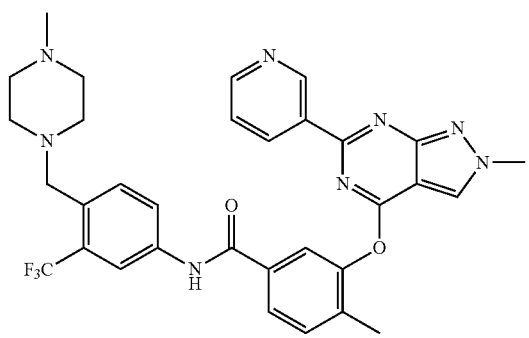
IV-i-2
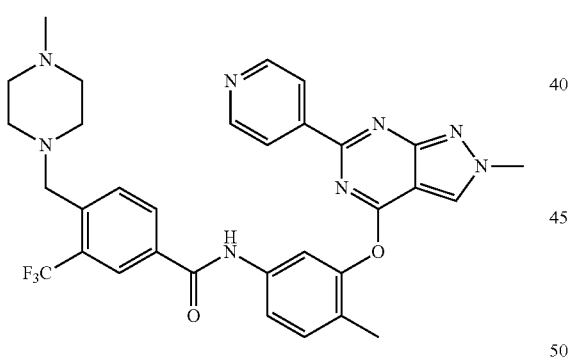
IV-m-2
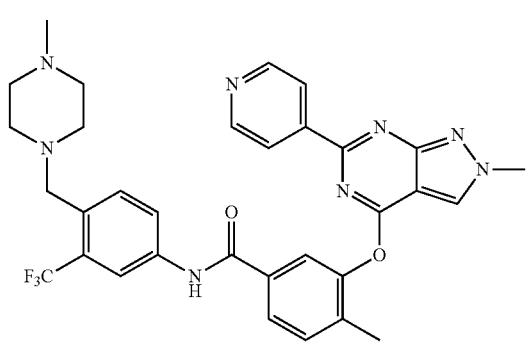
IV-l-1
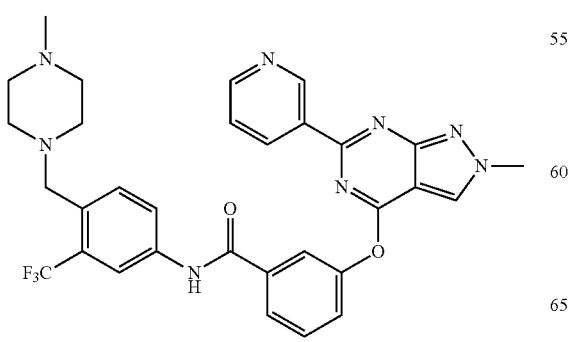
IV-n-1
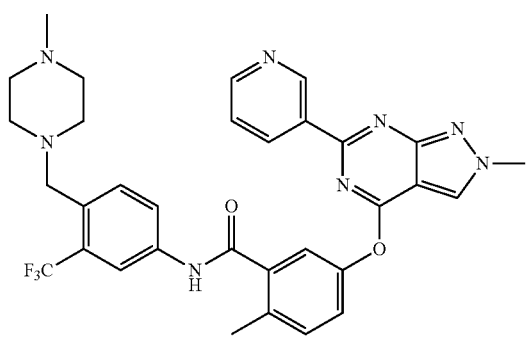

-continued
IV-n-2
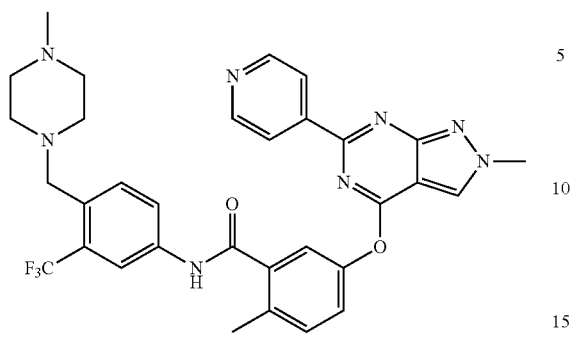
IV-n-6
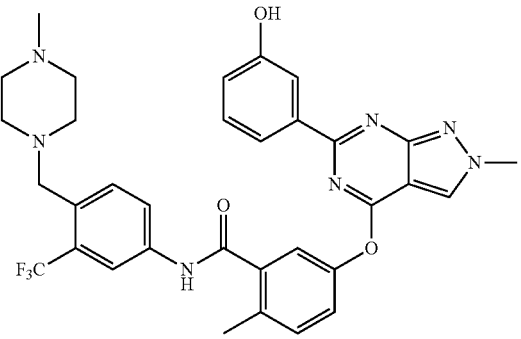
IV-n-3
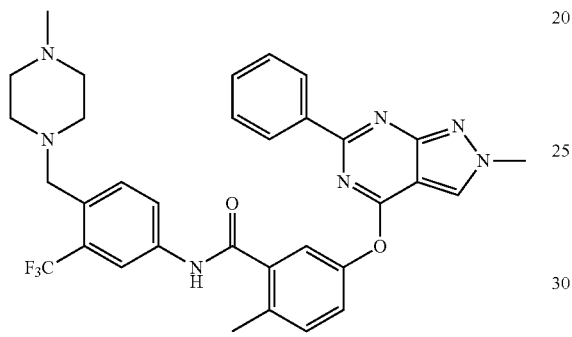
IV-n-7
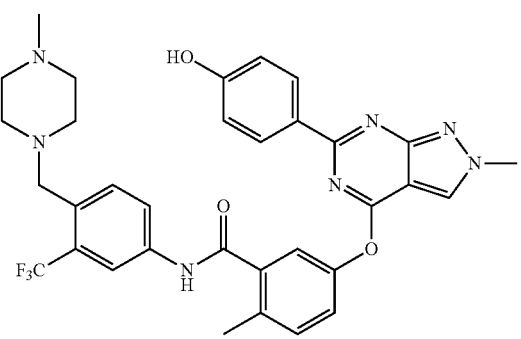
IV-n-4
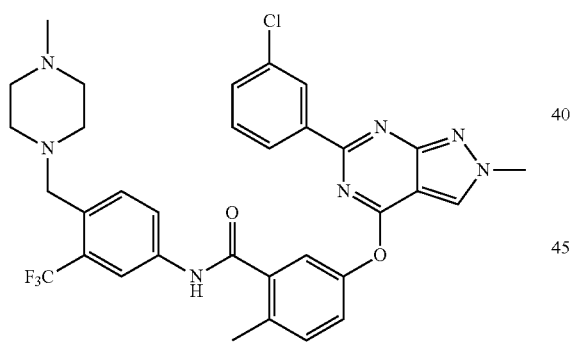
IV-n-8
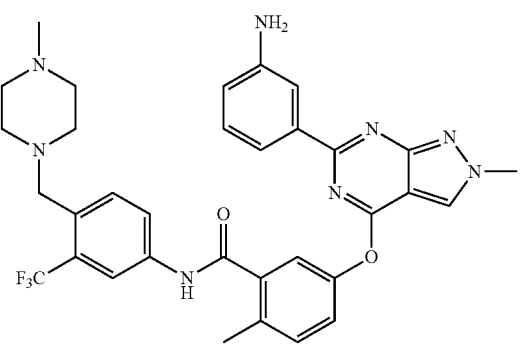
IV-n-5
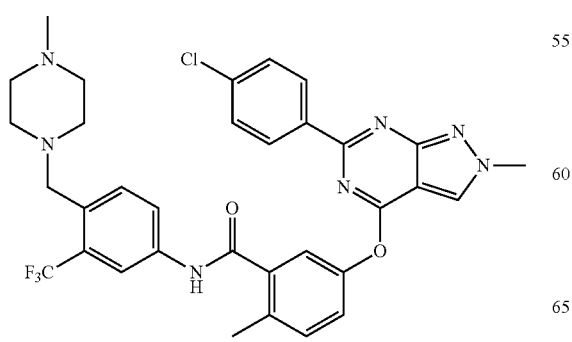
IV-n-9
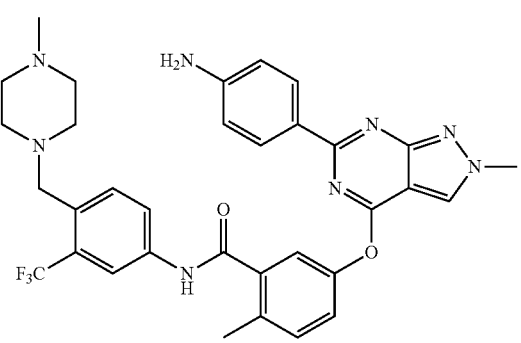

IV-n-10
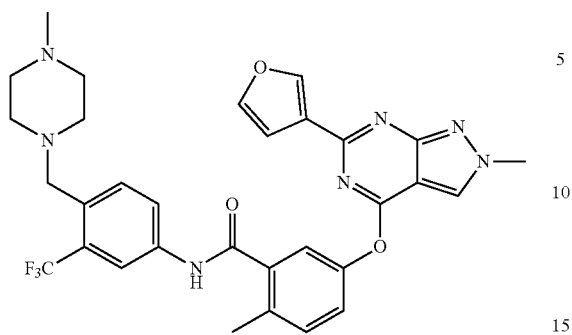
IV-n-11
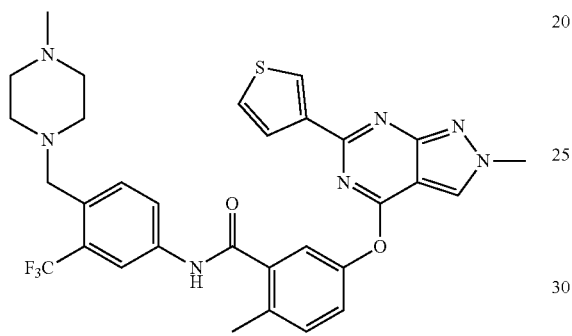
IV-o-1
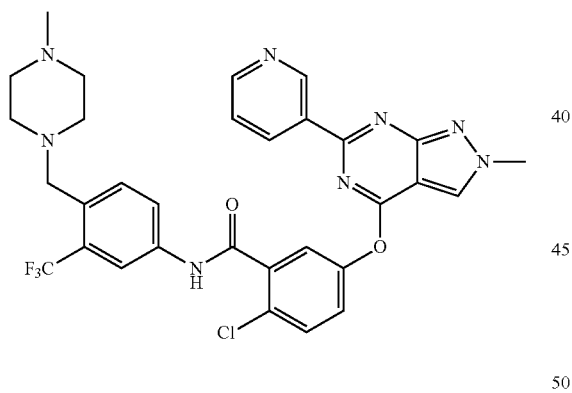
IV-o-2
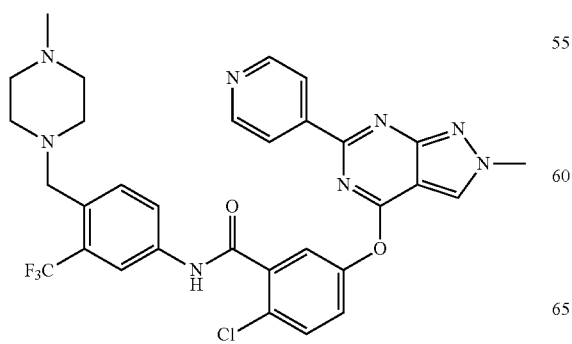
IV-o-3
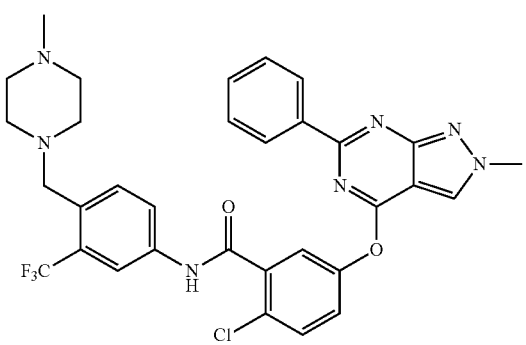
IV-o-4
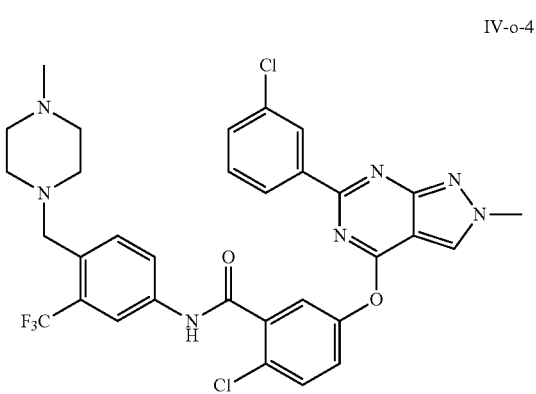
IV-o-5
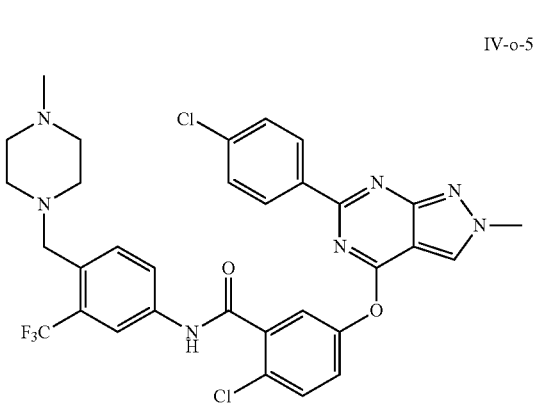
IV-o-6
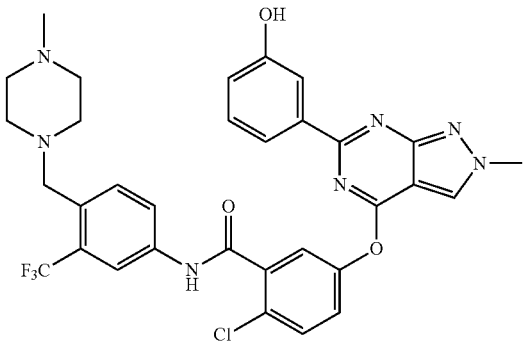

IV-o-7
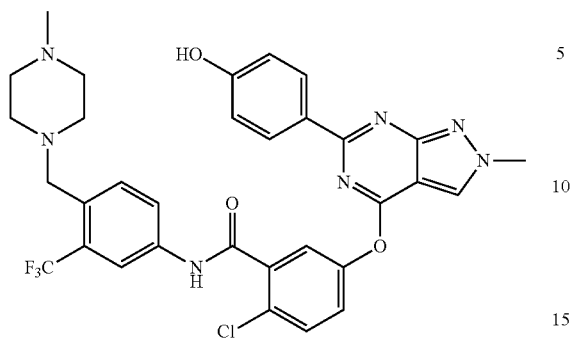
IV-o-11
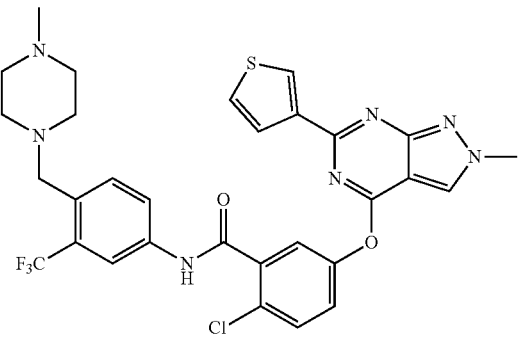
IV-o-8
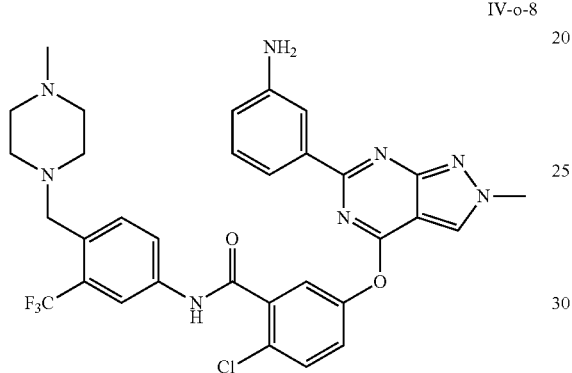
IV-o-12
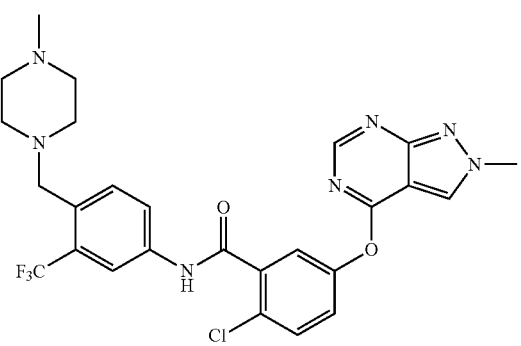
IV-o-9
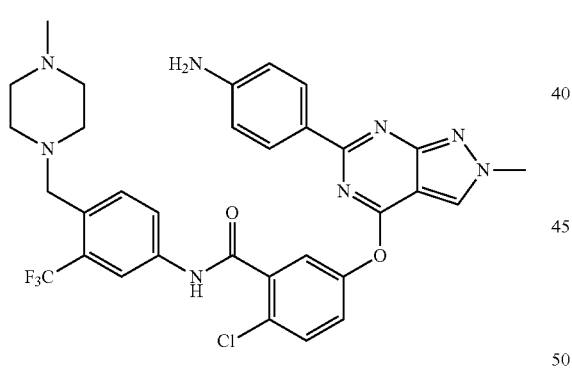
IV-r-1
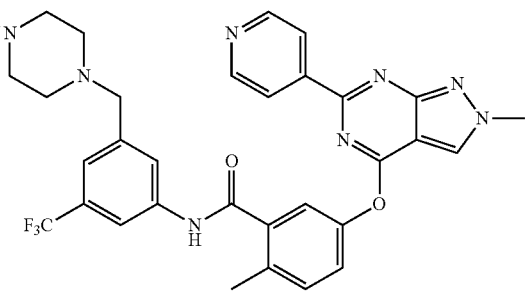
IV-o-10
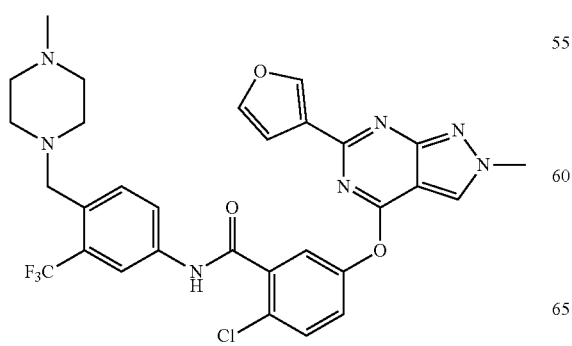
IV-t-1
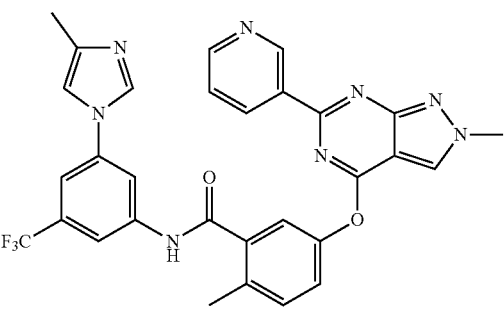

VI-h-1
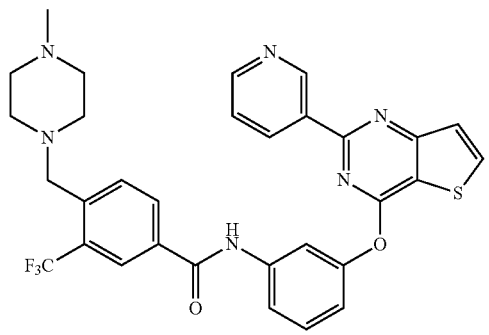
VI-j-1
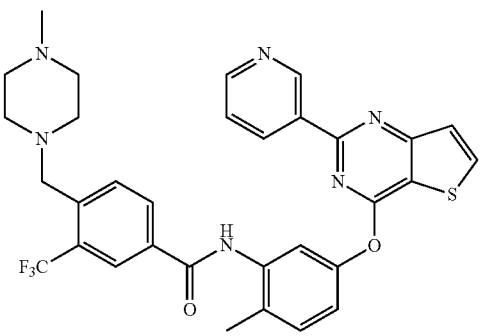
VI-h-2
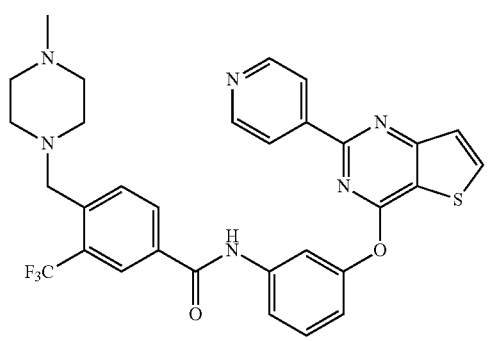
VI-j-2
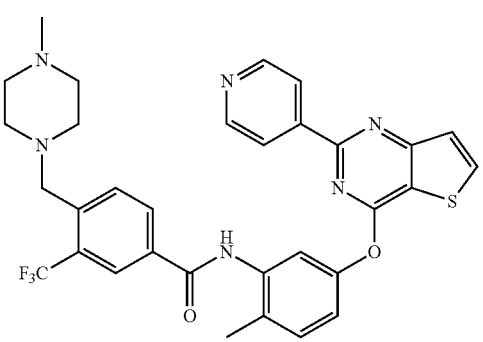
VI-i-1
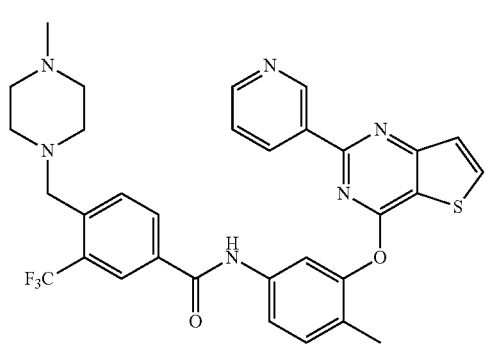
VI-l-1
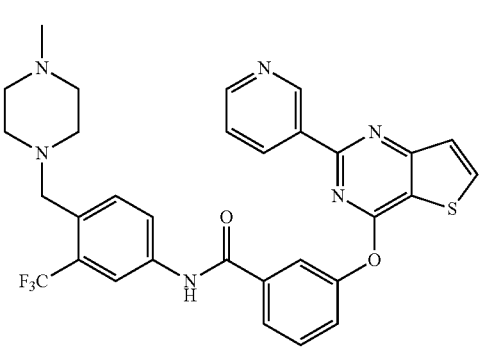
VI-i-2
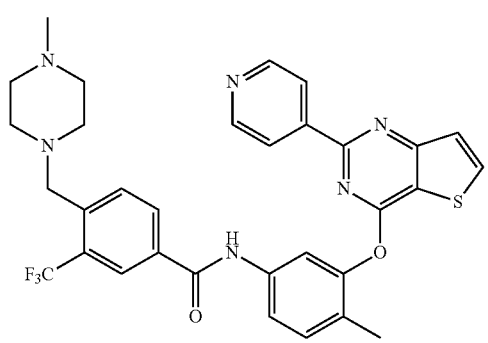
VI-m-1
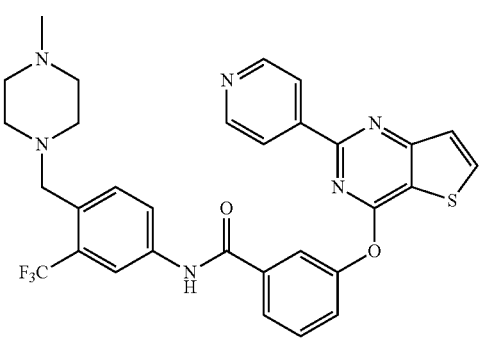

343
-continued

VI-n-1
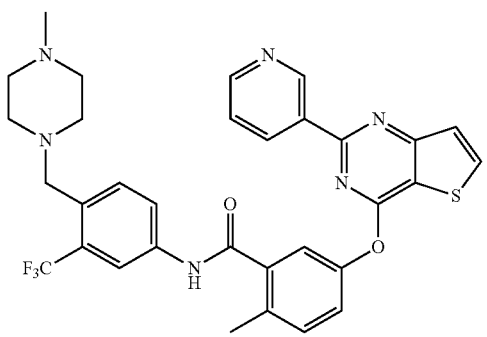

VI-o-1
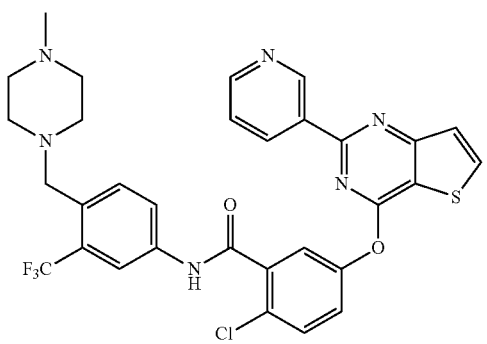

VI-o-2
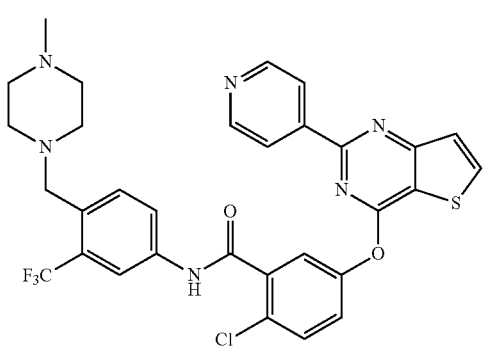

VI-p-1
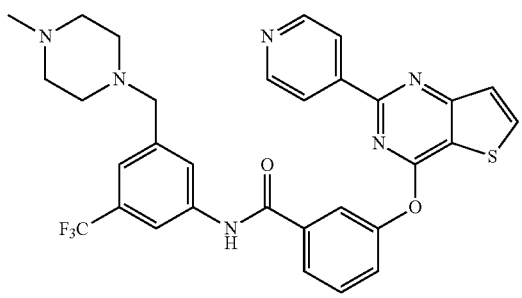

344
-continued

VI-p-2
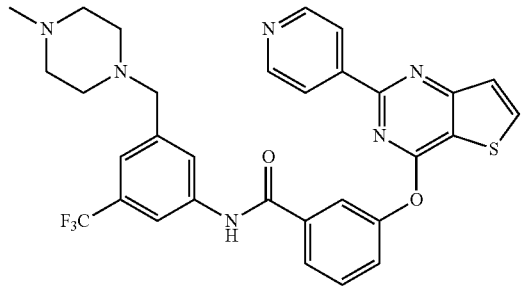

VI-q-1
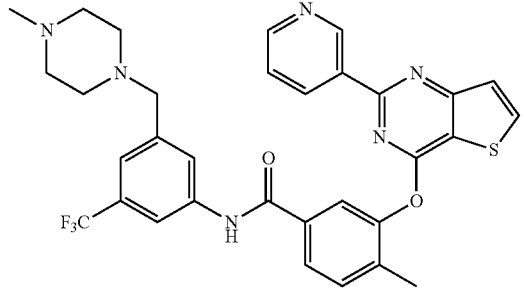

and

VI-q-2
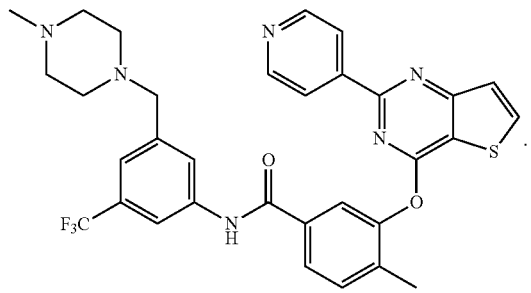

8. A pharmaceutical composition, comprising a compound or a pharmaceutically acceptable salt thereof according to claim 1 and a pharmaceutically acceptable carrier, diluent, or excipient.

9. A preparation method of a compound according to claim 1, comprising the following steps:
   a) reacting a compound of formula 1 with a compound of formula 2 under alkaline conditions to obtain a compound of formula 3:

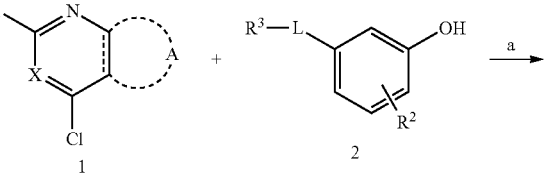

-continued

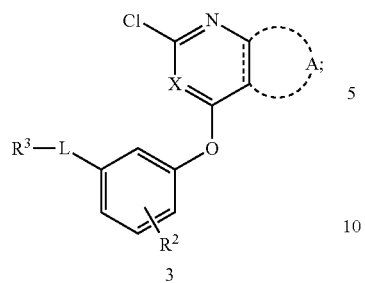

3 b) reacting the compound of formula 3 under Suzuki coupling reaction or Buchwald coupling reaction or basic conditions to obtain a compound of any one of formulae I, II, III, IV and VI:

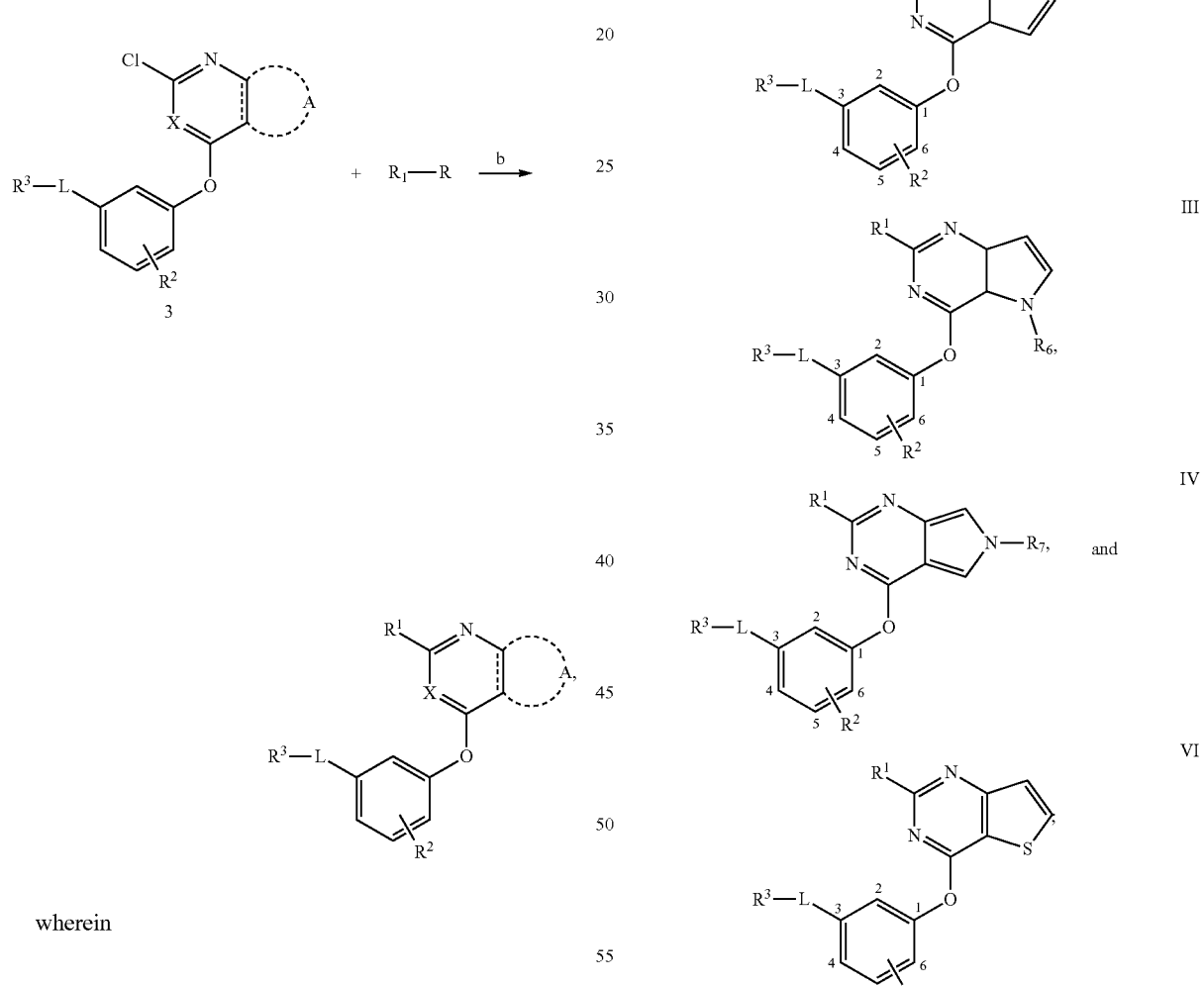

wherein

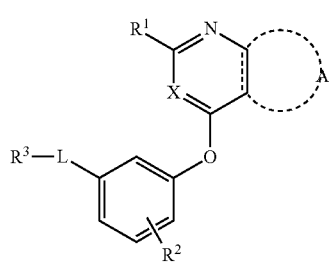

is selected from:

$R_1$, $R_2$, $R_3$, $R_4$, $R_5$, $R_6$, $R_7$ and L are as defined in claim 1; R refers to a reactive group selected from hydrogen, boric acid group, or borate ester group.

10. A preparation method according to claim 9, characterized in that:

a) in the step of preparing the compound of formula 3, the base used is selected from an organic base or an inorganic base;

b) in the step of preparing the compound of any one of formulae I, II, III, IV and VI, when the reaction is Suzuki coupling reaction, the metal catalyst used is a transition metal catalyst selected from Pd(dppf)Cl$_2$·CH$_2$Cl$_2$, Pd(OAc)$_2$, Pd(PPh$_3$)$_4$, Ni(cod$_2$), and Ni(dppf)Cl$_2$; the solvent used is selected from toluene, tetrahydrofuran, N,N-dimethylformamide, water, and mixed solvents; the base used is selected from sodium carbonate, potassium carbonate, cesium carbonate, potassium carbonate, sodium hydroxide, barium hydroxide, potassium fluoride, cesium fluoride, and sodium tert-butoxide;

c) in the step of preparing the compound of any one of formulae I, II, III, IV and VI, when the reaction is Buchwald coupling reaction, the metal catalyst used is a transition metal catalyst selected from Pd$_2$(dba)$_3$, Pd(OAc)$_2$, and Pd(dppf)Cl$_2$·CH$_2$Cl$_2$; the solvent used is selected from toluene, tetrahydrofuran, N,N-dimethylformamide, and tert-butanol; the base used is selected from potassium carbonate, cesium carbonate, sodium tert-butoxide, and lithium hexamethyldisilazide (LHMDS);

d) in the step of preparing the compound of any one of formulae I, II, III, IV and VI, when the reaction is under alkaline conditions, the base used is selected from organic bases and inorganic bases; the solvent used is selected from toluene, tetrahydrofuran, N,N-dimethylformamide, and tert-butanol.

11. A method of treating a disease associated with RET kinase accompanied by abnormal cell proliferation, morphological changes, or hyperkinesia in a subject, or treating a disease associated with angiogenesis or cancer metastasis in a subject, comprising administering the compound according to claim 1 or a pharmaceutically acceptable salt thereof to the subject, wherein the disease is lung adenocarcinoma.

12. A method of treating a disease associated with RET kinase accompanied by abnormal cell proliferation, morphological changes, or hyperkinesia in a subject, or treating a disease associated with angiogenesis or cancer metastasis in a subject, comprising administering the compound according to claim 7 to the subject, wherein the disease is lung adenocarcinoma.

* * * * *

UNITED STATES PATENT AND TRADEMARK OFFICE
CERTIFICATE OF CORRECTION

PATENT NO. : 11,319,322 B2
APPLICATION NO. : 16/626015
DATED : May 3, 2022
INVENTOR(S) : Xianming Deng et al.

Page 1 of 7

It is certified that error appears in the above-identified patent and that said Letters Patent is hereby corrected as shown below:

In the Claims

In Claim 1, at Column 249, Line 1, the text: --wherein: for-- should be added before Formula I.

In Claim 4, at Column 263, Lines 39-44, the formulae:

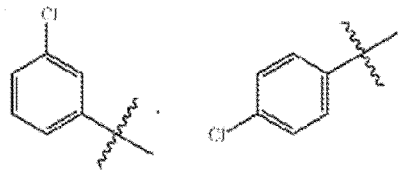

Should be replaced with the formulae:

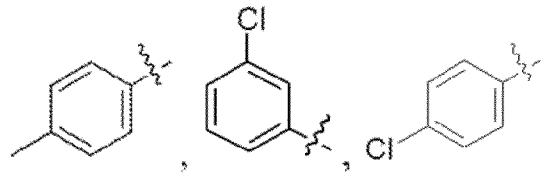

In Claim 5, at Column 265, Lines 1-12, the formula:

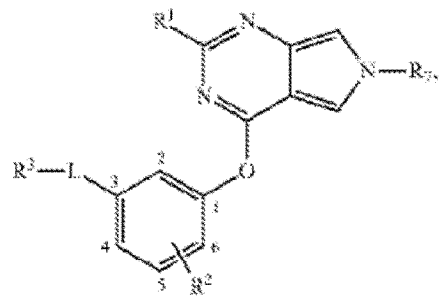

Signed and Sealed this
First Day of November, 2022

Katherine Kelly Vidal
*Director of the United States Patent and Trademark Office*

CERTIFICATE OF CORRECTION (continued)
U.S. Pat. No. 11,319,322 B2

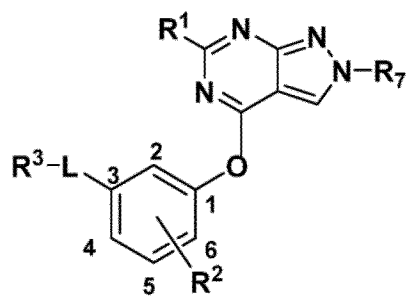

Should be replaced with the formula:

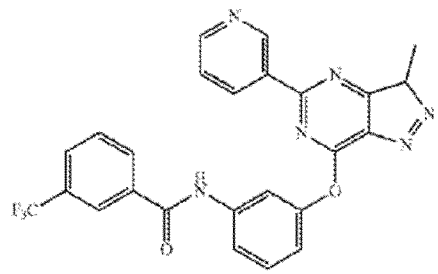

In Claim 7, at Column 267, Lines 54-65, the formula:

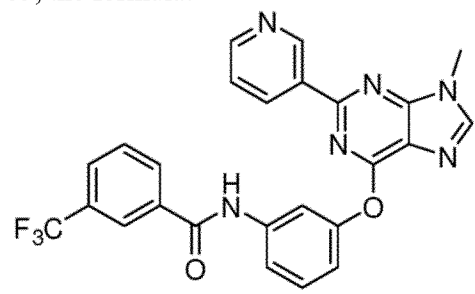

Should be replaced with the formula:

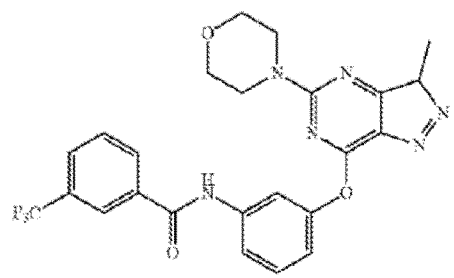

In Claim 7, at Column 268, Lines 3-13, the formula:

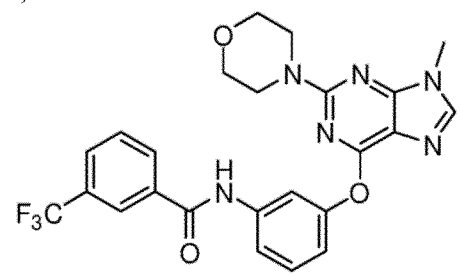

Should be replaced with the formula:

In Claim 7, at Column 268, Lines 15-29, the formula:
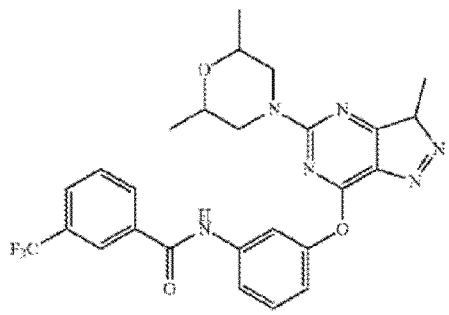
Should be replaced with the formula:
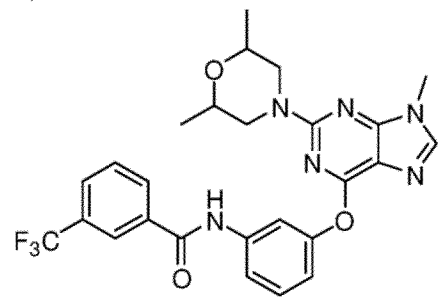
In Claim 7, at Column 268, Lines 30-41, the formula:
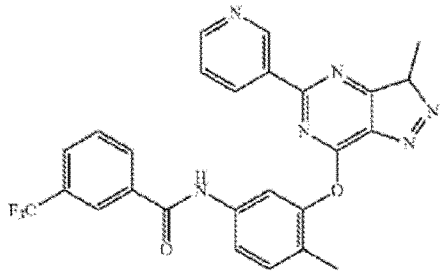
Should be replaced with the formula:
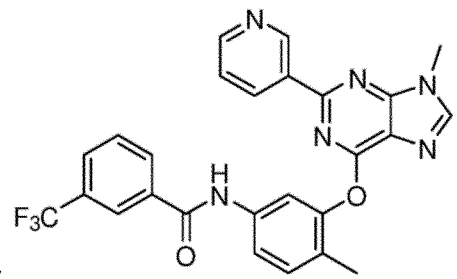
In Claim 7, at Column 268, Lines 43-53, the formula:
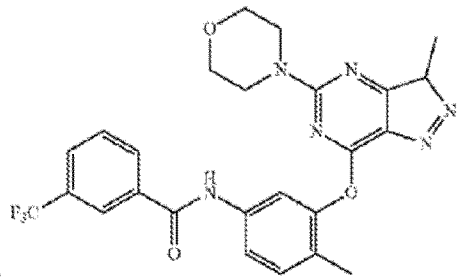

CERTIFICATE OF CORRECTION (continued)
U.S. Pat. No. 11,319,322 B2

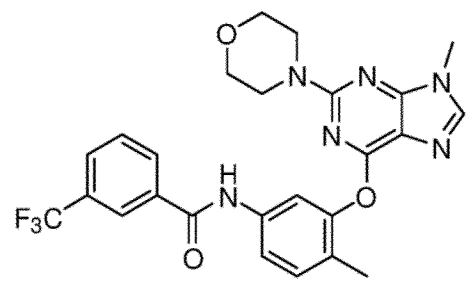

Should be replaced with the formula:

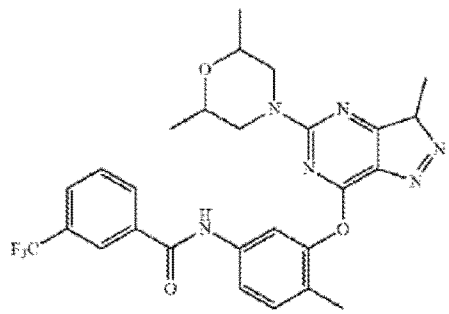

In Claim 7, at Column 268, Lines 54-68, the formula:

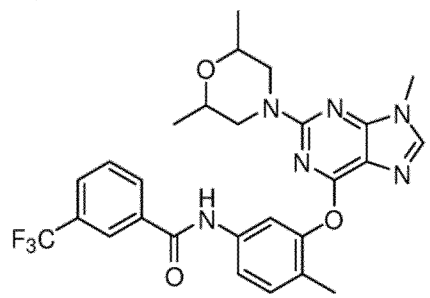

Should be replaced with the formula:

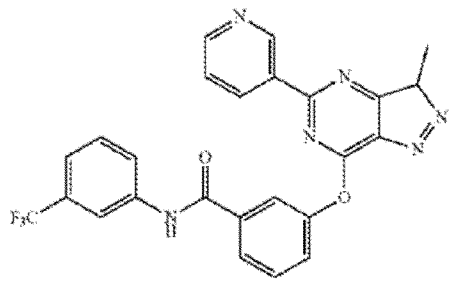

In Claim 7, at Column 269, Lines 3-12, the formula:

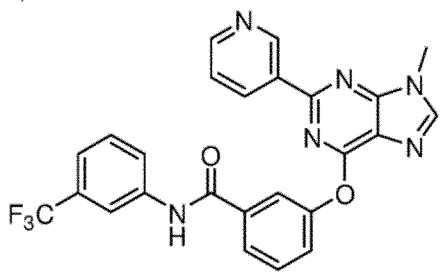

Should be replaced with the formula:

In Claim 7, at Column 269, Lines 15-26, the formula:
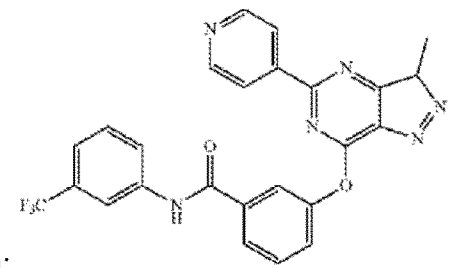
Should be replaced with the formula:
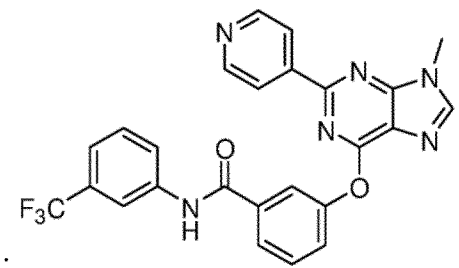
In Claim 7, at Column 318, Lines 35-50, the formula:
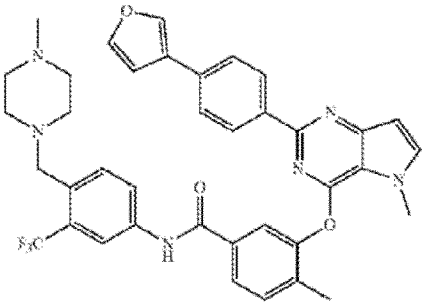
Should be replaced with the formula:
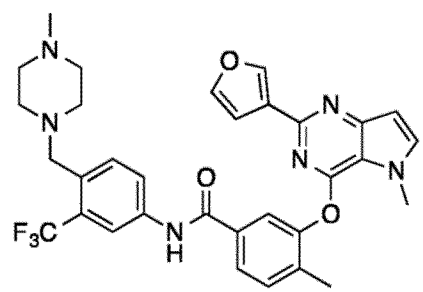
In Claim 7, at Column 318, Lines 53-67, the formula:
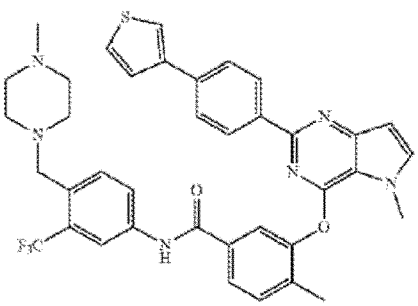

CERTIFICATE OF CORRECTION (continued)
U.S. Pat. No. 11,319,322 B2

Page 6 of 7

Should be replaced with the formula: 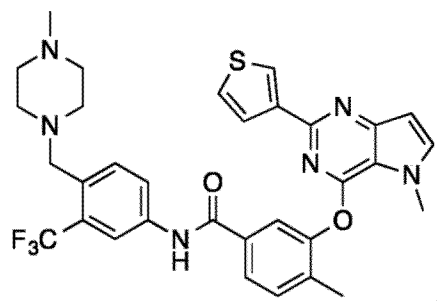 .

In Claim 9, at Column 346, Lines 4-15, the formula: 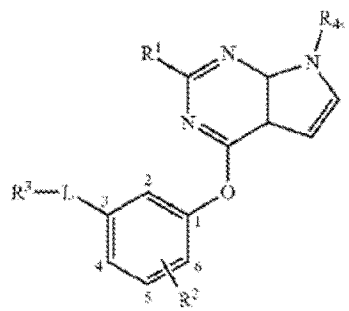

Should be replaced with the formula: 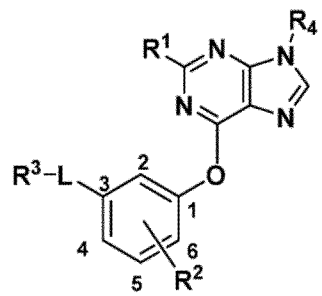 .

In Claim 9, at Column 346, Lines 16-26, the formula: 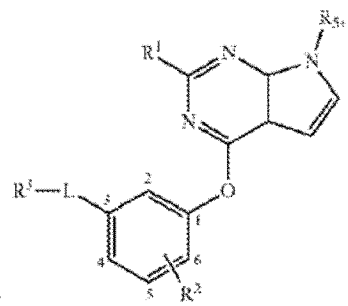

Should be replaced with the formula: 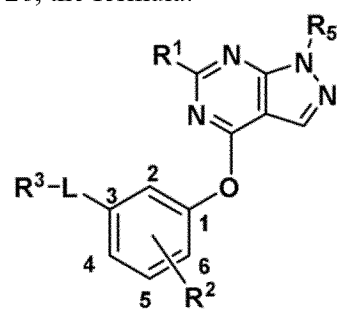 .

CERTIFICATE OF CORRECTION (continued)
U.S. Pat. No. 11,319,322 B2

In Claim 9, at Column 346, Lines 37-47, the formula:

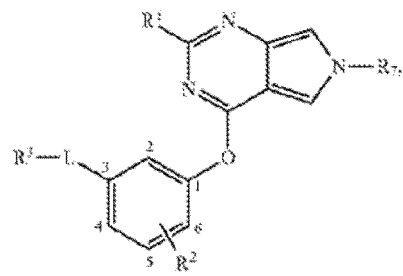

Should be replaced with the formula: